(12) United States Patent
McMinn et al.

(10) Patent No.: US 11,078,233 B2
(45) Date of Patent: *Aug. 3, 2021

(54) TRIPEPTIDE EPOXY KETONE PROTEASE INHIBITORS

(71) Applicant: Onyx Therapeutics, Inc., Thousand Oaks, CA (US)

(72) Inventors: Dustin McMinn, Pacifica, CA (US); Henry Johnson, San Bruno, CA (US); Simeon Bowers, Oakland, CA (US); David C. Moebius, Westwood, MA (US)

(73) Assignee: Onyx Therapeutics, Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/818,731

(22) Filed: Mar. 13, 2020

(65) Prior Publication Data

US 2020/0207809 A1  Jul. 2, 2020

Related U.S. Application Data

(60) Division of application No. 15/251,688, filed on Aug. 30, 2016, now Pat. No. 10,647,744, which is a
(Continued)

(30) Foreign Application Priority Data

Mar. 13, 2014 (AR) .............................. P140100970

(51) Int. Cl.
| | | |
|---|---|---|
| *C07K 5/08* | (2006.01) | |
| *C07K 5/097* | (2006.01) | |
| *C07D 405/12* | (2006.01) | |
| *C07D 409/12* | (2006.01) | |
| *C07D 303/32* | (2006.01) | |
| *C07K 5/062* | (2006.01) | |
| *C07K 5/02* | (2006.01) | |
| *C07K 5/06* | (2006.01) | |
| *C07K 5/078* | (2006.01) | |
| *C07K 5/065* | (2006.01) | |
| *C07K 5/072* | (2006.01) | |
| *C07K 5/083* | (2006.01) | |

(Continued)

(52) U.S. Cl.
CPC ............ *C07K 5/0821* (2013.01); *A61K 38/06* (2013.01); *C07D 303/32* (2013.01); *C07D 405/12* (2013.01); *C07D 409/12* (2013.01); *C07K 5/0202* (2013.01); *C07K 5/0205* (2013.01); *C07K 5/0606* (2013.01); *C07K 5/06026* (2013.01); *C07K 5/06069* (2013.01); *C07K 5/06078* (2013.01); *C07K 5/06113* (2013.01); *C07K 5/06121* (2013.01); *C07K 5/06139* (2013.01); *C07K 5/06147* (2013.01); *C07K 5/06173* (2013.01); *C07K 5/06191* (2013.01); *C07K 5/0806* (2013.01); *A61K 38/00* (2013.01)

(58) Field of Classification Search
CPC .............. C07K 5/0821; C07K 5/06121; C07K 5/06069; C07K 5/06078; C07K 5/06147; C07K 5/06173; C07K 5/06191; C07K 5/0205; C07K 5/0202; C07K 5/06139; C07K 5/06113; C07K 5/0606; C07K 5/06026; C07K 5/0806; A61K 38/06; A61K 38/00; C07D 405/12; C07D 303/32; C07D 409/12
See application file for complete search history.

(56) References Cited

U.S. PATENT DOCUMENTS

| | | |
|---|---|---|
| 4,522,811 A | 6/1985 | Eppstein et al. |
| 5,340,736 A | 8/1994 | Goldberg |

(Continued)

FOREIGN PATENT DOCUMENTS

| | | |
|---|---|---|
| CN | 101014612 A | 8/2007 |
| JP | 2009-514971 A | 4/2009 |

(Continued)

OTHER PUBLICATIONS

Adams, The proteasome: a suitable antineoplastic target, Nat. Rev. Cancer, 4(5):349-60 (2004).
(Continued)

*Primary Examiner* — Sudhaker Katakam
(74) *Attorney, Agent, or Firm* — Marshall, Gerstein & Borun LLP

(57) ABSTRACT

Provided herein are tripeptide epoxy ketone protease inhibitors, methods of their preparation, related pharmaceutical compositions, and methods of using the same. For example, provided herein are compounds of Formula (X):

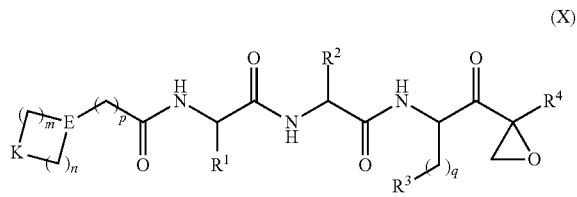

and pharmaceutically acceptable salts and compositions including the same. The compounds and compositions provided herein may be used, for example, in the treatment of diseases including inflammation and neurodegenerative disease.

27 Claims, No Drawings

Related U.S. Application Data continuation of application No. 14/210,806, filed on Mar. 14, 2014, now Pat. No. 9,434,761.

(60) Provisional application No. 61/941,798, filed on Feb. 19, 2014, provisional application No. 61/883,843, filed on Sep. 27, 2013, provisional application No. 61/883,798, filed on Sep. 27, 2013, provisional application No. 61/856,847, filed on Jul. 22, 2013, provisional application No. 61/847,780, filed on Jul. 18, 2013, provisional application No. 61/785,608, filed on Mar. 14, 2013, provisional application No. 61/786,086, filed on Mar. 14, 2013.

(51) Int. Cl.
*A61K 38/06* (2006.01)
*A61K 38/00* (2006.01)

(56) References Cited

U.S. PATENT DOCUMENTS

| | | | |
|---|---|---|---|
| 6,468,798 | B1 | 10/2002 | Debs et al. |
| 6,471,996 | B1 | 10/2002 | Sokoll et al. |
| 6,472,375 | B1 | 10/2002 | Hoon et al. |
| 7,232,818 | B2 | 6/2007 | Smyth et al. |
| 7,417,042 | B2 | 8/2008 | Smyth et al. |
| 7,589,066 | B2 | 9/2009 | Orlowski et al. |
| 7,687,456 | B2 | 3/2010 | Zhou et al. |
| 7,691,852 | B2 | 4/2010 | Shenk et al. |
| 7,737,112 | B2 | 6/2010 | Lewis et al. |
| 8,088,741 | B2 | 1/2012 | Smyth et al. |
| 9,434,761 | B2 | 9/2016 | McMinn et al. |
| 10,647,744 | B2 * | 5/2020 | McMinn ................ A61P 13/12 |
| 2003/0216325 | A1 | 11/2003 | Saksena et al. |
| 2007/0105786 | A1 | 5/2007 | Zhou et al. |
| 2008/0090785 | A1 | 4/2008 | Smyth et al. |
| 2013/0303482 | A1 | 11/2013 | Lewis et al. |

FOREIGN PATENT DOCUMENTS

| | | |
|---|---|---|
| JP | 2009-541327 A | 11/2009 |
| WO | 98/10779 A1 | 3/1998 |
| WO | 2007/056464 A1 | 5/2007 |
| WO | 2007/149512 A2 | 12/2007 |
| WO | 2010/048298 A1 | 4/2010 |

OTHER PUBLICATIONS

Basler et al, The immunoproteasome: a novel drug target for autoimmune diseases, Clinical and Experimental Rheumatology, 33: S-74-S-79 (2015).
Basler et al., Co-inhibition of immunoproteasome subunits LMP2 and LMP7 is required to block autoimmunity, EMBO Reports, 19:e46512 (2018).
Basler et al., Inhibition of the immunoproteasome ameliorates experimental autoimmune encephalomyelitis, EMBO Molecular Medicine, 6:226-238 (2014).
Basler et al., Prevention of experimental colitis by a selective inhibitor of the immunoproteasome, J. Immunol., 185:634-41 (2010).
Berge et al., Pharmaceutical salts, J. Pharm. Sci., 66(1):1-19 (1977).
Braun et al., Targeting NF-kappaB in hematologic malignancies, Cell Death Differ., 13(5):748-58 (2006).
Brzezinski et al., Low Neurotoxicity of Onx-0914 Supports the Idea of Specific Immunoproteasome Inhibition as a Side-Effect-Limiting, Therapeutic Stragegy, Eur. J. Microbiol. Immunol., 7(3):234-45 (2017).
Chapatte et al., Processing of tumor-associated antigen by the proteasomes of dendritic cells controls in vivo T-cell responses, Cancer Res., 66(10):5461-8 (2006).

Chen et al., Inhibition of immunoproteasome reduces infarction volume and attenuates inflammatory reaction in a rat model of ischemic stroke, Cell Death and Disease, 6:e1626 (2015).
Chen et al., Proteasome inhibitor ameliorates severe acute pancreatitis and associated lung injury of rats, World J Gastroenterol, 14(20):3249-3253 (2008).
Ciechanover, The ubiquitin-proteasome proteolytic pathway, Cell, 79(1):13-21 (1994).
Cilloni et al., Nuclear factor kB as a target for new drug development in myeloid malignancies, Haematologica, 92(9):1224-9 (2007).
Cohen, AIDS mood upbeat—for a change, Science, 267:959-60 (1995).
Collins, Endothelial nuclear factor—kappa B and the initiation of the atherosclerotic lesion, Lab. Invest., 68(5):499-508 (1993).
Demo et al., Antitumor activity of PR-171, a novel irreversible inhibitor of the proteasome, Cancer Res., 67(13):6383-91 (2007).
Farini et al., Therapeutic potential of immunoproteasome inhibition in Duchenne muscular dystrophy, Molecular Therapy, 24(11):1898-1912 (2016).
Garrett et al., Selective inhibitors of the osteoblast proteasome stimulate bone formation in vivo and in vitro, J. Clin. Invest., 111(11):1771-82 (2003).
Gonzalez et al., Proteasome function is required for encystation of Entamoeba invadens, Arch. Med. Res., 28 Spec No. 139-40 (1997).
Hamajima et al., Intranasal administration of HIV-DNA vaccine formulated with a polymer, carboxymethylcellulose, augments mucosal antibody production and cell-mediated immune response, Clin. Immunol. Immunopathol., 88(2):205-10 (1998).
Hardy, The secret life of the hair follicle, Trends Genet., 8(2):55-61 (1992).
Harris et al., Effects of transforming growth factor beta on bone nodule formation and expression of bone morphogenetic protein 2, osteocalcin, osteopontin, alkaline phosphatase, and type I collagen mRNA in long-term cultures of fetal rat calvarial osteoblasts, J. Bone Miner. Res., 9(6):855-63 (1994).
Ho et al., LMP2-specific inhibitors: chemical genetic tools for proteasome biology, Chem. Biol., 14(4):419-30 (2007).
Huber et al., Immuno- and Constitutive Proteasome Crystal Structures Reveal Differences in Substrate and Inhibitor Specificity, Cell, 148:727-738 (2012).
Ichikawa et al., Novel proteasome inhibitors have a beneficial effect in murine lupus via the dual inhibition of type I interferon and autoantibody secreting cells, Arthritis and Rheumatism, 64:493-503 (2012).
International Application No. PCT/US2014/026980, International Preliminary Report on Patentability, dated Sep. 24, 2015.
International Application No. PCT/US2014/026980, International Search Report and Written Opinion, dated Jul. 28, 2014.
International Application No. PCT/US2014/026987, International Preliminary Report on Patentability, dated Sep. 24, 2015.
International Application No. PCT/US2014/026987, International Search Report and Written Opinion, dated Jul. 30, 2014.
Johnson et al., Required immunoproteasome subunit inhibition profile for anti-inflammatory efficacy and clinical candidate KZR-616 ((2S,3R)-N-((S)-3-(Cyclopent-1-en-1-yl)-1-((R)-2-methyloxiran-2-yl)-1-oxo-propan-2-yl)-3-hydroxy-3-(4-methoxyphenyl)-2((S)-2-)2-morpholinoacetamido-) propanamido) propenamide), J. Med. Chem., 61:11127-11143 (2018).
Kalim et al., Immunoproteasome subunit LMP7 deficiency and inhibition suppresses Th1 and Th17 but enhances regulatory T cell differentiation, J. Immunol., 189:4182-93 (2012).
Kojima et al., Two-way cleavage of beta-amyloid protein precursor by multicatalytic proteinase, FEBS Lett., 304(1):57-60 (1992).
Kuek et al., Immune-mediated inflammatory diseases (IMIDs) and biologic therapy: a medical revolution, Postgrad Med. J., 83:251-260 (2007).
Kumatori et al., Abnormally high expression of proteasomes in human leukemic cells, Proc. Natl. Acad. Sci. USA, 87(18):7071-5 (1990).
Lee et al., The immunoproteasome: an emerging therapeutic target. Curr. Top. Med. Chem. 11(23):2923-30 (2011).
Liu et al., ONX-0914, a selective inhibitor of immunoproteasome, ameliorates experimental autoimmune myasthenia gravis by modulating humoral response, J. Neuroimmunol., 311:71-78 (2017).

(56) References Cited

OTHER PUBLICATIONS

Liu et al., PR-957, a selective inhibitor of immunoproteasome subunit low-MW polypeptide 7, attenuates experimental autoimmune neuritis by suppressing Th 17-cell differentiation and regulating cytokine production, FASEB Journal, 31(4):1756-1766 (2018).
Meiners et al., Ubiquitin-Proteasome Pathway as a New Target for the Prevention of Restenosis, Circulation, 105:483-489 (2002).
Meng et al., Epoxomicin, a potent and selective proteasome inhibitor, exhibits in vivo anti-inflammatory activity, Proc. Natl. Acad. Sci. USA, 96:10403 (1999).
Moebius et al., Immunoproteasomes are essential for survival and expansion of T cells in virus-infected mice, Eur. J. Immunol., 40:3439-3449 (2010).
Muchamuel et al., "A selective inhibitor of the immunoproteasome subunit NMP7 blocks cytokine production and attenuates progression of experimental arthritis," Nat. Med., 15:781-787 (2009).
Muchamuel et al., KZR-616, A selective inhibitor of the immunoproteasome, Blocks the disease progression in multiple models of systemic lupus erythematosus (SLE), Annals of the Rheumatic Diseases, 77:685 (2018).
Mundt S, et al., Inhibition and deficiency of the immunoproteasome subunit LMP7 attenuates LCMV-induced meningitis, Eur. J. Immunol., 00:1-10 (2015).
Nagayama et al., Prophylactic and therapeutic efficacies of a selective inhibitor of the immunoproteasome for Hashimoto's thyroiditis, but not for Graves' hyperthyroidism, in mice, Clin. Exp. Immunol., 168:268-273 (2012).
Palombella et al., The ubiquitin-proteasome pathway is required for processing the NF-kappa B1 precursor protein and the activation of NF-kappa B, Cell, 78(5):773-85 (1994).
Parlati et al., Carfilzomib can induce tumor cell death through selective inhibition of the chymotrypsin-like activity of the proteasome, Blood, 114(16):3439-47 (2009).
Patani et al., Bioisosterism: A Rational Approach in Drug Design, Chem. Rev., 96:3147-3176 (1996).
Paugam et al., Characterization and role of protozoan parasite proteasomes, Trends Parasitol., 19(2):55-9 (2003).
Purves et al., Life: The science of biology, 7th ed. W. H. Freeman & Co, 2004, G-3.
Qureshi et al., The proteasome as a lipopolysaccharide-binding protein in macrophages: differential effects of proteasome inhibition on lipopolysaccharide-induced signaling events, J. Immunol., 171(3):1515-25 (2003).
Rolfe et al., The ubiquitin-mediated proteolytic pathway as a therapeutic area, J. Mol. Med. (Berl.), 75(1):5-17 (1997).
Rosenblum et al., Mechanisms of human autoimmunity, J Clin Invest., 125(6):2228-2233 (2015).
Screen et al., Nature of pharmacophore influences active site specificity of proteasome inhibitors. J. Biol. Chem., 285(51):40125-34 (2010).
Semren et al., Validation of the 2nd Generation Proteasome Inhibitor Oprozomib for Local Therapy of Pulmonary Fibrosis, PLOS One, 10(9):e0136188 (2015).
Sharma et al., "Near-infrared activity-based fluorescent probe for LMP7: A chemical proteomics tool for immunoproteasome in living cells," Chembiochem, 13:1899-1903 (2012).
Shimada et al., Proteasome inhibitors improve the function of mutant lysosomal-glucosidase in fibroblasts from Pompe disease patient carrying c.546G>T mutation, Biochem. Biophys. Res. Commun., 415(2):274-8 (2011).
Simsek et al., Hepatitis B virus large and middle glycoproteins are degraded by a proteasome pathway in glucosidase-inhibited cells but not in cells with functional glucosidase enzyme, J. Virol., 79(20):12914-20 (2005).
Szalay et al., Ongoing coxsackievirus myocarditis is associated with increased formation and activity of myocardial immunoproteasomes, Am. J. Pathol., 168(5):1542-52 (2006).
Thanos et al., NF-kappa B: a lesson in family values, Cell, 80(4):529-32 (1995).
Traenckner et al., A proteasome inhibitor prevents activation of NF-kappa B and stabilizes a newly phosphorylated form of I kappa B-alpha that is still bound to NF-kappa B, EMBO J., 13(22):5433-41 (1994).
Verbrugge et al., Inactivating PSMB5 mutations and P-glycoprotein (multidrug resistance-associated protein/ATP-binding cassette B1) mediate resistance to proteasome inhibitors: ex vivo efficacy of (immuno)proteasome inhibitors in mononuclear blood cells from patients with rheumatoid arthritis, J. Pharmacol. Exp. Ther., 341(1):174-82 (2012).
Wang et al., Human autoimmune diseases: a comprehensive update, Journal of Internal Medicine, 278(4):369-295 (2015).
Wehenkel et al., A selective inhibitor of the immunoproteasome subunit LMP2 induces apoptosis in PC-3 cells and suppresses tumour growth in nude mice, Br. J. Cancer, 107(1):53-62 (2012).
Yamamoto, Mechanisms of Autoimmunity, JMAJ., 47(9):403-406 (2004).
Yu et al., The ubiquitin-proteasome system facilitates the transfer of murine coronavirus from endosome to cytoplasm during virus entry, J. Virol., 79(1):644-8 (2005).
Zilberberg et al., Inhibition of the Immunoproteasome Subunit LMP7 with ONX 0914 Ameliorates Graft-versus-Host Disease in an MHC-Matched Minor Histocompatibility Antigen-Disparate Murine Model, Biol Blood Marrow Transplant, 21:1555-1564 (2015).

* cited by examiner

TRIPEPTIDE EPOXY KETONE PROTEASE INHIBITORS

CROSS-REFERENCE TO RELATED APPLICATIONS

This is a continuation of U.S. patent application Ser. No. 14/210,806, filed Mar. 14, 2014, which claims the benefit of U.S. Provisional Application Nos. 61/941,798 (filed Feb. 19, 2014), 61/883,798 (filed on Sep. 27, 2013), 61/856,847 (filed on Jul. 22, 2013), 61/847,780 (filed on Jul. 18, 2013), 61/786,086 (filed on Mar. 14, 2013), 61/883,843 (filed on Sep. 27, 2013), and 61/785,608 (filed on Mar. 14, 2013), each of which is incorporated herein by reference in its entirety.

BACKGROUND OF THE INVENTION

Field of the Invention

This disclosure relates to tripeptide epoxy ketone protease inhibitors including methods of making and using the same.

Description of Related Technology

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multi-catalytic protease, which cleaves proteins into short peptides through the action of its three major proteolytic activities. While having a general function in intracellular protein turnover, proteasome-mediated degradation also plays a key role in many processes such as major histocompatibility complex (MHC) class I antigen presentation, apoptosis, cell growth regulation, NF-κB activation, antigen processing, and transduction of pro-inflammatory signals.

The 20S proteasome is a 700 kDa cylindrical-shaped multicatalytic protease complex comprised of 28 subunits organized into four rings. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteasomes thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three interferon-γ-inducible β subunits (LMP7, LMP2 and MECL1), which replace their normal counterparts, β5, β1 and β7 respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in β subunits and the exchange of γ interferon-inducing β subunits alter these activities to various degrees.

New compositions and methods for preparing and formulating proteasome inhibitor(s) would be useful.

SUMMARY OF THE INVENTION

Provided herein are compounds of general formula (X) or (I):

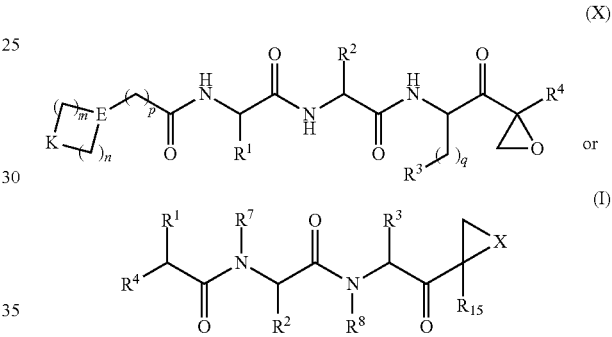

with substituents defined as discussed in detail below.

Also provided herein is a pharmaceutical composition comprising a pharmaceutically acceptable carrier or diluent and a compound provided herein, or a pharmaceutically acceptable salt thereof.

The compounds can compositions provided herein are useful in the treatment of diseases or disorders, such inflammation and neurodegenerative disease. Specifically contemplated diseases include, but are not limited to, rheumatoid arthritis, lupus, multiple sclerosis, and Crohn's disease. Accordingly, provided herein is a method of treating such a disease or disorder in a patient, the method comprising administering a therapeutically effective amount of a compound or composition as provided herein to cause a therapeutic effect.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

DETAILED DESCRIPTION OF THE INVENTION

Definitions

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

As used herein, chemical structures which contain one or more stereocenters depicted with dashed and bold bonds (i.e., ⋯⋯ and ━) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

Resolution of racemic mixtures of compounds can be carried out by any of numerous methods known in the art. An exemplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethyl amine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "$C_{x-y}$alkyl" refers to substituted or unsubstituted saturated hydrocarbon groups, including straight-chain alkyl and branched-chain alkyl groups that contain from x to y carbons in the chain. For example, $C_{1-7}$alkyl refers to an alkyl groups having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond, respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term, "$C_{x-y}$alkoxyalkyl" refers to a $C_{x-y}$alkyl group, as previously defined, substituted with an alkoxy group. For example, the term "$C_{1-6}$alkoxyalkyl" refers to a $C_{1-6}$alkyl group substituted with an alkoxy group, thereby forming an ether.

The term, "$C_{x-y}$aralkyl" refers to a $C_{x-y}$alkyl group, as previously defined, substituted with an aryl group. For example, the term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

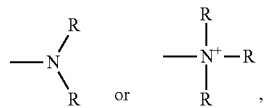

where each R group independently represents a hydrogen, an alkyl, an alkenyl, —$(CH_2)_b$-T, or two of the R groups taken together with the N atom to which they are attached complete a heterocycle having from 4 to 8 atoms in the ring structure; T represents an aryl, a cycloalkyl, a cycloalkenyl, a heterocyclyl or a polycyclyl; and b is zero or an integer from 1 to 8. In certain embodiments, an amino group is basic, meaning its protonated form has a pKa above 7.00. In some embodiments, the terms "amine" and "amino" refer to a moiety that is covalently bonded to a unsubstituted or substituted nitrogen atom.

The terms "amide" and "amido" are art-recognized as an amino-substituted carbonyl and include a moiety that can be represented by the general formula:

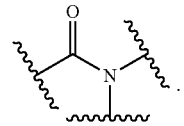

In some embodiments, the amide will not include imides, which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. In some embodiments, an aryl ring can be substituted with a halogen, such as fluorine.

The terms "carbocycle" and "carbocyclyl", as used herein, refer to a 3- to 7-membered non-aromatic substituted or unsubstituted ring in which each atom of the ring is carbon. The ring may be completely saturated or may have one or more unsaturated bonds such that the ring remains non-aromatic. The terms "carbocycle" and "carbocyclyl" also include polycyclic ring systems having two or more cyclic rings in which one or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls. Carbocyclyls include cyclopropyl, cyclopentyl, cyclopentenyl, cyclohexyl, cyclohexylmethyl, and 4-methylcyclohexyl. Examples of polycyclic carbocyclyls include bicyclo[2.2.1]heptanyl, spiro[2.4]heptanyl, norbornyl, and adamantyl.

The term "cycloalkyl" as used herein refers to a 3- to 7-membered saturated substituted or unsubstituted ring in which each atom of the ring is carbon. The term "cycloalkyl" also includes polycyclic ring systems having two or more cyclic rings in which one or more carbon atoms are common to two adjoining rings wherein at least one of the rings is a cycloalkyl.

The term "cycloalkenyl" as used herein refers to a 3- to 7-membered substituted or unsubstituted ring in which each atom of the ring is carbon. The ring has one or more unsaturated bonds such that the ring remains non-aromatic. The term "cycloalkenyl" also includes polycyclic ring systems having two or more cyclic rings in which one or more carbon atoms are common to two adjoining rings wherein at least one of the rings is a cycloalkenyl.

The term "carbonyl" is art-recognized and includes moieties containing a C=O group, such as, for example, those represented by the general formulae:

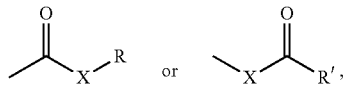

wherein X is a bond or represents an oxygen or a sulfur, and R represents a hydrogen, an alkyl, an alkenyl, —(CH$_2$)$_b$-T or a pharmaceutically acceptable salt, R' represents a hydrogen, an alkyl, an alkenyl or —(CH$_2$)$_b$-T, where m and T are as defined above. Where X is an oxygen and R or R' is not hydrogen, the formula represents an "ester". Where X is an oxygen and R is a hydrogen, the formula represents a "carboxylic acid".

The term, "C$_{x-y}$heteroaralkyl" refers to a C$_{x-y}$alkyl group, as previously defined, substituted with a heteroaryl group. For example, the term "C$_{1-6}$heteroaralkyl", as used herein, refers to a C$_{1-6}$alkyl group substituted with a heteroaryl group.

The term "heteroaryl" includes substituted or unsubstituted aromatic 5- to 7-membered ring structures, for example, 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine, and pyrimidine, and the like. In some embodiments, a heteroaryl ring can be substituted with a halogen, such as fluorine.

The term "heteroatom" as used herein means an atom of any element other than carbon or hydrogen. For example, heteroatoms include nitrogen, oxygen, phosphorus, and sulfur.

The term "heterocyclyl" or "heterocyclic group" refers to substituted or unsubstituted non-aromatic 3- to 10-membered ring structures, for example, 3- to 7-membered rings, whose ring structures include one to four heteroatoms. The ring may be completely saturated (e.g., heterocycloalkyl) or may have one or more unsaturated bonds such that the ring remains non-aromatic (e.g., heterocycloalkenyl). The term "heterocyclyl" or "heterocyclic group" also includes polycyclic ring systems having one or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term, "C$_{x-y}$hydroxyalkyl" refers to a C$_{x-y}$alkyl group, as previously defined, substituted with a hydroxy group. For example, the term "C$_{1-6}$hydroxyalkyl" refers to a C$_{1-6}$alkyl group substituted with a hydroxy group.

The term "thioether" refers to an alkyl group, as defined above, having a sulfur moiety attached thereto. In some embodiments, the "thioether" is represented by —S— alkyl. Representative thioether groups include methylthio, ethylthio, and the like.

The term "substituted," refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include, for example, an alkyl, alkenyl, alkynyl, a halogen, a hydroxyl, a carbonyl (such as a carboxyl, an ester, a thioester, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a carbocyclyl (e.g., cycloalkyl, cycloalkenyl), a heterocyclyl (e.g., heterocycloalkyl), an aralkyl, a heteroaralkyl, or an aromatic (i.e., aryl) or heteroaromatic (i.e., heteroaryl) moiety. It will be understood by those skilled in the art that the moieties substituted on the hydrocarbon chain can themselves be substituted, if appropriate. In some embodiments, the substituent is a halogen, such as fluorine. When a chemical functional group includes more than one substituent, the substituents can be bound to the same carbon atom or to two or more different carbon atoms. A substituted chemical functional group can itself include one or more substituents.

In some embodiments, the compounds provided herein, or salts thereof, are substantially isolated or purified. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds, or salt thereof. Methods for isolating compounds and their salts are routine in the art.

The term "prophylactic or therapeutic" treatment is art-recognized and includes administration to the host of one or more of the subject compositions. If the subject composition is administered prior to clinical manifestation of the unwanted condition (e.g., disease or other unwanted state of the host animal) then the treatment is prophylactic, (i.e., it protects the host against developing the unwanted condition), whereas if the subject composition is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes. In some embodiments, a compound of the disclosure preferentially inhibits the immunoproteasome.

The term "i20S" as used herein refers to the 20S immunoproteasome.

The term "c20S" as used herein refers to the constitutive 20S proteasome.

As used herein, the term "inhibitor" is meant to describe a compound that blocks or reduces an activity of an enzyme or system of enzymes, receptors, or other pharmacological target (for example, inhibition of proteolytic cleavage of standard fluorogenic peptide substrates such as succinyl-Leu-Leu-Val-Tyr-AMC, Boc-Leu-Leu-Arg-AMC and Z-Leu-Leu-Glu-AMC, inhibition of various catalytic activities of the 20S proteasome). An inhibitor can act with competitive, uncompetitive, or noncompetitive inhibition. An inhibitor can bind reversibly or irreversibly, and therefore, the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

A "therapeutically effective amount" of a compound with respect to the subject method of treatment, refers to an amount of the compound(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a patient condition.

Compounds

In one aspect, the disclosure provides a compound having a structure of Formula (X), or a pharmaceutically acceptable salt thereof:

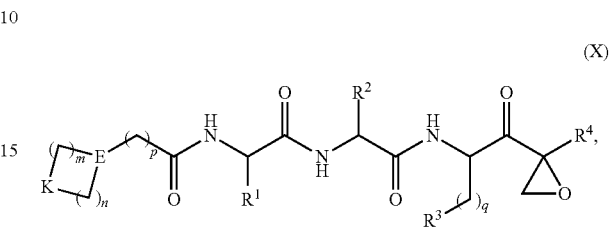

(X)

wherein:
m and n each independently are 0, 1 or 2, and m+n=2, 3, or 4;
p is 0 or 1;
q is 0, 1, or 2;
K is selected from the group consisting of $CR^5R^6$, $NR^7$, $N(C=O)OR^7$, —NH—(C=O)—, O, S, SO, and $SO_2$;
E is N or $CR^7$;
$R^1$ is selected from the group consisting of H, $C_{1-6}$alkyl, $C_{2-6}$alkenyl, $C_{2-6}$alkynyl, $C_{3-6}$cycloalkyl, and 3-6 membered heterocycloalkyl, wherein $R^1$ is optionally substituted with one or more substituents selected from the group consisting of halo, $OR^7$, $SR^7$, $N(R^7)_2$, CN, and $(C=O)N(R^7)_2$;
$R^2$ is $C_{1-2}$alkylene-G or (C=O)-G; wherein G is selected from the group consisting of aryl, heteroaryl, and pyridinone, with the proviso that when $R^2$ is $CH_2$phenyl, the phenyl is substituted with one or more substituents selected from the group consisting of $OR^7$, halo, $C_{1-3}$alkyl, $OCF_3$, $SO_2R^7$, $(C=O)N(R^7)_2$, CN, and $SO_2N(R^7)_2$;
$R^3$ is selected from the group consisting of $C_{3-7}$cycloalkyl, $C_{3-7}$cycloalkenyl, a 3-7 membered heterocycloalkyl, and a 3-7 membered heterocycloalkenyl, wherein $R^3$ is optionally substituted with one or more substituents selected from the group consisting of halo, =O, $OR^7$, $SR^7$, $N(R^7)_2$, $O(C=O)N(R^7)_2$, and $C_{1-6}$alkyl;
$R^4$ is H or $C_{1-3}$alkyl;
$R^5$ and $R^6$ are each independently selected from the group consisting of H, OH, halo, $C_{1-3}$alkyl, and $CF_3$, or $R^5$ and $R^6$ together with the carbon to which they are attached form C=O or

wherein W is O or $NR^7$, and r is 1, 2 or 3; and each $R^7$ is independently H or $C_{1-6}$alkyl.

In some embodiments, m is 0. In various embodiments, m is 1. In some embodiments, m is 2.

In some embodiments, n is 2. In some embodiments, n is 1. In some embodiments, n is 0.

In some embodiments, m+n is 2. In various embodiments, m+n is 3. In various embodiments, m+n is 4.

In some embodiments, p is 0, and in various embodiments, p is 1.

In some embodiments, q is 0. In some embodiments, q is 1. In various embodiments, q is 2.

In some embodiments, p is 0 and m+n is 4. In various embodiments p is 1 and m+n is 4. In various embodiments, p is 0 and m+n is 3. In various embodiments, p is 1 and m+n is 3. In some embodiments, p is 0 and m+n is 2. In some embodiments, p is 1 and m+n is 2.

In some embodiments, K is $CR^5R^6$. In some of these embodiments, $R^5$ and $R^6$ are each independently H, OH, F, $CH_3$, or $CH_2CH_3$, or $R^5$ and $R^6$ together with the carbon to which they are attached from C=O or

where r is 1. For example, K is selected from CH(OH), $C(CH_3)(OH)$, C=O, $CH_2$, $CF_2$, CH(Cl), $CH(CF_3)$,

and $COH(CH_3)$. In some cases, K is CH(OH). In various embodiments, K is $NR^7$, and $R^7$ is H, $CH_2CH_3$, or $CH_3$. For example, K can include $NCH_3$ or $NCH_2CH_3$. In some embodiments, K is $N(C=O)OR^7$ (e.g., N(C=O)OH or $N(C=O)OCH_3$), —NH—(C=O)—, S, SO, or $SO_2$. In various embodiments, K is O.

In some embodiments, E is N. In other embodiments, E is $CR^7$, such as, for example, CH or $C(CH_3)$. In various embodiments, E is N or CH. In some cases, E is N or CH and K is O, $CH_2$, or CH(OH).

In some exemplary embodiments,

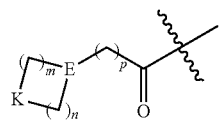

is selected from the group consisting of:

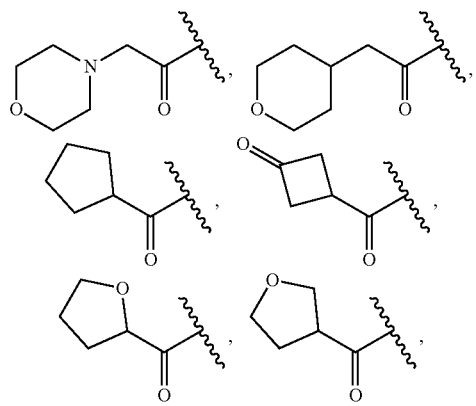

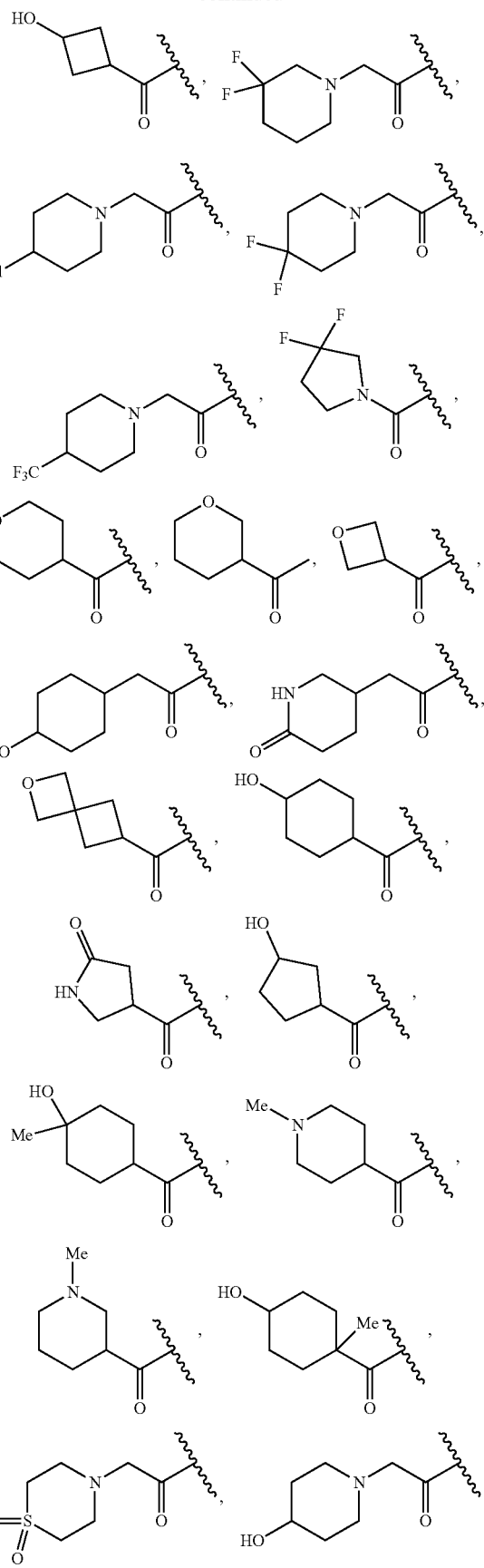

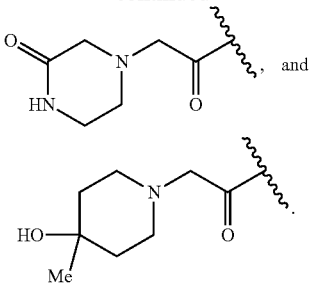, and

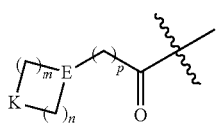

In various cases,

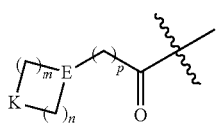

is selected from

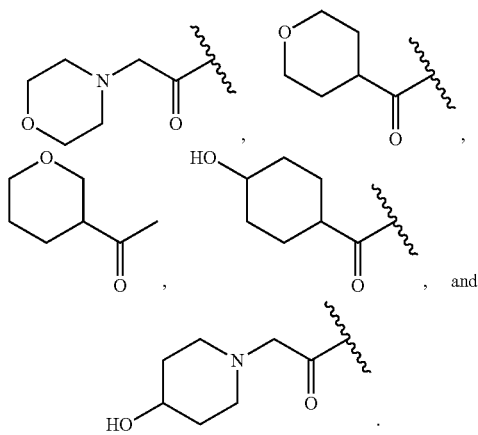, and

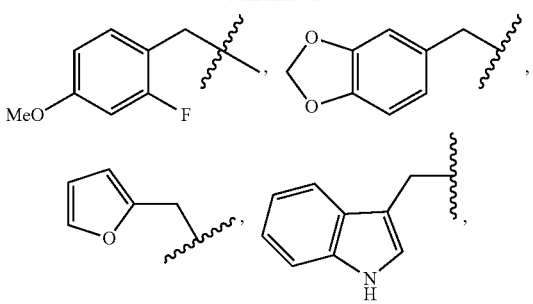

In some embodiments, $R^1$ is $C_{1-6}$alkyl or $R^1$ is $C_{1-3}$alkyl, such as, $CH_3$, $CH_2OH$, $CF_3$, $CH(OH)CH_3$, $CH_2CN$, or $CH_2CH_3$. For example, $R^1$ can be selected from $CH_3$, $CH_2OH$ and $CH_2CN$. In various embodiments, $R^1$ is $C_{2-6}$alkenyl, such as $CH_2CH=CH_2$; or $C_{2-6}$alkynyl, such as $CH_2C\equiv CH$. In some embodiments, $R^1$ is $C_{3-6}$cycloalkyl, such as, for example, cyclopropyl, cyclobutyl, cyclopentyl, or cyclohexyl. In various embodiments, $R^1$ is a 3-6 membered heterocycloalkyl, such as, for example, oxetanyl, tetrahydrofuranyl, or piperadinyl.

In some embodiments, $R^2$ is $C_{1-2}$alkylene-heteroaryl, such as, for example, $CH_2$-heteroaryl. In various embodiments, $R^2$ is $C_{1-2}$alkylene-pyridinone. In various embodiments, $R^2$ is $C_{1-2}$alkylene-aryl. In some embodiments, $R^2$ is $CH_2$-aryl. In some cases, $R^2$ is selected from the group consisting of:

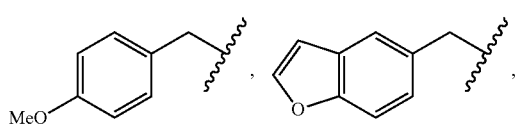

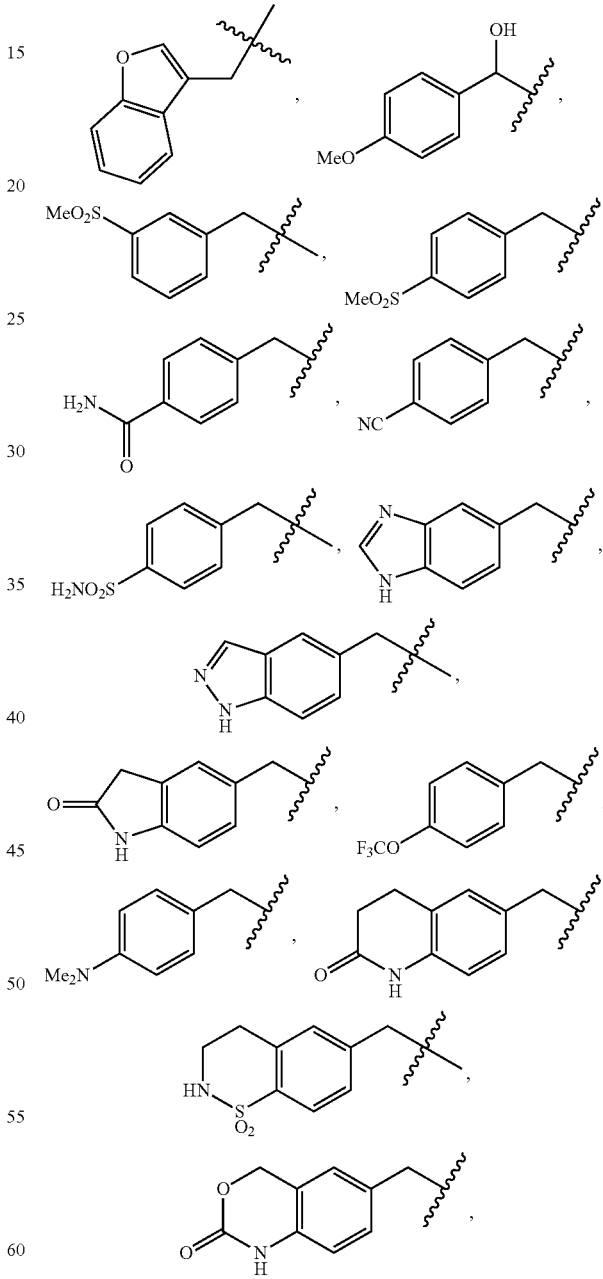

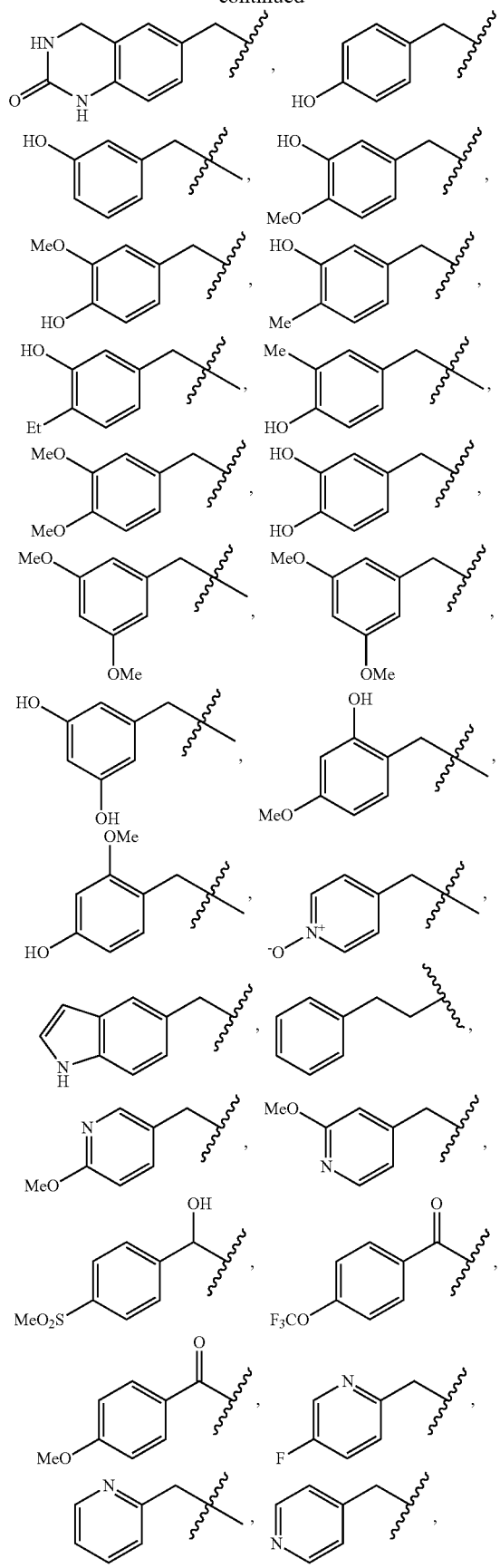
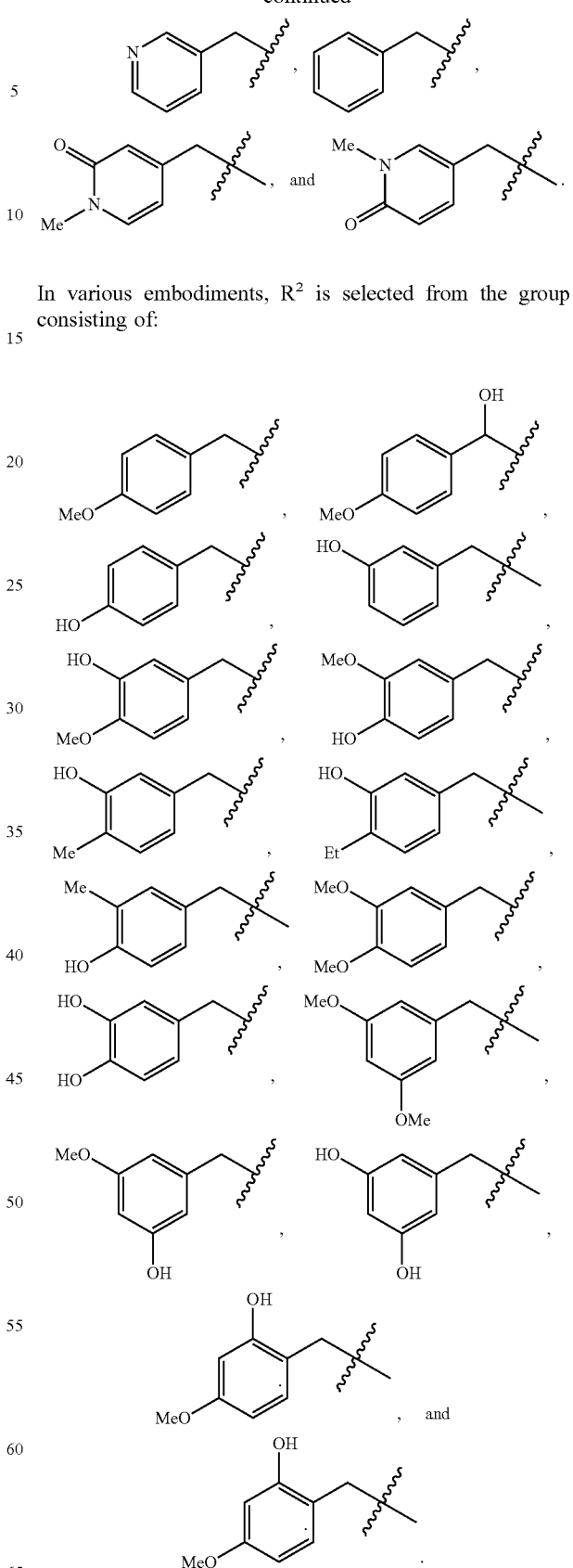
In various embodiments, $R^2$ is selected from the group consisting of:

In some cases, R² is [structures shown: 4-methoxybenzyl; 3-hydroxy-4-methoxybenzyl; 1-(4-methoxyphenyl)-1-hydroxymethyl; 3-hydroxy-4-methylbenzyl], or .

In various embodiments, R² is selected from the group consisting of: [structures shown: benzo[1,3]dioxol-5-ylmethyl; benzofuran-3-ylmethyl; benzofuran-5-ylmethyl; indol-3-ylmethyl; 2-oxoindolin-5-ylmethyl; indol-5-ylmethyl; benzimidazol-5-ylmethyl; 1H-indazol-5-ylmethyl; 2-oxo-1,2,3,4-tetrahydroquinolin-6-ylmethyl; 1,1-dioxo-3,4-dihydro-2H-benzo[e][1,2]thiazin-6-ylmethyl; 1,1-dioxo-3,4-dihydro-2H-benzo[e][1,2]thiazin-6-ylmethyl; 2-oxo-1,2,3,4-tetrahydroquinazolin-6-ylmethyl], and

[continued structure: 2-oxo-1,4-dihydro-2H-benzo[d][1,3]oxazin-6-ylmethyl].

In some embodiments, R² is selected from the group consisting of: [structures shown: (5-fluoropyridin-2-yl)methyl; pyridin-2-ylmethyl; pyridin-4-ylmethyl; pyridin-3-ylmethyl; (2-methoxypyridin-4-yl)methyl; (6-methoxypyridin-3-yl)methyl; (1-oxidopyridin-4-yl)methyl; and furan-2-ylmethyl].

In some cases, R² is selected from the group consisting of: [structures shown: benzyl; phenethyl/phenylpropyl; (4-methoxy-2-fluorophenyl)methyl; (4-trifluoromethoxyphenyl)methyl; (4-cyanophenyl)methyl; (3-methylsulfonylphenyl)methyl; (4-methylsulfonylphenyl)methyl; (4-sulfamoylphenyl)methyl; 1-hydroxy-1-(4-methylsulfonylphenyl)methyl; (4-dimethylaminophenyl)methyl; (4-carbamoylphenyl)methyl; (1-methyl-2-oxo-1,2-dihydropyridin-4-yl)methyl], -continued

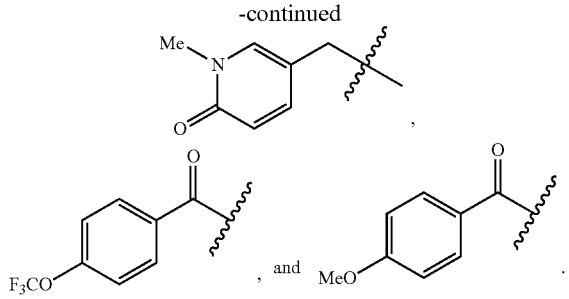

In various embodiments, $R^3$ is $C_{3-7}$cycloalkyl, such as, for example, cyclopropyl, cyclobutyl, cyclopentyl, or cyclohexyl. In some embodiments, the $C_{3-7}$cycloalkyl is substituted with at least one substituent selected from the group consisting of OH, F, Me, $NH_2$, and $O(CO)NH_2$. In some cases, $R^3$ is cyclopentyl or cyclohexyl. In various embodiments, $R^3$ is $C_{3-7}$cycloalkenyl, such as cyclopentenyl or cyclohexenyl. In some of these embodiments, the $C_{3-7}$cycloalkenyl is substituted with at least one substituent selected from the group consisting of OH and Me. In various embodiments, $R^3$ is a 3-7 membered heterocycloalkyl, such as, for example, tetrohydrofuranyl, tetrahydropyranyl, pyrrolindinyl, or pyrrolidinonyl. In some embodiments, $R^3$ is a 3-7 membered heterocycloalkenyl, such as, for example, dihydropyranyl or dihydrofuranyl. For example, $R^3$ can be selected from the group consisting of:

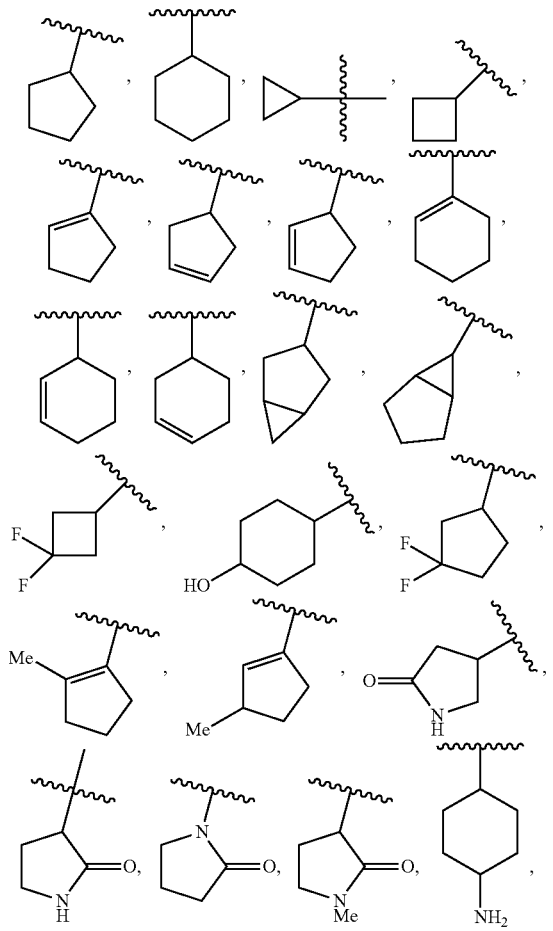

-continued

In some cases, $R^3$ is

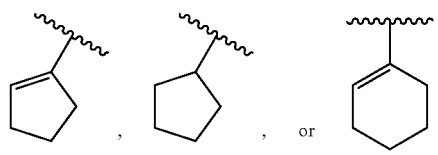 [SMILES: *C1=CCCC1 ; *C1CCCC1 ; *C1=CCCCC1]

In some cases, $R^3$ is

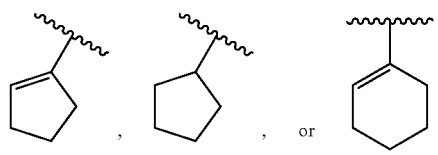 [SMILES: *C1=CCCC1 ; *C1CCCC1 ; *C1=CCCCC1]

and q is 0 or 1, or q is 1.

In some embodiments, $R^4$ is $C_{1-3}$alkyl, such as methyl or ethyl. In various embodiments, $R^4$ is H. In some case, $R^4$ is methyl.

Specifically contemplated is a compound of Formula X including

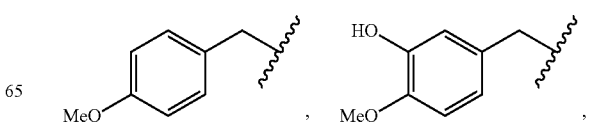

as described in paragraph [0053], $R^1$ as described in paragraph [0054], $R^2$ as described in paragraph [0055], $R^3$ as described in paragraph [0056], and $R^4$ as described in paragraph [0057].

In some exemplary embodiments: m and n are each independently 2; p is 1; q is 1; K is $CR^5R^6$ or O; E is N or $CR^7$; $R^1$ is $CH_3$, $CH_2OH$, $CH(OH)CH_3$, $CH_2CN$, or oxetanyl; $R^2$ is

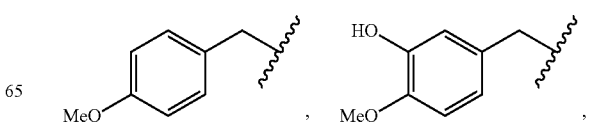

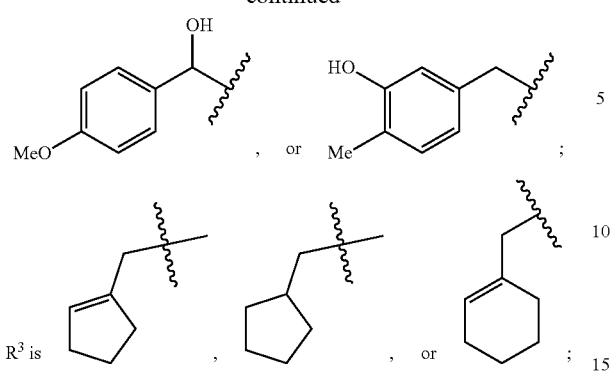
R⁴ is methyl; R⁵ is H; R⁶ is OH; and R⁷ is H.
In some embodiments, a compound of Formula (X) is selected from:
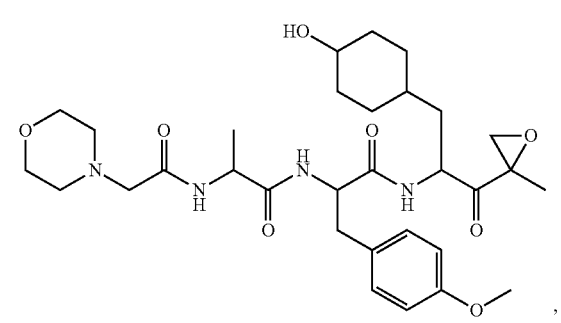
,
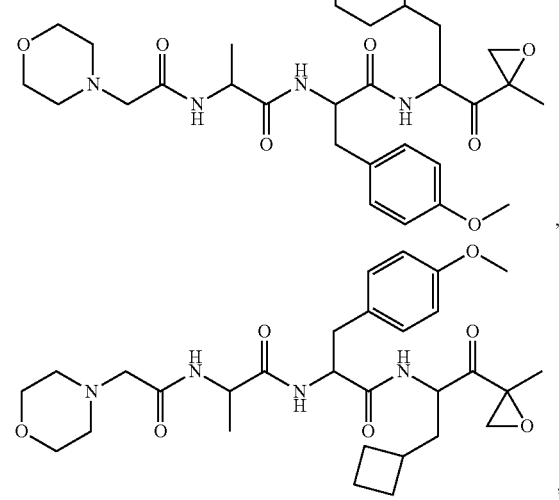
,
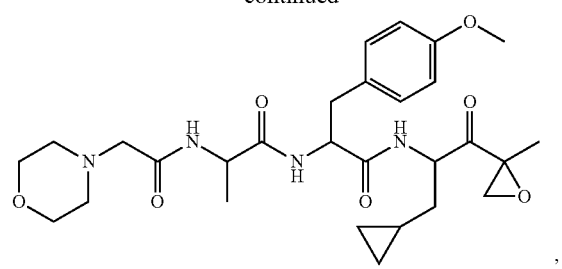
,
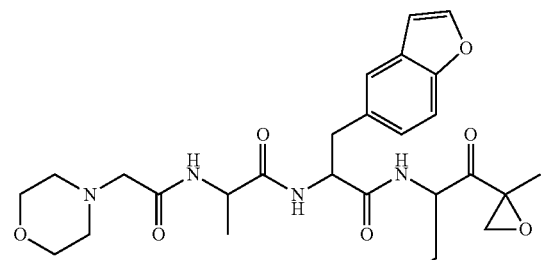
,
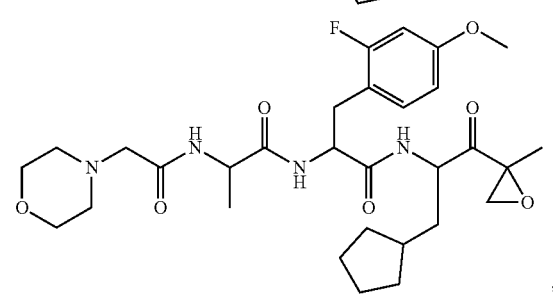
,
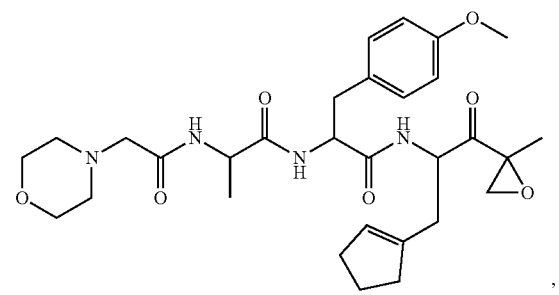
,
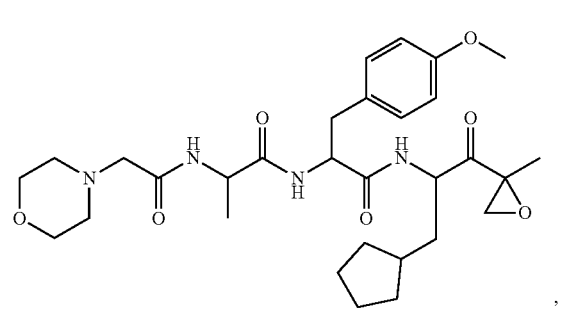
,

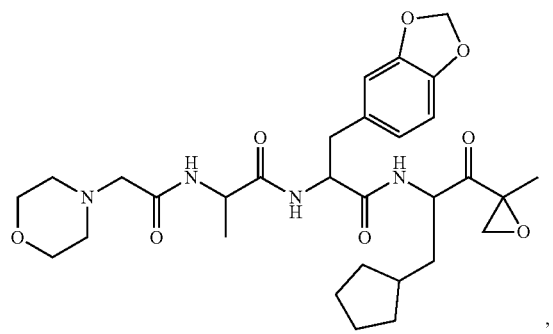
,
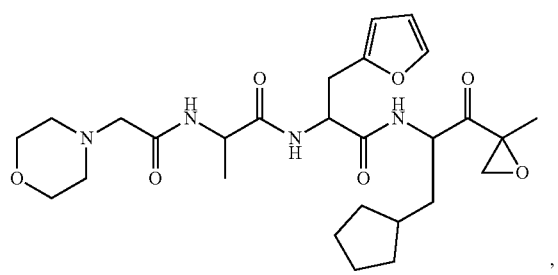
,
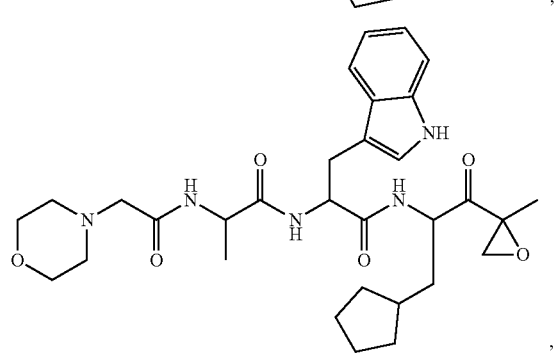
,
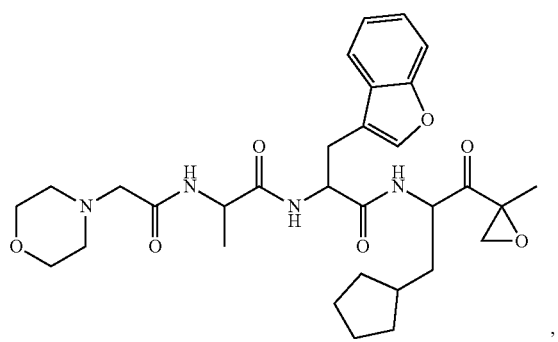
,
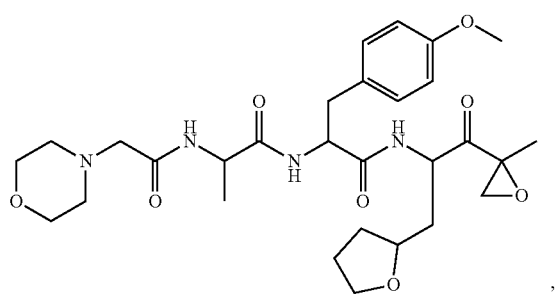
,
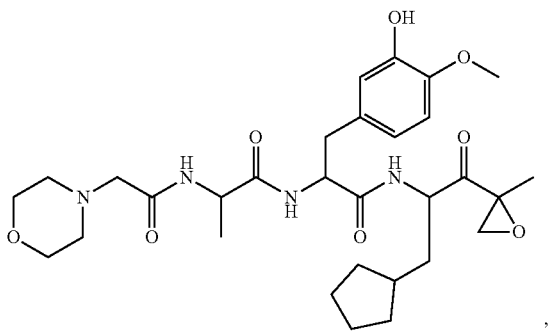
,
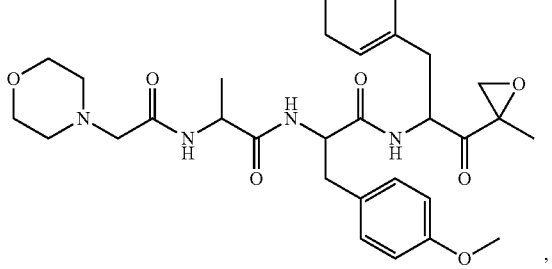
,
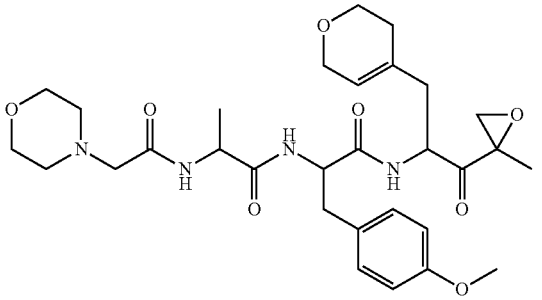
,
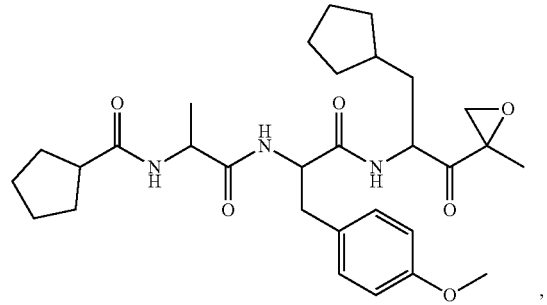
,
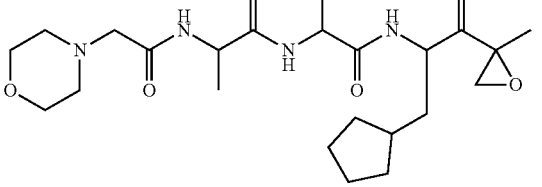
,

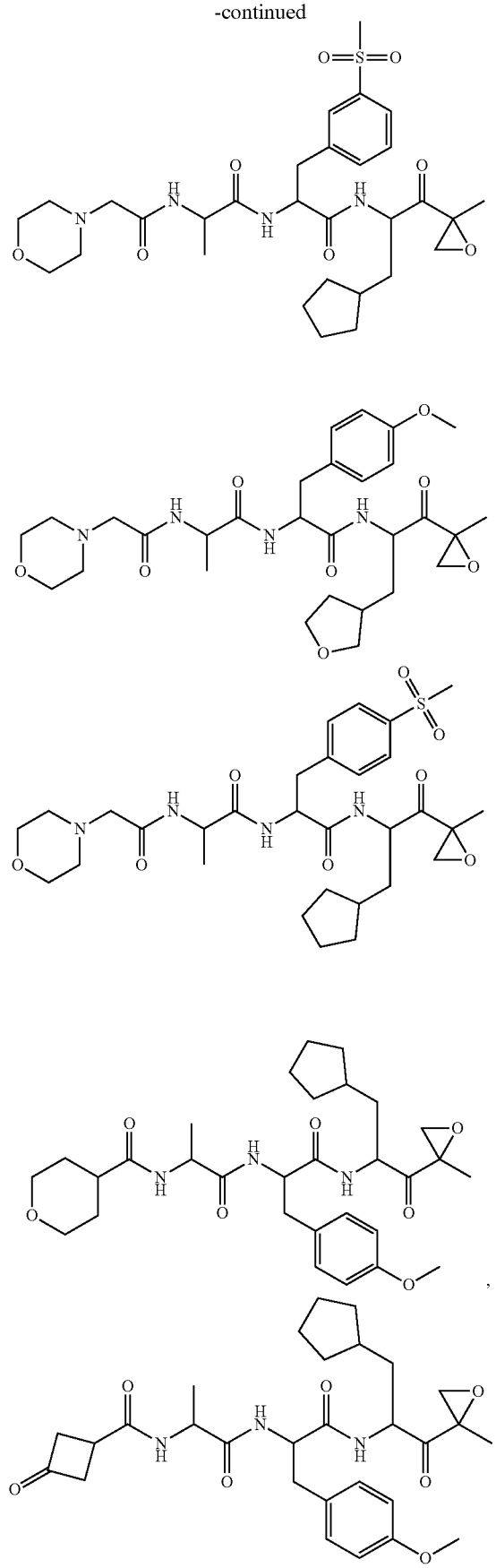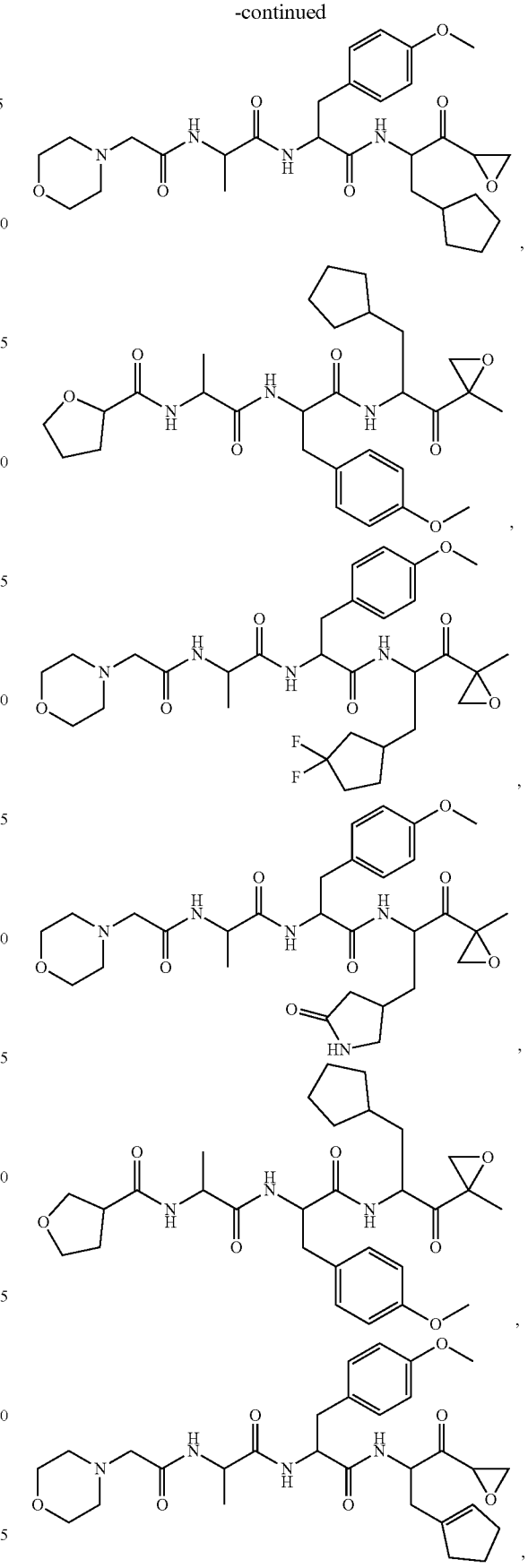

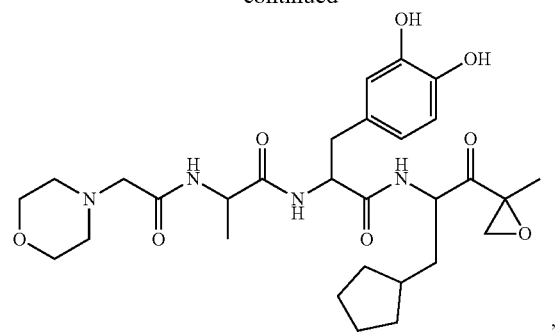
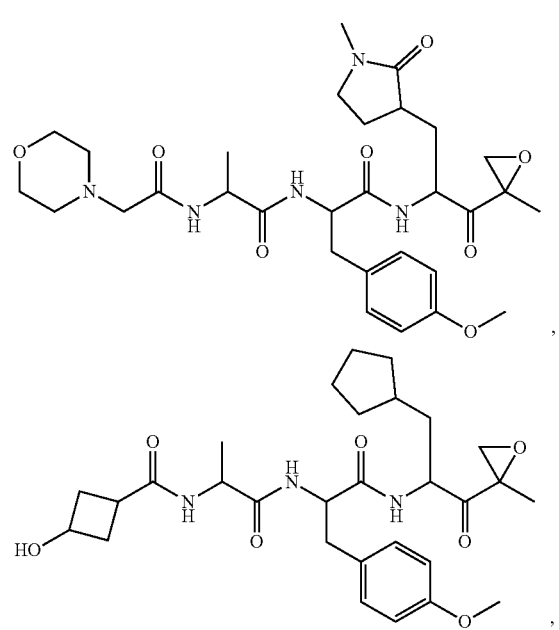
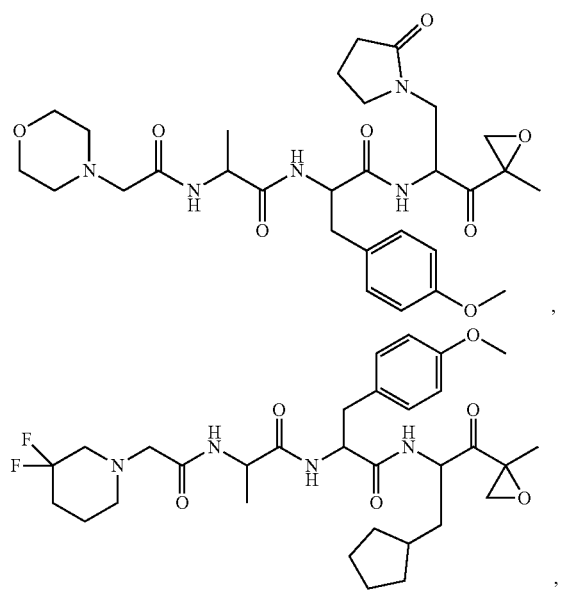
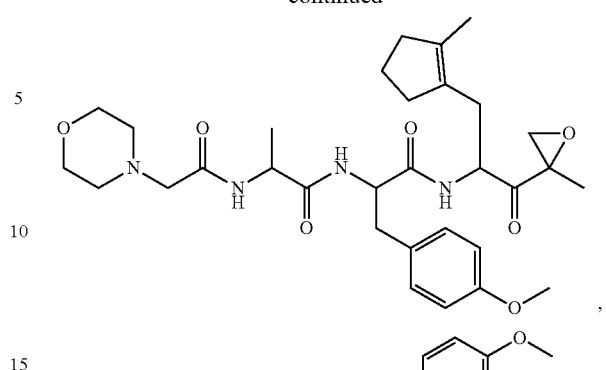
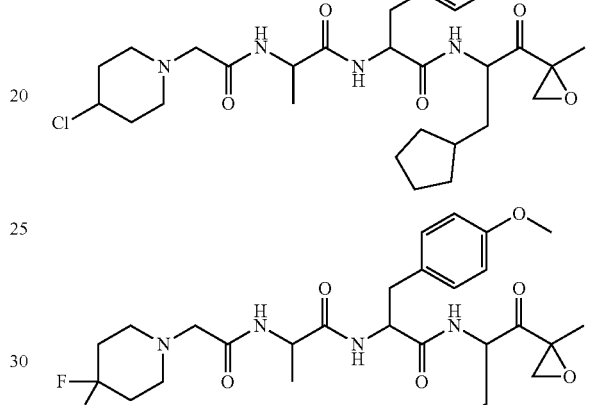
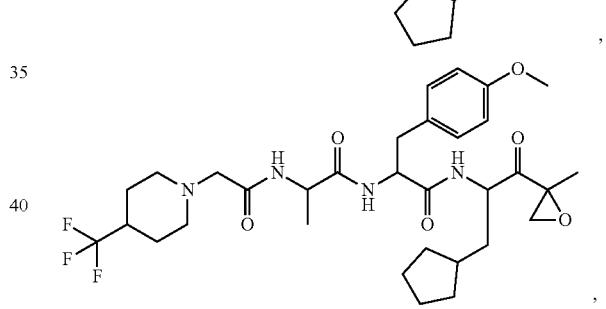
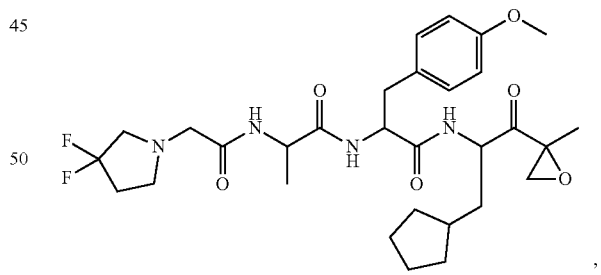
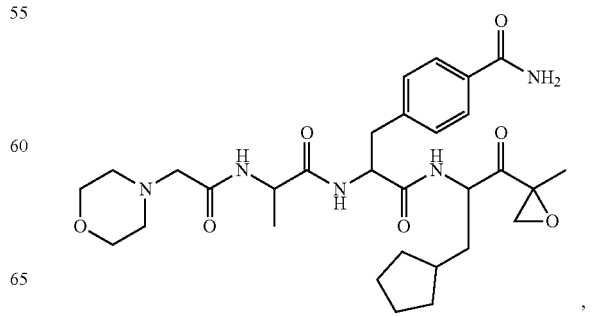

27
-continued
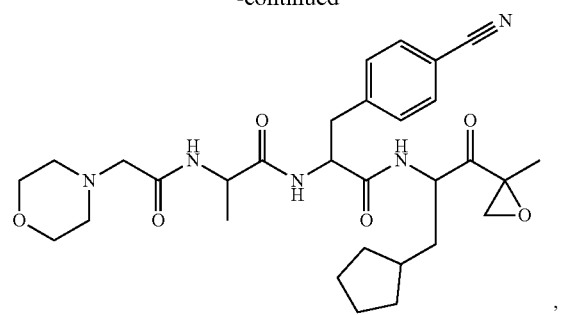
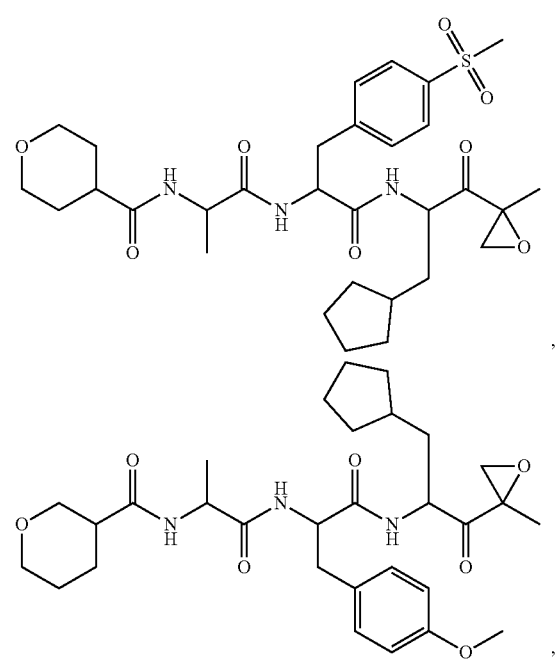
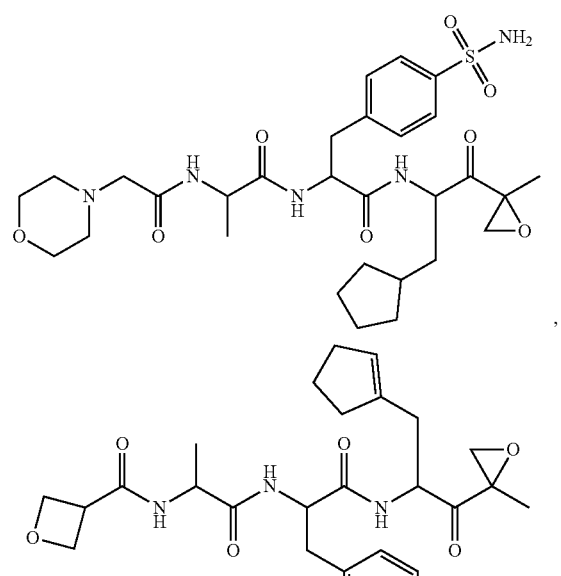
28
-continued
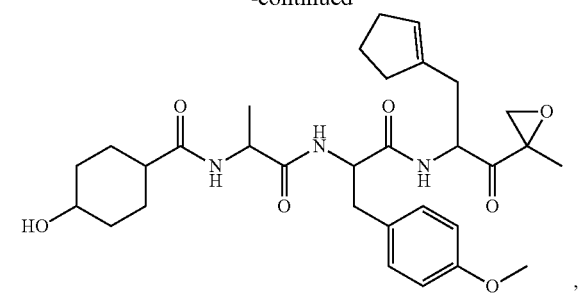
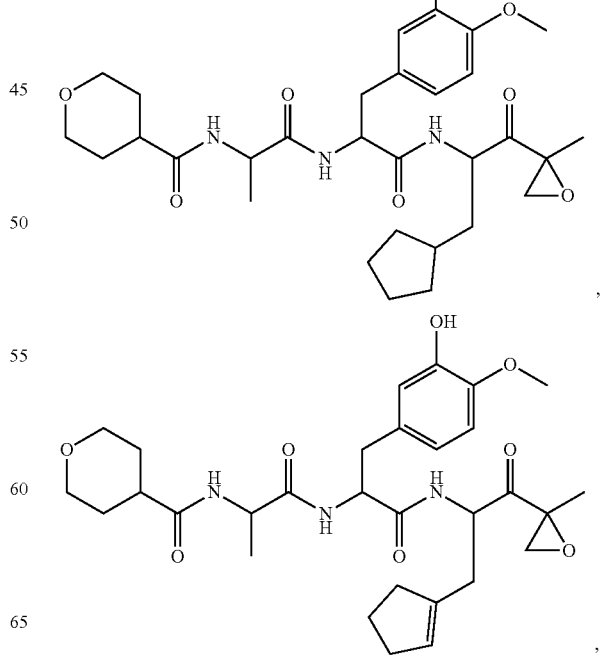

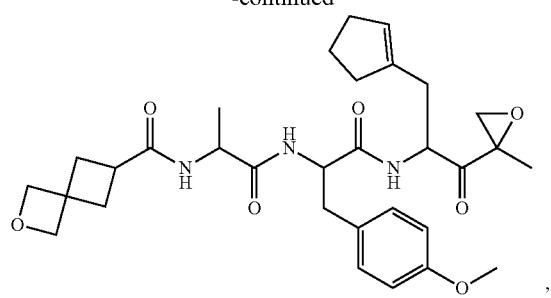
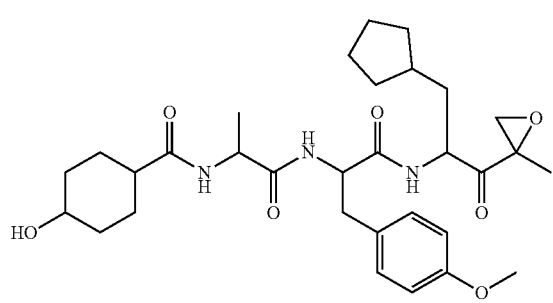
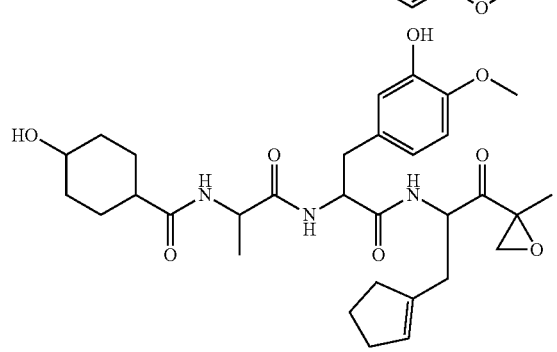
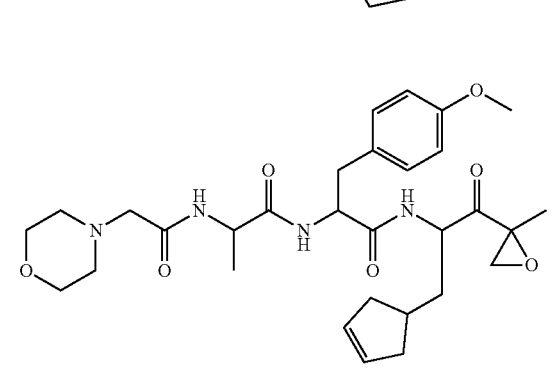
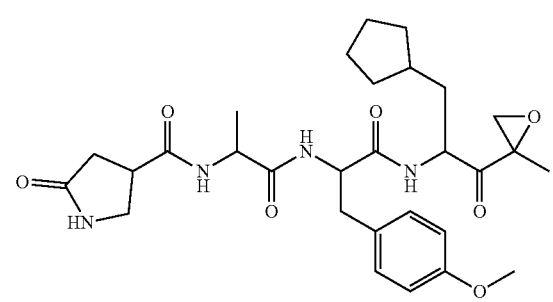
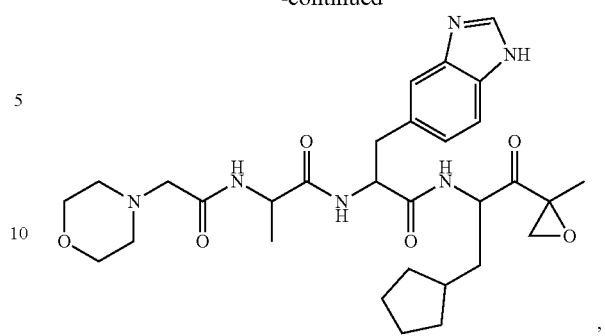
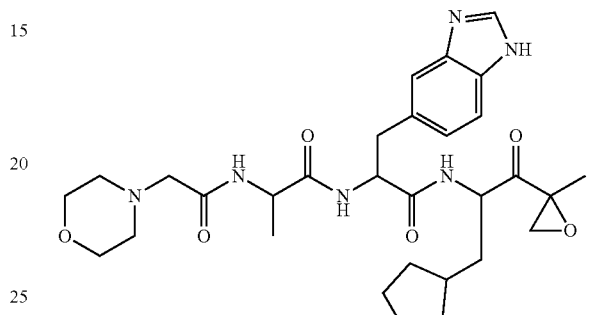
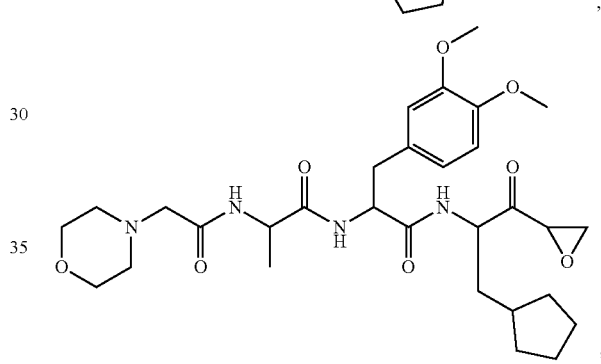
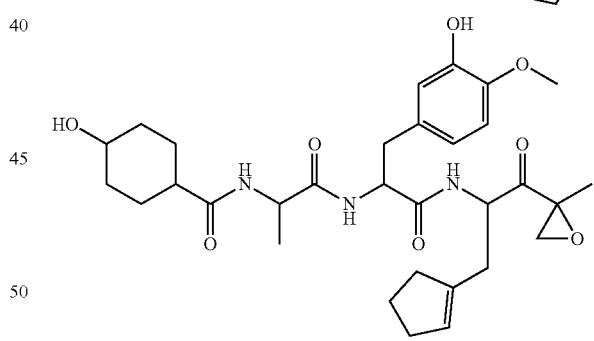
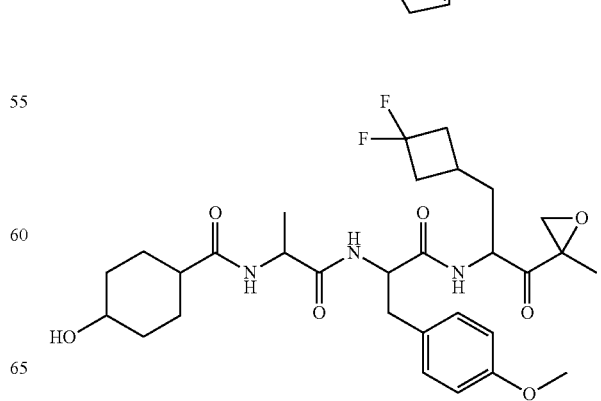

31
-continued
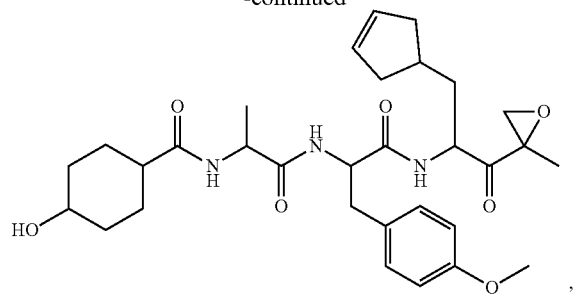
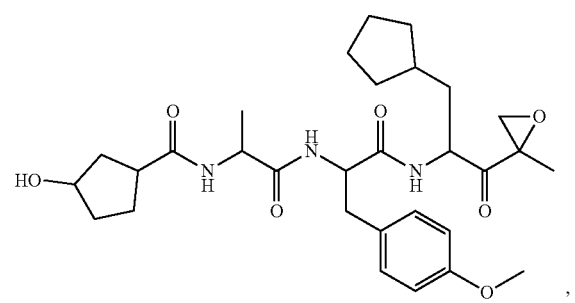
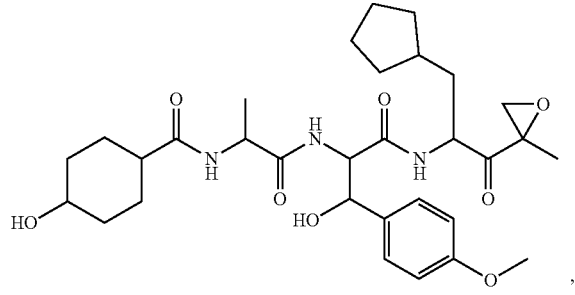
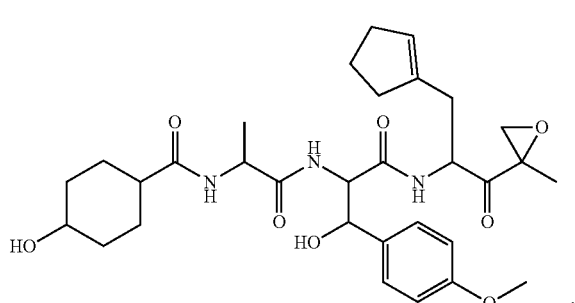
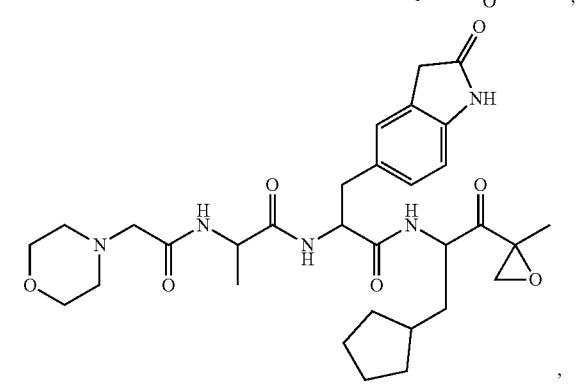
32
-continued
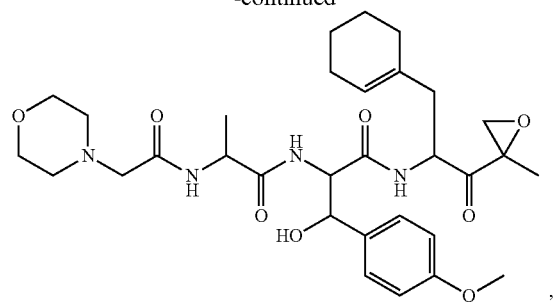
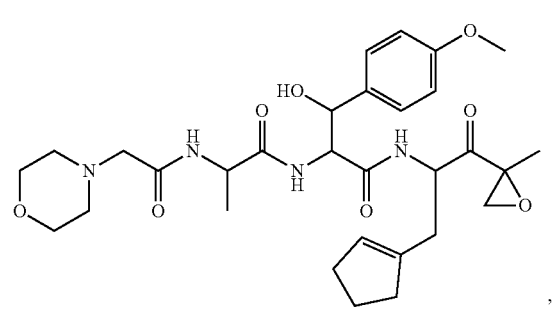
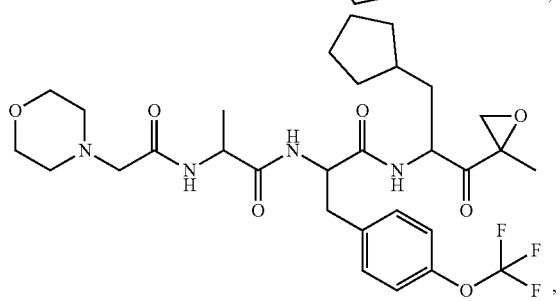
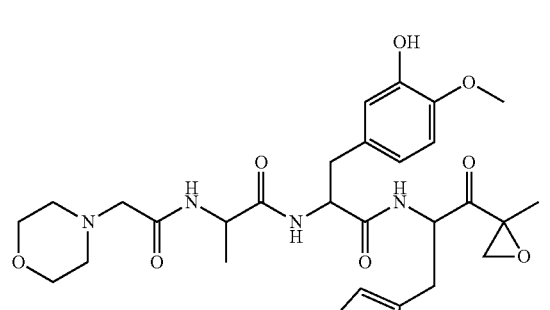
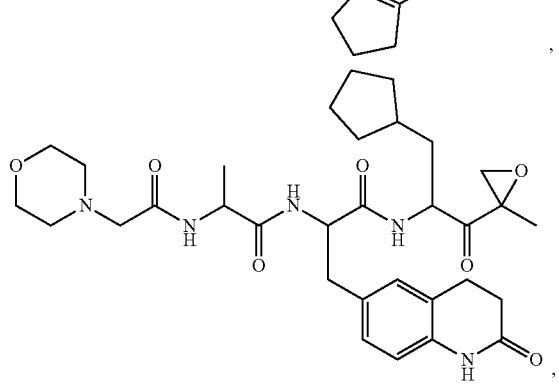

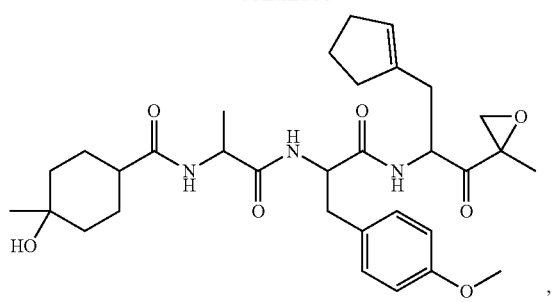
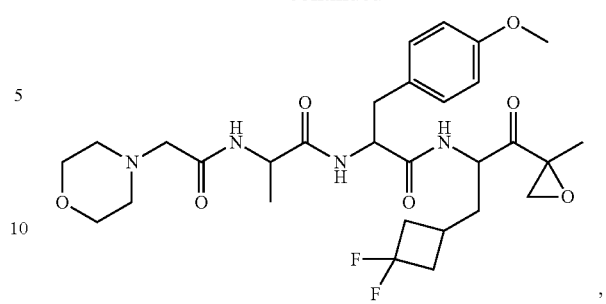
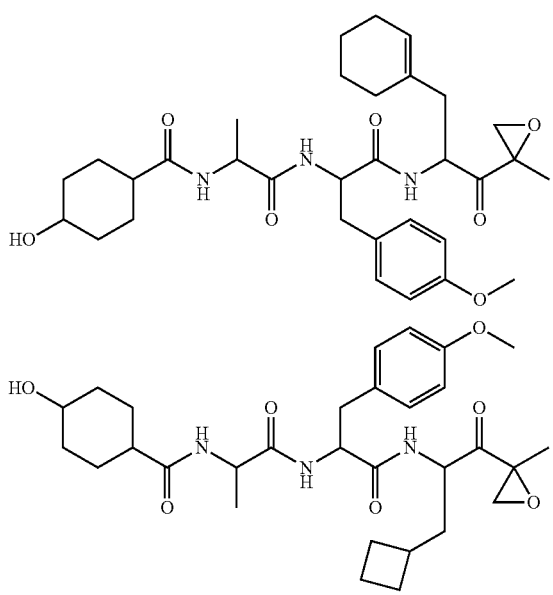
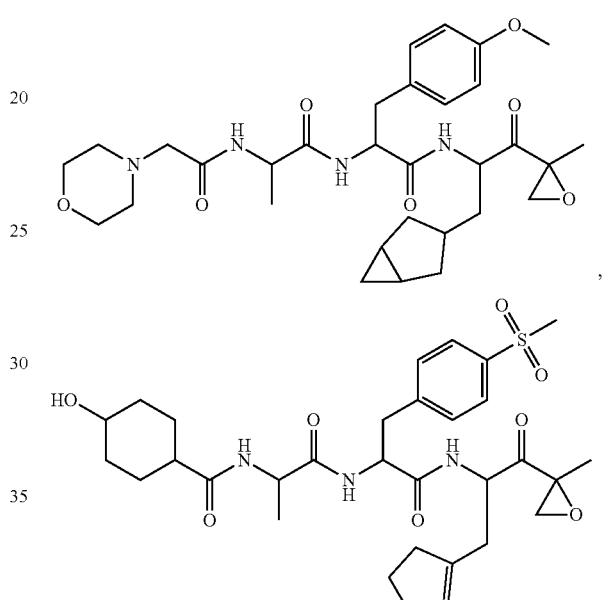
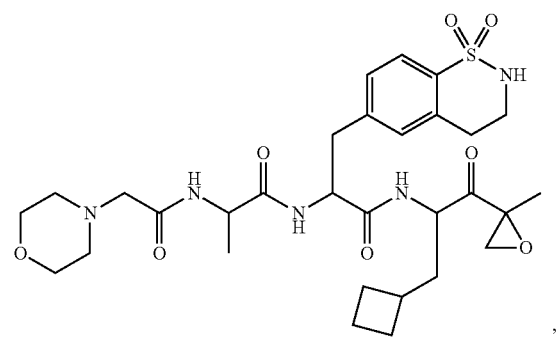
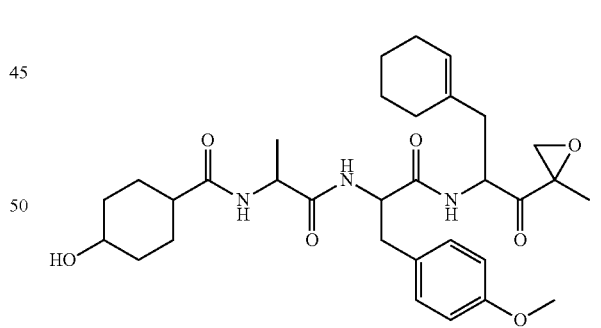
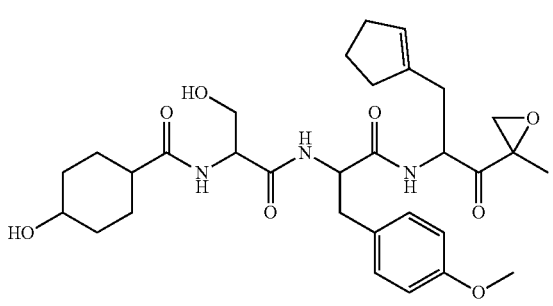
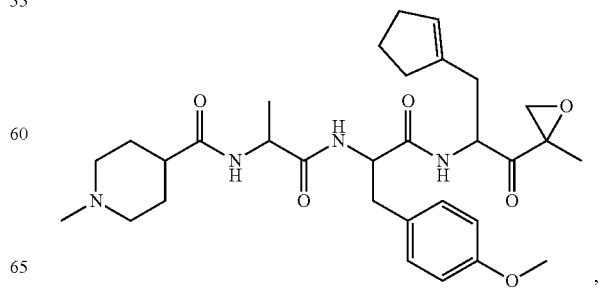

35
-continued
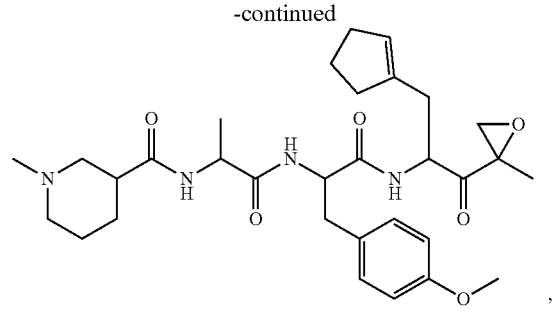
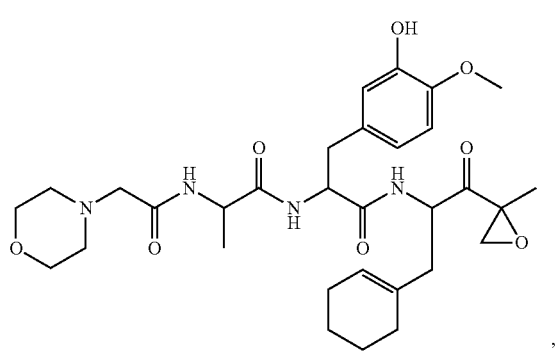
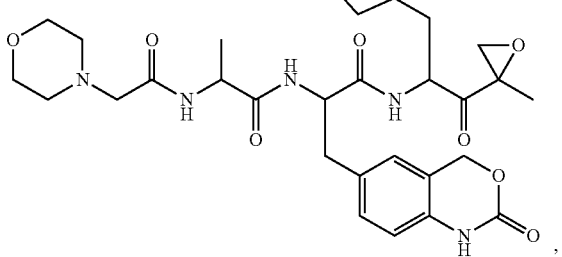
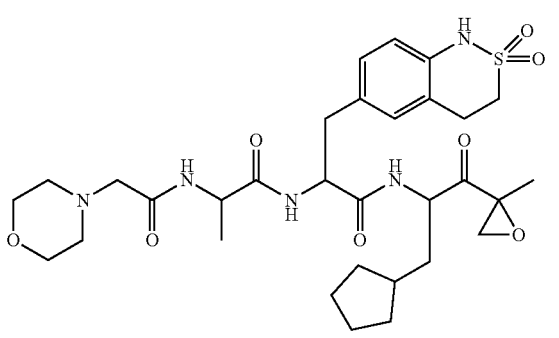
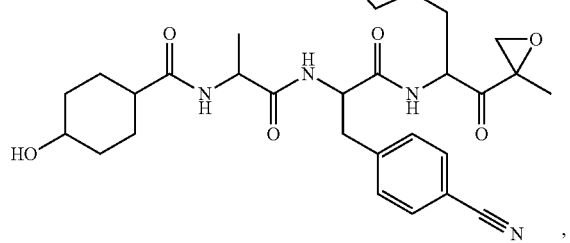
36
-continued
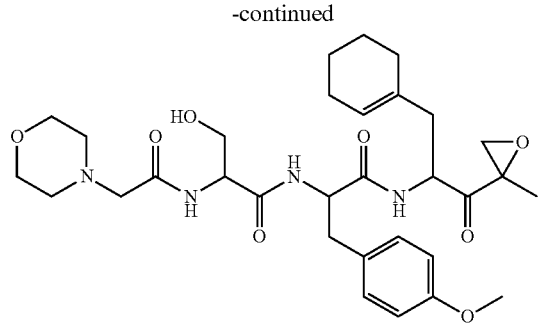
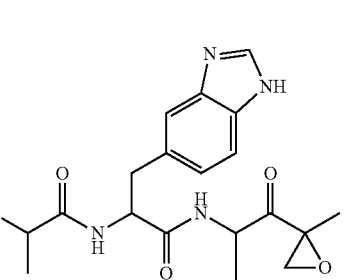
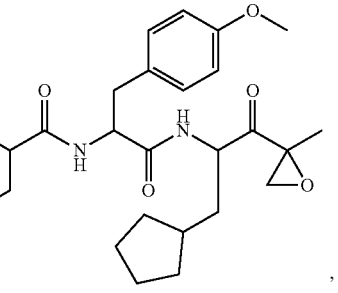
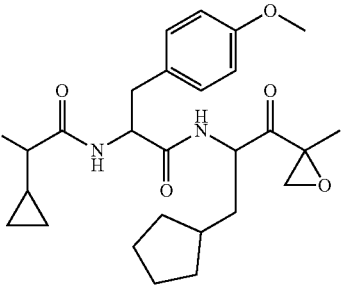
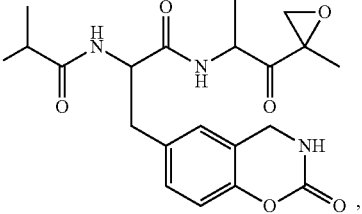

37
-continued
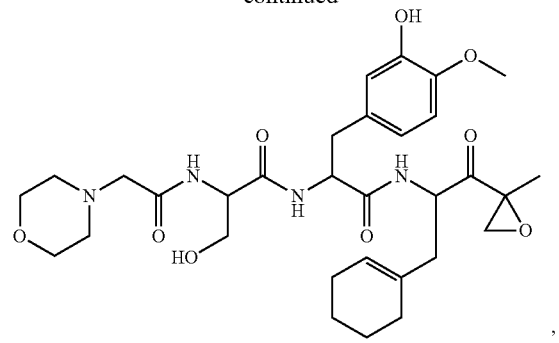
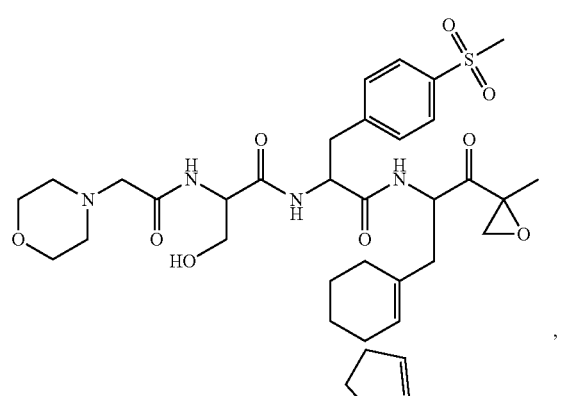
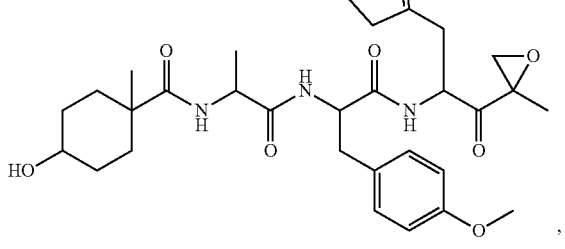
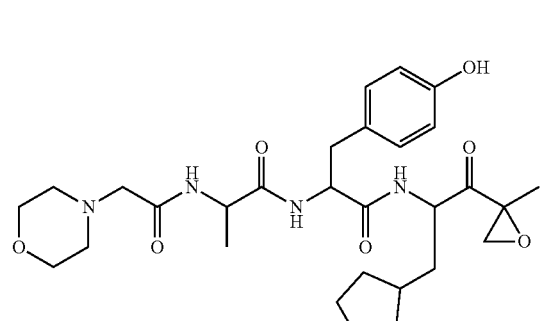
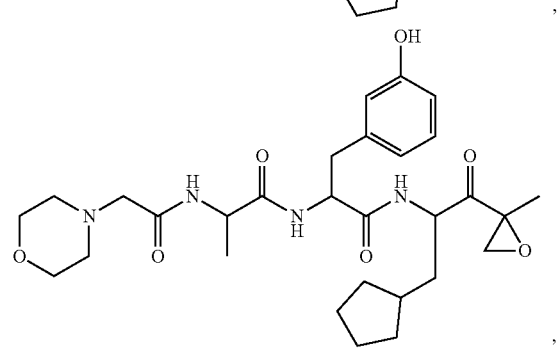
38
-continued
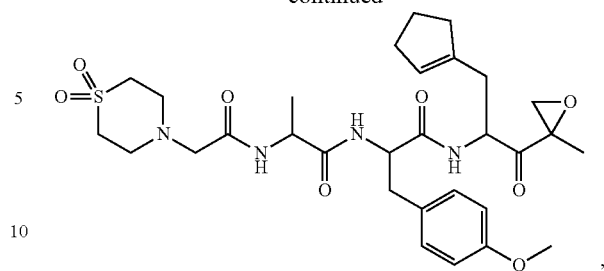
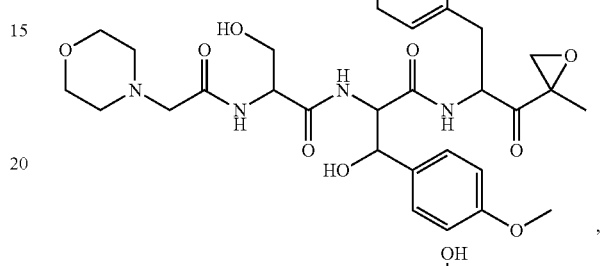
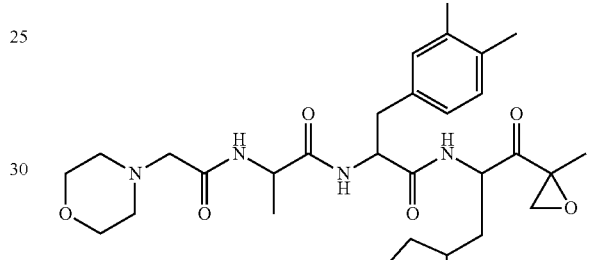
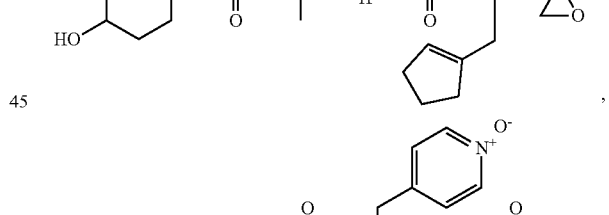
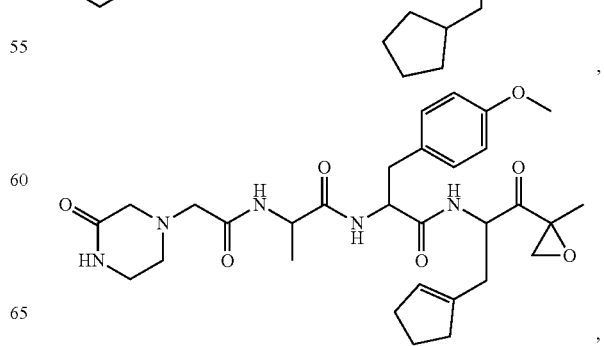

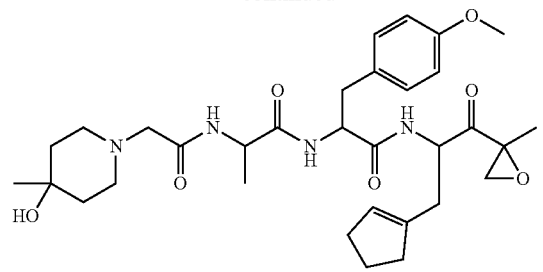
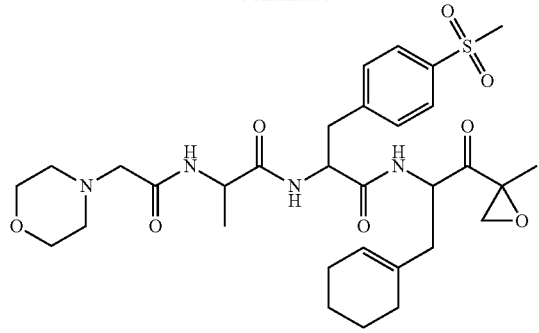
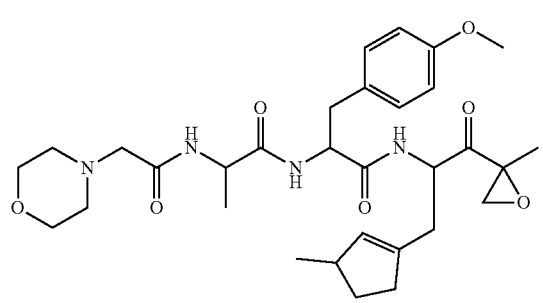
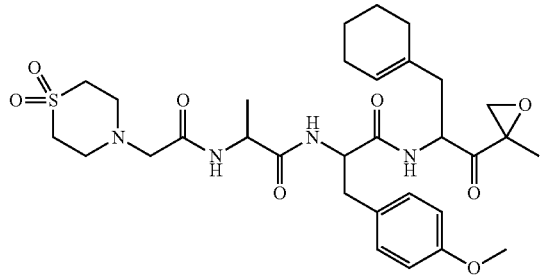
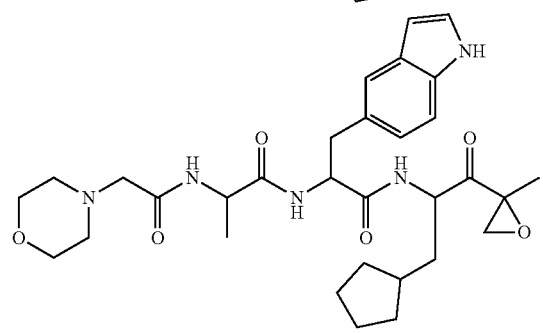
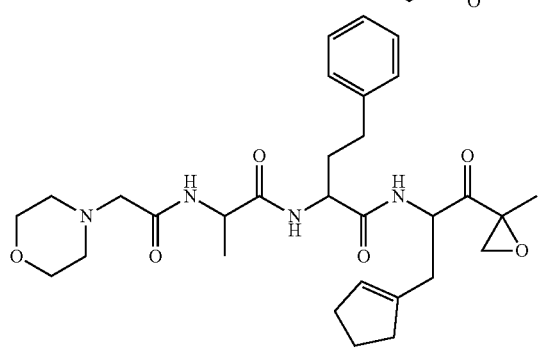
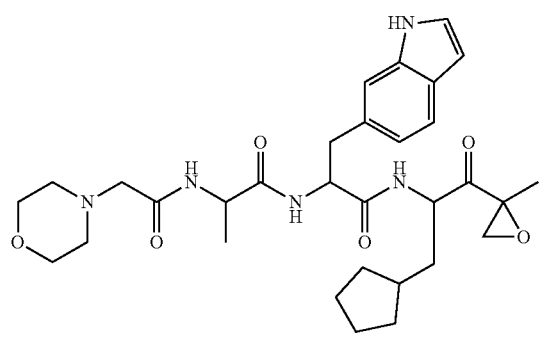
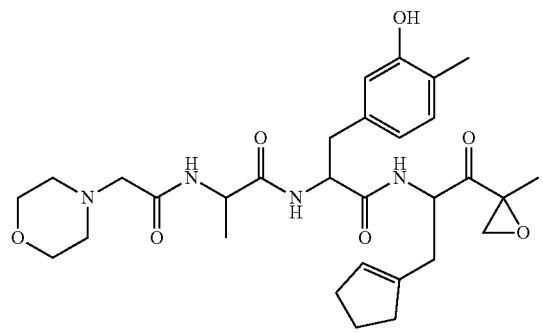
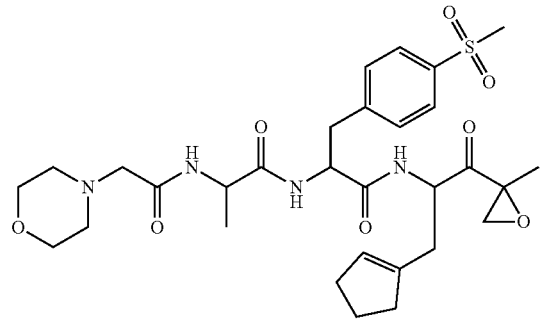
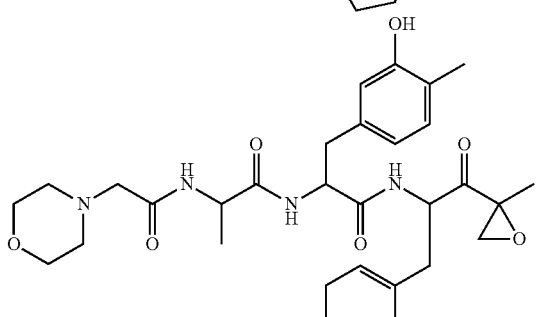

-continued
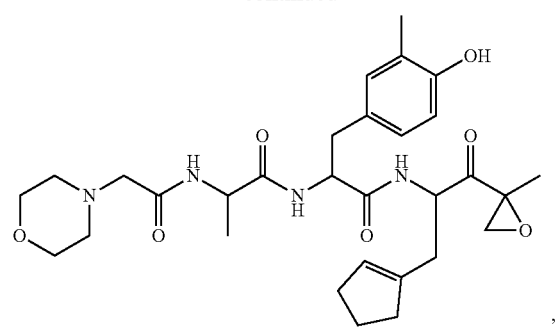
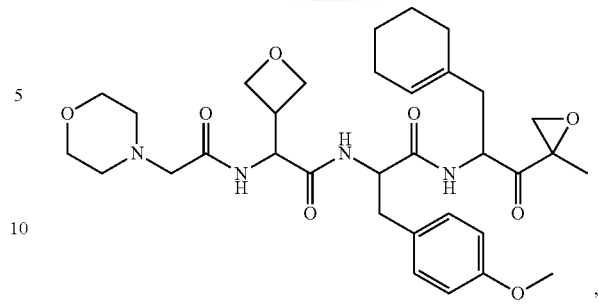
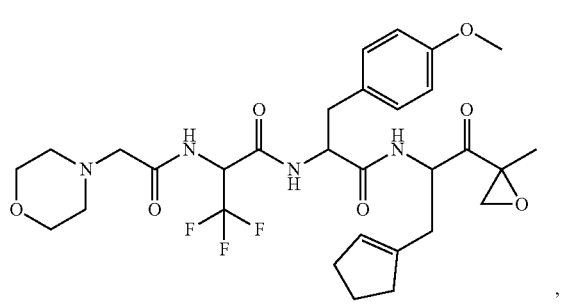
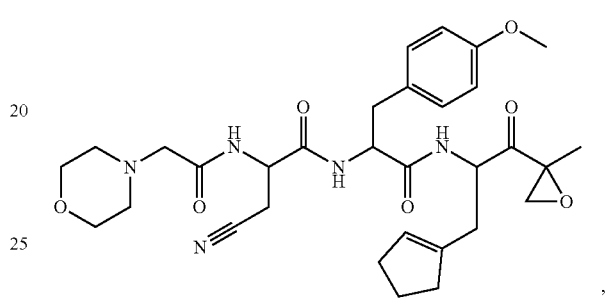
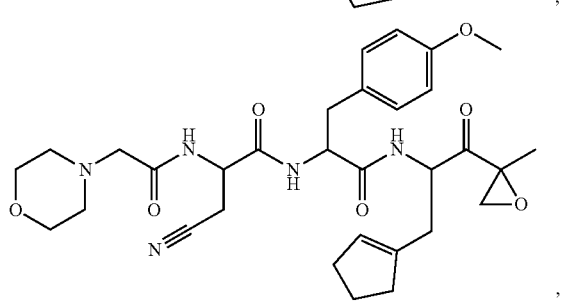
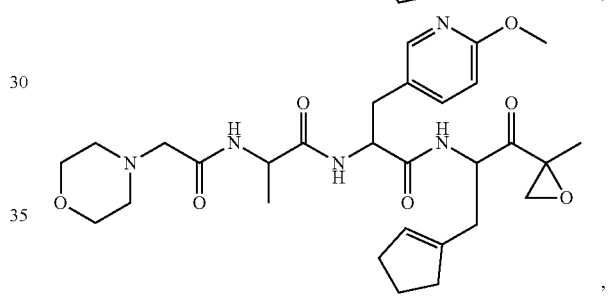
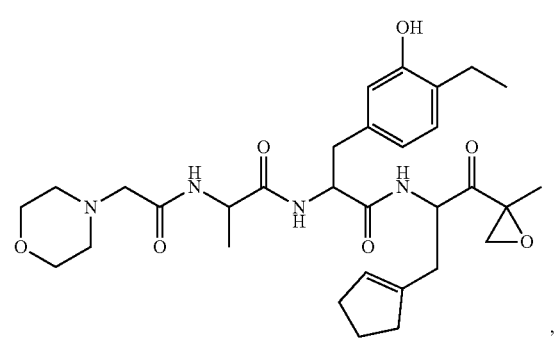
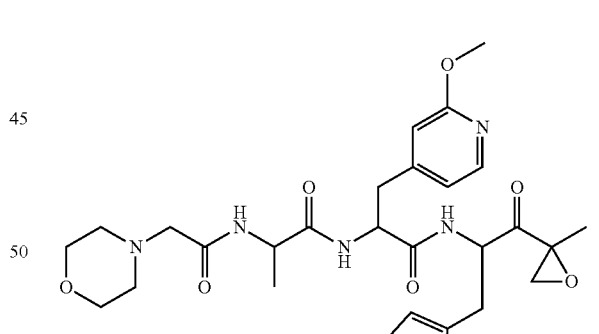
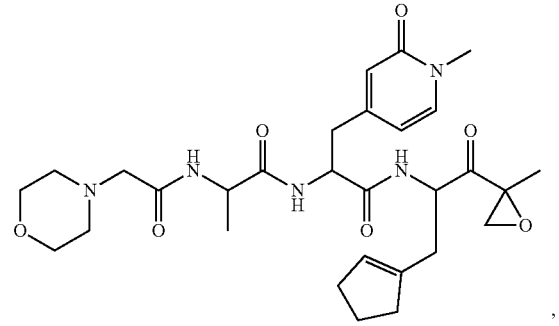
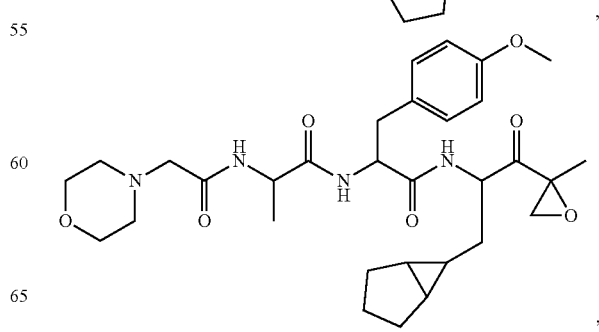

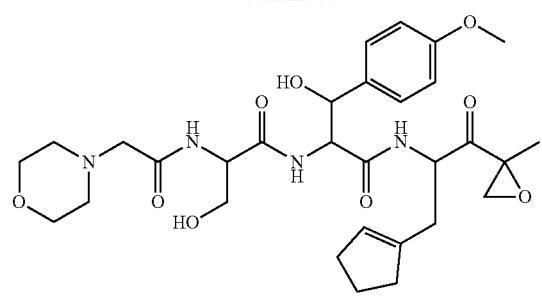
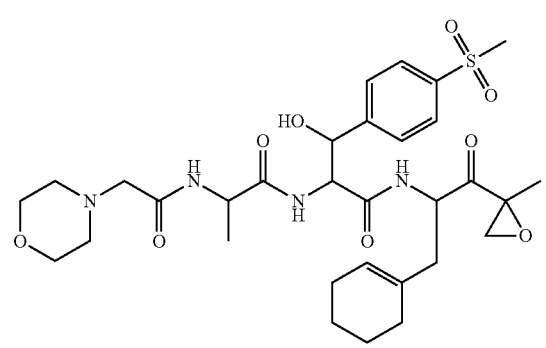
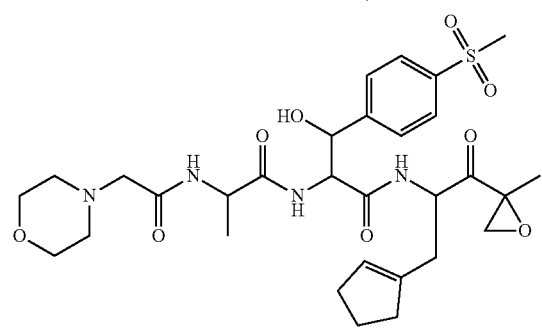
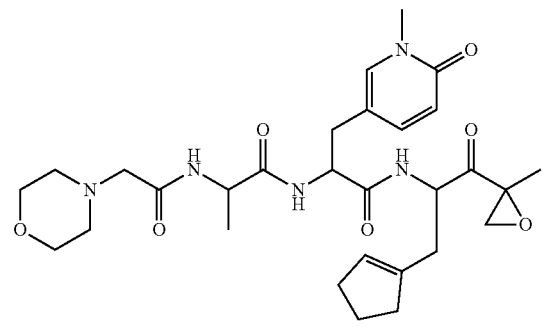
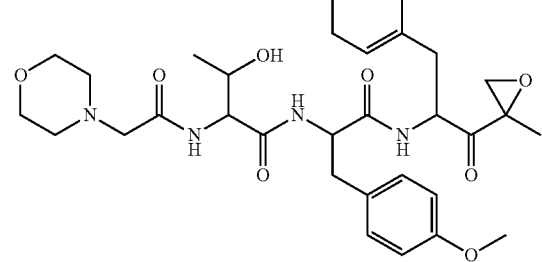
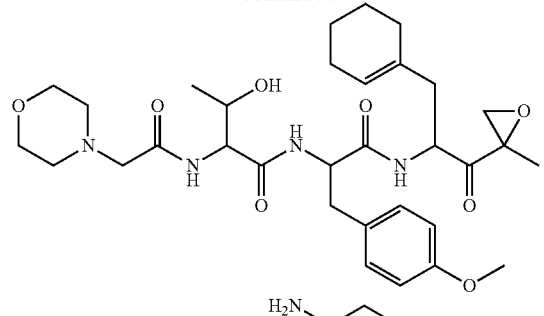
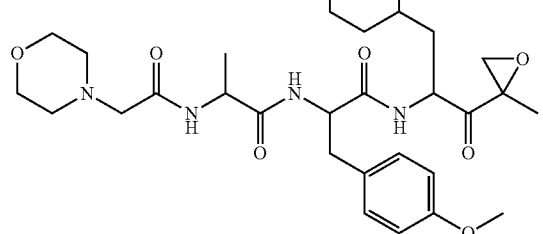
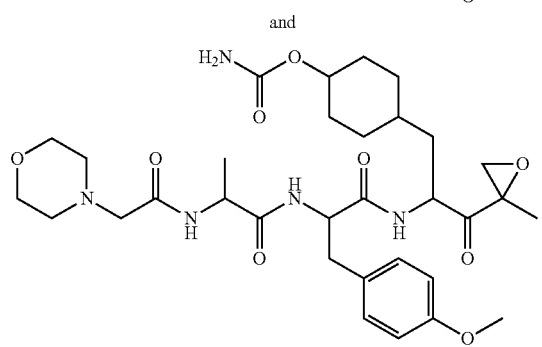
or a pharmaceutically acceptable salt thereof.
In some exemplary embodiments, a compound of Formula (X) is selected from the group consisting of:
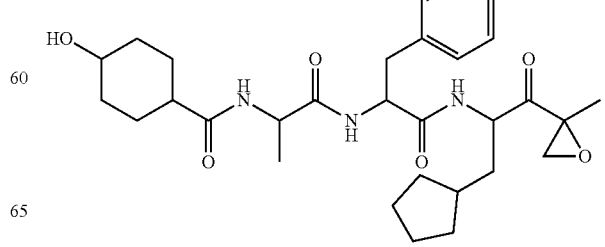

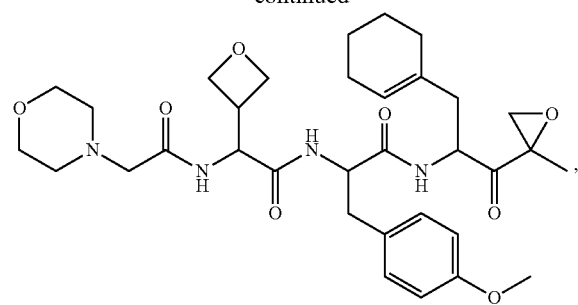
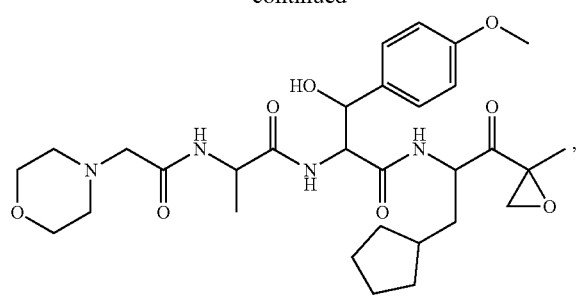
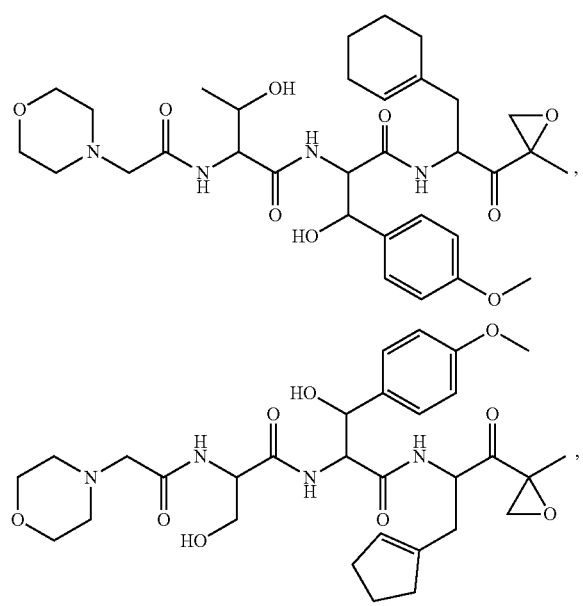
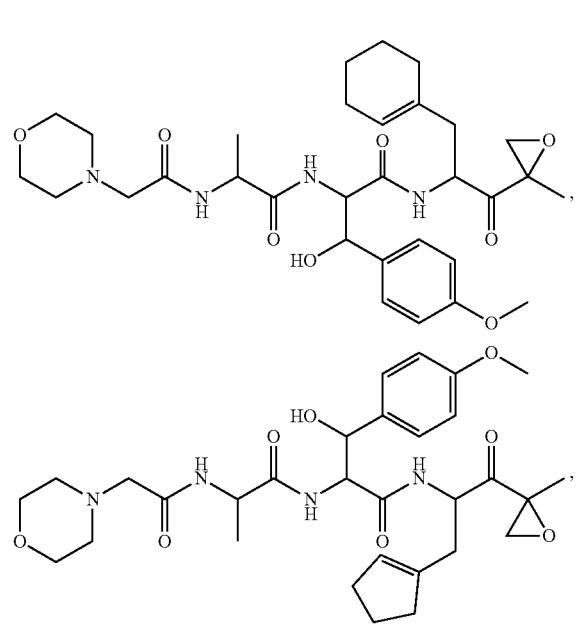
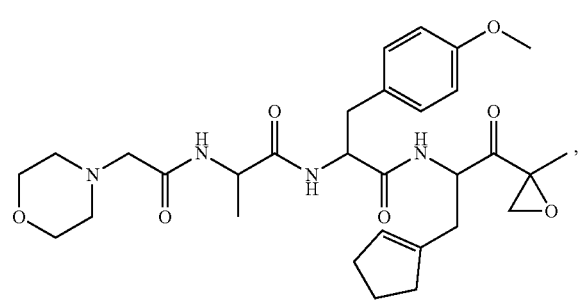
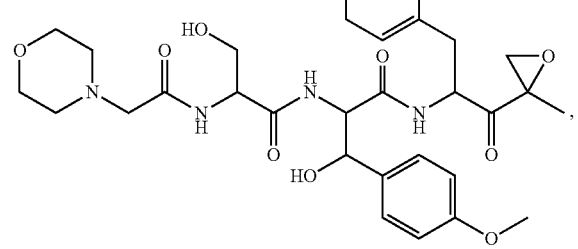
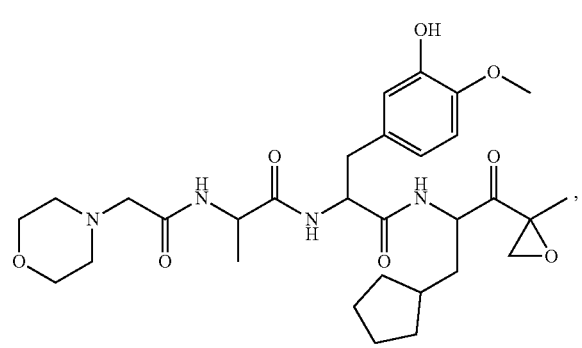
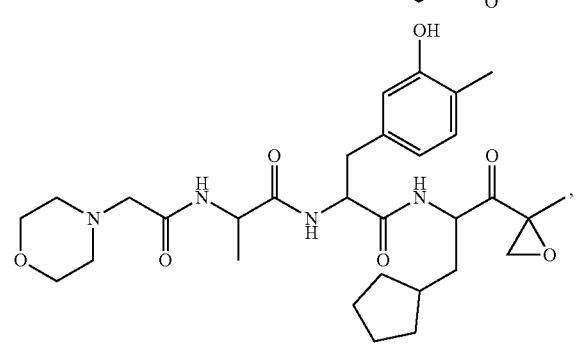

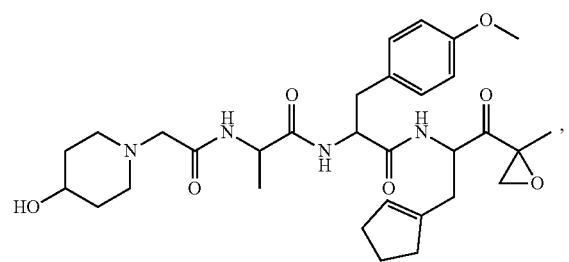
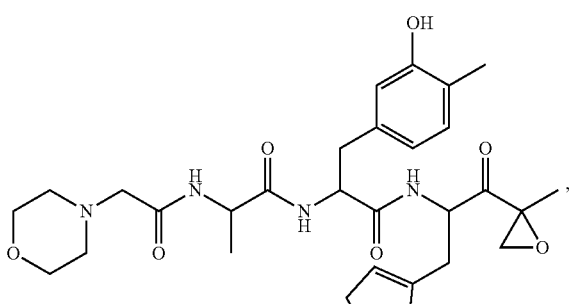
and
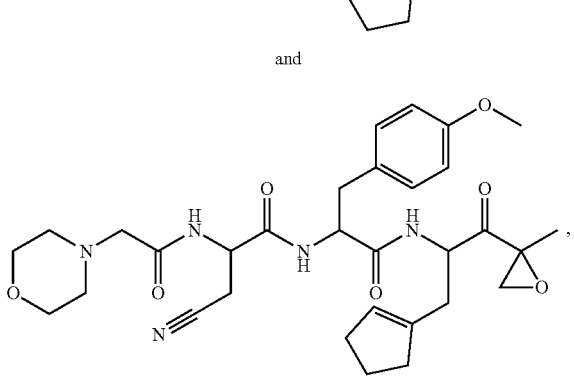
or a pharmaceutically acceptable salt thereof.
For example, a compound of Formula (X) can be selected from the group consisting of:
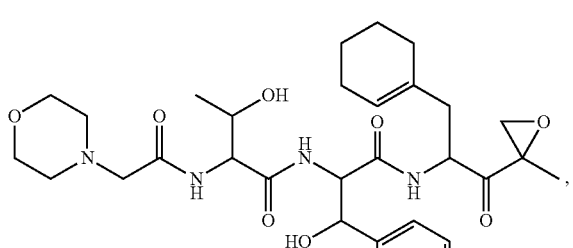
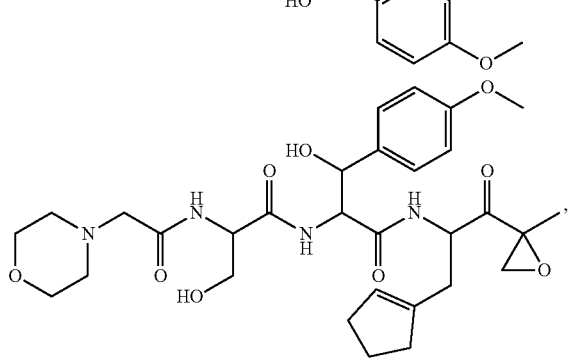
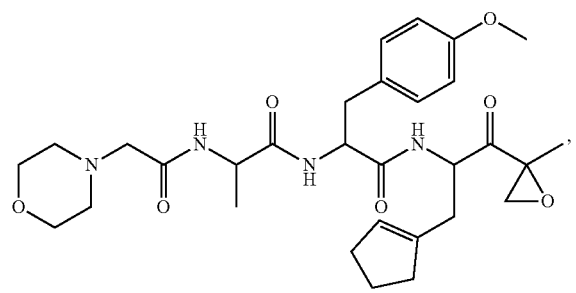
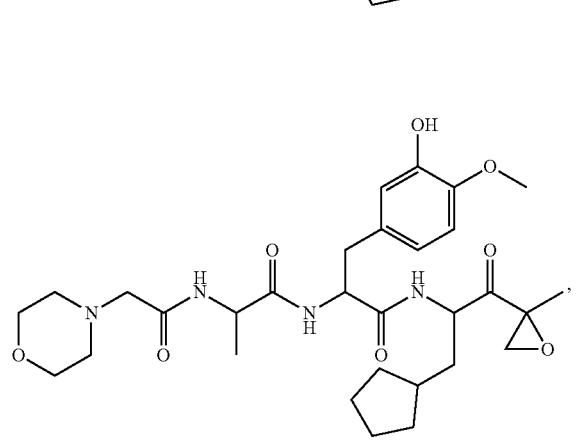
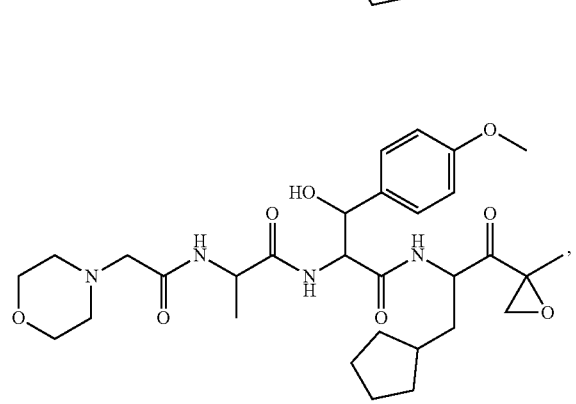
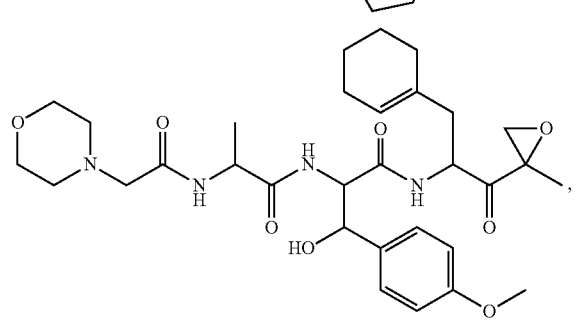
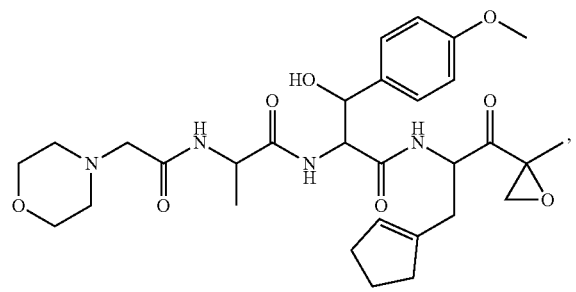

-continued
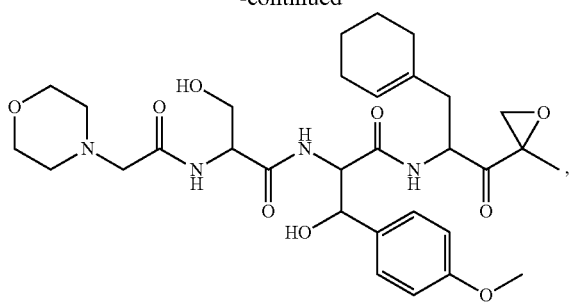
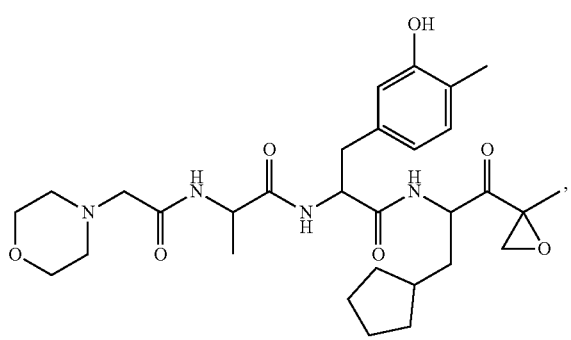
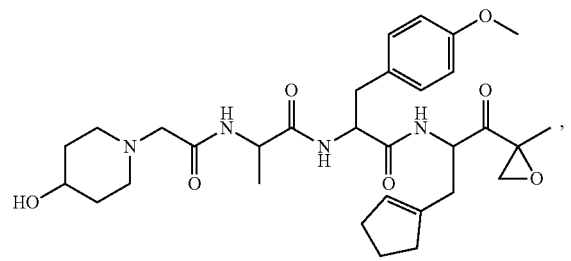
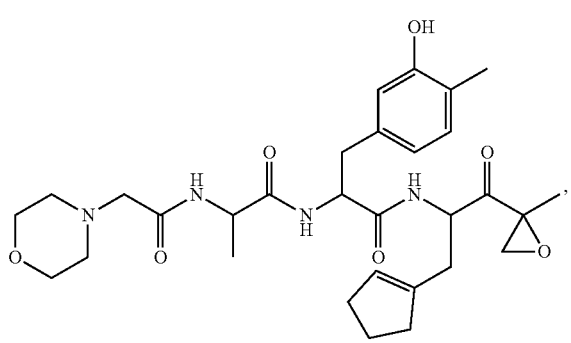
and
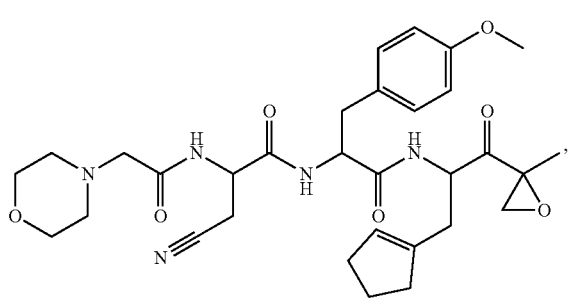
or a pharmaceutically acceptable salt thereof.
In various embodiments, a compound of Formula (X) has a stereochemical configuration:
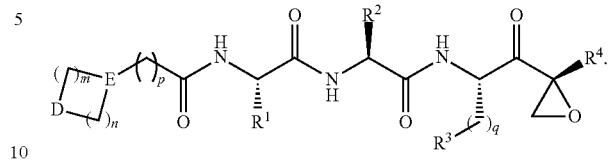
In various embodiments, a compound of Formula (X) is selected from:
C-1001
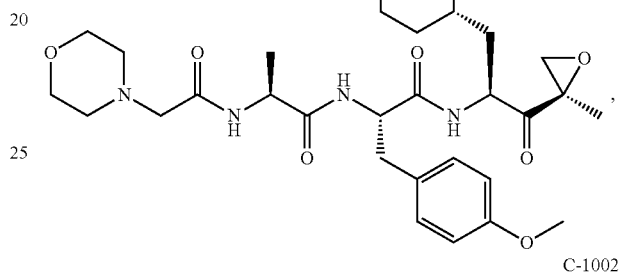
C-1002
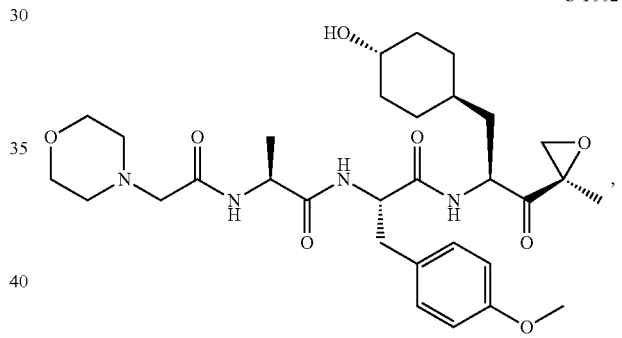
C-1003
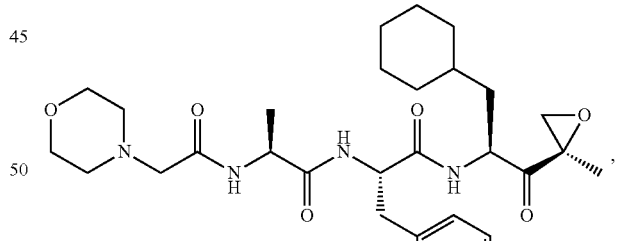
C-1004
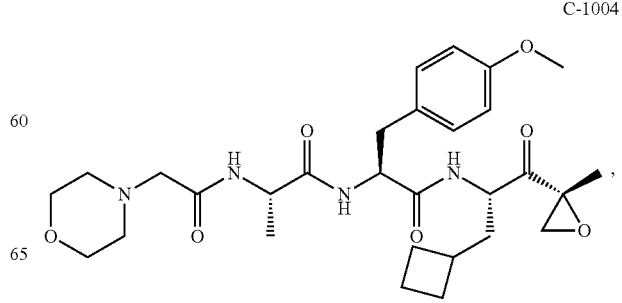

C-1005
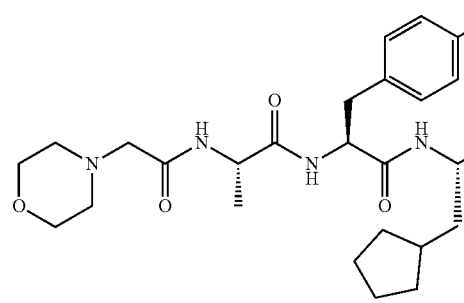
C-1006
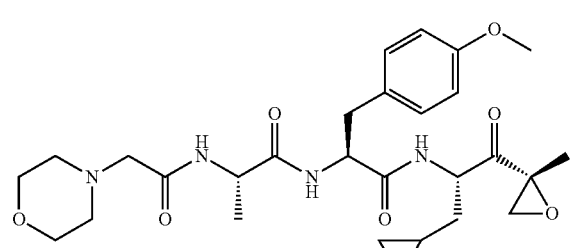
C-1007
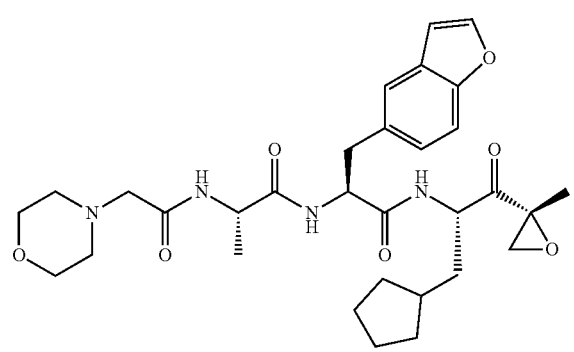
C-1008
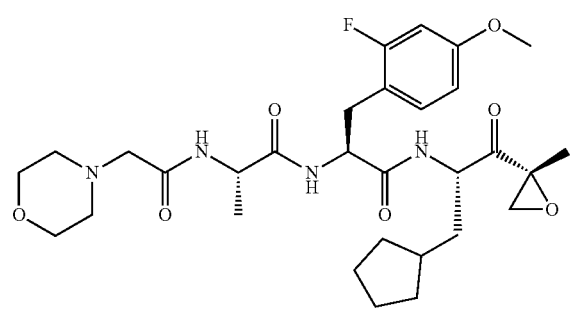
C-1009
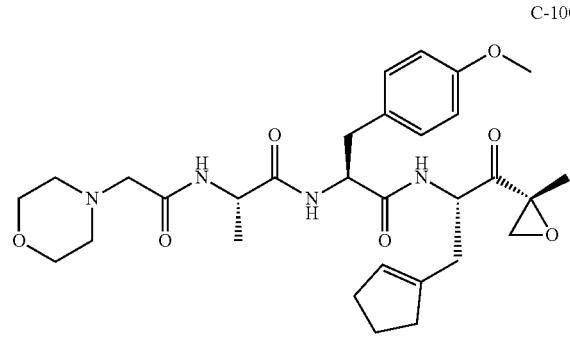
C-1010
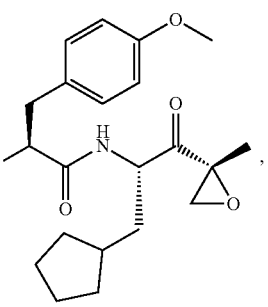
C-1011
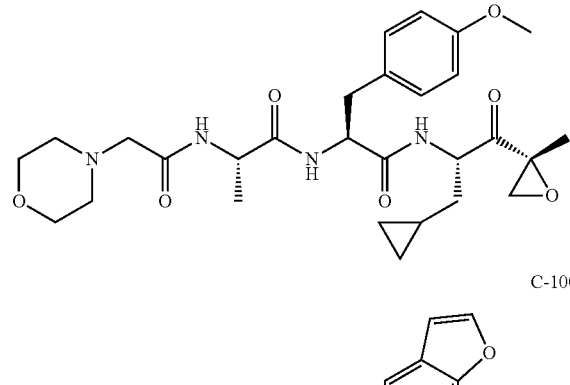
C-1012
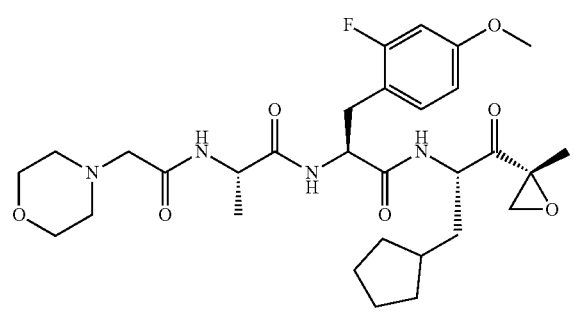
C-1013
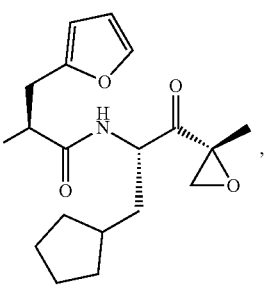

C-1014
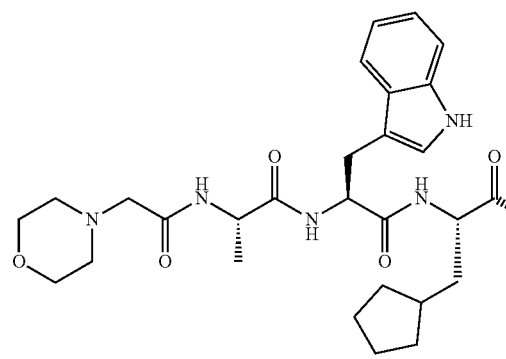
C-1015
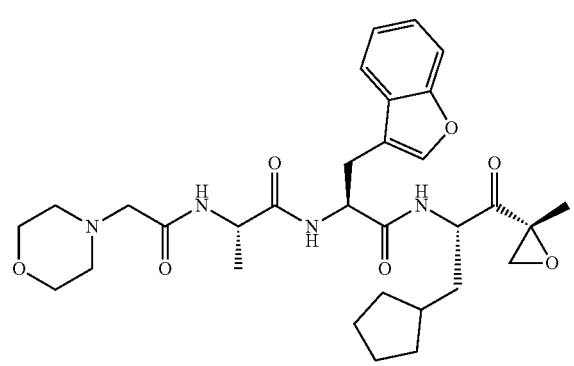
C-1016
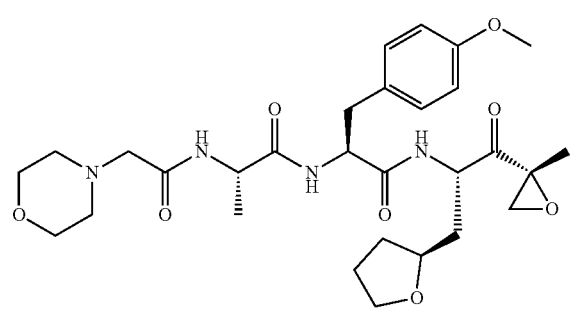
C-1017
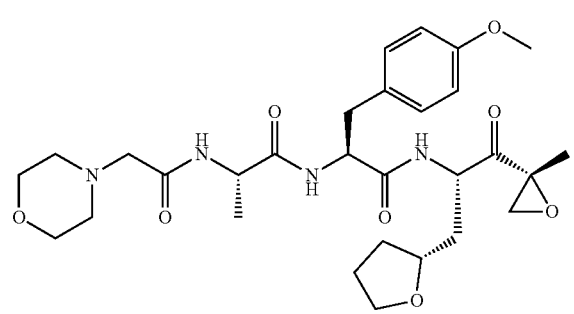
C-1018
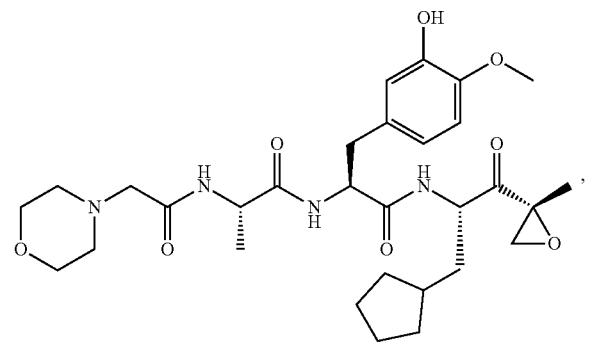
C-1019
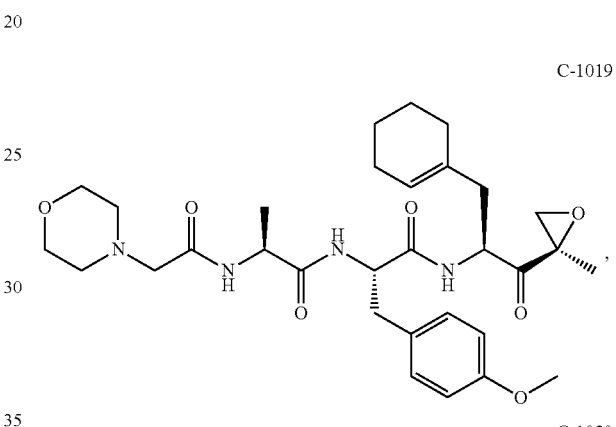
C-1020
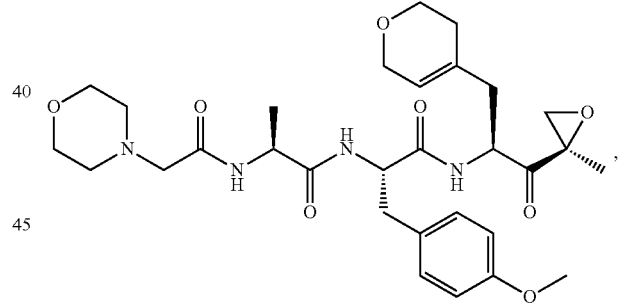
C-1021
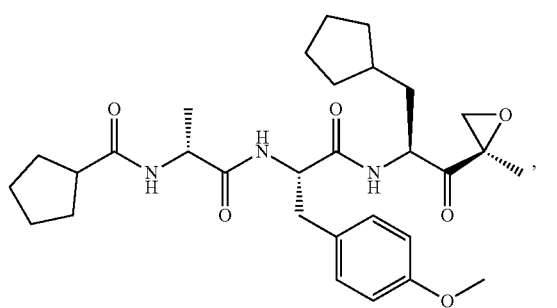

-continued
C-1022
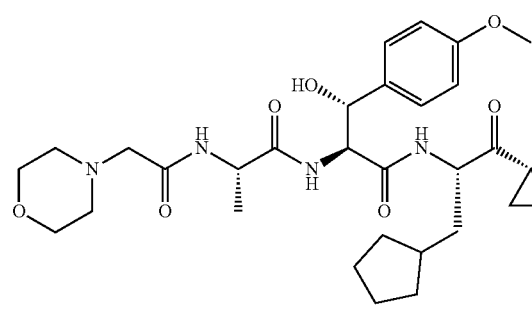
C-1023
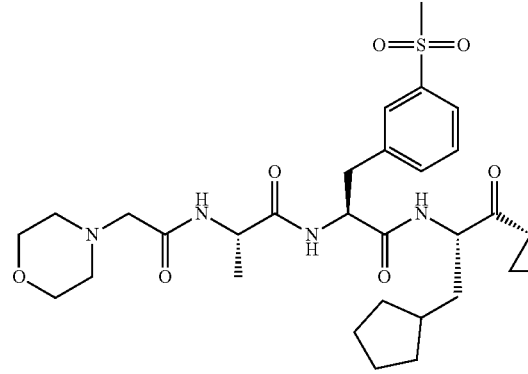
C-1024
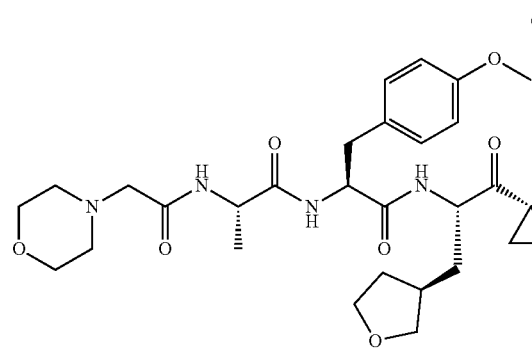
C-1025
-continued
C-1026
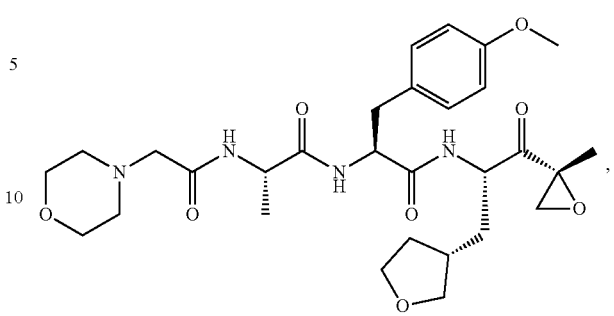
C-1027
C-1028
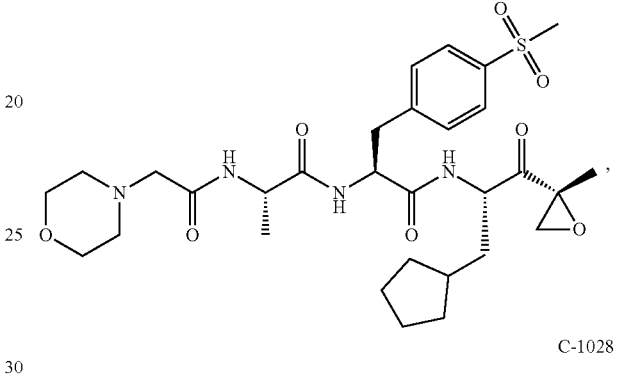
C-1029
C-1030
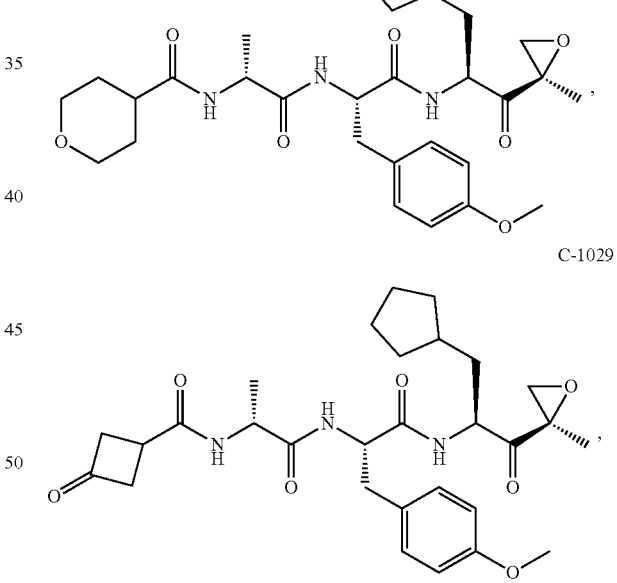

C-1031
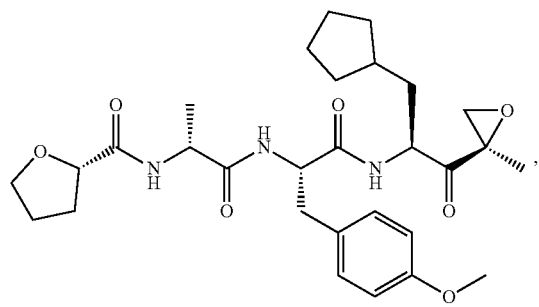
C-1032
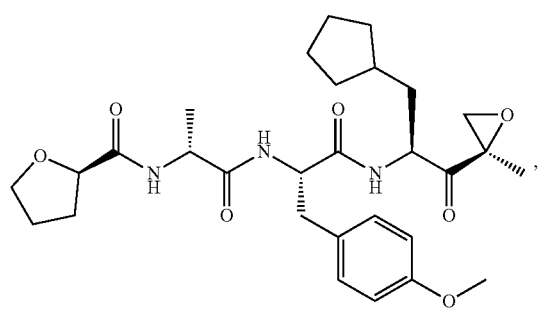
C-1033
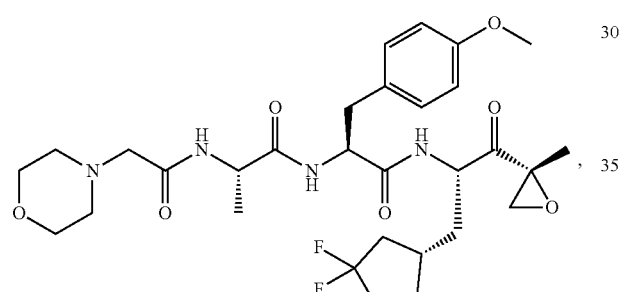
C-1034
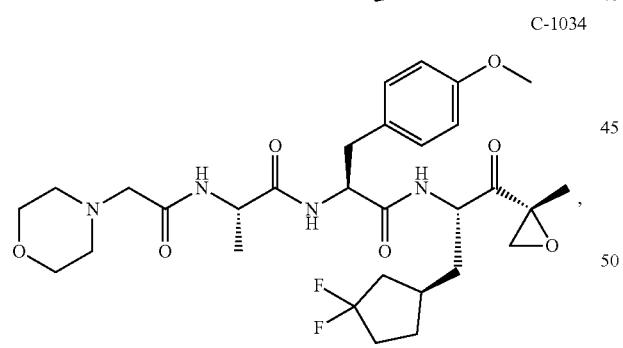
C-1035
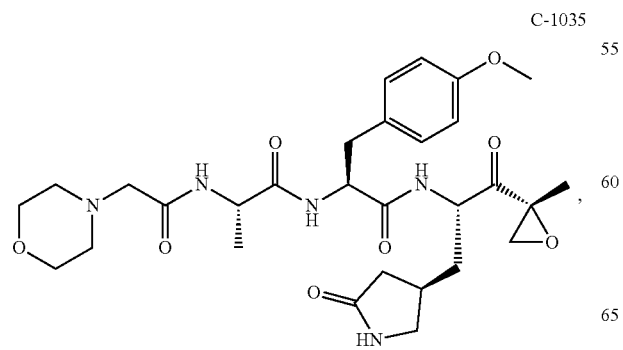
C-1036
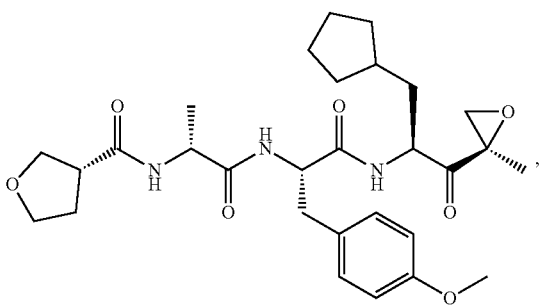
C-1037
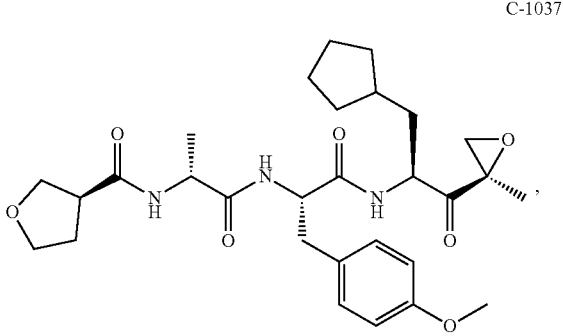
C-1038
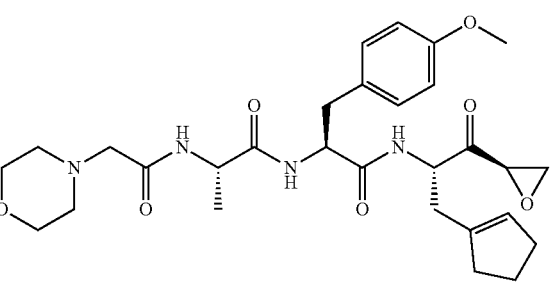
C-1039
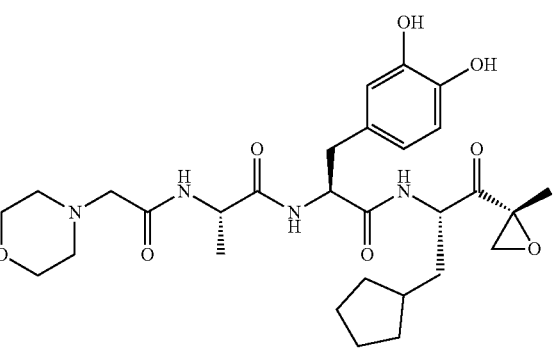

C-1040
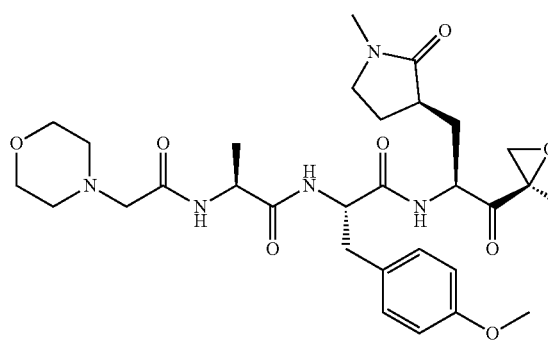
C-1041
C-1042
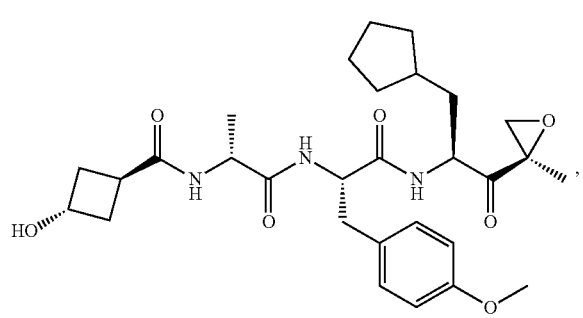
C-1043
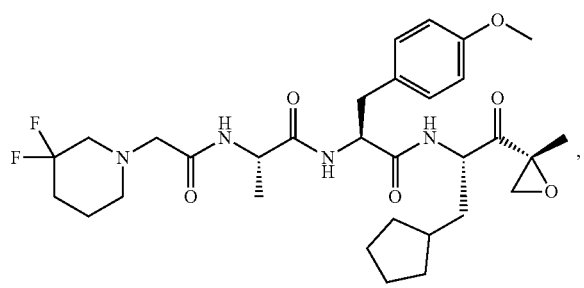
C-1044
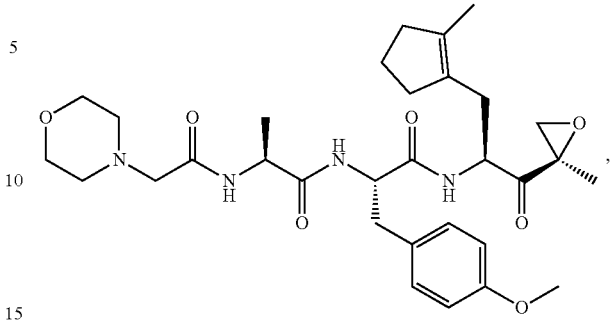
C-1045
C-1046
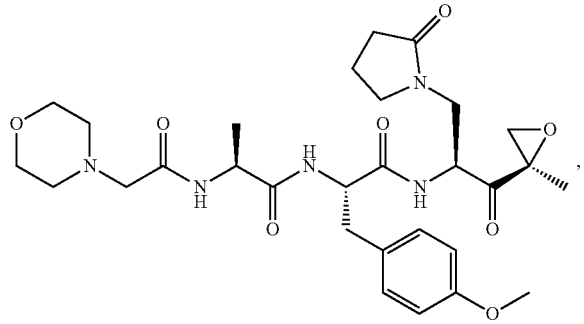
C-1047
C-1048

C-1049
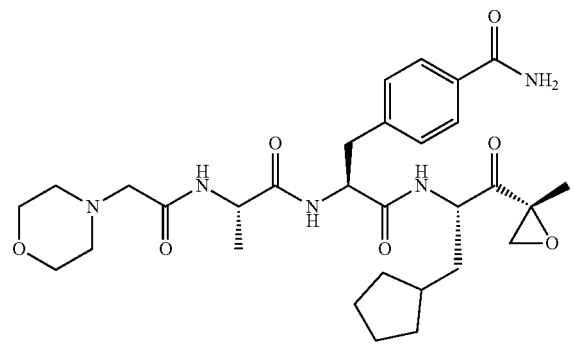
C-1053
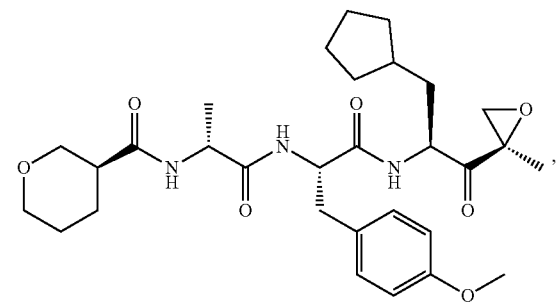
C-1050
C-1054
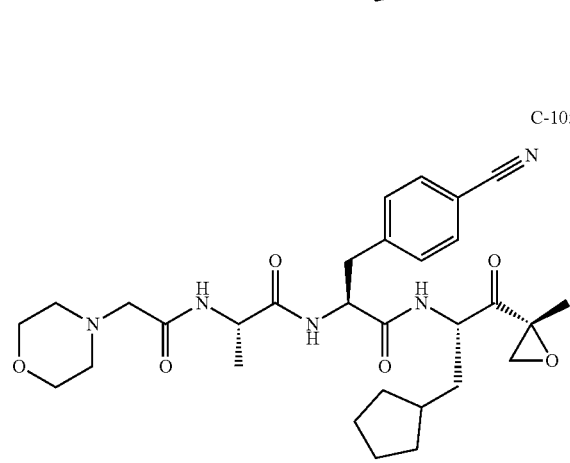
C-1055
C-1051
C-1056
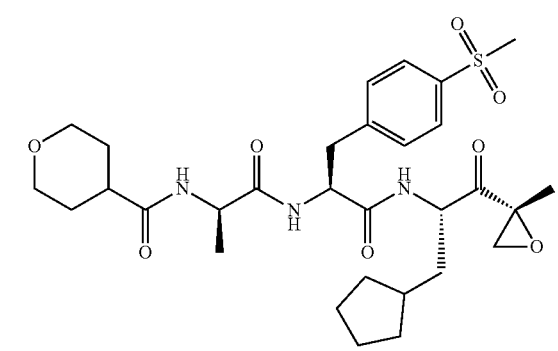
C-1052
C-1057
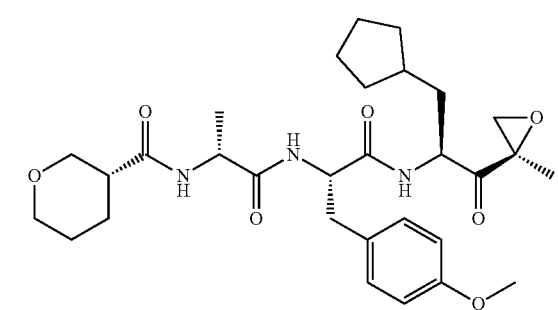

-continued
C-1058
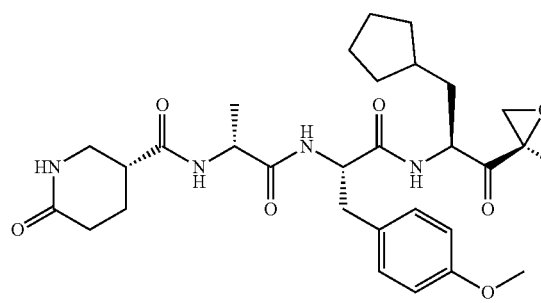
C-1062
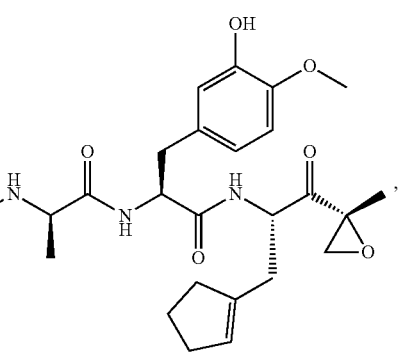
C-1059
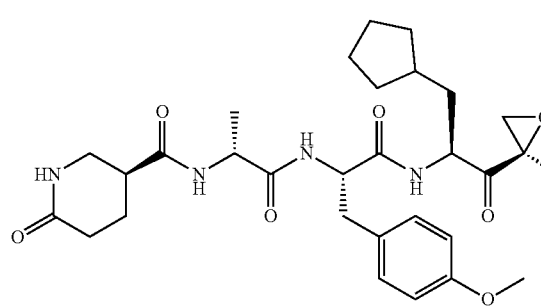
C-1063
C-1060
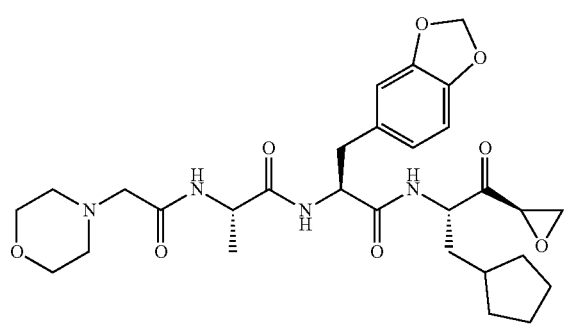
C-1064
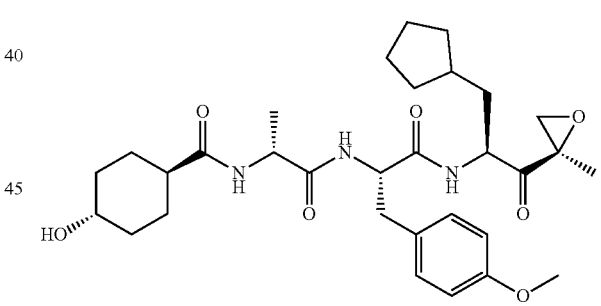
C-1061
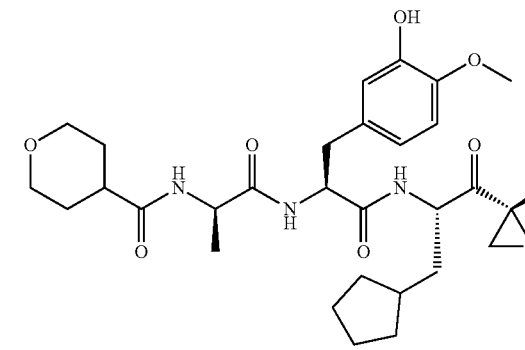
C-1065
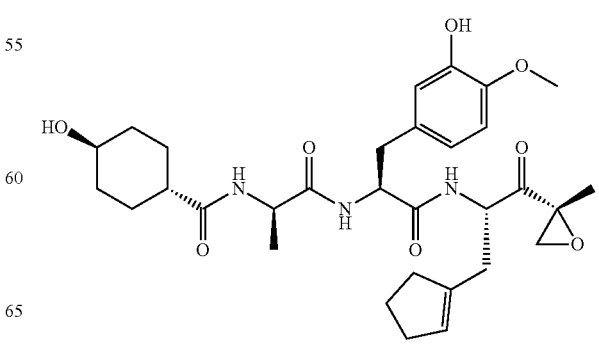

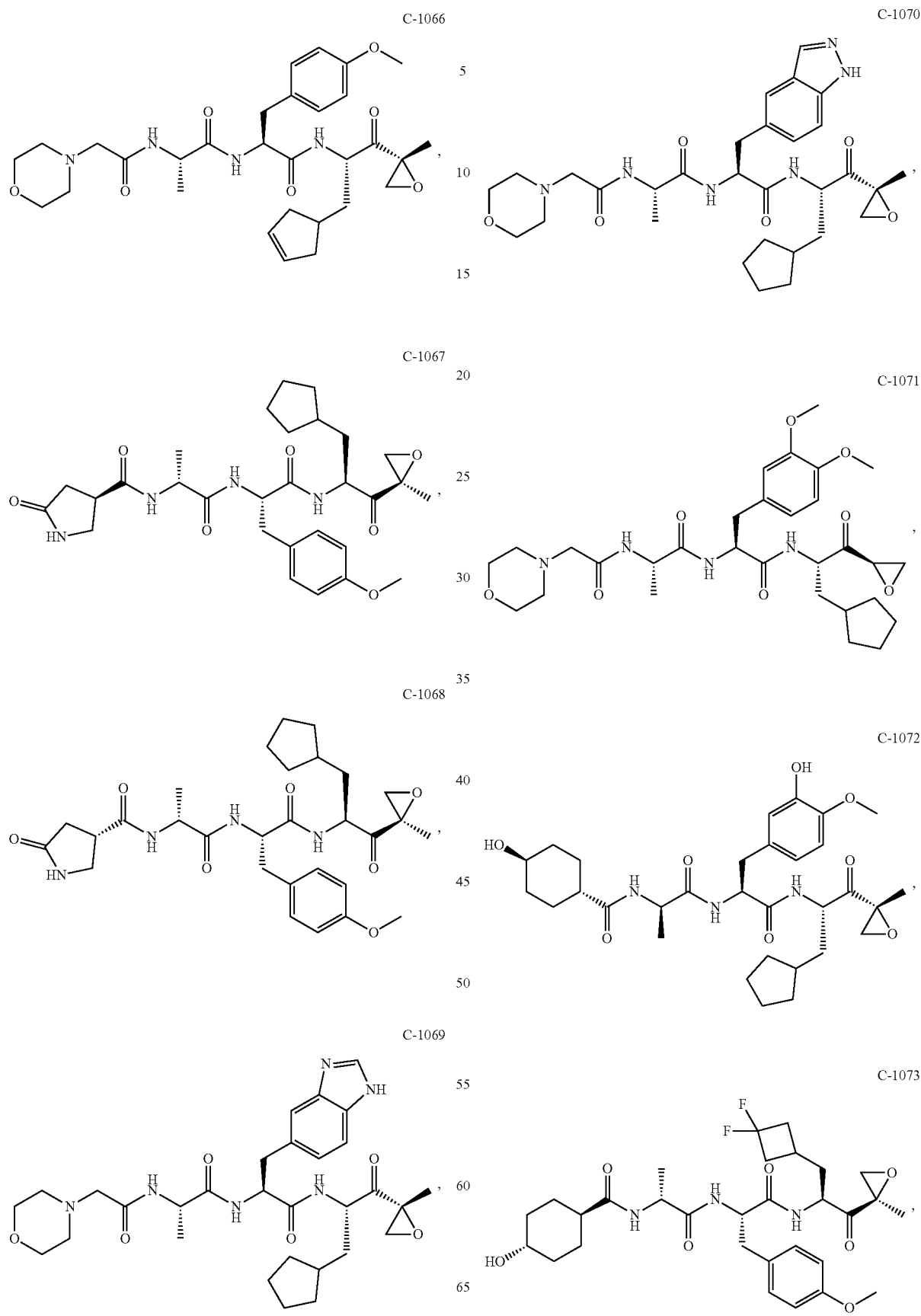

C-1074
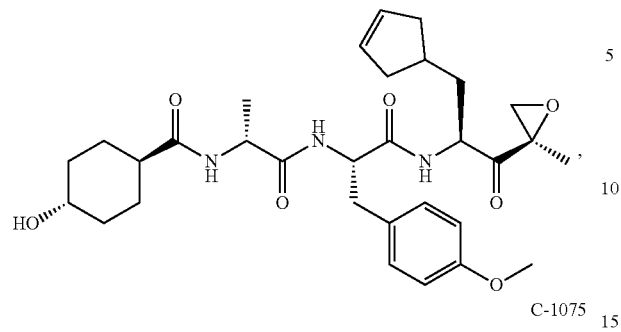
C-1079
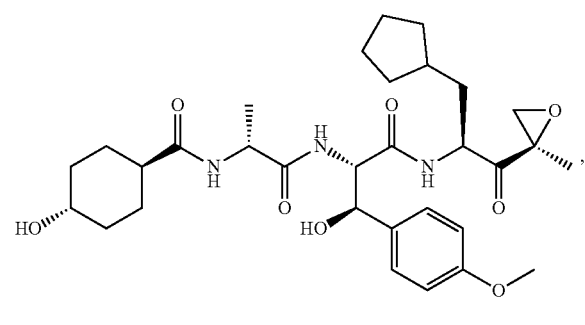
C-1075
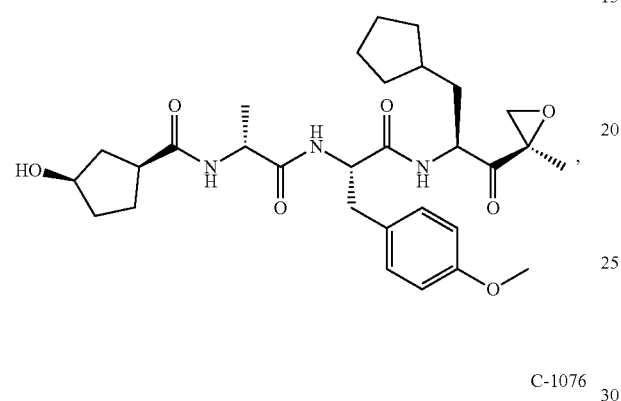
C-1080
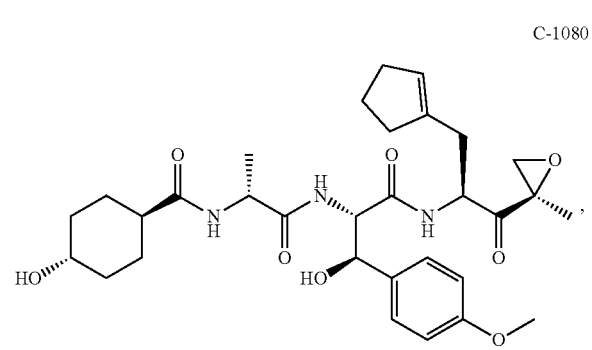
C-1076
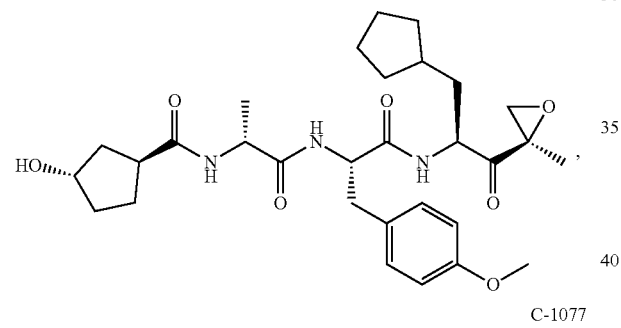
C-1081
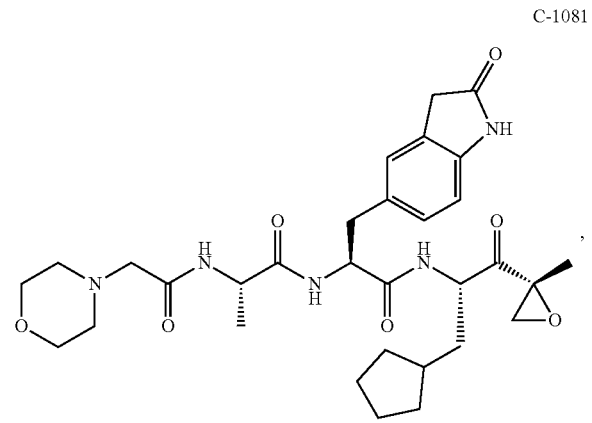
C-1077
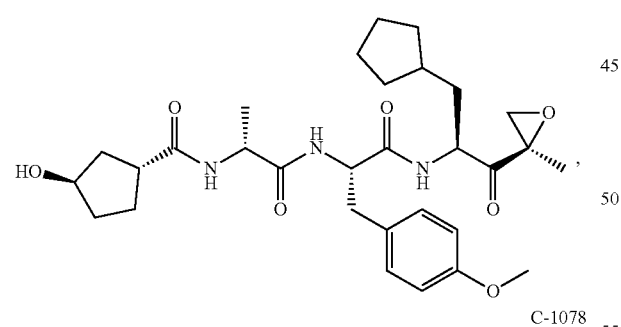
C-1078
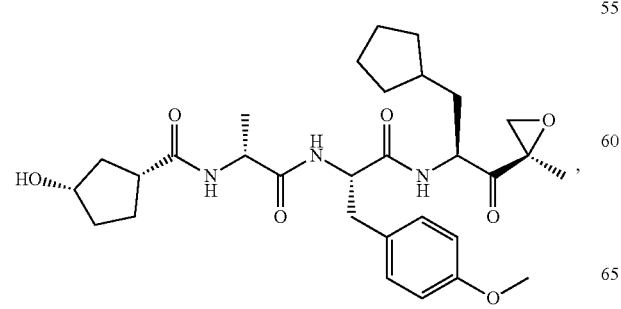
C-1082
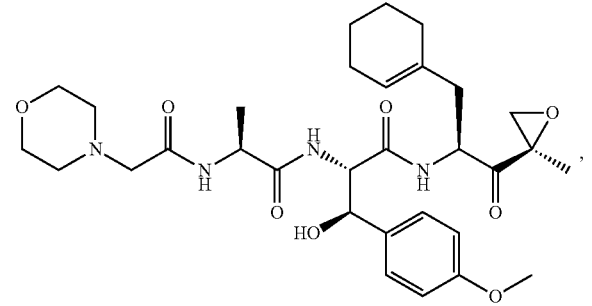

C-1083
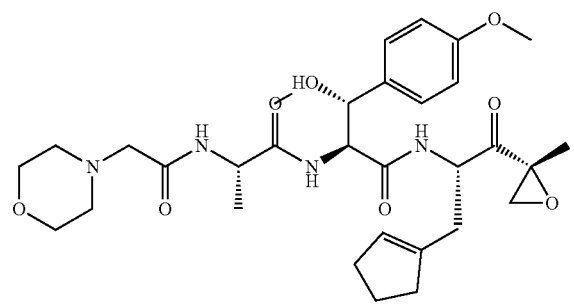
C-1087
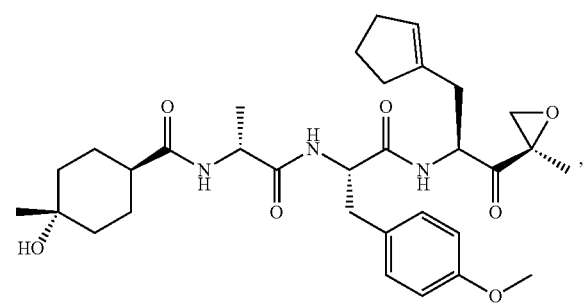
C-1084
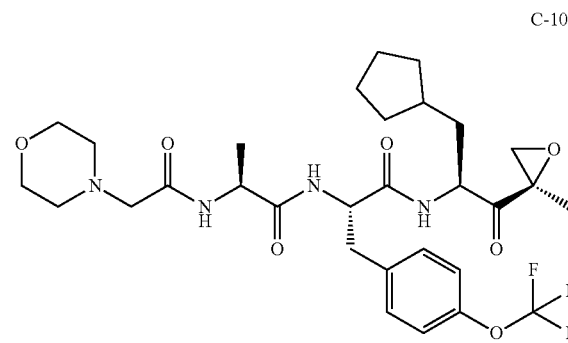
C-1088
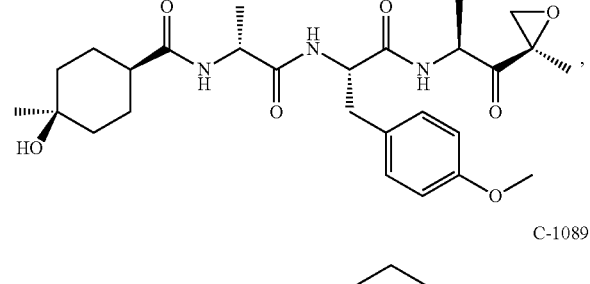
C-1085
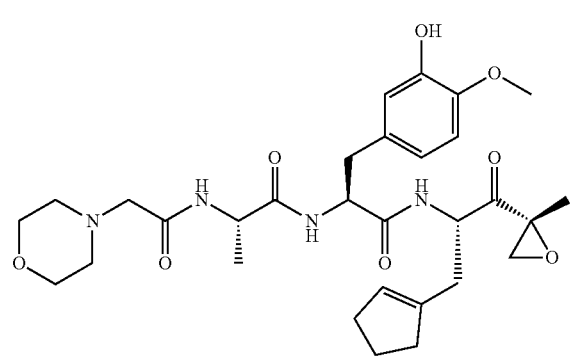
C-1089
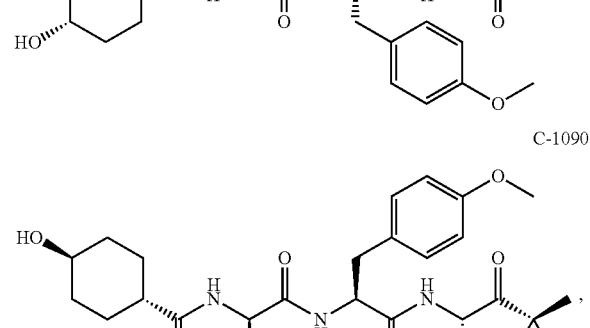
C-1090
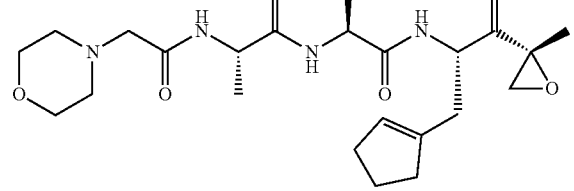
C-1086
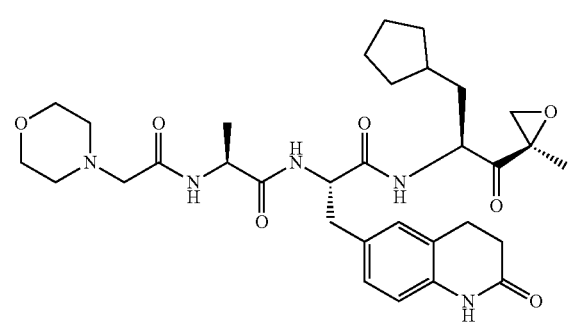
C-1091
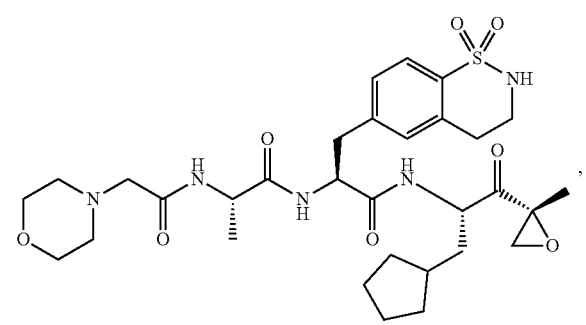

C-1092
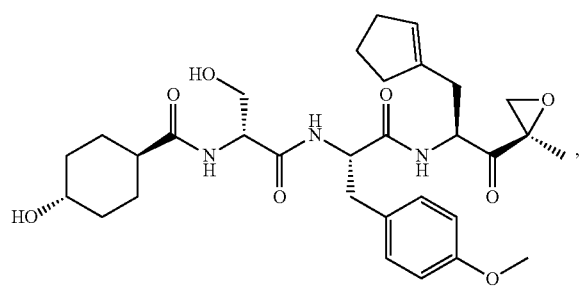
C-1097
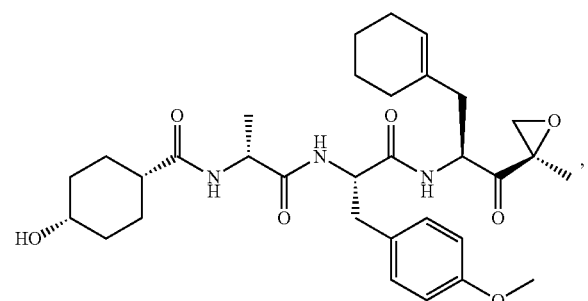
C-1093
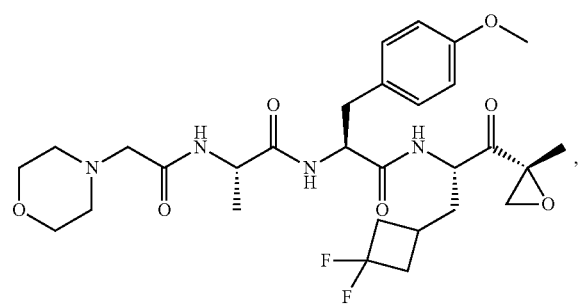
C-1098
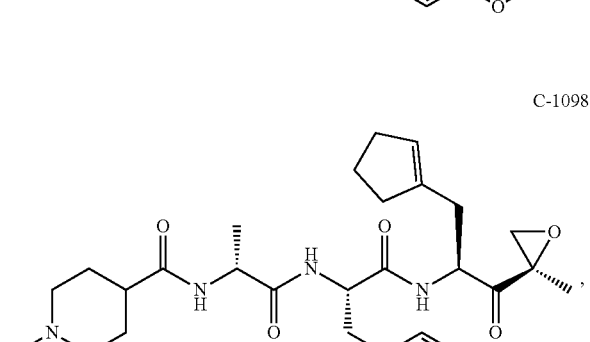
C-1094
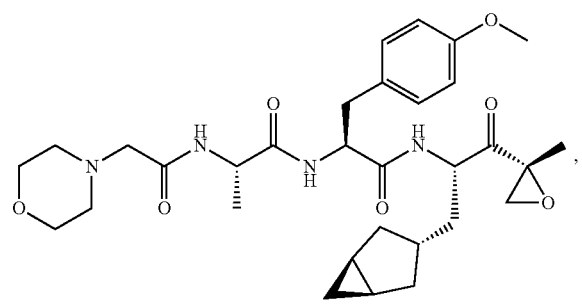
C-1099
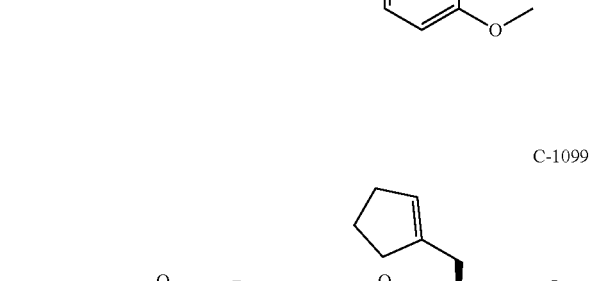
C-1095
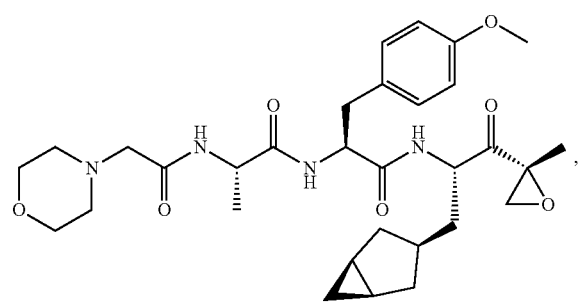
C-1100
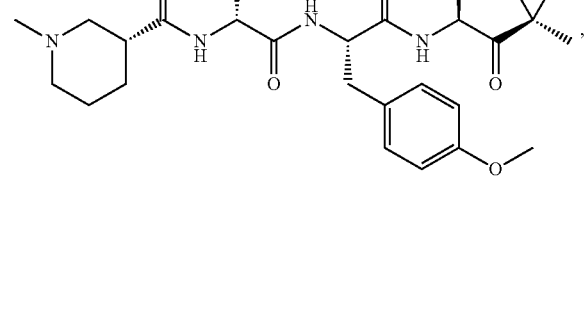
C-1096
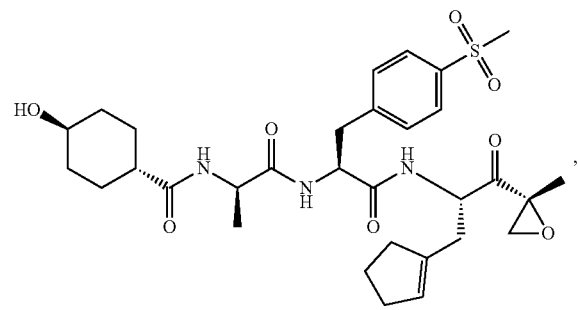
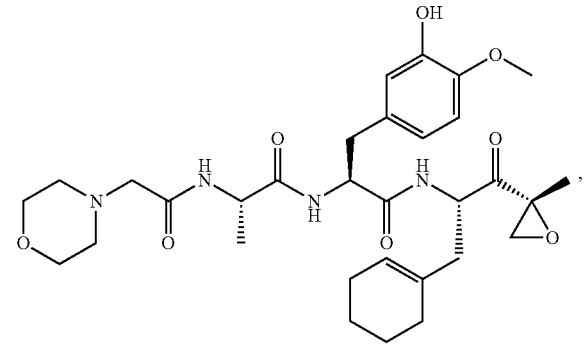

C-1101
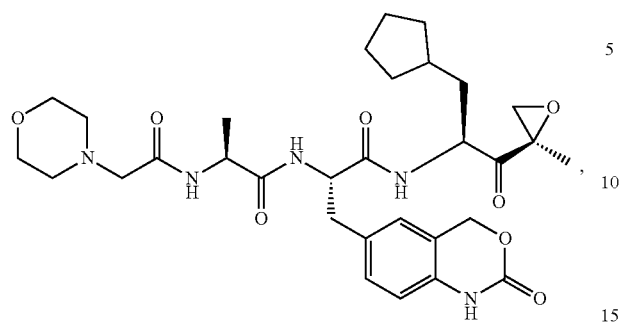
C-1105
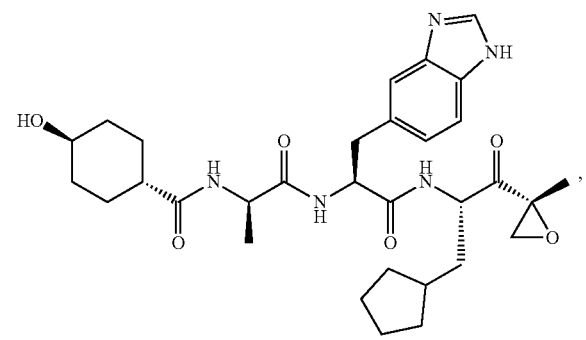
C-1102
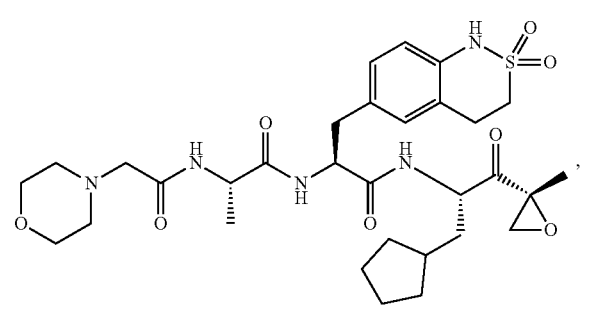
C-1106
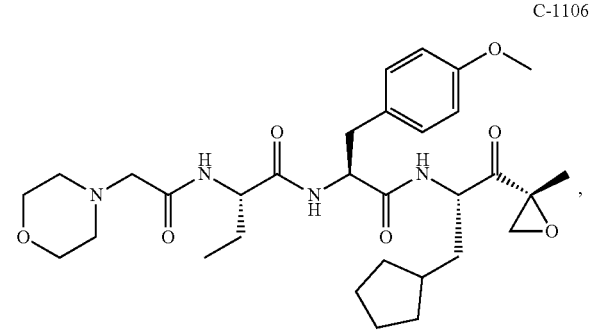
C-1103
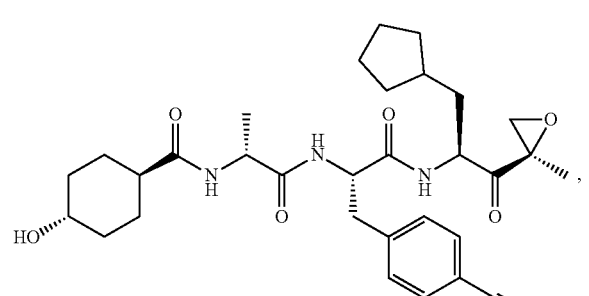
C-1107
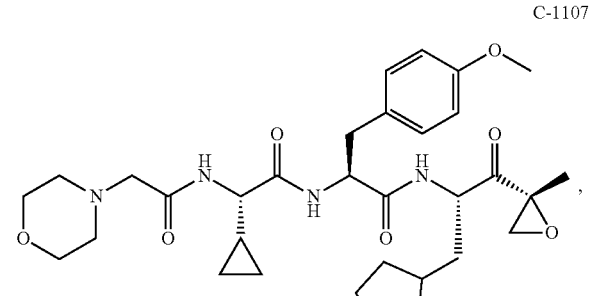
C-1104
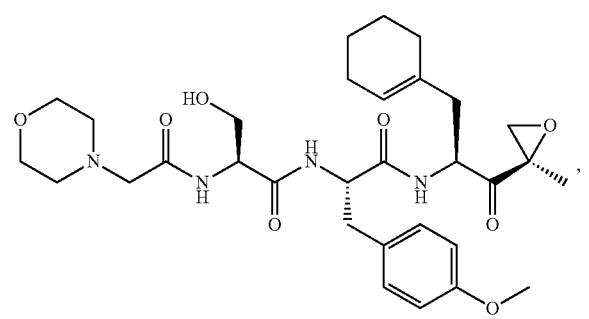
C-1108
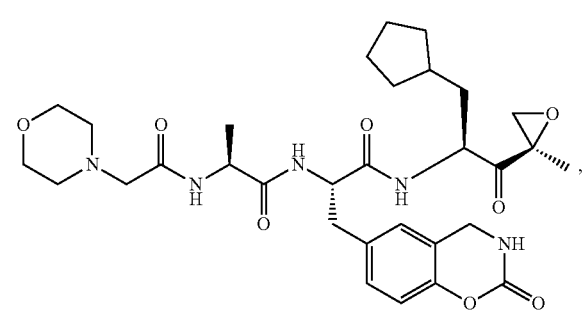

C-1109
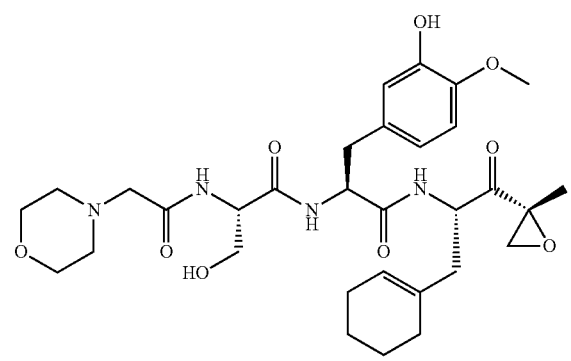
C-1113
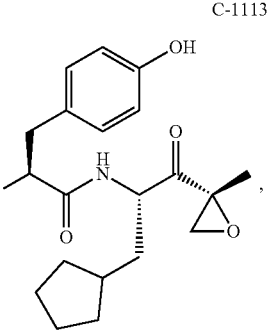
C-1110
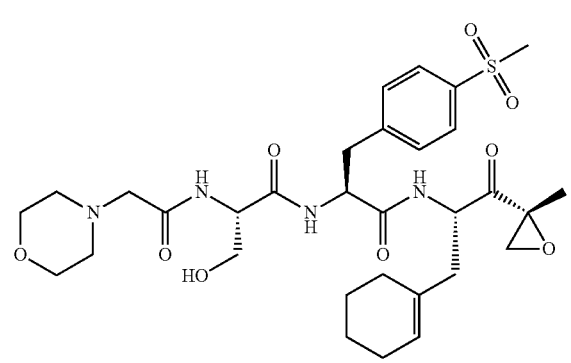
C-1114
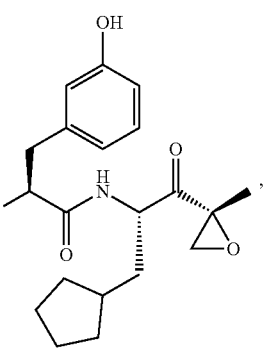
C-1111
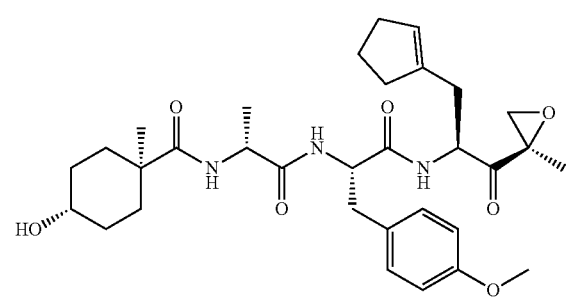
C-1115
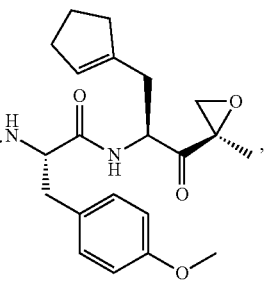
C-1112
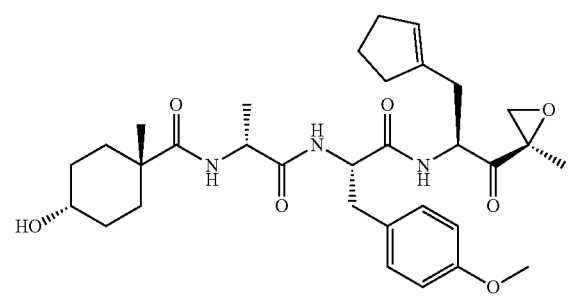
C-1116
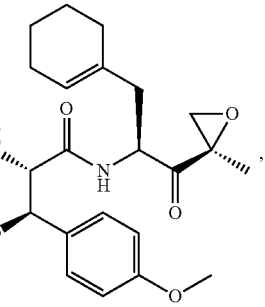

-continued
C-1117
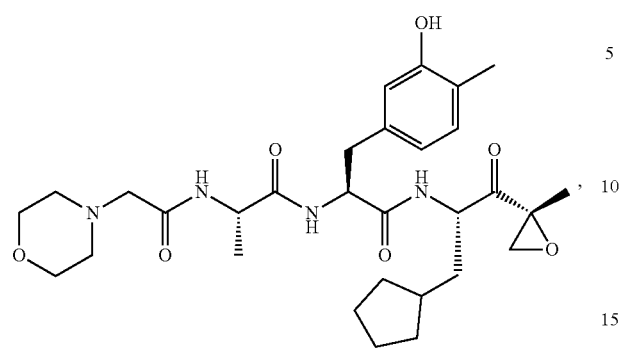
C-1118
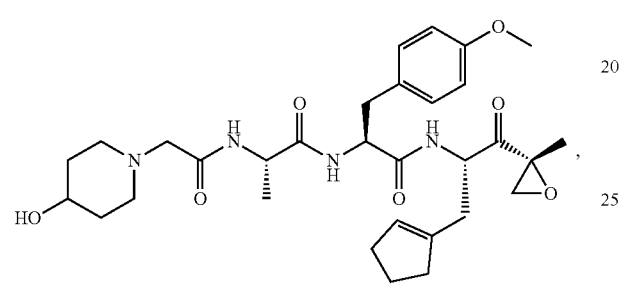
C-1119
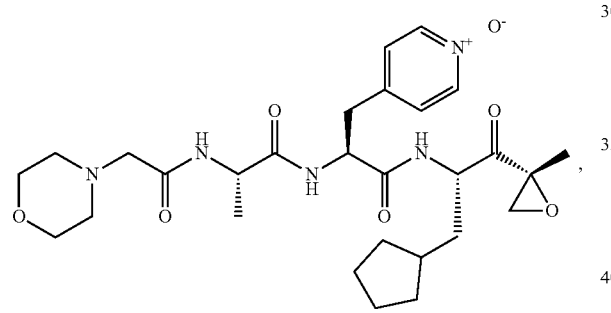
C-1120
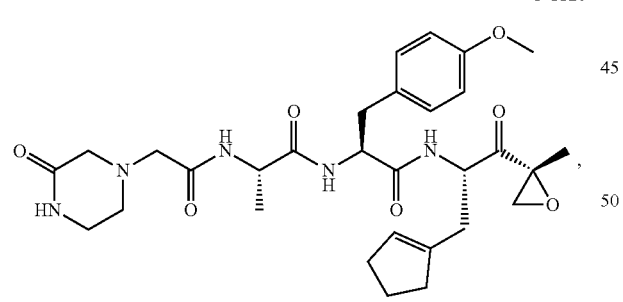
C-1121
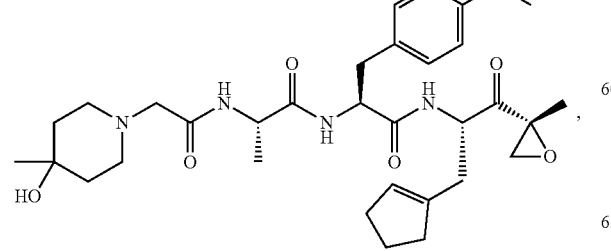
-continued
C-1122
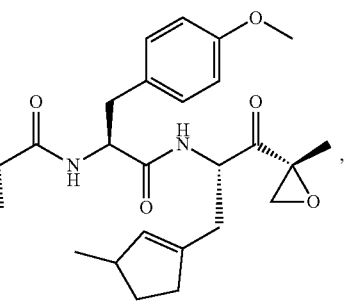
C-1123
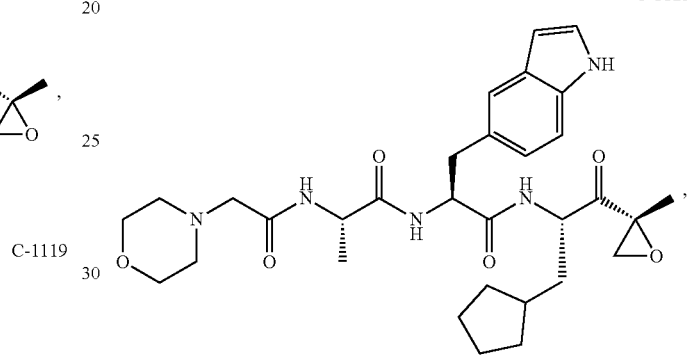
C-1124
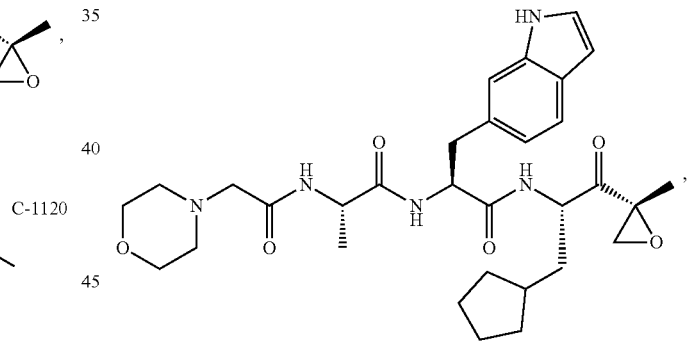
C-1125
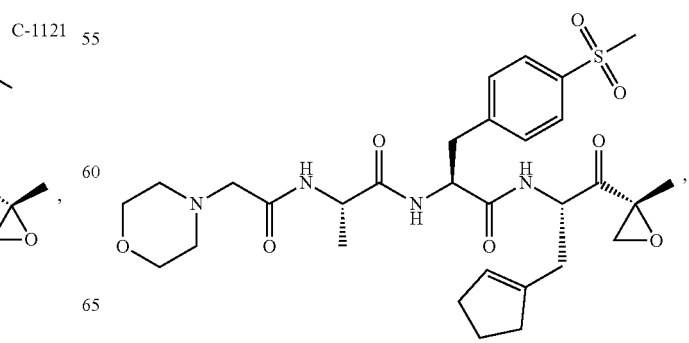

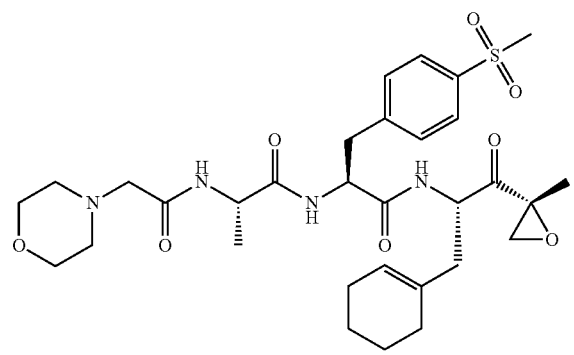
C-1126
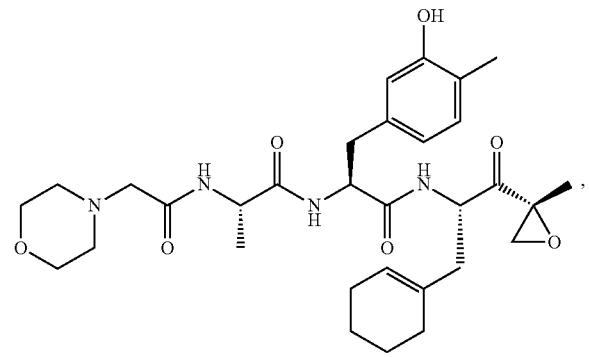
C-1130
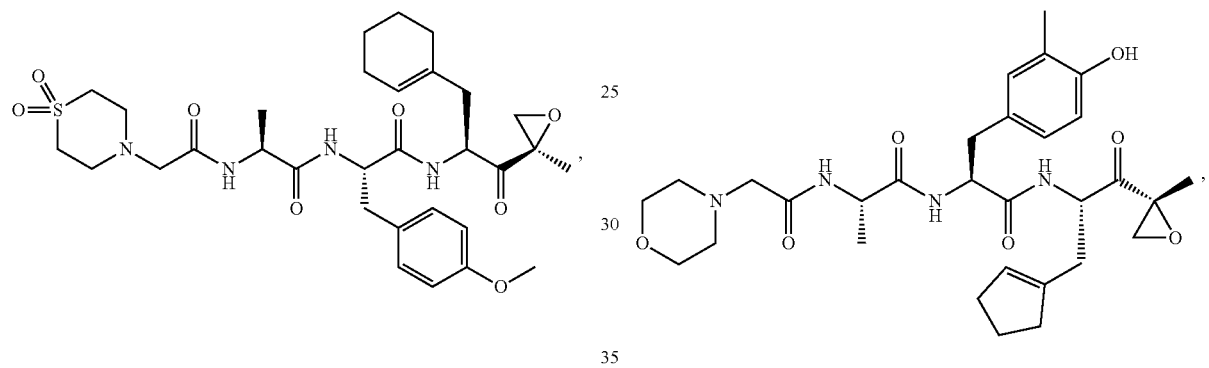
C-1127, C-1131
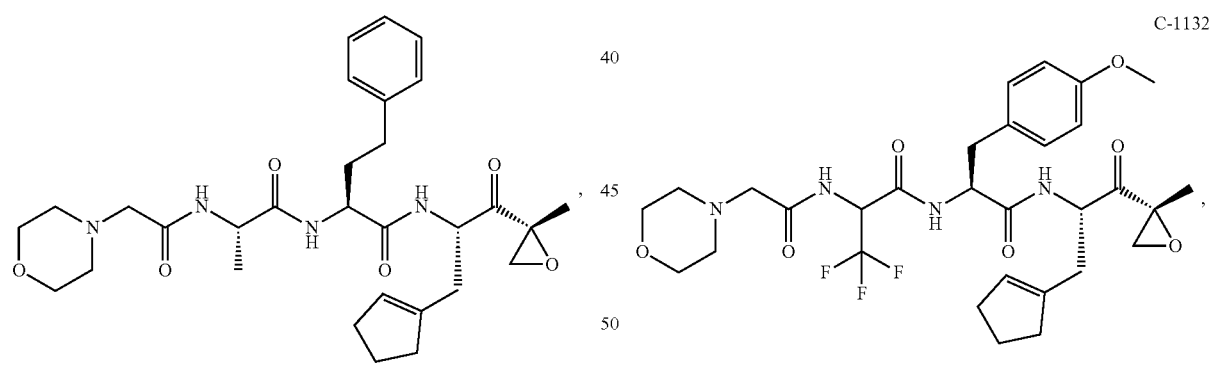
C-1128, C-1132
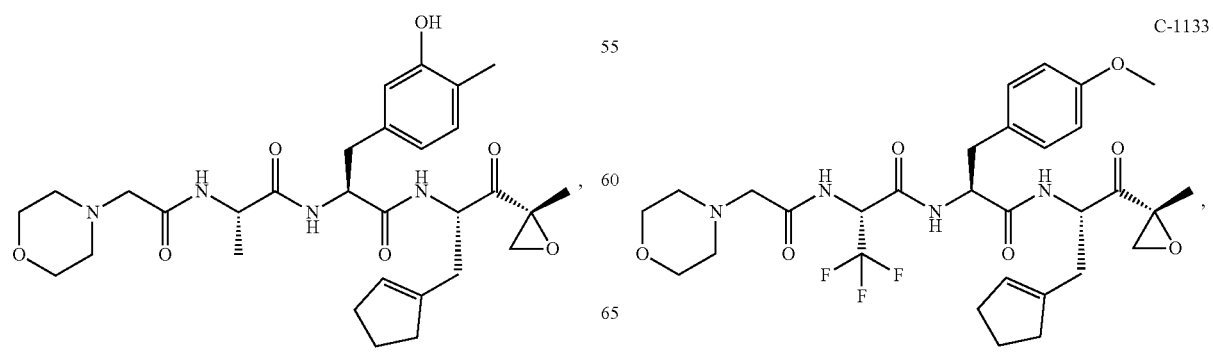
C-1129, C-1133

C-1134
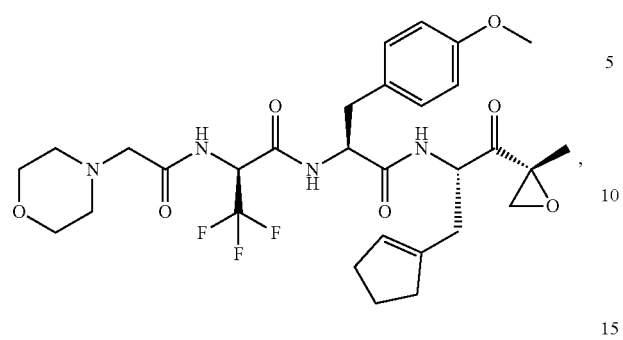
C-1138
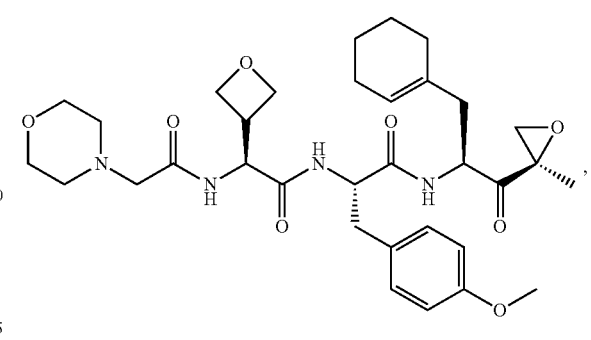
C-1135
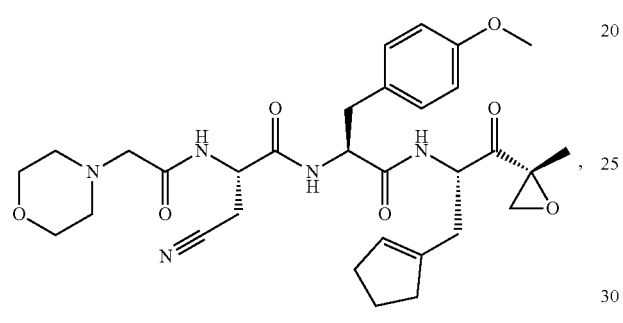
C-1139
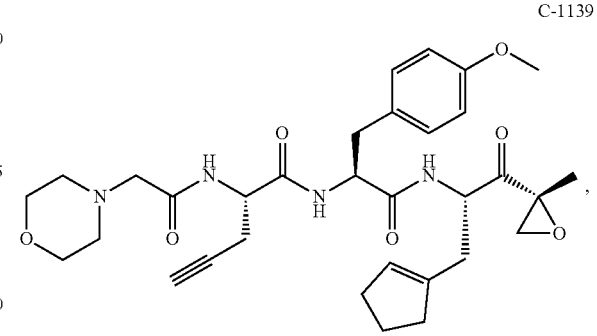
C-1136
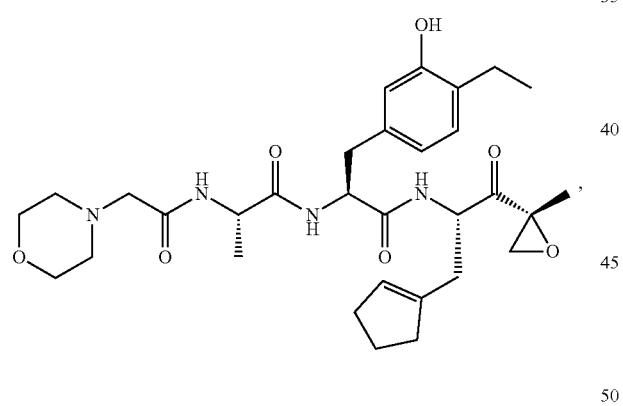
C-1140
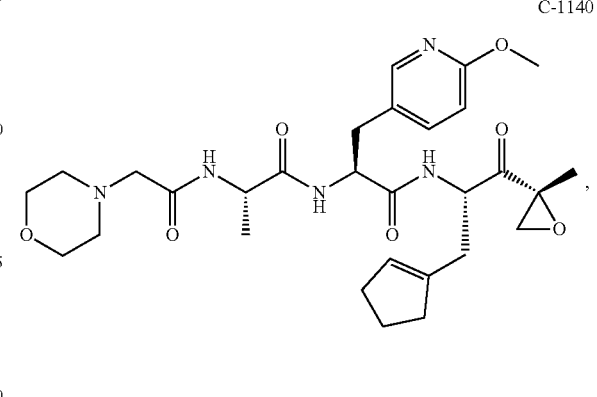
C-1137
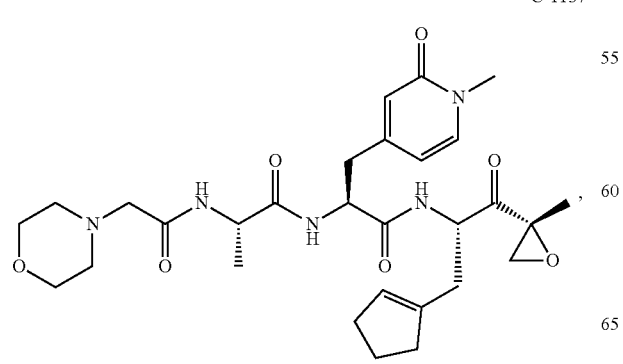
C-1141
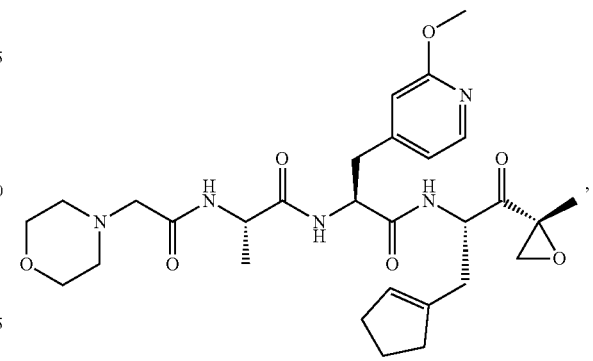

C-1142
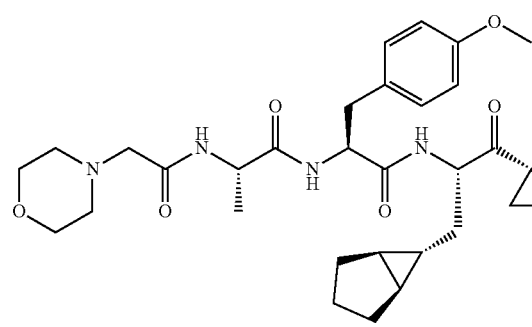
C-1143
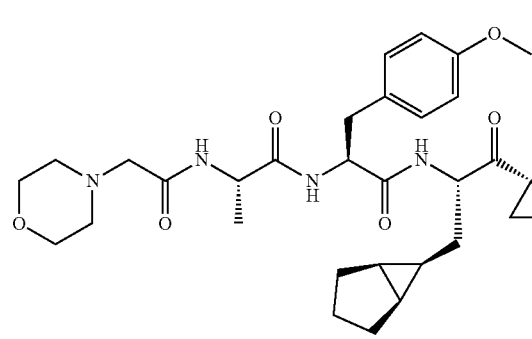
C-1144
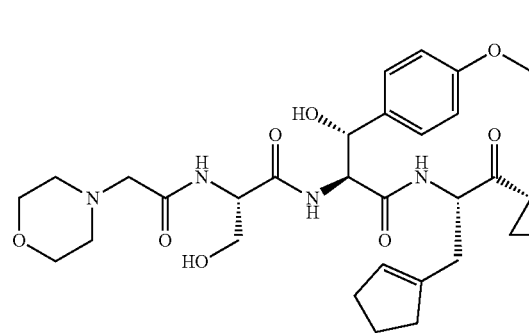
C-1145
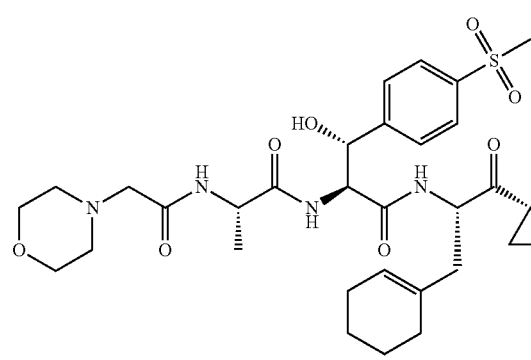
C-1146
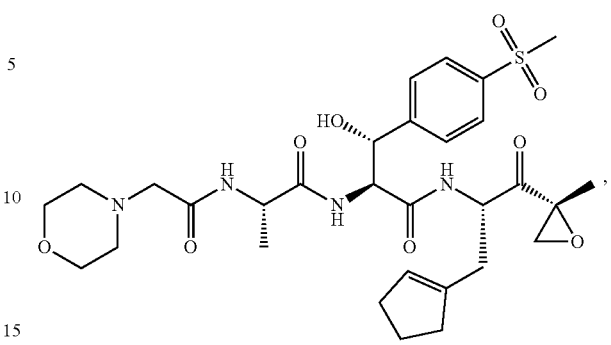
C-1147
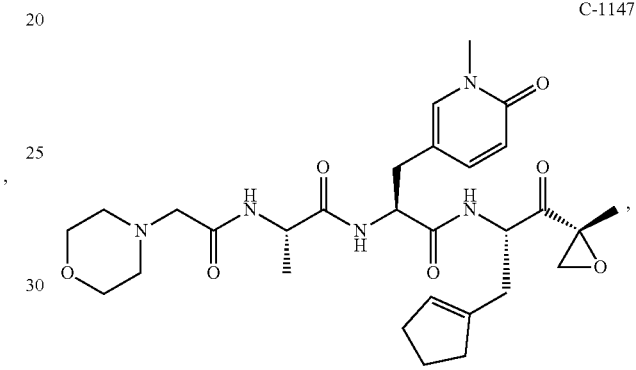
C-1148
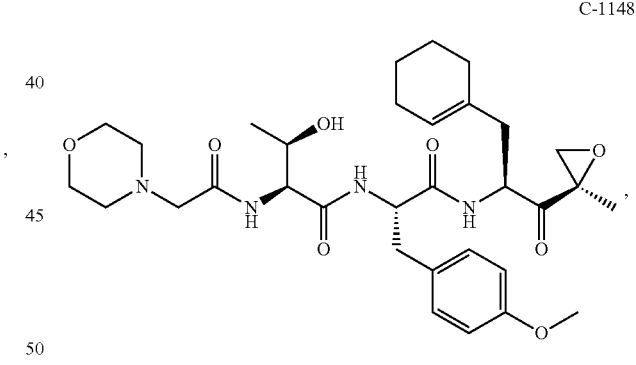
C-1149
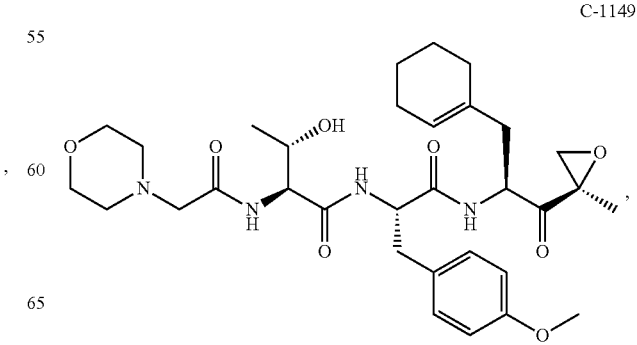

-continued

C-1150

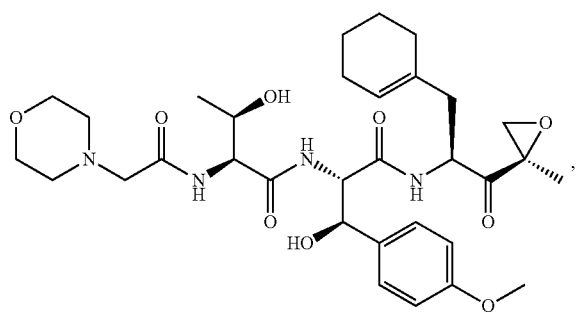

C-1151

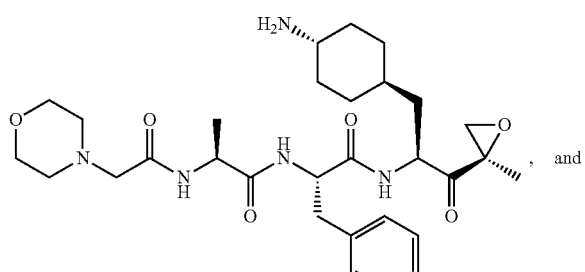

and

C-1152

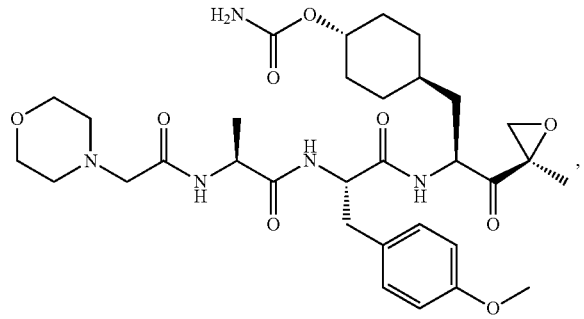

or a pharmaceutically acceptable salt thereof.

In some exemplary embodiments, the disclosure provides a compound selected from the group consisting of: C-1009, C-1018, C-1022, C-1056, C-1057, C-1072, C-1082, C-1083, C-1116, C-1117, C-118, C-1129, C-1135, C-1138, C-1144, and C-1150, or a pharmaceutically acceptable salt thereof.

For example, the disclosure provides a compound selected from the group consisting of: C-1009, C-1018, C-1022, C-1082, C-1083, C-1116, C-1117, C-1118, C-1129, C-1135, C-1144, and C-1150, or a pharmaceutically acceptable salt thereof.

In another aspect, the disclosure provides a tripeptide epoxy ketone compound having a structure selected from:

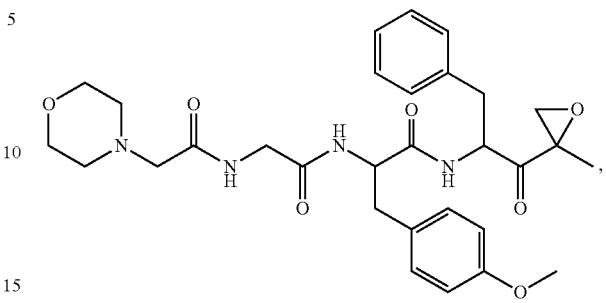

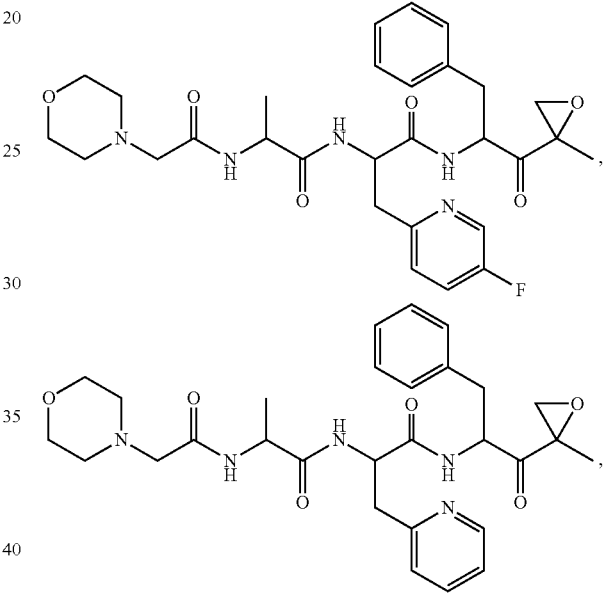

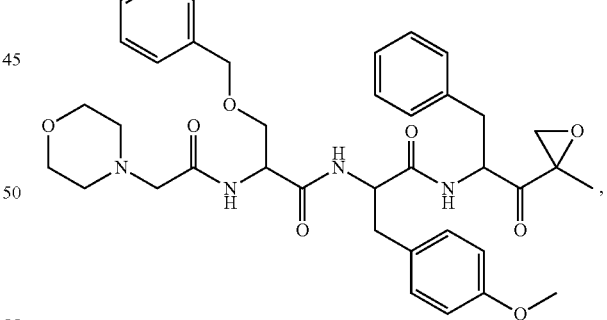

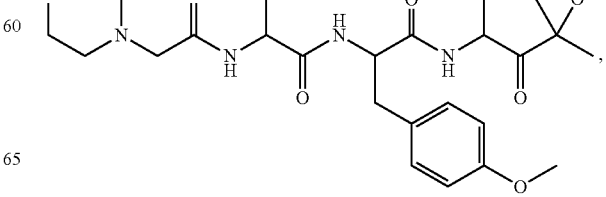

87
-continued
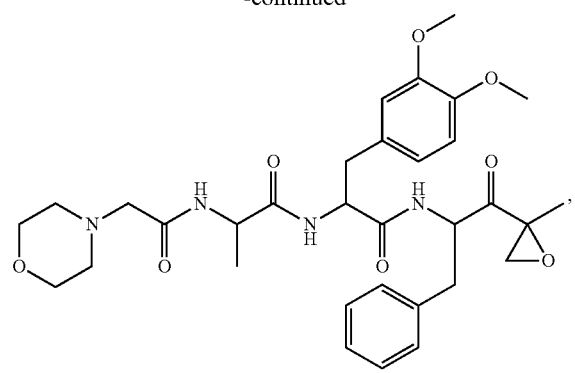
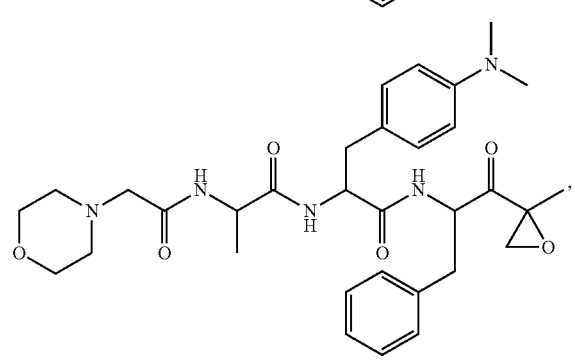
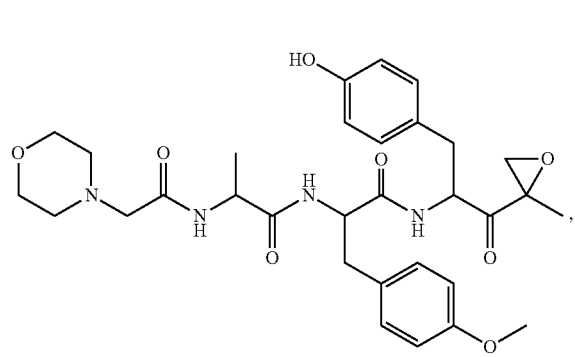
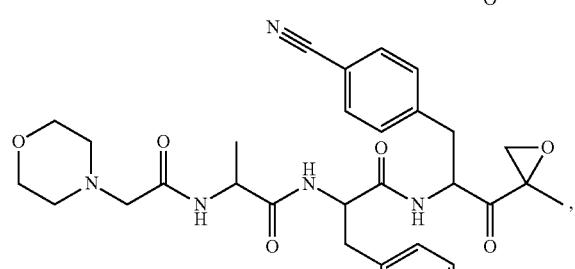
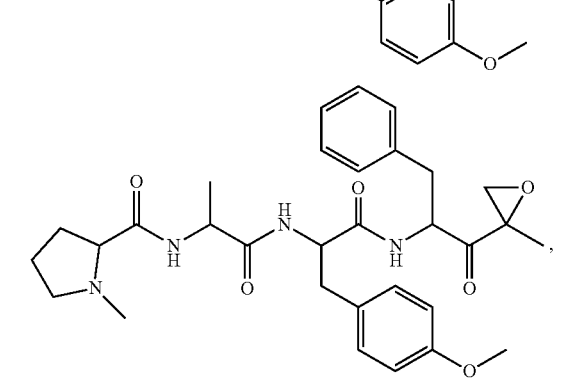
88
-continued
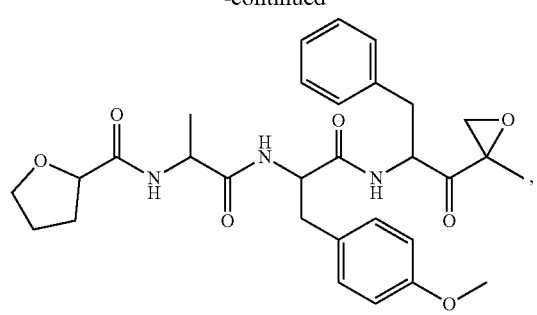
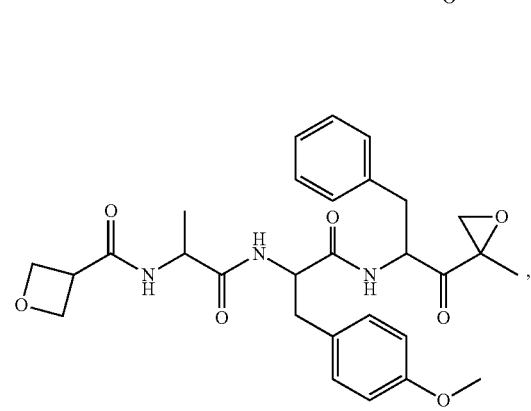
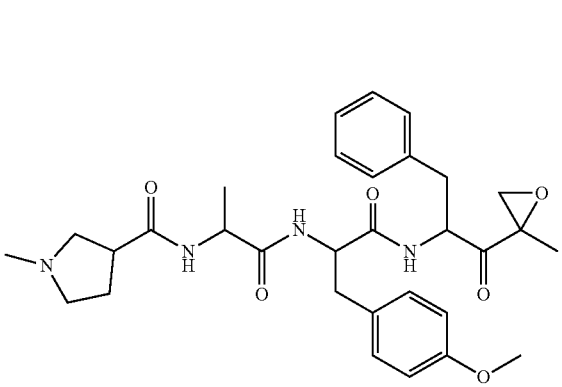
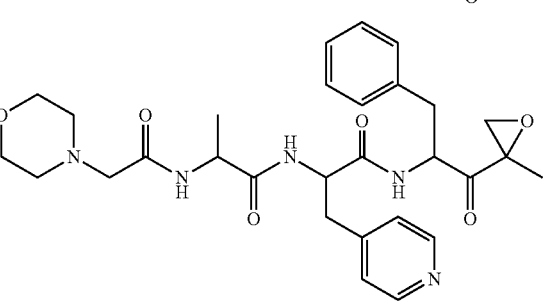
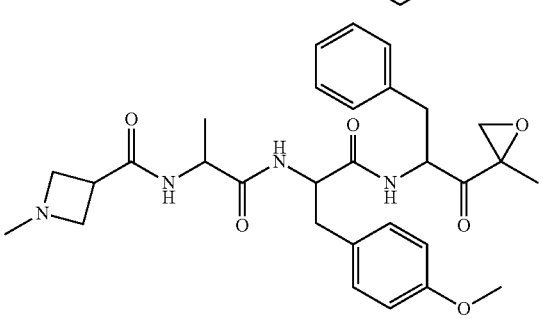

89
-continued
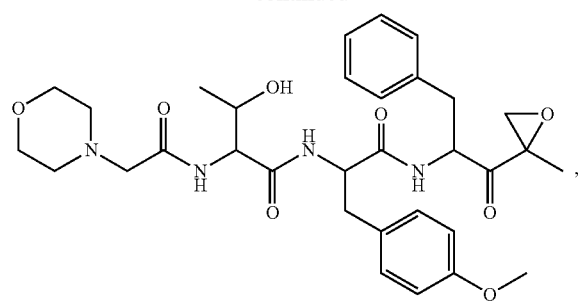
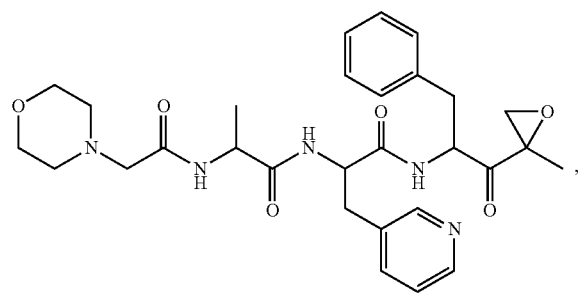
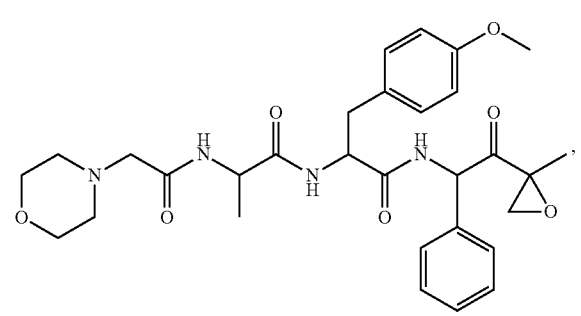
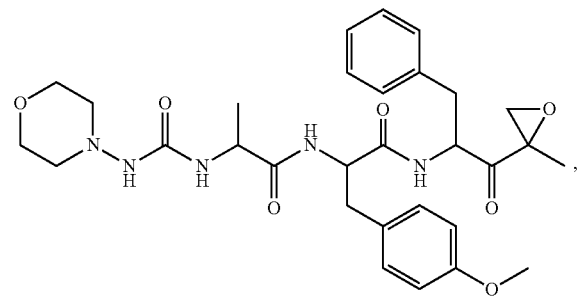
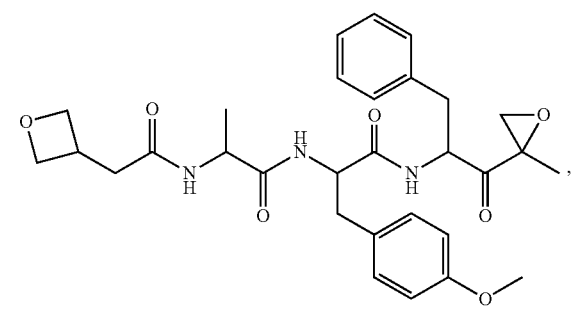
90
-continued
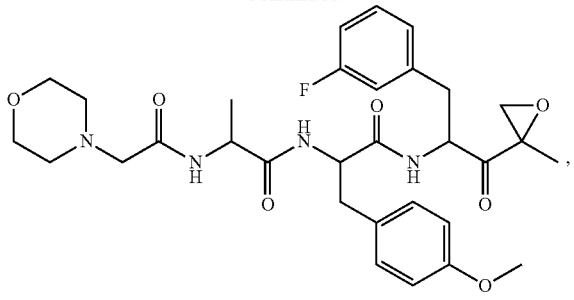
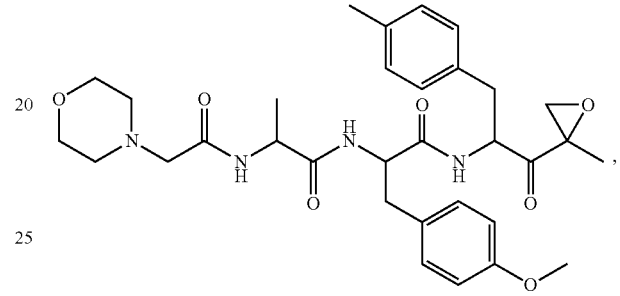
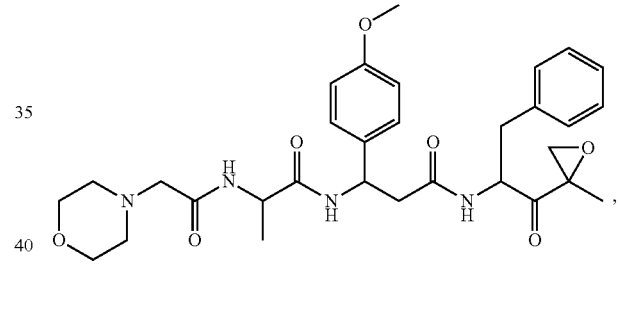
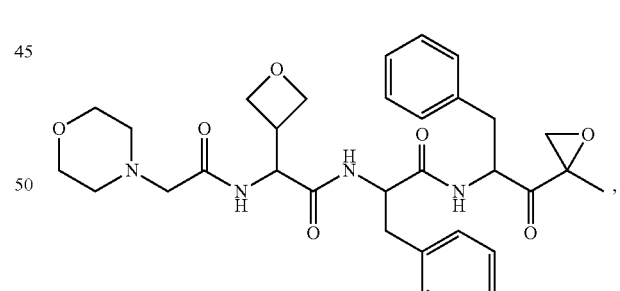
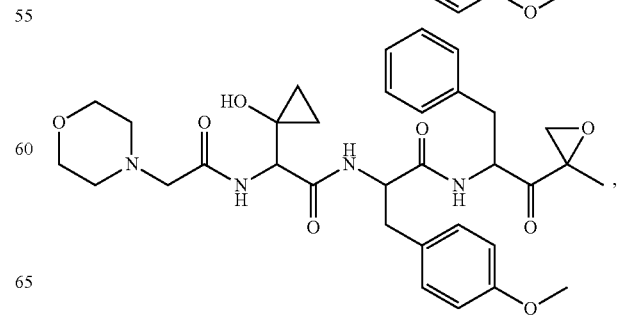

91
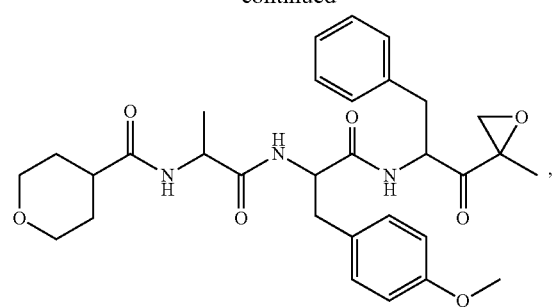
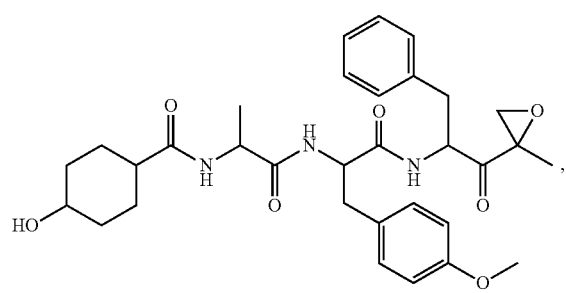
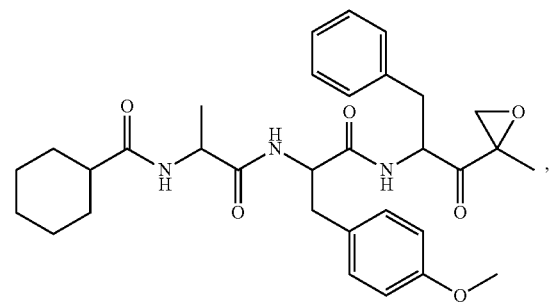
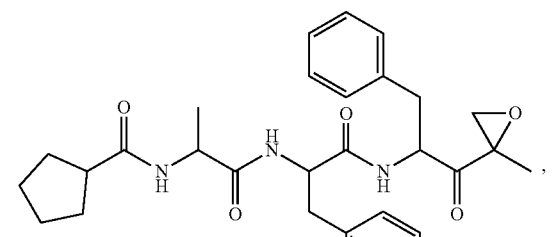
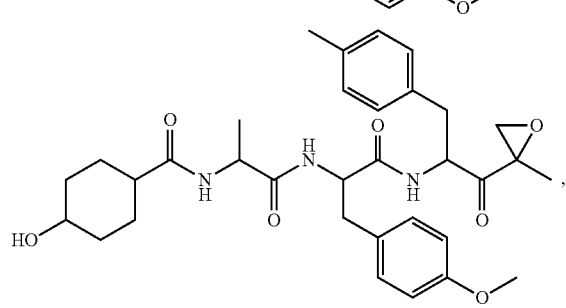
92
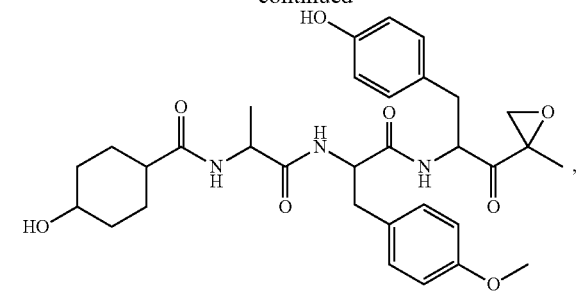
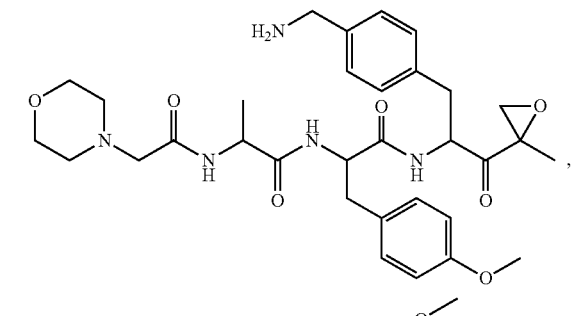
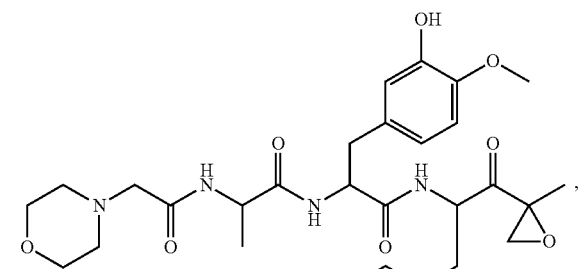
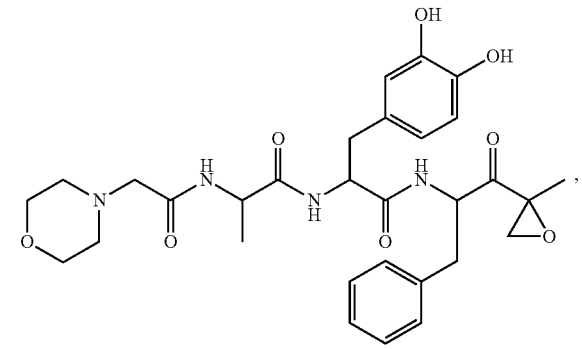

93
-continued
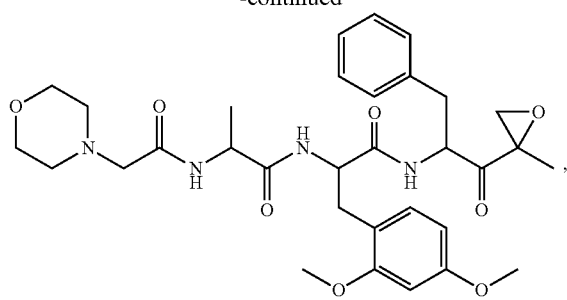
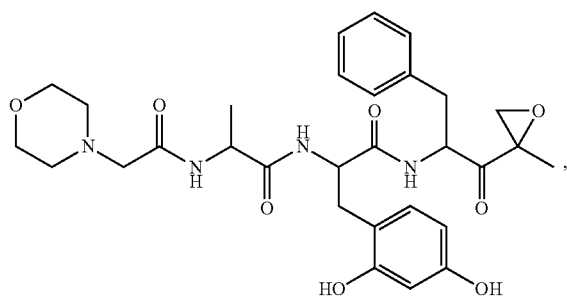
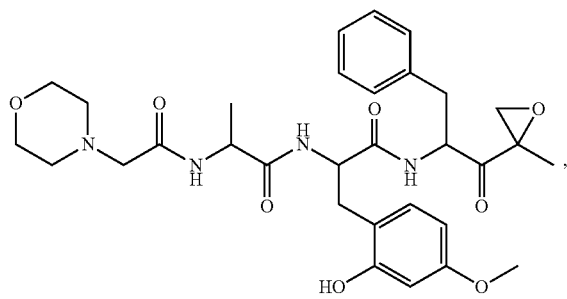
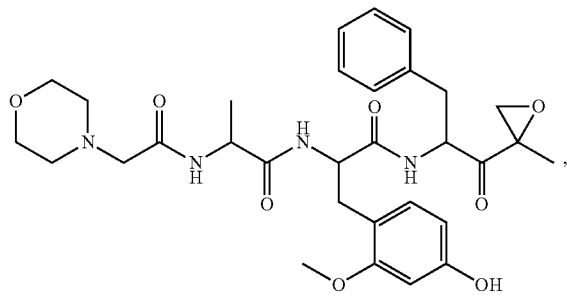
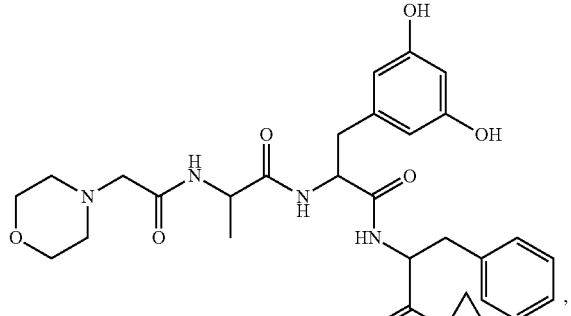
94
-continued
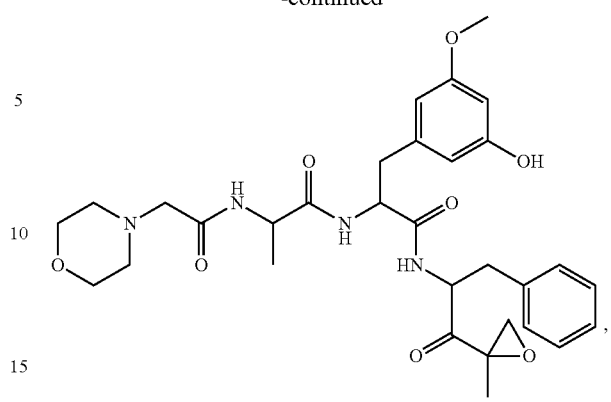
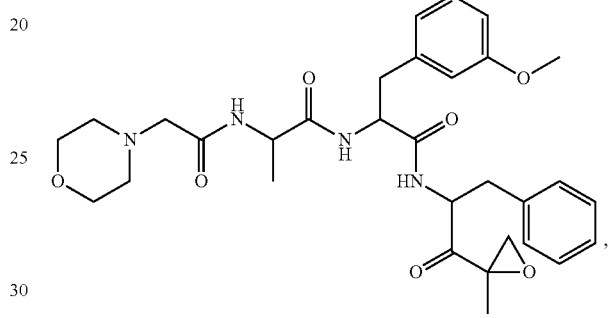
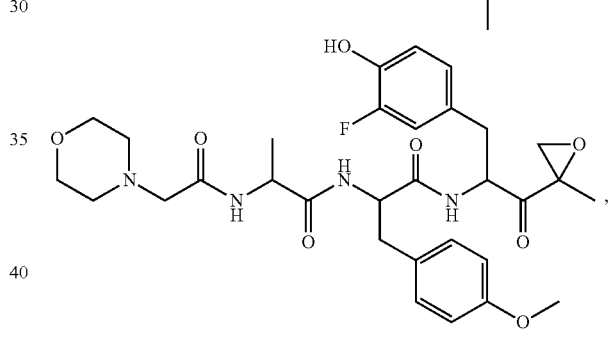
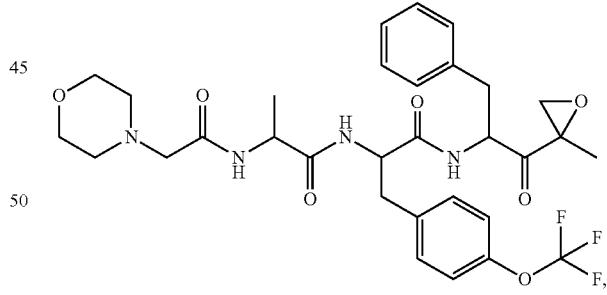
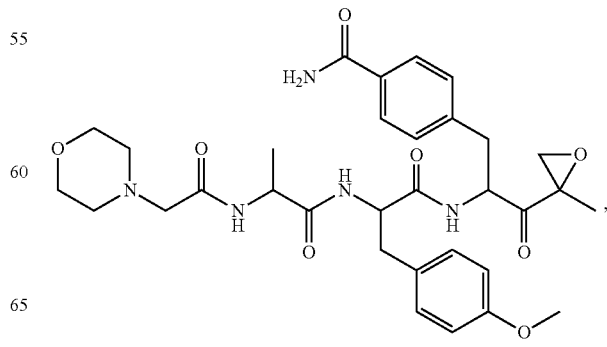

95
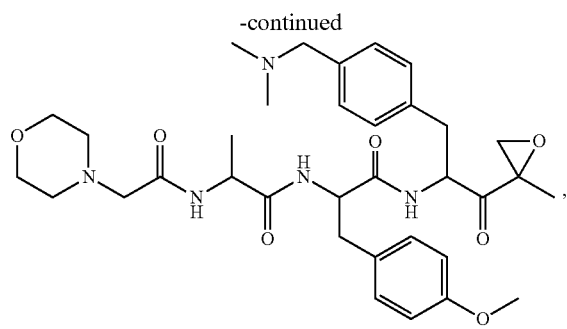
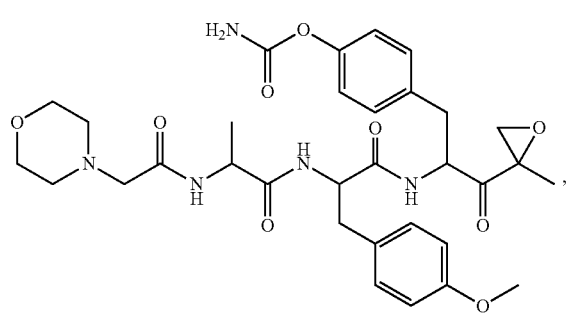
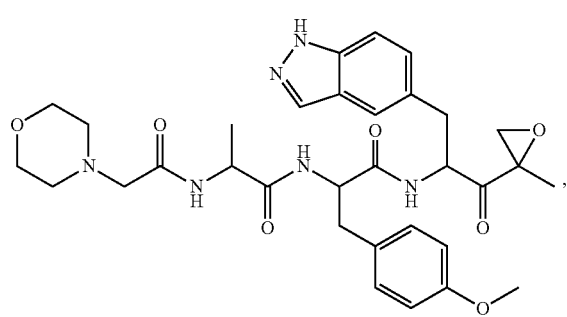
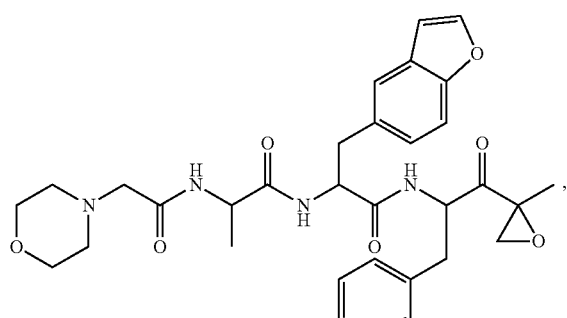
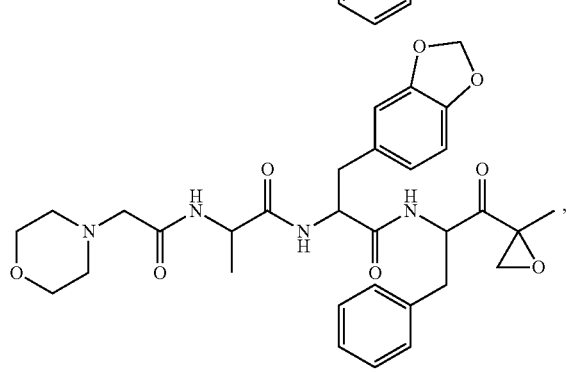
96
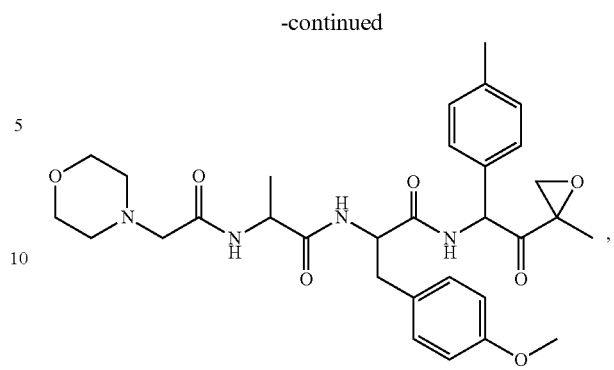
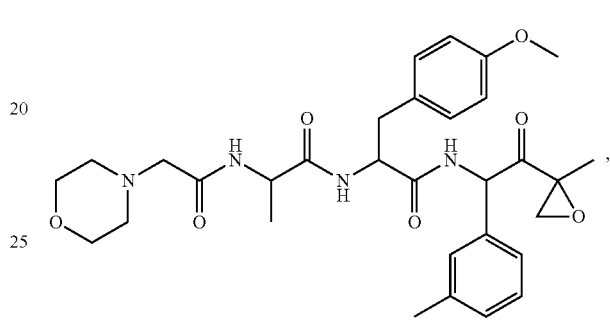
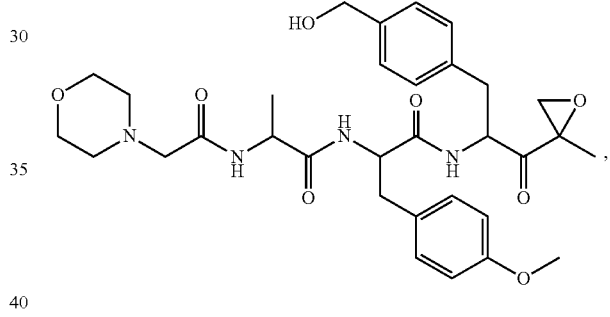
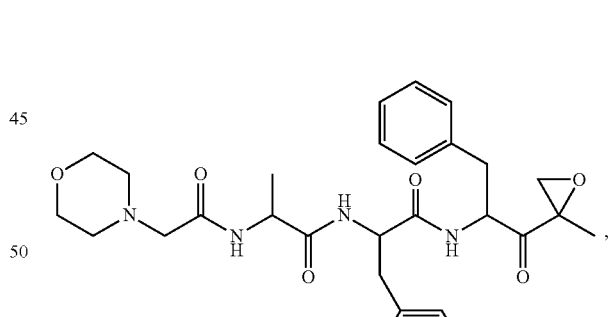
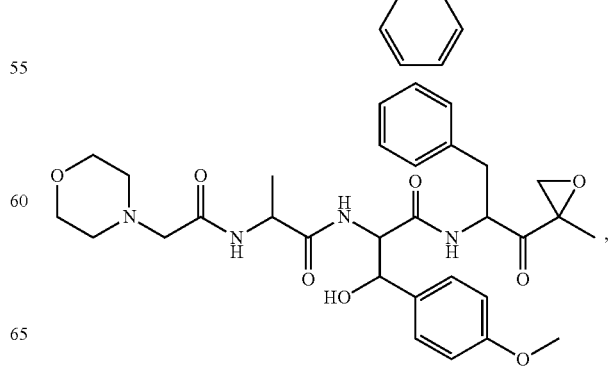

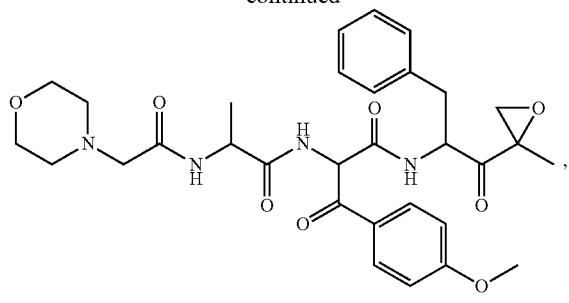
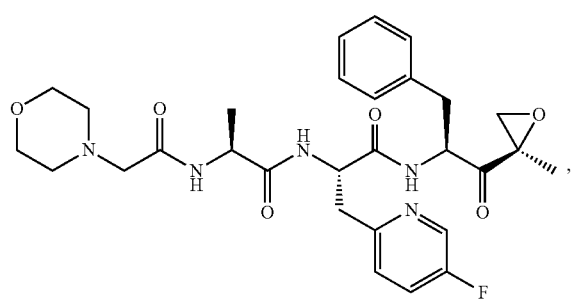
C-1154
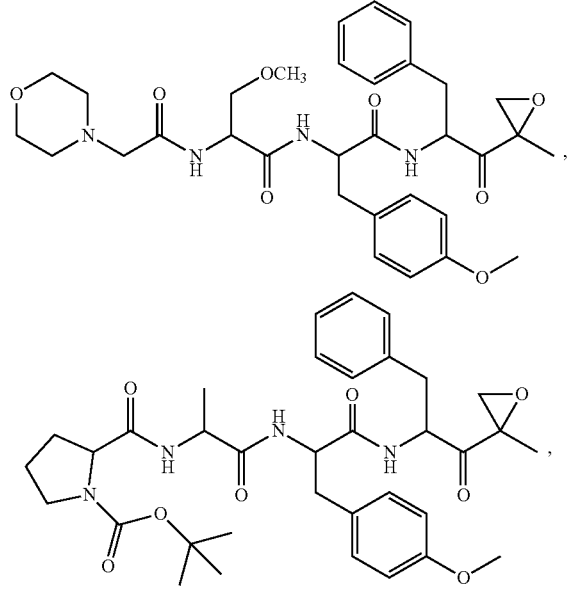
and
or a pharmaceutically acceptable salt thereof.
For example, the disclosure provides a tripeptide epoxy ketone compound selected from the group consisting of:
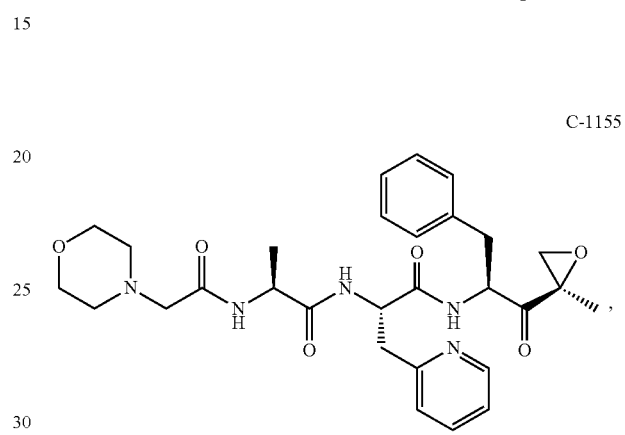
C-1155
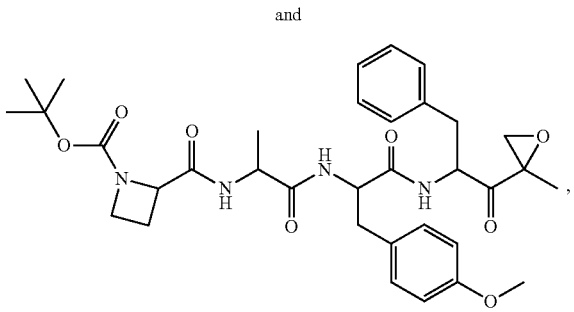
C-1153
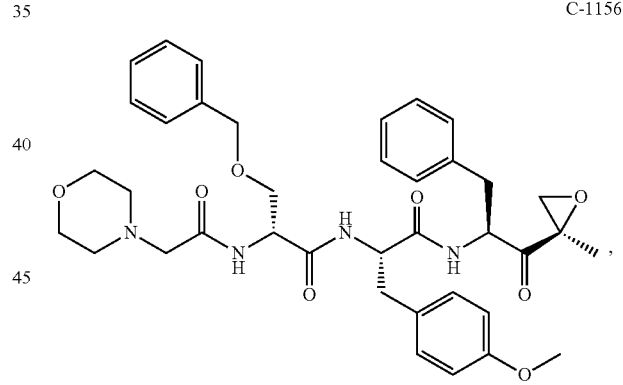
C-1156
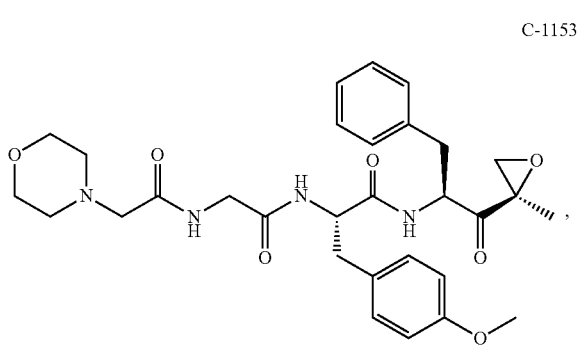
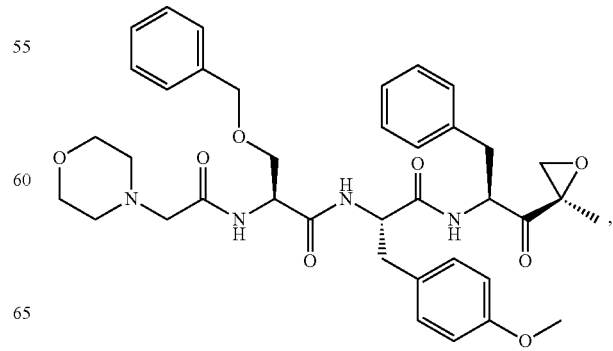
C-1157

C-1158
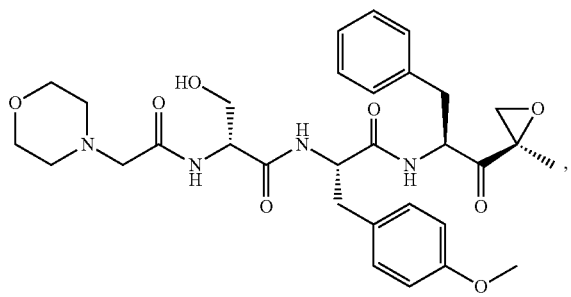
C-1159
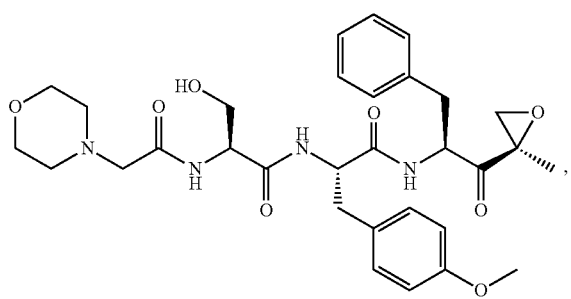
C-1160
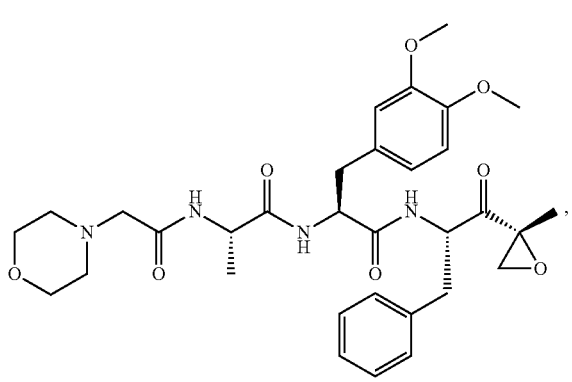
C-1161
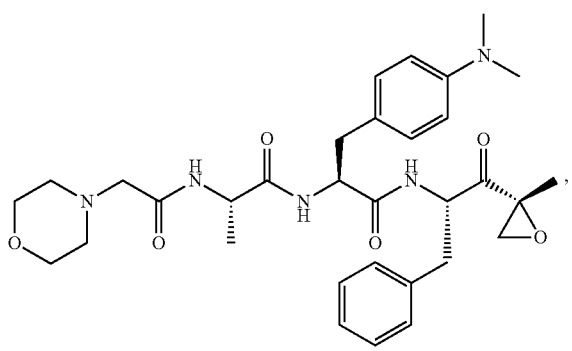
C-1162
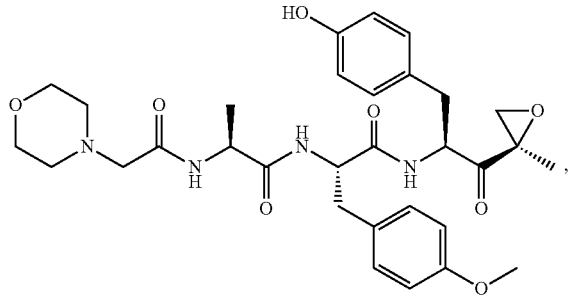
C-1163
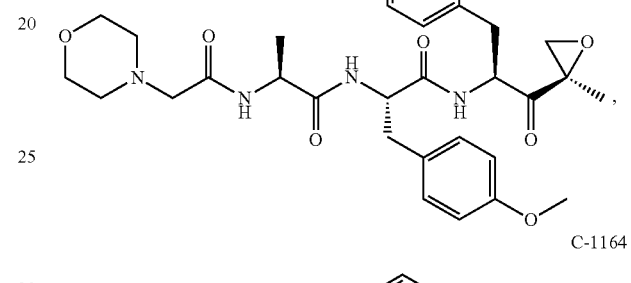
C-1164
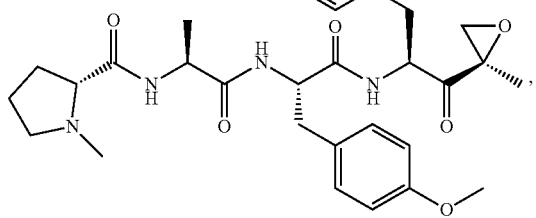
C-1165
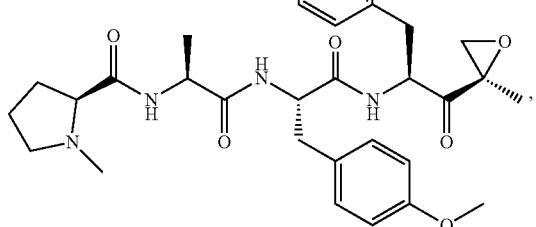
C-1166
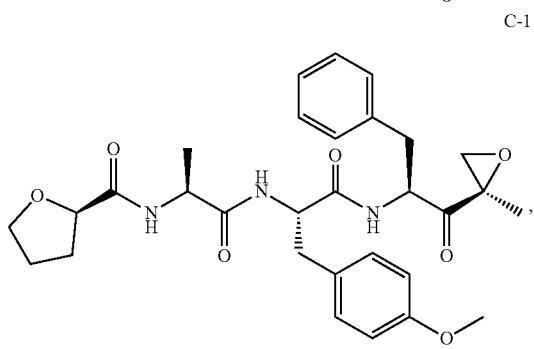

C-1167
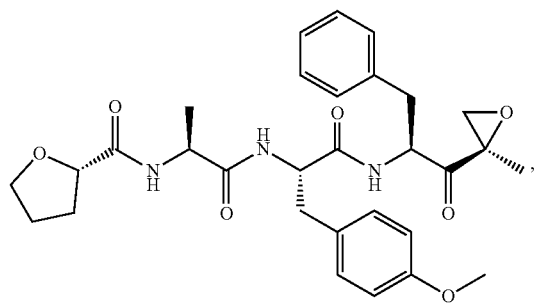
C-1168
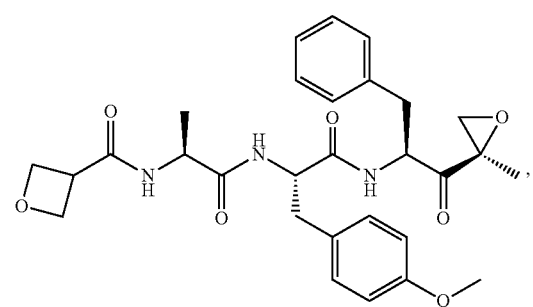
C-1169
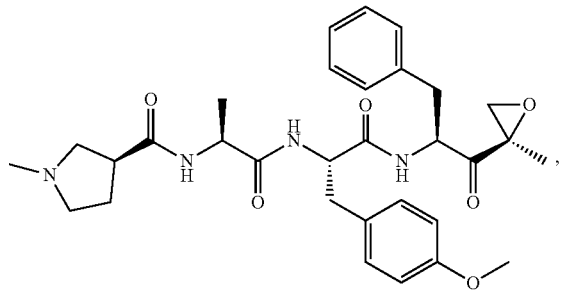
C-1170
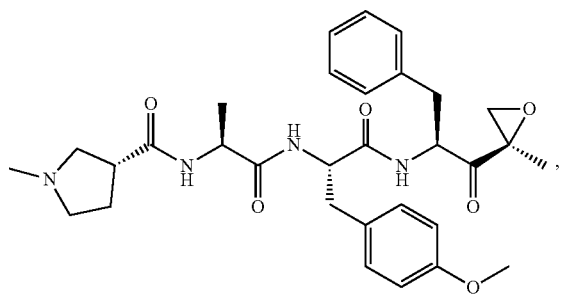
C-1171
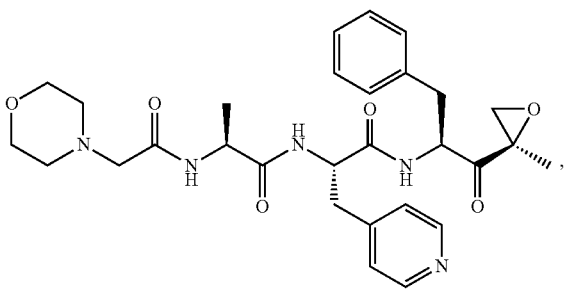
C-1172
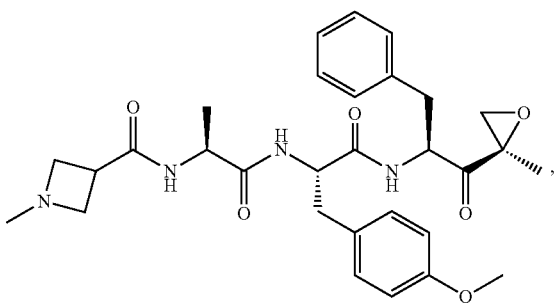
C-1173
C-1174
C-1175
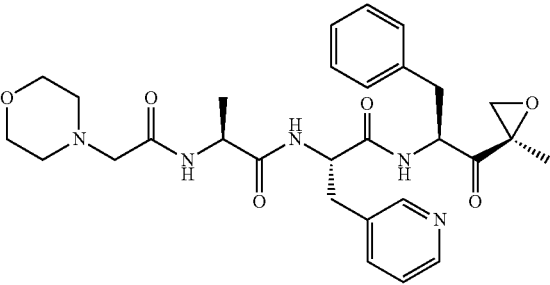
C-1176

C-1177
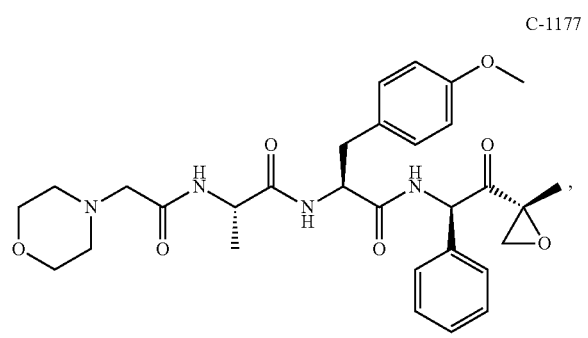
C-1178
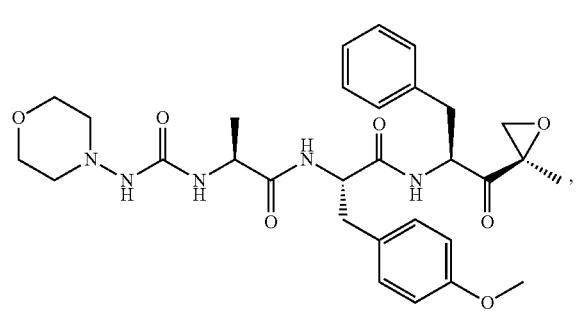
C-1179
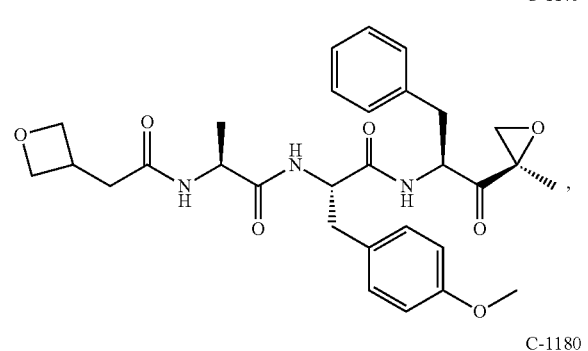
C-1180
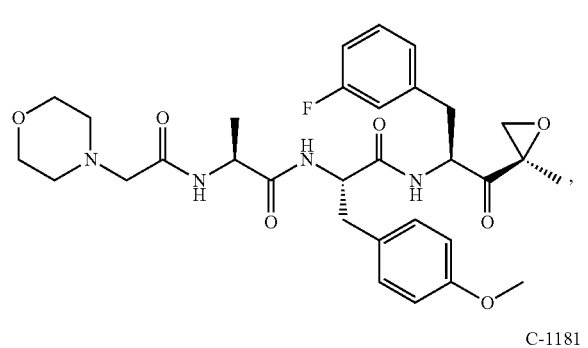
C-1181
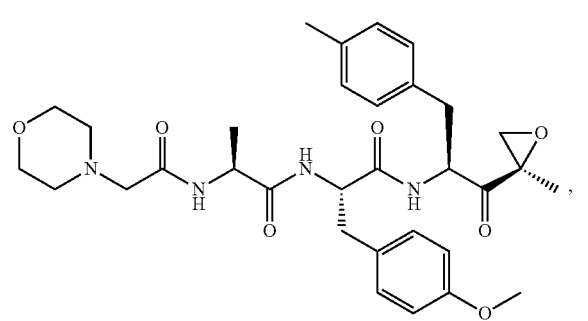
C-1182
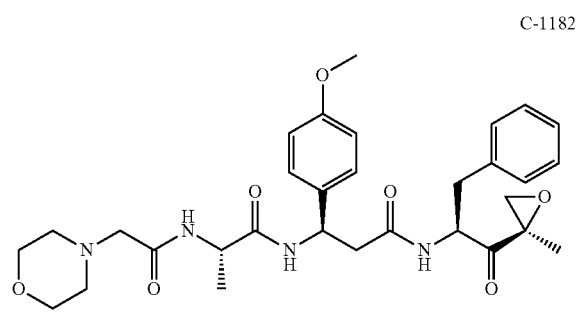
C-1183
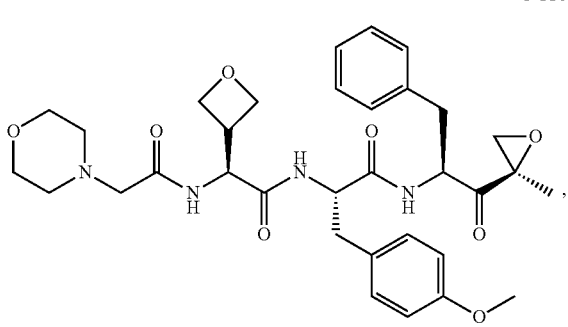
C-1184
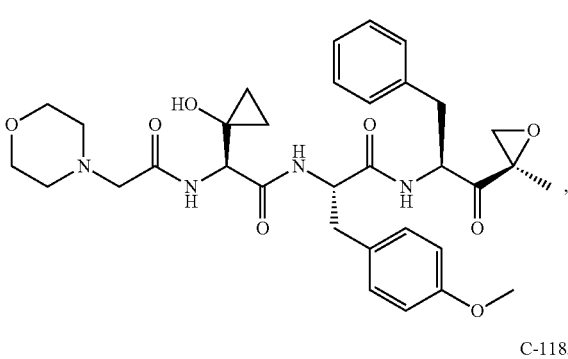
C-1185
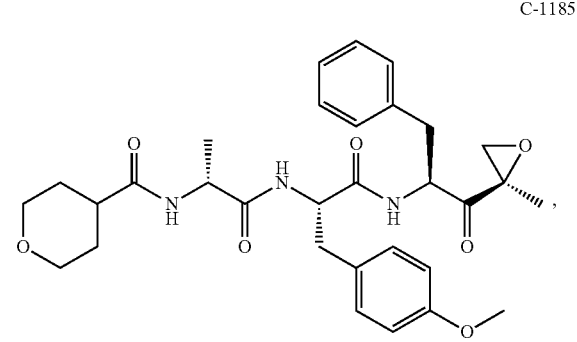
C-1186
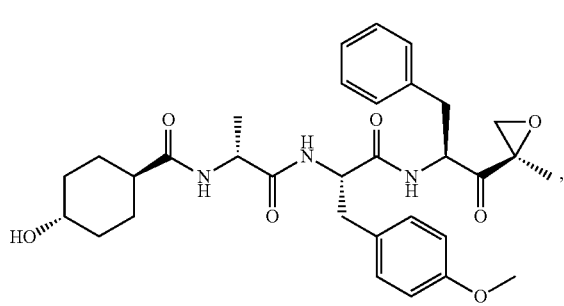

C-1187
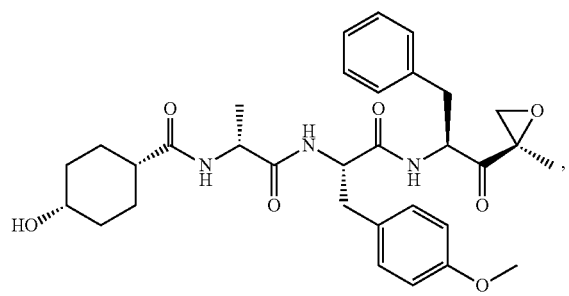
C-1188
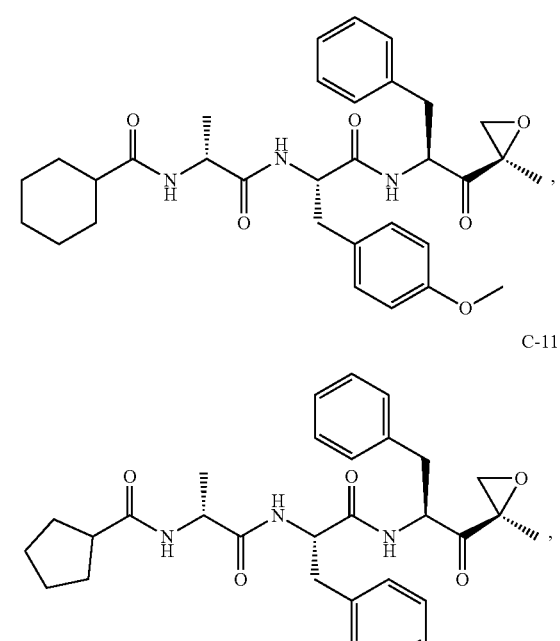
C-1189
C-1190
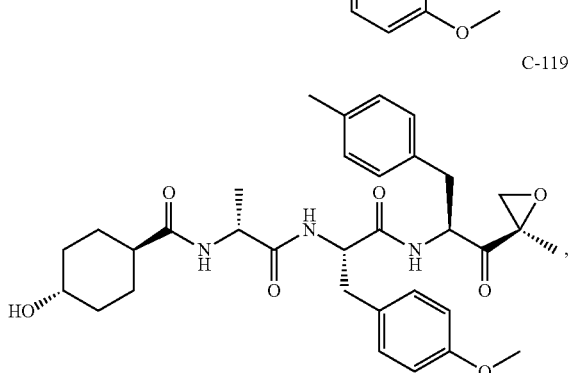
C-1191
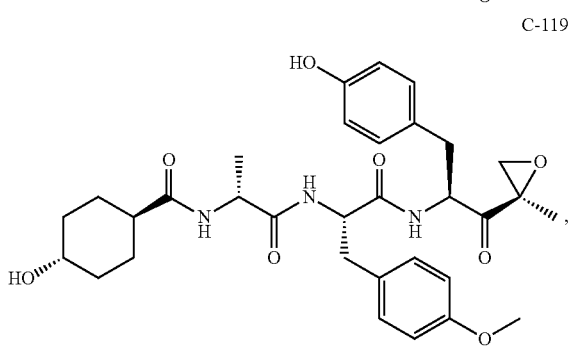
C-1192
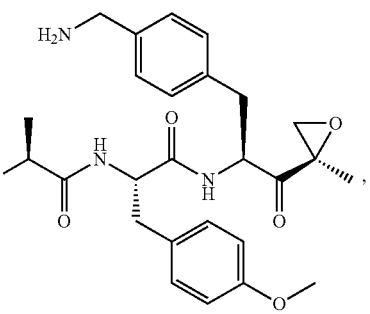
C-1193
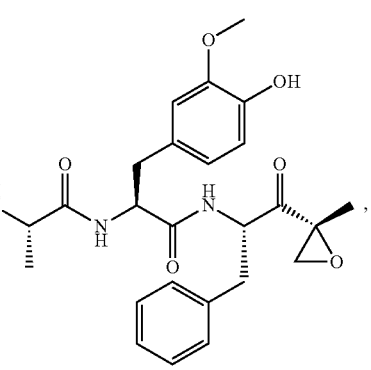
C-1194
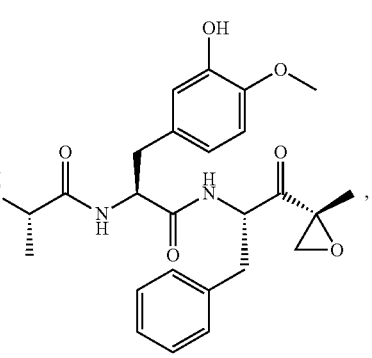
C-1195
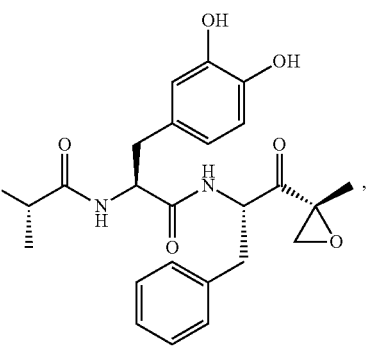

-continued
C-1196
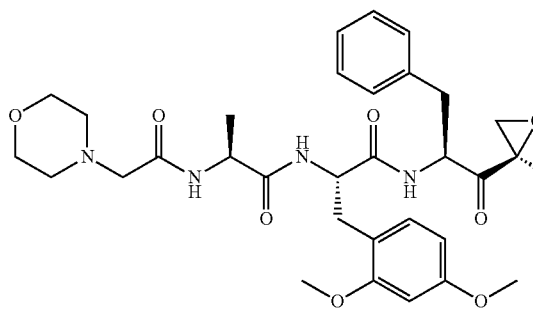
C-1197
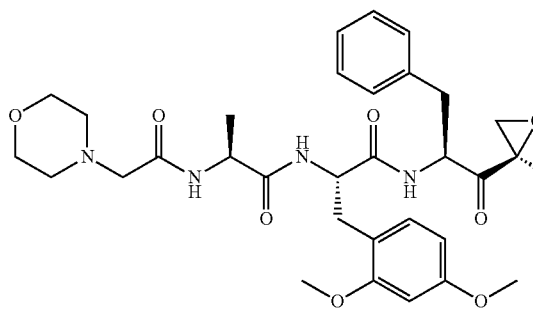
C-1198
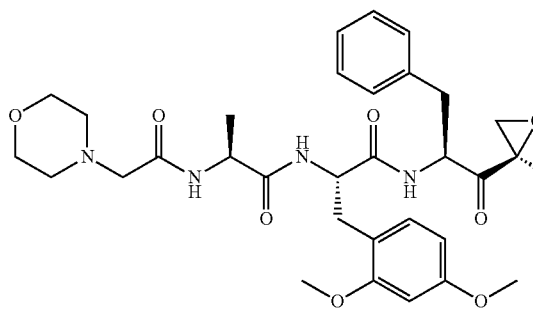
C-1199
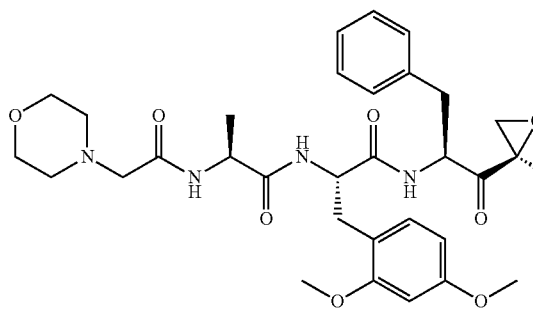
-continued
C-1200
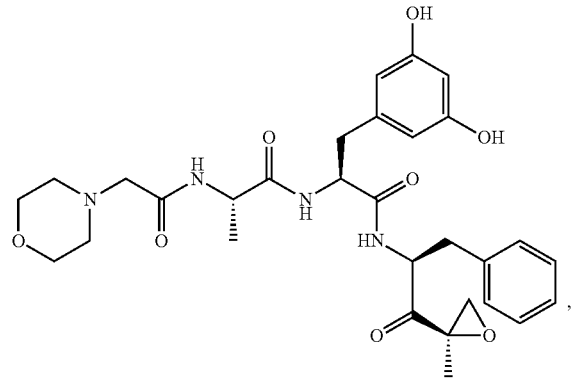
C-1201
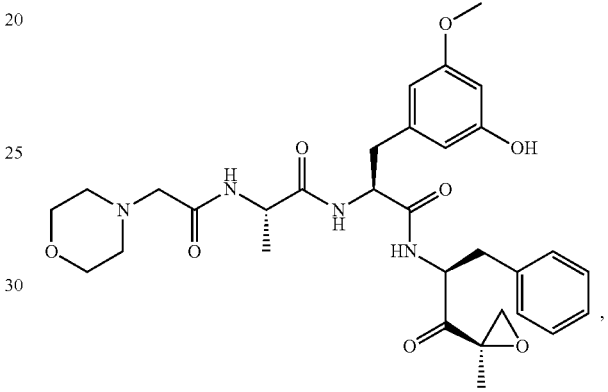
C-1202
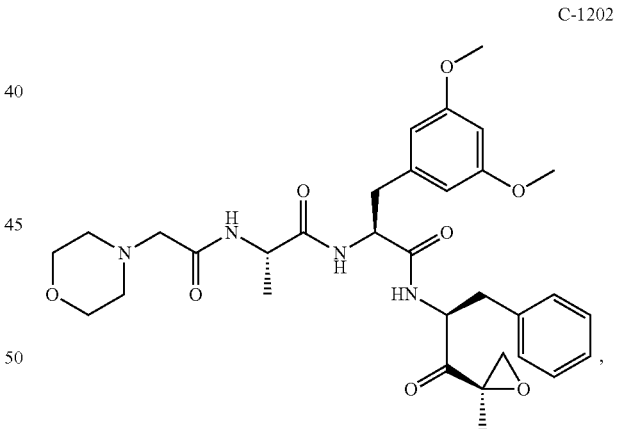
C-1203
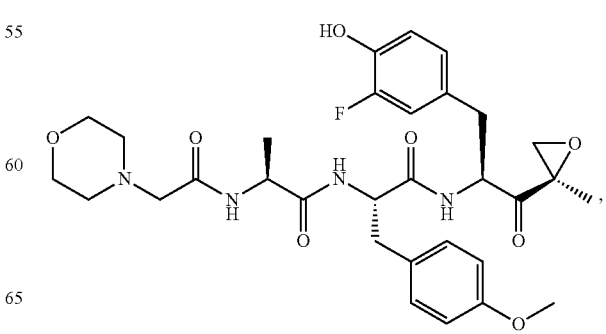

C-1204
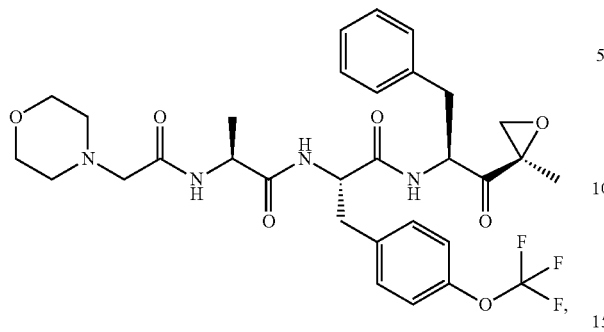
C-1208
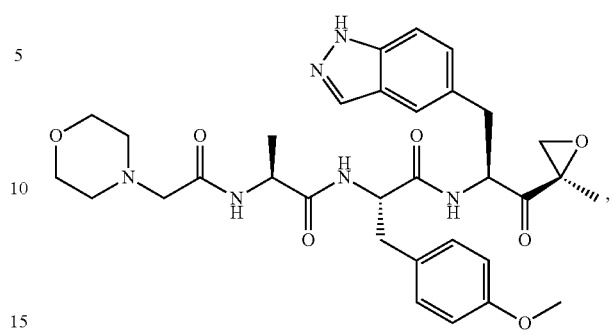
C-1205
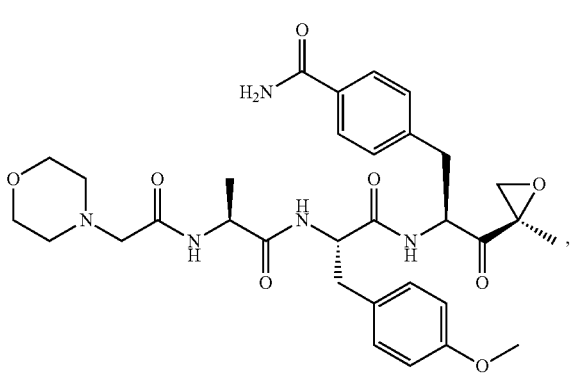
C-1209
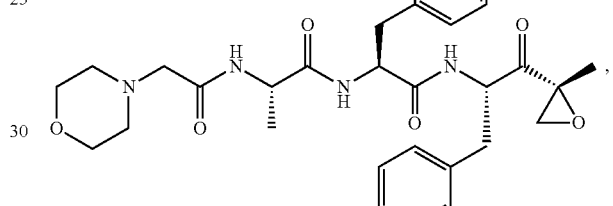
C-1206
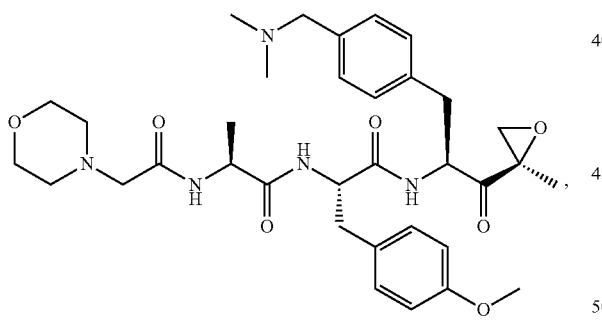
C-1210
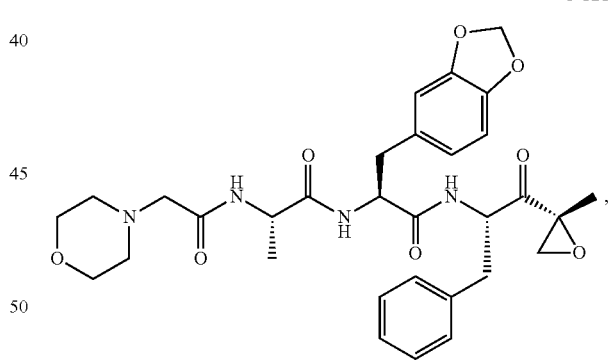
C-1207
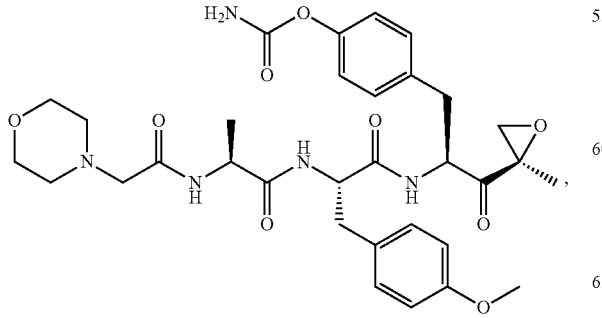
C-1211
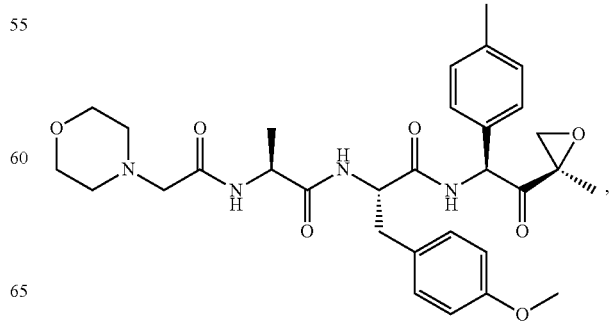

C-1212
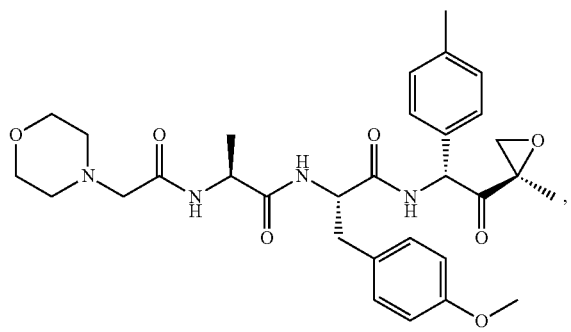
C-1216
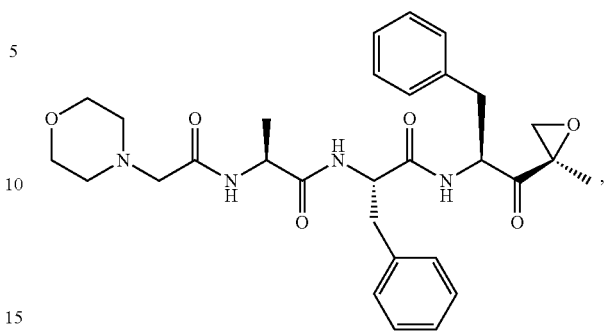
C-1213
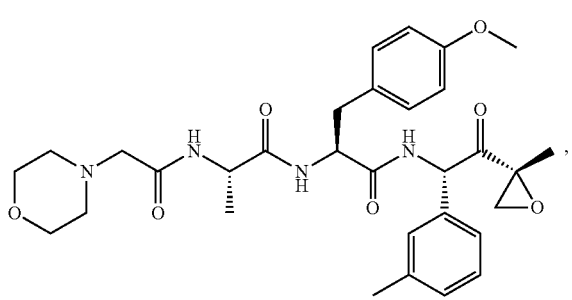
C-1217
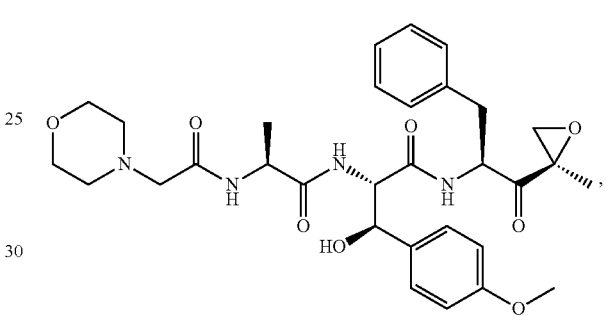
C-1214
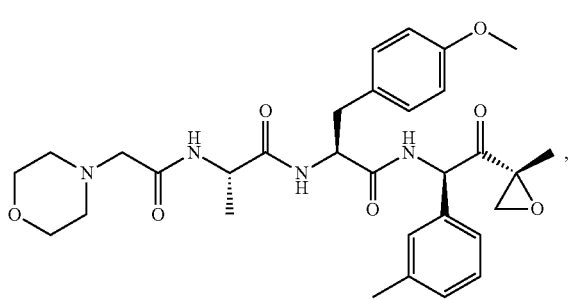
C-1218
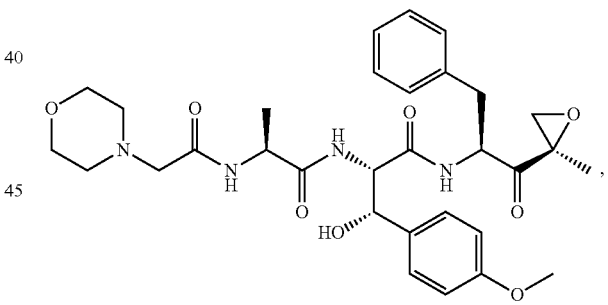
C-1215
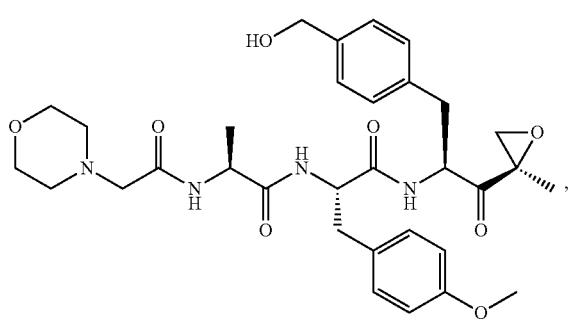
C-1219
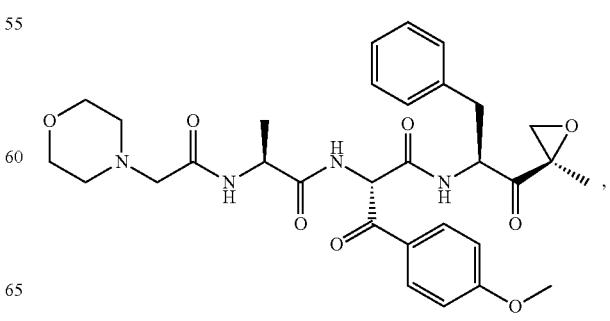

-continued
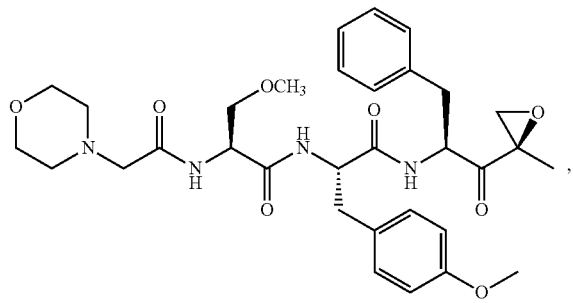
C-1220
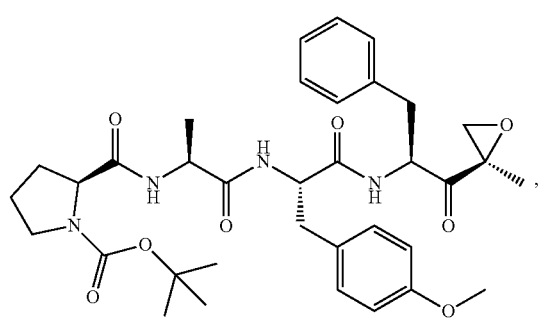
C-1221
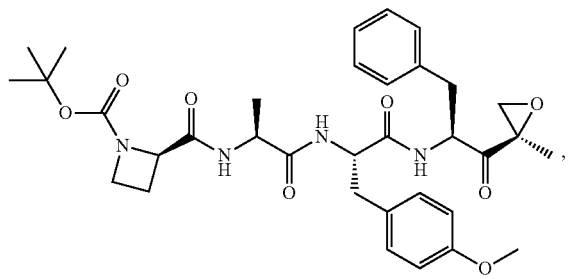
C-1222
and
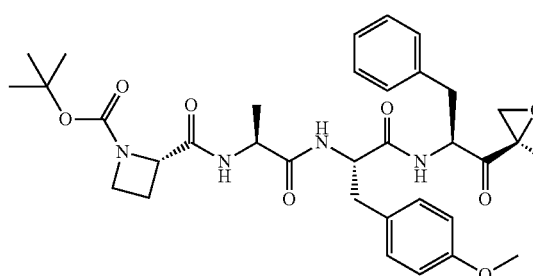
C-1211
or a pharmaceutically acceptable salt thereof.
In yet another aspect, the disclosure provides a tripeptide epoxy ketone compound selected from:
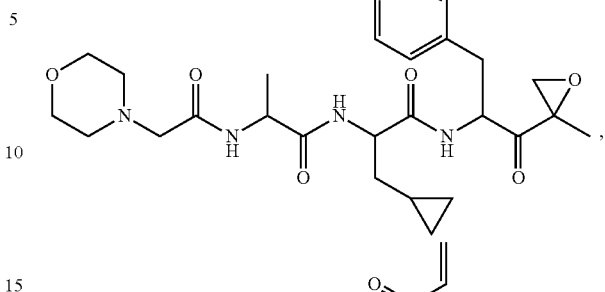
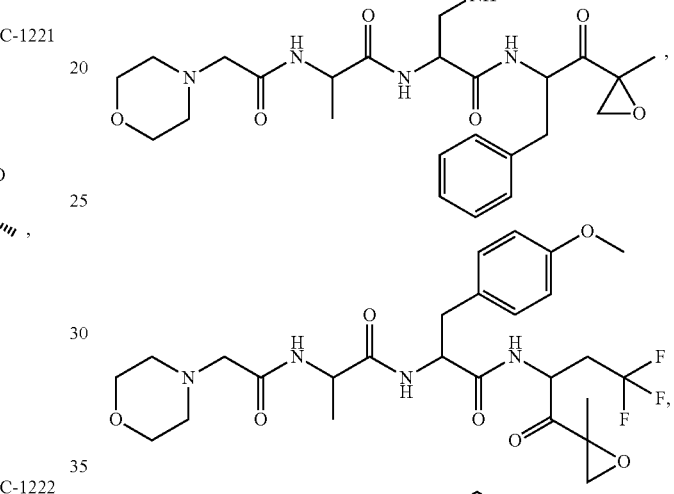
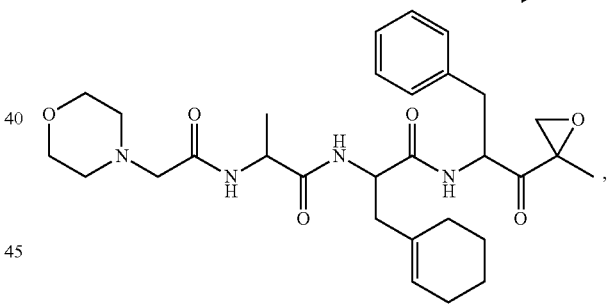
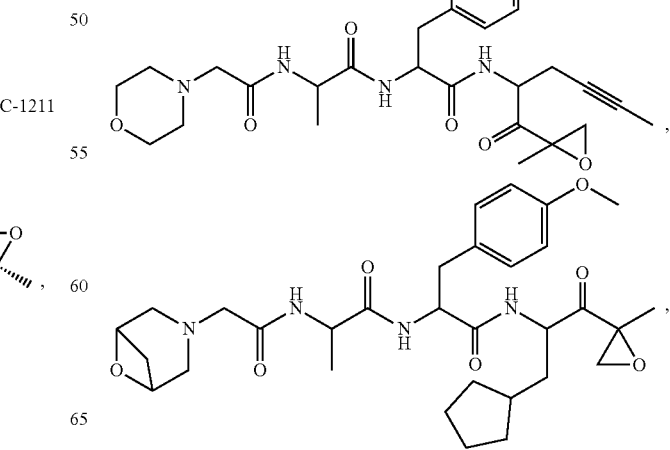

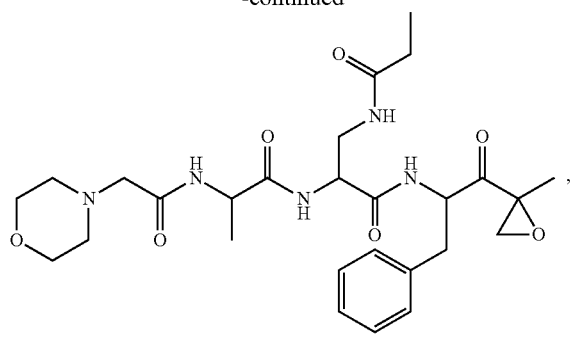
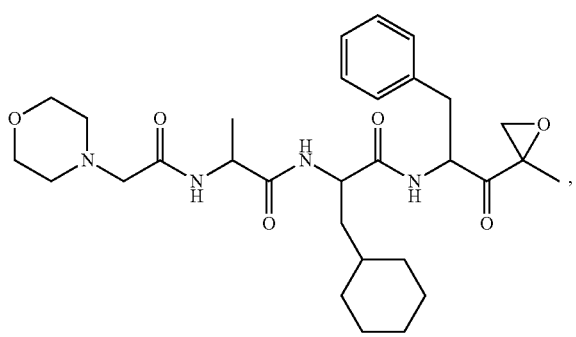
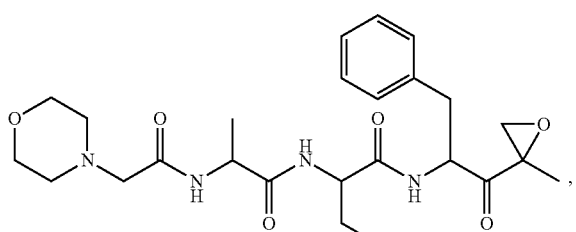
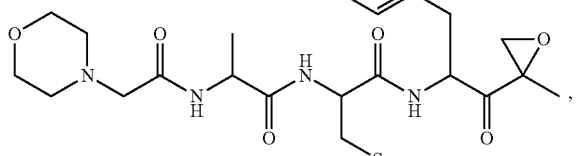
and
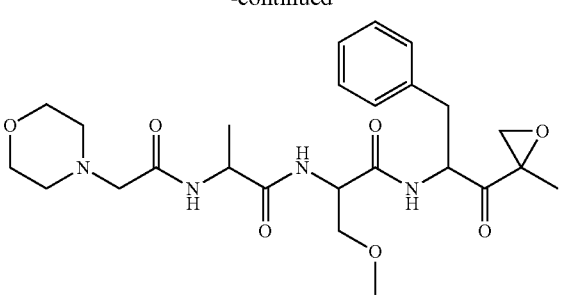
or a pharmaceutically acceptable salt thereof.
For example, the disclosure provides a tripeptide epoxy ketone compound selected from:
C-1224
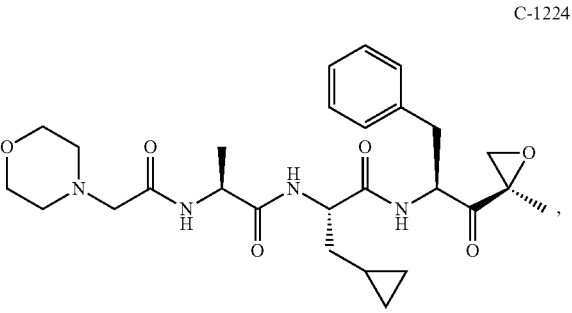
C-1225
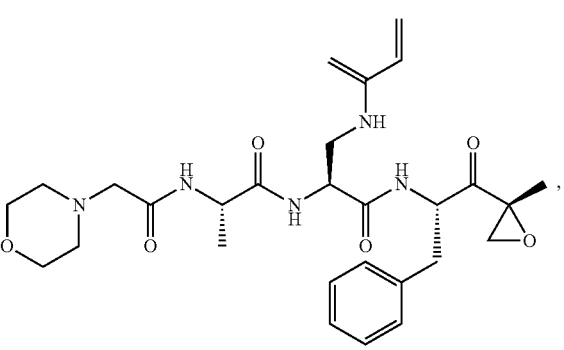
C-1226
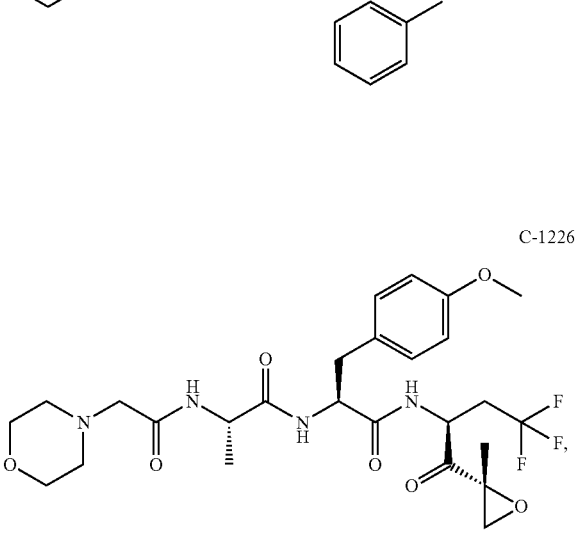

C-1227
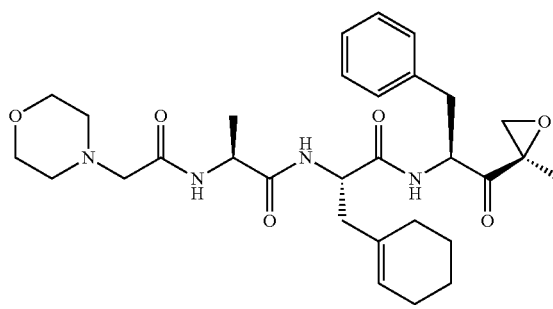
C-1228
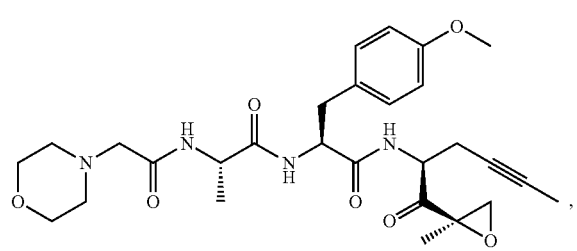
C-1229
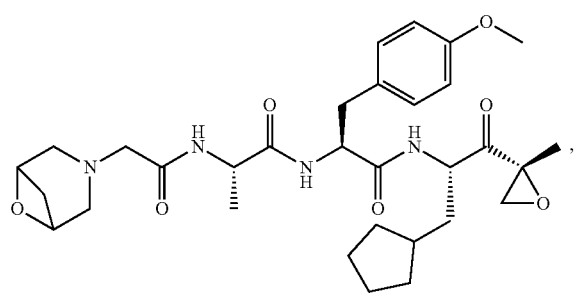
C-1230
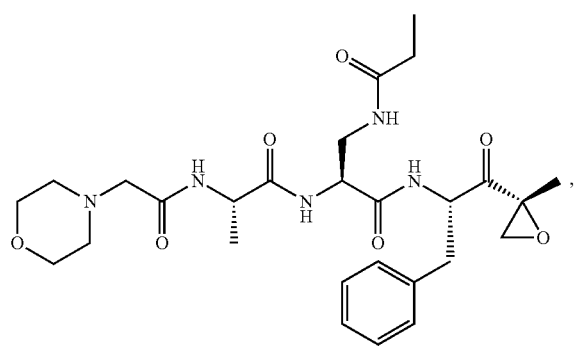
C-1231
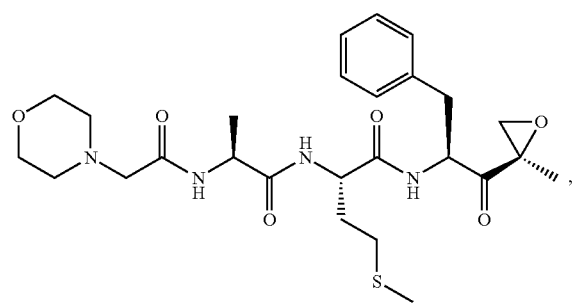
C-1232
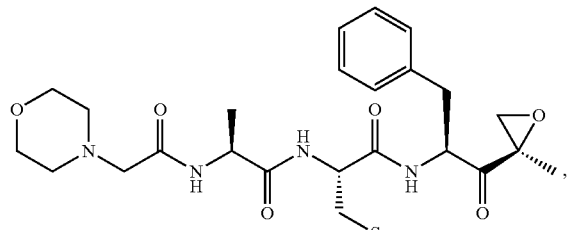
C-1233
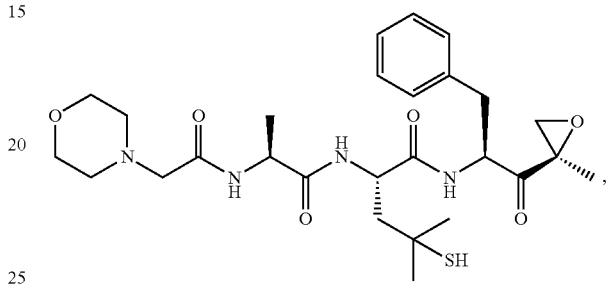
C-1234
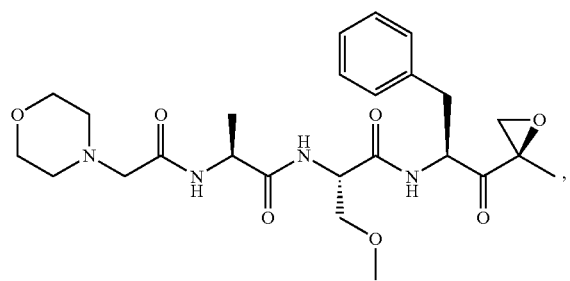
and
C-1235
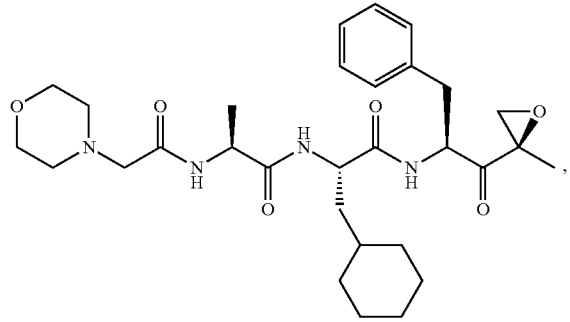
or a pharmaceutically acceptable salt thereof.
In still another aspect, provided herein is a compound having a structure of Formula (I), or a pharmaceutically acceptable salt thereof:
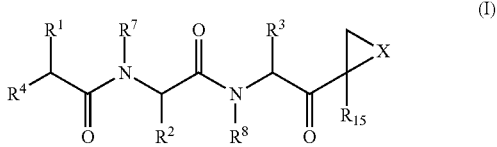
(I)

wherein:

B is absent;

L is C=O;

each M is independently absent or is $C_{1-12}$alkyl;

Q is absent;

X is O;

$R^1$ is selected from hydrogen, —$C_{1-6}$alkyl-B, $C_{1-6}$hydroxyalkyl, and $C_{1-6}$alkoxyalky;

$R^2$ is selected from

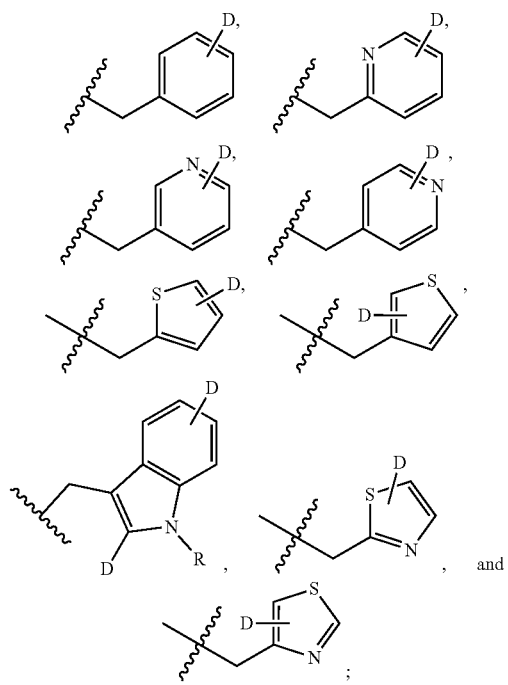

wherein D is selected from hydrogen, methoxy, t-butoxy, hydroxy, halogen, cyano, trifluoromethyl, and $C_{1-4}$alkyl, with the proviso that when $R^2$ is benzyl, D is other than hydrogen;

$R^3$ is selected from carbocyclylM- and carbocyclyl;

$R^4$ is $N(R^5)$L-Q-$R^6$;

$R^5$ is hydrogen;

$R^6$ is selected from heterocyclylM- and carbocyclylM-;

$R^7$ and $R^8$ are hydrogen; and $R^{15}$ is selected from hydrogen, $C_{1-6}$alkyl, and $C_{1-6}$hydroxyalkyl.

Therefore, a compound of Formula (I) can be represented as:

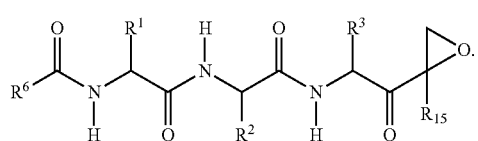

(IA)

In some embodiments, $R^{15}$ is selected from hydrogen, methyl, ethyl, hydroxymethyl, and 2-hydroxyethyl.

In some embodiments, $R^2$ is

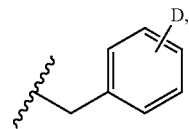

and D is selected from methoxy, hydroxy, trifluromethyl, and $C_{1-4}$alkyl.

In some embodiments, $R^6$ is heterocyclylM-, and in other embodiments, $R^6$ is carbocyclylM-.

In some embodiments,

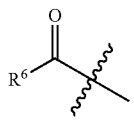

is selected from the group consisting of:

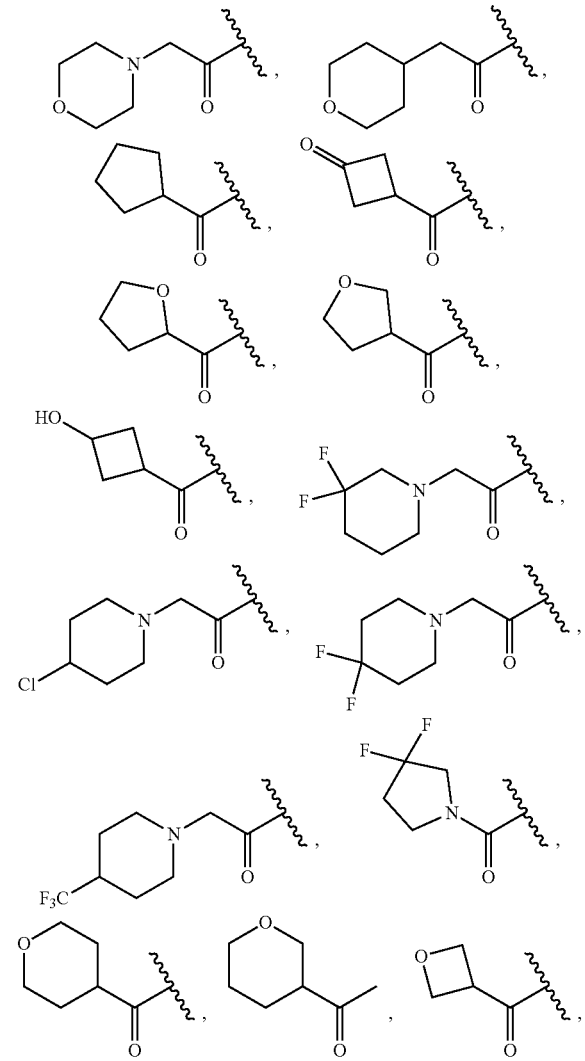

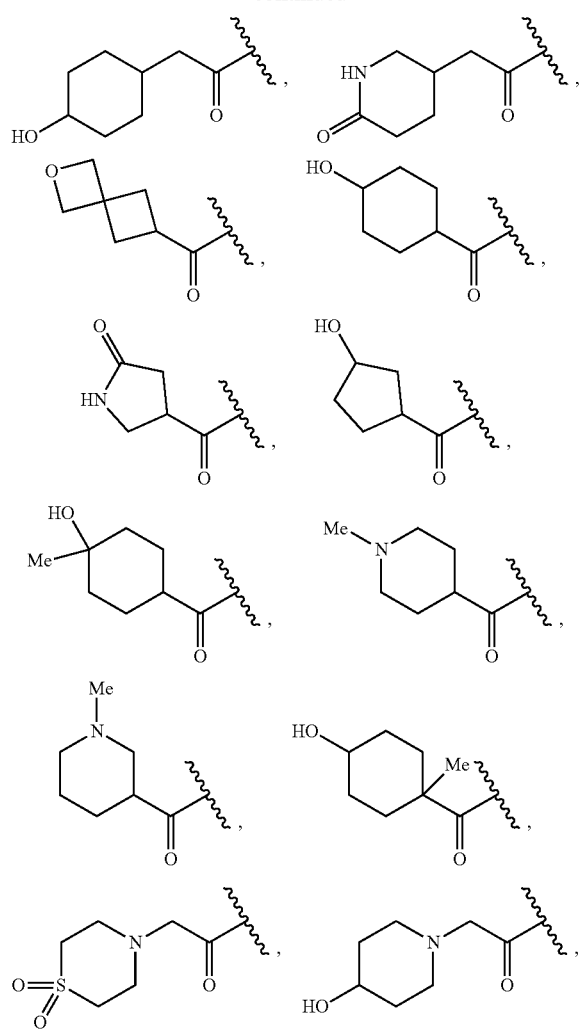
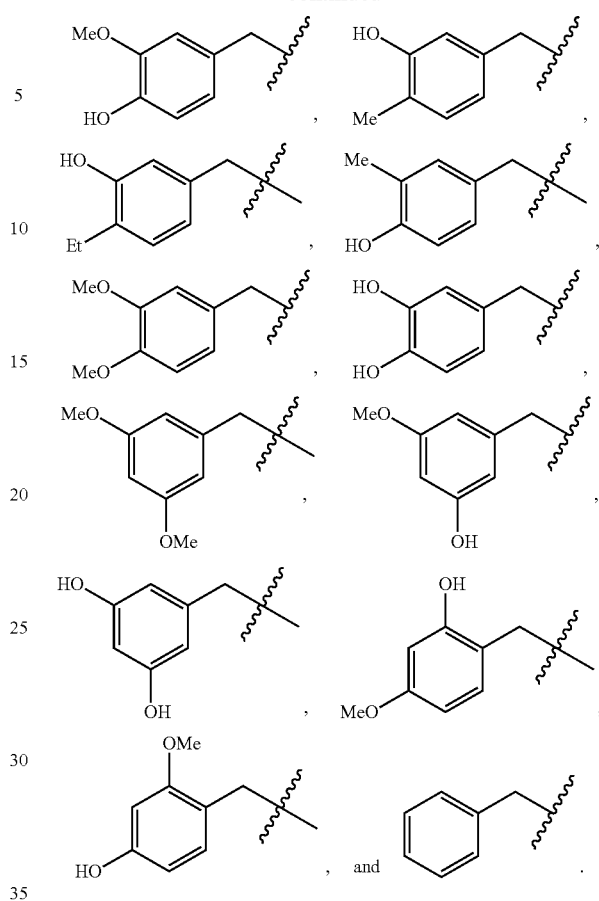
In some embodiments, $R^2$ is selected from the group consisting of:
In some embodiments, $R^3$ is carbocyclyl-. In various embodiments, $R^3$ is carbocyclylM- and M is $C_{1-12}$alkyl. In some embodiments, $R^3$ is carbocyclylCH$_2$-, where the carbocyclyl is selected from the group consisting of:
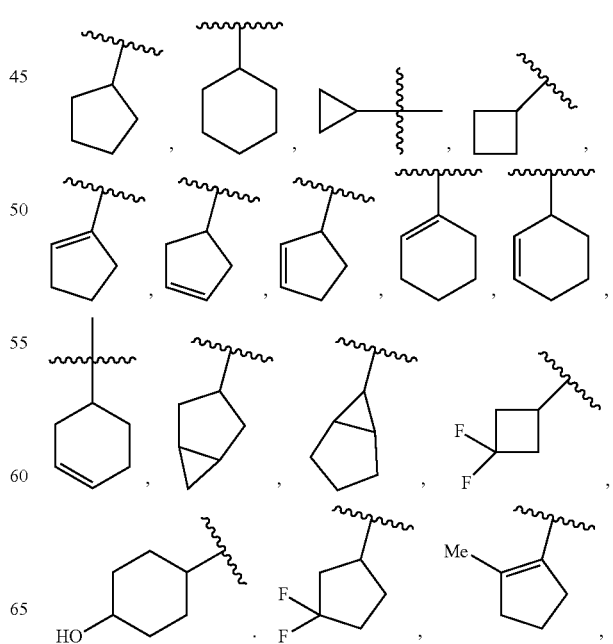

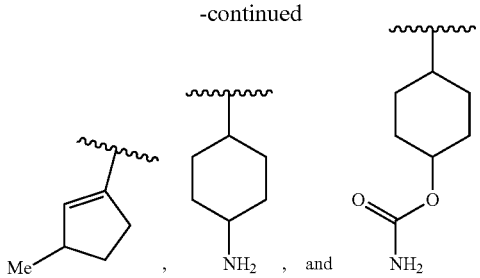

In some embodiments, $R^3$ is carbocycylCH$_2$—, wherein the carbocyclyl is

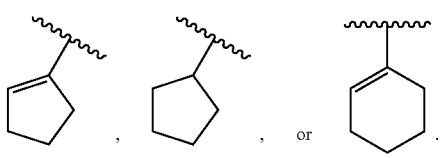 [SMILES: *C1=CCCC1 ; *C1CCCC1 ; *C1=CCCCC1]

The compounds provided herein can be synthesized using conventional techniques using readily available starting materials. In general, the compounds provided herein are conveniently obtained via standard organic chemistry synthesis methods. For example, the compounds provided herein may be prepared using the methods described herein or using the synthetic methods described in U.S. Pat. Nos. 7,232,818; 7,417,042; 7,687,456; 7,691,852; and 8,088,741, each of which is incorporated by reference in its entirety.

Methods of Use

The compounds disclosed herein can be inhibitors of immunoproteasome (iP). In some cases, a compound as disclosed herein inhibits the iP subunit LMP7. LMP7 activity can be inhibited by at least 10%, at least 20%, at least 30%, at least 40%, at least 50%, at least 60%, at least 70%, or at least 80%, as measured in a proteasome subunit assay as described below in the examples. One or more additional iP subunits can be inhibited by a compound as disclosed herein, such as LMP2, MECL-1, δ 1, δ 2, and δ 5. In various embodiments, a compound disclosed herein inhibits LMP7 and one or both of LMP2 and MECL-1. The compounds disclosed herein can reduce cytokine activity or expression, e.g., one or more of L-2, MHC-I, L-6, TNFα, and IFN-β. Thus, provided are methods wherein a compound as disclosed herein inhibits expression or activity of one or more of IL-2, MHC-I, IL-6, TNFα, and IFN-β by at least 10%, at least 20%, at least 30%, at least 40%, at least 50%, at least 60%, at least 70%, or at least 80%, as measured in an assay as described below in the examples.

The biological consequences of proteasome inhibition are numerous. Proteasome inhibition has been suggested as a prevention and/or treatment of a multitude of diseases including, but not limited to, neurotoxic/degenerative diseases, Alzheimer, ischemic conditions, inflammation, autoimmune diseases, HIV, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, and bone and hair growth diseases. Therefore, pharmaceutical formulations for proteasome-specific compounds, such as the epoxy ketone class of molecules, provide a means of administering a drug to a patient and treating these conditions.

The proteasome regulates NF-κB, which in turn regulates genes involved in the immune and inflammatory response. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., Cell (1994) 78:773-785). Thus, provided herein are methods of affecting the level of expression of IL-2, MHC-I, IL-6, TNFα, IFN-β or any of the other previously-mentioned proteins, each method comprising administering to a patient a therapeutically effective amount of a compound or composition disclosed herein.

Also provided herein is a method of treating an autoimmune disease in a patient comprising administering a therapeutically effective amount of the compound described herein. An "autoimmune disease" as used herein is a disease or disorder arising from and directed against an individual's own tissues. Examples of autoimmune diseases include, but are not limited to, inflammatory responses such as inflammatory skin diseases including psoriasis and dermatitis (e.g., atopic dermatitis); systemic scleroderma and sclerosis; responses associated with inflammatory bowel disease (such as Crohn's disease and ulcerative colitis); respiratory distress syndrome (including adult respiratory distress syndrome (ARDS)); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Beheet disease; giant cell arteritis; immune complex nephritis; IgA nephropathy; IgM polyneuropathies; immune thrombocytopenic purpura (ITP) or autoimmune thrombocytopenia.

The immune system screens for autologous cells that are virally infected, have undergone oncogenic transformation or present unfamiliar peptides on their surface. Intracellular proteolysis generate small peptides for presentation to T-lymphocytes to induce MHC class I-mediated immune responses. Thus, provided herein is a method of using a compound or composition provided herein as an immunomodulatory agent for inhibiting or altering antigen presentation in a cell, comprising exposing the cell (or administering to a patient) to the compound described herein. Specific embodiments include a method of treating graft or transplant-related diseases, such as graft-versus-host disease or host versus-graft disease in a patient, comprising administering a therapeutically effective amount of the compound described herein. The term "graft" as used herein refers to biological material derived from a donor for transplantation into a recipient. Grafts include such diverse material as, for example, isolated cells such as islet cells; tissue such as the amniotic membrane of a newborn; bone marrow; hematopoietic precursor cells; ocular tissue, such as corneal tissue; and organs such as skin, heart, liver, spleen, pancreas, thyroid lobe, lung, kidney, and tubular organs (e.g., intestine, blood vessels, or esophagus). The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. In some cases, the donor and recipient is the same patient. In some embodiments, the graft is bone marrow or an organ such as heart and the donor of the graft and the host are matched for HLA class II antigens.

Proteasome inhibition has also been associated with inhibition of NF-κB activation and stabilization of p53 levels. Thus, compositions provided herein may also be used to inhibit NF-κB activation, and stabilize p53 levels in cell culture. Since NF-κB is a key regulator of inflammation, it is an attractive target for anti-inflammatory therapeutic intervention. Thus, compositions provided herein may be useful for the treatment of conditions associated with inflammation, including, but not limited to COPD, psoriasis, asthma, bronchitis, emphysema, and cystic fibrosis.

The disclosed compositions can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include 0-amyloid protein and regulatory proteins such as cyclins and transcription factor NF-κB.

In some embodiments, a composition provided herein is useful for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis, and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of 3-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the β-subunit of human macropain (Kojima, S. et al., *Fed. Eur. Biochem. Soc.*, (1992) 304:57-60). The APP-processing enzyme cleaves at the Gln15-Lys16 bond; in the presence of calcium ion, the enzyme also cleaves at the Met-1-Asp1 bond, and the Asp1-Ala2 bonds to release the extracellular domain of β-AP.

Therefore, provided herein is a method of treating Alzheimer's disease, including administering to a patient a therapeutically effective amount of a composition disclosed herein. Such treatment includes reducing the rate of β-AP processing, reducing the rate of β-AP plaque formation, reducing the rate of β-AP generation, and reducing the clinical signs of Alzheimer's disease.

Also provided herein are methods of treating cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Peptide proteasome inhibitors (e.g., a compound or composition provided herein) are useful for treating conditions such as cancer, chronic infectious diseases, fever, muscle disuse (atrophy) and denervation, nerve injury, fasting, renal failure associated with acidosis, kidney disease, and hepatic failure. See, e.g., Goldberg, U.S. Pat. No. 5,340,736, which is incorporated herein by reference in its entirety. Methods of treatment include: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a patient) with an effective amount of a pharmaceutical composition disclosed herein to reduce the rate of muscle protein degradation in the cell; reduce the rate of intracellular protein degradation in the cell; and/or reduce the rate of degradation of p53 protein in the cell. In some embodiments, the methods include administering to a patient a therapeutically effective amount of a pharmaceutical composition disclosed herein.

Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activates transcription of target genes upon TGF-β stimulation is regulated by proteasome activity. However, accelerated degradation of the TGF-β signaling components has been observed in cancers and other hyperproliferative conditions. Thus, in certain embodiments, a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases, and extrinsic lung disorders) is provided. The treatment of burn victims is often hampered by fibrosis, thus, in some embodiments a compound provided herein may be administered by topical or systemic administration to treat burns. Wound closure following surgery is often associated with disfiguring scars, which may be prevented by inhibition of fibrosis. Thus, in certain embodiments, a method for the prevention or reduction of scarring is provided herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., Cell (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., Cell (1994) 78:773-785). Some embodiments include methods of affecting the level of expression of IL-2, MHC-I, IL-6, TNFα, IFN-β, or any of the other previously-mentioned proteins, each method including administering to a patient a therapeutically effective amount of a composition disclosed herein. Complexes including p50 are rapid mediators of acute inflammatory and immune responses (Thanos, D. and Maniatis, T., Cell (1995) 80:529-532).

NF-κB also participates in the expression of the cell adhesion genes that encode E-selectin, P-selectin, ICAM, and VCAM-1 (Collins, T., Lab. Invest. (1993) 68:499-508). In some embodiments, a method for inhibiting cell adhesion (e.g., cell adhesion mediated by E-selectin, P-selectin, ICAM, or VCAM-1) is provided, including contacting a cell with an effective amount of a pharmaceutical composition disclosed herein. In some embodiments, a method for inhibiting cell adhesion (e.g., cell adhesion mediated by E-selectin, P-selectin, ICAM, or VCAM-1) is provided, including administering to a patient a therapeutically effective amount of a pharmaceutical composition disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB. It has been demonstrated that the severity of injury resulting in hypoxia can be reduced with the administration of a proteasome inhibitor. Thus, provided herein is a method of treating an ischemic condition or reperfusion injury comprising administering to a patient in need of such treatment a therapeutically effective amount of a compound provided herein. Examples of such conditions or injuries include, but are not limited to, acute coronary syndrome (vulnerable plaques), arterial occlusive disease (cardiac, cerebral, peripheral arterial, and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj 14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., Science, (1995) 267:960). Provided herein is a method for inhibiting or reducing HIV infection in a patient, and a method for decreasing the level of viral gene expression, each method including administering to the patient a therapeutically effective amount of a composition disclosed herein.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice which developed chronic myocarditis (Szalay et al, Am J Pathol 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronvirus. Yu and Lai (J Virol 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate. Inhibiting the proteasome degradation pathway causes a significant reduction in the amount of secreted envelope proteins (Simsek et al, J Virol 79:12914-12920, 2005). In addition to HBV, other hepatitis viruses (A, C, D and E) may also utilize the ubiquitin-proteasome degradation pathway for secretion, morphogenesis and pathogenesis. Accordingly, in certain embodiments, a method for treating viral infection, such as SARS or hepatitis A, B, C, D and E, is provided comprising contacting a cell with an effective amount of the compound disclosed herein. In some embodiments, a method for treating viral infection, such as SARS or hepatitis A, B, C, D and E, is provided comprising administering to a patient a therapeutically effective amount of the compound disclosed herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., J. Immun. (2003) 171: 1515-1525). Therefore, in certain embodiments, compositions as provided herein may be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a composition described herein. In some embodiments, the cell is contacted with an effective amount of a compound or composition provided herein to inhibit antigen presentation in the cell. A further embodiment is a method for suppressing the immune system of a patient (e.g., inhibiting transplant rejection, allergy, asthma), including administering to the patient a therapeutically effective amount of a composition described herein. Compositions provided herein can also be used to treat autoimmune diseases such as lupus, rheumatoid arthritis, multiple sclerosis, and inflammatory bowel diseases such as ulcerative colitis and Crohn's disease.

Another embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. *Cell* (1994) 78:773-785; and Traenckner, et al., *EMBO J.* (1994) 13:5433-5441). In some embodiments, a method for inhibiting IκB-α degradation is provided, including contacting a cell with a composition described herein. In some embodiments, a cell is contacted with an effective amount of the composition to inhibit IκB-α degradation. A further embodiment is a method for reducing the cellular content of NF-κB in a cell, muscle, organ, or patient, including contacting the cell, muscle, organ, or patient with a composition described herein. In some embodiments, a cell is contacted with an effective amount of the composition to reduce the cellular content of NF-κB in a cell.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Further provided herein are methods for affecting cyclin-dependent eukaryotic cell cycles, including exposing a cell (in vitro or in vivo) to a composition disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with p34cdc2 protein kinase or related kinases. The proteolysis targeting signal is localized to amino acids 42-RAAL-GNISEN-50 (destruction box). There is evidence that cyclin is converted to a form vulnerable to a ubiquitin ligase or that a cyclin-specific ligase is activated during mitosis (Ciechanover, A., Cell, (1994) 79:13-21). Inhibition of the proteasome inhibits cyclin degradation, and therefore inhibits cell proliferation, for example, in cyclin-related cancers (Kumatori et al., Proc. Natl. Acad. Sci. USA (1990) 87:7071-7075). Provided herein is a method for treating a proliferative disease in a patient (e.g., cancer, psoriasis, or restenosis), including administering to the patient a therapeutically effective amount of a composition disclosed herein. Also provided herein is a method for treating cyclin-related inflammation in a patient, including administering to a patient a therapeutically effective amount of a composition described herein.

In another embodiment, the disclosed compositions are useful for the treatment of a parasitic infection, such as infections caused by protozoan parasites. The proteasome of these parasites is considered to be involved primarily in cell differentiation and replication activities (Paugam et al., *Trends Parasitol.* 2003, 19(2): 55-59). Furthermore, *Entamoeba* species have been shown to lose encystation capacity when exposed to proteasome inhibitors (Gonzales, et al., *Arch. Med. Res.* 1997, 28, Spec No: 139-140). In certain such embodiments, the disclosed compositions are useful for the treatment of parasitic infections in humans caused by a protozoan parasite selected from *Plasmodium* sps. (including *P. falciparum, P. vivax, P. malariae,* and *P. ovale,* which cause malaria), *Trypanosoma* sps. (including *T. cruzi,* which causes Chagas' disease, and *T. brucei* which causes African sleeping sickness), *Leishmania* sps. (including L. amazonesis, *L. donovani, L. infantum, L. mexicana,* etc.), *Pneumocystis carinii* (a protozoan known to cause pneumonia in AIDS and other immunosuppressed patients), *Toxoplasma gondii, Entamoeba histolytica, Entamoeba invadens,* and *Giardia lamblia.* In certain embodiments, the disclosed compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona,* and *Neurospora crassa.* Other compounds useful as proteasome inhibitors in the treatment of parasitic diseases are described in WO 98/10779, which is incorporated herein in its entirety.

In certain embodiments, the disclosed compositions inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

Prokaryotes have what is equivalent to the eukaryote 20S proteasome particle. Albeit, the subunit composition of the prokaryote 20S particle is simpler than that of eukaryotes, it has the ability to hydrolyze peptide bonds in a similar manner. For example, the nucleophilic attack on the peptide bond occurs through the threonine residue on the N-terminus of the β-subunits. In some embodiments, a method of treating prokaryotic infections is provided, comprising administering to a patient a therapeutically effective amount of a compound or composition provided herein. Prokaryotic infections may include diseases caused by either mycobacteria (such as tuberculosis, leprosy or Buruli Ulcer) or archaebacteria.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed compositions may be useful in the treatment and/or prevention of diseases associated with bone loss, such as osteoporosis.

Provided herein is a method for treating a disease or condition selected from autoimmune disease, graft or transplant-related condition, neurodegenerative disease, fibrotic-associated condition, ischemic-related conditions, infection (viral, parasitic or prokaryotic), and diseases associated with bone loss, comprising administering a compound as provided herein.

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., *Trans Genet* (1992) 8:55-61 describes evidence that bone morphogenetic proteins (BMPs), are differentially expressed in hair follicles during development. Harris, S. E., et al., *J Bone Miner Res* (1994) 9:855-863 describes the effects of TGF-β on expression of BMP-2 and other substances in bone cells. BMP-2 expression in mature follicles also occurs during maturation and after the period of cell proliferation (Hardy, et al. (1992, supra). Thus, compounds provided herein may also be useful for hair follicle growth stimulation.

Also provided herein is a method for treating a lysosomal storage disorder by administration of a compound as disclosed herein. Lysosomal storage disorders are a group of diseases resulting from the abnormal metabolism of various substrates, including glycosphingolipids, glycogen, mucopolysaccharides, and glycoproteins. The metabolism of exo- and endogenous high molecular weight compounds normally occurs in the lysosomes, and the process is normally regulated in a stepwise process by degradation enzymes. Therefore, a deficient activity in one enzyme may impair the process, resulting in an accumulation of particular substrates. It has been shown that inhibition of the proteasome can improve the function of certain substrates in patients suffering from a lysosomal storage disorder (Y. Shimada et al. *Biochem. Biophys. Res. Commun.* (2011) 415(2):274-8). Most of these diseases can be clinically classified into subtypes: i) infantile-onset; ii) juvenile-onset; or iii) late-onset. The infantile-onset forms are often the most severe usually with no residual enzyme activity. The later-onset forms are often milder with low, but often detectable residual enzyme activity. The severity of the juvenile-onset forms are in between the infantile-onset and late-onset forms. Non-limiting examples of such disorders include: Pompe disease, Gaucher disease, Fabry disease, GM1-gangliosidosis, Tay-Sachs disease, Sandhoff disease, Niemann-Pick disease, Krabbe disease, Farber disease, Metachromatic leukodystrophy, Hurler-Scheie disease, Hunter disease, Sanfilippo disease A, Sanfilippo disease B, Sanfilippo disease C, Sanfilippo disease D, Morquio disease A, Morquio disease B, Maroteaux-Lamy disease, Sly disease, α-mannosidosis, β-mannosidosis, fucosidosis, sialidosis, and Schindler-Kanzaki disease. One embodiment, therefore, is a method of treating Pompe disease, including administering to a patient a therapeutically effective amount of a composition provided herein.

The disclosed compositions are also useful as diagnostic agents (e.g., in diagnostic kits or for use in clinical laboratories) for screening for proteins (e.g., enzymes, transcription factors) processed by Ntn hydrolases, including the proteasome. The disclosed compositions are also useful as research reagents for specifically binding the X/MB1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a composition disclosed herein; exposing the compound-exposed organism, cell preparation, or cell extract to a signal; and monitoring the process or output. The high selectivity of the compounds disclosed herein permits rapid and accurate elimination or implication of the Ntn (for example, the 20S proteasome) in a given cellular, developmental, or physiological process.

Pharmaceutical Compositions and Administration

The methods provided herein include the manufacture and use of pharmaceutical compositions, which include one or more of the compounds provided herein. Also included are the pharmaceutical compositions themselves. In some embodiments, the compounds provided herein can be formulated as described in U.S. Pat. No. 7,737,112 and U.S. application Ser. No. 13/614,829, each of which is incorporated herein by reference in its entirety. Pharmaceutical compositions typically include a pharmaceutically acceptable carrier.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted 3-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Formulations suitable for oral administration may be in the form of capsules (e.g., gelatin capsules), cachets, pills, tablets, lozenges (using a flavored basis, usually sucrose and acacia or tragacanth), powders, troches, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound provided herein as an active ingredient. A composition may also be administered as a bolus, electuary, or paste. Oral compositions generally include an inert diluent or an edible carrier.

Pharmaceutically compatible binding agents, and/or adjuvant materials can be included as part of an oral composition. In solid dosage forms for oral administration (capsules, tablets, pills, dragees, powders, granules, and the like), the active ingredient can be mixed with one or more pharmaceutically acceptable carriers, such as sodium citrate or dicalcium phosphate, and/or any of the following: (1) fillers or extenders, such as starches, cyclodextrins, lactose, sucrose, saccharin, glucose, mannitol, and/or silicic acid; (2) binders, such as, for example, carboxymethylcellulose, microcrystalline cellulose, gum tragacanth, alginates, gelatin, polyvinyl pyrrolidone, sucrose, and/or acacia; (3) humectants, such as glycerol; (4) disintegrating agents, such as agar-agar, calcium carbonate, potato, corn, or tapioca starch, alginic acid, Primogel, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, Sterotes, solid polyethylene glycols, sodium lauryl sulfate, and mixtures thereof; (10) a glidant, such as colloidal silicon dioxide; (11) coloring agents; and (12) a flavoring agent such as peppermint, methyl salicylate, or orange flavoring. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of a powdered compound moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, microspheres, and/or nanoparticles. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions suitable for parenteral administration can include one or more compounds provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, N.J.). In all cases, the composition must be sterile and should be fluid to the extent that easy syringability exists. Proper fluidity can be maintained, for example, by the use of coating materials, such as lecithin, by the maintenance of the required particle size in the case of dispersions, and by the use of surfactants.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798. Additionally, intranasal delivery can be accomplished, as described in, inter alia, Hamajima et al., *Clin. Immunol. Immunopathol.*, 88(2), 205-10 (1998). Liposomes (e.g., as described in U.S. Pat. No. 6,472,375, which is incorporated herein by reference in its entirety), microencapsulation and nanoencapsulation can also be used. Biodegradable targetable microparticle delivery systems or biodegradable targetable nanoparticle delivery systems can also be used (e.g., as described in U.S. Pat. No. 6,471,996, which is incorporated herein by reference in its entirety).

Systemic administration of a therapeutic compound as described herein can also be by transmucosal or transdermal means. Dosage forms for the topical or transdermal administration of a compound provided herein include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The ointments, pastes, creams, and gels may contain, in addition to one or more compounds provided herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound provided herein, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound provided herein can be administered by aerosol. This is accomplished by preparing an aqueous aerosol, liposomal preparation, or solid particles containing a compound or composition provided herein. A nonaqueous (e.g., fluorocarbon propellant) suspension could be used. In some embodiments, sonic nebulizers are used because they minimize exposing the agent to shear, which can result in degradation of the compound.

Ordinarily, an aqueous aerosol can be made by formulating an aqueous solution or suspension of the agent together with conventional pharmaceutically acceptable carriers and stabilizers. The carriers and stabilizers vary with the requirements of the particular composition, but typically include nonionic surfactants (TWEEN® (polysorbates), PLURONIC® (poloxamers), sorbitan esters, lecithin, CREMOPHOR® (polyethoxylates)), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a compound provided herein to the body. Such dosage forms can be made by dissolving or dispersing the agent in the proper medium. Absorption enhancers can also be used to increase the flux of the compound across the skin. The rate of such flux can be controlled by either providing a rate controlling membrane or dispersing the compound in a polymer matrix or gel.

The pharmaceutical compositions can also be prepared in the form of suppositories or retention enemas for rectal and/or vaginal delivery. Formulations presented as a suppository can be prepared by mixing one or more compounds provided herein with one or more suitable nonirritating excipients or carriers comprising, for example, cocoa butter, glycerides, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety.

As described above, the preparations of one or more compounds provided herein may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. In some embodiments, administration is oral.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection, and infusion.

The phrases "systemic administration", "administered systemically", "peripheral administration", and "administered peripherally" as used herein mean the administration of a ligand, drug, or other material via route other than directly into the central nervous system, such that it enters the patient's system and thus, is subject to metabolism and other like processes, for example, subcutaneous administration.

A compound provided herein may be administered to humans and other animals for therapy by any suitable route of administration, including orally, nasally, as by, for example, a spray, rectally, intravaginally, parenterally, intracisternally, and topically, as by powders, ointments or drops, including buccally and sublingually. Regardless of the route of administration selected, a compound provided herein, which may be used in a suitable hydrated form, and/or the pharmaceutical compositions provided herein, is formulated into a pharmaceutically acceptable dosage form by conventional methods known to those of skill in the art. In another embodiment, the pharmaceutical composition is an oral solution or a parenteral solution. Another embodiment is a freeze-dried preparation that can be reconstituted prior to administration. As a solid, this formulation may also include tablets, capsules or powders.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

The pharmaceutical compositions can be included in a container, pack, or dispenser together with instructions for administration.

Also provided herein is a conjoint therapy wherein one or more other therapeutic agents are administered with a compound or a pharmaceutical composition comprising a compound provided herein. Such conjoint treatment may be achieved by way of the simultaneous, sequential, or separate dosing of the individual components of the treatment. Non-limiting examples of conjoint therapies include those provided in WO 2010/048298, which is incorporated herein in its entirety.

In certain embodiments, a composition provided herein is conjointly administered with one or more other proteasome inhibitor(s) (see, e.g., U.S. Pat. Nos. 7,232,818 and 8,088,741, each of which is incorporated herein by reference in its entirety). Additional examples of proteasome inhibitors include bortezomib, MLN9708, marizomib, carfilzomib (see, e.g., U.S. Pat. No. 7,417,042), and those compounds disclosed in U.S. Pat. Nos. 7,687,456 and 7,691,852, each of which is incorporated herein by reference in its entirety.

In certain embodiments, a pharmaceutical composition as provided herein is conjointly administered with a cytokine. Cytokines include, but are not limited to, Interferon-$\gamma$, -$\alpha$, and -$\beta$, Interleukins 1-8, 10 and 12, Granulocyte Monocyte Colony-Stimulating factor (GM-CSF), TNF-$\alpha$ and -$\beta$, and TGF-$\beta$.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In some embodiments, a pharmaceutical composition provided herein is conjointly administered with an immunotherapeutic agent. Suitable immunotherapeutic agents may include, but are not limited to, MDR modulators (e.g., verapamil, valspordar, biricodar, tariquidar, laniquidar), cyclosporine, thalidomide, lenalidomide (REVLIMID®), pomalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib, and trastuzumab.

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

EXAMPLES

General Experimental Methods

Nuclear Magnetic Resonance (NMR) spectra were recorded at 400 MHz for $^1$H. Chemical shifts ($\delta$) are given in ppm downfield from tetramethylsilane, an internal standard, and coupling constants (J-values) are in hertz (Hz).

Mass spectrometry (MS) was used to confirm the mass of the compounds by ionizing the compounds to generate charged molecules or molecule fragments and measuring their mass-to-charge ratios (m/z). As the ionization method, EI (electron impact) ionization was used.

Synthetic Procedures-Tripeptide Epoxy Ketone Compounds

Example 1

(1r,4R)—N—((R)-1-(((S)-1-(((S)-3-(Cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxy-4-methylcyclohexanecarboxamide (C-1087)

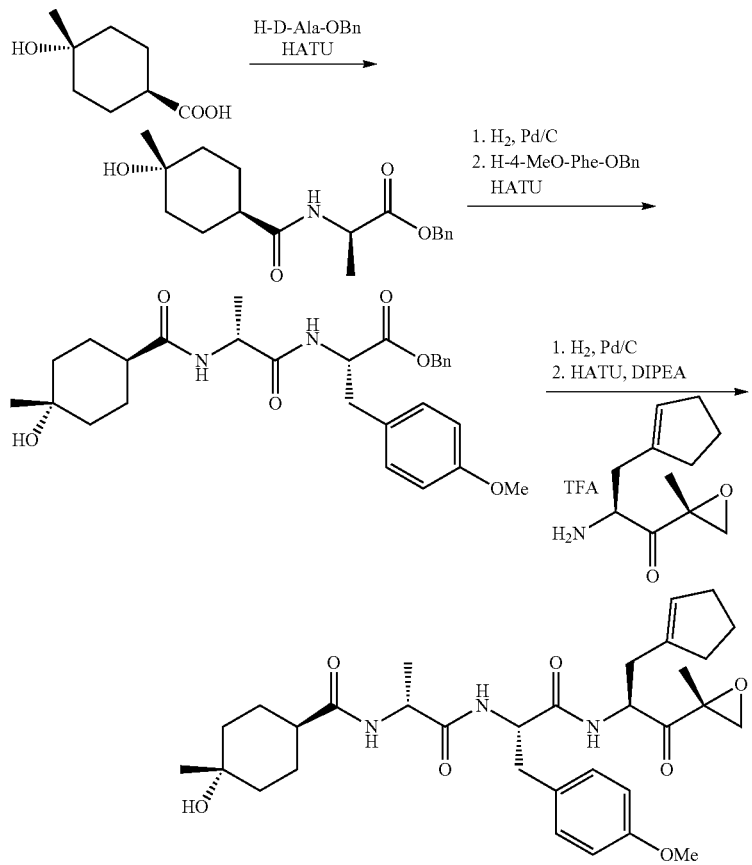

1-[Bis(dimethylamino)methylene]-1H-1,2,3-triazolo[4,5-b]pyridinium 3-oxid hexafluorophosphate (HATU; 751 mg, 1.98 mmol) and N,N-Diisopropylethylamine (DIPEA; 1.15 mL, 6.58 mmol) were added to a solution of the acid (260 mg, 1.64 mmol) and (R)-benzyl 2-aminopropanoate (355 mg, 1.98 mmol) in dimethylformamide (DMF; 5 mL) at 0° C. The reaction mixture was allowed to warm to ambient temperature and stirred for 0.5 h. Water (20 mL) was added and the resulting mixture was extracted with ethyl acetate (EtOAc; 50 mL×3). The combined organic layers were washed with water (100 mL) and brine (100 mL), dried over anhydrous sodium sulfate and concentrated. The residue was purified by flash column chromatography on silica gel (petroleum ether/EtOAc=2:3) to afford (R)-benzyl 2-((1r, 4r)-4-hydroxy-4-methylcyclohexanecarboxamido)propanoate (320 mg, 61% yield) as an off-white solid.

To a solution of (R)-Benzyl 2-((1r, 4r)-4-hydroxy-4-methylcyclohexanecarboxamido)propanoate (320 mg, 1.0 mmol) in THF (10 mL) was added palladium on carbon (Pd/C; 30 mg, 10%). The mixture was stirred under hydrogen atmosphere (1 atm) at ambient temperature for 2 h. The mixture was filtered through a pad of Celite and the filtrate was concentrated under reduced pressure to afford the corresponding acid (230 mg, quantitative) as a colorless solid, which was used in the next step without further purification.

HATU (458 mg, 1.2 mmol) and DIPEA (0.70 mL, 4.0 mmol) were added to a solution of the acid (230 mg, 1.645 mmol) and (S)-benzyl 2-amino-3-(4-methoxyphenyl) propanoate (hydrochloric acid (HCl) salt, 323 mg, 1.0 mmol) in DMF (7 mL) at 0° C. The reaction mixture was allowed to warm to ambient temperature and stirred for 0.5 h. Water (20 mL) was added and the resulting mixture was extracted with EtOAc (50 mL×3). The combined organic layers were washed with water (100 mL) and brine (100 mL), dried over anhydrous sodium sulfate and concentrated. The residue was purified by flash column chromatography on silica gel (petroleum ether/EtOAc=1:2) to afford (S)-2-((R)-2-((1r,4r)-4-hydroxy-4-methylcyclohexanecarboxamido)propanamido)-3-(4-methoxyphenyl)propanoic acid (315 mg, 63% yield) as an off-white solid.

To a solution of (S)-2-((R)-2-((1r,4r)-4-hydroxy-4-methylcyclohexanecarboxamido)propanamido)-3-(4-methoxyphenyl)propanoic acid (315 mg, 0.64 mmol) in THF (10 mL) was added Pd/C (30 mg, 10%). The mixture was stirred under hydrogen atmosphere (1 atm) at ambient temperature for 2 h. The mixture was filtered through a pad of Celite and the filtrate was concentrated under reduced pressure to afford compound (R)-2-((1r,4R)-4-hydroxy-4-methylcyclohexanecarboxamido)propanoic acid (260 mg, quantitative) as a colorless solid, which was used in the next step without further purification.

HATU (308 mg, 0.81 mmol) and DIPEA (0.2 mL, 1.15 mmol) were added to a solution of (R)-2-((1r,4R)-4-hydroxy-4-methylcyclohexanecarboxamido)propanoic acid (260 mg, 0.64 mmol) and (S)-2-amino-3-(cyclopent-1-en-1-yl)-1-((R)-2-methyloxiran-2-yl)propan-1-one (190 mg, 0.64 mmol) in DMF (6 mL) at 0° C. The reaction mixture was allowed to warm to ambient temperature and stirred for 0.5 h. Water (20 mL) was added and the resulting mixture was extracted with EtOAc (50 mL×3). The combined organic layers were washed with water (100 mL) and brine (100 mL), dried over anhydrous sodium sulfate and concentrated. The residue was purified by flash column chromatography on silica gel (EtOAc) to afford (1 r,4R)—N—((R)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxy-4-methylcyclohexanecarboxamide (260 mg, 63% yield) as an off-white solid. $^1$H NMR (300 MHz, deuterated chloroform (CDCl$_3$)): δ 7.16 (d, J=8.4 Hz, 2H), 6.83 (m, 1H), 6.82 (d, J=8.4 Hz, 2H), 6.35 (m, 1H), 6.16 (m, 1H), 5.32 (m, 1H), 4.56 (m, 2H), 4.36 (m, 1H), 3.78 (s, 3H), 3.29 (m, 1H), 2.98 (m, 2H), 2.89 (m, 1H), 2.26 (m, 1H), 2.05 (m, 5H), 1.86-1.78 (m, 6H), 1.48 (d, J=6.3 Hz, 3H), 1.43 (m, 2H), 1.26 (m, 4H), 1.23 (s, 3H), 0.87 (m, 3H). MS (EI) for $C_{32}H_{45}N_3O_7$, found 606.3 [M+Na]$^+$.

(1s,4S)—N—((R)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxy-4-methylcyclohexanecarboxamide (C-1088): $^1$H NMR (300 MHz, CDCl$_3$): δ 7.16 (d, J=8.7 Hz, 2H), 6.82 (d, J=8.4 Hz, 2H), 6.60 (d, J=7.2 Hz, 1H), 6.16 (d, J=7.2 Hz, 2H), 5.30 (m, 1H), 4.56 (m, 2H), 4.36 (m, 1H), 3.79 (s, 3H), 3.28 (d, J=5.1 Hz, 1H), 2.99 (m, 2H), 2.89 (m, 1H), 2.26 (m, 2H), 2.18-2.15 (m, 6H), 1.85-1.64 (m, 9H), 1.47 (d, J=6.3 Hz, 3H), 1.27-1.24 (m, 6H). MS (EI) for $C_{32}H_{45}N_3O_7$, found 606.3 [M+Na]$^+$.

Example 2

(S)—N—((S)-3-(Cyclohex-1-en-1-yl)-1-((R)-2-methyloxiran-2-yl)-1-oxopropan-2-yl)-2-((S)-3-hydroxy-2-(2-morpholinoacetamido)propanamido)-3-(3-hydroxy-4-methoxyphenyl)propanamide (C-1109)

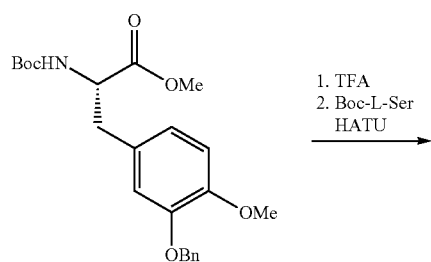

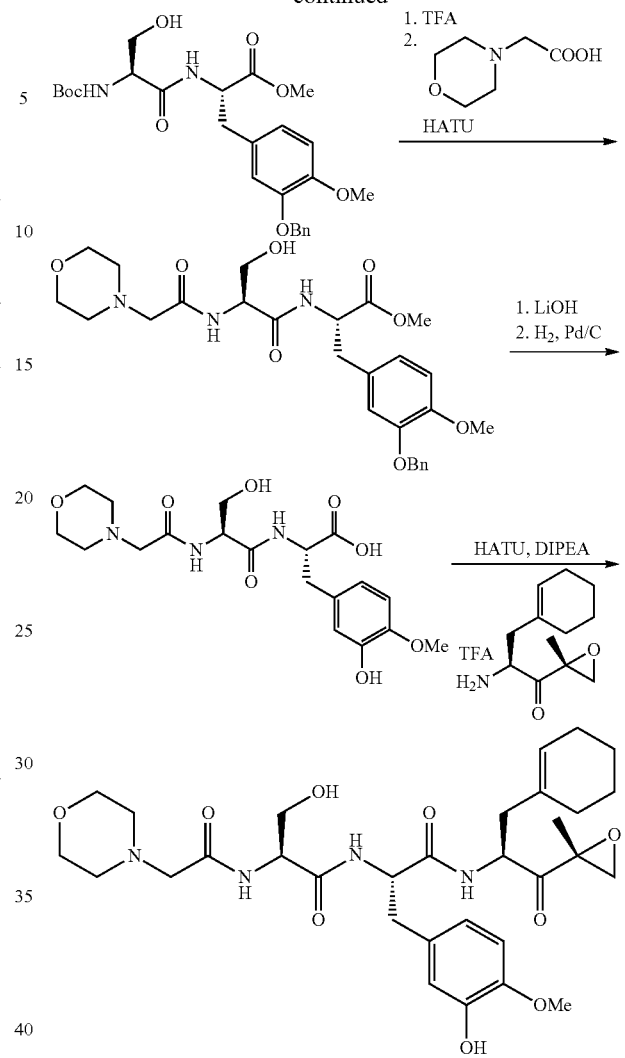

Trifluoroacetic acid (TFA; 25 mL) was added to a solution of (S)-methyl 3-(3-(benzyloxy)-4-methoxyphenyl)-2-((tert-butoxycarbonyl)amino)propanoate (5.00 g, 12.0 mmol) in dichloromethane (CH$_2$Cl$_2$; 50 mL) at 0° C. with stirring. The mixture was stirred for 1 h and then concentrated to dryness. The residue was azeotroped three times with EtOAc (20 mL for each portion) to remove residual TFA to afford crude compound (S)-methyl 2-amino-3-(3-(benzyloxy)-4-methoxyphenyl)propanoate as its TFA salt.

Crude (S)-methyl 2-amino-3-(3-(benzyloxy)-4-methoxyphenyl)propanoate (TFA salt, 12 mmol) was dissolved in DMF (50 mL) followed by addition of Boc-L-serine (2.47 g, 12 mmol), HATU (6.87 g, 18.1 mmol) and DIPEA (10 mL) at 0° C. with stirring. The reaction mixture was allowed to warm to ambient temperature and stirred for 3 h. EtOAc (200 mL) and water (200 mL) was added and two layers were separated. The aqueous phase was extracted with EtOAc (100 mL×3) and the combined organic phases were washed with brine (200 mL×3), dried over anhydrous sodium sulfate, and concentrated. The residue was purified by flash column chromatography on silica gel (CH$_2$Cl$_2$/methanol (MeOH)=20:1) to afford (S)-methyl 3-(3-(benzyloxy)-4-methoxyphenyl)-2-((S)-2-((tert-butoxycarbonyl)amino)-3-hydroxypropanamido)propanoate (4.4 g, 73% yield).

TFA (20 mL) was added to a solution of (S)-methyl 3-(3-(benzyloxy)-4-methoxyphenyl)-2-((S)-2-((tert-butoxycarbonyl)amino)-3-hydroxypropanamido)propanoate (4.4 g, 8.7 mmol) in CH$_2$Cl$_2$ (50 mL) at 0° C. with stirring. The mixture was stirred for 1 h and then concentrated to dryness. The residue was azeotroped three times with EtOAc (20 mL for each portion) to remove residual TFA to afford crude (S)-methyl 2-((S)-2-amino-3-hydroxypropanamido)-3-(3-(benzyloxy)-4-methoxyphenyl)propanoate as its TFA salt.

Crude (S)-methyl 2-((S)-2-amino-3-hydroxypropanamido)-3-(3-(benzyloxy)-4-methoxyphenyl)propanoate (TFA salt, 8.7 mmol) was dissolved in DMF (50 mL) followed by addition of 2-morpholinoacetic acid (1.3 g, 8.7 mmol), HATU (5.0 g, 13.1 mmol) and DIPEA (5.0 mL) at 0° C. with stirring. The reaction mixture was allowed to warm to ambient temperature and stirred for 3 h. EtOAc (200 mL) and water (200 mL) was added and two layers were separated. The aqueous phase was extracted with EtOAc (100 mL×3) and the combined organic phases were washed with brine (200 mL×3), dried over anhydrous sodium sulfate, and concentrated. The residue was purified by flash column chromatography on silica gel (CH$_2$Cl$_2$/EtOAc/MeOH=20:10:1) to afford (S)-methyl 3-(3-(benzyloxy)-4-methoxyphenyl)-2-((S)-3-hydroxy-2-(2-morpholinoacetamido)propanamido)propanoate (2.9 g, 62% yield).

(S)-methyl 3-(3-(benzyloxy)-4-methoxyphenyl)-2-((S)-3-hydroxy-2-(2-morpholinoacetamido)propanamido)propanoate (1.0 g, 1.9 mmol) was treated with a solution of lithium hydroxide-H$_2$O (400 mg, 10 mmol) in water/THF (50 mL/20 mL) for 2 h. THF was removed and the aqueous phase was acidified to pH=3-4 with 1N HCl followed by concentration to dryness to afford the corresponding acid.

The acid was dissolved in MeOH (20 mL) and Pd/C (1 g, 10%) was added. The mixture was stirred under hydrogen atmosphere (1 atm) at ambient temperature overnight and then filtered through a pad of celite. The filtrate was concentrated under reduced pressure to afford (S)-2-((S)-3-hydroxy-2-(2-morpholinoacetamido)propanamido)-3-(3-hydroxy-4-methoxyphenyl)propanoic acid (520 mg, 64% yield) as a colorless solid.

HATU (570 mg, 1.5 mmol) and DIPEA (1.48 mL) were added to a solution of (S)-2-((S)-3-hydroxy-2-(2-morpholinoacetamido)propanamido)-3-(3-hydroxy-4-methoxyphenyl)propanoic acid (425 mg, 1 mmol) and (S)-2-amino-3-(cyclohex-1-en-1-yl)-1-((R)-2-methyloxiran-2-yl)propan-1-one (TFA salt, 1 mmol) in DMF (20 mL) at 0° C. with stirring. The reaction mixture was allowed to warm to ambient temperature and stirred for 3 h. EtOAc (100 mL) and water (100 mL) was added and the two layers were separated. The aqueous phase was extracted with EtOAc (50 mL×3) and the combined organic phases were washed with brine (200 mL×3), dried over anhydrous sodium sulfate and concentrated. The residue was purified by flash column chromatography on silica gel (CH$_2$Cl$_2$/EtOAc/MeOH=20: 10:0.2) to afford (S)—N—((S)-3-(cyclohex-1-en-1-yl)-1-((R)-2-methyloxiran-2-yl)-1-oxopropan-2-yl)-2-((S)-3-hydroxy-2-(2-morpholinoacetamido)propanamido)-3-(3-hydroxy-4-methoxyphenyl)propanamide (220 mg, 35% yield). $^1$H NMR (300 MHz, DMSO-d$_6$): δ 8.74 (s, 1H), 8.22 (d, J=7.5 Hz, 1H), 8.02 (d, J=8.1 Hz, 1H), 7.78 (m, 1H), 6.73 (d, J=8.4 Hz, 1H), 6.63 (s, 1H), 6.54 (m, 1H), 5.39 (m, 1H), 5.03 (m, 1H), 4.40-4.60 (m, 2H), 4.30 (m, 1H), 3.71 (s, 3H), 3.60 (m, 4H), 3.50 (m, 2H), 3.22 (m, 1H), 2.80-3.10 (m, 3H), 2.40 (m, 3H), 2.20 (m, 2H), 1.90-2.10 (m, 4H), 1.50-1.70 (m, 4H), 1.37 (s, 3H), 1.00-1.30 (m, 3H). MS (EI) for C$_{31}$H$_{44}$N$_4$O$_9$, found 617.3 (MH)$^+$.

The following compounds were synthesized in a similar manner:

(S)—N—((S)-3-cyclopentyl-1-((R)-2-methyloxiran-2-yl)-1-oxopropan-2-yl)-3-(4-methoxyphenyl)-2-((R)-2-(2-(tetrahydro-2H-pyran-4-yl)acetamido)propanamido)propanamide (C-1011): $^1$H NMR (300 MHz, CDCl$_3$): δ 7.12 (d, J=8.4 Hz, 2H), 6.83 (d, J=8.7 Hz, 2H), 6.58 (d, J=7.8 Hz, 1H), 6.49 (d, J=7.8 Hz, 1H), 6.23 (d, J=7.5 Hz, 1H), 4.62 (m, 1H), 4.47 (m, 1H), 4.37 (m, 1H), 3.94 (m, 2H), 3.80 (s, 3H), 3.36 (m, 2H), 3.29 (d, J=5.1 Hz, 1H), 3.00 (m, 2H), 2.90 (d, J=4.8 Hz, 1H), 2.15 (m, 2H), 2.07 (m, 1H), 1.51 (s, 3H), 1.32 (d, J=6.6 Hz, 3H), 1.06-1.83 (m, 15H). MS (EI) for C$_{31}$H$_{45}$N$_3$O$_7$, found 572.5 (MH)$^+$.

(S)—N—((S)-3-cyclopentyl-1-((R)-2-methyloxiran-2-yl)-1-oxopropan-2-yl)-3-(4-methoxyphenyl)-2-((S)-2-(2-(tetrahydro-2H-pyran-4-yl)acetamido)propanamido)propanamide (C-1010): $^1$H NMR (CDCl$_3$, 300 MHz): δ 7.11 (d, J=8.7 Hz, 2H), 6.81 (d, J=8.7 Hz, 2H), 6.75 (d, J=6.6 Hz, 2H), 6.38-6.43 (m, 1H), 6.20-6.27 (m, 1H), 4.62-4.65 (m, 1H), 4.47-4.53 (m, 2H), 3.92-3.98 (m, 2H), 3.79 (s, 3H), 3.41 (t, J=8.7 Hz, 2H), 3.23 (d, J=4.8 Hz, 1H), 2.95-3.03 (m, 2H), 2.90 (d, J=4.8 Hz, 1H), 2.06-2.13 (m, 2H), 1.53-1.92 (m, 11H), 1.52 (s, 3H), 1.39 (d, J=7.5 Hz, 3H), 1.03-1.36 (m, 4H). MS (EI) for C$_{31}$H$_{45}$N$_3$O$_7$, found 572.3 (MH)$^+$.

Example 3

(S)—N—((S)-3-(Cyclohex-1-en-1-yl)-1-((R)-2-methyloxiran-2-yl)-1-oxopropan-2-yl)-2-((S)-3-hydroxy-2-(2-morpholinoacetamido)propanamido)-3-(4-(methyl sulfonyl)phenyl)propanamide (C-1110)

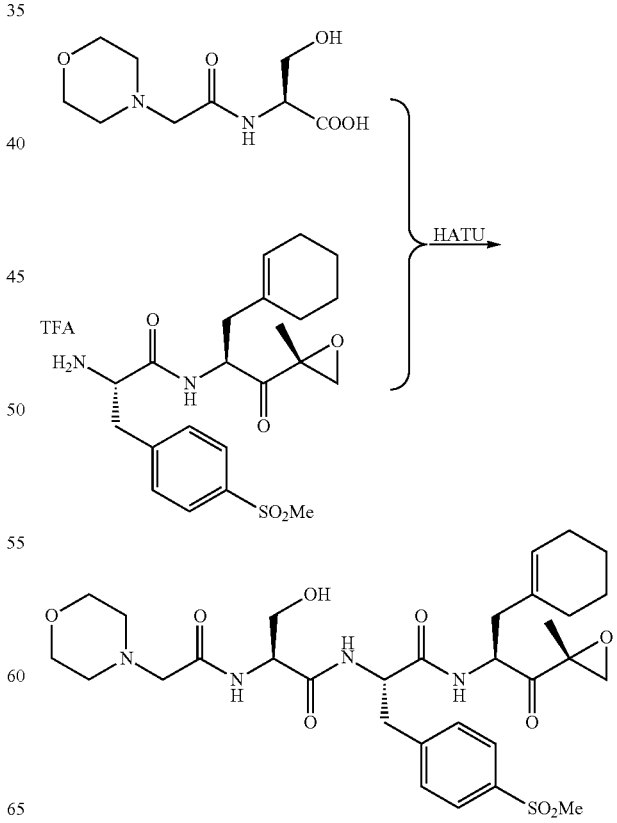

HATU (502 mg, 1.3 mmol) and DIPEA (1.35 mL) were added to a solution of (S)-3-hydroxy-2-(2-morpholinoacetamido)propanoic acid (225 mg, 0.97 mmol) and (S)-2-amino-N—((S)-3-(cyclohex-1-en-1-yl)-1-((R)-2-methyloxiran-2-yl)-1-oxopropan-2-yl)-3-(4-(methylsulfonyl)phenyl)propanamide (0.88 mmol) in DMF (20 mL) at 0° C. with stirring. The reaction mixture was allowed to warm to ambient temperature and stirred for 3 h. EtOAc (100 mL) and water (100 mL) was added and the two layers were separated. The aqueous phase was extracted with EtOAc (50 mL×3). The combined organic phases were washed with brine (200 mL×3), dried over anhydrous sodium sulfate and concentrated. The residue was purified by flash column chromatography on silica gel ($CH_2Cl_2$/EtOAc/MeOH=20:10:0.2) to afford (S)—N—((S)-3-(cyclohex-1-en-1-yl)-1-((R)-2-methyloxiran-2-yl)-1-oxopropan-2-yl)-2-((S)-3-hydroxy-2-(2-morpholinoacetamido)propanamido)-3-(4-(methylsulfonyl)phenyl)propanamide (200 mg, 35% yield). $^1$H NMR (300 MHz, DMSO-$d_6$): δ 8.33 (d, J=7.2 Hz, 1H), 8.13 (d, J=8.4 Hz, 1H), 7.78 (d, J=8.1 Hz, 2H), 7.69 (d, J=7.8 Hz, 1H), 7.46 (d, J=7.8 Hz, 2H), 5.40 (m, 1H), 5.05 (m, 1H), 4.45-4.70 (m, 2H), 4.30 (m, 1H), 3.57 (m, 4H), 3.50 (m, 2H), 3.22 (m, 1H), 3.20 (s, 3H), 3.10 (m, 1H), 2.80-3.00 (m, 4H), 2.40 (m, 2H), 2.20 (m, 2H), 1.90-2.10 (m, 4H), 1.50-1.70 (m, 3H), 1.37 (s, 3H), 1.00-1.30 (m, 3H). MS (EI) for $C_{31}H_{44}N_4O_9S$, found 649.0 $(MH)^+$.

The following compounds were synthesized in a similar manner:

(1r,4R)—N—((R)-1-(((S)-1-(((S)-3-cyclopentyl-1-((R)-2-methyloxiran-2-yl)-1-oxopropan-2-yl)amino)-3-(3-hydroxy-4-methoxyphenyl)-1-oxopropan-2-yl)amino)-1-oxopropan-2-yl)-4-hydroxycyclohexanecarboxamide (C-1072): $^1$H NMR (400 MHz, CDCl$_3$ δ 8.70 (s, 1H), 8.20 (d, J=7.0 Hz, 1H), 7.98 (d, J=8.7 Hz, 1H), 7.82 (d, J=7.2 Hz, 1H), 6.74 (d, J=8.3 Hz, 1H), 6.62 (d, J=2.0 Hz, 1H), 6.55 (dd, J=8.2, 2.0 Hz, 1H), 4.52 (d, J=4.5 Hz, 1H), 4.47-4.34 (m, 1H), 4.34-4.21 (m, 1H), 4.15 (p, J=7.1, 7.1, 7.0, 7.0 Hz, 1H), 3.70 (s, 3H), 3.28 (td, J=10.7, 10.6, 5.3 Hz, 1H), 3.21 (d, J=5.3 Hz, 1H), 3.00 (d, J=5.3 Hz, 1H), 2.87 (dd, J=13.8, 3.7 Hz, 1H), 2.04 (ddt, J=11.9, 8.4, 3.4, 3.4 Hz, 1H), 1.96-1.84 (m, 1H), 1.84-1.43 (m, 13H), 1.40 (s, 3H), 1.23 (s, 2H), 1.15-0.99 (m, 4H), 0.95 (d, J=7.0 Hz, 3H). MS (EI) for $C_{31}H_{45}N_3O_8$, found 588.0 $(MH)^+$.

(S)—N—((S)-3-(cyclopent-1-en-1-yl)-1-((R)-2-methyloxiran-2-yl)-1-oxopropan-2-yl)-3-(3-hydroxy-4-methoxyphenyl)-2-((S)-2-(2-morpholinoacetamido)propanamido)propanamide (C-1085): $^1$H NMR (400 MHz, CDCl$_3$) δ 7.50 (d, J=7.7 Hz, 1H), 6.83-6.63 (m, 4H), 6.16 (d, J=7.0 Hz, 1H), 5.34 (s, 1H), 4.58 (ddd, J=8.6, 7.1, 4.7 Hz, 1H), 4.51 (q, J=6.9, 6.9, 6.9 Hz, 1H), 4.43 (q, J=7.2, 7.2, 7.1 Hz, 1H), 3.86 (s, 3H), 3.81-3.65 (m, 4H), 3.27 (d, J=4.9 Hz, 1H), 3.18 (qd, J=7.5, 7.4, 7.4, 4.4 Hz, 1H), 3.02 (s, 2H), 2.97-2.86 (m, 3H), 2.59-2.44 (m, 4H), 2.30-2.21 (m, 3H), 2.18 (t, J=7.4, 7.4 Hz, 2H), 1.83 (dt, J=13.6, 6.9, 6.9 Hz, 2H), 1.70-1.66 (m, 2H), 1.44 (d, J=6.6 Hz, 3H), 1.36 (d, J=7.1 Hz, 3H). MS (EI) for $C_{30}H_{42}N_4O_8$, found 587.0 $(MH)^+$.

(1r,4R)—N—((R)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-3-hydroxy-1-oxopropan-2-yl)-4-hydroxycyclohexanecarboxamide (C-1092): $^1$H NMR (400 MHz, CDCl$_3$) δ 7.13 (d, J=8.8 Hz, 2H), 6.98 (d, J=7.7 Hz, 1H), 6.82 (d, J=8.7 Hz, 2H), 6.55 (d, J=7.0 Hz, 1H), 6.21 (d, J=7.3 Hz, 1H), 5.32 (s, 1H), 4.65-4.46 (m, 2H), 4.35 (ddd, J=7.2, 4.6, 3.1 Hz, 1H), 4.02 (dd, J=11.4, 3.0 Hz, 1H), 3.78 (s, 3H), 3.70-3.49 (m, 2H), 3.26 (d, J=5.3 Hz, 1H), 2.99 (dd, J=6.7, 3.4 Hz, 2H), 2.89 (d, J=4.9 Hz, 1H), 2.48 (dd, J=15.0, 6.5 Hz, 1H), 2.29-1.97 (m, 9H), 1.96-1.37 (m, 9H), 1.33-1.24 (m, 3H). MS (EI) for $C_{31}H_{43}N_3O_8$, found 586.0 $(MH)^+$.

(S)—N—((S)-3-(cyclohex-1-en-1-yl)-1-((R)-2-methyloxiran-2-yl)-1-oxopropan-2-yl)-3-(4-(methylsulfonyl)phenyl)-2-((S)-2-(2-morpholinoacetamido)propanamido)propanamide (C-1126): $^1$H NMR (300 MHz, DMSO-$d_6$): δ 8.33 (d, J=7.2 Hz, 1H), 8.15 (d, J=8.4 Hz, 1H), 7.80 (d, J=7.8 Hz, 2H), 7.73 (d, J=7.8 Hz, 1H), 7.46 (d, J=7.8 Hz, 2H), 5.40 (m, 1H), 4.45-4.70 (m, 2H), 4.25 (m, 1H), 3.56 (m, 4H), 3.10-3.2 (m, 4H), 3.00-3.10 (m, 2H), 2.80-3.00 (m, 3H), 2.40 (m, 4H), 2.20 (m, 1H), 1.80-2.10 (m, 5H), 1.50-1.70 (m, 3H), 1.38 (s, 3H), 1.13 (d, J=6.9 Hz, 3H). MS (EI) for $C_{31}H_{44}N_4O_8S$, found 633.3 $(MH)^+$.

(1S,3S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxycyclopentanecarboxamide (C-1076): $^1$H NMR (300 MHz, DMSO-$d_6$): δ 10.96 (br s, 1H), 8.31 (d, J=7.2 Hz, 1H), 8.03 (d, J=8.1 Hz, 1H), 7.72 (d, J=7.2 Hz, 1H), 7.35 (m, 1H), 7.22 (d, J=8.1 Hz, 1H), 6.79 (d, J=8.4 Hz, 1H), 6.31 (s, 1H), 4.40 (m, 1H), 4.26 (m, 2H), 3.49 (m, 4H), 3.17 (d, J=5.1 Hz, 1H), 3.02 (m, 3H), 2.79 (m, 3H), 2.29 (m, 4H), 1.99 (m, 1H), 1.72 (m, 2H), 1.65 (m, 4H), 1.50 (s, 3H), 1.14 (d, J=6.6 Hz, 3H). MS (EI) for $C_{31}H_{43}N_5O_6$, found 582.4 $(MH)^+$.

(1r,4R)—N—((R)-1-(((S)-1-(((S)-3-(cyclopent-3-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxycyclohexanecarboxamide (C-1074): $^1$H NMR (500 MHz, CDCl$_3$) δ 7.15-7.00 (m, 2H), 6.85-6.76 (m, 2H), 6.58 (d, J=8.0 Hz, 1H), 6.47 (d, J=8.0 Hz, 1H), 6.12 (d, J=7.0 Hz, 1H), 5.64 (ddd, J=7.6, 5.9, 3.9 Hz, 2H), 4.60 (q, J=6.6, 6.6, 6.6 Hz, 1H), 4.51 (ddd, J=9.8, 8.1, 3.5 Hz, 1H), 4.34 (p, J=7.0, 7.0, 7.0, 7.0 Hz, 1H), 3.77 (s, 3H), 3.59 (tt, J=10.6, 10.6, 4.9, 4.9 Hz, 1H), 3.26 (d, J=5.0 Hz, 1H), 3.05 (dd, J=14.1, 6.7 Hz, 1H), 2.95 (dd, J=14.1, 6.4 Hz, 1H), 2.89 (d, J=5.0 Hz, 1H), 2.44 (dd, J=11.9, 7.0 Hz, 2H), 2.34-1.93 (m, 6H), 1.93-1.78 (m, 3H), 1.78-1.59 (m, 3H), 1.55-1.40 (m, 6H), 1.27 (d, J=7.0 Hz, 4H). MS (EI) for $C_{31}H_{43}N_3O_7$, found 570.0 $(MH)^+$.

(S)—N—((S)-3-(cyclopent-1-en-1-yl)-1-((R)-2-methyloxiran-2-yl)-1-oxopropan-2-yl)-3-(4-(methylsulfonyl)phenyl)-2-((S)-2-(2-morpholinoacetamido)propanamido)propanamide (C-1125): $^1$H NMR (300 MHz, DMSO-$d_6$): δ 8.40 (d, J=7.5 Hz, 1H), 8.18 (d, J=8.4 Hz, 1H), 7.80 (d, J=7.8 Hz, 2H), 7.75 (d, J=7.2 Hz, 1H), 7.48 (d, J=7.8 Hz, 2H), 5.41 (m, 1H), 4.45-4.70 (m, 2H), 4.25 (m, 1H), 3.56 (m, 4H), 3.20 (s, 3H), 3.00-3.10 (m, 2H), 2.80-3.00 (m, 4H), 2.40 (m, 4H), 2.10-2.30 (m, 4H), 1.70-1.90 (m, 2H), 1.39 (s, 3H), 1.13 (d, J=6.9 Hz, 3H). MS (EI) for $C_{30}H_{42}N_4O_8S$, found 618.7 $(MH)^+$.

(1R,3S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxycyclopentanecarboxamide (C-1078): $^1$H NMR (300 MHz, DMSO-$d_6$): δ 8.23 (d, J=6.9 Hz, 1H), 8.04 (d, J=8.4 Hz, 1H), 7.92 (d, J=6.9 Hz, 1H), 7.10 (d, J=8.4 Hz, 2H), 6.78 (d, J=8.4 Hz, 2H), 4.45 (m, 2H), 4.30 (m, 1H), 4.10-4.20 (m, 2H), 3.69 (s, 3H), 3.20 (m, 1H), 2.90-3.10 (m, 2H), 2.80 (m, 1H), 2.60 (m, 1H), 1.40-2.00 (m, 13H), 1.40 (s, 3H), 1.00-1.20 (m, 2H), 0.95 (d, J=6.9 Hz, 3H). MS (EI) for $C_{30}H_{43}N_3O_7$, found 558.2 $(MH)^+$.

(1R,3R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxycyclopentanecarboxamide (C-1077): $^1$H NMR (300 MHz, DMSO-$d_6$): δ 8.26 (d, J=6.3 Hz, 1H), 8.04 (d, J=8.1 Hz, 1H), 7.93 (d, J=7.2 Hz, 1H), 7.10 (d, J=8.4 Hz, 2H), 6.78 (d, J=8.4 Hz, 2H), 4.75 (m, 1H), 4.45 (m, 1H), 4.30 (m, 1H), 4.20 (m, 1H), 4.10 (m, 1H), 3.69 (s, 3H), 3.20 (m, 1H), 2.90-3.10 (m, 2H), 2.50-2.70 (m, 2H), 1.40-2.00 (m, 13H), 1.40 (s, 3H), 1.00-1.20 (m, 2H), 0.95 (d, J=6.9 Hz, 3H). MS (EI) for $C_{30}H_{43}N_3O_7$, found 558.2 (MH)$^+$.

(1S,3R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxycyclopentanecarboxamide (C-1075): $^1$H NMR (300 MHz, DMSO-$d_6$): δ 8.24 (d, J=7.2 Hz, 1H), 8.04 (d, J=8.7 Hz, 1H), 7.93 (d, J=6.9 Hz, 1H), 7.10 (d, J=8.4 Hz, 2H), 6.78 (d, J=8.4 Hz, 2H), 4.45 (m, 2H), 4.30 (m, 1H), 4.10-4.20 (m, 2H), 3.70 (s, 3H), 3.20 (m, 1H), 2.90-3.10 (m, 2H), 2.80 (m, 1H), 2.60 (m, 1H), 1.40-2.00 (m, 13H), 1.40 (s, 3H), 1.00-1.20 (m, 2H), 0.95 (d, J=6.9 Hz, 3H). MS (EI) for $C_{30}H_{43}N_3O_7$, found 558.3 (MH)$^+$.

(1r,4R)—N—((R)-1-(((S)-1-(((S)-3-(cyclopent-1-en-1-yl)-1-((R)-2-methyloxiran-2-yl)-1-oxopropan-2-yl)amino)-3-(4-(methylsulfonyl)phenyl)-1-oxopropan-2-yl)amino)-1-oxopropan-2-yl)-4-hydroxycyclohexanecarboxamide (C-1096): $^1$H NMR (300 MHz, DMSO-$d_6$): δ 8.35 (d, J=6.9 Hz, 1H), 8.08 (d, J=8.4 Hz, 1H), 7.80 (d, J=8.4 Hz, 2H), 7.45 (d, J=8.4 Hz, 2H), 5.42 (m, 1H), 4.40-4.70 (m, 3H), 4.15 (m, 1H), 3.30-3.60 (m, 2H), 3.20 (s, 3H), 3.15 (m, 1H), 3.00 (m, 1H), 2.80 (m, 1H), 2.40 (m, 1H), 2.20-2.40 (m, 5H), 2.05 (m, 2H), 1.70-1.90 (m, 4H), 1.60 (m, 2H), 1.38 (s, 3H), 1.00-1.30 (m, 4H), 0.90 (d, J=7.2 Hz, 3H). MS (EI) for $C_{31}H_{43}N_3O_8S$, found 618.4 (MH)$^+$.

Example 4

(1r,4R)—N—((R)-1-(((S)-1-(((S)-3-(Cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxy-1-methylcyclohexanecarboxamide (C-111)

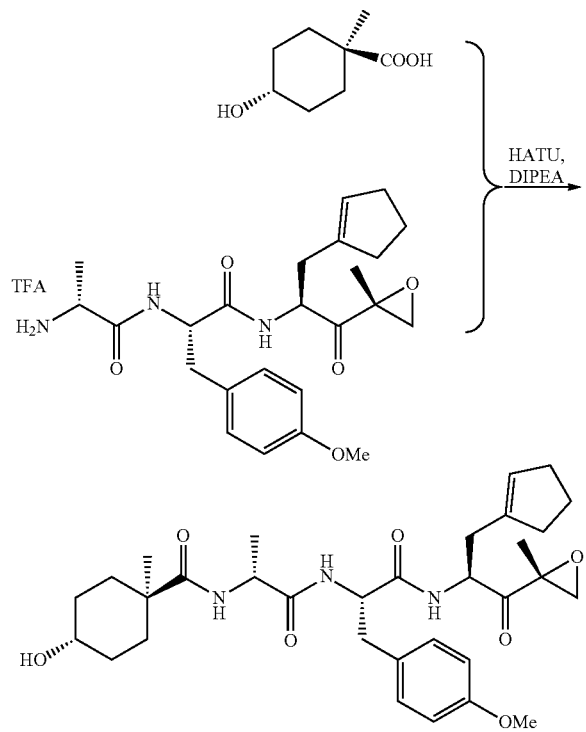

HATU (472 mg, 1.20 mmol) and DIPEA (1.48 mL) were added to a solution of (S)-2-((R)-2-aminopropanamido)-N—((S)-3-(cyclopent-1-en-1-yl)-1-((R)-2-methyloxiran-2-yl)-1-oxopropan-2-yl)-3-(4-methoxyphenyl)propanamide (TFA salt, 460 mg, 0.85 mmol) and trans-4-hydroxy-1-methylcyclohexanecarboxylic acid (131 mg, 0.83 mmol) in DMF (20 mL) at 0° C. with stirring. The reaction mixture was allowed to warm to ambient temperature and stirred for 3 h. EtOAc (100 mL) and water (100 mL) was added. The two layers were separated and the aqueous phase was extracted with EtOAc (50 mL×3). The combined organic phases were washed with brine (200 mL×3), dried over anhydrous sodium sulfate, and concentrated. The residue was purified by flash column chromatography on silica gel (CH$_2$Cl$_2$/EtOAc/MeOH=20:10:0.1) to afford (1r,4R)—N—((R)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxy-1-methylcyclohexanecarboxamide (150 mg, 30% yield). $^1$H NMR (300 MHz, DMSO-$d_6$): δ 8.33 (d, J=6.6 Hz, 1H), 7.96 (d, J=8.4 Hz, 1H), 7.38 (d, J=7.2 Hz, 1H), 7.10 (d, J=8.4 Hz, 2H), 6.78 (d, J=8.4 Hz, 2H), 5.40 (s, 1H), 4.40-4.60 (m, 2H), 4.20 (m, 1H), 3.69 (s, 3H), 3.20-3.60 (m, 2H), 3.22 (m, 1H), 2.90-3.10 (m, 2H), 2.40-2.60 (m, 2H), 2.10-2.30 (m, 5H), 2.05 (m, 2H), 1.75 (m, 2H), 1.55 (m, 2H), 1.23 (s, 3H), 1.00-1.30 (m, 5H), 0.96 (d, J=6.9 Hz, 3H). MS (EI) for $C_{32}H_{45}N_3O_7$, found 584.2 (MH)$^+$.

The following compounds were synthesized in a similar manner:

(R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-5-oxopyrrolidine-3-carboxamide (C-1067): $^1$H NMR (300 MHz, DMSO-$d_6$): δ 8.23 (d, J=6.9 Hz, 1H), 8.14 (m, 2H), 7.54 (br s, 1H), 7.11 (d, J=8.4 Hz, 2H), 6.78 (d, J=8.7 Hz, 2H), 4.31 (m, 1H), 4.29 (m, 1H), 4.21 (m, 1H), 3.70 (s, 3H), 3.21 (m, 3H), 3.02 (m, 2H), 2.60 (m, 1H), 2.22 (d, J=8.1 Hz, 2H), 2.02 (m, 1H), 1.73 (m, 2H), 1.57 (m, 2H), 1.48 (m, 4H), 1.41 (s, 3H), 1.13 (m, 2H), 0.95 (d, J=7.2 Hz, 3H). MS (EI) for $C_{29}H_{40}N_4O_7$, found 555.2 (M-H)$^-$.

(S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-5-oxopyrrolidine-3-carboxamide (C-1068): $^1$H NMR (300 MHz, DMSO-$d_6$): δ 8.27 (d, J=7.5 Hz, 1H), 8.15 (m, 2H), 7.57 (br s, 1H), 7.12 (d, J=7.8 Hz, 2H), 6.79 (d, J=8.7 Hz, 2H), 4.32 (m, 1H), 4.30 (m, 1H), 4.21 (m, 1H), 3.71 (s, 3H), 3.23 (m, 3H), 3.02 (m, 2H), 2.60 (m, 1H), 2.22 (m, 2H), 2.02 (m, 1H), 1.73 (m, 2H), 1.57 (m, 2H), 1.48 (m, 4H), 1.42 (s, 3H), 1.13 (m, 3H), 0.95 (d, J=7.2 Hz, 3H). MS (EI) for $C_{29}H_{40}N_4O_7$, found 557.3 (MH)$^-$.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)cyclopentanecarboxamide (C-1021): $^1$H NMR (300 MHz, DMSO-$d_6$): δ 8.23 (d, J=6.3 Hz, 1H), 8.02 (d, J=7.8 Hz, 1H), 7.86 (d, J=7.2 Hz, 1H), 7.10 (d, J=4.8 Hz, 2H), 6.76 (d, J=8.4 Hz, 2H), 4.41 (m, 1H), 4.27 (m, 1H), 4.13 (m, 1H), 3.68 (s, 3H), 3.00 (m, 2H), 2.96 (m, 2H), 2.54 (m, 2H), 1.90 (m, 1H), 1.72 (m, 4H), 1.54 (m, 10H), 1.39 (s, 3H), 1.07 (m, 3H), 0.93 (d, J=6.9 Hz, 3H). MS (EI) for $C_{30}H_{43}N_3O_6$, found 540.4 (MH)$^-$.

(S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)tetrahydrofuran-3-carboxamide (C-1037): $^1$H NMR (300 MHz, DMSO-$d_6$): δ 8.23 (d, J=6.9 Hz, 1H), 8.08-8.12 (m, 2H), 7.12 (d, J=8.4 Hz, 2H), 6.79 (d, J=8.4 Hz, 2H), 4.58 (m, 1H), 4.30 (m, 1H), 4.20 (m, 1H), 3.81 (m, 1H), 3.70 (s, 3H), 3.65 (m, 1H), 3.55 (m. 1H), 3.22 (d, J=4.8 Hz, 1H), 2.90-3.10 (m, 3H), 2.50-2.70 (m, 2H), 1.80-2.00 (m, 3H), 1.50-1.80 (m, 7H), 1.42 (s, 3H), 1.00-1.30 (m, 3H), 0.96 (d, J=6.6 Hz, 3H). MS (EI) for $C_{29}H_{41}N_3O_7$, found 542.2 (MH)⁻.

(S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)tetrahydro-2H-pyran-3-carboxamide (C-1053): ¹H NMR (300 MHz, DMSO-d₆): δ 8.25 (d, J=7.2 Hz, 1H), 7.90-8.10 (m, 2H), 7.12 (d, J=8.4 Hz, 2H), 6.79 (d, J=8.4 Hz, 2H), 4.45 (m, 1H), 4.30 (m, 1H), 4.18 (m, 1H), 3.80 (m, 2H), 3.71 (s, 3H), 3.20-3.40 (m, 3H), 2.90-3.10 (m, 2H), 2.65 (m, 1H), 2.40 (m, 1H), 1.90 (m, 1H), 1.50-1.85 (m, 10H), 1.41 (s, 3H), 1.00-1.30 (m, 2H), 0.95 (d, J=6.6 Hz, 3H). MS (EI) for $C_{30}H_{43}N_3O_7$, found 556.3 (MH)⁻.

(R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)tetrahydro-2H-pyran-3-carboxamide (C-1052): ¹H NMR (300 MHz, DMSO-d₆): δ 8.23 (d, J=7.2 Hz, 1H), 7.90-8.10 (m, 2H), 7.12 (d, J=8.4 Hz, 2H), 6.79 (d, J=8.4 Hz, 2H), 4.45 (m, 1H), 4.30 (m, 1H), 4.18 (m, 1H), 3.80 (m, 1H), 3.71 (s, 3H), 3.20-3.30 (m, 3H), 2.90-3.10 (m, 2H), 2.65 (m, 1H), 2.40 (m, 1H), 1.90 (m, 1H), 1.50-1.85 (m, 11H), 1.41 (s, 3H), 1.00-1.30 (m, 2H), 0.97 (d, J=6.6 Hz, 3H). ). MS (EI) for $C_{30}H_{43}N_3O_7$, found 556.3 (MH)⁻.

(1s,4S)—N—((R)-1-(((S)-1-((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxycyclohexanecarboxamide (C-1056): ¹H NMR (400 MHz, CDCl₃) δ 7.20-7.04 (m, 2H), 6.90-6.68 (m, 3H), 6.32 (d, J=7.1 Hz, 1H), 6.21 (d, J=7.1 Hz, 1H), 5.32 (s, 1H), 4.57 (q, J=7.0, 6.6, 6.6 Hz, 2H), 4.43 (p, J=7.0, 7.0, 6.9, 6.9 Hz, 1H), 3.93 (s, 1H), 3.78 (s, 3H), 3.28 (d, J=4.9 Hz, 1H), 2.98 (p, J=7.3, 7.3, 7.2, 7.2 Hz, 2H), 2.88 (d, J=5.0 Hz, 1H), 2.49 (d, J=14.1 Hz, 1H), 2.21 (ddd, J=21.9, 13.1, 7.9 Hz, 6H), 2.02-1.70 (m, 7H), 1.70-1.52 (m, 4H), 1.48 (s, 3H), 1.26 (d, J=7.0 Hz, 3H). MS (EI) for $C_{31}H_{43}N_3O_7$, found 570.0 (MH)⁺.

N—((R)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)oxetane-3-carboxamide (C-1055): ¹H NMR (400 MHz, CDCl₃) δ 7.22-7.08 (m, 2H), 6.92-6.74 (m, 2H), 6.58 (d, J=7.7 Hz, 1H), 6.25 (d, J=6.9 Hz, 1H), 6.17 (d, J=7.0 Hz, 1H), 5.31 (s, 1H), 4.91-4.66 (m, 4H), 4.55 (q, J=7.6, 7.6, 6.8 Hz, 2H), 4.40 (p, J=7.1, 7.1, 7.1, 7.1 Hz, 1H), 3.79 (s, 4H), 3.26 (d, J=5.0 Hz, 1H), 3.08-2.93 (m, 2H), 2.93-2.81 (m, 1H), 2.49 (dd, J=14.1, 2.7 Hz, 1H), 2.24-2.18 (m, 5H), 1.92-1.70 (m, 2H), 1.49 (s, 3H), 1.28 (d, J=7.0 Hz, 3H). MS (EI) for $C_{28}H_{37}N_3O_7$, found 528.0 (MH)⁺.

(1r,4R)—N—((R)-1-(((S)-1-((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxycyclohexanecarboxamide (C-1057): ¹H NMR (400 MHz, CDCl₃) δ 7.19-7.09 (m, 2H), 6.88-6.71 (m, 2H), 6.53 (d, J=7.7 Hz, 1H), 6.10 (dd, J=12.8, 7.0 Hz, 2H), 5.30 (s, 1H), 4.54 (td, J=7.9, 6.8, 3.4 Hz, 2H), 4.36 (p, J=7.0, 7.0, 7.0, 7.0 Hz, 1H), 3.78 (s, 3H), 3.61 (td, J=10.8, 10.7, 5.5 Hz, 1H), 3.28 (d, J=5.0 Hz, 1H), 2.97 (qd, J=14.1, 14.0, 14.0, 6.7 Hz, 2H), 2.89 (d, J=5.0 Hz, 1H), 2.45 (s, 1H), 2.36-2.20 (m, 3H), 2.19-2.10 (m, 2H), 2.04 (dt, J=11.7, 3.4, 3.4 Hz, 3H), 1.95-1.69 (m, 4H), 1.58-1.36 (m, 6H), 1.26 (d, J=7.0 Hz, 4H). MS (EI) for $C_{31}H_{43}N_3O_7$, found 570.0 (MH)⁺.

(S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-6-oxopiperidine-3-carboxamide (C-1059): ¹H NMR (300 MHz, DMSO-d₆): δ 8.25 (d, J=7.5 Hz, 1H), 8.06-8.12 (m, 2H), 7.43 (s, 1H), 7.12 (d, J=8.4 Hz, 2H), 6.79 (d, J=8.4 Hz, 2H), 4.45 (m, 1H), 4.30 (m, 1H), 4.18 (m, 1H), 3.71 (s, 3H), 3.10-3.30 (m, 3H), 2.90-3.10 (m, 2H), 2.50-2.70 (m, 2H), 2.10 (m, 2H), 1.50-1.85 (m, 9H), 1.41 (s, 3H), 1.00-1.30 (m, 4H), 0.95 (d, J=6.6 Hz, 3H). MS (EI) for $C_{30}H_{42}N_4O_7$, found 571.0 (MH)⁺.

(R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-6-oxopiperidine-3-carboxamide (C-1058): ¹H NMR (300 MHz, CDCl₃): δ 7.40 (m, 1H), 7.33 (m, 2H), 6.92-6.86 (m, 3H), 6.40 (d, J=7.2 Hz, 1H), 4.91 (m, 1H), 4.68 (m, 1H), 4.47-4.43 (m, 2H), 4.40 (m, 1H), 3.81 (s, 3H), 3.74-3.72 (m, 4H), 3.25 (d, J=4.8 Hz, 1H), 2.99 (m, 1H), 2.91 (d, J=4.8 Hz, 1H), 2.51 (m, 4H), 1.74-1.63 (m, 4H), 1.61 (m, 5H), 1.53 (s, 3H), 1.33 (d, J=6.9 Hz, 3H), 1.28-1.20 (m, 3H). MS (EI) for $C_{30}H_{44}N_4O_8$, found 589.3 (MH)⁺.

(1r,4R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxycyclohexanecarboxamide (C-1064): ¹H NMR (400 MHz, CDCl₃) δ 8.22 (d, J=7.0 Hz, 1H), 7.95 (d, J=8.7 Hz, 1H), 7.81 (d, J=7.2 Hz, 1H), 7.26-7.00 (m, 2H), 6.96-6.69 (m, 2H), 4.50 (d, J=3.7 Hz, 1H), 4.43 (td, J=10.1, 9.5, 3.9 Hz, 1H), 4.29 (q, J=7.2, 7.2, 7.2 Hz, 1H), 4.24-4.07 (m, 1H), 3.28 (s, 1H), 3.21 (s, 1H), 3.00 (d, J=5.3 Hz, 1H), 2.95 (dd, J=13.8, 3.8 Hz, 1H), 2.60 (dd, J=13.9, 10.2 Hz, 1H), 2.07 (s, 1H), 1.84-1.77 (m, 2H), 1.76-1.43 (m, 8H), 1.40 (s, 3H), 1.36-1.21 (m, 2H), 1.21-1.00 (m, 4H), 0.94 (d, J=7.1 Hz, 3H). MS (EI) for $C_{31}H_{45}N_3O_7$, found 572.3 (MH)⁺.

(R)—N—((R)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-1-methylpiperidine-3-carboxamide (C-1099): ¹H NMR (300 MHz, DMSO-d₆): δ 8.28 (d, J=7.2 Hz, 1H), 8.02 (m, 2H), 7.12 (d, J=8.7 Hz, 2H), 6.78 (d, J=8.7 Hz, 2H), 5.42 (m, 1H), 4.62 (m, 1H), 4.48 (m, 1H), 4.18 (m, 1H), 3.71 (s, 3H), 3.22 (d, J=5.4 Hz, 1H), 2.99 (d, J=5.4 Hz, 1H), 2.91 (m, 1H), 2.62 (m, 3H), 2.51 (m, 2H), 2.37 (m, 4H), 2.10 (d, J=5.4 Hz, 3H), 1.89-1.78 (m, 4H), 1.83 (m, 2H), 1.44 (s, 3H), 1.38 (m, 2H), 0.96 (d, J=7.2 Hz, 3H). MS (EI) for $C_{31}H_{44}N_4O_6$, found 569.4 (MH)⁺.

N—((R)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-1-methylpiperidine-4-carboxamide (C-1098): ¹H NMR (300 MHz, DMSO-d₆): δ 8.27 (d, J=7.2 Hz, 1H), 8.00 (d, J=8.7 Hz, 1H), 7.86 (d, J=7.2 Hz, 1H), 7.10 (d, J=8.7 Hz, 2H), 6.77 (d, J=8.7 Hz, 2H), 5.41 (m, 1H), 4.62 (m, 2H), 4.19 (m, 1H), 3.70 (s, 3H), 3.22 (d, J=5.1 Hz, 1H), 2.99 (d, J=5.4 Hz, 1H), 2.91 (m, 1H), 2.62 (m, 2H), 2.59 (m, 1H), 2.50 (m, 2H), 2.21 (m, 4H), 1.94 (m, 3H), 1.85 (m, 3H), 1.77 (m, 4H), 1.51 (s, 3H), 1.38 (m, 2H), 0.94 (d, J=6.9 Hz, 3H). MS (EI) for $C_{31}H_{44}N_4O_6$, found 569.3 (MH)⁺.

(1s,4S)—N—((R)-1-(((S)-1-(((S)-3-(cyclohex-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxycyclohexanecarboxamide (C-1097): ¹H NMR (400 MHz, CDCl3): 7.18-7.16 (m, 2H), 6.85-8.82 (m, 2H), 6.85-6.56 (m, 2H), 6.58-6.56 (m, 1H), 6.06-6.02 (m, 2H), 5.27 (s, 1H), 4.53-4.51 (m, 2H), 4.40-4.36 (m, 1H), 3.95-3.91 (m, 1H), 3.78 (s, 3H), 3.31-3.30 (m, 1H), 3.01-

2.88 (m, 3H), 2.41-2.32 (m, 1H), 2.25-2.18 (m, 1H), 1.98-1.44 (m, 19H), 1.29 (m 3H). MS (EI) for $C_{32}H_{45}N_3O_7$, found 584.0 (MH)$^+$.

(2S)-2-((2S)-2-(2-(6-oxa-3-azabicyclo[3.1.1]heptan-3-yl)acetamido)propanamido)-N—((S)-3-cyclopentyl-1-((R)-2-methyloxiran-2-yl)-1-oxopropan-2-yl)-3-(4-methoxyphenyl)propanamide (C-1229): $^1$H NMR (400 MHz, DMSO-d6): 8.31-8.05 (m, 4H), 7.74-7.72 (m, 1H), 7.12-7.10 (m, 2H), 6.80-6.77 (m, 2H), 4.49-4.22 (m, 5H), 3.70 (s 3H), 3.66-3.58 (m, 4H), 3.32 (s, 3H), 3.19-3.10 (m, 4H), 3.04-2.90 (m, 3H), 2.78-2.60 (m, 2H), 2.22-2.21 (m, 1H), 1.90-1.42 (m, 4H), 1.41 (s, 3H), 1.16-1.14 (d, 3H). MS (EI) for $C_{31}H_{44}N_4O_7$, found 585.0 (MH)$^+$.

(1s,4S)—N—((R)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxy-1-methylcyclohexanecarboxamide (C-1112): $^1$H NMR (300 MHz, DMSO-d$_6$): δ 8.30 (d, J=6.9 Hz, 1H), 7.93 (d, J=8.7 Hz, 1H), 7.33 (d, J=7.2 Hz, 1H), 7.08 (d, J=8.4 Hz, 2H), 6.78 (d, J=8.4 Hz, 2H), 5.40 (s, 1H), 4.40-4.60 (m, 2H), 4.37 (m, 1H), 4.20 (m, 1H), 3.69 (s, 3H), 3.45 (m, 1H), 3.22 (m, 1H), 2.90-3.10 (m, 2H), 2.40-2.60 (m, 4H), 2.15-2.30 (m, 5H), 1.75-1.85 (m, 2H), 1.40-1.70 (m, 6H), 1.38 (s, 3H), 1.00-1.30 (m, 2H), 0.96 (d, J=6.9 Hz, 3H). MS (EI) for $C_{32}H_{45}N_3O_7$, found 582.1 (MH)$^-$.

Example 5

(S)—N—((S)-3-(Cyclopent-1-en-1-yl)-1-((R)-2-methyloxiran-2-yl)-1-oxopropan-2-yl)-2-((S)-2-(2-morpholinoacetamido)propanamido)-4-phenylbutanamide (C-1128)

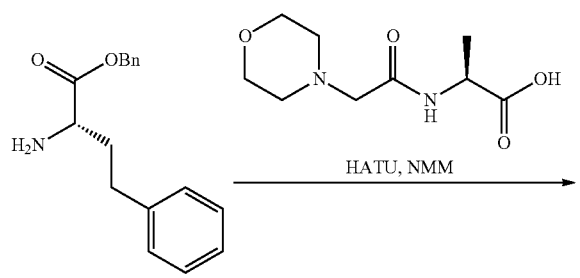

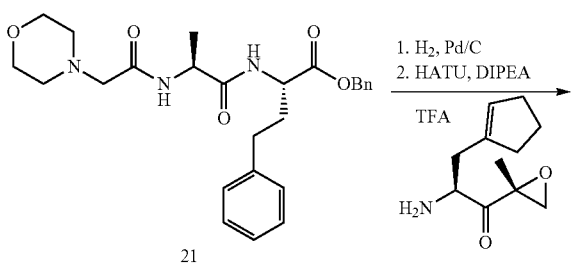

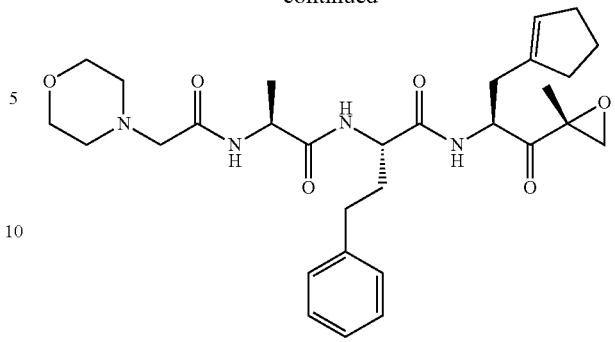

N-Methylmorpholine (1.09 g, 10.8 mmol) was added to a mixture of (S)-2-(2-morpholinoacetamido)propanoic acid (0.58 g, 2.7 mmol), (S)-benzyl 2-amino-4-phenylbutanoate (TFA salt, 1.03 g, 2.7 mmol) and HATU (1.13 g, 2.97 mmol) in dichloromethane (50 mL) at 0° C. The reaction mixture was allowed to warm to ambient temperature and stirred for 1 h. Water (50 mL) was added and the resulting mixture was extracted with dichloromethane (50 mL×3). The organic extracts were combined, dried over anhydrous sodium sulfate, and concentrated. The residue was purified by flash column chromatography on silica gel (dichloromethane/methanol=100:1 to 10:1) to afford (S)-benzyl 2-((S)-2-(2-morpholinoacetamido)propanamido)-4-phenylbutanoate (0.9 g, 71% yield).

(S)-Benzyl 2-((S)-2-(2-morpholinoacetamido)propanamido)-4-phenylbutanoate (0.62 g, 1.3 mmol) was hydrogenated in the presence of Pd/C (0.1 g) in methanol (20 mL) for 1 h at ambient temperature. Pd/C was filtered off and the filtrate was concentrated to afford the corresponding acid.

The acid was dissolved in dichloromethane (30 mL) and treated with (S)-2-amino-3-(cyclopent-1-en-1-yl)-1-((R)-2-methyloxiran-2-yl)propan-1-one (0.450 g, 1.33 mmol) and HATU (0.560 g, 1.46 mmol). N-Methylmorpholine (0.53 g, 5.2 mmol) was added to the solution at 0° C. The reaction mixture was allowed to warm to ambient temperature and stirred for 1 h. Water (50 mL) was added and the resulting mixture was extracted with dichloromethane (50 mL×3). The organic extracts were combined, dried over anhydrous sodium sulfate, and concentrated. The residue was purified by flash column chromatography on silica gel (dichloromethane/methanol=100:1 to 20:1) and prep-TLC to afford (S)—N—((S)-3-(cyclopent-1-en-1-yl)-1-((R)-2-methyloxiran-2-yl)-1-oxopropan-2-yl)-2-((S)-2-(2-morpholinoacetamido)propanamido)-4-phenylbutanamide (195 mg, 26% yield). $^1$H NMR (300 MHz, DMSO-d$_6$): δ 8.22 (d, J=6.9 Hz, 1H), 8.13 (d, J=7.5 Hz, 1H), 7.87 (d, J=7.5 Hz, 1H), 7.28 (m, 2H), 7.17 (m, 3H), 5.41 (m, 1H), 4.49 (m, 1H), 4.37 (m, 2H), 4.28 (m, 1H), 3.58 (m, 4H), 3.22 (d, J=5.1 Hz, 1H), 2.97 (m, 1H), 2.92 (m, 2H), 2.43 (m, 4H), 2.24 (m, 5H), 1.83 (m, 4H), 1.37 (s, 3H), 1.23 (m, 2H), 1.22 (d, J=6.9 Hz, 3H). MS (EI) for $C_{30}H_{42}N_4O_6$, found 555.6 (MH)$^+$.

The following compounds were synthesized in a similar manner:

(S)—N—((S)-3-cyclopentyl-1-((R)-oxiran-2-yl)-1-oxopropan-2-yl)-3-(3,4-dimethoxyphenyl)-2-((S)-2-(2-morpholinoacetamido)propanamido)propanamide (C-1071): $^1$H NMR (300 MHz, DMSO-d$_6$): δ 8.49 (d, J=8.1 Hz, 1H), 8.26 (d, J=8.7 Hz, 1H), 7.83 (d, J=8.7 Hz, 1H), 6.71-6.86 (m, 3H), 4.53 (m, 1H), 4.28 (m, 2H), 3.72 (s, 3H), 3.69 (s, 3H), 3.55 (m, 4H), 2.62-3.03 (m, 6H), 2.37 (m, 4H), 1.40-1.97 (m, 9H), 1.24 (s, 3H), 1.16 (d, J=6.9 Hz, 3H). MS (EI) for C$_{30}$H$_{44}$N$_4$O$_8$, found 587.3 (MH)$^-$.

(S)—N—((S)-3-cyclopentyl-1-((R)-2-methyloxiran-2-yl)-1-oxopropan-2-yl)-3-(4-(methylsulfonyl)phenyl)-2-((S)-2-(2-morpholinoacetamido)propanamido)propanamide (C-1027): $^1$H NMR (300 MHz, DMSO-d$_6$): δ 8.38 (d, J=7.2 Hz, 1H), 8.15 (d, J=8.1 Hz, 1H), 7.80 (d, J=8.4 Hz, 2H), 7.73 (d, J=7.8 Hz, 1H), 7.49 (d, J=8.4 Hz, 2H), 4.60 (m, 1H), 4.20-4.40 (m, 2H), 3.60 (m, 4H), 3.44 (m. 1H), 3.18 (s, 3H), 3.10-3.20 (m, 2H), 2.80-3.00 (m, 3H), 2.40 (m, 4H), 1.40-2.00 (m, 7H), 1.40 (s, 3H), 1.16 (d, J=6.6 Hz, 3H). MS (EI) for C$_{30}$H$_{44}$N$_4$O$_8$S, found 621.3 (MH)$^+$.

(S)—N—((S)-3-cyclopentyl-1-((R)-2-methyloxiran-2-yl)-1-oxopropan-2-yl)-3-(3-(methylsulfonyl)phenyl)-2-((S)-2-(2-morpholinoacetamido)propanamido)propanamide (C-1024): $^1$H NMR (300 MHz, DMSO-d$_6$): δ 8.42 (d, J=7.5 Hz, 1H), 8.15 (d, J=8.1 Hz, 1H), 7.70-7.90 (m, 3H), 7.50-7.60 (m, 2H), 4.60 (m, 1H), 4.20-4.40 (m, 2H), 3.60 (m, 4H), 3.44 (m. 1H), 3.18 (s, 3H), 3.10-3.20 (m, 2H), 2.80-3.00 (m, 3H), 2.40 (m, 4H), 1.40-2.00 (m, 7H), 1.40 (s, 3H), 1.16 (d, J=6.6 Hz, 3H). MS (EI) for C$_{30}$H$_{44}$N$_4$O$_8$S, found 621.3 (MH)$^+$.

(S)-3-(4-cyanophenyl)-N—((S)-3-cyclopentyl-1-((R)-2-methyloxiran-2-yl)-1-oxopropan-2-yl)-2-((S)-2-(2-morpholinoacetamido)propanamido)propanamide (C-1050): $^1$H NMR (300 MHz, DMSO-d$_6$): δ 8.35 (d, J=6.9 Hz, 1H), 8.15 (d, J=8.1 Hz, 1H), 7.75 (br s, 1H), 7.72 (d, J=8.1 Hz, 2H), 7.42 (d, J=7.8 Hz, 2H), 4.61 (m, 1H), 4.26 (m, 2H), 3.56 (m, 4H), 3.17 (d, J=5.1 Hz, 1H), 2.73-3.10 (m, 5H), 2.37 (m, 4H), 1.42-2.03 (m, 11H), 1.42 (s, 3H), 0.86 (d, J=6.6 Hz, 3H). MS (EI) for C$_{30}$H$_{41}$N$_5$O$_6$, found 566.5 (MH)$^-$.

4-((S)-3-(((S)-3-cyclopentyl-1-((R)-2-methyloxiran-2-yl)-1-oxopropan-2-yl)amino)-2-((S)-2-(2-morpholinoacetamido)propanamido)-3-oxopropyl)$_b$ enzamide (C-1049): $^1$H NMR (300 MHz, DMSO-d$_6$): δ 8.34 (d, J=6.9 Hz, 1H), 8.11 (d, J=8.1 Hz, 1H), 7.90 (br s, 1H), 7.76 (d, J=8.4 Hz, 2H), 7.71 (m, 1H), 7.29 (m, 1H), 7.28 (d, J=7.8 Hz, 2H), 4.62 (m, 1H), 4.28 (m, 2H), 3.55 (m, 4H), 3.18 (d, J=5.1 Hz, 1H), 2.71-3.06 (m, 5H), 2.35 (m, 4H), 1.42-1.89 (m, 11H), 1.42 (s, 3H), 1.15 (d, J=6.9 Hz, 3H). MS (EI) for C$_{30}$H$_{43}$N$_5$O$_7$, found 584.4 (MH)$^-$.

(S)—N—((S)-3-cyclopentyl-1-((R)-2-methyloxiran-2-yl)-1-oxopropan-2-yl)-2-((S)-2-(2-morpholinoacetamido)propanamido)-3-(4-sulfamoylphenyl)propanamide (C-1054): $^1$H NMR (300 MHz, DMSO-d$_6$): δ 8.37 (d, J=7.2 Hz, 1H), 8.11 (d, J=8.4 Hz, 1H), 7.76 (d, J=7.8 Hz, 1H), 7.69 (d, J=8.1 Hz, 2H), 7.39 (d, J=8.1 Hz, 2H), 7.29 (br s, 2H), 4.56 (m, 1H), 4.27 (m, 2H), 3.56 (m, 4H), 3.16 (d, J=5.4 Hz, 1H), 2.74-3.11 (m, 5H), 2.38 (m, 4H), 1.42-1.91 (m, 11H), 1.42 (s, 3H), 1.15 (d, J=6.9 Hz, 3H). MS (EI) for C$_{29}$H$_{43}$N$_5$O$_8$S, found 622.3 (MH)$^+$.

Example 6

(S)—N—((S)-3-(Cyclohex-1-en-1-yl)-1-((R)-2-methyloxiran-2-yl)-1-oxopropan-2-yl)-3-(4-methoxyphenyl)-2-((S)-2-(2-morpholinoacetamido)-2-(oxetan-3-yl)acetamido)propanamide (C-1138)

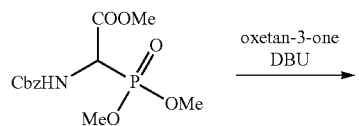

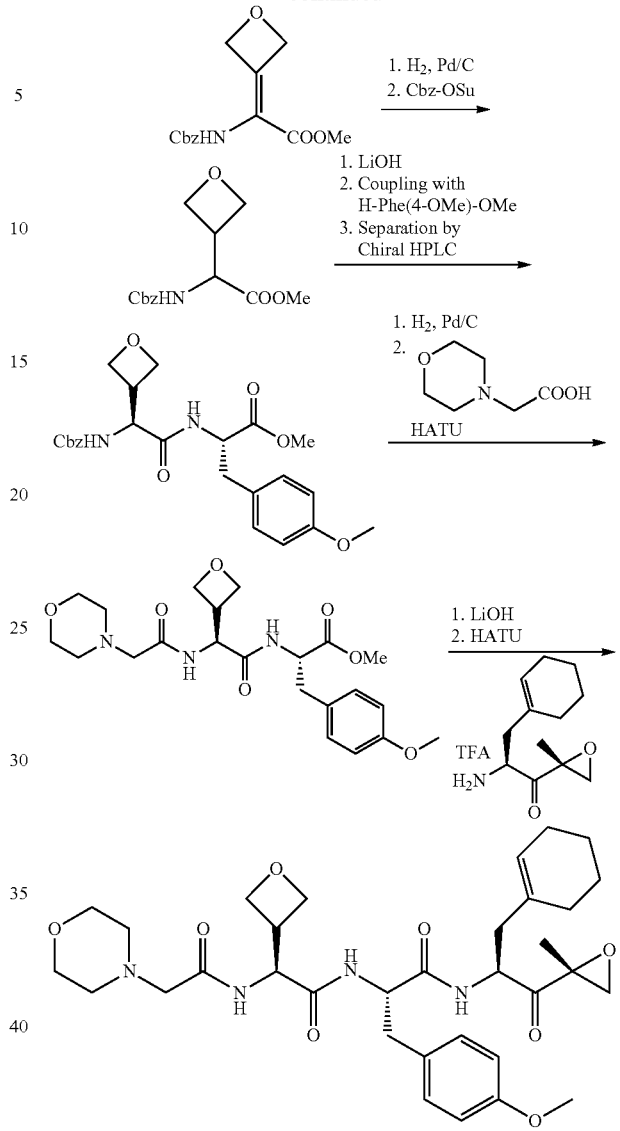

1,8-Diazabicycloundec-7-ene (DBU; 16.25 g, 95 mmol) was added dropwise to a solution of N-benzyloxy carbonyl-(phosphono glycine trimethylester) (23.0 g, 70.0 mmol) and oxetan-3-one (5.0 g, 70 mmol) in methylene chloride (200 mL) at ambient temperature under N$_2$. The reaction mixture was stirred for 48 h at ambient temperature. The solvent was removed and the residue was dissolved in EtOAc (500 mL). The resulting solution was washed with 5% aqueous KHSO$_4$ (300 mL×2), saturated aqueous NaHCO$_3$ (300 mL×3), and brine (200 mL×1), respectively. The organic phase was dried over anhydrous sodium sulfate and concentrated. The residue was purified by flash column chromatography on silica gel (Hexane/EtOAc=5:1) to afford methyl 2-(benzyloxycarbonylamino)-2-(oxetan-3-ylidene)acetate (13.5 g, 69% yield).

Pd/C (10%, 5.0 g) was added to a solution of methyl 2-(benzyloxycarbonylamino)-2-(oxetan-3-ylidene)acetate (10.0 g, 36 mmol) in MeOH (100 mL). The suspension was stirred under hydrogen atmosphere at ambient temperature for 12 h. The catalyst was filtered off and washed with MeOH (100 mL). The filtrate and washings were combined followed by addition of benzyloxycarbonyl N-succinimide (Cbz-OSu; 10.0 g, 40 mmol) and triethylamine (15.2 mL, 108 mmol). The reaction mixture was stirred for 12 h at ambient temperature and then concentrated. The residue was purified by flash column chromatography on silica gel (Hexane/EtOAc=5:1) to afford methyl 2-(benzyloxycarbonylamino)-2-(oxetan-3-yl)acetate (4.3 g, 41% yield) as a yellow solid.

A solution of LiOH (650 mg, 27.0 mmol) in water (10 mL) was added to a solution methyl 2-(benzyloxycarbonylamino)-2-(oxetan-3-yl)acetate (2.5 g, 9.0 mmol) in tetrahydrofuran (THF; 50 mL) at 0° C. with stirring. The reaction mixture was stirred for 12 h and then acidified with 2 N aqueous HCl to pH=3. Most of the solvent was removed and the remaining mixture was extracted with EtOAc (50 mL×3). The combined organic phases were washed with brine (50 mL×1), dried over anhydrous sodium sulfate and concentrated to afford the corresponding acid (2.0 g), which was used directly without further purification.

4-(4,6-Dimethoxy-1,3,5-triazin-2-yl)-4-methylmorpholinium chloride (DMTMM; 4.4 g, 16 mmol) and N-methylmorpholine (3.2 g, 32 mmol) were added to a solution of the acid (2.0 g, 8.0 mmol) and L-4-methoxylphenylalanine methyl ester hydrochloride (2.0 g, 8.2 mmol) in methylene chloride (100 mL) at 0° C. with stirring. The suspension was stirred for 1 h at ambient temperature and then washed with 5% aqueous KHSO$_4$ (100 mL×2), saturated aqueous NaHCO$_3$ (100 mL×3), and brine (50 mL×1), respectively. The organic phase was dried over anhydrous sodium sulfate and concentrated. The residue was purified by flash column chromatography on silica gel (Hexane/EtOAc=3:1) to afford a mixture of two diastereomers (2.5 g), which was further separated by chiral prep-HPLC to give (S)-methyl 2-((S)-2-(benzyloxycarbonylamino)-2-(oxetan-3-yl)acetamido)-3-(4-methoxyphenyl)propanoate (1.1 g, 26% yield) as a colorless solid.

Pd/C (10%, 1.0 g) was added to a solution of (S)-methyl 2-((S)-2-(benzyloxycarbonylamino)-2-(oxetan-3-yl)acetamido)-3-(4-methoxyphenyl)propanoate (600 mg, 1.30 mmol) in MeOH (10 mL). The suspension was stirred under hydrogen atmosphere at ambient temperature for 2 h. The catalyst was filtered off and washed with MeOH (10 mL). The filtrate and washings were combined and concentrated to dryness.

The residue was dissolved in methylene chloride (50 mL) followed by addition of 2-morpholinoacetic acid (190 mg, 1.30 mmol), HATU (550 mg, 1.40 mmol) and DIPEA (0.70 mL, 410 mmol) at 0° C. The reaction mixture was allowed to warm to ambient temperature and stirred for 0.5 h. Saturated aqueous NaHCO$_3$ (20 mL) was added and two phases were separated. The aqueous phase was extracted with CH$_2$Cl$_2$ (20 mL×3). The combined organic phases were washed with brine (20 mL×3), dried over anhydrous sodium sulfate and concentrated. The residue was purified by flash column chromatography on silica gel (CH$_2$Cl$_2$/MeOH=50:1) to afford (S)-methyl 3-(4-methoxyphenyl)-2-((S)-2-(2-morpholinoacetamido)-2-(oxetan-3-yl) acetamido)propanoate (280 mg, 48% yield).

A solution of LiOH (70 mg, 2.8 mmol) in water (10 mL) was added to a solution of (S)-methyl 3-(4-methoxyphenyl)-2-((S)-2-(2-morpholinoacetamido)-2-(oxetan-3-yl)acetamido)propanoate (340 mg, 0.760 mmol) in THF (10 mL) at 0° C. with stirring. The reaction mixture was stirred for 3 h and then acidified with 2N aqueous HCl to pH=3. The mixture was concentrated to dryness to afford the corresponding acid (350 mg), which was used directly without further purification.

HATU (320 mg, 0.800 mmol) and DIPEA (0.5 mL) were added to a solution of the acid (350 mg, 0.760 mmol) and (S)-2-amino-3-(cyclohex-1-en-1-yl)-1-((R)-2-methyloxiran-2-yl)propan-1-one (TFA salt, 0.8 mmol) in DMF (20 mL) at 0° C. with stirring. The suspension was allowed to warm to ambient temperature and stirred for 1 h. The mixture was diluted with EtOAc (100 mL) and then washed with 5% aqueous KHSO$_4$ (50 mL×3), saturated aqueous NaHCO$_3$ (50 mL×3), and brine (50 mL×1) respectively. The organic phase was dried over anhydrous sodium sulfate and concentrated. The residue was purified by flash column chromatography on silica gel (CH$_2$Cl$_2$/EtOAc/MeOH=20:10:0.5) to afford (S)—N—((S)-3-(cyclohex-1-en-1-yl)-1-((R)-2-methyloxiran-2-yl)-1-oxopropan-2-yl)-3-(4-methoxyphenyl)-2-((S)-2-(2-morpholinoacetamido)-2-(oxetan-3-yl)acetamido)propanamide (120 mg, 25% yield over two steps) as a yellow solid. $^1$H NMR (300 MHz, DMSO-d$_6$): δ 8.28 (d, J=7.5 Hz, 1H), 8.16 (d, J=7.2 Hz, 1H), 7.90 (d, J=7.8 Hz, 1H), 7.10 (d, J=7.2 Hz, 2H), 6.78 (d, J=7.2 Hz, 2H), 5.38 (m, 1H), 4.62 (m, 1H), 4.40-4.60 (m, 4H), 4.20-4.40 (m, 2H), 3.70 (s, 3H), 3.54 (m, 4H), 3.20 (m, 1H), 2.90-3.10 (m, 4H), 2.75 (m, 1H), 2.20-2.50 (m, 6H), 1.80-2.10 (m, 5H), 1.50-1.70 (m, 4H), 1.37 (s, 3H). MS (EI) for C$_{33}$H$_{46}$N$_4$O$_8$, found 627.2 (MH)$^+$.

Example 7

(S)—N—((S)-1-(((S)-3-(Cyclopent-1-en-1-yl)-1-((R)-2-methyloxiran-2-yl)-1-oxopropan-2-yl)amino)-3-(4-methoxyphenyl)-1-oxopropan-2-yl)-2-(2-morpholinoacetamido)pent-4-ynamide (C-1139)

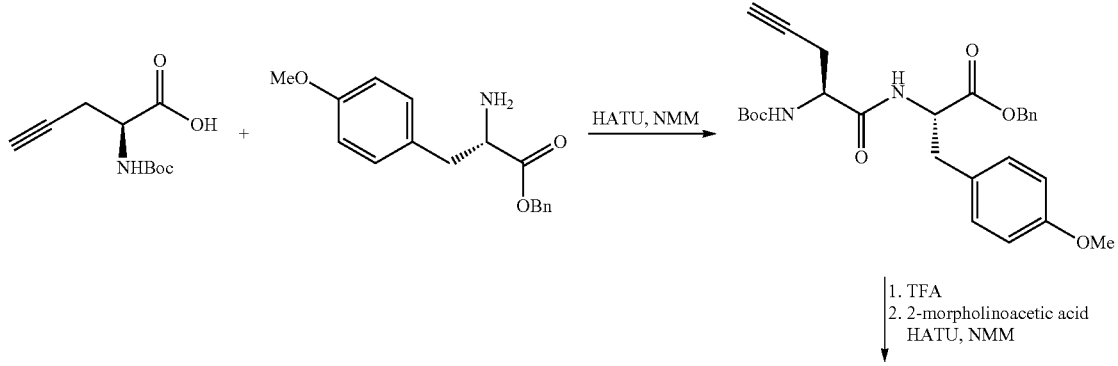

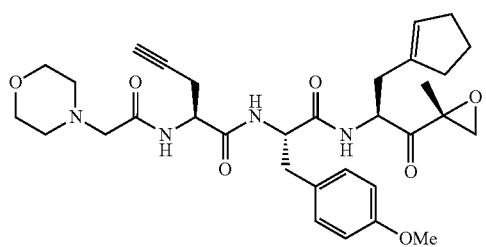 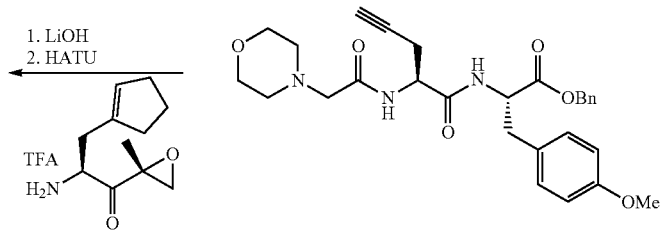

1. LiOH
2. HATU

TFA
H₂N

HATU (1.2 g, 3.1 mmol) was added to a solution of (S)-2-(tert-butoxycarbonylamino) pent-4-ynoic acid (0.6 g, 2.8 mmol) and (S)-benzyl 2-amino-3-(4-methoxyphenyl) propanoate (HCl salt, 1.0 g, 3.1 mmol) in dichloromethane (20 mL) at 0° C. N-Methylmorpholine (1.20 mL, 11.3 mmol) was added and the reaction mixture was allowed to warm to ambient temperature and stirred for 1 h. Water (20 mL) was added and the resulting mixture was extracted with dichloromethane (20 mL×3). The organic extracts were combined, dried over anhydrous sodium sulfate, and concentrated. The residue was purified by flash column chromatography on silica gel (petroleum ether/EtOAc=10:1 to 5:1) to afford (S)-benzyl 2-((S)-2-(tert-butoxycarbonylamino)pent-4-ynamido)-3-(4-methoxy phenyl)propanoate (1.1 g, 81% yield) as a colorless solid.

(S)-Benzyl 2-((S)-2-(tert-butoxycarbonylamino)pent-4-ynamido)-3-(4-methoxy phenyl)propanoate (1.1 g, 2.3 mmol) was dissolved in dichloromethane (10 mL) and treated with TFA (1.5 mL) for 1 h at ambient temperature. The solvent was removed and the residue was added to a solution of 2-morpholinoacetic acid (0.33 g, 2.3 mmol) and HATU (1.0 g, 2.6 mmol) in dichloromethane (20 mL). N-Methylmorpholine (0.63 mL, 5.7 mmol) was added at 0° C. The reaction mixture was allowed to warm to ambient temperature and stirred for 1 h. Water (20 mL) was added and the resulting mixture was extracted with dichloromethane (20 mL×3). The organic extracts were combined, dried over anhydrous sodium sulfate, and concentrated. The residue was purified by flash column chromatography on silica gel (dichloromethane/methanol=200:1 to 100:1) to afford (S)-Benzyl 3-(4-methoxyphenyl)-2-((S)-2-(2-morpholinoacetamido)pent-4-ynamido)propanoate (0.8 g, 69% yield) as a colorless solid.

A solution of (S)-benzyl 3-(4-methoxyphenyl)-2-((S)-2-(2-morpholinoacetamido)pent-4-ynamido)propanoate (0.8 g, 1.6 mmol) in water/THF (5 mL/3 mL) was treated with LiOH—H₂O (0.13 g, 3.1 mmol) for 1 h at ambient temperature. The mixture was neutralized to pH=7 with concentrated aqueous HCl and then concentrated under vacuum to dryness.

The residue was added to a mixture of (S)-2-amino-3-(cyclopent-1-en-1-yl)-1-((R)-2-methyloxiran-2-yl)propan-1-one (0.50 g, 1.6 mmol) and HATU (0.66 g, 1.7 mmol) in dichloromethane (20 mL). N-Methylmorpholine (0.43 mL, 4.0 mmol) was added at 0° C. The reaction mixture was allowed to warm to ambient temperature and stirred for 1 h. Water (30 mL) was added and the resulting mixture was extracted with dichloromethane (30 mL×3). The organic extracts were combined, dried over anhydrous sodium sulfate, and concentrated. The residue was purified by flash column chromatography on silica gel (dichloromethane/methanol=200:1 to 80:1) to afford (S)—N—((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)-2-(2-morpholinoacetamido)pent-4-ynamide (130 mg, 14% yield). ¹H NMR (300 MHz, DMSO-d₆): δ 8.35 (d, J=7.2 Hz, 1H), 8.09 (d, J=8.4 Hz, 1H), 7.86 (d, J=8.4 Hz, 1H), 7.10 (d, J=8.4 Hz, 2H), 6.78 (d, J=8.4 Hz, 2H), 5.40 (m, 1H), 4.49 (m, 3H), 3.70 (s, 3H), 3.57 (m, 4H), 3.18 (d, J=5.1 Hz, 1H), 2.99 (d, J=5.1 Hz, 1H), 2.84 (m, 2H), 2.63 (m, 2H), 2.41 (m, 6H), 2.23 (m, 6H), 1.80 (m, 2H), 1.38 (s, 3H). MS (EI) for C₃₂H₄₂N₄O₇, found 595.28 (MH)⁺.

The following compounds were synthesized in a similar manner:

(S)—N—((S)-3-cyclopentyl-1-((R)-2-methyloxiran-2-yl)-1-oxopropan-2-yl)-3-(furan-2-yl)-2-((S)-2-(2-morpholinoacetamido)propanamido)propanamide (C-1013): ¹H NMR (300 MHz, CDCl₃): δ 7.60 (br s, 1H), 7.32 (m, 1H), 6.80 (d, 1H), 6.50 (d, 1H), 6.28 (m, 1H), 6.12 (d, J=3.3 Hz, 1H), 4.72 (m, 1H), 4.46 (m, 2H), 3.78 (m, 4H), 3.67 (m, 1H), 3.26 (d, J=4.8 Hz, 1H), 3.16-3.06 (m, 4H), 2.57 (m, 1H), 1.74 (m, 4H), 1.73-1.64 (m, 10H), 1.55 (d, 3H), 1.48-0.92 (m, 3H). MS (EI) for C₂₇H₄₀N₄O₇, found 533.4 (MH)⁺.

N—((R)-1-(((S)-1-(((S)-3-cyclopentyl-1-((R)-2-methyloxiran-2-yl)-1-oxopropan-2-yl)amino)-3-(4-(methylsulfonyl)phenyl)-1-oxopropan-2-yl)amino)-1-oxopropan-2-yl) tetrahydro-2H-pyran-4-carboxamide (C-1051): ¹H NMR (300 MHz, DMSO-d₆): δ 8.32 (d, J=6.3 Hz, 1H), 8.14 (d, J=8.7 Hz, 1H), 7.90 (d, J=6.9 Hz, 1H), 7.80 (d, J=8.1 Hz, 2H), 7.47 (d, J=8.1 Hz, 2H), 4.65 (m, 1H), 4.30 (m, 1H), 4.15 (m, 1H), 3.40 (m, 2H), 3.30 (m, 2H), 3.18 (s, 3H), 3.15 (m, 1H), 3.08 (m, 1H), 2.82 (m, 1H), 2.40 (m, 1H), 1.95 (m, 1H), 1.40-1.80 (m, 12H), 1.42 (s, 3H), 1.00-1.30 (m, 2H), 0.94 (d, J=6.9 Hz, 3H). MS (EI) for C₃₀H₄₃N₃O₈S, found 606.0 (MH)⁻.

(1r,4R)—N—((R)-1-(((2S,3R)-1-(((S)-3-(cyclopent-1-en-1-yl)-1-((R)-2-methyloxiran-2-yl)-1-oxopropan-2-yl)amino)-3-hydroxy-3-(4-methoxyphenyl)-1-oxopropan-2-yl)amino)-1-oxopropan-2-yl)-4-hydroxycyclohexanecarboxamide (C-1080): ¹H NMR (400 MHz, CDCl₃) δ 7.94 (dd, J=13.9, 7.1 Hz, 2H), 7.73 (d, J=9.0 Hz, 1H), 7.24 (s, 2H), 6.94-6.68 (m, 2H), 5.53 (s, 1H), 5.41 (s, 1H), 5.02 (s, 1H), 4.56 (q, J=7.7, 7.7, 7.7 Hz, 1H), 4.30 (dd, J=9.0, 2.8 Hz, 1H), 4.23 (p, J=7.0, 7.0, 7.0, 7.0 Hz, 1H), 3.71 (s, 3H), 3.21 (d, J=5.2 Hz, 1H), 2.96 (d, J=5.2 Hz, 1H), 2.50 (tt, J=3.3, 3.3, 1.7, 1.7 Hz, 3H), 2.44 (dd, J=14.5, 5.6 Hz, 1H), 2.38-2.12 (m, 5H), 2.12-2.01 (m, 1H), 1.80 (d, J=7.2 Hz, 4H), 1.73-1.59 (m, 2H), 1.44-1.24 (m, 4H), 1.09 (d, J=13.2 Hz, 2H), 0.98 (d, J=7.1 Hz, 3H). MS (EI) for C₃₁H₄₃N₃O₈, found 584.3 (MH)⁻.

(1r,4R)—N—((R)-1-(((2S,3R)-1-(((S)-3-cyclopentyl-1-((R)-2-methyloxiran-2-yl)-1-oxopropan-2-yl)amino)-3-hydroxy-3-(4-methoxyphenyl)-1-oxopropan-2-yl)amino)-1-oxopropan-2-yl)-4-hydroxycyclohexanecarboxamide (C-1079): ¹H NMR (400 MHz, CDCl₃) δ 7.97 (d, J=6.3 Hz, 1H), 7.93 (d, J=7.1 Hz, 1H), 7.85 (d, J=9.1 Hz, 1H), 7.24 (d, J=8.7 Hz, 2H), 6.92-6.74 (m, 2H), 5.54 (d, J=4.7 Hz, 1H), 5.08 (dd, J=4.5, 2.5 Hz, 1H), 4.54 (d, J=4.5 Hz, 1H), 4.33

(ddd, J=10.2, 7.2, 3.9 Hz, 1H), 4.30-4.18 (m, 2H), 3.70 (s, 3H), 3.29 (dd, J=9.8, 5.2 Hz, 2H), 2.99 (d, J=5.3 Hz, 1H), 2.05 (tt, J=11.8, 11.8, 3.4, 3.4 Hz, 1H), 1.98-1.89 (m, 1H), 1.87-1.43 (m, 13H), 1.39 (s, 3H), 1.37-1.22 (m, 2H), 1.22-1.00 (m, 2H), 0.96 (d, J=7.0 Hz, 3H). MS (EI) for $C_{31}H_{45}N_3O_8$, found 586.3 (MH)$^+$.

(S)—N—((S)-1-(((S)-3-cyclopentyl-1-((R)-2-methyloxiran-2-yl)-1-oxopropan-2-yl)amino)-3-(4-methoxyphenyl)-1-oxopropan-2-yl)-2-(2-morpholinoacetamido)butanamide (C-1106): $^1$H NMR (300 MHz, CDCl$_3$): δ 7.51 (br s, 1H), 7.11 (d, J=8.4 Hz, 2H), 6.79 (d, J=8.4 Hz, 2H), 6.68 (d, J=6.9 Hz, 1H), 6.27 (d, J=6.9 Hz, 1H), 4.61 (m, 1H), 4.52 (m, 1H), 4.28 (m, 1H), 3.77 (s, 3H), 3.72 (m, 4H), 3.24 (d, J=4.8 Hz, 1H), 2.85-3.07 (m, 5H), 2.50 (m, 4H), 1.51 (s, 3H), 0.83-1.95 (m, 16H). MS (EI) for $C_{31}H_{46}N_4O_7$, 587.7 (MH)$^+$.

(S)—N—((S)-3-cyclopentyl-1-((R)-2-methyloxiran-2-yl)-1-oxopropan-2-yl)-2-((S)-2-cyclopropyl-2-(2-morpholinoacetamido)acetamido)-3-(4-methoxyphenyl)propanamide (C-1107): $^1$H NMR (300 MHz, CDCl$_3$): δ 7.72 (br s, 1H), 7.12 (d, J=8.7 Hz, 2H), 6.80 (d, J=8.4 Hz, 2H), 6.78 (d, J=3.6 Hz, 1H), 6.31 (d, J=3.6 Hz, 1H), 4.46-4.67 (m, 2H), 3.77 (s, 3H), 3.75 (m, 5H), 3.25 (d, J=4.8 Hz, 1H), 2.85-3.16 (m, 5H), 2.54 (m, 4H), 1.57 (s, 3H), 0.39-1.83 (m, 16H). MS (EI) for $C_{32}H_{46}N_4O_7$, 599.1 (MH)$^+$.

Example 8

(S)—N—((S)-3-(Cyclopent-1-en-1-yl)-1-((R)-2-methyloxiran-2-yl)-1-oxopropan-2-yl)-3-(2-methoxypyridin-4-yl)-2-((S)-2-(2-morpholinoacetamido)propanamido)propanamide (C-1141)

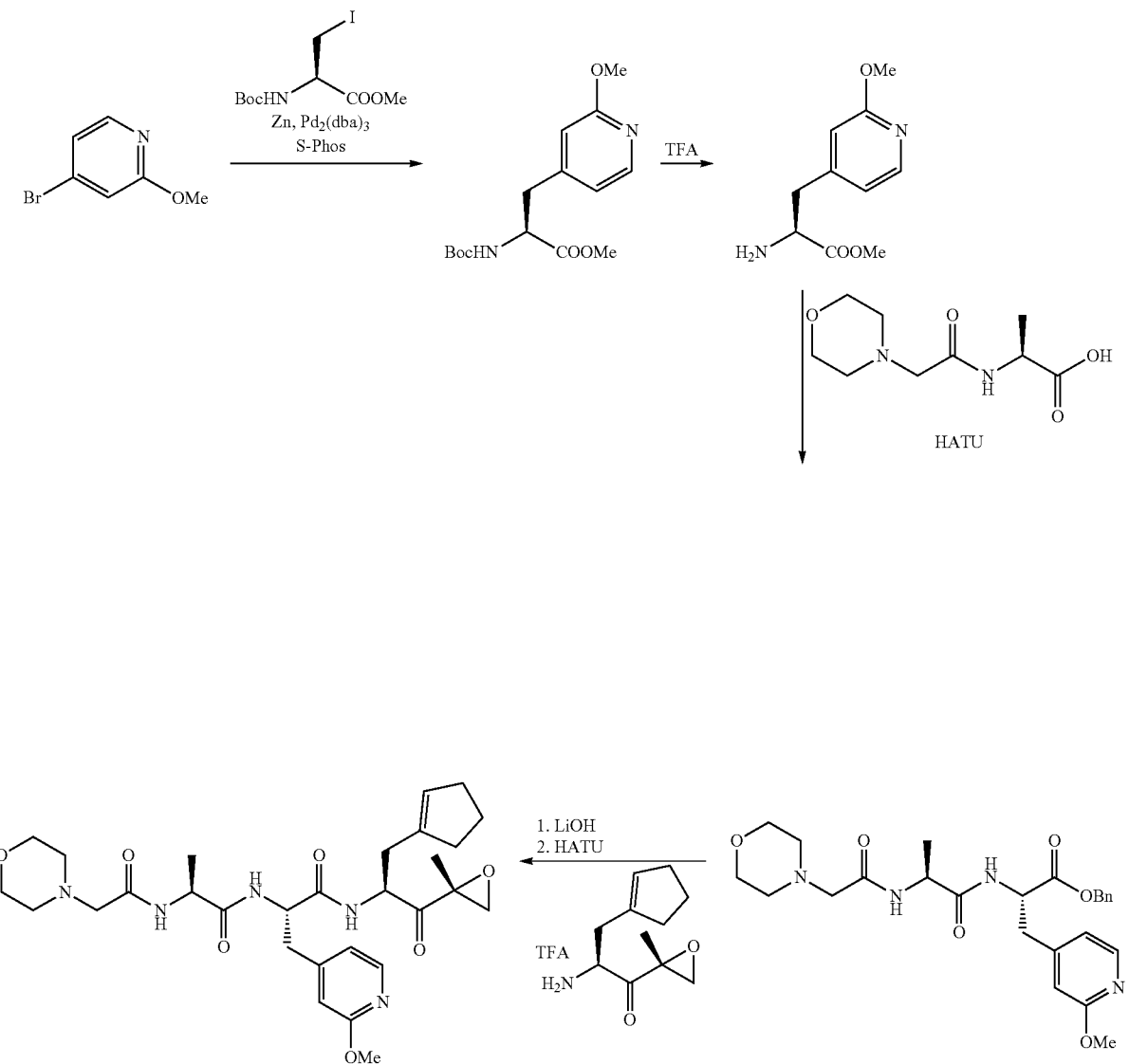

Dry DMF (30 mL) was added to zinc dust (2.78 g, 42.6 mmol) in a flame dried bottom flask under $N_2$. (R)-Methyl 2-(tert-butoxycarbonylamino)-3-iodopropanoate (3.85 g, 11.7 mmol) was added followed by a catalytic amount of iodine (1.06 g, 0.10 mmol). The mixture was stirred at ambient temperature for 0.5 h. $Pd_2(dba)_3$ (487 mg, 0.050 mmol), S-Phos (437 g, 0.100 mmol) and 4-bromo-2-methoxypyridine (2.00 g, 10.6 mmol) were added. The reaction mixture was heated at 60° C. for 6 h and then cooled to ambient temperature. EtOAc (200 mL) and water (200 mL) were added. The organic phase was separated, washed with water (300 mL×3) and brine (300 mL×1), dried over anhydrous sodium sulfate, and concentrated. The residue was purified by flash column chromatography on silica gel (hexane/EtOAc=2:1) to afford (S)-methyl 2-(tert-butoxycarbonylamino)-3-(2-methoxypyridin-4-yl)propanoate (2.4 g, 73% yield).

TFA (5 mL) was added to a solution of (S)-methyl 2-(tert-butoxycarbonylamino)-3-(2-methoxypyridin-4-yl)propanoate (2.4 g, 7.7 mmol) in $CH_2Cl_2$ (10 mL) at 0° C. with stirring. The mixture was stirred for 1 h and then concentrated to dryness. The residue was azeotroped three times with EtOAc (10 mL for each portion) to remove residual TFA to afford crude (S)-methyl 2-amino-3-(2-methoxypyridin-4-yl)propanoate as its TFA salt.

The crude (S)-methyl 2-amino-3-(2-methoxypyridin-4-yl)propanoate (TFA salt, 7.7 mmol) was dissolved in DMF (10 mL). (S)-2-(2-morpholinoacetamido)propanoic acid (1.7 g, 7.7 mmol), HATU (4.40 g, 11.6 mmol) and DIPEA (1 mL) were added at 0° C. with stirring. The reaction mixture was allowed to warm to ambient temperature and stirred for 3 h. EtOAc (100 mL) and water (100 mL) was added and two layers were separated. The aqueous phase was extracted with EtOAc (30 mL×3) and the combined organic phases were washed with brine (50 mL×3), dried over anhydrous sodium sulfate, and concentrated. The residue was purified by flash column chromatography on silica gel ($CH_2Cl_2$/MeOH=20:1) to afford (S)-methyl 3-(2-methoxypyridin-4-yl)-2-((S)-2-(2-morpholinoacetamido)propanamido)propanoate (1.5 g, 48% yield).

(S)-methyl 3-(2-methoxypyridin-4-yl)-2-((S)-2-(2-morpholinoacetamido)propanamido)propanoate (800 mg, 2.00 mmol) was treated with a solution of lithium hydroxide-$H_2O$ (329 mg, 7.80 mmol) in water/THF (10 mL/10 mL) for 30 min. THF was removed and the aqueous phase was acidified to pH=3-4 with 1N aqueous HCl. The resulting mixture was concentrated to dryness to afford the corresponding acid, which was used directly without further purification.

The acid was dissolved in DMF (20 mL) and compound (S)-2-amino-3-(cyclopent-1-en-1-yl)-1-((R)-2-methyloxiran-2-yl)propan-1-one (2.00 mmol), HATU (1.12 g, 2.90 mmol) and DIPEA (1 mL) were added at 0° C. with stirring. The reaction mixture was allowed to warm to ambient temperature and stirred for 3 h. EtOAc (100 mL) and water (100 mL) was added and two layers were separated. The aqueous phase was extracted with EtOAc (30 mL×3) and the combined organic phases were washed with brine (50 mL×3), dried over anhydrous sodium sulfate, and concentrated. The residue was purified by flash column chromatography on silica gel ($CH_2Cl_2$/EtOAc/MeOH=20:10:1) to afford (S)—N—((S)-3-(cyclopent-1-en-1-yl)-1-((R)-2-methyloxiran-2-yl)-1-oxopropan-2-yl)-3-(2-methoxypyridin-4-yl)-2-((S)-2-(2-morpholinoacetamido)propanamido)propanamide (330 mg, 29% yield over two steps). $^1$H NMR (300 MHz, DMSO-$d_6$): δ 8.38 (d, J=7.2 Hz, 1H), 8.14 (d, J=8.7 Hz, 1H), 8.00 (d, J=8.4 Hz, 1H), 7.75 (d, J=8.4 Hz, 1H), 6.84 (d, J=8.1 Hz, 1H), 6.35 (s, 1H), 5.77 (m, 1H), 4.50-4.70 (m, 2H), 4.25 (m, 1H), 3.80 (s, 3H), 3.57 (m, 4H), 3.20 (m, 1H), 3.05 (m, 1H), 2.80-3.00 (m, 3H), 2.70 (m, 1H), 2.37 (m, 4H), 2.10-2.30 (m, 5H), 1.80 (m, 1H), 1.39 (s, 3H), 1.15 (d, J=6.9 Hz, 3H). MS (EI) for $C_{29}H_{41}N_5O_7$, found 572.2 (MH)$^+$.

The following compounds were synthesized in a similar manner:

(S)—N—((S)-3-cyclopentyl-1-((R)-2-methyloxiran-2-yl)-1-oxopropan-2-yl)-3-(1H-indol-5-yl)-2-((S)-2-(2-morpholinoacetamido)propanamido)propanamide (C-1123): $^1$H NMR (300 MHz, DMSO-$d_6$): δ 10.96 (br s, 1H), 8.31 (d, J=7.2 Hz, 1H), 8.03 (d, J=8.1 Hz, 1H), 7.72 (d, J=7.2 Hz, 1H), 7.35 (m, 1H), 7.22 (d, J=8.1 Hz, 1H), 6.79 (d, J=8.4 Hz, 1H), 6.31 (s, 1H), 4.40 (m, 1H), 4.26 (m, 2H), 3.49 (m, 4H), 3.17 (d, J=5.1 Hz, 1H), 3.02 (m, 3H), 2.79 (m, 3H), 2.29 (m, 4H), 1.99 (m, 1H), 1.72 (m, 2H), 1.65 (m, 4H), 1.50 (s, 3H), 1.14 (d, J=6.6 Hz, 3H). MS (EI) for $C_{31}H_{43}N_5O_6$, found 582.4 (MH)$^+$.

(S)—N—((S)-3-cyclopentyl-1-((R)-2-methyloxiran-2-yl)-1-oxopropan-2-yl)-3-(1H-indol-6-yl)-2-((S)-2-(2-morpholinoacetamido)propanamido)propanamide (C-1124): $^1$H NMR (300 MHz, DMSO-$d_6$): δ 10.97 (br s, 1H), 8.32 (d, J=7.5 Hz, 1H), 8.10 (d, J=8.4 Hz, 1H), 7.71 (d, J=6.9 Hz, 1H), 7.36 (d, J=7.8 Hz, 1H), 7.25 (m, 2H), 6.79 (d, J=7.8 Hz, 1H), 6.34 (s, 1H), 4.34 (m, 1H), 4.26 (m, 2H), 3.49 (m, 4H), 3.17 (d, J=5.4 Hz, 1H), 3.09 (m, 1H), 3.04 (m, 1H), 2.98 (m, 1H), 2.84 (m, 3H), 2.29 (m, 4H), 1.90 (m, 1H), 1.71 (m, 2H), 1.65 (m, 4H), 1.50 (s, 3H), 1.15 (d, J=6.6 Hz, 3H). LC-MS for $C_{31}H_{43}N_5O_6$, found 582.4 (MH)$^+$.

(S)—N—((S)-3-cyclopentyl-1-((R)-2-methyloxiran-2-yl)-1-oxopropan-2-yl)-3-(2-fluoro-4-methoxyphenyl)-2-((S)-2-(2-morpholinoacetamido)propanamido)propanamide (C-1008): $^1$H NMR (300 MHz, DMSO-$d_6$): δ 8.10 (d, J=7.5 Hz, 1H), 8.04 (d, J=8.7 Hz, 1H), 7.75 (d, J=7.2 Hz, 1H), 7.06 (m, 1H), 6.83 (m, 1H), 6.61 (m, 1H), 4.55 (m, 1H), 4.33 (m, 1H), 4.23 (m, 1H), 3.80 (s, 3H), 3.60 (m, 4H), 3.19 (m. 1H), 3.01 (m, 1H), 2.80-3.00 (m, 3H), 2.75 (m, 1H), 2.40 (m, 4H), 1.95 (m, 1H), 1.50-1.85 (m, 7H), 1.40 (s, 3H), 1.00-1.20 (m, 2H), 1.26 (d, J=6.6 Hz, 3H). MS (EI) for $C_{30}H_{43}FN_4O_7$, found 591.3 (MH)$^+$.

(S)-3-(benzofuran-5-yl)-N—((S)-3-cyclopentyl-1-((R)-2-methyloxiran-2-yl)-1-oxopropan-2-yl)-2-((S)-2-(2-morpholinoacetamido)propanamido)propanamide (C-1007): $^1$H NMR (300 MHz, DMSO-$d_6$): δ 8.35 (d, J=7.5 Hz, 1H), 8.10 (d, J=9.0 Hz, 1H), 7.94 (d, J=1.5 Hz, 1H), 7.71 (d, J=7.8 Hz, 1H), 7.40-7.50 (m, 2H), 7.18 (d, J=8.4 Hz, 1H), 6.87 (m, 1H), 4.39 (m, 1H), 4.28 (m, 1H), 4.28 (m, 1H), 3.50 (m, 4H), 3.20 (m. 1H), 3.10 (m, 1H), 3.01 (m, 1H), 2.80-3.00 (m, 3H), 2.29 (m, 4H), 1.95 (m, 1H), 1.50-1.85 (m, 7H), 1.40 (s, 3H), 1.00-1.20 (m, 2H), 1.26 (d, J=6.6 Hz, 3H). MS (EI) for $C_{31}H_{42}N_4O_7$, found 583.3 (MH)$^+$.

(S)-3-(benzo[d][1,3]dioxol-5-yl)-N—((S)-3-cyclopentyl-1-((R)-2-methyloxiran-2-yl)-1-oxopropan-2-yl)-2-((S)-2-(2-morpholinoacetamido)propanamido)propanamide (C-1012): $^1$H NMR (300 MHz, DMSO-$d_6$): δ 8.30 (d, J=7.2 Hz, 1H), 8.02 (d, J=8.7 Hz, 1H), 7.77 (d, J=7.5 Hz, 1H), 6.75-6.79 (m, 2H), 6.65 (m, 5H), 5.95 (s, 2H), 4.48 (m, 1H), 4.29 (m, 1H), 4.28 (m, 1H), 3.60 (m, 4H), 3.57 (s, 2H), 3.18 (m. 1H), 3.05 (m, 1H), 2.90 (m, 2H), 2.75 (m, 1H), 2.40 (m, 4H), 1.95 (m, 1H), 1.50-1.85 (m, 4H), 1.40 (s, 3H), 1.00-1.20 (m, 2H), 1.26 (d, J=6.6 Hz, 3H). MS (EI) for $C_{30}H_{42}N_4O_8$, found 587.6 (MH)$^+$.

(S)—N—((S)-3-cyclopentyl-1-((R)-2-methyloxiran-2-yl)-1-oxopropan-2-yl)-3-(1H-indol-3-yl)-2-((S)-2-(2-morpholinoacetamido)propanamido)propanamide (C-1014): $^1$H NMR (300 MHz, DMSO-$d_6$): δ 10.84 (br s, 1H), 8.30 (d, J=7.2 Hz, 1H), 8.06 (d, J=8.1 Hz, 1H), 7.76 (d, J=7.5 Hz, 1H), 7.57 (d, J=7.5 Hz, 1H), 7.30 (d, J=8.1 Hz, 1H), 6.95-7.15 (m, 3H), 4.55 (m, 1H), 4.20-4.40 (m, 2H), 3.60 (m, 4H), 3.10-3.20 (m, 2H), 2.80-3.00 (m, 4H), 2.40 (m, 4H), 1.95 (m, 1H), 1.50-1.85 (m, 7H), 1.40 (s, 3H), 1.00-1.20 (m, 2H), 1.26 (d, J=6.6 Hz, 3H). MS (EI) for $C_{31}H_{43}N_5O_6$, found 582.3 (MH)$^+$.

(S)-3-(benzofuran-3-yl)-N—((S)-3-cyclopentyl-1-((R)-2-methyloxiran-2-yl)-1-oxopropan-2-yl)-2-((S)-2-(2-morpholinoacetamido)propanamido)propanamide (C-1015): $^1$H NMR (300 MHz, DMSO-$d_6$): δ 8.20 (d, J=7.5 Hz, 1H), 7.77 (d, J=7.5 Hz, 1H), 7.60-7.70 (m, 2H), 7.54 (d, J=7.5 Hz, 1H), 7.20-7.30 (m, 2H), 4.65 (m, 1H), 4.20-4.40 (m, 2H), 3.55 (m, 4H), 3.16 (m, 1H), 2.95-3.10 (m, 2H), 2.90 (m, 2H), 2.40 (m, 4H), 1.95 (m, 1H), 1.50-1.85 (m, 7H), 1.40 (s, 3H), 1.00-1.20 (m, 2H), 1.26 (d, J=6.6 Hz, 3H). MS (EI) for $C_{31}H_{42}N_4O_7$, found 583.5 (MH)$^+$.

(S)—N—((S)-3-cyclopentyl-1-((R)-2-methyloxiran-2-yl)-1-oxopropan-2-yl)-2-((S)-2-(2-morpholinoacetamido)propanamido)-3-(4-(trifluoromethoxy)phenyl)propanamide (C-1084): $^1$H NMR (300 MHz, DMSO-$d_6$): δ 8.34 (d, J=6.9 Hz, 1H), 8.12 (d, J=8.4 Hz, 1H), 7.74 (d, J=7.8 Hz, 1H), 7.33 (d, J=8.4 Hz, 2H), 7.22 (d, J=8.1 Hz, 2H), 4.56 (m, 1H), 4.30 (m, 2H), 3.56 (m, 4H), 3.17 (d, J=5.1 Hz, 1H), 2.65-3.03 (m, 5H), 2.37 (m, 4H), 1.41-2.01 (m, 11H), 1.41 (s, 3H), 1.13 (d, J=6.9 Hz, 3H). MS (EI) for $C_{30}H_{41}F_3N_4O_7$, found 627.3 (MH)$^+$.

(S)—N—((S)-3-cyclopentyl-1-((R)-2-methyloxiran-2-yl)-1-oxopropan-2-yl)-2-((S)-2-(2-morpholinoacetamido)propanamido)-3-(2-oxoindolin-5-yl)propanamide (C-1081): $^1$H NMR (300 MHz, DMSO-$d_6$): δ 10.31 (s, 1H), 8.32 (d, J=7.2 Hz, 1H), 8.06 (d, J=8.4 Hz, 1H), 7.75 (d, J=7.8 Hz, 1H), 6.90-7.10 (m, 2H), 6.65 (m, 1H), 4.50 (m, 1H), 4.20-4.40 (m, 2H), 3.60 (m, 4H), 3.18 (m, 1H), 3.05 (m, 1H), 2.80-3.00 (m, 5H), 2.60 (m, 1H), 2.30-2.50 (m, 4H), 1.50-1.95 (m, 7H), 1.40 (s, 3H), 1.26 (d, J=6.6 Hz, 3H). MS (EI) for $C_{31}H_{43}N_5O_7$, found 596.3 (MH)$^-$.

(S)—N—((S)-3-cyclopentyl-1-((R)-2-methyloxiran-2-yl)-1-oxopropan-2-yl)-2-((S)-2-(2-morpholinoacetamido)propanamido)-3-(2-oxo-1,2,3,4-tetrahydroquinolin-6-yl)propanamide (C-1086): $^1$H NMR (300 MHz, DMSO-$d_6$): δ 10.02 (s, 1H), 8.32 (d, J=7.2 Hz, 1H), 8.03 (d, J=8.4 Hz, 1H), 7.75 (d, J=7.8 Hz, 1H), 6.90-7.00 (m, 2H), 6.68 (m, 1H), 4.48 (m, 1H), 4.20-4.30 (m, 2H), 3.56 (m, 4H), 3.18 (m, 1H), 3.05 (m, 1H), 2.80-3.00 (m, 5H), 2.60 (m, 1H), 2.30-2.50 (m, 6H), 1.50-1.95 (m, 7H), 1.40 (s, 3H), 1.26 (d, J=6.6 Hz, 3H). MS (EI) for $C_{32}H_{45}N_5O_7$, found 612.7 (MH)$^+$.

(S)—N—((S)-3-cyclopentyl-1-((R)-2-methyloxiran-2-yl)-1-oxopropan-2-yl)-3-(1,1-dioxido-3,4-dihydro-2H-benzo[e][1,2]thiazin-6-yl)-2-((S)-2-(2-morpholinoacetamido)propanamido)propanamide (C-1091): $^1$H NMR (300 MHz, DMSO-$d_6$): δ 8.40 (d, J=7.2 Hz, 1H), 8.10 (d, J=8.1 Hz, 1H), 7.78 (d, J=7.8 Hz, 1H), 7.57 (d, J=8.1 Hz, 1H), 7.39 (m, 1H), 7.26 (d, J=8.4 Hz, 2H), 7.18 (s, 1H), 4.63 (m, 1H), 4.30 (m, 2H), 3.58 (m, 6H), 3.17 (d, J=5.1 Hz, 1H), 2.97 (m, 2H), 2.89 (m, 4H), 2.75 (m, 1H), 2.39 (m, 4H), 1.42-1.92 (m, 10H), 1.42 (s, 3H), 1.16 (d, J=6.9 Hz, 3H). MS (EI) for $C_{31}H_{45}N_5O_8S$, found 648.52 (MH)$^+$.

(S)—N—((S)-3-(cyclopent-1-en-1-yl)-1-((R)-2-methyloxiran-2-yl)-1-oxopropan-2-yl)-3-(1-methyl-6-oxo-1,6-dihydropyridin-3-yl)-2-((S)-2-(2-morpholinoacetamido)propanamido)propanamide (C-1147): $^1$H NMR (300 MHz, DMSO-$d_6$): δ 8.37 (d, J=6.9 Hz, 1H), 8.08 (d, J=8.1 Hz, 1H), 7.79 (d, J=7.5 Hz, 1H), 7.37 (s, 1H), 7.27 (d, J=9.3 Hz, 1H), 6.25 (d, J=9.0 Hz, 1H), 5.40 (m, 1H), 4.47 (m, 2H), 4.32 (m, 1H), 3.56 (m, 4H), 3.20 (m, 2H), 2.99 (d, J=5.7 Hz, 1H), 2.90 (m, 2H), 2.66 (m, 2H), 2.38 (m, 7H), 2.23 (m, 5H), 1.79 (m, 2H), 1.38 (s, 3H), 1.16 (d, J=6.9 Hz, 3H), 0.84 (m, 2H). MS (EI) for $C_{29}H_{41}N_5O_7$, 572.3 (MH)$^+$.

(S)—N—((S)-3-(cyclopent-1-en-1-yl)-1-((R)-2-methyloxiran-2-yl)-1-oxopropan-2-yl)-3-(6-methoxypyridin-3-yl)-2-((S)-2-(2-morpholinoacetamido)propanamido)propanamide (C-1140): $^1$H NMR (300 MHz, DMSO-$d_6$): δ 8.36 (d, J=7.2 Hz, 1H), 8.11 (d, J=8.7 Hz, 1H), 7.93 (s, 1H), 7.75 (d, J=8.1 Hz, 1H), 7.53 (d, J=8.4 Hz, 1H), 6.68 (d, J=8.4 Hz, 1H), 5.40 (m, 1H), 4.51 (m, 2H), 4.27 (m, 1H), 3.79 (s, 3H), 3.55 (m, 4H), 3.18 (d, J=5.1 Hz, 1H), 2.99 (m, 1H), 2.86 (m, 3H), 2.65 (m, 1H), 2.37 (m, 4H), 2.24 (m, 6H), 1.79 (m, 2H), 1.38 (s, 3H), 1.14 (d, J=6.9 Hz, 3H). MS (EI) for $C_{29}H_{41}N_5O_7$, found 572.3 (MH)$^+$.

(S)—N—((S)-3-(cyclopent-1-en-1-yl)-1-((R)-2-methyloxiran-2-yl)-1-oxopropan-2-yl)-3-(1-methyl-2-oxo-1,2-dihydropyridin-4-yl)-2-((S)-2-(2-morpholinoacetamido)propanamido)propanamide (C-1137): $^1$H NMR (300 MHz, DMSO-$d_6$): δ 8.35 (d, J=7.2 Hz, 1H), 8.11 (d, J=8.4 Hz, 1H), 7.78 (d, J=7.5 Hz, 1H), 7.55 (d, J=6.0 Hz, 1H), 6.18 (s, 1H), 6.11 (d, J=7.2 Hz, 1H), 5.40 (s, 1H), 4.51 (m, 2H), 4.27 (m, 1H), 3.58 (m, 4H), 3.35 (s, 3H), 3.18 (d, J=4.8 Hz, 1H), 2.97 (d, J=6.9 Hz, 1H), 2.90 (m, 2H), 2.76 (m, 1H), 2.39 (m, 4H), 2.23 (m, 5H), 1.80 (m, 2H), 1.38 (s, 3H), 1.16 (d, J=6.9 Hz, 3H). MS (EI) for $C_{29}H_{41}N_5O_7$, found 571.9 (MH)$^+$.

(S)—N—((S)-3-(cyclopent-1-en-1-yl)-1-((R)-2-methyloxiran-2-yl)-1-oxopropan-2-yl)-3-(4-ethyl-3-hydroxyphenyl)-2-((S)-2-(2-morpholinoacetamido)propanamido)propanamide (C-1136): $^1$H NMR (300 MHz, DMSO-$d_6$): δ 9.07 (s, 1H), 8.27 (d, J=7.5 Hz, 1H), 8.09 (d, J=7.5 Hz, 1H), 7.78 (d, J=7.5 Hz, 1H), 6.90 (d, J=7.8 Hz, 1H), 6.62 (s, 1H), 6.56 (d, J=7.8 Hz, 1H), 5.40 (s, 1H), 4.51 (m, 2H), 4.28 (m, 1H), 3.57 (m, 4H), 3.18 (d, J=4.8 Hz, 1H), 2.98 (d, J=5.1 Hz, 1H), 2.91 (m, 2H), 2.88 (m, 1H), 2.47 (m, 2H), 2.38 (m, 4H), 2.24 (m, 5H), 1.79 (m, 2H), 1.38 (s, 3H), 1.16 (d, J=6.3 Hz, 3H), 1.10 (t, J=7.5 Hz, 3H). MS (EI) for $C_{31}H_{44}N_4O_7$, found 584.9 (MH)$^+$.

(S)—N—((S)-3-(cyclopent-1-en-1-yl)-1-((R)-2-methyloxiran-2-yl)-1-oxopropan-2-yl)-3-(4-hydroxy-3-methylphenyl)-2-((S)-2-(2-morpholinoacetamido)propanamido)propanamide (C-1131): $^1$H NMR (300 MHz, DMSO-$d_6$): δ 9.03 (s, 1H), 8.29 (d, J=7.2 Hz, 1H), 7.98 (d, J=8.4 Hz, 1H), 7.75 (d, J=7.2 Hz, 1H), 6.86 (s, 1H), 6.78 (d, J=8.1 Hz, 1H), 6.59 (d, J=8.1 Hz, 1H), 5.39 (s, 1H), 4.35 (m, 1H), 4.28 (m, 1H), 4.06 (m, 1H), 3.55 (m, 4H), 3.18 (d, J=5.1 Hz, 1H), 2.97 (d, J=4.8 Hz, 1H), 2.91 (m, 3H), 2.36 (m, 4H), 2.21 (m, 5H), 2.03 (s, 3H), 1.76 (m, 2H), 1.38 (s, 3H), 1.14 (d, J=6.6 Hz, 3H). MS (EI) for $C_{30}H_{42}N_4O_7$, found 570.8 (MH)$^+$.

(S)—N—((S)-3-cyclopentyl-1-((R)-2-methyloxiran-2-yl)-1-oxopropan-2-yl)-3-(3-hydroxyphenyl)-2-((S)-2-(2-morpholinoacetamido)propanamido)propanamide (C-1114): $^1$H NMR (300 MHz, DMSO-$d_6$): δ 9.21 (s, 1H), 8.30 (d, J=7.2 Hz, 1H), 8.07 (d, J=8.4 Hz, 1H), 7.75 (d, J=7.5 Hz, 1H), 6.99 (m, 1H), 6.50-6.70 (m, 2H), 4.50 (m, 1H), 4.15-4.30 (m, 2H), 3.60 (m, 4H), 3.16 (m, 1H), 3.00 (m, 1H), 2.80-3.00 (m, 3H), 2.70 (m, 1H), 2.30 (m, 4H), 1.41-2.00 (m, 9H), 1.41 (s, 3H), 1.15 (d, J=6.9 Hz, 3H). MS (EI) for $C_{29}H_{42}N_4O_7$, found 559.2 (MH)$^+$.

(S)—N—((S)-3-cyclopentyl-1-((R)-2-methyloxiran-2-yl)-1-oxopropan-2-yl)-3-(4-hydroxyphenyl)-2-((S)-2-(2-morpholinoacetamido)propanamido)propanamide (C-1113): $^1$H NMR (300 MHz, DMSO-$d_6$): δ 9.17 (s, 1H), 8.29 (d, J=6.6 Hz, 1H), 8.02 (d, J=7.2 Hz, 1H), 7.74 (d, J=7.8 Hz, 1H), 6.98 (d, J=8.4 Hz, 2H), 6.60 (d, J=8.1 Hz, 2H), 4.45 (m, 1H), 4.28 (m, 2H), 4.22 (m, 1H), 3.57 (m, 4H), 3.17 (d, J=8.4 Hz, 1H), 2.86 (d, J=5.4 Hz, 1H), 2.63 (m, 3H), 2.60 (m, 1H), 2.38 (m, 4H), 1.72 (m, 1H), 1.70 (m, 2H), 1.66 (m, 6H), 1.41 (s, 3H), 1.15 (d, J=6.6 Hz, 3H). MS (EI) for $C_{29}H_{42}N_4O_7$, found 559.2 (MH)$^+$.

(S)—N—((S)-3-cyclopentyl-1-((R)-2-methyloxiran-2-yl)-1-oxopropan-2-yl)-2-((S)-2-(2-morpholinoacetamido)propanamido)-3-(2-oxo-3,4-dihydro-2H-benzo[e][1,3]oxazin-6-yl)propanamide (C-1108): $^1$H NMR (300 MHz, DMSO-d$_6$): δ 8.36 (d, J=6.3 Hz, 1H), 8.10 (d, J=7.8 Hz, 1H), 7.95 (s, 1H), 7.74 (d, J=7.5 Hz, 1H), 7.10 (d, J=7.5 Hz, 1H), 7.04 (s, 1H), 6.86 (d, J=8.1 Hz, 1H), 4.50 (m, 1H), 4.35 (s, 2H), 4.30 (m, 2H), 3.55 (m, 4H), 3.17 (d, J=4.5 Hz, 1H), 2.70-3.06 (m, 4H), 2.63 (m, 1H), 2.36 (m, 4H), 1.31-2.02 (m, 11H), 1.48 (s, 3H), 1.15 (d, J=6.3 Hz, 3H). MS (EI) for $C_{31}H_{43}N_5O_8$, found 636.0 [M+Na]$^+$.

(S)-3-(1H-benzo[d]imidazol-5-yl)-N—((S)-3-cyclopentyl-1-((R)-2-methyloxiran-2-yl)-1-oxopropan-2-yl)-2-((S)-2-(2-morpholinoacetamido)propanamido)propanamide (C-1069): $^1$H NMR (300 MHz, DMSO-d$_6$): δ 8.33 (m, 1H), 8.32 (d, J=6.9 Hz, 1H), 8.14 (s, 1H), 8.09 (d, J=8.4 Hz, 1H), 7.71 (d, J=7.8 Hz, 1H), 7.42 (m, 2H), 7.07 (d, J=8.4 Hz, 1H), 4.57 (m, 1H), 4.25 (m, 2H), 3.50 (m, 4H), 3.18 (d, J=4.5 Hz, 1H), 2.71-3.15 (m, 5H), 2.31 (m, 4H), 1.41-2.03 (m, 11H), 1.40 (s, 3H), 1.14 (d, J=6.9 Hz, 3H). MS (EI) for $C_{30}H_{42}N_6O_6$, found 583.4 (MH)$^+$.

(S)—N—((S)-3-cyclopentyl-1-((R)-2-methyloxiran-2-yl)-1-oxopropan-2-yl)-3-(1H-indazol-5-yl)-2-((S)-2-(2-morpholinoacetamido)propanamido)propanamide (C-1070): $^1$H NMR (300 MHz, DMSO-d$_6$): δ 12.94 (s, 1H), 8.35 (m, 1H), 8.10 (d, J=8.7 Hz, 1H), 7.96 (s, 1H), 7.68 (d, J=6.0 Hz, 1H), 7.54 (s, 1H), 7.39 (d, J=8.4 Hz, 1H), 7.24 (d, J=8.4 Hz, 1H), 4.62 (m, 1H), 4.30 (m, 2H), 3.49 (m, 4H), 2.70-3.25 (m, 6H), 2.26 (m, 4H), 1.41-1.93 (m, 10H), 1.40 (s, 3H), 1.14 (d, J=6.9 Hz, 3H). MS (EI) for $C_{30}H_{42}N_6O_6$, found 583.4 (MH)$^+$.

(1r,4R)—N—((R)-1-(((S)-3-(1H-benzo[d]imidazol-5-yl)-1-(((S)-3-cyclopentyl-1-((R)-2-methyloxiran-2-yl)-1-oxopropan-2-yl)amino)-1-oxopropan-2-yl)amino)-1-oxopropan-2-yl)-4-hydroxycyclohexanecarboxamide (C-1105): $^1$H NMR (300 MHz, CDCl$_3$): δ 12.47 (br s, 1H), 8.29 (d, J=6.9 Hz, 1H), 8.17 (s, 1H), 8.09 (d, J=8.7 Hz, 1H), 7.79 (d, J=6.9 Hz, 1H), 7.42 (m, 2H), 7.06 (d, J=6.9 Hz, 1H), 4.52 (m, 2H), 4.27 (m, 1H), 4.15 (m, 1H), 2.69-3.27 (m, 6H), 0.91-2.03 (m, 19H), 1.41 (s, 3H), 0.87 (d, J=6.9 Hz, 3H). MS (EI) for $C_{31}H_{43}N_5O_6$, 582.22 (MH)$^+$.

(1r,4R)—N—((R)-1-(((S)-3-(4-cyanophenyl)-1-(((S)-3-cyclopentyl-1-((R)-2-methyloxiran-2-yl)-1-oxopropan-2-yl)amino)-1-oxopropan-2-yl)amino)-1-oxopropan-2-yl)-4-hydroxycyclohexanecarboxamide (C-1103): $^1$H NMR (300 MHz, DMSO-d$_6$): δ 8.29 (d, J=6.9 Hz, 1H), 8.11 (d, J=9.0 Hz, 1H), 7.82 (d, J=7.2 Hz, 1H), 7.71 (d, J=8.1 Hz, 2H), 7.39 (d, J=8.1 Hz, 2H), 4.53 (m, 2H), 4.30 (m, 1H), 4.11 (m, 1H), 3.30 (m, 1H), 3.22 (d, J=4.8 Hz, 1H), 3.10 (m, 1H), 3.02 (d, J=5.1 Hz, 1H), 2.80 (m, 1H), 1.83 (m, 1H), 1.79 (m, 1H), 1.73 (m, 3H), 1.53 (m, 4H), 1.48 (m, 4H), 1.37 (s, 3H), 1.33 (m, 3H), 1.25 (m, 4H), 0.91 (d, J=6.9 Hz, 3H). MS (EI) for $C_{31}H_{42}N_4O_6$, found 567.3 (MH)$^+$.

(S)—N—((S)-3-cyclopentyl-1-((R)-2-methyloxiran-2-yl)-1-oxopropan-2-yl)-3-(2,2-dioxido-3,4-dihydro-1H-benzo[c][1,2]thiazin-6-yl)-2-((S)-2-(2-morpholinoacetamido)propanamido)propanamide (C-1102): $^1$H NMR (300 MHz, DMSO-d$_6$): δ 10.00 (s, 1H), 8.33 (d, J=7.2 Hz, 1H), 8.03 (d, J=8.4 Hz, 1H), 7.80 (m, 1H), 6.90-7.10 (m, 2H), 6.62 (d, J=8.1 Hz, 1H), 4.50 (m, 1H), 4.20-4.30 (m, 2H), 3.60 (m, 4H), 3.20-3.30 (m, 4H), 3.10 (m, 1H), 3.00 (m, 1H), 2.80-3.00 (m, 3H), 2.70 (m, 1H), 2.30 (m, 4H), 1.41-2.00 (m, 9H), 1.41 (s, 3H), 1.15 (d, J=6.9 Hz, 3H). MS (EI) for $C_{31}H_{45}N_5O_8S$, found 648.5 (MH)$^+$.

N—((S)-3-cyclopentyl-1-((R)-2-methyloxiran-2-yl)-1-oxopropan-2-yl)-2-((S)-2-(2-morpholinoacetamido)propanamido)-3-(2-oxo-2,4-dihydro-1H-benzo[d][1,3]oxazin-6-yl)propanamide (C-1101): $^1$H NMR (300 MHz, DMSO-d$_6$): δ 10.14 (br s, 1H), 8.40 (d, J=6.9 Hz, 1H), 8.17 (d, J=8.7 Hz, 1H), 7.79 (d, J=7.8 Hz, 1H), 7.08 (d, J=8.1 Hz, 1H), 7.02 (s, 1H), 6.75 (d, J=8.1 Hz, 1H), 5.21 (s, 2H), 4.43 (m, 1H), 4.29 (m, 2H), 3.55 (m, 4H), 3.16 (d, J=4.8 Hz, 1H), 2.61-3.06 (m, 5H), 2.36 (m, 4H), 1.41-1.97 (m, 11H), 1.41 (s, 3H), 1.16 (d, J=6.6 Hz, 3H). MS (EI) for $C_{31}H_{43}N_5O_8$, found 614.8 (MH)$^+$.

(S)-3-(benzo[d][1,3]dioxol-5-yl)-N—((S)-3-cyclopentyl-1-((R)-oxiran-2-yl)-1-oxopropan-2-yl)-2-((S)-2-(2-morpholinoacetamido)propanamido)propanamide (C-1060): $^1$H NMR (300 MHz, CDCl$_3$): δ 7.51 (d, J=4.5 Hz, 2H), 6.81 (d, J=6.6 Hz, 1H), 6.76-6.64 (m, 3H), 6.46 (d, J=6.6 Hz, 1H), 5.94 (s, 2H), 4.57-4.42 (m, 3H), 3.79 (s, 3H), 3.51 (m, 1H), 3.13 (m, 2H), 3.01-2.99 (m, 4H), 2.37 (m, 4H), 1.76 (m, 5H), 1.69-1.53 (m, 6H), 1.39 (d, J=6.9 Hz, 3H). MS (EI) for $C_{29}H_{40}N_4O_8$, found 573.4 (MH$^+$).

(S)—N—((S)-3-cyclopentyl-1-((R)-2-methyloxiran-2-yl)-1-oxopropan-2-yl)-3-(3-hydroxy-4-methoxyphenyl)-2-((S)-2-(2-morpholinoacetamido)propanamido)propanamide (C-1018): $^1$H NMR (300 MHz, DMSO-d$_6$): δ 8.73 (s, 1H), 8.26 (d, J=7.2 Hz, 1H), 8.04 (d, J=8.1 Hz, 1H), 7.75 (d, J=7.8 Hz, 1H), 6.74 (d, J=8.4 Hz, 1H), 6.66 (d, J=1.8 Hz, 1H), 6.60-6.58 (m, 1H), 4.49-4.43 (m, 1H), 4.35-4.20 (m, 2H), 3.72 (s, 3H), 3.68-3.60 (m, 4H), 3.22-3.18 (m. 1H), 3.01-2.80 (m, 4H), 2.65-2.58 (m, 1H), 2.45-2.34 (m, 4H), 1.91-1.81 (m, 1H), 1.85-1.50 (m, 7H), 1.40 (s, 3H), 1.20-1.00 (m, 2H), 1.26 (d, J=6.6 Hz, 3H). MS (EI) for $C_{30}H_{44}N_4O_8$, found 589.7 (MH$^+$).

Example 9

(S)—N—((S)-3-((1R,3r,5S)-Bicyclo[3.1.0]hexan-3-yl)-1-((R)-2-methyloxiran-2-yl)-1-oxopropan-2-yl)-3-(4-methoxyphenyl)-2-((S)-2-(2-morpholinoacetamido)propanamido)propanamide (C-1095)

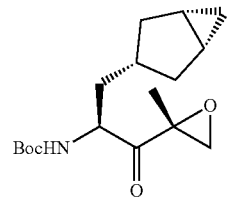
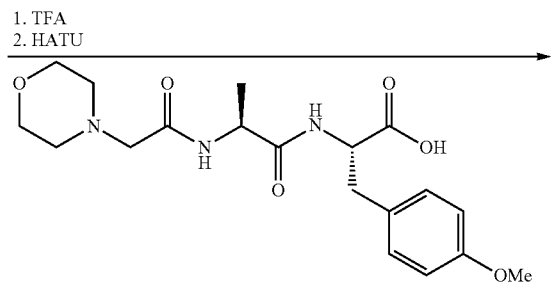

-continued

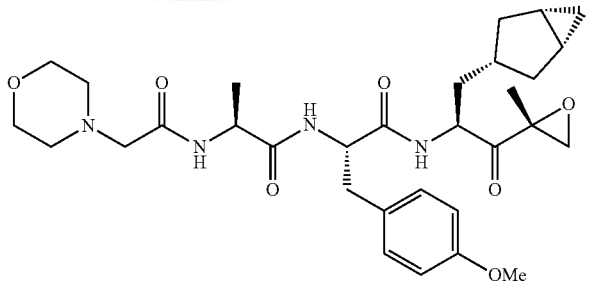

TFA (5 mL) was added to solution of tert-butyl ((R)-3-((1R,3r,5S)-bicyclo[3.1.0]hexan-3-yl)-1-((R)-2-methyloxiran-2-yl)-1-oxopropan-2-yl)carbamate (310 mg, 1.1 mmol) in CH$_2$Cl$_2$ (16 mL) at 0° C. with stirring. The mixture was stirred for 1 h and concentrated to dryness. The residue was azeotroped three times with EtOAc (5 mL for each portion) to remove residual TFA to afford (S)-2-amino-3-((1R,3r,5S)-bicyclo[3.1.0]hexan-3-yl)-1-((R)-2-methyloxiran-2-yl)propan-1-one (quantitative) as its TFA salt.

(S)-2-Amino-3-((1R,3r,5S)-bicyclo[3.1.0]hexan-3-yl)-1-((R)-2-methyloxiran-2-yl)propan-1-one (TFA salt) was dissolved in DMF (20 mL) and (S)-3-(4-methoxyphenyl)-2-((S)-2-(2-morpholinoacetamido)propanamido)propanoic acid (670 mg, 1.70 mmol), HATU (710 mg, 1.80 mmol) and DIPEA (1.48 mL) were added at 0° C. with stirring. The reaction mixture was allowed to warm to ambient temperature and stirred for 3 h. EtOAc (100 mL) and water (100 mL) was added and two layers were separated. The aqueous phase was extracted with EtOAc (50 mL×3). The combined organics were washed with brine (200 mL×3), dried over anhydrous sodium sulfate, and concentrated. The residue was purified by flash column chromatography on silica gel (CH$_2$Cl$_2$/EtOAc/MeOH=20:10:0.1) to afford (S)—N—((S)-3-((1R,3r,5S)-bicyclo[3.1.0]hexan-3-yl)-1-((R)-2-methyloxiran-2-yl)-1-oxopropan-2-yl)-3-(4-methoxyphenyl)-2-((S)-2-(2-morpholinoacetamido)propanamido)propanamide (350 mg, 54% yield). $^1$H NMR (300 MHz, DMSO-d$_6$): δ 8.25 (d, J=6.9 Hz, 1H), 8.09 (d, J=8.1 Hz, 1H), 7.75 (d, J=7.5 Hz, 1H), 7.13 (d, J=8.4 Hz, 2H), 6.80 (d, J=8.4 Hz, 2H), 4.45 (m, 1H), 4.20-4.40 (m, 2H), 3.71 (s, 3H), 3.56 (m, 4H), 3.15 (m, 1H), 3.05 (m, 1H), 2.80-3.00 (m, 3H), 2.65 (m, 1H), 2.35 (m, 4H), 1.70-1.80 (m, 2H), 1.40-1.60 (m, 3H), 1.42 (s, 3H), 1.10-1.30 (m, 3H), 1.16 (d, J=6.9 Hz, 3H). MS (EI) for C$_{31}$H$_{44}$N$_4$O$_7$, found 585.1 (MH$^+$).

The following compounds were synthesized in a similar manner:

(S)—N—((S)-3-((1R,3s,5S)-bicyclo[3.1.0]hexan-3-yl)-1-((R)-2-methyloxiran-2-yl)-1-oxopropan-2-yl)-3-(4-methoxyphenyl)-2-((S)-2-(2-morpholinoacetamido)propanamido)propanamide (C-1094): $^1$H NMR (300 MHz, DMSO-d$_6$): δ 8.25 (d, J=6.9 Hz, 1H), 8.09 (d, J=8.1 Hz, 1H), 7.75 (d, J=7.5 Hz, 1H), 7.13 (d, J=8.4 Hz, 2H), 6.80 (d, J=8.4 Hz, 2H), 4.45 (m, 1H), 4.20-4.40 (m, 2H), 3.71 (s, 3H), 3.56 (m, 4H), 3.15 (m, 1H), 3.05 (m, 1H), 2.80-3.00 (m, 3H), 2.65 (m, 1H), 2.35 (m, 4H), 1.70-1.80 (m, 2H), 1.40-1.60 (m, 3H), 1.42 (s, 3H), 1.10-1.30 (m, 3H), 1.16 (d, J=6.9 Hz, 3H). LC-MS for C$_{31}$H$_{44}$N$_4$O$_7$, found 585.1 (MH$^+$).

(S)—N—((S)-3-((1r,4S)-4-hydroxycyclohexyl)-1-((R)-2-methyloxiran-2-yl)-1-oxopropan-2-yl)-3-(4-methoxyphenyl)-2-((S)-2-(2-morpholinoacetamido)propanamido)propanamide (C-1002): $^1$H NMR (400 MHz, CDCl$_3$) δ 7.44 (d, J=7.3 Hz, 1H), 7.10 (d, J=8.6 Hz, 2H), 6.80 (d, J=8.6 Hz, 2H), 6.72 (d, J=7.5 Hz, 1H), 6.29 (d, J=8.0 Hz, 1H), 4.54 (q, J=7.2, 7.1, 7.1 Hz, 2H), 4.41 (p, J=7.6, 7.6, 7.4, 7.4 Hz, 1H), 3.84-3.64 (m, 8H), 3.63-3.45 (m, 1H), 3.23 (d, J=4.9 Hz, 1H), 3.11-2.79 (m, 5H), 2.64-2.43 (m, 4H), 2.01-1.83 (m, 5H), 1.64 (dt, J=12.8, 2.9, 2.9 Hz, 1H), 1.55-1.46 (m, 3H), 1.36 (d, J=8.0 Hz, 3H), 1.32-1.12 (m, 4H), 1.07-0.91 (m, 2H). MS (EI) for C$_{31}$H$_{46}$N$_4$O$_8$, found 603.4 (MH$^+$).

(S)—N—((S)-3-((1s,4R)-4-hydroxycyclohexyl)-1-((R)-2-methyloxiran-2-yl)-1-oxopropan-2-yl)-3-(4-methoxyphenyl)-2-((S)-2-(2-morpholinoacetamido)propanamido)propanamide (C-1001): $^1$H NMR (400 MHz, CDCl$_3$) δ 7.43 (d, J=7.5 Hz, 1H), 7.10 (d, J=8.6 Hz, 2H), 6.79 (d, J=8.6 Hz, 2H), 6.74 (d, J=7.5 Hz, 1H), 6.28 (d, J=7.9 Hz, 1H), 4.65-4.49 (m, 2H), 4.42 (p, J=7.2, 7.2, 7.2, 7.2 Hz, 1H), 3.77 (s, 3H), 3.69 (t, J=4.5, 4.5 Hz, 4H), 3.23 (d, J=5.0 Hz, 1H), 3.07-2.81 (m, 5H), 2.45 (d, J=7.5 Hz, 4H), 1.87-1.61 (m, 4H), 1.50-1.12 (m, 15H). MS (EI) for C$_{31}$H$_{46}$N$_4$O$_8$, found 603.4 (MH$^+$).

(S)—N—((S)-3-cyclopropyl-1-((R)-2-methyloxiran-2-yl)-1-oxopropan-2-yl)-3-(4-methoxyphenyl)-2-((S)-2-(2-morpholinoacetamido)propanamido)propanamide (C-1006): $^1$H NMR (400 MHz, CDCl$_3$) δ 7.43 (d, J=7.7 Hz, 1H), 7.13 (d, J=8.5 Hz, 2H), 6.80 (d, J=8.5 Hz, 2H), 6.69 (d, J=7.4 Hz, 1H), 6.36 (d, J=7.5 Hz, 1H), 4.64-4.49 (m, 2H), 4.49-4.34 (m, 1H), 3.77 (s, 3H), 3.70 (t, J=4.5, 4.5 Hz, 4H), 3.23 (d, J=5.0 Hz, 1H), 2.98 (dd, J=13.6, 7.0 Hz, 3H), 2.89 (dd, J=10.7, 5.7 Hz, 2H), 2.52-2.39 (m, 4H), 1.58-1.45 (m, 4H), 1.36 (d, J=11.1 Hz, 3H), 1.24-1.12 (m, 1H), 0.56 (s, 1H), 0.05-0.07 (m, 3H). MS (EI) for C$_{28}$H$_{40}$N$_4$O$_7$, 545.0 found (MH$^+$).

(S)—N—((S)-3-cyclopentyl-1-((R)-2-methyloxiran-2-yl)-1-oxopropan-2-yl)-3-(4-methoxyphenyl)-2-((S)-2-(2-morpholinoacetamido)propanamido)propanamide (C-1005): $^1$H NMR (400 MHz, CDCl$_3$) δ 7.42 (d, J=7.5 Hz, 1H), 7.16-7.05 (m, 2H), 6.87-6.75 (m, 2H), 6.64 (d, J=7.5 Hz, 1H), 6.22 (d, J=7.9 Hz, 1H), 4.64-4.34 (m, 3H), 3.77 (s, 3H), 3.70 (t, J=4.6, 4.6 Hz, 4H), 3.24 (d, J=5.0 Hz, 1H), 3.07-2.79 (m, 5H), 2.54-2.35 (m, 4H), 1.77-1.43 (m, 12H), 1.36 (d, J=7.1 Hz, 3H), 1.11 (s, 1H), 0.96 (s, 1H). MS (EI) for C$_{30}$H$_{44}$N$_4$O$_7$, found 571.3 (MH$^+$).

(S)—N—((S)-3-cyclobutyl-1-((R)-2-methyloxiran-2-yl)-1-oxopropan-2-yl)-3-(4-methoxyphenyl)-2-((S)-2-(2-morpholinoacetamido)propanamido)propanamide (C-1004): $^1$H NMR (400 MHz, CDCl$_3$) δ 7.45 (d, J=7.6 Hz, 1H), 7.18-7.07 (m, 2H), 6.87-6.76 (m, 2H), 6.69 (d, J=7.6 Hz, 1H), 6.19 (d, J=7.8 Hz, 1H), 4.53 (q, J=7.0, 7.0, 7.0 Hz, 1H), 4.46-4.31 (m, 2H), 3.78 (s, 3H), 3.71 (t, J=4.6, 4.6 Hz, 4H), 3.20 (d, J=5.0 Hz, 1H), 3.09-2.80 (m, 5H), 2.59-2.39 (m, 4H), 2.32-2.07 (m, 3H), 2.06-1.89 (m, 2H), 1.89-1.71 (m, 2H), 1.69-1.59 (m, 1H), 1.58-1.41 (m, 4H), 1.37 (d, J=7.1 Hz, 3H). MS (EI) for C$_{29}$H$_{42}$N$_4$O$_7$, found 559.1 (MH$^+$).

(S)-3-(4-methoxyphenyl)-N—((S)-1-((R)-2-methyloxiran-2-yl)-1-oxo-3-((S)-tetrahydrofuran-2-yl)propan-2-yl)-2-((S)-2-(2-morpholinoacetamido)propanamido)propanamide (C-1016): $^1$H NMR (300 MHz, CDCl$_3$): δ 7.42 (m, 1H), 7.17 (d, J=8.7 Hz, 2H), 6.95 (d, J=7.5 Hz, 1H), 6.82 (d, J=8.7 Hz, 2H), 6.67 (d, J=7.8 Hz, 1H), 4.61 (m, 1H), 4.59 (m, 1H), 4.45 (m, 1H), 3.81 (s, 3H), 3.79-3.72 (m, 6H), 3.25 (d, J=5.1 Hz, 1H), 3.00 (m, 3H), 2.91 (d, J=5.1 Hz, 1H), 2.53 (m, 4H), 2.01 (m, 2H), 1.85-1.64 (m, 5H), 1.55 (s, 3H), 1.38 (d, J=6.9 Hz, 3H), 1.15 (d, J=6.0 Hz, 1H). MS (EI) for C$_{29}$H$_{42}$N$_4$O$_8$, found 575.5 (MH)$^+$.

(S)-3-(4-methoxyphenyl)-N—((S)-1-((R)-2-methyloxiran-2-yl)-1-oxo-3-((R)-tetrahydrofuran-2-yl)propan-2-yl)-2-((S)-2-(2-morpholinoacetamido)propanamido)propanamide (C-1017): $^1$H NMR (300 MHz, CDCl$_3$): δ 7.42 (m, 1H), 7.15 (m, 3H), 6.82 (d, J=8.7 Hz, 2H), 6.60 (m, 1H), 4.62-4.60 (m, 2H), 4.44 (m, 1H), 3.80 (m, 1H), 3.79 (s, 3H), 3.79-3.72 (m, 6H), 3.32 (d, J=4.8 Hz, 1H), 3.05-2.89 (m, 5H), 2.52-2.49 (m, 4H), 1.91-1.81 (m, 6H), 1.53 (s, 3H), 1.37 (d, J=6.6 Hz, 3H). MS (EI) for C$_{29}$H$_{42}$N$_4$O$_8$, found 575.7 (MH)$^+$.

(S)—N—((S)-3-(cyclohex-1-en-1-yl)-1-((R)-2-methyloxiran-2-yl)-1-oxopropan-2-yl)-3-(4-methoxyphenyl)-2-((S)-2-(2-morpholinoacetamido)propanamido)propanamide (C-1019): $^1$H NMR (300 MHz, DMSO-d$_6$): δ 8.25 (d, J=7.5 Hz, 1H), 8.03 (d, J=8.1 Hz, 1H), 7.73 (d, J=7.2 Hz, 1H), 7.11 (m, 2H), 6.78 (m, 2H), 4.81 (m, 1H), 5.40 (s, 1H), 4.52 (m, 2H), 4.21 (m, 1H), 3.71 (s, 1H), 3.33 (m, 4H), 3.20 (m, 1H), 2.98 (m, 1H), 2.95 (m, 2H), 2.50 (m, 1H), 2.36 (m, 4H), 2.20 (m, 1H), 1.99 (m, 6H), 1.54 (m, 4H), 1.37 (s, 3H), 1.16 (m, 3H). MS (EI) for C$_{31}$H$_{44}$N$_4$O$_7$, found 585.4 (MH)$^+$.

(S)—N—((S)-3-(3,6-dihydro-2H-pyran-4-yl)-1-((R)-2-methyloxiran-2-yl)-1-oxopropan-2-yl)-3-(4-methoxyphenyl)-2-((S)-2-(2-morpholinoacetamido)propanamido)propanamide (C-1020): $^1$H NMR (300 MHz, CDCl$_3$): δ 7.17 (d, J=8.7 Hz, 2H), 6.84 (d, J=8.7 Hz, 2H), 6.81 (m, 1H), 6.14 (m, 1H), 5.37 (s, 1H), 4.56 (m, 2H), 4.34 (m, 1H), 4.06 (m, 2H), 3.80 (s, 3H), 3.79-3.72 (m, 4H), 3.29 (d, J=4.8 Hz, 1H), 3.01-2.93 (m, 5H), 2.51 (m, 4H), 2.04 (m, 2H), 1.68 (m, 3H), 1.52 (s, 3H), 1.37 (d, J=6.9 Hz, 3H). MS (EI) for C$_{30}$H$_{42}$N$_4$O$_8$, found 587.7 (MH)$^+$.

(S)—N—((S)-3-((S)-3,3-difluorocyclopentyl)-1-((R)-2-methyloxiran-2-yl)-1-oxopropan-2-yl)-3-(4-methoxyphenyl)-2-((S)-2-(2-morpholinoacetamido)propanamido)propanamide (C-1033): $^1$H NMR (300 MHz, CDCl$_3$): δ 7.47 (d, J=7.5 Hz, 1H), 7.10 (d, J=8.4 Hz, 2H), 6.81 (d, J=8.7 Hz, 2H), 6.72 (d, J=7.8 Hz, 1H), 6.50 (d, J=7.8 Hz, 1H), 4.56 (m, 1H), 4.42 (m, 2H), 3.79 (s, 3H), 3.75 (m, 4H), 3.22 (d, J=4.8 Hz, 1H), 2.91-3.10 (m, 5H), 2.51 (m, 4H), 1.69-2.38 (m, 9H), 1.52 (s, 3H), 1.36 (d, J=5.7 Hz, 3H). MS (EI) for C$_{30}$H$_{42}$F$_2$N$_4$O$_7$, found 609.4 (MH)$^+$.

(S)—N—((S)-3-((R)-3,3-difluorocyclopentyl)-1-((R)-2-methyloxiran-2-yl)-1-oxopropan-2-yl)-3-(4-methoxyphenyl)-2-((S)-2-(2-morpholinoacetamido)propanamido)propanamide (C-1034): $^1$H NMR (300 MHz, CDCl$_3$): δ 7.45 (d, J=7.2 Hz, 1H), 7.10 (d, J=8.4 Hz, 2H), 6.81 (d, J=8.7 Hz, 2H), 6.69 (d, J=7.8 Hz, 1H), 6.51 (d, J=7.8 Hz, 1H), 4.55 (m, 1H), 4.40 (m, 2H), 3.79 (s, 3H), 3.73 (m, 4H), 3.23 (d, J=5.1 Hz, 1H), 2.87-3.13 (m, 5H), 2.50 (m, 4H), 1.62-2.18 (m, 9H), 1.52 (s, 3H), 1.39 (d, J=5.7 Hz, 3H). MS (EI) for C$_{30}$H$_{42}$F$_2$N$_4$O$_7$, found 609.4 (MH)$^+$.

(2S)-3-(4-methoxyphenyl)-N-((2S)-3-(1-methyl-2-oxopyrrolidin-3-yl)-1-((R)-2-methyloxiran-2-yl)-1-oxopropan-2-yl)-2-((S)-2-(2-morpholinoacetamido) propanamido)propanamide (C-1040): $^1$H NMR (300 MHz, CDCl$_3$): δ 8.50 (d, J=8.1 Hz, 1H), 7.56 (d, J=8.1 Hz, 1H), 7.10 (m, 2H), 6.77 (m, 2H), 4.74 (m, 1H), 4.50 (m, 1H), 4.32 (m, 1H), 4.13 (m, 1H), 3.76 (s, 3H), 3.74-3.68 (m, 4H), 3.60 (m, 3H), 3.35 (m, 1H), 3.35-3.04 (m, 4H), 3.00-2.85 (m, 2H), 2.80 (m, 3H), 2.47 (m, 4H), 2.45-2.06 (m, 1H), 1.57-1.60 (m, 2H), 1.58 (s, 3H), 1.42 (d, J=6.9 Hz, 3H). MS (EI) for C$_{30}$H$_{43}$N$_5$O$_8$, found 603.0 (MH)$^+$.

(2S)-3-(4-methoxyphenyl)-N-((2S)-1-((R)-2-methyloxiran-2-yl)-1-oxo-3-(5-oxopyrrolidin-3-yl)propan-2-yl)-2-((S)-2-(2-morpholinoacetamido) propanamido)propanamide (C-1035): $^1$H NMR (300 MHz, CDCl$_3$): δ 8.07 (d, J=8.1 Hz, 1H), 7.56 (d, J=8.1 Hz, 1H), 7.38 (d, J=8.4 Hz, 1H), 7.07 (d, J=8.4 Hz, 2H), 6.77 (m, 2H), 4.74 (m, 2H), 4.47 (m, 2H), 3.76 (s, 3H), 3.71-3.68 (m, 4H), 3.33 (m, 3H), 3.06 (m, 1H), 2.92 (m, 3H), 2.47 (m, 4H), 2.40 (m, 4H), 1.80 (m, 2H), 1.52 (s, 3H), 1.38 (d, J=6.9 Hz, 3H). MS (EI) for C$_{29}$H$_{41}$N$_5$O$_8$, found 588.6 (MH)$^+$.

(1r,3R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-hydroxycyclobutanecarboxamide (C-1041): $^1$H NMR (300 MHz, DMSO-d$_6$): δ 7.11 (d, J=8.7 Hz, 2H), 6.83 (d, J=8.7 Hz, 2H), 6.68-6.85 (m, 2H), 6.45-6.70 (m, 1H), 4.65-4.75 (m, 2H), 6.42 (m, 2H), 5.88 (m, 1H), 5.10 (s, 2H), 4.80-4.83 (m, 1H), 4.63-4.66 (m, 1H), 4.48-4.53 (m, 2H), 4.30-4.40 (m, 1H), 3.80 (s, 3H), 3.32 (d, J=5.1 Hz, 1H), 3.11 (dd, J=4.2, 13.8 Hz, 1H), 2.89-2.99 (m, 2H), 2.48-2.54 (m, 4H), 2.14-2.22 (m, 2H), 1.40-1.80 (m, 3H), 1.44 (s, 3H), 1.29 (d, J=6.9 Hz, 3H), 1.08-1.20 (m, 1H). MS (EI) for C$_{29}$H$_{41}$N$_3$O$_7$, found 544.3 (MH)$^+$.

(S)-3-(4-methoxyphenyl)-N—((S)-1-((R)-2-methyloxiran-2-yl)-1-oxo-3-(2-oxopyrrolidin-1-yl)propan-2-yl)-2-((S)-2-(2-morpholinoacetamido) propanamido)propanamide (C-1042): $^1$H NMR (300 MHz, DMSO-d$_6$): δ 7.65 (m, 1H), 7.30-7.60 (m, 2H), 7.05-7.15 (m, 2H), 6.70-6.85 (m, 3H), 4.40-4.70 (m, 3H), 3.78 (s, 3H), 3.60-3.75 (m, 4H), 3.30-3.60 (m, 3H), 3.15 (m, 1H), 2.80-3.00 (m, 4H), 2.30-2.60 (m, 6H), 1.80-2.10 (m, 3H), 1.39 (s, 3H), 1.20-1.30 (m, 3H). MS (EI) for C$_{29}$H$_{41}$N$_5$O$_8$, found 588.4 (MH)$^+$. ). MS (EI) for C$_{29}$H$_{41}$N$_5$O$_8$, found 588.4 (MH)$^+$.

(S)-3-(4-methoxyphenyl)-N—((S)-3-(2-methyl cyclopent-1-en-1-yl)-1-((R)-2-methyloxiran-2-yl)-1-oxopropan-2-yl)-2-((S)-2-(2-morpholinoacetamido) propanamido)propanamide (C-1044): $^1$H NMR (300 MHz, CD$_3$OD): δ 8.31 (d, J=7.8 Hz, 1H), 8.05 (d, J=7.8 Hz, 1H), 7.74 (d, J=7.5 Hz, 1H), 7.11 (d, J=8.7 Hz, 2H), 6.78 (d, J=8.7 Hz, 2H), 4.28-4.54 (m, 2H), 4.22-4.30 (m, 1H), 3.71 (s, 3H), 3.56 (br s, 4H), 3.18 (d, J=5.1 Hz, 1H), 2.82-2.98 (m, 4H), 2.64-2.67 (m, 1H), 2.35-2.45 (m, 5H), 2.13-2.26 (m, 5H), 1.71 (t, J=7.2 Hz, 1H), 1.57 (s, 3H), 1.39 (s, 3H), 1.16 (d, J=6.9 Hz, 3H). MS (EI) for C$_{31}$H$_{44}$N$_4$O$_7$, found 585.4 (MH)$^+$.

(1r,4R)—N—((R)-1-(((S)-1-(((S)-3-(3,3-difluorocyclobutyl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxycyclohexanecarboxamide (C-1073): $^1$H NMR (400 MHz, CDCl$_3$) δ 8.25 (d, J=7.1 Hz, 1H), 7.99 (d, J=8.6 Hz, 1H), 7.83 (d, J=7.1 Hz, 1H), 7.19-7.02 (m, 2H), 6.87-6.63 (m, 2H), 4.50 (d, J=4.5 Hz, 1H), 4.41 (ddd, J=10.2, 8.7, 3.9 Hz, 1H), 4.30-4.20 (m, 1H), 4.13 (p, J=7.1, 7.1, 7.1, 7.1 Hz, 1H), 4.08-3.95 (m, 1H), 3.69 (s, 3H), 3.26 (s, 1H), 3.21 (d, J=5.1 Hz, 1H), 3.03 (d, J=5.2 Hz, 1H), 2.94 (dd, J=13.8, 3.8 Hz, 1H), 2.77-2.56 (m, 3H), 2.10-1.99 (m, 1H), 1.62 (s, 5H), 1.41 (s, 2H), 1.14-1.00 (m, 2H), 0.95 (d, J=7.1 Hz, 2H). MS (EI) for C$_{30}$H$_{41}$F$_2$N$_3$O$_7$, found 594.0 (MH)$^+$.

(1r,4R)—N—((R)-1-(((S)-1-(((S)-3-(cyclopent-1-en-1-yl)-1-((R)-2-methyloxiran-2-yl)-1-oxopropan-2-yl)amino)-3-(3-hydroxy-4-methoxyphenyl)-1-oxopropan-2-yl)amino)-1-oxopropan-2-yl)-4-hydroxycyclohexanecarboxamide (C-1065): $^1$H NMR (300 MHz, DMSO-d$_6$): δ 8.70 (br s, 1H), 8.24 (d, J=7.2 Hz, 1H), 7.95 (d, J=8.7 Hz, 1H), 7.80 (d, J=7.5 Hz, 1H), 6.74 (d, J=8.1 Hz, 1H), 6.62 (m, 1H), 6.55 (d, J=8.1 Hz, 1H), 5.40 (br s, 1H), 4.51 (d, J=4.5 Hz, 2H), 4.30 (m, 1H), 4.18 (m, 1H), 3.70 (s, 3H), 3.28 (m, 1H), 3.16 (d, J=5.4 Hz, 1H), 2.98 (m, J=5.4 Hz, 1H), 2.70 (m, 1H), 2.62 (m, 2H), 2.48 (m, 2H), 2.24 (m, 3H), 1.94 (m, 1H), 1.80 (m, 4H), 1.63 (m, 2H), 1.37 (s, 3H), 1.32 (m, 2H), 1.28 (m, 2H), 0.95 (d, J=7.2 Hz, 3H). MS (EI) for C$_{31}$H$_{43}$N$_3$O$_8$, found 586.3 (MH)$^+$.

(S)—N—((S)-3-(cyclopent-3-en-1-yl)-1-((R)-2-methyloxiran-2-yl)-1-oxopropan-2-yl)-3-(4-methoxyphenyl)-2-((S)-2-(2-morpholinoacetamido)propanamido)propanamide (C-1066): $^1$H NMR (300 MHz, DMSO-d$_6$): δ 8.36 (d, J=7.2 Hz, 1H), 8.08 (d, J=8.4 Hz, 1H), 7.75 (d, J=7.8 Hz, 1H), 7.13 (d, J=8.4 Hz, 2H), 6.80 (d, J=8.4 Hz, 2H), 5.68 (m, 2H), 4.50 (m, 1H), 4.20-4.40 (m, 2H), 3.75 (s, 3H), 3.70 (m, 4H), 3.15 (m, 1H), 3.05 (m, 1H), 2.80-3.00 (m, 3H), 2.65 (m, 1H), 2.35 (m, 4H), 1.90-2.10 (m, 2H), 1.60 (m, 1H), 1.50 (m, 1H), 1.42 (s, 3H), 1.14 (d, J=6.9 Hz, 3H). MS (EI) for C$_{30}$H$_{42}$N$_4$O$_7$, found 571.64 (MH)$^+$. MS (EI) for C$_{30}$H$_{42}$N$_4$O$_7$, found 571.3 (MH)$^+$.

(1r,4R)—N—((R)-1-(((S)-1-(((S)-3-(cyclohex-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxycyclohexanecarboxamide (C-1089): $^1$H NMR (300 MHz, DMSO-d$_6$): δ 8.26 (m, 1H), 7.79 (d, J=6.9 Hz, 1H), 7.65 (d, J=7.5 Hz, 1H), 7.10 (d, J=8.7 Hz, 2H), 6.78 (d, J=8.4 Hz, 2H), 5.41 (m, 1H), 4.53 (m, 2H), 4.40 (m, 1H), 4.08 (m, 1H), 3.70 (s, 3H), 3.34 (m, 2H), 3.25 (m, 2H), 2.93 (m, 2H), 2.10 (m, 1H), 1.99-1.80 (m, 8H), 1.66-1.46 (m, 3H), 1.37 (d, J=6.9 Hz, 3H), 1.29 (m, 2H), 1.14 (m, 2H), 0.94 (d, J=6.9 Hz, 3H). MS (EI) for C$_{32}$H$_{45}$N$_3$O$_7$, found 584.4 (MH)$^+$.

(1r,4R)—N—((R)-1-(((S)-1-(((S)-3-cyclobutyl-1-((R)-2-methyloxiran-2-yl)-1-oxopropan-2-yl)amino)-3-(4-methoxyphenyl)-1-oxopropan-2-yl)amino)-1-oxopropan-2-yl)-4-hydroxycyclohexanecarboxamide (C-1090): $^1$H NMR (300 MHz, CDCl$_3$): δ 7.11 (d, J=8.4 Hz, 2H), 6.82 (d, J=9.0 Hz, 2H), 6.76 (m, 1H), 6.52 (m, 1H), 6.33 (m, 1H), 4.44 (m, 1H), 4.39 (m, 2H), 3.79 (s, 3H), 3.56 (m, 1H), 3.23 (d, J=5.1 Hz, 1H), 2.99 (m, 2H), 2.88 (m, 1H), 2.08 (m, 1H), 2.06-2.02 (m, 4H), 1.99-1.77 (m, 8H), 1.65 (m, 2H), 1.64 (m, 5H), 1.27 (m, 5H). MS (EI) for C$_{30}$H$_{43}$N$_3$O$_7$, found 558.3 (MH)$^+$.

(S)—N—((S)-3-((1R,5S,6s)-bicyclo[3.1.0]hexan-6-yl)-1-((R)-2-methyloxiran-2-yl)-1-oxopropan-2-yl)-3-(4-methoxyphenyl)-2-((S)-2-(2-morpholinoacetamido)propanamido)propanamide (C-1143): $^1$H NMR (300 MHz, DMSO-d$_6$): δ 8.37 (d, J=6.9 Hz, 1H), 8.03 (d, J=8.4 Hz, 1H), 7.72 (d, J=7.8 Hz, 1H), 7.11 (d, J=8.4 Hz, 1H), 6.78 (d, J=8.7 Hz, 2H), 4.64 (m, 1H), 4.37 (m, 1H), 4.26 (m, 1H), 3.70 (s, 3H), 3.56 (m, 4H), 3.23 (d, J=4.8 Hz, 1H), 2.94 (m, 1H), 2.90 (m, 3H), 2.86 (m, 1H), 2.36 (m, 4H), 1.99 (m, 3H), 1.80 (m, 4H), 1.34 (m, 3H), 1.30-1.28 (m, 3H), 1.16 (d, J=5.1 Hz, 3H), 1.13 (m, 1H). MS (EI) for C$_{31}$H$_{44}$N$_4$O$_7$, found 585.43 (MH)$^+$.

(S)—N—((S)-3-(3,3-difluorocyclobutyl)-1-((R)-2-methyloxiran-2-yl)-1-oxopropan-2-yl)-3-(4-methoxyphenyl)-2-((S)-2-(2-morpholinoacetamido)propanamido)propanamide (C-1093): $^1$H NMR (400 MHz, CDCl$_3$) δ 8.24 (d, J=7.2 Hz, 1H), 8.15 (s, 1H), 8.02 (d, J=8.6 Hz, 1H), 7.81 (d, J=7.3 Hz, 1H), 7.17-6.99 (m, 2H), 6.86-6.70 (m, 2H), 5.41 (s, 1H), 4.52 (s, 3H), 4.47-4.35 (m, 3H), 4.18 (p, J=7.2, 7.2, 7.0, 7.0 Hz, 1H), 3.71 (s, 3H), 3.62 (pd, J=6.6, 6.6, 6.6, 6.6, 3.9 Hz, 2H), 3.22 (d, J=5.3 Hz, 1H), 3.14 (qd, J=7.4, 7.3, 7.3, 4.3 Hz, 2H), 3.02-2.95 (m, 1H), 2.97-2.88 (m, 1H), 2.88-2.72 (m, 2H), 2.59 (dd, J=13.9, 10.3 Hz, 1H), 2.42 (dd, J=14.1, 4.7 Hz, 1H), 2.34-2.11 (m, 2H), 1.90-1.70 (m, 2H), 1.38 (s, 3H), 0.92 (d, J=7.1 Hz, 3H). MS (EI) for C$_{29}$H$_{40}$F$_2$N$_4$O$_7$, found 585.43 (MH)$^+$.

(S)-3-(4-methoxyphenyl)-N—((S)-1-((R)-2-methyloxiran-2-yl)-1-oxo-3-((R)-tetrahydrofuran-3-yl)propan-2-yl)-2-((S)-2-(2-morpholinoacetamido)propanamido)propanamide (C-1026): $^1$H NMR (300 MHz, DMSO-d$_6$): δ 8.36 (d, J=7.5 Hz, 1H), 8.08 (d, J=8.1 Hz, 1H), 7.75 (d, J=7.5 Hz, 1H), 7.13 (d, J=8.4 Hz, 2H), 6.80 (d, J=8.4 Hz, 2H), 4.50 (m, 1H), 4.20-4.30 (m, 2H), 3.75 (m, 4H), 3.60-3.70 (m, 5H), 3.30 (m, 1H), 3.15 (m, 1H), 3.00 (m, 1H), 2.80-3.00 (m, 3H), 2.70 (m, 1H), 2.35 (m, 4H), 2.20 (m, 1H), 2.00 (m, 1H), 1.70 (m, 1H), 1.50-1.70 (m, 2H), 1.42 (s, 3H), 1.14 (d, J=6.9 Hz, 3H). MS (EI) for C$_{29}$H$_{42}$N$_4$O$_8$, found 575.5 (MH)$^+$.

(S)—N—((S)-3-((1R,5S,6r)-bicyclo[3.1.0]hexan-6-yl)-1-((R)-2-methyloxiran-2-yl)-1-oxopropan-2-yl)-3-(4-methoxyphenyl)-2-((S)-2-(2-morpholinoacetamido) propanamido)propanamide (C-1142): $^1$H NMR (300 MHz, CDCl$_3$): δ 7.65 (br s, 1H), 7.13 (d, J=8.4 Hz, 2H), 6.80 (m, 3H), 6.36 (m, 1H), 4.56 (m, 2H), 4.43 (m, 1H), 3.78 (s, 3H), 3.75 (m, 4H), 3.21 (d, J=4.8 Hz, 1H), 3.06-2.94 (m, 4H), 2.88 (d, J=4.8 Hz, 1H), 2.57 (m, 4H), 1.69-1.41 (m, 4H), 1.41 (m, 3H), 1.36 (d, J=7.2 Hz, 3H), 1.28 (m, 1H), 1.20 (m, 1H), 0.96 (m, 1H), 0.95 (m, 1H), 0.88 (m, 2H), 0.37 (m, 1H). MS (EI) for C$_{31}$H$_{44}$N$_4$O$_7$, found 585.3 (MH)$^+$.

(S)-3-(4-methoxyphenyl)-N—((S)-1-((R)-2-methyloxiran-2-yl)-1-oxo-3-((S)-tetrahydrofuran-3-yl)propan-2-yl)-2-((S)-2-(2-morpholinoacetamido)propanamido) propanamide (C-1025): $^1$H NMR (300 MHz, DMSO-d$_6$): δ 8.45 (d, J=6.9 Hz, 1H), 8.22 (d, J=8.1 Hz, 1H), 7.80 (d, J=7.5 Hz, 1H), 7.15 (d, J=8.4 Hz, 2H), 6.80 (d, J=8.4 Hz, 2H), 4.45 (m, 1H), 4.20-4.30 (m, 2H), 3.80 (m, 2H), 3.75 (s, 3H), 3.60-3.70 (m, 6H), 3.10-3.30 (m, 3H), 3.05 (m, 1H), 2.80-3.00 (m, 3H), 2.75 (m, 1H), 2.35 (m, 4H), 2.20 (m, 1H), 1.95 (m, 1H), 1.50-1.70 (m, 1H), 1.42 (s, 3H), 1.16 (d, J=6.9 Hz, 3H). MS (EI) for C$_{29}$H$_{42}$N$_4$O$_8$, found 575.4 (MH)$^+$.

(2S)-3-(4-methoxyphenyl)-N-((2S)-3-(3-methyl cyclopent-1-en-1-yl)-1-((R)-2-methyloxiran-2-yl)-1-oxopropan-2-yl)-2-((S)-2-(2-morpholinoacetamido) propanamido)propanamide (C-1122): $^1$H NMR (300 MHz, DMSO-d$_6$): δ 8.35 (m, 1H), 8.07 (d, J=8.4 Hz, 1H), 7.73 (d, J=7.5 Hz, 1H), 7.13 (d, J=8.4 Hz, 2H), 6.79 (d, J=8.4 Hz, 2H), 5.31 (m, 1H), 4.50-4.60 (m, 2H), 4.25 (m, 1H), 3.70 (s, 3H), 3.50 (m, 4H), 3.18 (m, 1H), 2.95 (m, 1H), 2.80-2.90 (m, 3H), 2.65 (m, 1H), 2.35 (m, 4H), 1.70-2.10 (m, 4H), 1.38 (s, 3H), 1.14 (d, J=6.9 Hz, 3H), 0.39 (m, 3H). MS (EI) for C$_{31}$H$_{44}$N$_4$O$_7$, found 585.2 (MH)$^+$.

(S)—N—((S)-3-cyclohexyl-1-((R)-2-methyloxiran-2-yl)-1-oxopropan-2-yl)-3-(4-methoxyphenyl)-2-((S)-2-(2-morpholinoacetamido)propanamido)propanamide (C-1003): $^1$H NMR (400 MHz, CDCl$_3$) δ 7.42 (d, J=8.0 Hz, 1H), 7.19-7.01 (m, 2H), 6.90-6.77 (m, 2H), 6.63 (d, J=7.8 Hz, 1H), 6.17 (d, J=7.5 Hz, 1H), 4.66-4.47 (m, 2H), 4.41 (p, J=7.1, 7.1, 6.8, 6.8 Hz, 1H), 3.78 (s, 3H), 3.70 (t, J=4.6, 4.6 Hz, 4H), 3.26 (d, J=5.0 Hz, 1H), 3.11-2.93 (m, 3H), 2.93-2.80 (m, 2H), 2.60-2.35 (m, 4H), 1.84-1.51 (m, 11H), 1.30-1.00 (m, 6H), 1.02-0.75 (m, 2H). MS (EI) for C$_{31}$H$_{46}$N$_4$O$_7$, found 587.4 (M$^+$).

(S)—N—((S)-3-cyclopentyl-1-((R)-oxiran-2-yl)-1-oxopropan-2-yl)-3-(4-methoxyphenyl)-2-((S)-2-(2-morpholinoacetamido)propanamido)propanamide (C-1030): $^1$H NMR (300 MHz, CDCl$_3$): δ 7.40 (m, 1H), 7.13 (d, J=8.4 Hz, 2H), 6.82 (d, J=8.7 Hz, 2H), 6.76 (d, J=8.1 Hz, 1H), 6.47 (d, J=8.1 Hz, 1H), 4.61 (m, 1H), 4.49 (m, 1H), 4.42 (m, 1H), 3.79 (s, 3H), 3.74 (m, 4H), 3.51 (m, 1H), 3.13-3.10 (m, 4H), 3.08-3.03 (m, 2H), 2.50 (m, 4H), 1.74 (m, 2H), 1.63 (m, 1H), 1.53 (m, 2H), 1.34 (d, J=8.4 Hz, 3H), 1.27 (m, 3H), 0.85-1.16 (m, 3H). MS (EI) for $C_{29}H_{42}N_4O_7$, found 559.8 (MH$^+$).

(S)—N—((S)-3-(cyclopent-1-en-1-yl)-1-((R)-oxiran-2-yl)-1-oxopropan-2-yl)-3-(4-methoxyphenyl)-2-((S)-2-(2-morpholinoacetamido)propanamido)propanamide (C-1038): $^1$H NMR (300 MHz, CDCl$_3$): δ 7.40 (m, 1H), 7.13 (d, J=8.4 Hz, 2H), 6.82 (d, J=8.7 Hz, 2H), 6.76 (d, J=8.1 Hz, 1H), 6.47 (d, J=8.1 Hz, 1H), 5.37 (m, 1H), 4.58 (m, 1H), 4.53 (m, 1H), 4.42 (m, 1H), 3.80 (s, 3H), 3.74 (m, 4H), 3.51 (m, 1H), 3.13-3.10 (m, 4H), 3.08-3.03 (m, 1H), 2.58 (m, 4H), 2.35-2.19 (m, 5H), 1.87 (m, 2H), 1.37 (d, J=8.4 Hz, 3H). MS (EI) for $C_{29}H_{40}N_4O_7$, found 557.3 (MH$^+$).

Example 10

(S)-3-Cyano-N—((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)-2-(2-morpholinoacetamido)propanamide (C-1135)

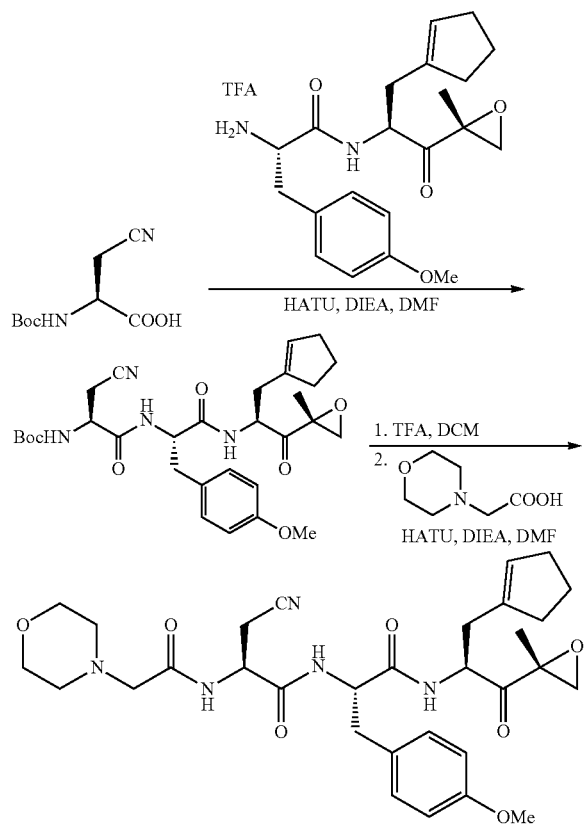

Sequentially HATU (1.21 g, 3.20 mmol) and DIEA (1.35 mL, 7.8 mmol) were added to a 0° C. solution of (S)-2-(tert-butoxycarbonylamino)-3-cyanopropanoic acid and (S)-2-amino-N—((S)-3-(cyclopent-1-en-1-yl)-1-((R)-2-methyloxiran-2-yl)-1-oxopropan-2-yl)-3-(4-methoxyphenyl)propanamide (TFA salt, 2.1 mmol) in DMF (20 mL). The reaction mixture was allowed to warm to ambient temperature and stirred for 3 h. EtOAc (100 mL) and water (100 mL) was added. The aqueous layer was extracted with EtOAc (50 mL×3). The combined organic phases were washed with brine (200 mL×3), dried over anhydrous sodium sulfate, and concentrated. The residue was purified by flash column chromatography on silica gel (EtOAc/hexane=1:2) to afford tert-butyl ((S)-3-cyano-1-(((S)-1-(((S)-3-(cyclopent-1-en-1-yl)-1-((R)-2-methyl oxiran-2-yl)-1-oxopropan-2-yl)amino)-3-(4-methoxyphenyl)-1-oxopropan-2-yl) amino)-1-oxopropan-2-yl)carbamate (590 mg, 45% yield).

To a solution of tert-butyl ((S)-3-cyano-1-(((S)-1-(((S)-3-(cyclopent-1-en-1-yl)-1-((R)-2-methyl oxiran-2-yl)-1-oxopropan-2-yl)amino)-3-(4-methoxyphenyl)-1-oxopropan-2-yl) amino)-1-oxopropan-2-yl)carbamate (0.59 g, 1.0 mmol) in DCM (10 mL) was added TFA (5 mL). The reaction mixture was stirred for 15 min at ambient temperature then concentrated to dryness to afford (S)-2-amino-3-cyano-N—((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)propanamide (650 mg, quant.) as its TFA salt, which was used directly without further purification.

Sequentially HATU (0.61 g, 1.6 mmol) and DIEA (1.35 mL, 7.8 mmol) were added to a 0° C. solution of (S)-2-amino-3-cyano-N—((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)propanamide (1 mmol) and 2-morpholinoacetic acid (160 mg, 1.10 mmol) in DMF (20 mL) with stirring. The reaction mixture was allowed to warm to ambient temperature and stirred for 3 h. EtOAc (100 mL) and water (100 mL) was added. The two layers were separated and the aqueous phase was extracted with EtOAc (50 mL×3). The combined organic phases were washed with brine (200 mL×3), dried over anhydrous sodium sulfate, and concentrated. The residue was purified by flash column chromatography on silica gel (EtOAc/hexane=1:2) to afford (S)-3-cyano-N—((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)-2-(2-morpholinoacetamido)propanamide (210 mg, 35% yield). $^1$H NMR (300 MHz, DMSO-d$_6$): δ 8.44 (d, J=6.6 Hz, 1H), 8.16 (d, J=7.5 Hz, 1H), 8.08 (d, J=8.1 Hz, 1H), 7.10 (d, J=8.4 Hz, 2H), 6.78 (d, J=8.4 Hz, 2H), 5.40 (s, 1H), 4.60-4.35 (m, 3H), 3.70 (s, 3H), 3.62-3.57 (m, 4H), 3.18 (m, 1H), 3.05-2.80 (m, 3H), 2.65 (m, 1H), 2.50-2.10 (m, 10H), 1.90-1.70 (m, 2H), 1.37 (s, 3H). MS(EI) for $C_{31}H_{41}N_5O_7$, found 596.3 (MH)$^+$.

The following compounds were synthesized in a similar manner:

N—((R)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)-2-oxaspiro[3.3]heptane-6-carboxamide (C-1063): $^1$H NMR (400 MHz, CDCl$_3$) δ 8.24 (d, J=7.2 Hz, 1H), 8.15 (s, 1H), 8.02 (d, J=8.6 Hz, 1H), 7.81 (d, J=7.3 Hz, 1H), 7.17-6.99 (m, 2H), 6.86-6.70 (m, 2H), 5.41 (s, 1H), 4.52 (s, 3H), 4.47-4.35 (m, 3H), 4.18 (p, J=7.2, 7.2, 7.0, 7.0 Hz, 1H), 3.71 (s, 3H), 3.62 (pd, J=6.6, 6.6, 6.6, 6.6, 3.9 Hz, 2H), 3.22 (d, J=5.3 Hz, 1H), 3.14 (qd, J=7.4, 7.3, 7.3, 4.3 Hz, 2H), 3.02-2.95 (m, 1H), 2.97-2.88 (m, 1H), 2.88-2.72 (m, 1H), 2.59 (dd, J=13.9, 10.3 Hz, 1H), 2.42 (dd, J=14.1, 4.7 Hz, 1H), 2.34-2.11 (m, 4H), 1.90-1.70 (m, 2H), 1.38 (s, 3H), 0.92 (d, J=7.1 Hz, 3H). MS(EI) for $C_3, H_{41}N_3O_7$, found 568.0 (MH)$^+$.

N—((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)-3,3,3-trifluoro-2-(2-morpholinoacetamido)propanamide (C-1134): $^1$H NMR (300 MHz, DMSO-d$_6$): δ 8.95 (m, 1H), 8.52 (m, 1H), 8.24 (m, 1H), 8.05 (m, 1H), 7.15 (m, 2H), 6.78 (dd, J=7.2 Hz, 2H), 5.20-5.50 (m, 2H), 4.40-4.60 (m, 2H), 3.70 (s, 3H), 3.60 (m, 4H), 3.18 (m, 1H), 2.80-3.10 (m, 3H), 2.65 (m, 1H), 2.30-2.50 (m, 5H), 2.10-2.30 (m, 4H), 2.00 (m, 1H), 1.70-1.90 (m, 2H), 1.38 (s, 3H). MS (EI) for $C_{30}H_{39}F_3N_4O_7$, found 625.8 (MH)+.

(R)—N—((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)-3,3,3-trifluoro-2-(2-morpholinoacetamido)propanamide (C-1132): $^1$H NMR (300 MHz, DMSO-$d_6$): δ 8.95 (m, 1H), 8.52 (m, 1H), 8.24 (m, 1H), 8.05 (m, 1H), 7.15 (m, 2H), 6.78 (2d, J=7.2 Hz, 2H), 5.20-5.50 (m, 2H), 4.40-4.60 (m, 2H), 3.70 (s, 3H), 3.60 (m, 4H), 3.18 (m, 1H), 2.80-3.10 (m, 3H), 2.65 (m, 1H), 2.30-2.50 (m, 5H), 2.10-2.30 (m, 4H), 2.00 (m, 1H), 1.70-1.90 (m, 2H), 1.38 (s, 3H). LC-MS for $C_{30}H_{39}F_3N_4O_7$, found 625.7 (MH)+.

Example 11

(S)—N—((S)-3-(Cyclopent-1-en-1-yl)-1-((R)-2-methyloxiran-2-yl)-1-oxopropan-2-yl)-3-(4-methoxyphenyl)-2-((S)-2-(2-morpholinoacetamido)propanamido)propanamide (C-1009)

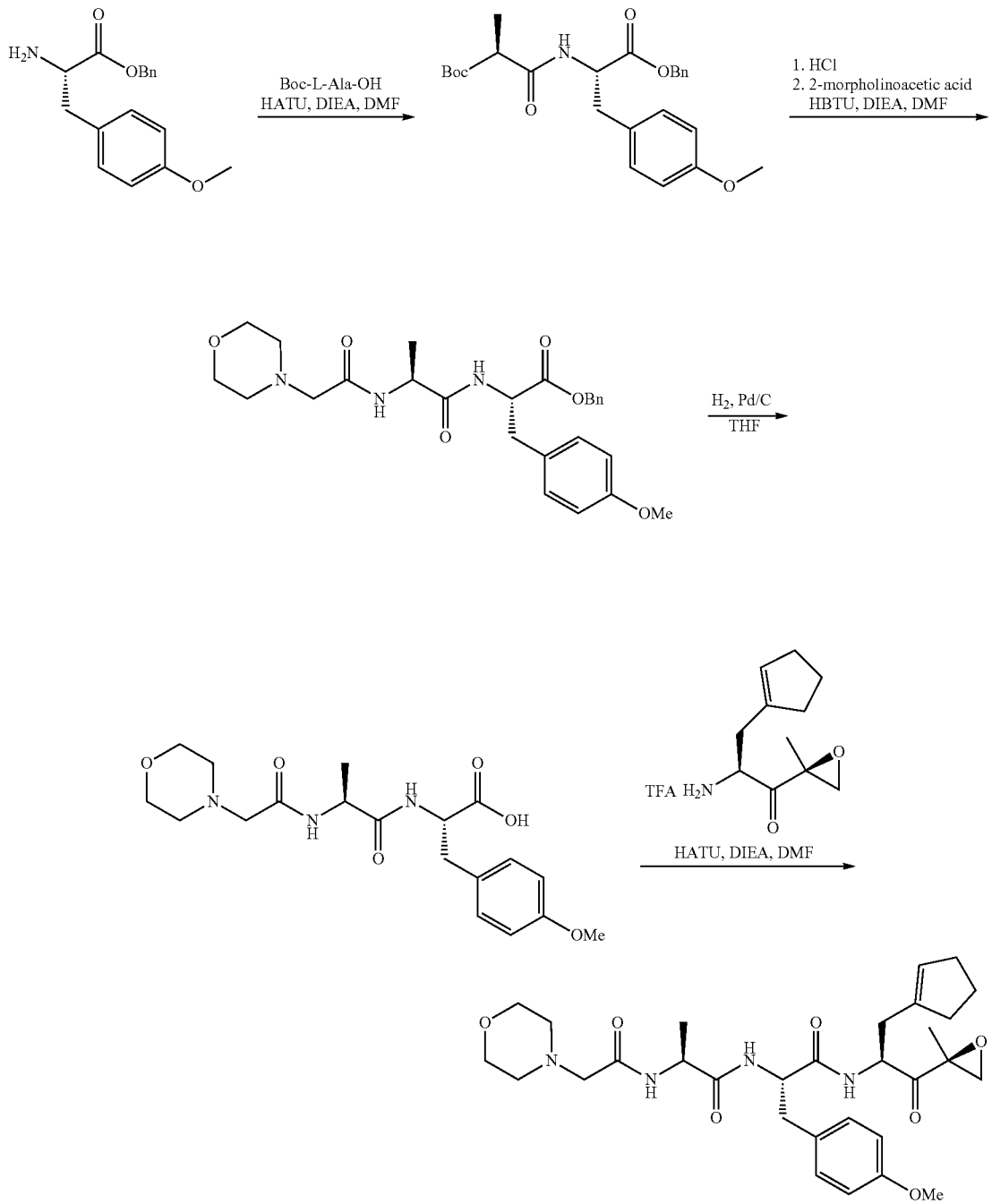

Sequentially HATU (19.3 g, 51.0 mmol) and DIEA (29.6 mL, 170 mmol) were added to a 0° C. solution of Boc-L-alanine (7.70 g, 40.7 mmol) and L-4-MeO-phenylalanine benzyl ester p-toluenesulfonate salt (15.0 g, 34.0 mmol) in DMF (200 mL) with stirring. The reaction mixture was allowed to warm to ambient temperature and stirred for 12 h. The mixture was then concentrated and the residue was purified by flash column chromatography on silica gel (hexane/EtOAc=3:1) to afford (S)-benzyl 2-((S)-2-((tert-butoxycarbonyl)amino)propanamido)-3-(4-methoxyphenyl)propanoate (13.7 g, 88% yield).

A solution of (S)-benzyl 2-((S)-2-((tert-butoxycarbonyl)amino)propanamido)-3-(4-methoxyphenyl)propanoate (29.0 g, 63.6 mmol) in 3 N HCl-EtOAc (150 mL) was stirred for 1 h at ambient temperature. The mixture was concentrated and the residue was washed with petroleum ether (100 mL) to afford (S)-benzyl 2-((S)-2-aminopropanamido)-3-(4-methoxyphenyl)propanoate as an HCl salt (quant.), which was used directly in the next step without further purification.

To a solution of (S)-benzyl 2-((S)-2-aminopropanamido)-3-(4-methoxyphenyl)propanoate (HCl salt, 21.0 g, 53.5 mmol) in DMF (200 mL) at 0° C. was added HBTU (30.4 g, 80.3 mmol) and HOBt (10.8 g, 80.3 mmol). The mixture was stirred for 5 min then 2-morpholinoacetic acid (8.15 g, 56.2 mmol) and DIEA (46.5 mL, 214 mmol) were added. The reaction mixture was stirred at ambient temperature for 30 min. Saturated aqueous $NaHCO_3$ (200 mL) was then added and the resulting mixture was extracted with EtOAc (300 mL×2). The combined extracts were washed with brine (400 mL), dried over anhydrous sodium sulfate, and concentrated. Purification of the residue by flash column chromatography on silica gel (heptane to EtOAc/heptane=3:2) afforded (S)-benzyl 3-(4-methoxyphenyl)-2-((S)-2-(2-morpholinoacetamido)propanamido)propanoate (23.0 g, 89% yield) as a colorless solid.

A mixture of (S)-benzyl 3-(4-methoxyphenyl)-2-((S)-2-(2-morpholinoacetamido)propanamido)propanoate (5.00 g, 10.4 mmol) and Pd/C (10%, 1.0 g) in THF (50 mL) was stirred under a hydrogen atmosphere for 2 h. The mixture was filtered and concentrated to afford (S)-3-(4-methoxyphenyl)-2-((S)-2-(2-morpholinoacetamido)propanamido)propanoic acid (3.3 g, 94% yield) as a colorless solid. $^1$H NMR (300 MHz, DMSO-$d_6$): δ 8.24 (d, J=8.1 Hz, 1H), 7.76 (d, J=7.8 Hz, 1H), 7.13 (m, 2H), 6.82 (m, 2H), 4.35 (m, 2H), 3.71 (s, 3H), 3.63-3.56 (m, 4H), 2.99-2.65 (m, 4H), 2.41-2.38 (m, 4H), 1.20 (d, J=6.9 Hz, 3H). MS (EI) for $C_{19}H_{27}N_3O_6$, found 394.5 (MH$^+$).

To a solution of (S)-3-(4-methoxyphenyl)-2-((S)-2-(2-morpholinoacetamido)propanamido)propanoic acid (850 mg, crude) and (S)-2-amino-3-(cyclopent-1-en-1-yl)-1-((R)-2-methyloxiran-2-yl)propan-1-one (TFA salt, 200 mg, 0.680 mmol) in DCM (10 mL) was added HATU (283 mg, 0.750 mmol). The mixture was cooled to 0° C. and basified with DIEA to pH=8. The reaction mixture was stirred at ambient temperature for 30 min and water (30 mL) was added. The resulting mixture was extracted with DCM (30 mL×2) and the extracts were combined, dried over anhydrous sodium sulfate, and concentrated. The residue was purified by flash column chromatography on silica gel (petroleum ether/EtOAc=2:1 to 1:2, then DCM/methanol=70:1) to afford (S)—N—((S)-3-(cyclopent-1-en-1-yl)-1-((R)-2-methyloxiran-2-yl)-1-oxopropan-2-yl)-3-(4-methoxyphenyl)-2-((S)-2-(2-morpholinoacetamido)propanamido) (170 mg, 18%) as a colorless solid. $^1$H NMR (300 MHz, CDCl$_3$): δ 7.29 (br. s, 1H), 7.16 (d, J=8.7 Hz, 2H), 6.83 (d, J=8.7 Hz, 2H), 6.74 (d, J=7.2 Hz, 1H), 6.10 (d, J=7.2 Hz, 1H), 5.33 (s, 1H), 4.56-4.44 (m, 2H), 3.80 (s, 3H), 3.75-3.73 (m, 4H), 3.29 (d, J=4.8 Hz, 1H), 3.00-2.91 (m, 5H), 2.53-2.47 (m, 5H), 2.27-2.16 (m, 5H), 1.90-1.81 (m, 1H), 1.73 (s, 3H), 1.37 (d, J=7.2 Hz, 3H). MS (EI) for $C_{30}H_{42}N_4O_7$, found 571.4 (MH)$^+$.

The following compounds were synthesized in a similar manner:

(S)—N—((S)-3-(cyclohex-1-en-1-yl)-1-((R)-2-methyloxiran-2-yl)-1-oxopropan-2-yl)-2-((S)-2-(2-(1,1-dioxidothiomorpholino)acetamido)propanamido)-3-(4-methoxyphenyl)propanamide (C-1127): $^1$H NMR (300 MHz, DMSO-$d_6$): δ 8.25 (d, J=6.0 Hz, 1H), 7.96 (d, J=6.3 Hz, 1H), 7.87 (d, J=6.9 Hz, 1H), 7.10 (d, J=6.3 Hz, 2H), 6.78 (d, J=6.3 Hz, 2H), 5.38 (m, 1H), 4.50 (m, 2H), 4.28 (m, 1H), 3.70 (s, 3H), 3.18 (m, 1H), 2.99-3.15 (m, 5H), 2.81-2.97 (m, 6H), 2.62 (m, 1H), 2.23 (m, 1H), 1.83-2.11 (m, 6H), 1.42-1.63 (m, 4H), 1.36 (s, 3H), 1.16 (d, J=4.8 Hz, 3H). MS (EI) for $C_{31}H_{44}N_4O_8S$, found 633.2 (MH)$^+$.

(S)—N—((S)-3-(cyclopent-1-en-1-yl)-1-((R)-2-methyloxiran-2-yl)-1-oxopropan-2-yl)-2-((S)-2-(2-(1,1-dioxidothiomorpholino)acetamido)propanamido)-3-(4-methoxyphenyl)propanamide (C-1115): $^1$H NMR (300 MHz, DMSO-$d_6$): δ 8.31 (d, J=6.9 Hz, 1H), 7.97 (d, J=8.1 Hz, 1H), 7.88 (d, J=7.5 Hz, 1H), 7.11 (d, J=8.4 Hz, 2H), 6.79 (d, J=8.1 Hz, 2H), 5.40 (s, 1H), 4.49 (m, 2H), 4.29 (m, 1H), 3.70 (s, 3H), 2.68-3.23 (m, 10H), 1.81-2.72 (m, 4H), 2.24 (m, 4H), 2.21 (m, 1H), 1.97 (m, 1H), 1.79 (m, 2H), 1.37 (s, 3H), 1.16 (d, J=6.9 Hz, 3H). MS (EI) for $C_{30}H_{42}N_4O_8S$, found 619.2 (MH)$^+$.

(S)—N—((S)-3-(cyclopent-1-en-1-yl)-1-((R)-2-methyloxiran-2-yl)-1-oxopropan-2-yl)-2-((S)-2-(2-(4-hydroxy-4-methylpiperidin-1-yl)acetamido)propanamido)-3-(4-methoxyphenyl)propanamide (C-1121): $^1$H NMR (300 MHz, DMSO-$d_6$): δ 8.30 (d, J=6.9 Hz, 1H), 8.10 (d, J=8.1 Hz, 1H), 7.70 (d, J=7.2 Hz, 1H), 7.11 (d, J=8.4 Hz, 2H), 6.79 (d, J=8.4 Hz, 2H), 5.40 (br s, 1H), 4.51 (m, 2H), 4.27 (m, 1H), 4.13 (m, 1H), 3.70 (s, 3H), 3.50 (m, 1H), 3.18 (d, J=5.1 Hz, 1H), 2.98 (d, J=5.1 Hz, 1H), 2.84 (m, 3H), 2.64 (m, 1H), 2.37 (m, 4H), 2.24 (m, 4H), 1.77 (m, 2H), 1.45 (m, 4H), 1.43 (s, 3H), 1.17 (m, 4H), 1.14 (d, J=6.6 Hz, 3H). MS (EI) for $C_{32}H_{46}N_4O_7$, found 597.5 (MH)$^-$.

(S)—N—((S)-3-(cyclopent-1-en-1-yl)-1-((R)-2-methyloxiran-2-yl)-1-oxopropan-2-yl)-3-(4-methoxyphenyl)-2-((S)-2-(2-(3-oxopiperazin-1-yl)acetamido)propanamido)propanamide (C-1120): $^1$H NMR (300 MHz, DMSO-$d_6$): δ 8.31 (d, J=7.2 Hz, 1H), 8.06 (d, J=8.4 Hz, 1H), 7.80 (m, 2H), 7.12 (d, J=8.4 Hz, 2H), 6.78 (d, J=8.7 Hz, 2H), 5.40 (m, 1H), 4.49 (m, 2H), 4.27 (m, 1H), 3.70 (s, 3H), 3.18 (d, J=5.1 Hz, 1H), 3.13 (m, 2H), 2.73-3.09 (m, 6H), 2.65 (m, 1H), 2.56 (m, 2H), 2.37 (m, 1H), 2.23 (m, 5H), 1.79 (m, 2H), 1.40 (s, 3H), 1.15 (d, J=6.9 Hz, 3H). MS (EI) for $C_{30}H_{41}N_5O_7$, found 584.4 (MH)$^+$.

4-((S)-3-(((S)-3-cyclopentyl-1-((R)-2-methyloxiran-2-yl)-1-oxopropan-2-yl)amino)-2-((S)-2-(2-morpholinoacetamido)propanamido)-3-oxopropyl)pyridine 1-oxide (C-1119): $^1$H NMR (300 MHz, DMSO-$d_6$): δ 8.43 (d, J=6.9 Hz, 1H), 8.21 (d, J=8.4 Hz, 1H), 8.07 (d, J=6.6 Hz, 2H), 7.78 (d, J=7.5 Hz, 1H), 7.23 (d, J=6.9 Hz, 2H), 4.61 (m, 1H), 4.28 (m, 2H), 3.57 (m, 4H), 3.03 (m, 2H), 3.00 (m, 2H), 2.97 (m, 3H), 2.39 (m, 4H), 1.75 (m, 1H), 1.69 (m, 2H), 1.65 (m, 6H), 1.49 (d, J=5.1 Hz, 3H), 1.15 (d, J=6.9 Hz, 3H). MS (EI) for $C_{28}H_{41}N_5O_7$, found 560.2 (MH)$^+$.

(S)—N—((S)-3-(cyclohex-1-en-1-yl)-1-((R)-2-methyloxiran-2-yl)-1-oxopropan-2-yl)-2-((S)-3-hydroxy-2-(2-morpholinoacetamido)propanamido)-3-(4-methoxyphenyl)propanamide (C-1104): $^1$H NMR (300 MHz, CDCl$_3$): δ 7.88 (m, 1H), 7.16 (d, J=8.9 Hz, 2H), 6.94 (d, J=7.8 Hz, 1H), 6.82

(d, J=8.4 Hz, 2H), 6.18 (d, J=6.6 Hz, 1H), 5.28 (br s, 1H), 4.56 (m, 2H), 4.50 (m, 1H), 4.02 (m, 1H), 3.78 (s, 3H), 3.74-3.71 (m, 4H), 3.62 (m, 2H), 3.29 (d, J=4.8 Hz, 1H), 3.03-2.97 (m, 4H), 2.50 (m, 4H), 2.34 (m, 2H), 1.89 (m, 5H), 1.60 (m, 3H), 1.53 (s, 3H). MS (EI) for $C_{31}H_{44}N_4O_8$, found 601.8 (MH)$^+$.

Example 12

(2S,3R)—N—((S)-3-Cyclopentyl-1-((R)-2-methyl-oxiran-2-yl)-1-oxopropan-2-yl)-3-hydroxy-3-(4-methoxyphenyl)-2-((S)-2-(2-morpholinoacetamido)propanamido)propanamide (C-1022)

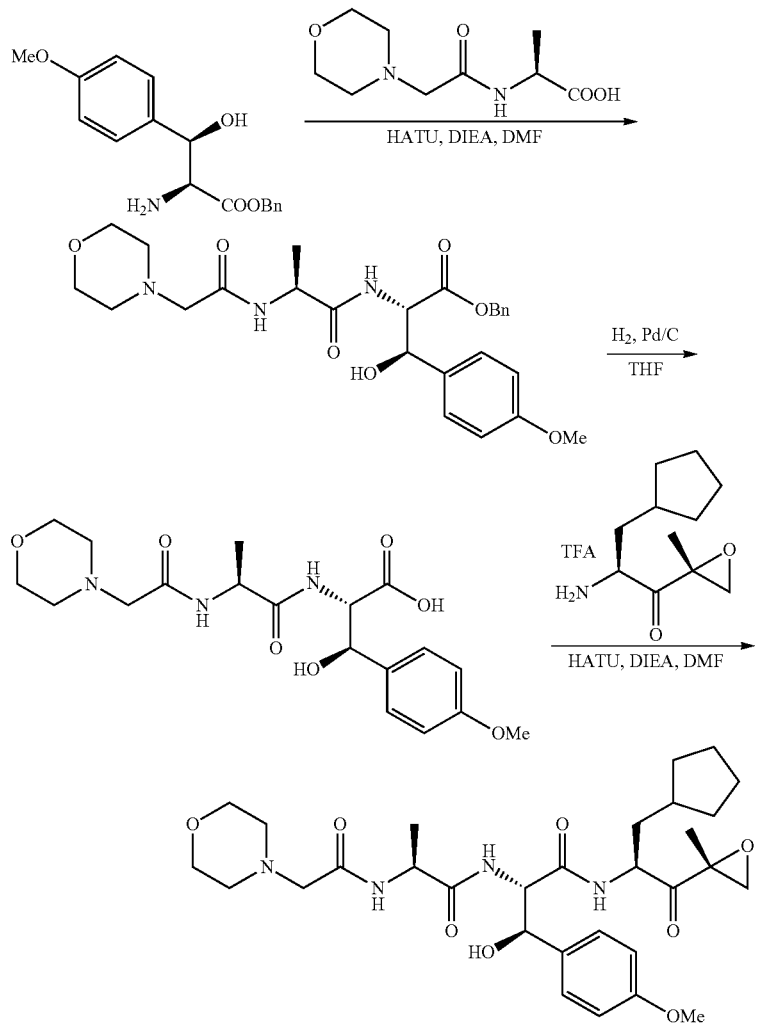

Sequentially HATU (3.41 g, 8.96 mmol) and DIEA (2.60 mL, 15.0 mmol) were added to a 0° C. solution of (2S,3R)-benzyl 2-amino-3-hydroxy-3-(4-methoxyphenyl) propanoate (2.30 g, 7.47 mmol) and (S)-2-(2-morpholinoacetamido) propanoic acid (1.61 g, 7.47 mmol) in DMF (35 mL). The reaction mixture was allowed to warm to ambient temperature and stirred for 1 h. The mixture was concentrated and the residue was purified by flash column chromatography on silica gel (petroleum ether/EtOAc=2:1 to 1:2) to afford (2S,3R)-benzyl 3-hydroxy-3-(4-methoxyphenyl)-2-((S)-2-(2-morpholino acetamido)propanamido)propanoate (2.04 g, 54% yield) as a colorless solid.

To a solution of (2S,3R)-benzyl 3-hydroxy-3-(4-methoxyphenyl)-2-((S)-2-(2-morpholino acetamido)propanamido)propanoate (2.0 g, 4.0 mmol) in THF (40 mL) was added Pd/C (500 mg, 10%). The mixture was stirred under a hydrogen atmosphere (1 atm) at ambient temperature overnight and then filtered through a pad of celite. The filtrate was concentrated under reduced pressure and the residue was washed with EtOAc (10 mL) to afford (2S,3R)-3-hydroxy-3-(4-methoxyphenyl)-2-((S)-2-(2-morpholinoacetamido)propanamido)propanoic acid (1.30 g, 78% yield) as a colorless solid.

$^1$H NMR (300 MHz, DMSO-d$_6$): δ 8.08 (d, J=8.7 Hz, 1H), 7.74 (d, J=8.4 Hz, 1H), 7.27 (d, J=8.4 Hz, 2H), 6.81 (d, J=8.7 Hz, 2H), 5.10-5.07 (m, 1H), 4.41-4.39 (m, 2H), 3.71 (s, 3H), 3.56-3.55 (m, 4H), 2.97-2.73 (m, 2H), 2.38-2.35 (m, 4H), 1.16 (d, J=6.9 Hz, 3H). MS (EI) for $C_{19}H_{27}N_3O_7$, found 410.2 (MH)$^+$.

Sequentially HATU (1.84 g, 4.80 mmol) and DIEA (0.63 mL, 20 mmol) were added to a 0° C. solution of (2S,3R)-3-hydroxy-3-(4-methoxyphenyl)-2-((S)-2-(2-morpholinoacetamido)propanamido)propanoic acid (1.65 g, 4.00 mmol) and (S)-2-amino-3-cyclopentyl-1-((R)-2-methyloxiran-2-yl)

propan-1-one (1.2 g, 4.0 mmol) in DMF (30 mL). The reaction mixture was allowed to warm to ambient temperature and stirred for 30 min. The mixture was concentrated and the residue was purified by flash column chromatography on silica gel (petroleum ether/EtOAc=2:1 to EtOAc) to afford (2S,3R)—N—((S)-3-cyclopentyl-1-((R)-2-methyloxiran-2-yl)-1-oxopropan-2-yl)-3-hydroxy-3-(4-methoxyphenyl)-2-((S)-2-(2-morpholinoacetamido)propanamido)propanamide (1.45 g, 61% yield) as a colorless solid. $^1$H NMR (300 MHz, CDCl$_3$): δ 7.40 (d, J=5.7 Hz, 1H), 7.32-7.22 (m, 2H), 7.06-6.99 (m, 2H), 6.82 (d, J=8.7 Hz, 2H), 5.26-5.21 (m, 1H), 4.68-4.60 (m, 2H), 4.58-4.39 (m, 2H), 4.01-3.85 (m, 1H), 3.81 (s, 3H), 3.74-3.72 (m, 4H), 3.25 (d, J=4.8 Hz, 1H), 2.99-2.85 (m, 2H), 2.53-2.39 (m, 4H), 1.74-1.61 (m, 8H), 1.53 (s, 3H), 1.33 (d, J=6.9 Hz, 3H), 1.28-1.20 (m, 3H). MS(EI) for C$_{30}$H$_{44}$N$_4$O$_8$, found 589.3 (MH)$^+$.

The following compounds were synthesized in a similar manner:

(2S,3R)—N—((S)-3-(cyclohex-1-en-1-yl)-1-((R)-2-methyloxiran-2-yl)-1-oxopropan-2-yl)-3-hydroxy-3-(4-methoxyphenyl)-2-((S)-2-(2-morpholinoacetamido)propanamido)propanamide (C-1082): $^1$H NMR (300 MHz, CDCl$_3$): δ 7.43-7.40 (m, 1H), 7.27-7.25 (m, 2H), 7.00 (d, J=8.7 Hz, 1H), 6.84 (d, J=4.8 Hz, 1H), 6.83-6.81 (m, 2H), 5.45-5.44 (m, 1H), 5.21-5.20 (m, 1H), 4.61-4.58 (m, 2H), 4.46-4.38 (m, 1H), 3.77 (s, 3H), 3.72-3.66 (m, 4H), 3.26 (d, J=4.8 Hz, 1H), 2.91-2.89 (m, 3H), 2.60-2.32 (m, 4H), 2.07-1.95 (m, 4H), 1.69-1.40 (s, 7H), 1.31 (d, J=6.9 Hz, 3H). MS(EI) for C$_{31}$H$_{44}$N$_4$O$_8$, found 601.3 (MH)$^+$.

(2S,3R)—N—((S)-3-(cyclopent-1-en-1-yl)-1-((R)-2-methyloxiran-2-yl)-1-oxopropan-2-yl)-3-hydroxy-3-(4-methoxyphenyl)-2-((S)-2-(2-morpholinoacetamido)propanamido)propanamide (C-1083): $^1$H NMR (300 MHz, CDCl$_3$): δ 7.43 (d, J=7.5 Hz, 1H), 7.29-7.23 (m, 2H), 7.01 (d, J=7.5 Hz, 1H), 6.95 (d, J=7.5 Hz, 1H), 6.84 (d, J=8.7 Hz, 2H), 5.48-5.46 (m, 1H), 5.25-5.22 (m, 1H), 4.63-4.60 (m, 2H), 4.50-4.42 (m, 1H), 3.80 (s, 3H), 3.70-3.66 (m, 4H), 3.28 (d, J=5.1 Hz, 1H), 2.99-2.92 (m, 3H), 2.62-2.22 (m, 10H), 1.89-1.84 (m, 2H), 1.54 (s, 3H), 1.33 (d, J=6.9 Hz, 3H). MS(EI) for C$_{30}$H$_{42}$N$_4$O$_8$, found 587.4 (MH)$^+$.

Example 13

(2S,3R)—N—((S)-3-(Cyclohex-1-en-1-yl)-1-((R)-2-methyloxiran-2-yl)-1-oxopropan-2-yl)-3-hydroxy-2-((S)-3-hydroxy-2-(2-morpholinoacetamido)propanamido)-3-(4-methoxyphenyl)propanamide (C-1116)

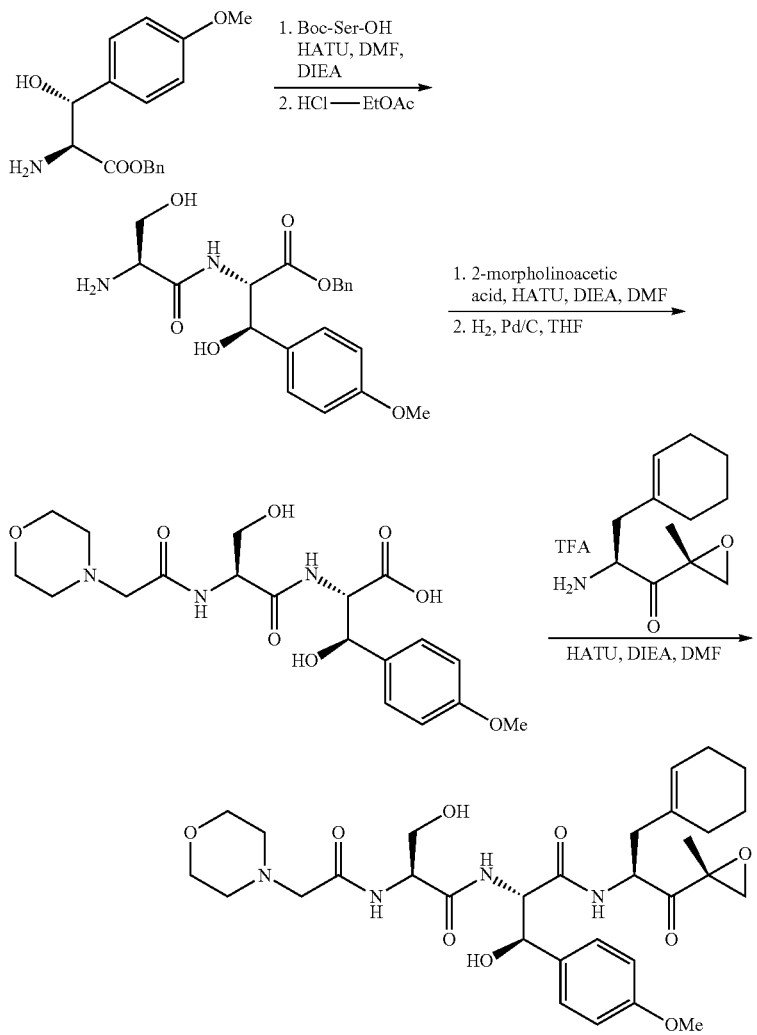

Sequentially HATU (645 mg, 1.70 mmol) and DIEA (0.99 mL, 5.7 mmol) were added to a 0° C. solution of (2S,3R)-benzyl 2-amino-3-hydroxy-3-(4-methoxyphenyl)propanoate (HCl salt, 477 mg, 1.41 mmol) and Boc-Ser-OH (290 mg, 1.41 mmol) in DMF (8 mL). The reaction mixture was allowed to warm to ambient temperature and stirred for 30 min. The mixture was concentrated and the residue was purified by flash column chromatography on silica gel (petroleum ether/EtOAc=2:1) twice to afford (2S,3R)-benzyl 2-((S)-2-((tert-butoxycarbonyl)amino)-3-hydroxypropanamido)-3-hydroxy-3-(4-methoxyphenyl)propanoate (646 mg, 93% yield) as a colorless solid.

To HCl-EtOAc (5 N, 10 mL) was added a solution of (2S,3R)-benzyl 2-((S)-2-((tert-butoxycarbonyl)amino)-3-hydroxypropanamido)-3-hydroxy-3-(4-methoxyphenyl)propanoate (646 mg, 1.32 mmol) in DCM (10 mL). The mixture was stirred at ambient temperature for 30 min and then concentrated. The residue was washed with diethyl ether (5 mL) to afford (2S,3R)-benzyl 2-((S)-2-amino-3-hydroxypropanamido)-3-hydroxy-3-(4-methoxyphenyl)propanoate (HCl salt, 474 mg, 85% yield) as a colorless solid.

Sequentially HATU (509 mg, 1.34 mmol) and DIEA (0.78 mL, 4.5 mmol) were added to a 0° C. solution of (2S,3R)-benzyl 2-((S)-2-amino-3-hydroxypropanamido)-3-hydroxy-3-(4-methoxyphenyl)propanoate (HCl salt, 474 mg, 1.12 mmol) and 2-morpholinoacetic acid (162 mg, 1.12 mmol) in DMF (8 mL). The reaction mixture was allowed to warm to ambient temperature and stirred for 30 min. The mixture was concentrated and the residue was washed with EtOAc to afford (2S,3R)-benzyl 3-hydroxy-2-((S)-3-hydroxy-2-(2-morpholinoacetamido)propanamido)-3-(4-methoxyphenyl)propanoate (349 mg, 67% yield) as a colorless solid.

To a solution of (2S,3R)-benzyl 3-hydroxy-2-((S)-3-hydroxy-2-(2-morpholinoacetamido)propanamido)-3-(4-methoxyphenyl)propanoate (349 mg, 0.680 mmol) in THF (20 mL) was added Pd/C (100 mg, 10%). The mixture was stirred under a hydrogen atmosphere (1 atm) at ambient temperature overnight then filtered through a pad of celite. The filtrate was concentrated to afford (2S,3R)-3-hydroxy-2-((S)-3-hydroxy-2-(2-morpholinoacetamido)propanamido)-3-(4-methoxyphenyl)propanoic acid (121 mg, 42% yield) as a colorless solid.

Sequentially HATU (537 mg, 1.41 mmol) and DIEA (1.02 mL, 5.88 mmol) were added to a 0° C. solution of (2S,3R)-3-hydroxy-2-((S)-3-hydroxy-2-(2-morpholinoacetamido)propanamido)-3-(4-methoxyphenyl)propanoic acid (500 mg, 1.18 mmol) and (S)-2-amino-3-(cyclohex-1-en-1-yl)-1-((R)-2-methyloxiran-2-yl)propan-1-one (TFA salt, 364 mg, 1.18 mmol) in DMF (10 mL). The reaction mixture was allowed to warm to ambient temperature and stirred for 30 min. The mixture was concentrated and the residue was purified by flash column chromatography on silica gel (DCM/MeOH=50:1 to 30:1) twice to afford (2S,3R)—N—((S)-3-(cyclohex-1-en-1-yl)-1-((R)-2-methyloxiran-2-yl)-1-oxopropan-2-yl)-3-hydroxy-2-((S)-3-hydroxy-2-(2-morpholinoacetamido)propanamido)-3-(4-methoxyphenyl)propanamide (500 mg, 57% yield) as a colorless solid. ¹H NMR (300 MHz, DMSO-d₆): δ 7.97 (d, J=7.5 Hz, 1H), 7.86 (d, J=9.0 Hz, 1H), 7.75 (d, J=7.5 Hz, 1H), 7.26 (d, J=8.7 Hz, 2H), 6.80 (d, J=8.7 Hz, 2H), 5.61 (d, J=4.5 Hz, 1H), 5.40-5.38 (m, 1H), 5.23-5.21 (m, 1H), 5.04-5.02 (m, 1H), 4.62-4.51 (m, 1H), 4.45-4.35 (m, 2H), 3.71 (s, 3H), 3.68-3.41 (m, 6H), 3.33 (s, 1H), 3.21 (d, J=5.1 Hz, 1H), 2.97-2.80 (m, 3H), 2.39-2.21 (m, 4H), 2.11-1.71 (m, 4H), 1.56-1.40 (m, 4H), 1.26 (s, 3H), 1.28-1.22 (m, 1H). MS(EI) for C₃₁H₄₄N₄O₉, found 617.4 (MH)⁺.

The following compounds were synthesized in a similar manner:

(2S,3R)—N—((S)-3-(cyclopent-1-en-1-yl)-1-((R)-2-methyloxiran-2-yl)-1-oxopropan-2-yl)-3-hydroxy-2-((S)-3-hydroxy-2-(2-morpholinoacetamido)propanamido)-3-(4-methoxyphenyl)propanamide (C-1144): ¹H NMR (300 MHz, DMSO-d₆): δ 8.03 (d, J=7.2 Hz, 1H), 7.92 (d, J=8.7 Hz, 1H), 7.74 (d, J=7.8 Hz, 1H), 7.25 (d, J=8.7 Hz, 2H), 6.81 (d, J=8.7 Hz, 2H), 5.63 (d, J=4.5 Hz, 1H), 5.41 (s, 1H), 5.25 (m, 1H), 5.04 (m, 1H), 4.41 (m, 1H), 4.37 (m, 2H), 4.30 (m, 2H), 3.71 (s, 3H), 3.67 (m, 1H), 3.55 (m, 4H), 3.35 (m, 1H), 3.20 (d, J=5.4 Hz, 1H), 2.97 (m, 2H), 2.89 (m, 1H), 2.39 (m, 4H), 2.25 (m, 4H), 1.82 (m, 2H), 1.36 (s, 3H). MS (EI) for C₃₀H₄₂N₄O₉, found 603.28 (MH)⁺.

(2S,3S)—N—((S)-3-cyclopentyl-1-((R)-2-methyloxiran-2-yl)-1-oxopropan-2-yl)-3-hydroxy-3-(4-methoxyphenyl)-2-((S)-2-(2-morpholinoacetamido)propanamido)propanamide (C-1023): ¹H NMR (300 MHz, CDCl₃): δ 7.40 (m, 1H), 7.33 (m, 2H), 6.92-6.86 (m, 3H), 6.40 (d, J=7.2 Hz, 1H), 4.91 (m, 1H), 4.68 (m, 1H), 4.47-4.43 (m, 2H), 4.40 (m, 1H), 3.81 (s, 3H), 3.74-3.72 (m, 4H), 3.25 (d, J=4.8 Hz, 1H), 2.99 (m, 1H), 2.91 (d, J=4.8 Hz, 1H), 2.51 (m, 4H), 1.74-1.63 (m, 4H), 1.61 (m, 5H), 1.53 (s, 3H), 1.33 (d, J=6.9 Hz, 3H), 1.28-1.20 (m, 3H). MS (EI) for C₃₀H₄₄N₄O₈, found 589.3 (MH)⁺.

Example 14

(S)—N—((S)-3-Cyclopentyl-1-((R)-2-methyloxiran-2-yl)-1-oxopropan-2-yl)-3-(3-hydroxy-4-methylphenyl)-2-((S)-2-(2-morpholinoacetamido)propanamido)propanamide (C-1117)

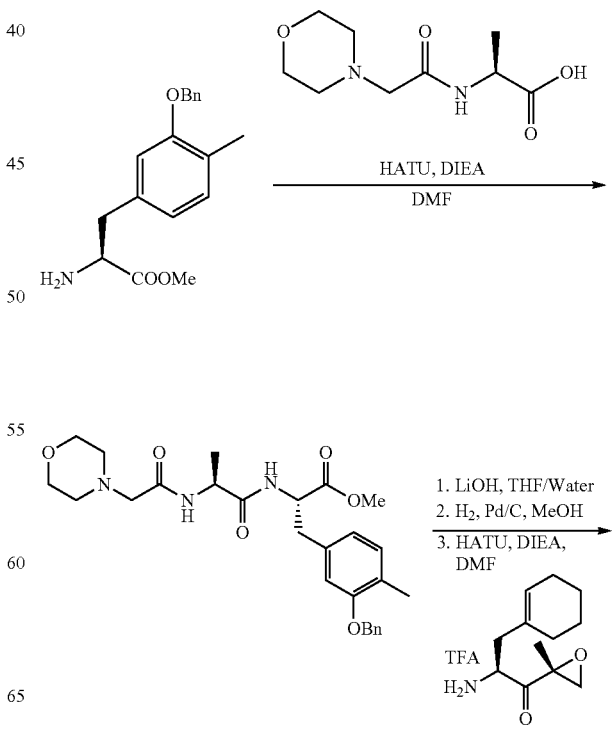

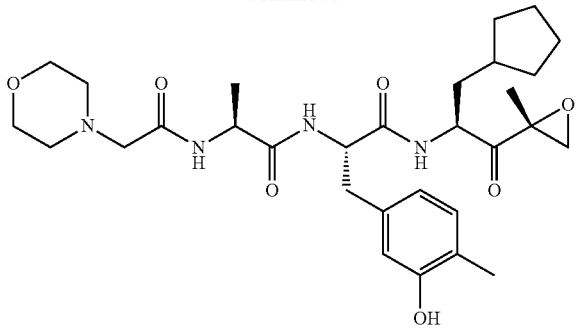

Crude (S)-methyl 2-amino-3-(3-(benzyloxy)-4-methylphenyl)propanoate (TFA salt, 2.5 mmol) was dissolved in DMF (5 mL) and (S)-2-(2-morpholinoacetamido)propanoic acid (0.65 g, 3.0 mmol), HATU (1.43 g, 3.70 mmol), and DIEA (1.0 mL) were added at 0° C. with stirring. The reaction mixture was allowed to warm to ambient temperature and stirred for 3 h. EtOAc (100 mL) and water (100 mL) was added. The aqueous phase was extracted with EtOAc (30 mL×3) and the combined organic phases were washed with brine (50 mL×3), dried over anhydrous sodium sulfate, and concentrated. The residue was purified by flash column chromatography on silica gel (DCM/MeOH=20:1) to afford (S)-Methyl 3-(3-(benzyloxy)-4-methylphenyl)-2-((S)-2-(2-morpholinoacetamido) propanamido)propanoate (1.2 g, 96% yield).

(S)-Methyl 3-(3-(benzyloxy)-4-methylphenyl)-2-((S)-2-(2-morpholinoacetamido) propanamido)propanoate (1.2 g, 2.4 mmol) was treated with a solution of lithium hydroxide-$H_2O$ (300 mg, 7.2 mmol) in water/THF (10 mL/10 mL) for 30 min. The THF was removed and the aqueous phase was acidified to pH=3-4 with 1 N HCl and then concentrated to dryness to afford (S)-3-(3-(benzyloxy)-4-methylphenyl)-2-((S)-2-(2-morpholinoacetamido)propanamido)propanoic acid, which was used directly without further purification.

The crude (S)-3-(3-(benzyloxy)-4-methylphenyl)-2-((S)-2-(2-morpholinoacetamido)propanamido)propanoic acid was dissolved in MeOH (20 mL) and Pd/C (10%, 1.0 g) was added. The suspension was stirred under a hydrogen atmosphere at ambient temperature for 12 h. The Pd/C was filtered off and washed with MeOH (5 mL). The filtrate and washings were combined and concentrated to dryness.

(S)-3-(3-Hydroxy-4-methylphenyl)-2-((S)-2-(2-morpholinoacetamido)propanamido)propanoic acid was dissolved in DMF (5 mL) and (S)-2-amino-3-cyclopentyl-1-((R)-2-methyloxiran-2-yl)propan-1-one (TFA salt, 0.40 g, 1.3 mmol), HATU (0.65 g, 1.9 mmol) and DIEA (0.5 mL) were added at 0° C. with stirring. The reaction mixture was allowed to warm to ambient temperature and stirred for 3 h. EtOAc (100 mL) and water (100 mL) was added and the two layers were separated. The aqueous phase was extracted with EtOAc (30 mL×3) and the combined organic phases were washed with brine (50 mL×3), dried over anhydrous sodium sulfate, and concentrated. The residue was purified by flash column chromatography on silica gel (DCM/EtOAc/MeOH=20:10:1) to afford (S)—N—((S)-3-cyclopentyl-1-((R)-2-methyloxiran-2-yl)-1-oxopropan-2-yl)-3-(3-hydroxy-4-methylphenyl)-2-((S)-2-(2-morpholinoacetamido)propanamido)propanamide (150 mg, 11% yield over three steps). $^1$H NMR (300 MHz, DMSO-$d_6$): δ 9.06 (s, 1H), 8.26 (d, J=7.2 Hz, 1H), 8.06 (d, J=8.7 Hz, 1H), 7.75 (d, J=7.5 Hz, 1H), 6.89 (d, J=7.8 Hz, 1H), 6.61 (s, 1H), 6.53 (d, J=7.2 Hz, 1H), 4.51-4.39 (m, 1H), 4.30-4.15 (m, 2H), 3.69-3.61 (m, 4H), 3.17 (d, J=5.4 Hz, 1H), 3.00 (d, J=5.1 Hz, 1H), 2.90-2.81 (m, 3H), 2.42-2.30 (m, 4H), 2.04 (s, 3H), 1.91-1.42 (m, 7H), 1.41 (s, 3H), 1.30-1.02 (m, 6H). MS(EI) for $C_{30}H_{44}N_4O_7$, found 573.3 $(MH)^+$.

The following compounds were synthesized in a similar manner:

(S)—N—((S)-3-cyclopentyl-1-((R)-2-methyloxiran-2-yl)-1-oxopropan-2-yl)-3-(3,4-dihydroxyphenyl)-2-((S)-2-(2-morpholinoacetamido)propanamido)propanamide (C-1039): $^1$H NMR (300 MHz, DMSO-$d_6$): δ 8.69 (s, 1H), 8.63 (s, 1H), 8.25 (d, J=7.2 Hz, 1H), 8.01 (d, J=8.7 Hz, 1H), 7.77 (d, J=6.3 Hz, 1H), 6.55-6.65 (m, 2H), 6.45 (m, 1H), 4.45 (m, 1H), 4.20-4.40 (m, 2H), 3.60 (m, 4H), 3.18 (m. 1H), 3.05 (m, 1H), 2.90 (m, 2H), 2.80 (m, 1H), 2.40 (m, 4H), 1.95 (m, 1H), 1.50-1.85 (m, 7H), 1.40 (s, 3H), 1.00-1.20 (m, 2H), 1.26 (d, J=6.6 Hz, 3H). MS(EI) for $C_{29}H_{42}N_4O_8$, found 575.0 $(MH)^+$.

N—((R)-1-(((S)-1-(((S)-3-cyclopentyl-1-((R)-2-methyloxiran-2-yl)-1-oxopropan-2-yl)amino)-3-(3-hydroxy-4-methoxyphenyl)-1-oxopropan-2-yl)amino)-1-oxopropan-2-yl)tetrahydro-2H-pyran-4-carboxamide (C-1061): $^1$H NMR (300 MHz, DMSO-$d_6$): δ 8.77 (br s, 1H), 8.22 (d, J=6.9 Hz, 1H), 8.04 (d, J=8.7 Hz, 1H), 7.93 (d, J=6.9 Hz, 1H), 6.75 (d, J=8.4 Hz, 1H), 6.64 (s, 1H), 6.57 (d, J=8.1 Hz, 1H), 4.39 (m, 1H), 4.27 (m, 1H), 4.18 (m 1H), 3.82 (s, 3H), 3.22-3.43 (m, 3H), 3.01 (d, J=5.4 Hz, 1H), 2.88 (m, 1H), 2.51 (m, 1H), 2.40 (s, 2H), 1.41 (s, 3H), 1.13-1.98 (m, 15H), 0.99 (d, J=6.9 Hz, 3H). MS (EI) for $C_{30}H_{43}N_3O_8$, found 574.4 $(MH)^+$.

N—((R)-1-(((S)-1-(((S)-3-(cyclopent-1-en-1-yl)-1-((R)-2-methyloxiran-2-yl)-1-oxopropan-2-yl)amino)-3-(3-hydroxy-4-methoxyphenyl)-1-oxopropan-2-yl)amino)-1-oxopropan-2-yl)tetrahydro-2H-pyran-4-carboxamide (C-1062): $^1$H NMR (300 MHz, DMSO-$d_6$): δ 8.70 (s, 1H), 8.24 (d, J=7.2 Hz, 1H), 8.01 (d, J=7.2 Hz, 1H), 7.87 (d, J=7.5 Hz, 1H), 7.12 (d, J=8.4 Hz, 1H), 6.75 (d, J=8.1 Hz, 1H), 6.63 (m, 1H), 6.58 (d, J=8.7 Hz, 1H), 5.42 (s, 1H), 4.52 (m, 1H), 4.40 (m, 1H), 4.22 (m, 1H), 3.81 (m, 2H), 3.71 (s, 3H), 3.31-3.23 (m, 3H), 3.00 (m, 1H), 2.94 (m, 1H), 2.50 (m, 2H), 2.24 (m, 4H), 1.83 (m, 2H), 1.80 (m, 4H), 1.38 (s, 3H), 0.97 (d, J=6.9 Hz, 3H). MS (EI) for $C_{28}H_{41}N_3O_7$, found 532.4 $(MH)^+$.

(S)—N—((S)-3-(cyclopent-1-en-1-yl)-1-((R)-2-methyloxiran-2-yl)-1-oxopropan-2-yl)-3-(3-hydroxy-4-methylphenyl)-2-((S)-2-(2-morpholinoacetamido)propanamido)propanamide (C-1129): $^1$H NMR (300 MHz, DMSO-$d_6$): δ 9.08 (s, 1H), 8.28 (d, J=7.2 Hz, 1H), 8.07 (d, J=8.4 Hz, 1H), 7.77 (d, J=7.8 Hz, 1H), 6.88 (d, J=7.8 Hz, 1H), 6.61 (s, 1H), 6.53 (d, J=7.2 Hz, 1H), 5.76-5.74 (m, 1H), 4.50-4.40 (m, 2H), 4.29-4.21 (m, 1H), 3.57-3.54 (m, 4H), 3.35 (s, 1H), 3.19 (d, J=5.1 Hz, 1H), 3.00-2.72 (m, 5H), 2.58-2.10 (m, 10H), 1.79-1.39 (m, 2H), 1.39 (s, 3H), 1.15 (d, J=6.9 Hz, 3H). MS(EI) for $C_{30}H_{42}N_4O_7$, found 572.0 $(MH)^+$.

(S)—N—((S)-3-(cyclohex-1-en-1-yl)-1-((R)-2-methyloxiran-2-yl)-1-oxopropan-2-yl)-3-(3-hydroxy-4-methylphenyl)-2-((S)-2-(2-morpholinoacetamido)propanamido)propanamide (C-1130): $^1$H NMR (300 MHz, DMSO-$d_6$): δ 9.08 (s, 1H), 8.22 (d, J=7.2 Hz, 1H), 8.07 (d, J=8.4 Hz, 1H), 7.77 (d, J=7.8 Hz, 1H), 6.88 (d, J=7.8 Hz, 1H), 6.61 (s, 1H), 6.53 (d, J=7.2 Hz, 1H), 5.77 (m, 1H), 4.40-4.50 (m, 2H), 4.25 (m, 1H), 3.55 (m, 4H), 3.19 (m, 1H), 3.00 (m, 1H), 2.80-3.00 (m, 3H), 2.70 (m, 1H), 2.30 (m, 4H), 2.20 (m, 1H), 1.80-2.10 (m, 5H), 1.50-1.70 (m, 4H), 1.37 (s, 3H), 1.15 (d, J=6.9 Hz, 3H). MS (EI) for $C_{31}H_{44}N_4O_7$, found 586.25 $(MH)^+$.

Example 15

(S)—N—((S)-3-(Cyclopent-1-en-1-yl)-1-((R)-2-methyloxiran-2-yl)-1-oxopropan-2-yl)-2-((S)-2-(2-(4-hydroxypiperidin-1-yl)acetamido)propanamido)-3-(4-methoxyphenyl)propanamide (C-1118)

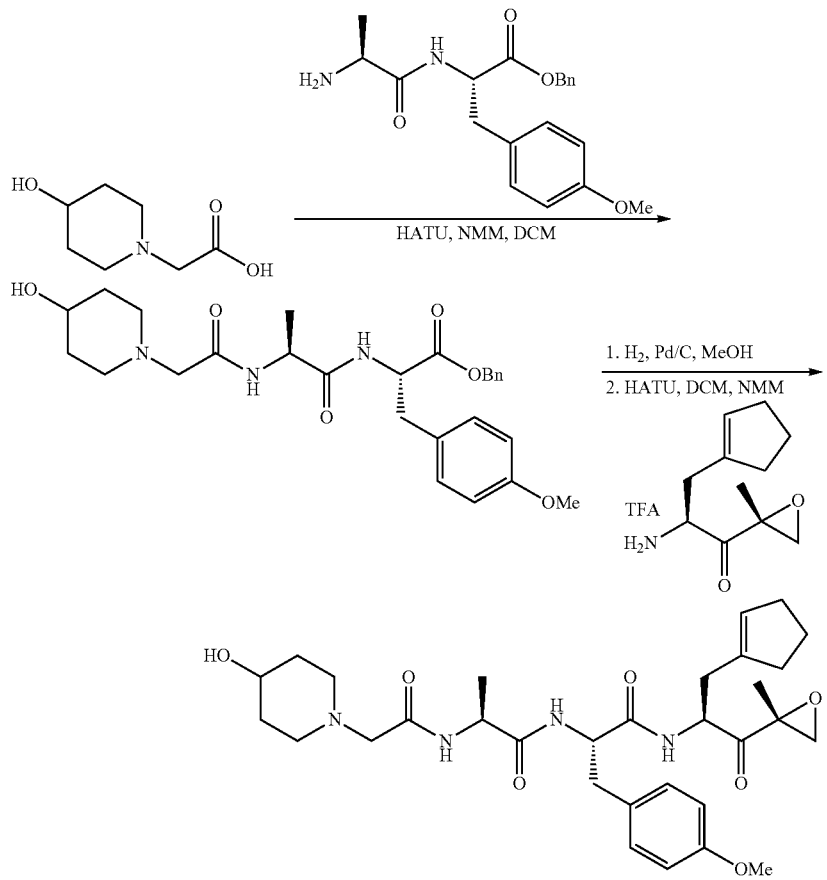

To a solution of 2-(4-hydroxypiperidin-1-yl)acetic acid (0.41 g, 2.6 mmol) and (S)-benzyl 2-((S)-2-aminopropanamido)-3-(4-methoxyphenyl)propanoate (HCl salt, 0.93 g, 2.6 mmol) in dichloromethane (30 mL) at 0° C. was added HATU (1.1 g, 2.9 mmol) followed by N-methylmorpholine (1.05 g, 10.4 mmol). The reaction mixture was allowed to warm to ambient temperature and stirred for 1 h. Water (30 mL) was added and the resulting mixture was extracted with dichloromethane (30 mL×3). The organic extracts were combined, dried over anhydrous sodium sulfate, and concentrated. The residue was purified by flash column chromatography on silica gel (petroleum ether/dichloromethane=5:1 to 1:1) to afford (S)-benzyl 2-((S)-2-(2-(4-hydroxypiperidin-1-yl)acetamido)propanamido)-3-(4-methoxyphenyl)propanoate (1.1 g, 87% yield) as a colorless solid.

A mixture of (S)-benzyl 2-((S)-2-(2-(4-hydroxypiperidin-1-yl)acetamido)propanamido)-3-(4-methoxyphenyl)propanoate (0.50 g, 1.0 mmol) and Pd/C (0.1 g) in methanol (20 mL) was hydrogenated for 1 h at ambient temperature. The Pd/C was filtered off and the filtrate was concentrated.

The residue was dissolved in dichloromethane (20 mL) followed by addition of (S)-2-amino-3-(cyclopent-1-en-1-yl)-1-((R)-2-methyloxiran-2-yl)propan-1-one (TFA salt, 0.300 g, 1.02 mmol) and HATU (0.40 g, 1.0 mmol). N-Methylmorpholine (0.36 g, 3.8 mmol) was added to the solution at 0° C. The reaction mixture was allowed to warm to ambient temperature and stirred for 1 h. Water (20 mL) was added and the resulting mixture was extracted with dichloromethane (20 mL×3). The organic extracts were combined, dried over anhydrous sodium sulfate, and concentrated. The residue was purified by flash column chromatography on silica gel (dichloromethane/methanol=200:1 to 80:1) and preparative TLC to afford (S)—N—((S)-3-(cyclopent-1-en-1-yl)-1-((R)-2-methyloxiran-2-yl)-1-oxopropan-2-yl)-2-((S)-2-(2-(4-hydroxypiperidin-1-yl)acetamido)propanamido)-3-(4-methoxyphenyl)propanamide (151 mg, 26% yield). $^1$H NMR (300 MHz, DMSO-$d_6$): δ 8.30 (d, J=7.2 Hz, 1H), 8.09 (d, J=8.1 Hz, 1H), 7.71 (br. s, 1H), 7.12 (d, J=8.4 Hz, 2H), 6.78 (d, J=8.4 Hz, 2H), 5.40 (s, 1H), 4.58 (br. s, 1H), 4.52-4.41 (m, 2H), 4.32-4.26 (m, 1H), 3.70 (s, 3H), 3.49-3.35 (m, 1H), 3.34 (s, 1H), 3.18 (d, J=5.1 Hz, 1H), 2.98 (d, J=5.1 Hz, 1H), 2.92-2.72 (m, 3H), 2.63-2.35 (m, 5H), 2.29-1.91 (m, 7H), 1.85-1.70 (m, 4H), 1.38 (s, 3H), 1.14 (d, J=6.9 Hz, 3H). MS(EI) for $C_{31}H_{44}N_4O_7$, found 585.2 (MH)$^+$.

The following compounds were synthesized in similar manner:

(S)—N—((S)-3-cyclopentyl-1-((R)-2-methyloxiran-2-yl)-1-oxopropan-2-yl)-2-((S)-2-(2-(3,3-difluoropyrrolidin-1-yl)acetamido)propanamido)-3-(4-methoxyphenyl)propanamide (C-1048): $^1$H NMR (300 MHz, CDCl$_3$): δ 8.27 (d, J=6.9 Hz, 1H), 7.97 (d, J=7.2 Hz, 1H), 7.78 (d, J=7.8 Hz, 1H), 7.12 (d, J=8.4 Hz, 2H), 6.79 (d, J=8.1 Hz, 2H), 4.30 (m, 1H), 4.27 (m, 1H), 3.71 (s, 3H), 3.17 (d, J=5.1 Hz, 1H), 3.10 (m, 2H), 2.90 (m, 2H), 2.77 (m, 2H), 2.70 (m, 2H), 2.23 (m, 2H), 1.85 (m, 2H), 1.61-1.49 (m, 7H), 1.45 (s, 3H), 1.15 (d, J=6.9 Hz, 3H). MS(EI) for $C_{30}H_{42}F_2N_4O_6$, found 593.4 (MH)$^+$.

(S)—N—((S)-3-cyclopentyl-1-((R)-2-methyloxiran-2-yl)-1-oxopropan-2-yl)-3-(4-methoxyphenyl)-2-((S)-2-(2-(4-(trifluoromethyl)piperidin-1-yl)acetamido)propanamido) propanamide (C-1047): $^1$H NMR (300 MHz, CDCl$_3$): δ 7.13 (d, J=8.7 Hz, 2H), 6.81 (d, J=8.4 Hz, 2H), 6.75 (d, J=8.1 Hz, 1H), 6.40 (d, J=8.1 Hz, 1H), 4.60 (m, 1H), 4.58 (m, 1H), 4.51 (m, 1H), 3.94 (s, 2H), 3.79 (s, 3H), 3.27 (d, J=4.8 Hz, 1H), 3.00 (m, 3H), 2.97 (m, 4H), 2.18 (m, 3H), 2.18 (m, 3H), 1.90 (m, 3H), 1.72-1.68 (m, 5H), 1.52 (m, 3H), 1.39 (d, J=6.9 Hz, 3H), 1.44-1.27 (m, 3H). MS(EI) for $C_{32}H_{45}F_3N_4O_6$, found 639.0 (MH)$^+$.

(S)—N—((S)-3-cyclopentyl-1-((R)-2-methyloxiran-2-yl)-1-oxopropan-2-yl)-2-((S)-2-(2-(4,4-difluoropiperidin-1-yl)acetamido)propanamido)-3-(4-methoxyphenyl)propanamide (C-1046): $^1$H NMR (300 MHz, CDCl$_3$): δ 7.13 (d, J=8.7 Hz, 2H), 6.82 (d, J=8.4 Hz, 2H), 6.74 (d, J=8.1 Hz, 1H), 6.40 (d, J=8.1 Hz, 1H), 4.59 (m, 1H), 4.57 (m, 1H), 4.48 (m, 1H), 3.79 (s, 3H), 3.25 (d, J=5.1 Hz, 1H), 3.04-2.91 (m, 3H), 2.90 (m, 2H), 2.63-2.59 (m, 4H), 2.02 (m, 4H), 1.98 (m, 1H), 1.70 (m, 4H), 1.64 (m, 3H), 1.52 (m, 5H), 1.37 (d, J=6.9 Hz, 3H), 1.27 (m, 1H), 1.25 (m, 1H). MS(EI) for $C_{31}H_{44}F_2N_4O_6$, found 607.4 (MH)$^+$.

(S)-2-((S)-2-(2-(4-chloropiperidin-1-yl)acetamido)propanamido)-N—((S)-3-cyclopentyl-1-((R)-2-methyloxiran-2-yl)-1-oxopropan-2-yl)-3-(4-methoxyphenyl)propanamide (C-1045): $^1$H NMR (300 MHz, CDCl$_3$): δ 7.13 (d, J=8.7 Hz, 2H), 6.82 (d, J=8.4 Hz, 2H), 6.78 (d, J=8.1 Hz, 1H), 6.40 (d, J=8.1 Hz, 1H), 4.59 (m, 1H), 4.57 (m, 1H), 4.48 (m, 1H), 4.13 (m, 1H), 3.78 (s, 3H), 3.26 (d, J=5.1 Hz, 1H), 3.02-2.97 (m, 3H), 2.90 (m, 2H), 2.73 (m, 2H), 2.42 (m, 2H), 2.09 (m, 2H), 1.92 (m, 4H), 1.87 (m, 4H), 1.73 (m, 4H), 1.52 (m, 3H), 1.41 (d, J=6.9 Hz, 3H), 1.38 (m, 1H), 1.36 (m, 1H). MS(EI) for $C_{31}H_{45}ClN_4O_6$, found 605.4 (MH)$^+$.

(S)—N—((S)-3-cyclopentyl-1-((R)-2-methyloxiran-2-yl)-1-oxopropan-2-yl)-2-((S)-2-(2-(3,3-difluoropiperidin-1-yl)acetamido)propanamido)-3-(4-methoxyphenyl)propanamide (C-1043): $^1$H NMR (300 MHz, CDCl$_3$): δ 7.13 (d, J=8.7 Hz, 2H), 6.82 (d, J=8.4 Hz, 2H), 6.77 (d, J=8.1 Hz, 1H), 6.40 (d, J=8.1 Hz, 1H), 4.60 (m, 1H), 4.58 (m, 1H), 4.39 (m, 1H), 3.94 (s, 2H), 3.79 (s, 3H), 3.27 (d, J=4.8 Hz, 1H), 3.00 (m, 4H), 2.90 (m, 2H), 2.88 (m, 2H), 2.50 (m, 2H), 1.94 (m, 2H), 1.89 (m, 3H), 1.70 (m, 2H), 1.60 (m, 2H), 1.51 (s, 3H), 1.37 (d, J=6.9 Hz, 3H), 1.36-1.27 (m, 4H). MS(EI) for $C_{31}H_{44}F_2N_4O_6$, found 607.4 (MH)$^+$.

(R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)tetrahydrofuran-3-carboxamide (C-1036): $^1$H NMR (300 MHz, DMSO-d$_6$): δ 8.23 (d, J=6.9 Hz, 1H), 8.07-8.11 (m, 2H), 7.12 (d, J=8.4 Hz, 2H), 6.79 (d, J=8.4 Hz, 2H), 4.55 (m, 1H), 4.33 (m, 1H), 4.20 (m, 1H), 3.80 (m, 1H), 3.75 (s, 3H), 3.55-3.75 (m, 2H), 3.22 (d, J=4.8 Hz, 1H), 2.90-3.10 (m, 3H), 2.65 (m, 1H), 1.80-2.05 (m, 3H), 1.50-1.80 (m, 7H), 1.42 (s, 3H), 1.00-1.30 (m, 2H), 0.96 (d, J=6.6 Hz, 3H). MS(EI) for $C_{29}H_{41}N_3O_7$, found 544.0 (MH)$^+$.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)tetrahydro-2H-pyran-4-carboxamide (C-1028): $^1$H NMR (300 MHz, CDCl$_3$): δ 7.11 (d, J=8.7 Hz, 2H), 6.83 (d, J=8.4 Hz, 2H), 6.65 (m, 1H), 6.52 (m, 1H), 6.29 (m, 1H), 4.64 (m, 1H), 4.52 (m, 1H), 4.40 (m, 1H), 4.03 (d, J=3.3 Hz, 1H), 3.99 (d, J=2.7 Hz, 1H), 3.80 (s, 3H), 3.40 (m, 2H), 3.28 (d, J=5.1 Hz, 1H), 3.04 (m, 2H), 2.89 (m, 1H), 2.42 (m, 1H), 1.80-1.75 (m, 6H), 1.68 (m, 4H), 1.55 (m, 5H), 1.30 (d, J=6.9 Hz, 3H), 1.20 (m, 2H), 1.06 (m, 1H). MS (EI) for $C_{30}H_{43}N_3O_7$, found 558.6 (MH)$^+$.

N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)-3-oxocyclobutanecarboxamide (C-1029): $^1$H NMR (300 MHz, CDCl$_3$): δ 7.12 (d, J=8.4 Hz, 2H), 6.83 (d, J=8.7 Hz, 2H), 6.49 (m, 3H), 4.66 (m, 1H), 4.52 (m, 1H), 4.40 (m, 1H), 3.81 (s, 3H), 3.45-3.43 (m, 3H), 3.30-2.92 (m, 5H), 2.92 (m, 2H), 1.98 (m, 4H), 1.74 (m, 6H), 1.33 (d, J=6.6 Hz, 3H), 1.30 (m, 2H), 1.26 (m, 1H). MS (EI) for $C_{29}H_{39}N_3O_7$, found 542.6 (MH)$^+$.

(S)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)tetrahydrofuran-2-carboxamide (C-1031): $^1$H NMR (300 MHz, DMSO-d$_6$): δ 8.33 (d, J=7.2 Hz, 1H), 8.12 (d, J=8.4 Hz, 1H), 7.57 (d, J=7.8 Hz, 1H), 7.12 (d, J=8.4 Hz, 2H), 6.79 (d, J=8.4 Hz, 2H), 4.50 (m, 1H), 4.15-4.40 (m, 3H), 3.70-3.90 (m, 2H), 3.71 (s, 3H), 3.20 (d, J=5.1 Hz, 1H), 2.90-3.10 (m, 2H), 2.65 (m, 1H), 2.10 (m, 1H), 1.50-1.90 (m, 10H), 1.41 (s, 3H), 1.00-1.30 (m, 4H), 0.99 (d, J=6.6 Hz, 3H). MS(EI) for $C_{29}H_{41}N_3O_7$, found 544.0 (MH)$^+$.

(R)—N—((R)-1-(((S)-1-(((S)-3-cyclopentyl-1-((R)-2-methyloxiran-2-yl)-1-oxopropan-2-yl)amino)-3-(4-methoxyphenyl)-1-oxopropan-2-yl)amino)-1-oxopropan-2-yl)tetrahydrofuran-2-carboxamide (C-1032): $^1$H NMR (300 MHz, DMSO-d$_6$): δ 8.33 (d, J=7.2 Hz, 1H), 8.20 (d, J=8.7 Hz, 1H), 7.60 (d, J=7.5 Hz, 1H), 7.12 (d, J=8.4 Hz, 2H), 6.79 (d, J=8.4 Hz, 2H), 4.50 (m, 1H), 4.15-4.40 (m, 3H), 3.70-3.90 (m, 2H), 3.71 (s, 3H), 3.20 (d, J=5.1 Hz, 1H), 2.90-3.10 (m, 2H), 2.65 (m, 1H), 2.10 (m, 1H), 1.50-1.90 (m, 10H), 1.41 (s, 3H), 1.00-1.30 (m, 4H), 0.99 (d, J=6.6 Hz, 3H). MS(EI) for $C_{29}H_{41}N_3O_7$, found 544.0 (MH)$^+$.

Example 16

(2S,3R)—N—((S)-1-(((S)-3-(Cyclohex-1-en-1-yl)-1-((R)-2-methyloxiran-2-yl)-1-oxopropan-2-yl) amino)-3-(4-methoxyphenyl)-1-oxopropan-2-yl)-3-hydroxy-2-(2-morpholinoacetamido)butanamide (C-1148)

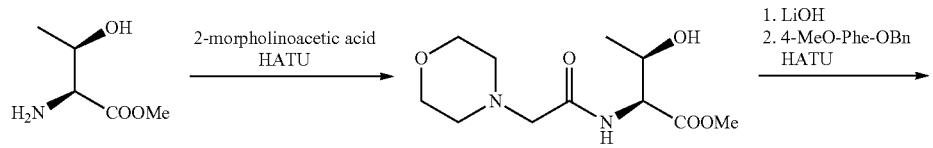

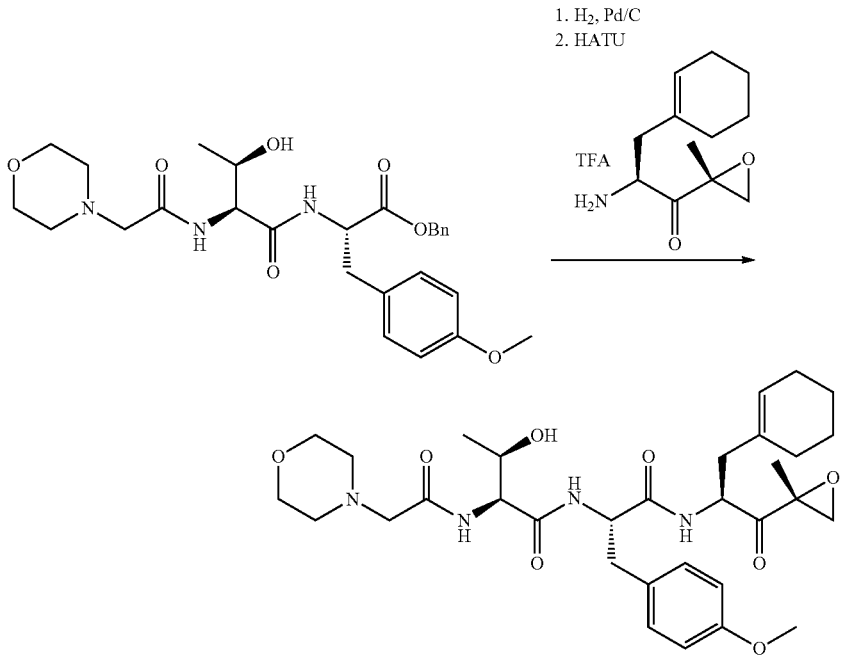

HATU (7.66 g, 20.1 mmol) was added to a solution of 2-morpholinoacetic acid (2.44 g, 16.8 mmol) and (2S,3R)-methyl 2-amino-3-hydroxybutanoate hydrochloride (2.84 g, 16.8 mmol) in dichloromethane (20 mL) at 0° C. N-Methylmorpholine (5.1 g, 50.4 mmol) was added and the reaction mixture was allowed to warm to ambient temperature and stirred for 1 h. The mixture was concentrated and the residue was purified by flash column chromatography on silica gel (dichloromethane/methanol=100:1 to 60:1) to afford (2S,3R)-methyl 3-hydroxy-2-(2-morpholinoacetamido)butanoate (2.1 g, 48% yield).

A solution of (2S,3R)-methyl 3-hydroxy-2-(2-morpholinoacetamido)butanoate (0.35 g, 1.3 mmol) in water/THF (5 mL/3 mL) was treated with LiOH—H$_2$O (0.11 g, 2.6 mmol) for 1 h at ambient temperature. The mixture was neutralized to pH=7 with concentrated HCl and then concentrated to dryness.

The residue was added to a solution of 4-MeO-Phe-OBn (TFA salt, 0.52 g, 1.3 mmol) and HATU (1.0 g, 2.6 mmol) in dichloromethane (20 mL). N-Methylmorpholine (0.63 mL, 5.7 mmol) was added at 0° C. and the reaction mixture was allowed to warm to ambient temperature and stirred for 1 h. The mixture was concentrated and the residue was purified by flash column chromatography on silica gel (dichloromethane/methanol=50:1 to 10:1) to afford (S)-benzyl 2-((2S,3R)-3-hydroxy-2-(2-morpholinoacetamido)butanamido)-3-(4-methoxyphenyl)propanoate (0.5 g, 72% yield).

A solution of (S)-benzyl 2-((2S,3R)-3-hydroxy-2-(2-morpholinoacetamido)butanamido)-3-(4-methoxyphenyl)propanoate (0.5 g, 1.0 mmol) in methanol (10 mL) was stirred under hydrogen atmosphere in the presence of Pd/C (0.1 g) for 1 h at ambient temperature. Pd/C was filtered off and the filtrate was concentrated to dryness.

The residue was added to a mixture of compound tert-butyl ((S)-3-(cyclohex-1-en-1-yl)-1-((R)-2-methyloxiran-2-yl)-1-oxopropan-2-yl)carbamate (TFA salt, 0.32 g, 1.0 mmol) and HATU (0.46 g, 1.2 mmol) in DCM (20 mL). N-Methyl morpholine (0.43 mL, 4.0 mmol) was added to the solution at 0° C. The reaction mixture was allowed to warm to ambient temperature and stirred for 1 h. Water (30 mL) was added and the resulting mixture was extracted with EtOAc (30 mL×3). The organic extracts were combined, dried over anhydrous sodium sulfate and concentrated. The residue was purified by flash column chromatography on silica gel (dichloromethane/methanol=200:1 to 120:1) to afford (2S,3R)—N—((S)-1-(((S)-3-(cyclohex-1-en-1-yl)-1-((R)-2-methyloxiran-2-yl)-1-oxopropan-2-yl)amino)-3-(4-methoxyphenyl)-1-oxopropan-2-yl)-3-hydroxy-2-(2-morpholinoacetamido)butanamide (270 mg, 45% yield). $^1$H NMR (300 MHz, DMSO-d$_6$): δ 8.28 (d, J=7.2 Hz, 1H), 7.93 (d, J=8.4 Hz, 1H), 7.63 (d, J=4.8 Hz, 1H), 7.09 (d, J=8.4 Hz, 2H), 6.76 (d, J=8.4 Hz, 2H), 5.77 (s, 1H), 5.40 (m, 1H), 5.02 (d, J=5.1 Hz, 1H) 4.51 (m, 2H), 4.19 (m, 1H), 3.95 (m, 1H), 3.70 (s, 3H), 3.55 (m, 4H), 3.21 (d, J=5.1 Hz, 1H), 2.95 m, 2H), 2.89 (m, 2H), 2.65 (m, 1H), 2.39 (m, 3H), 2.23 (m, 1H), 1.78-2.09 (m, 5H), 1.56 (m, 4H), 1.37 (s, 3H), 0.95 (d, J=6.0 Hz, 3H). MS (EI) for C$_{32}$H$_{46}$N$_4$O$_8$, 616.2 (MH)$^+$.

The following compounds were synthesized in a similar manner:

(2S,3S)—N—((S)-1-(((S)-3-(cyclohex-1-en-1-yl)-1-((R)-2-methyloxiran-2-yl)-1-oxopropan-2-yl)amino)-3-(4-methoxyphenyl)-1-oxopropan-2-yl)-3-hydroxy-2-(2-morpholinoacetamido)butanamide (C-1150): $^1$H NMR (300 MHz, DMSO-d$_6$): δ 8.21 (d, J=6.9 Hz, 1H), 8.10 (d, J=8.4 Hz, 1H), 7.64 (d, J=8.7 Hz, 1H), 7.13 (d, J=8.4 Hz, 2H), 6.77 (d, J=8.4 Hz, 2H), 5.76 (s, 1H), 5.39 (m, 1H), 4.99 (d, J=4.5 Hz, 1H), 4.50 (m, 2H), 4.25 (m, 1H), 3.79 (m, 1H), 3.70 (s, 3H), 3.54 (m, 4H), 3.21 (d, J=5.1 Hz, 1H), 2.89 (m, 4H), 2.64 (m, 1H), 2.37 (m, 3H), 2.21 (m, 1H), 2.03 (m, 5H), 1.56 (m, 4H), 1.37 (s, 3H), 0.97 (d, J=6.3 Hz, 3H). MS (EI) for C$_{32}$H$_{46}$N$_4$O$_8$, found 615.2 (MH)$^+$.

(2S,3S)—N—((S)-1-(((S)-3-(cyclohex-1-en-1-yl)-1-((R)-2-methyloxiran-2-yl)-1-oxopropan-2-yl)amino)-3-(4-methoxyphenyl)-1-oxopropan-2-yl)-3-hydroxy-2-(2-morpholinoacetamido)butanamide (C-1149): $^1$H NMR (300

MHz, DMSO-d$_6$): δ 8.21 (d, J=6.9 Hz, 1H), 8.10 (d, J=8.4 Hz, 1H), 7.64 (d, J=8.7 Hz, 1H), 7.13 (d, J=8.4 Hz, 2H), 6.77 (d, J=8.4 Hz, 2H), 5.39 (m, 1H), 4.99 (d, J=4.5 Hz, 1H), 4.50 (m, 2H), 4.25 (m, 1H), 3.79 (m, 1H), 3.70 (s, 3H), 3.54 (m, 4H), 3.21 (d, J=5.1 Hz, 1H), 2.89 (m, 4H), 2.64 (m, 1H), 2.37 (m, 4H), 2.21 (m, 1H), 2.03 (m, 5H), 1.56 (m, 4H), 1.37 (s, 3H), 0.97 (d, J=6.3 Hz, 3H). MS (EI) for C$_{32}$H$_{46}$N$_4$O$_8$, found 615.2 (MH)$^+$.

Synthetic Procedures-Fragments

Example 17 tert-Butyl ((2S)-3-(3-methylcyclopent-1-en-1-yl)-1-((R)-2-methyloxiran-2-yl)-1-oxopropan-2-yl)carbamate

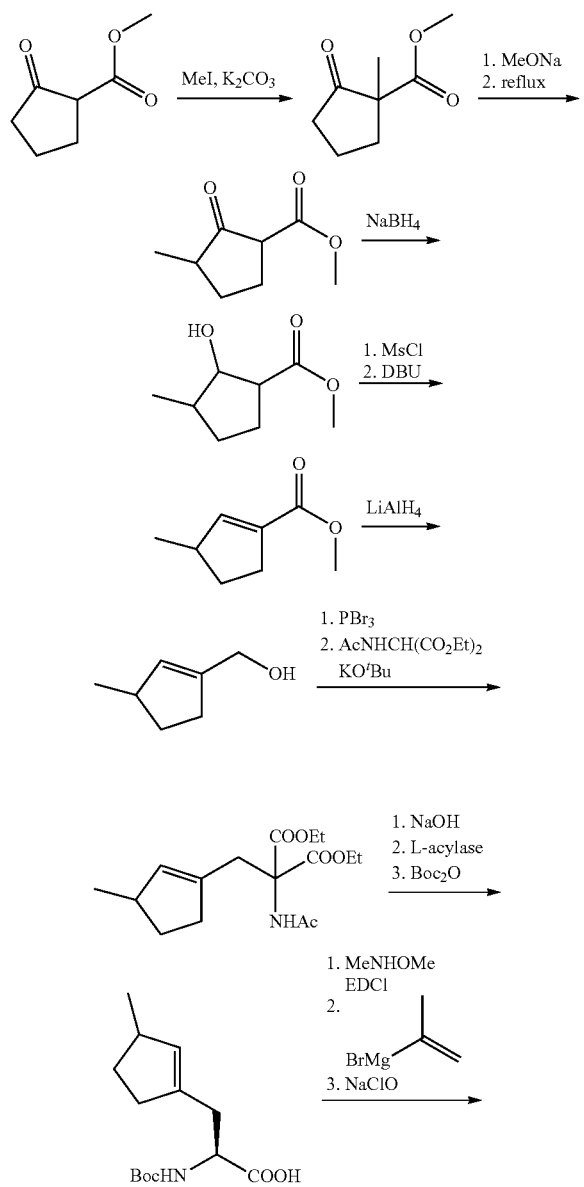

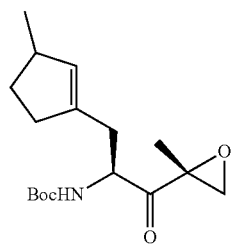

A mixture of methyl 2-oxocyclopentanecarboxylate (67 g, 0.47 mol), K$_2$CO$_3$ (163 g, 1.18 mol) and MeI (167 g, 1.18 mol) in acetone (500 mL) was heated under reflux for 12 h. The mixture was cooled to ambient temperature and then concentrated. The residue was dissolved in EtOAc (800 mL) and the resulting solution was washed with saturated aqueous NaHCO$_3$ (500 mL×3) and brine (300 mL×1), dried over anhydrous sodium sulfate, and concentrated to dryness. The residue was purified by distillation to afford methyl 1-methyl-2-oxocyclopentanecarboxylate (60.5 g, 82% yield).

Methyl 1-methyl-2-oxocyclopentanecarboxylate (61.0 g, 0.39 mol) was added dropwise to a freshly prepared solution of NaOMe (0.78 mol) in MeOH (1 L) at ambient temperature. The solution was heated under reflux for 3 h and then concentrated. The residue was dissolved in toluene (1 L) and the resulting solution was heated under reflux for 5 h. The mixture was cooled to ambient temperature, washed with saturated aqueous NaHCO$_3$ (500 mL×3) and brine (300 mL×1), dried over anhydrous sodium sulfate, and concentrated to dryness. The residue was purified by distillation to afford methyl 3-methyl-2-oxocyclopentanecarboxylate (39.0 g, 64% yield).

NaBH$_4$ (9.98 g, 0.260 mol) was added in portions to a solution of methyl 3-methyl-2-oxocyclopentanecarboxylate (41.2 g, 0.26 mol) in MeOH (250 mL) at 0° C. The reaction mixture was allowed to warm to ambient temperature and stirred for 5 h. The reaction was quenched with saturated aqueous NH$_4$Cl (500 mL) and the resulting mixture was extracted with EtOAc (250 mL×5). The combined organic phases were washed with brine (500 mL×2), dried over anhydrous sodium sulfate, and concentrated to afford methyl 2-hydroxy-3-methylcyclopentanecarboxylate (34.0 g).

Et$_3$N (295 mL, 2.1 mol) and DMAP (2.59 g, 21.2 mmol) were added sequentially to a solution of methyl 2-hydroxy-3-methylcyclopentanecarboxylate (33.5 g, 0.21 mol) in CH$_2$Cl$_2$ (800 mL) at 0° C. Then MsCl (65.6 mL, 0.85 mol) was added dropwise over 1 h. The reaction mixture was stirred at 0° C. for 1 h and then allowed to warm to ambient temperature and stirred for 8 h. Water (500 mL) was added and the two layers were separated. The organic layer was washed with aqueous HCl (1N, 200 mL×3), saturated aqueous NaHCO$_3$ (200 mL×3), and brine (300 mL×1), respectively. The organic solution was dried over anhydrous sodium sulfate and concentrated to dryness.

The residue was dissolved in CH$_2$Cl$_2$ (600 mL) and cooled to 0° C. A solution of DBU (53.2 mL, 0.36 mol) in CH$_2$Cl$_2$ (100 mL) was added dropwise. The reaction mixture was allowed to warm to ambient temperature and stirred overnight. Water (200 mL) was added and the two layers were separated. The organic layer was washed with aqueous HCl (1N, 200 mL×3), saturated aqueous NaHCO$_3$ (200 mL×3), and brine (300 mL×1), respectively. The organic solution was dried over anhydrous sodium sulfate and concentrated to dryness. The residue was purified by distillation to afford methyl 3-methylcyclopent-1-enecarboxylate (15.3 g, 38% yield over three steps).

A suspension of LiAlH$_4$ (7.4 g, 190 mol) in THF (100 mL) was cooled to 0° C. under nitrogen. A solution of methyl 3-methylcyclopent-1-enecarboxylate (26.0 g, 170 mmol) in THF (100 mL) was added dropwise. The reaction mixture was allowed to warm to ambient temperature and stirred for 5 h. The reaction was quenched with water (7.4 mL), 15% aqueous NaOH (7.4 mL) and water (22.2 mL) carefully. The resulting mixture was filtered and washed with THF (100 mL×3). The filtrate and washings were combined and concentrated to dryness to afford crude (3-methylcyclopent-1-en-1-yl)methanol (18.6 g) as an oil.

Phosphorous tribromide (8 mL, 83 mmol) was added to a solution of (3-methylcyclopent-1-en-1-yl)methanol (18.5 g, 165 mmol) in Et$_2$O (300 mL) at −10° C. with stirring. The mixture was allowed to warm to ambient temperature and stirred for 3 h. The reaction was quenched with ice-water (100 mL). The organic phase was separated, washed with saturated aqueous NaHCO$_3$ (100 mL×3) and brine (100 mL×1), dried over anhydrous sodium sulfate, and concentrated to dryness to afford the corresponding bromide (24.0 g).

Potassium tert-butoxide (16.9 g, 0.15 mol) was added in portions to a solution of diethyl 2-acetamidomalonate (25.3 g, 0.12 mol) in DMF (100 mL) while maintaining the temperature below 10° C. After the addition was complete, the suspension was stirred for 0.5 h at 10° C. and the bromide (24.0 g) was added dropwise. The reaction mixture was stirred for 10 h at ambient temperature and water (500 mL) was added. The resulting mixture was extracted with EtOAc (500 mL×3). The combine organic phases were washed with saturated aqueous NaHCO$_3$ (500 mL×3), 5% aqueous KHSO$_4$ (500 mL×3), and brine (300 mL×1), respectively. The organic phase was dried over anhydrous sodium sulfate and concentrated to dryness. The residue was purified by flash column chromatography on silica gel (hexanes/EtOAc=10:1) to afford diethyl 2-acetamido-2-((3-methylcyclopent-1-enyl)methyl)malonate (34.4 g, 67% yield).

Diethyl 2-acetamido-2-((3-methylcyclopent-1-enyl)methyl)malonate (34.4 g, 0.110 mol) was dissolved in ethanol (200 mL) and 1N aqueous NaOH (200 mL, 0.2 mol) was added. The solution was heated under reflux for 8 h and then cooled to ambient temperature. The organic solvent was removed and the remaining aqueous solution was washed with ethyl ether (50 mL×3) and acidified with 2N aqueous hydrochloric acid to pH=3. The resulting mixture was extracted with EtOAc (200 mL×6) and the combined organic phases were washed with brine (200 mL×1), dried over anhydrous sodium sulfate, and concentrated to dryness.

The residue was suspended in water (500 mL) and aqueous NaOH (1N) was added dropwise to adjust to pH=7.5. The mixture was stirred for 30 min at 37° C. and then filtered. L-Acylase (5.0 g) was added to the filtrate and the mixture was stirred for 40 h at 37° C. The mixture was cooled to ambient temperature and purified by ion-exchange resin (732 #, 100 g) to afford the corresponding L-amino acid.

L-Amino acid was dissolved in water and acetone (1:1, 200 mL) and the solution was basified with 2N aqueous NaOH to pH=8. Boc$_2$O (22.0 g, 0.1 mmol) was added and the reaction mixture was stirred for 12 h at ambient temperature. The organic solvent was removed and the remaining aqueous solution was washed with ethyl ether (200 mL×3) and acidified with 2N aqueous hydrochloric acid to pH=3. The resulting mixture was extracted with EtOAc (200 mL×6). The combined organic phases were washed with brine (100 mL×1), dried over anhydrous sodium sulfate, and concentrated to afford (2S)-2-(tert-Butoxycarbonyl amino)-3-(3-methylcyclopent-1-enyl)propanoic acid (4.8 g, 16% yield), which was used directly without further purification.

Triethylamine (1.3 mL, 9.7 mmol) was added to a suspension of dimethylhydroxyl amine hydrochloride (1.86 g, 9.7 mmol) and (2S)-2-(tert-butoxycarbonylamino)-3-(3-methylcyclopent-1-enyl)propanoic acid (2.6 g, 9.7 mmol) in methylene dichloride (50 mL) at 0° C. followed by addition of EDCI (1.86 g, 9.7 mmol). The reaction mixture was stirred overnight at ambient temperature and water (30 mL) was added. The organic layer was separated and washed with 5% aqueous KHSO$_4$ (30 mL×3), saturated aqueous NaHCO$_3$ (50 mL×3), and brine (50 mL×1), respectively. The organic phase was dried over anhydrous sodium sulfate and concentrated. The residue was purified by flash column chromatography on silica gel (hexanes/EtOAc=10:1) to afford the corresponding Weinreb amide.

The amide was dissolved in THF (50 mL) and a freshly prepared solution of isopropenylmagnesium bromide (75 mmol) in THF was added dropwise at 0° C. with stirring. The reaction mixture was stirred at 0° C. for 5 h and then quenched with saturated aqueous NH$_4$Cl (100 mL). The resulting mixture was extracted with EtOAc (100 mL×3). The combined organic layers were washed with 5% aqueous KHSO$_4$ (100 mL×3), saturated aqueous NaHCO$_3$ (100 mL×3), and brine (50 mL×1), respectively. The organic phase was dried over anhydrous sodium sulfate and concentrated. The residue was purified by flash column chromatography on silica gel (hexanes/EtOAc=10:1) to afford the corresponding enone (2.1 g, 69% yield).

Aqueous NaClO (10%, 16.3 mL, 22 mmol) was added dropwise to a solution of the enone (2.1 g, 6.7 mmol) in DMF (50 mL) at −10° C. with stirring. The reaction mixture was stirred for 2 h at −10° C. and water (300 mL) was added. The resulting mixture was extracted with EtOAc (100 mL×3). The combined organic layers were washed with 5% aqueous KHSO$_4$ (100 mL×3), saturated aqueous NaHCO$_3$ (100 mL×3), and brine (100 mL×1) respectively. The organic phase was dried over anhydrous sodium sulfate and concentrated. The residue was purified by flash column chromatography on silica gel (hexanes/EtOAc=5:1) to afford tert-butyl (2S)-3-(3-methylcyclopent-1-enyl)-1-((R)-2-methyloxiran-2-yl)-1-oxopropan-2-ylcarbamate (1.1 g, 50% yield).

tert-Butyl ((R)-3-(cyclopent-3-en-1-yl)-1-((R)-2-methyloxiran-2-yl)-1-oxopropan-2-yl)carbamate was synthesized in a similar manner starting from (S)-2-((tert-butoxycarbonyl)amino)-3-(cyclopent-3-en-1-yl)propanoic acid.

Example 18 tert-Butyl ((S)-1-((R)-2-methyloxiran-2-yl)-1-oxo-3-((R)-tetrahydrofuran-3-yl)propan-2-yl)carbamate and tert-Butyl (S)-1-((R)-2-methyloxiran-2-yl)-1-oxo-3-((S)-tetrahydrofuran-3-yl) propan-2-ylcarbamate

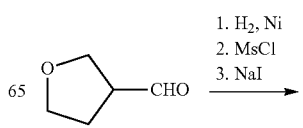

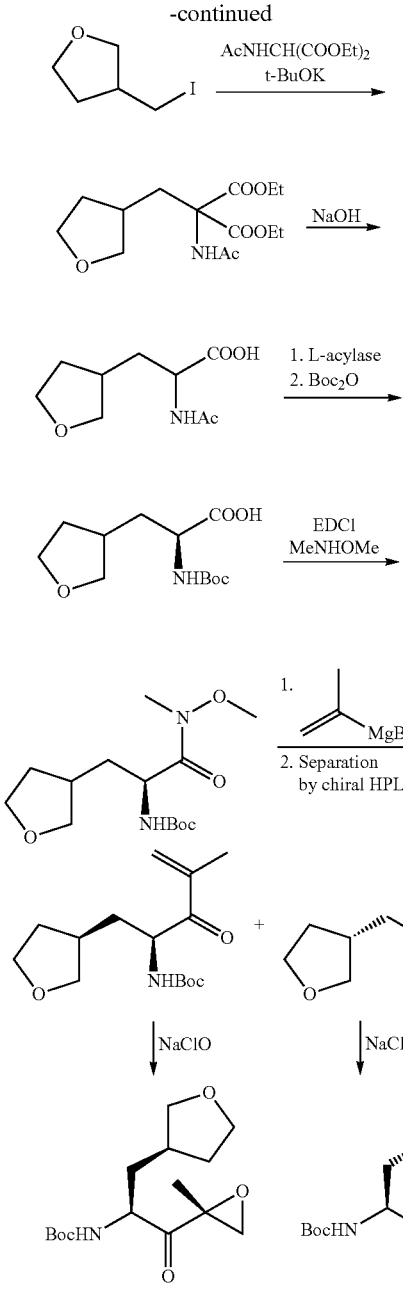

A mixture of Raney Ni (50 g) and tetrahydrofuran-3-carbaldehyde (100 g, 50% aqueous, 1.0 mol) was stirred under hydrogen atmosphere at ambient temperature for 12 h. The catalyst was filtered off and washed with water (20 mL). The filtrate and washings were combined and the solvent was removed by azeotroping with toluene. The residue was distilled to afford tetrahydro-3-furanmethanol (45 g) as a colorless oil.

Triethylamine (13.7 mL, 98 mmol) was added to a solution of tetrahydro-3-furanmethanol (10.0 g, 98 mmol) in methylene chloride (100 mL) at 0° C. followed by addition of methanesulfonyl chloride (12.3 g, 108 mmol) dropwise. The reaction mixture was stirred at 0° C. for 1 h and then allowed to warm to ambient temperature and stirred overnight. Aqueous hydrochloric acid (1N, 100 mL) was added and the two layers were separated. The organic layer was washed with 1N aqueous hydrochloric acid (100 mL×2), saturated aqueous sodium bicarbonate (100 mL×3), and brine (50 mL×1), respectively. The organic phase was dried over anhydrous sodium sulfate and concentrated to afford crude mesylate of tetrahydro-3-furanmethanol.

The mesylate was dissolved in acetone (1 L) and sodium iodide (45.0 g, 0.3 mol) was added. The suspension was heated under reflux overnight. The mixture was cooled to ambient temperature and filtered. The filtration cake was washed with cold acetone (50 mL). The filtrate and washings were combined and concentrated. Ethyl ether (100 mL) was added to the residue and the resulting precipitate was filtered off and washed with ethyl ether (100 mL×2). The filtrate and washings were concentrated and the residue was distilled to afford 3-(iodomethyl)tetrahydrofuran (20.1 g, 95% yield) as a yellow oil.

The remainder of the synthesis was carried out in a similar manner to the synthesis of tert-butyl (2S)-3-(3-methylcyclopent-1-enyl)-1-((R)-2-methyloxiran-2-yl)-1-oxopropan-2-ylcarbamate.

The stereochemical configuration was confirmed by x-ray crystallographic analysis.

Example 19 tert-Butyl ((S)-1-((R)-2-methyloxiran-2-yl)-1-oxo-3-((R)-tetrahydrofuran-2-yl)propan-2-yl)carbamate and tert-butyl ((S)-1-((R)-2-methyloxiran-2-yl)-1-oxo-3-((S)-tetrahydrofuran-2-yl)propan-2-yl)carbamate

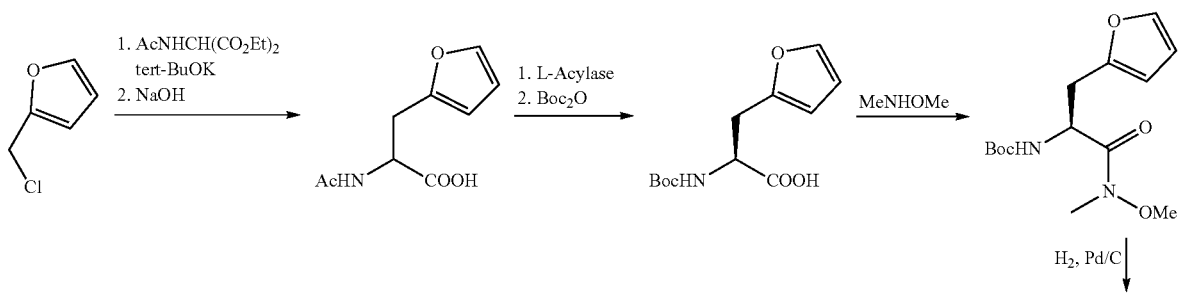

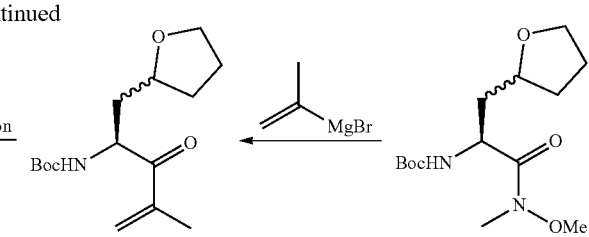

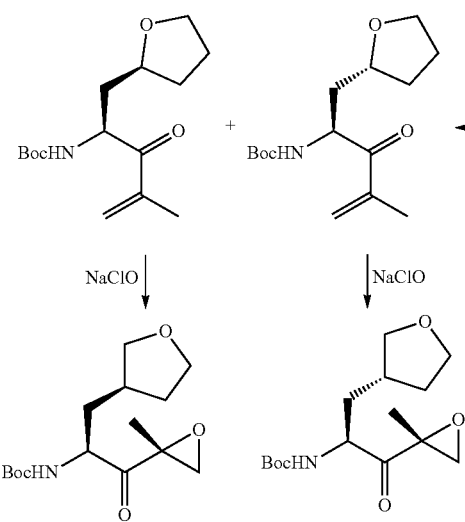

The synthesis was carried out in a similar manner to tert-Butyl ((S)-1-((R)-2-methyloxiran-2-yl)-1-oxo-3-((R)-tetrahydrofuran-3-yl)propan-2-yl)carbamate and tert-Butyl (S)-1-((R)-2-methyloxiran-2-yl)-1-oxo-3-((S)-tetrahydrofuran-3-yl) propan-2-ylcarbamate and the reduction of (S)-tert-Butyl 3-(furan-2-yl)-1-(methoxy(methyl)amino)-1-oxopropan-2-yl carbamate was carried out as follows:

To a solution of (S)-tert-Butyl 3-(furan-2-yl)-1-(methoxy(methyl)amino)-1-oxopropan-2-yl carbamate (8.6 g, 28.9 mol) in ethyl acetate (400 mL) was added Pd/C (2.0 g, 10%). The mixture was stirred under hydrogen atmosphere (1 atm) at 80° C. overnight and then cooled to room temperature. The mixture was filtered through a pad of Celite and the filtrate was concentrated under reduced pressure to afford (S)-tert-Butyl 1-(methoxy(methyl)amino)-1-oxo-3-(tetrahydrofuran-2-yl)propan-2-ylcarbamate (8.4 g, 96% yield) as a viscous oil, which was used in the next step without further purification.

The stereochemical configuration was confirmed by x-ray crystallographic analysis.

Example 20 tert-Butyl ((S)-3-((1R,5S,6r)-bicyclo[3.1.0]hexan-6-yl)-1-((R)-2-methyloxiran-2-yl)-1-oxopropan-2-yl)carbamate

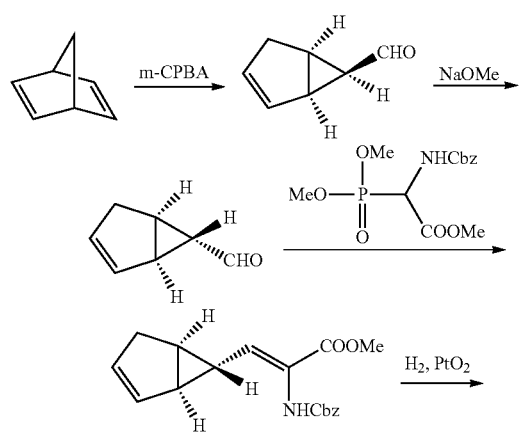

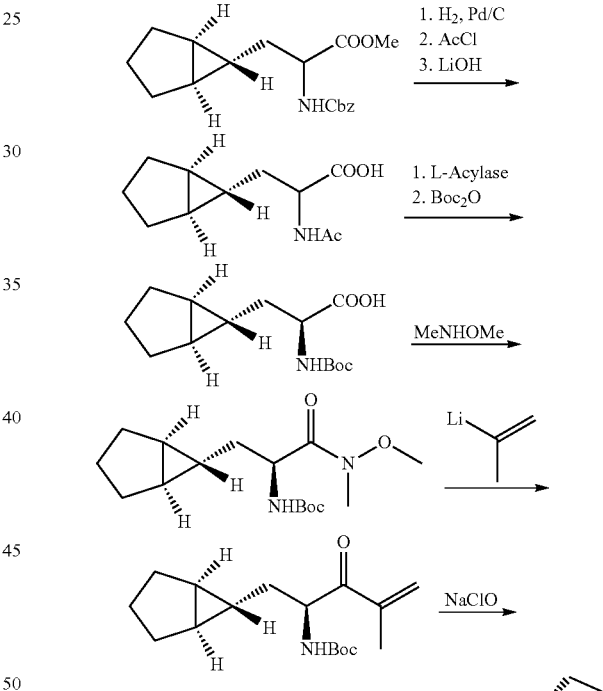

To a solution of norbornadiene (10.0 g, 108 mmol) in CH$_2$Cl$_2$ (400 mL) was added m-CPBA (22.1 g, 108 mmol) in portions over 1 h at 0° C. The reaction mixture was stirred for 1.5 h at ambient temperature and then filtered. The filtrate was washed with cold 5% aqueous NaHCO$_3$ (200 mL) and cold water (200 mL), dried over anhydrous sodium sulfate, and concentrated to afford (1S,5R,6R)-bicyclo[3.1.0]hex-2-ene-6-carbaldehyde as a clear oil.

(1S,5R,6R)-bicyclo[3.1.0]Hex-2-ene-6-carbaldehyde was taken up in methanol (150 mL) and NaOMe (8.15 g, 151 mmol) was added. The mixture was heated under reflux for 24 h and then cooled to ambient temperature. The mixture was diluted with water and extracted with Et₂O (200 mL×2). The combined organic layers were washed with water (100 mL) and brine (100 mL), dried over anhydrous sodium sulfate and concentrated. The residue was purified by flash column chromatography on silica gel (petroleum ether/EtOAc=10:1) to afford trans-bicyclo[3.1.0]hex-2-ene-6-carbaldehyde (2.7 g, 23% yield over two steps) as a light yellow oil.

A mixture of trans-bicyclo[3.1.0]hex-2-ene-6-carbaldehyde (5.0 g, 6.3 mmol), methyl 2-(benzyloxycarbonylamino)-2-(dimethoxyphosphoryl)acetate (23.0 g, 69.4 mol) and DBU (11.0 g, 69.4 mmol) in DCM (150 mL) was stirred at ambient temperature for 1 h. The mixture was poured into saturated aqueous NH₄Cl (150 mL) and then extracted with DCM (100 mL×2). The combined organic layers were washed with saturated aqueous NH₄Cl (100 mL×2) and brine (100 mL), dried over anhydrous sodium sulfate, and concentrated. The residue was purified by flash column chromatography on silica gel (petroleum ether/EtOAc=10:1 to 4:1) to afford methyl 2-(benzyloxycarbonylamino)-3-(trans-bicyclo[3.1.0]hex-2-en-6-yl)acrylate (7.0 g, 48% yield over two steps) as a colorless oil.

To a solution of methyl 2-(benzyloxycarbonylamino)-3-(trans-bicyclo[3.1.0]hex-2-en-6-yl)acrylate (10.0 g, 33 mmol) in methanol (200 mL) was added PtO₂ (0.8 g). The mixture was stirred under hydrogen atmosphere for 2 h. The mixture was filtered through a pad of Celite and then concentrated to afford crude methyl 2-(benzyloxycarbonylamino)-3-(trans-bicyclo[3.1.0]hexan-6-yl) propanoate, which was used directly without further purification.

To a solution of crude methyl 2-(benzyloxycarbonylamino)-3-(trans-bicyclo[3.1.0]hexan-6-yl) propanoate (10.0 g, 31.0 mmol) in methanol (300 mL) was added Pd/C (10%, 1.0 g). The mixture was stirred under hydrogen atmosphere for 12 h. The mixture was filtered through a pad of Celite and then concentrated. The residue was purified by flash column chromatography on silica gel (petroleum ether/EtOAc=20:1 to 4:1) and prep-HPLC to afford the corresponding amine (0.9 g, 9% yield over two steps) as a colorless oil.

To a solution of amine (0.52 g, 2.82 mmol) in DCM (20 mL) containing Et₃N (0.96 mL, 7.06 mmol) was added AcCl (0.3 g, 3.67 mmol) dropwise at 0° C. over 30 min. The reaction mixture was stirred for 1 h at 0° C. and saturated aqueous NaHCO₃ (20 mL) was added. The resulting mixture was extracted with DCM (20 mL) and the combined organic layers were concentrated to afford acetyl-amide (0.6 g, 94% yield) as a colorless oil.

To a mixture of acetyl-amide (0.60 g, 2.67 mmol) in THF (20 mL) and water (20 mL) was added lithium hydroxide (0.6 g, 14.6 mmol). The reaction mixture was stirred at ambient temperature for 0.5 h and diluted with water (50 mL). The solution was washed with EtOAc (50 mL) and the aqueous phase was adjusted to pH=4 with 2N aqueous HCl (20 mL). The resulting precipitate was collected by filtration and dried under vacuum to afford 2-acetamido-3-(trans-bicyclo[3.1.0]hexan-6-yl)propanoic acid (0.5 g, 89% yield) as a yellow solid.

A mixture of 2-acetamido-3-(trans-bicyclo[3.1.0]hexan-6-yl)propanoic acid (850 mg, 4.00 mmol) in water (5 mL) was adjusted to pH=8.5 with 1M aqueous NaOH. The mixture was filtered and the filtrate was heated to 38° C. and L-acylase (100 mg) was added. The mixture was stirred for 24 h and then filtrated. The filtrate was adjusted to pH=2-3 with 1N aqueous HCl and the resulting mixture was washed with EtOAc (20 mL×2).

The aqueous layer was adjusted to pH=8-9 and a solution of Boc₂O (658 mg, 3.0 mmol) in acetone (10 mL) was added. The reaction mixture was stirred at ambient temperature overnight and acetone was removed. The remaining mixture was adjusted to pH=3-4 and then extracted with EtOAc (20 mL×2). The combined extracts were concentrated to afford (S)-3-(trans-bicyclo[3.1.0]hexan-6-yl)-2-(tert-butoxycarbonylamino)propanoic acid (1.14 g, 28% yield over two steps) as a colorless oil.

The remainder of the synthesis was carried out according to the procedure for tert-butyl (2S)-3-(3-methylcyclopent-1-enyl)-1-((R)-2-methyloxiran-2-yl)-1-oxopropan-2-ylcarbamate.

Example 21 tert-Butyl ((S)-3-((1R,3r,5S)-bicyclo[3.1.0]hexan-3-yl)-1-((R)-2-methyloxiran-2-yl)-1-oxopropan-2-yl)carbamate

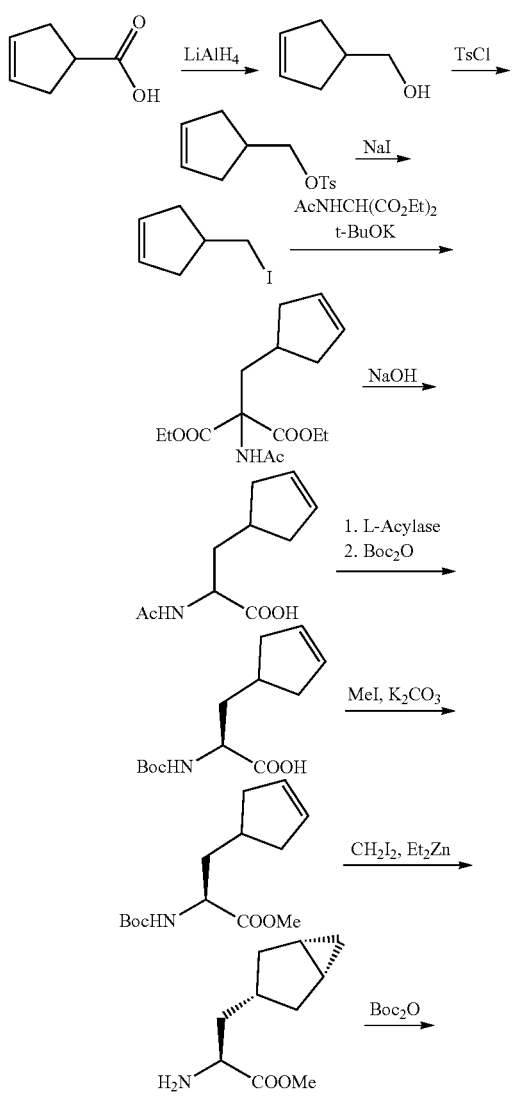

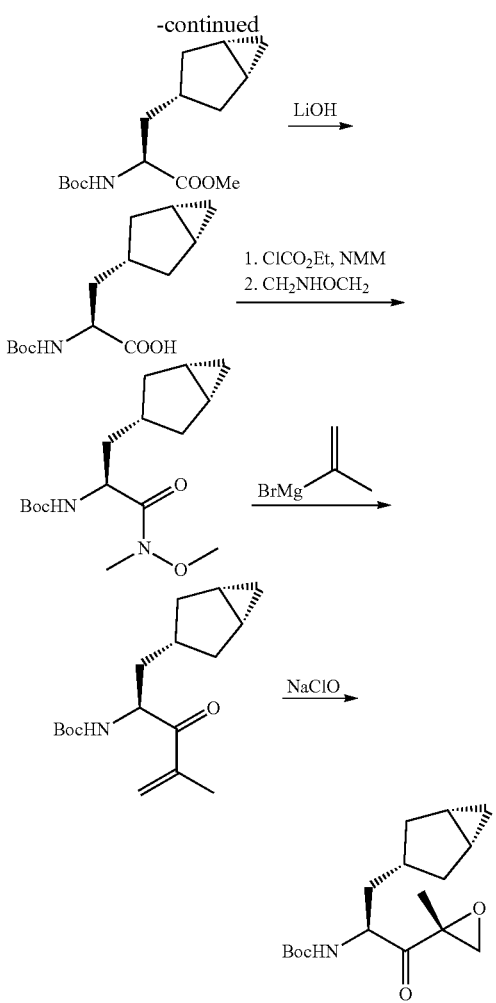

A suspension of LiAlH₄ (20.4 g, 0.54 mol) in THF (700 mL) was cooled to 0° C. under nitrogen. A solution of cyclopent-3-enecarboxylic acid (40.0 g, 0.36 mol) in THF (100 mL) was added dropwise. The cooling bath was removed and the reaction mixture was warmed to 40° C. and stirred for 2 h. The mixture was cooled to 0° C. again and water (24 mL) was added dropwise carefully. The resulting mixture was acidified with dilute aqueous HCl to pH=2-3 and then extracted with EtOAc (300 mL×2). The organics were combined, washed with saturated aqueous NaHCO₃ (300 mL×2) and brine (300 mL), dried over anhydrous sodium sulfate, and concentrated to afford cyclopent-3-enylmethanol as a light yellow oil (30.0 g, 85% yield).

To a solution of cyclopent-3-enylmethanol (71 g, 0.72 mol) in DCM (2.0 L) was added triethylamine (151 mL, 1.09 mol). The mixture was cooled to 0° C. and TsCl (179.4 g, 0.94 mol) was added in portions over 1.5 h. Then DMAP (4.4 g, 0.036 mol) was added and the reaction mixture was allowed to warm to ambient temperature and stirred under nitrogen overnight. Saturated aqueous NaHCO₃ (1.0 L) was added and the two phases were separated. The aqueous phase was extracted with DCM (500 mL). The organics were combined, washed with saturated aqueous NH₄Cl (1.0 L) and brine (1.0 L), dried over anhydrous sodium sulfate and concentrated to afford cyclopent-3-enylmethyl 4-methylbenzenesulfonate as a brown oil (174 g, 95% yield), which was used in the next step without further purification.

To a solution of cyclopent-3-enylmethyl 4-methylbenzenesulfonate (174 g, 0.690 mol) in acetone (2.0 L) was added NaI (311 g, 2.07 mol). The reaction mixture was stirred at 70° C. overnight and then cooled to ambient temperature. Water (2.0 L) was added and the mixture was extracted with DCM (1 L×2). The extracts were combined, dried over anhydrous sodium sulfate, and concentrated. The residue was purified by flash column chromatography on silica gel (petroleum ether) to afford 4-(iodomethyl)cyclopent-1-ene as a light yellow oil (119 g, 82% yield).

Example 22

(S)-3-((1R,3r,5S)-bicyclo[3.1.0]hexan-3-yl)-2-((tert-butoxycarbonyl)amino)propanoic acid was synthesized from (1R,3r,5S)-3-(iodomethyl)bicyclo[3.1.0]hexane in a similar manner to the synthesis of (2S)-2-(tert-butoxycarbonylamino)-3-(tetrahydrofuran-3-yl)propanoic acid To a solution of (S)-3-((1R,3r,5S)-bicyclo[3.1.0]hexan-3-yl)-2-((tert-butoxycarbonyl)amino)propanoic acid (4.0 g, 15.8 mmol) in DMF (120 mL) was added K₂CO₃ (3.3 g, 23.5 mmol). The mixture was stirred at ambient temperature for 0.5 h followed by addition of MeI (2.7 g, 18.8 mmol). The reaction mixture was stirred overnight and water (200 mL) was added. The resulting mixture was extracted with MTBE (200 mL×2). The organics were combined, washed with brine (300 mL), dried over anhydrous sodium sulfate, and concentrated to afford (S)-methyl 2-(tert-butoxycarbonylamino)-3-(cyclopent-3-enyl)propanoate (4.0 g, 95% yield) as a viscous oil, which was used in the next step without further purification.

To a solution of (S)-methyl 2-(tert-butoxycarbonylamino)-3-(cyclopent-3-enyl)propanoate (2.38 g, 8.86 mmol) in DCM (100 mL) at 0° C. was added Et₂Zn (1 M, 18.6 mL, 18.6 mmol) dropwise. The mixture was stirred for 15 min and a solution of CH₂I₂ (2.15 mL, 26.6 mmol) in DCM (13 mL) was added rapidly. The reaction mixture was stirred for 5 min and another portion of Et₂Zn (1 M, 9.75 mL, 9.75 mmol) was added followed by a solution of CH₂I₂ (2.15 mL, 26.6 mmol) in DCM (13 mL) again. The reaction mixture was allowed to warm to ambient temperature and stirred overnight. The mixture was cooled to 0° C. again and aqueous HCl (1 N) was added to adjust pH=1. Two phases were separated and the aqueous phase was basified with aqueous NaHCO₃ to pH=8-9 and then extracted with DCM (30 mL×3). The organics were combined, dried over anhydrous sodium sulfate, and concentrated to afford (S)-methyl 2-amino-3-((1R,3r,5S)-bicyclo[3.1.0]hexan-3-yl)propanoate (1.54 g, 95% yield) as a viscous oil, which was used in the next step without further purification.

(S)-Methyl 2-amino-3-((1R,3r,5S)-bicyclo[3.1.0]hexan-3-yl)propanoate (1.54 g, 8.4 mmol) was dissolved in THF (25 mL) and Boc₂ (2.20 g, 10.1 mmol) was added. The reaction mixture was stirred at ambient temperature for 3 h and then concentrated. The residue was purified by flash column chromatography on silica gel (petroleum ether/EtOAc=30:1) to afford (S)-methyl 3-((1R,3r,5S)-bicyclo[3.1.0]hexan-3-yl)-2-(tert-butoxycarbonylamino) propanoate (2.3 g, 96% yield) as a light yellow oil.

To a solution of (S)-methyl 3-((1R,3r,5S)-bicyclo[3.1.0]hexan-3-yl)-2-(tert-butoxycarbonylamino) propanoate (3.15 g, 11.1 mol) in water/THF (80 mL, 1:1) was added lithium hydroxide hydrate (1.40 g, 33.4 mol). The reaction mixture was stirred at ambient temperature for 2 h and then washed with EtOAc (50 mL×2). The organic phase was discarded and the aqueous phase was acidified with aqueous HCl to pH=3-4. The resulting mixture was extracted with DCM (100 mL×2) and the organics were combined and concentrated to afford (S)-3-((1R,3r,5S)-bicyclo[3.1.0]hexan-3-yl)-2-(tert-butoxycarbonylamino) propanoic acid (3.2 g, quantitative) as a viscous oil that was used in the next step without further purification.

To a solution of (S)-3-((1R,3r,5S)-bicyclo[3.1.0]hexan-3-yl)-2-(tert-butoxycarbonylamino) propanoic acid (3.2 g, 11.89 mmol) in THF/DCM (50 mL, 1:1) at 0° C. was added ethyl chloroformate (1.35 mL, 14.27 mmol) followed by addition of NMM (1.58 mL, 14.27 mmol) dropwise. The reaction mixture was stirred at 0° C. under nitrogen for 1 h (solution A).

To a solution of N,O-dimethylhydroxylamine (HCl salt, 1.39 g, 14.3 mmol) in DCM (40 mL) at 0° C. was added TEA (2.16 mL, 15.50 mmol) dropwise. This mixture was transferred into the flask charged with solution A. The resulting mixture was allowed to warm to ambient temperature and stirred for 2 h. Water (50 mL) was added and two layers were separated. The organic layer was washed with water (50 mL), dried over anhydrous sodium sulfate and concentrated. The residue was purified by flash column chromatography on silica gel (petroleum ether/EtOAc=10:1 to 5:1) to afford tert-butyl (S)-3-((1R,3r,5S)-bicyclo[3.1.0] hexan-3-yl)-1-(methoxy(methyl)amino)-1-oxopropan-2-yl-carbamate (3.0 g, 87% yield) as a colorless oil.

To a solution of tert-butyl (S)-3-((1R,3r,5S)-bicyclo [3.1.0]hexan-3-yl)-1-(methoxy(methyl)amino)-1-oxopropan-2-ylcarbamate (3.0 g, 9.6 mmol) in anhydrous THF (40 mL) was added freshly prepared prop-1-en-2-ylmagnesium bromide (38.4 mmol, 40 mL in THF) at 0° C. dropwise. The reaction mixture was stirred at 0° C. for 2 h and then quenched with saturated aqueous ammonium chloride (100 mL). The resulting mixture was extracted with EtOAc (50 mL×2) and the organic phases were combined, dried over anhydrous sodium sulfate and concentrated. The residue was purified by flash column chromatography on silica gel (petroleum ether/EtOAc=100:1 to 50:1) to afford tert-butyl (S)-1-((1R,3r,5S)-bicyclo[3.1.0]hexan-3-yl)-4-methyl-3-oxopent-4-en-2-ylcarbamate (1.1 g, 39% yield) as a colorless oil.

A solution of tert-butyl (S)-1-((1R,3r,5S)-bicyclo[3.1.0] hexan-3-yl)-4-methyl-3-oxopent-4-en-2-ylcarbamate (1.6 g, 5.5 mmol) in DMF (27 mL) was cooled to −20° C. and bleach (8.30 mL, 10.9 mmol, 10% active spice) was added dropwise under nitrogen. The reaction mixture was warmed to 0° C. and stirred for 2 h. Water (50 mL) was added and the resulting mixture was extracted with EtOAc (50 mL×2). The organic phases were combined, washed with brine (50 mL×2), dried over anhydrous sodium sulfate, and concentrated. The residue was purified by flash column chromatography on silica gel (petroleum ether/EtOAc=100:1) to afford tert-butyl ((S)-3-((1R,3r,5S)-bicyclo[3.1.0]hexan-3-yl)-1-((R)-2-methyloxiran-2-yl)-1-oxopropan-2-yl)carbamate (0.75 g, 44% yield) as a viscous oil. $^1$H NMR (CDCl$_3$, 300 MHz): δ 4.84 (d, J=8.4 Hz, 1H), 4.20 (t, J=9.0 Hz, 1H), 3.26 (t, J=5.1 Hz, 1H), 2.88 (t, J=5.1 Hz, 1H), 1.96 (dd, J=12.0, 6.0 Hz, 1H), 1.85 (dd, J=12.0, 6.6 Hz, 1H), 1.56-1.64 (m, 3H), 1.51 (s, 3H), 1.46 (s, 9H), 1.41-1.52 (m, 2H), 1.30-1.37 (m, 2H), 0.23-0.30 (m, 1H), 0.13-0.18 (m, 1H). MS (EI) for C$_{17}$H$_{27}$NO$_4$, found 332.2 [M+Na]$^+$. The stereochemical configuration was confirmed by x-ray crystallographic analysis.

Example 23 tert-Butyl ((S)-3-(2-methylcyclopent-1-en-1-yl)-1-((R)-2-methyloxiran-2-yl)-1-oxopropan-2-yl)carbamate

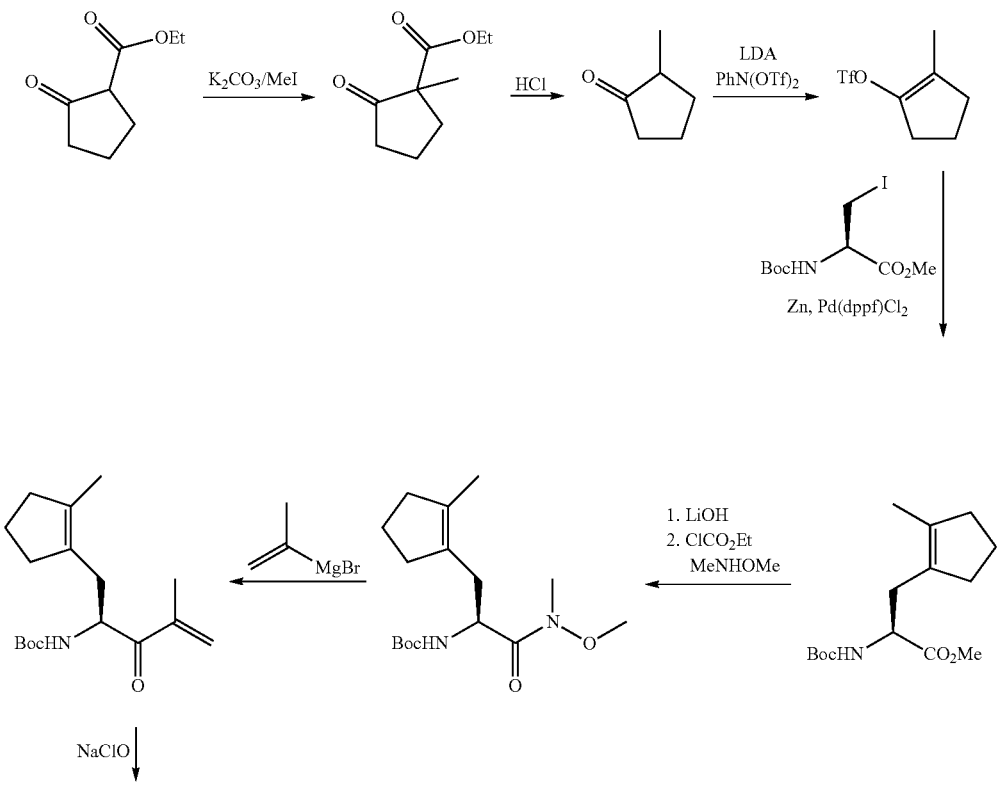

To a suspension of ethyl 2-oxocyclopentanecarboxylate (20.3 g, 0.130 mol) and $K_2CO_3$ (53.8 g, 0.390 mol) in acetone (90 mL) was added MeI (36.9 g, 0.250 mol) at ambient temperature. The reaction mixture was stirred for 30 min at ambient temperature and then heated under reflux for 1 h. Acetone was removed under reduced pressure and diethyl ether (200 mL) was added to the residue. The resulting mixture was stirred for 15 min and filtered. The filtrate was concentrated under reduced pressure followed by distillation under vacuum to afford ethyl 1-methyl-2-oxocyclopentanecarboxylate (20.5 g, 92% yield).

A mixture of ethyl 1-methyl-2-oxocyclopentanecarboxylate (20.0 g, 0.120 mol) in HCl (concentrated, 150 mL) was heated under reflux for 3 h. The mixture was cooled to ambient temperature and then extracted with DCM (150 mL×3). The combined organic phases were dried over anhydrous sodium sulfate and concentrated under reduced pressure to afford 2-methylcyclopentanone (9.5 g, 80% yield) as a colorless oil.

To a solution of 2-methylcyclopentanone (59.5 g, 0.610 mol) in THF (500 mL) was added LDA solution (2N, 303 mL, 0.610 mol) at −78° C. The mixture was stirred for 16 h at −78° C. followed by addition of a solution of N-phenyltriflimide (260 g, 0.730 mol) in THF (150 mL) at −78° C. via cannula. The reaction mixture was allowed to warm to ambient temperature and stirred for 16 h. The reaction was quenched with 10% aqueous NaOH (200 mL) and the resulting mixture was extracted with diethyl ether (300 mL×3). The combined organic phases were washed with brine, dried over anhydrous sodium sulfate, and concentrated. The crude oil was purified by flash column chromatography on silica gel (petroleum ether) to afford 2-methylcyclopent-1-en-1-yl trifluoromethanesulfonate (104 g, 74% yield).

To a suspension of Zn powder (11.7 g, 180 mmol) in freshly distilled DMF (20 mL) was added trimethylsilyl chloride (5.0 mL, 0.2 eq.) under $N_2$ atmosphere. The suspension was stirred vigorously for 35 min. The resulting pale orange supernatant was removed via a syringe. The activated Zn was washed with DMF (20 mL×2). To a suspension of the activated Zn powder in freshly distilled DMF (50 mL) was added methyl N-(tert-butoxycarbonyl)-3-iodo-L-alaninate (9.8 g, 30 mmol) at 0° C. The mixture was stirred for 5 min and the cooling bath was removed. The mixture was stirred for 20 min at ambient temperature. The grayish supernatant was transferred via a syringe into a dry flask under $N_2$ and the remaining zinc metal was washed with DMF (10 mL) followed by the transfer (solution A).

To a solution of 2-methylcyclopent-1-en-1-yl trifluoromethanesulfonate (8.60 g, 37.5 mmol) in DMF (18 mL) was added Pd(dppf)$Cl_2$ (1.2 g, 1.5 mmol). The resulting brown solution was stirred at ambient temperature for 20 min. The solution A was added at 0° C. and the reaction mixture was allowed to warm to ambient temperature and stirred for 16 h. The mixture was poured into water/EtOAc (1:1, 300 mL) and the resulting suspension was filtered through a pad of Celite. The two phases were separated and the aqueous phase was extracted with EtOAc (150 mL×2). The combined organics were washed with water (200 mL×2) and brine (200 mL), dried over anhydrous sodium sulfate, and concentrated. The residue was purified by flash column chromatography on silica gel (petroleum ether to petroleum ether/EtOAc=9:1) to afford (S)-methyl 2-((tert-butoxycarbonyl)amino)-3-(2-methylcyclopent-1-en-1-yl) propanoate (5.9 g, 68% yield) as a pale yellow oil.

To a solution of (S)-methyl 2-((tert-butoxycarbonyl) amino)-3-(2-methylcyclopent-1-en-1-yl) propanoate (35.0 g, 0.124 mol) in MeOH/$H_2O$ (250 mL/125 mL) was added LiOH—$H_2O$ (10.4 g, 0.25 mol) at 0° C. The reaction mixture was stirred for 1 h at 0° C. and then was adjusted to pH=7-8 with aqueous HCl (0.5 N). The organic solvent was removed under reduced pressure and the remaining mixture was adjusted to pH=10 with aqueous NaOH (0.5 N). The solution was washed with EtOAc (150 mL×2) and adjusted to pH=3-4 with aqueous HCl (0.5 N). The resulting mixture was extracted with EtOAc (150 mL×3) and the combined extracts were washed with water (100 mL) and brine (100 mL), dried over anhydrous sodium sulfate, and concentrated to afford the corresponding acid (32 g, 96% yield) as a pale yellow oil.

The remainder of the synthesis was carried out according to the procedure for tert-butyl ((S)-3-((1R,3r,5S)-bicyclo[3.1.0]hexan-3-yl)-1-((R)-2-methyloxiran-2-yl)-1-oxopropan-2-yl)carbamate.

Example 24 tert-Butyl ((S)-1-((R)-2-methyloxiran-2-yl)-1-oxo-3-(2-oxopyrrolidin-1-yl)propan-2-yl)carbamate

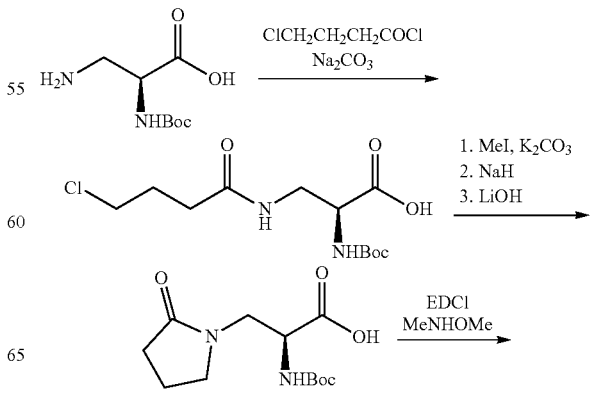

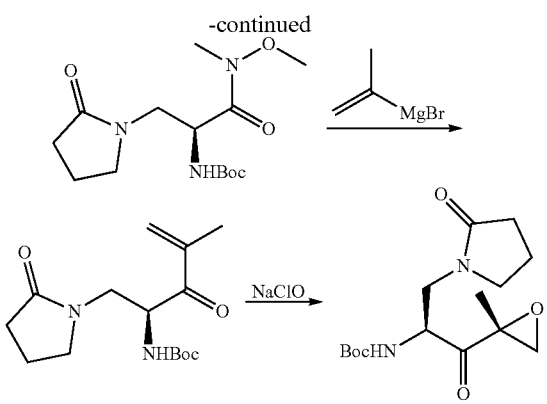

4-Chlorobutanoyl chloride (12.1 g, 86 mmol) was added to a solution of Boc-L-Dap (16.0 g, 78 mmol) in dioxane (160 mL) and 10% aqueous Na$_2$CO$_3$ (180 mL) at 0° C. dropwise. The reaction mixture was stirred at 0° C. for 1 h and then allowed to warm to ambient temperature and stirred overnight. The mixture was acidified with 1N aqueous hydrochloric acid to pH=3 and extracted with EtOAc (300 mL×3). The combined organic phases were washed with 1N aqueous hydrochloric acid (300 mL×3) and brine (300 mL×1), dried over anhydrous sodium sulfate, and concentrated to afford (S)-2-(tert-butoxycarbonylamino)-3-(4-chlorobutanamido)propanoic acid (15.5 g, 64% yield), which was used directly without further purification.

K$_2$CO$_3$ (7.0 g, 51 mmol) was added to a solution of (S)-2-(tert-butoxycarbonylamino)-3-(4-chlorobutanamido) propanoic acid (10.0 g, 34.0 mmol) in acetonitrile (100 mL) followed by addition of methyl iodine (5.6 g, 41 mmol). The suspension was heated at 50-60° C. for 4 h. After the mixture was cooled to ambient temperature, it was filtered and the filtration cake was washed with acetonitrile (50 mL). The filtrate and washings were combined and concentrated to dryness. The residue was purified by flash column chromatography on silica gel (Hexane/EtOAc=2:1) to afford the corresponding ester.

The ester was dissolved in DMF (100 mL) and NaH (60% suspension, 1.1 g, 45 mmol) was added at 0° C. The reaction mixture was stirred at 0° C. for 1 h and then allowed to warm to ambient temperature and stirred overnight. The reaction was quenched with ice-water (500 mL) and the resulting mixture was extracted with EtOAc (300 mL×3). The combined organic phases were washed with saturated aqueous NaHCO$_3$ (500 mL×3), 1N aqueous HCl (500 mL×3), and brine (300 mL×1), respectively. The organic phase was dried over anhydrous sodium sulfate and concentrated. The residue was purified by flash column chromatography on silica gel (Hexane/EtOAc=1:1) to afford the methyl ester (6.0 g, 57% yield) as an oil.

The methyl ester (6.0 g, 21 mmol) was dissolved in MeOH (20 mL) and a solution of LiOH (2.0 g, 84 mmol) in water (10 mL) was added at 0° C. with stirring. The reaction mixture was stirred for 3 h and then acidified with 2 N aqueous HCl to pH=3. The resulting mixture was concentrated to afford (S)-2-(tert-butoxycarbonylamino)-3-(2-oxopyrrolidin-1-yl)propanoic acid (4.1 g, 72% yield), which was used directly without further purification.

The remainder of the synthesis was carried out according to the procedure for tert-butyl (2S)-3-(3-methylcyclopent-1-enyl)-1-((R)-2-methyloxiran-2-yl)-1-oxopropan-2-ylcarbamate.

Example 25 tert-Butyl ((2S)-1-((R)-2-methyloxiran-2-yl)-1-oxo-3-(2-oxopyrrolidin-3-yl)propan-2-yl)carbamate

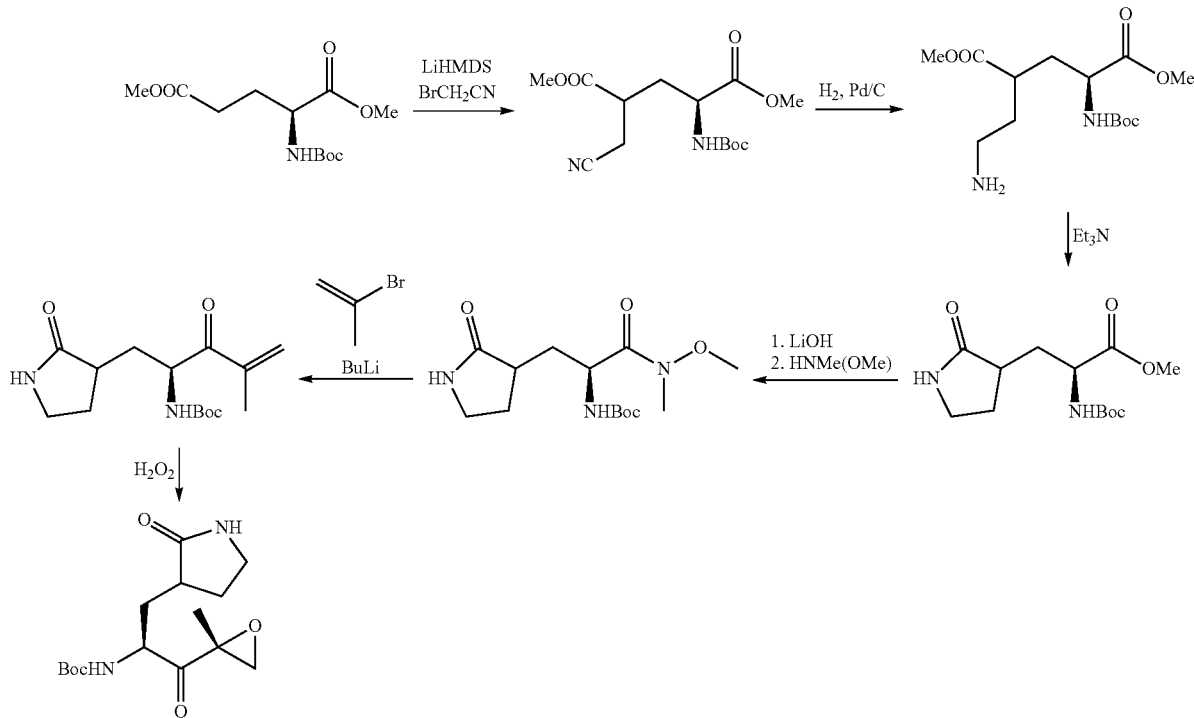

To a solution of Boc-Glu(OMe)-OMe (20.0 g, 72.6 mmol) in THF (50 mL) was added dropwise a solution of LiHMDS (26.3 g, 157 mmol) in THF (250 mL) at −78° C. under nitrogen atmosphere. The mixture was stirred at −78° C. for 1.5 h and bromoacetonitrile (13.0 g, 108 mmol) was added dropwise over 1 h while maintaining the temperature below −70° C. The reaction mixture was stirred at −78° C. for 2 h and quenched with pre-cooled methanol (10 mL) in one portion. The mixture was stirred for 10 min and then treated with a pre-cooled solution of acetic acid (9 mL) in THF (60 mL). The mixture was stirred for 10 min and poured into brine (200 mL). The resulting mixture was extracted with EtOAc (300 mL×2) and the combined extracts were dried over anhydrous sodium sulfate and concentrated under reduced pressure. The residue was purified by flash column chromatography on silica gel (heptanes/EtOAc=1:1) to afford (2S)-dimethyl 2-((tert-butoxycarbonyl)amino)-4-(cyanomethyl)pentanedioate (16.0 g, 70% yield) as a light brown oil.

To a solution of (2S)-dimethyl 2-((tert-butoxycarbonyl)amino)-4-(cyanomethyl)pentanedioate (10.0 g, 31.8 mmol) in AcOH (240 mL) was added 10% Pd/C (2.0 g) and the mixture was stirred under $H_2$ atmosphere (70 psi) for 3 h. The mixture was filtered through a pad of Celite and the filtrate was evaporated under reduced pressure. The residue was treated with MTBE and evaporated again to afford (4S)-dimethyl 2-(2-aminoethyl)-4-((tert-butoxycarbonyl)amino)pentanedioate (crude) as a light pink solid.

To a solution of (4S)-dimethyl 2-(2-aminoethyl)-4-((tert-butoxycarbonyl)amino)pentanedioate (crude) in THF (20 mL) was added $Et_3N$ (20 mL). The reaction mixture was stirred at 60° C. overnight and then cooled to ambient temperature. Water (50 mL) was added and the resulting mixture was extracted with methylene chloride (100 mL×2). The organic layers were combined, dried over anhydrous sodium sulfate, and concentrated under reduced pressure. The residue was purified by flash column chromatography on silica gel (heptanes/EtOAc=1:1) to afford (2S)-methyl 2-((tert-butoxycarbonyl)amino)-3-(2-oxopyrrolidin-3-yl)propanoate (5.5 g, 60% yield over two steps) as a light brown oil.

To a solution of (2S)-methyl 2-((tert-butoxycarbonyl)amino)-3-(2-oxopyrrolidin-3-yl)propanoate (5.5 g, 19 mmol) in methanol (50 mL) and water (25 mL) was added lithium hydroxide (1.6 g, 38 mmol). The mixture was stirred at ambient temperature for 1 h. The solution was diluted with water (50 mL) and washed with EtOAc (50 mL). The aqueous phase was adjusted to pH=2 with 0.1 N aqueous HCl and the resulting mixture was extracted with EtOAc (100 mL×2). The organic phases were combined, dried over anhydrous sodium sulfate, and concentrated to afford the corresponding acid (5.1 g, quantitative) as a yellow oil.

A mixture of dimethylhydroxylamine hydrochloride (1.14 g, 11.7 mmol), the acid (2.12 g, 7.80 mmol), EDCI (2.24 g, 11.7 mmol) and HOBt (1.58 g, 11.7 mmol) in DMF (10 mL) was cooled to 0° C. and triethylamine (3.0 mL, 23.3 mmol) was added. The reaction mixture was stirred at ambient temperature for 30 min and saturated aqueous sodium bicarbonate (50 mL) was added. The resulting mixture was extracted with EtOAc (50 mL×2). The combined extracts were dried over anhydrous sodium sulfate and concentrated under reduced pressure. The residue was purified by flash column chromatography on silica gel (petroleum ether/EtOAc=20:1) to afford tert-butyl ((2S)-1-(methoxy(methyl)amino)-1-oxo-3-(2-oxopyrrolidin-3-yl) propan-2-yl)carbamate (1.3 g, 53% yield) as a yellow oil.

n-BuLi (2.5 M, 3.17 mL, 7.9 mmol) was added dropwise to a solution of isopropenyl bromide (0.9 g, 8.3 mmol) in THF (15.0 mL) at −78° C. and the mixture was stirred at −78° C. for 30 min. A solution of tert-butyl ((2S)-1-(methoxy(methyl)amino)-1-oxo-3-(2-oxopyrrolidin-3-yl) propan-2-yl)carbamate (500 mg, 1.58 mmol) in THF (5.0 mL) was added dropwise. The reaction mixture was stirred at −78° C. for 3 h and then allowed to warm to ambient temperature and stirred for 12 h. Saturated aqueous $NH_4Cl$ (50 mL) was added and the resulting mixture was extracted with EtOAc (50 mL×2). The combined extracts were washed with brine, dried over anhydrous sodium sulfate, and concentrated. The residue was purified by flash column chromatography on silica gel (petroleum ether/EtOAc=20:1) to afford tert-butyl ((2S)-4-methyl-3-oxo-1-(2-oxopyrrolidin-3-yl)pent-4-en-2-yl)carbamate (200 mg, 42% yield) as a yellow oil.

To a solution of tert-butyl ((2S)-4-methyl-3-oxo-1-(2-oxopyrrolidin-3-yl)pent-4-en-2-yl)carbamate (200 mg, 0.67 mmol) in methanol (10 mL) at 0° C. was added 30% $H_2O_2$ (1.5 g, 1.4 mmol) followed by addition of benzonitrile (520 mg, 5.00 mmol) and DIPEA (0.87 mL, 5.0 mmol). The reaction mixture was stirred for 8 h at ambient temperature and then diluted with water (25 mL). The resulting mixture was extracted with EtOAc (50 mL×2). The combined extracts were washed with brine, dried over anhydrous sodium sulfate, and concentrated. The residue was purified by flash column chromatography on silica gel (heptanes/EtOAc=2:1) to afford tert-butyl ((S)-1-((R)-2-methyloxiran-2-yl)-1-oxo-3-(-2-oxopyrrolidin-3-yl) propan-2-yl)carbamate (95 mg, 45% yield) as a yellow oil.

Example 26 tert-Butyl ((2S)-3-(1-methyl-2-oxopyrrolidin-3-yl)-1-((R)-2-methyloxiran-2-yl)-1-oxopropan-2-yl)carbamate

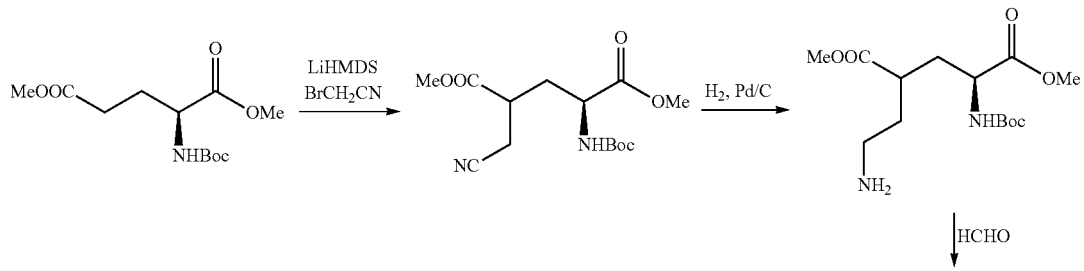

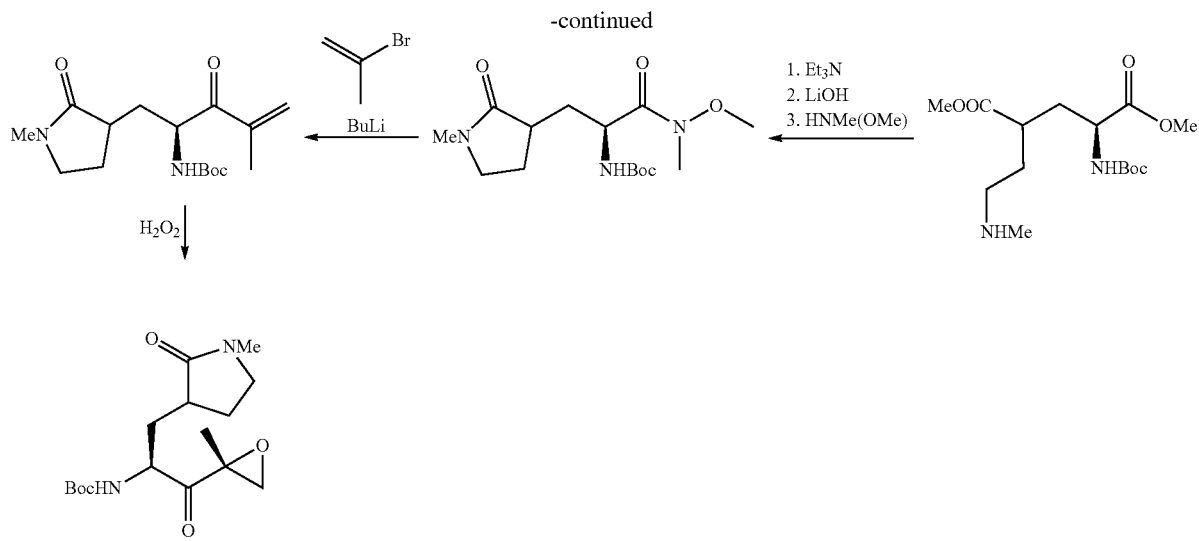

The synthesis of tert-butyl ((S)-3-((R)-1-methyl-2-oxopyrrolidin-3-yl)-1-((R)-2-methyloxiran-2-yl)-1-oxopropan-2-yl)carbamate was carried out in a similar manner to tert-butyl ((S)-1-((R)-2-methyloxiran-2-yl)-1-oxo-3-(-2-oxopyrrolidin-3-yl) propan-2-yl)carbamate.

The crude (4S)-dimethyl 2-(2-aminoethyl)-4-((tert-butoxycarbonyl)amino)pentanedioate (5.00 g, 15.7 mmol) was dissolved in methanol (100 mL) and 40% formaldehyde (1.0 g, 14 mmol) and Pd/C (0.8 g) were added. The mixture was stirred under H₂ atmosphere (20 psi) for 8 h at ambient temperature. The mixture was filtered through a pad of Celite and the filtrate was evaporated under reduced pressure to afford (2S)-dimethyl 2-((tert-butoxycarbonyl)amino)-4-(2-(methylamino)ethyl)pentane dioate (5.0 g, crude) as a dark brown oil.

Example 27

S)-2-Amino-3-((S)-3,3-difluorocyclopentyl)-1-((R)-2-methyloxiran-2-yl)propan-1-one and (S)-2-amino-3-((R)-3,3-difluorocyclopentyl)-1-((R)-2-methyloxiran-2-yl)propan-1-one

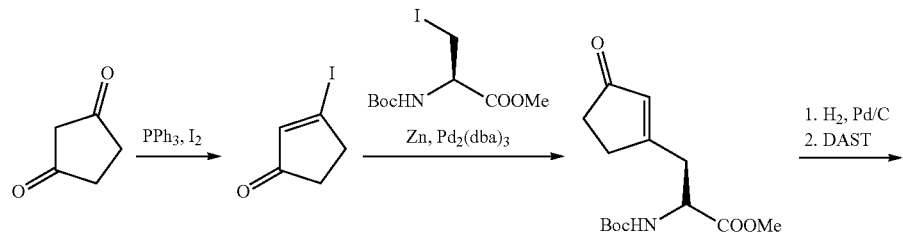

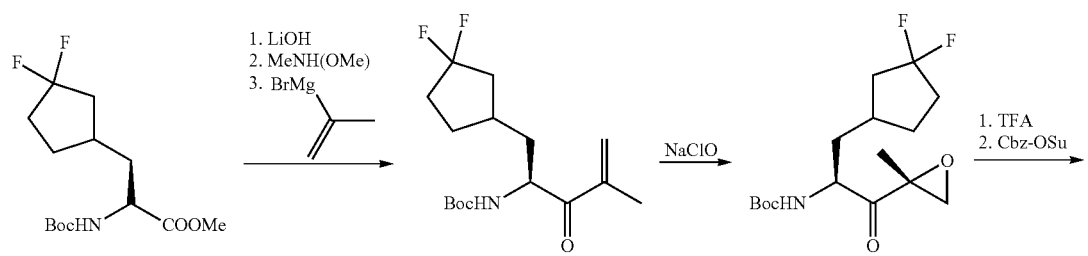

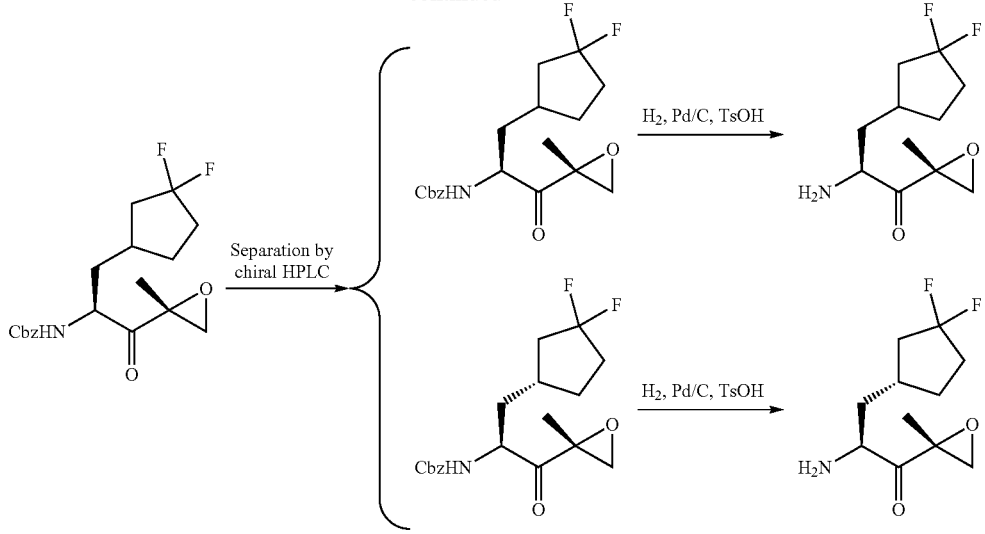

A mixture of iodine (121 g, 0.480 mol) and triphenylphosphine (135 g, 0.520 mol) in acetonitrile (600 mL) was stirred for 2 h at ambient temperature. Then cyclopentane-1,3-dione (39.2 g, 0.400 mol) and triethylamine (66.1 mL, 0.480 mol) were added. The reaction mixture was stirred overnight at 100° C. The mixture was cooled to ambient temperature and concentrated. The residue was purified by flash column chromatography on silica gel (petroleum ether/EtOAc=20:1 to 5:1) to afford 3-iodocyclopent-2-enone (56 g, 67% yield) as a colorless solid.

A solution of (R)-methyl 2-(tert-butoxycarbonylamino)-3-iodopropanoate (32.9 g, 0.100 mol) in DMF (20 mL) was added to a mixture of Zn (19.5 g, 0.300 mol) and iodine (6.6 g, 26 mmol) in DMF (30 mL) under nitrogen protection. The mixture was stirred for 1 h at ambient temperature. Then a solution of 3-iodocyclopent-2-enone (20.8 g, 0.100 mol) in DMF (50 mL), Pd$_2$(dba)$_3$ (2.3 g, 2.5 mmol) and S-Phos (2.1 g, 5.0 mmol) were added successively. The reaction mixture was stirred overnight at 50° C. The mixture was cooled to ambient temperature and water (100 mL) was added. The resulting mixture was extracted with EtOAc (150 mL×3). The combined organic extracts were dried over anhydrous sodium sulfate and concentrated. The residue was purified by flash column chromatography on silica gel (petroleum ether/EtOAc=5:1 to 2:1) to afford (S)-methyl 2-(tert-butoxycarbonylamino)-3-(3-oxocyclopent-1-enyl)propanoate (17 g, 60% yield) as a pale yellow oil.

A solution of (S)-methyl 2-(tert-butoxycarbonylamino)-3-(3-oxocyclopent-1-enyl)propanoate (23.0 g, 81.2 mmol) in methanol (100 mL) was hydrogenated in the presence of Pd/C (3.0 g) overnight at ambient temperature. Pd/C was filtered off and the filtrate was concentrated to give a colorless oil (22.0 g).

The crude cyclopentanone (22.0 g, 77.2 mmol) was dissolved in dichloromethane (100 mL) and DAST (37.3 g, 0.230 mol) was added. The reaction mixture was stirred for 2 d at ambient temperature and then poured into saturated aqueous sodium bicarbonate (100 mL). The two layers were separated and the aqueous layer was extracted with dichloromethane (100 mL×3). The organic extracts were combined, dried over anhydrous sodium sulfate, and concentrated. The residue was purified by flash column chromatography on silica gel (petroleum ether/EtOAc=30:1 to 10:1) to afford (2S)-methyl 2-(tert-butoxycarbonylamino)-3-(3,3-difluorocyclopentyl)propanoate (15 g, 63% yield) as a pale yellow oil.

LiOH—H$_2$O (6.2 g, 0.15 mol) was added to a mixture of (2S)-methyl 2-(tert-butoxycarbonylamino)-3-(3,3-difluorocyclopentyl)propanoate (15.0 g, 48.8 mmol) in water/THF (50 mL/50 mL). The reaction mixture was stirred for 1 h at ambient temperature. THF was removed and the remaining aqueous solution was acidified to pH=4-5 with 10% aqueous KHSO$_4$. The resulting mixture was extracted with EtOAc (100 mL×3). The organic extracts were combined, dried over anhydrous sodium sulfate, and concentrated to afford the corresponding acid (14.3 g) as a pale yellow oil, which was used directly without further purification.

The crude acid (14.3 g, 48.8 mmol) was dissolved in dichloromethane (100 mL) and N-methylmorpholine (4.93 g, 48.8 mmol) was added. The solution was cooled to 0° C. and isobutyl carbonochloridate (6.70 g, 48.8 mmol) was added dropwise. The mixture was stirred for 1 h at 0° C. followed by addition of a mixture of N,O-dimethylhydroxyl amine HCl salt (5.23 g, 53.7 mmol) and triethylamine (7.67 mL, 55.2 mmol) in dichloromethane (30 mL). The reaction mixture was stirred for 1 h at ambient temperature. The mixture was poured into water (150 mL) and the two phases were separated. The aqueous phase was extracted with EtOAc (100 mL×3). The organic phases were combined, dried over anhydrous sodium sulfate, and concentrated. The residue was purified by flash column chromatography on silica gel (petroleum ether/EtOAc=30:1 to 10:1) to afford the corresponding Weinreb amide (11.0 g) as a colorless oil.

The Weinreb amide (11.0 g, 32.7 mmol) was dissolved in THF (100 mL) and a solution of prop-1-en-2-ylmagnesium bromide (28.5 g, 0.200 mol) in THF (100 mL) was added at 0° C. The reaction mixture was stirred for 2 h at 0° C. and then 2 h at ambient temperature. The mixture was poured into 10% aqueous nitric acid (150 mL) and the resulting mixture was extracted with EtOAc (200 mL×3). The organic extracts were combined, dried over anhydrous sodium sulfate, and concentrated. The residue was purified by flash column chromatography on silica gel (petroleum ether/EtOAc=30:1 to 10:1) to afford tert-butyl (2R)-1-(3,3-difluorocyclopentyl)-4-methyl-3-oxopent-4-en-2-yl carbamate (4.5 g, 29% yield over three steps).

Aqueous NaClO (10%, 70.6 g, 94.6 mmol) was added dropwise to a solution of tert-Butyl (2R)-1-(3,3-difluorocyclopentyl)-4-methyl-3-oxopent-4-en-2-yl carbamate (5.00 g, 15.8 mmol) in DMF (20 mL) at −20° C. while maintaining the internal temperature below −10° C. The reaction mixture was stirred for 2 h at 0° C. and then overnight at ambient temperature. The mixture was poured into water (100 mL) and the resulting mixture was extracted with EtOAc (150 mL×3). The organic extracts were combined, dried over anhydrous sodium sulfate, and concentrated. The residue was purified by flash column chromatography on silica gel (petroleum ether/EtOAc=30:1 to 10:1) to afford tert-butyl (2S)-3-(3,3-difluorocyclopentyl)-1-((R)-2-methyloxiran-2-yl)-1-oxo propan-2-ylcarbamate (2.5 g, 48% yield).

TFA (1.71 g, 15.0 mmol) was added to a solution of tert-butyl (2S)-3-(3,3-difluorocyclopentyl)-1-((R)-2-methyloxiran-2-yl)-1-oxo propan-2-ylcarbamate (2.5 g, 7.5 mmol) in dichloromethane (10 mL). The reaction mixture was stirred for 2 h at ambient temperature and then concentrated to afford the amine (quantitative).

The amine (TFA salt, 7.5 mmol) was dissolved in 1,4-dioxane (30 mL) and then neutralized with saturated aqueous sodium bicarbonate to pH=8 at 0° C. Cbz-OSu (2.24 g, 9.0 mmol) was added and the reaction mixture was stirred for 3 h at ambient temperature. The mixture was extracted with EtOAc (50 mL×3). The organic extracts were combined, dried over anhydrous sodium sulfate, and concentrated. The residue was purified by flash column chromatography on silica gel (petroleum ether/EtOAc=30:1 to 10:1) to afford a mixture of diastereomers (2.4 g, 69% yield), which was further separated by chiral prep-HPLC to afford pure benzyl (S)-3-((S)-3,3-difluorocyclopentyl)-1-((R)-2-methyloxiran-2-yl)-1-oxo propan-2-ylcarbamate (1.1 g) and benzyl (S)-3-((R)-3,3-difluorocyclopentyl)-1-((R)-2-methyloxiran-2-yl)-1-oxo propan-2-ylcarbamate (0.7 g), respectively.

Benzyl (S)-3-((S)-3,3-difluorocyclopentyl)-1-((R)-2-methyloxiran-2-yl)-1-oxo propan-2-ylcarbamate (200 mg, 0.550 mmol) was hydrogenated in the presence of Pd/C (0.1 g) and p-TsOH-H$_2$O (104 mg, 0.550 mmol) in methanol (6 mL) for 1 h at 0-5° C. Pd/C was filtered off and then the filtrate was concentrated to dryness to provide (S)-2-amino-3-((S)-3,3-difluorocyclopentyl)-1-((R)-2-methyloxiran-2-yl)propan-1-one which was used immediately.

(S)-2-amino-3-((R)-3,3-difluorocyclopentyl)-1-((R)-2-methyloxiran-2-yl)propan-1-one was synthesized in a similar manner.

Example 28 tert-Butyl ((S)-3-((1r,4S)-4-((4-methoxybenzyl)oxy)cyclohexyl)-1-((R)-2-methyloxiran-2-yl)-1-oxopropan-2-yl)carbamate

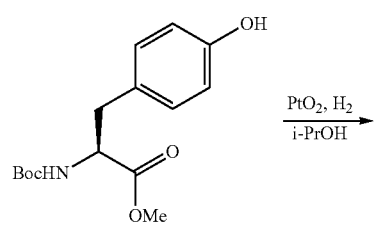

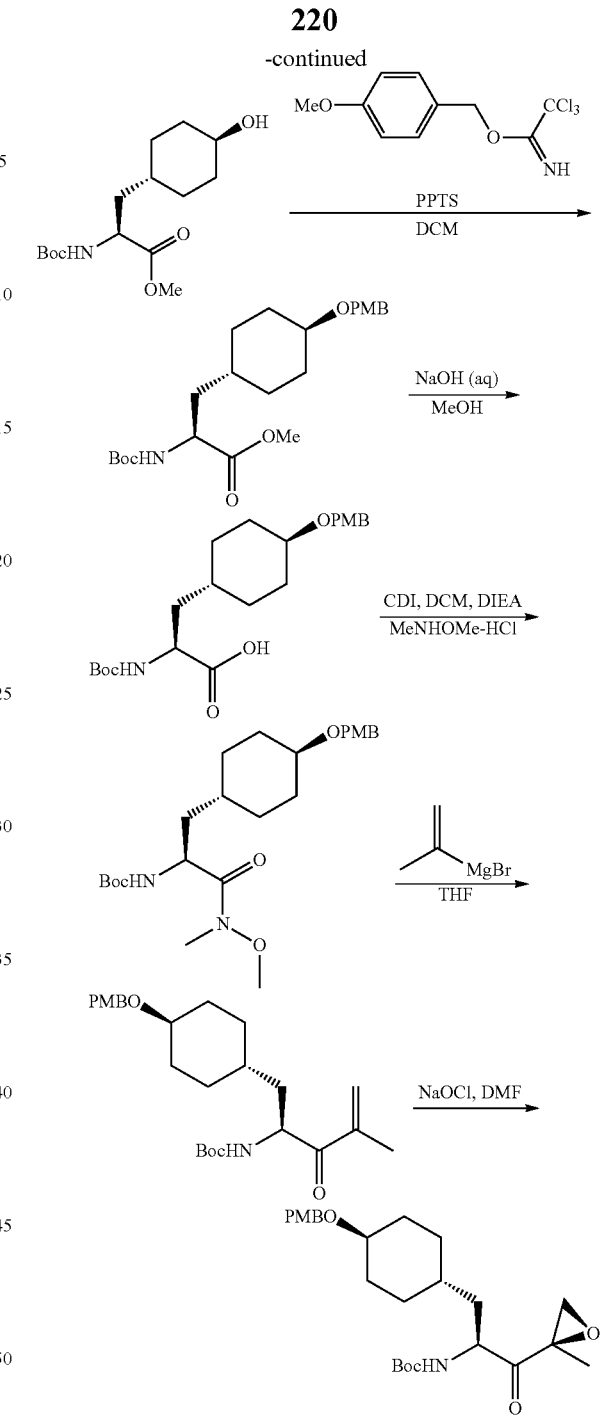

A mixture of (S)-methyl 2-((tert-butoxycarbonyl)amino)-3-(4-hydroxyphenyl)propanoate (15.0 g, 64.0 mmol), acetic acid (322 uL, 5.59 mmol), and platinum oxide (1.29 g, 5.66 mmol) in isopropanol (322 mL) in a Parr shaker jar was hydrogenated with hydrogen (60 psi) for 2 h. The mixture was filtered through a pad of Celite and concentrated. Purification by column chromatography (1:1 hexanes/EtOAc) provided a mixture of cis/trans isomers (33.0 g) that was recrystallized from EtOAc to provide -cis alcohol (S)-methyl 2-((tert-butoxycarbonyl)amino)-3-((1s,4R)-4-hydroxycyclohexyl)propanoate (1.93 g, 10%, 90% purity) as a colorless solid, -trans alcohol (S)-methyl 2-((tert-butoxycarbonyl)amino)-3-((1r,4S)-4-hydroxycyclohexyl)propanoate (1.41 mg, 7%, 85% purity) as clear oil, and over-reduced (S)-methyl 2-((tert-butoxycarbonyl)amino)-3-cyclohexyl-propanoate (10.3 g, 56%). The enriched isomer was used in the subsequent reaction without further purification.

A solution of (S)-methyl 2-((tert-butoxycarbonyl)amino)-3-((1r,4S)-4-hydroxycyclohexyl)propanoate (20.0 g, 66.5 mmol) in dichloromethane (200 mL) at 0° C. was added 2,2,2-trichloro-acetimidic acid 4-methoxy-benzyl ester (28.0 g, 99.7 mmol) and PPTS (1.67 g, 6.65 mmol). The reaction mixture was allowed to warm to ambient temperature over 24 h. Dichloromethane (200 mL) was added and the organic layers were washed with sodium bicarbonate (sat.), water, brine, and dried over sodium sulfate, filtered, and concentrated. Purification by column chromatography provided (S)-methyl 2-((tert-butoxycarbonyl)amino)-3-((1r,4S)-4-((4-methoxybenzyl)oxy)cyclohexyl)propanoate (23.0 g, 82%) as a colorless oil. $^1$H NMR (300 MHz, CDCl$_3$) δ 7.26 (d, J=8.7 Hz, 1H), 6.87 (d, J=8.7 Hz, 1H), 4.88 (d, J=8.1 Hz, 1H), 4.47 (s, 2H), 4.33 (m, 1H), 3.80 (s, 3H), 3.75 (s, 3H), 3.26 (m, 1H), 2.08 (m, 2H), 1.90 (m, 2H), 1.74-1.15 (m, 5H), 1.43 (s, 9H), 0.89 (m, 2H). MS (EI) for $C_{23}H_{35}NO_6$, found 444.2 [M+Na]$^+$.

To a solution of (S)-methyl 2-((tert-butoxycarbonyl)amino)-3-((1r,4S)-4-((4-methoxybenzyl)oxy)cyclohexyl)propanoate (15.0 g, 35.6 mmol) in MeOH (150 mL) at 0° C. was added NaOH (aq, 1 M, 71.2 mL, 71.2 mmol). The mixture was stirred at ambient temperature for 4 h. After removal of the solvent, the residue was diluted with dichloromethane (200 mL) and the solution was adjusted with HCl (1M) to pH 2-3. The organic layer was washed with water and brine, dried over sodium sulfate, filtered, and concentrated. Purification by column chromatography provided (S)-2-((tert-butoxycarbonyl)amino)-3-((1r,4S)-4-((4-methoxybenzyl)oxy)cyclohexyl)propanoic acid (12.5 g, 86%).

To a solution of (S)-2-((tert-butoxycarbonyl)amino)-3-((1r,4S)-4-((4-methoxybenzyl)oxy)cyclohexyl)propanoic acid (12.5 g, 30.7 mmol) in DCM (150 mL) at 0° C. was added carbonyl diimidazole (6.48 g, 40.0 mmol) and the mixture was stirred at 0° C. for 0.5 h. To the solution was added dimethylhydroxylamine hydrochloride (5.99 g, 61.4 mmol) and DIEA (7.90 g, 61.4 mmol). The mixture was allowed to warm to ambient temperature and stirred for 20 h. The organic layer was washed with water, 0.2 N HCl, sodium bicarbonate (sat.), water, brine, and dried over sodium sulfate. The organic layers were combined, filtered, and concentrated. Purification by column chromatography provided tert-butyl ((S)-1-(methoxy(methyl)amino)-3-((1r,4S)-4-((4-methoxybenzyl)oxy)cyclohexyl)-1-oxopropan-2-yl)carbamate (8.9 g, 64%).

To a solution of tert-butyl ((S)-1-(methoxy(methyl)amino)-3-((1r,4S)-4-((4-methoxybenzyl)oxy)cyclohexyl)-1-oxopropan-2-yl)carbamate (8.9 g, 19.8 mmol) in THF (50 mL) was added 2-propenylmagnesium bromide (0.5 M, 118 mL, 59.3 mmol) dropwise over 1 h. The mixture was stirred at −20° C. for 2 d then allowed to warm to ambient temperature. The mixture was stirred for an additional 2 h then poured into saturated aqueous NH$_4$Cl (400 mL) and stirred for 1 h. EtOAc (200 mL) was added and the mixture was adjusted with HCl (6 N) to pH 2-3. The organic layer was washed with water and brine, and dried over sodium sulfate. The solution was filtered, concentrated, and purified by silica gel column chromatography to provide tert-butyl ((S)-1-((1r,4S)-4-((4-methoxybenzyl)oxy)cyclohexyl)-4-methyl-3-oxopent-4-en-2-yl)carbamate (7.4 g, 87%).

To a solution of tert-butyl ((S)-1-((1r,4S)-4-((4-methoxybenzyl)oxy)cyclohexyl)-4-methyl-3-oxopent-4-en-2-yl)carbamate (7.40 g, 17.2 mmol, 1.0 eq) in DMF (130 mL) at −10° C. was added NaOCl (6% w/w, 42.6 mL, 34.4 mmol) at a rate to maintain an internal temperature below ≤−10° C. The mixture was stirred at 0° C. for 7 h then diluted with EtOAc (150 mL) and water (150 mL), and extracted with EtOAc (2×). The organic layers were washed with water and brine, dried over sodium sulfate, filtered, and concentrated. The crude residue was purified by column chromatography to provide tert-butyl ((S)-3-((1r,4S)-4-((4-methoxybenzyl)oxy)cyclohexyl)-1-((R)-2-methyloxiran-2-yl)-1-oxopropan-2-yl)carbamate (3.12 g, 41%). $^1$H NMR (300 MHz, CDCl$_3$) δ 7.27 (d, J=6.9 Hz, 1H), 6.87 (d, J=6.9 Hz, 1H), 4.84 (d, J=9.0 Hz, 1H), 4.47 (s, 2H), 4.31 (m, 1H), 3.79 (s, 3H), 3.27-3.25 (m, 2H), 2.88 (d, J=5.1 Hz, 1H), 2.11-1.84 (m, 3H), 1.72-1.65 (m, 2H), 1.51 (s, 3H), 1.48 (s, 9H), 1.50-0.98 (m, 6H). MS (EI) for $C_{25}H_{37}NO_6$, found 470.2 [M+Na]$^+$.

Example 29 tert-Butyl ((S)-3-cyclohexyl-1-((R)-2-methyloxiran-2-yl)-1-oxopropan-2-yl)carbamate

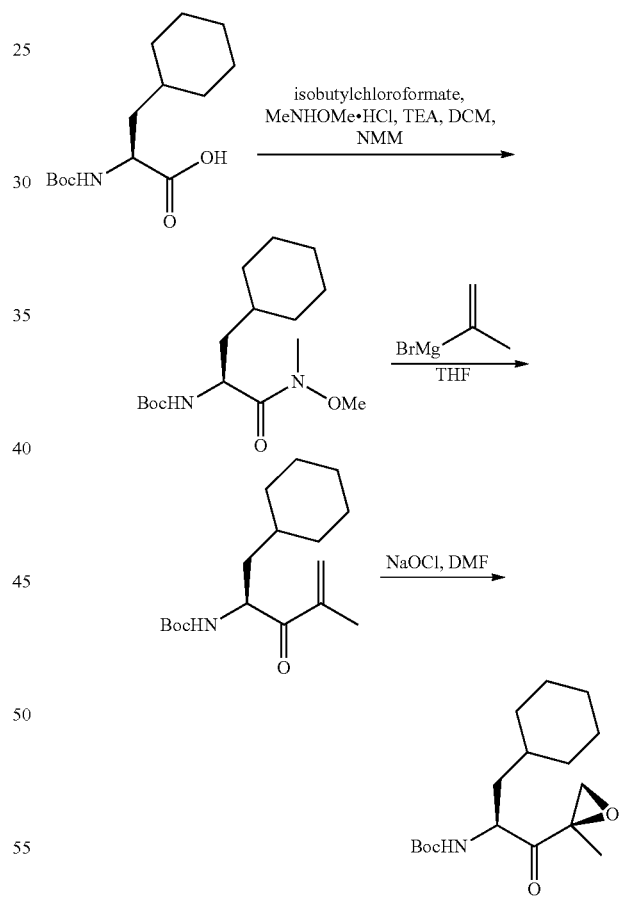

To a solution of dimethylhydroxylamine hydrochloride (3.98 g, 40.6 mmol) in DCM (50 mL) at 0° C. was added triethylamine (5.43 mL, 41.9 mmol). In a separate flask (S)-2-((tert-butoxycarbonyl)amino)-3-cyclohexylpropanoic acid (10.0 g, 36.9 mmol) in DCM (50 mL) and THF (50 mL) was cooled to 0° C. and isobutylchloroformate (4.83 mL, 36.9 mmol) was added followed by N-methylmorpholine (4.06 mL, 36.9 mmol). After 1 h it was added to the dimethylhydroxylamine mixture. The combined mixture was allowed to warm to ambient temperature over 16 h at which time it was quenched with water, washed with sodium bicarbonate (sat.), extracted with EtOAc (2×), washed with brine, dried with sodium sulfate, filtered, and concentrated. (S)-tert-Butyl (3-cyclohexyl-1-(methoxy(methyl)amino)-1-oxopropan-2-yl)carbamate (12.2 g) was provided as a colorless oil that was carried forward without further purification. MS (EI) for $C_{16}H_{30}N_2O_4$, found 215.3 [M-Boc]$^+$.

To (S)-tert-butyl (3-cyclohexyl-1-(methoxy(methyl) amino)-1-oxopropan-2-yl)carbamate (12.2 g, 38.9 mmol) in THF (150 mL) at 0° C. was added isopropenylmagnesium bromide (71.2 mL of a 1.5 N solution in methyl-THF, 0.107 mol) dropwise. After stirring at 0° C. for 2 h the mixture was quenched with heptane/citric acid (1:1). The product was extracted with EtOAc (2×), washed with brine, dried with sodium sulfate, filtered, and concentrated. The crude product was triturated from cold (0° C.) methanol to provide (S)-tert-butyl (1-cyclohexyl-4-methyl-3-oxopent-4-en-2-yl)carbamate (5.36 g, 49%) as a colorless crystalline solid. MS (EI) for $C_{17}H_{29}NO_3$, found 196.2 [M-Boc]$^+$.

To (S)-tert-butyl (1-cyclohexyl-4-methyl-3-oxopent-4-en-2-yl)carbamate (5.36 g, 18.1 mmol) in DMF at −10° C. was added NaOCl (47.1 mL of a 9.5% w/w solution, 36.2 mmol). Addition of NaOCl was performed at a rate to maintain an internal temperature of ≤−10° C. After the addition was complete the reaction mixture was transferred to an ice bath and stirred for an additional 2 h at which time it was diluted with water and EtOAc, extracted with EtOAc (2×), washed with brine, dried with sodium sulfate, filtered, and concentrated. Purification by column chromatography (3:1 heptane/EtOAc) provided tert-butyl ((S)-3-cyclohexyl-1-((R)-2-methyloxiran-2-yl)-1-oxopropan-2-yl)carbamate (3.68 g, 65%) as a colorless amorphous solid. MS (EI) for $C_{17}H_{29}NO_4$, found 310.2 (MH$^-$).

The following compounds were synthesized in a similar manner:

tert-butyl ((S)-3-cyclopropyl-1-((R)-2-methyloxiran-2-yl)-1-oxopropan-2-yl)carbamate tert-butyl ((S)-3-cyclobutyl-1-((R)-2-methyloxiran-2-yl)-1-oxopropan-2-yl)carbamate Example 30 tert-Butyl ((S)-3-cyclopentyl-1-((R)-oxiran-2-yl)-1-oxopropan-2-yl)carbamate

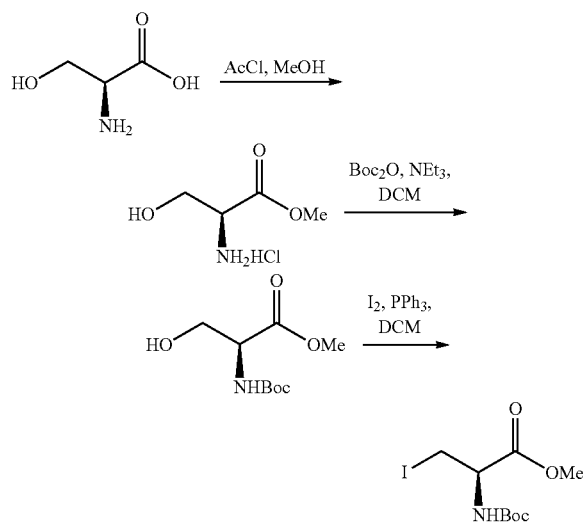

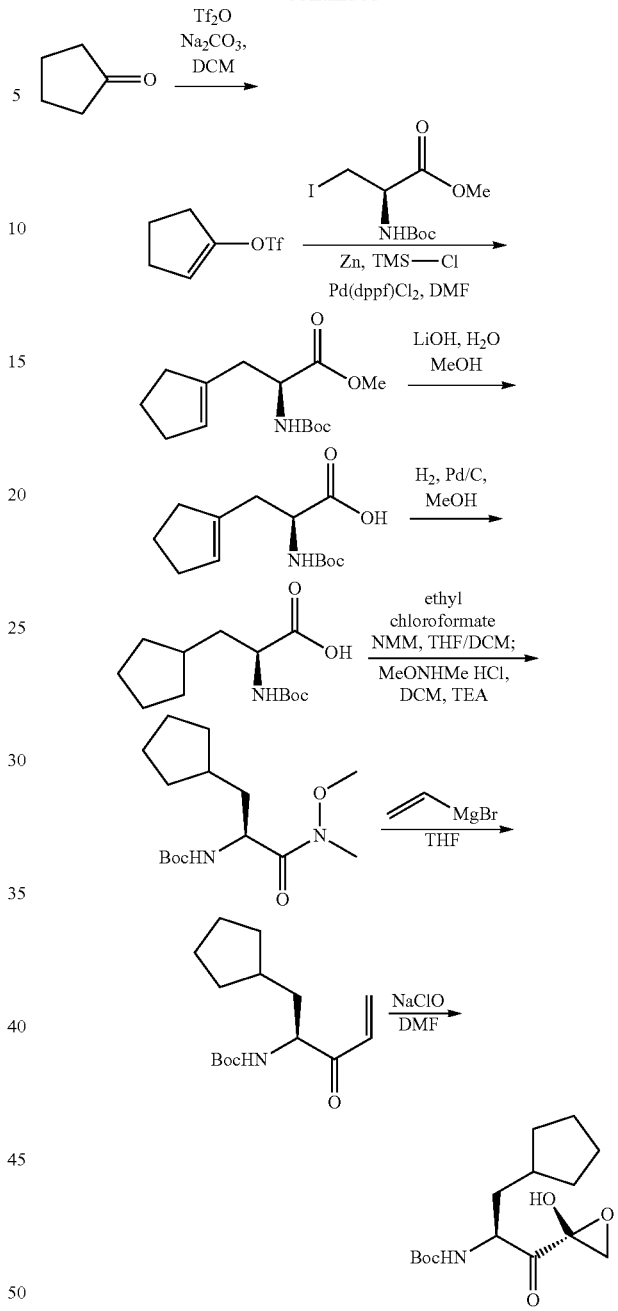

Methanol (450 mL) in a round-bottom flask was cooled to 0° C. and acetyl chloride (55 mL, 0.77 mol) was added dropwise. After completion of the addition, the mixture was stirred at ambient temperature for 10 min and H-Ser-OH (30 g, 0.29 mol) was added in three portions. The reaction mixture was heated at 80° C. for 2 h and then concentrated. The residue was dried under vacuum to afford (S)-methyl 2-amino-3-hydroxypropanoate hydrochloride (quantitative) as a colorless solid, which was used in the next step without further purification.

The crude (S)-methyl 2-amino-3-hydroxypropanoate hydrochloride (0.29 mol) was suspended in DCM (200 mL) and to this mixture was added triethylamine (79 mL, 0.57 mol) and Boc$_2$O (68 g, 0.31 mol) at 0° C. The cooling bath was removed and the reaction mixture was stirred at ambient temperature overnight and then diluted with MTBE (300 mL). The mixture was filtered and the filtrate was concentrated under reduced pressure. The residue was purified by flash column chromatography on silica gel to afford (S)-methyl 2-((tert-butoxycarbonyl)amino)-3-hydroxypropanoate (60 g, 94% yield) as a colorless oil.

A mixture of triphenylphosphine (131 g, 0.500 mol) and imidazole (34 g, 0.50 mol) in DCM (600 mL) was cooled to 0° C. and iodide (127 g, 0.50 mol) was added in small portions over 0.5 h. The cooling bath was removed and the mixture was stirred for 0.5 h. After the mixture was re-cooled to 0° C., a solution of (S)-methyl 2-((tert-butoxycarbonyl)amino)-3-hydroxypropanoate (73 g, 0.33 mol) in DCM (300 mL) was added dropwise. After the addition, the cooling bath was removed and the mixture was allowed to warm to ambient temperature and stirred for 1.5 h. The mixture was filtered and the filtrate was concentrated to remove most of the solvent. MTBE (400 mL) was added to the residue and the mixture was filtered to remove triphenylphosphine oxide. The filtrate was concentrated and the residue was purified by flash column chromatography on silica gel to afford (R)-methyl 2-((tert-butoxycarbonyl)amino)-3-iodopropanoate (74.0 g, 68% yield) as a colorless solid.

The synthesis of cyclopent-1-en-1-yl trifluoromethanesulfonate was described in the procedure for tert-Butyl ((S)-3-(cyclopent-1-en-1-yl)-1-((R)-2-methyloxiran-2-yl)-1-oxopropan-2-yl)carbamate To a suspension of zinc (123 g, 1.90 mol) in DMF (500 mL) was added TMSCl (46 mL) dropwise. The mixture was stirred at ambient temperature for 45 min. The upper clear liquid was drained out and the residue was washed with DMF (2×200 mL). The resulting solid was re-suspended in DMF (200 mL) and the mixture was cooled to 0° C. A solution of (R)-methyl 2-((tert-butoxycarbonyl)amino)-3-iodopropanoate (104 g, 0.320 mol) in DMF (300 mL) was added. The mixture was stirred at 0° C. under nitrogen for 20 min. The upper clear liquid was drained out and added dropwise to a solution of cyclopent-1-en-1-yl trifluoromethanesulfonate (90 g, 0.37 mol) and Pd(dppf)Cl$_2$ (3.9 g, 4.7 mmol) in DMF (500 mL). After addition, the reaction mixture was stirred at 50° C. under nitrogen overnight then cooled to ambient temperature. Brine (500 mL) was added and the resulting mixture was extracted with MTBE (3×300 mL). The organic layers were combined, washed with brine, and concentrated. The residue was purified by flash column chromatography on silica gel (petroleum ether/EtOAc=100:1 to 40:1) to afford (S)-methyl 2-((tert-butoxycarbonyl)amino)-3-(cyclopent-1-en-1-yl)propanoate as a viscous oil (62 g, 72% yield).

To a solution of (S)-methyl 2-((tert-butoxycarbonyl)amino)-3-(cyclopent-1-en-1-yl)propanoate (62 g, 0.23 mol) in water/methanol (900 mL, 2:1) was added lithium hydroxide hydrate (19.3 g, 0.460 mol). The reaction mixture was stirred at ambient temperature overnight and then concentrated to remove most of the methanol. The residue was washed with DCM (400 mL) and the aqueous phase was acidified with dilute HCl to pH=3-4. The resulting mixture was extracted with DCM (3×300 mL). The organic layers were combined and concentrated to afford (S)-2-((tert-butoxycarbonyl)amino)-3-(cyclopent-1-en-1-yl)propanoic acid (56 g, 95% yield) as viscous oil, which was used in the next step without further purification.

To a solution of (S)-2-((tert-butoxycarbonyl)amino)-3-(cyclopent-1-en-1-yl)propanoic acid (56 g, 0.22 mol) in methanol (500 mL) was added Pd/C (23 g, 0.022 mol, 10%). The mixture was stirred under a hydrogen atmosphere (1 atm) at ambient temperature overnight and then filtered through a pad of celite. The filtrate was concentrated under reduced pressure to afford (S)-2-((tert-butoxycarbonyl)amino)-3-cyclopentylpropanoic acid (55 g, 97% yield) as viscous oil, which was used in the next step without further purification.

To a flask charged with compound (S)-2-((tert-butoxycarbonyl)amino)-3-cyclopentylpropanoic acid (55.0 g, 214 mmol) was added THF/DCM (800 mL, 1:1). The solution was cooled to 0° C. and ethyl chloroformate (24.5 mL, 257 mmol) and NMM (28.4 mL, 257 mmol) was added dropwise sequentially. After addition, the mixture was stirred at 0° C. under nitrogen for 1 h. To the other flask charged with N,O-dimethylhydroxylamine HCl (25.0 g, 257 mmol) was added DCM (400 mL). The mixture was cooled to 0° C. and TEA (38.7 mL, 278 mmol) was added. The resulting mixture was transferred into the former reaction flask. The reaction mixture was allowed to warm to ambient temperature and stirred overnight. The reaction was then quenched with water (500 mL) and the two phases were separated. The organic phase was washed with water (500 mL), dried over anhydrous sodium sulfate, and concentrated to afford (S)-tert-butyl (3-cyclopentyl-1-(methoxy(methyl)amino)-1-oxopropan-2-yl)carbamate as colorless oil (60 g, 93% yield), which was used in the next step without further purification.

To a solution of (S)-tert-butyl (3-cyclopentyl-1-(methoxy(methyl)amino)-1-oxopropan-2-yl)carbamate (2.5 g, 8.3 mmol) in THF (35 mL) was added vinylmagnesium bromide (16.7 mL, 33.3 mol) at 0° C. dropwise. After completion of the addition, the reaction mixture was stirred at 0° C. for 2 h and then quenched with saturated aqueous ammonium chloride (30 mL). The resulting mixture was extracted with EtOAc (2×40 mL). The organic layers were combined, dried over anhydrous sodium sulfate, and concentrated. The residue was purified by flash column chromatography on silica gel (petroleum ether/EtOAc=100:1) to afford (S)-tert-butyl (1-cyclopentyl-3-oxopent-4-en-2-yl)carbamate as a yellow oil (854 mg, 38% yield).

A solution of (S)-tert-butyl (1-cyclopentyl-3-oxopent-4-en-2-yl)carbamate (854 mg, 3.20 mmol) in DMF (70 mL) was cooled to −20° C. and a bleach solution (9.50 mL, 12.8 mmol, 10% active spice) was added dropwise under nitrogen. The reaction mixture was warmed to 0° C. and stirred for 1.5 h. Water (70 mL) was added and the mixture was extracted with EtOAc (2×50 mL). The organic phases were combined, washed with brine (2×50 mL), dried over anhydrous sodium sulfate, and concentrated. The residue was purified by flash column chromatography on silica gel (petroleum ether/EtOAc=80:1) to afford tert-butyl ((S)-3-cyclopentyl-1-((R)-oxiran-2-yl)-1-oxopropan-2-yl)carbamate as a viscous oil (390 mg, contaminated with some impurities, 43% yield) as a yellow oil.

Example 31 tert-Butyl ((S)-3-(cyclopent-1-en-1-yl)-1-((R)-2-methyloxiran-2-yl)-1-oxopropan-2-yl)carbamate

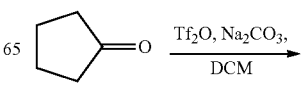

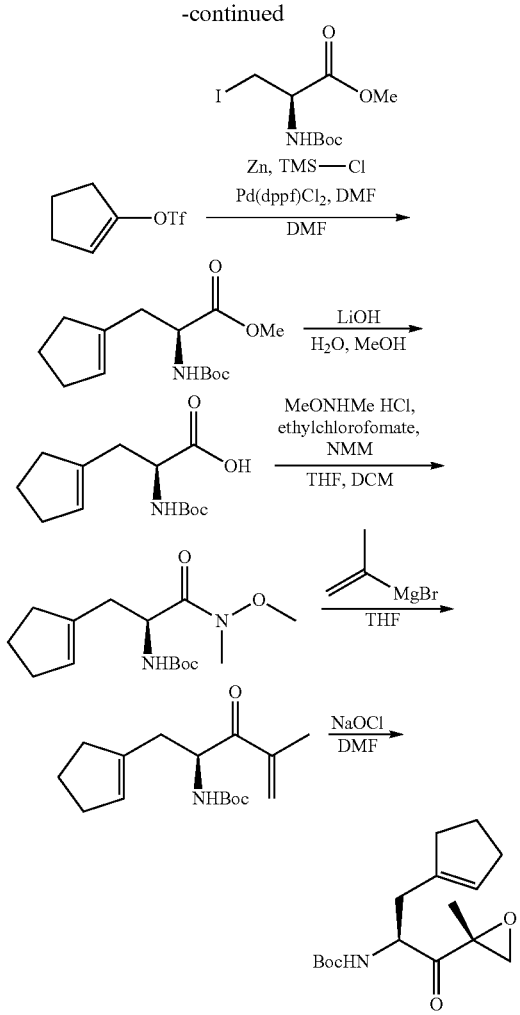

To a solution of cyclopentanone (55 g, 0.66 mol) in DCM (1.3 L) was added Na$_2$CO$_3$ (104 g, 0.980 mol) and the mixture was cooled to −20° C. Trifluoromethanesulfonic anhydride (121 mL, 0.720 mol) was added dropwise. After the addition, the cooling bath was removed and the reaction mixture was stirred at ambient temperature overnight. GC-MS analysis showed the reaction was not complete and additional trifluoromethane sulfonic anhydride (33 mL, 0.20 mol) was added. The reaction mixture was stirred for another 4 h then quenched with water (800 mL). The aqueous phase was extracted with DCM (300 mL). The organics were combined, washed with brine, and concentrated to afford cyclopentenyltrifluoromethanesulfonate as viscous oil (104 g, 73% yield), which was used in the next step without further purification.

To a suspension of zinc (123 g, 1.90 mol) in DMF (500 mL) was added TMSCl (46 mL) dropwise. The mixture was stirred at ambient temperature for 45 min. The upper clear liquid was removed and the residue was washed with DMF (200 mL×2). The resulting solid was re-suspended in DMF (200 mL) and the mixture was cooled to 0° C. A solution of (R)-methyl 2-((tert-butoxycarbonyl)amino)-3-iodopropanoate (104 g, 0.320 mol) in DMF (300 mL) was added. The mixture was stirred at 0° C. under nitrogen for 20 min. The upper clear liquid was removed and added to a solution of cyclopent-1-en-1-yl trifluoromethanesulfonate (90 g, 0.37 mol) and Pd(dppf)Cl$_2$ (3.9 g, 4.7 mmol) in DMF (500 mL) dropwise. After addition, the reaction mixture was stirred at 50° C. under nitrogen overnight then cooled to ambient temperature. Brine (500 mL) was added and the resulting mixture was extracted with MTBE (300 mL×3). The organics were combined, washed with brine, and concentrated. The residue was purified by flash column chromatography on silica gel (petroleum ether/EtOAc=100:1 to 40:1) to afford (S)-Methyl 2-(tert-butoxycarbonylamino)-3-cyclopentenylpropanoate as viscous oil (62 g, 72% yield). $^1$H NMR (300 MHz, CDCl$_3$): δ 5.48 (br s, 1H), 4.97 (d, J=6.6 Hz, 1H), 4.40-4.43 (m, 1H), 3.74 (s, 3H), 2.46-2.63 (m, 2H), 2.23-2.34 (m, 4H), 1.82-1.93 (m, 2H), 1.45 (s, 9H).

To a solution of (S)-methyl 2-(tert-butoxycarbonylamino)-3-cyclopentenylpropanoate (62 g, 0.23 mol) in water/methanol (900 mL, 2:1) was added lithium hydroxide hydrate (19.3 g, 0.460 mol). The reaction mixture was stirred at ambient temperature overnight and then concentrated to remove the majority of methanol. The residue was washed with DCM (400 mL) and the aqueous phase was acidified with diluted HCl to pH=3-4. The resulting mixture was extracted with DCM (300 mL×3). The organic layers were combined and concentrated to afford (S)-2-(tert-Butoxycarbonylamino)-3-cyclopentenylpropanoic acid (56 g, 95% yield) as viscous oil, which was used in the next step without further purification. $^1$H NMR (300 MHz, CDCl$_3$): δ 10.47 (br. s, 1H), 5.52 (br. s, 1H), 4.98 (d, J=8.1 Hz, 1H), 4.40-4.44 (m, 1H), 2.50-2.70 (m, 2H), 2.25-2.34 (m, 4H), 1.79-1.93 (m, 2H), 1.45 (s, 9H).

To a flask charged with (S)-2-(tert-Butoxycarbonylamino)-3-cyclopentenylpropanoic acid (55.0 g, 214 mmol) was added THF/DCM (800 mL, 1:1). The solution was cooled to 0° C. and ethyl chloroformate (24.5 mL, 257 mmol) and NMM (28.4 mL, 257 mmol) were added dropwise sequentially. After addition, the mixture was stirred at 0° C. under nitrogen for 1 h. To the other flask charged with N,O-dimethylhydroxylamine HCl (25 g, 257 mmol) was added DCM (400 mL). The mixture was cooled to 0° C. and TEA (38.7 mL, 278 mmol) was added. The resulting mixture was transferred into the former reaction flask. The reaction mixture was allowed to warm to ambient temperature and stirred overnight. The mixture was quenched with water (500 mL) and the organic phase was washed with water (500 mL), dried over anhydrous sodium sulfate, and concentrated to afford (S)-tert-butyl (3-(cyclopent-1-en-1-yl)-1-(methoxy(methyl)amino)-1-oxopropan-2-yl)carbamate as colorless oil (60 g, 93% yield), which was used in the next step without further purification.

To a solution of (S)-tert-butyl (3-(cyclopent-1-en-1-yl)-1-(methoxy(methyl)amino)-1-oxopropan-2-yl)carbamate (81 g, 0.27 mol) in THF (600 mL) was added freshly prepared prop-1-en-2-ylmagnesium bromide (96.0 mL, 1.08 mol) at 0° C. dropwise. After completion of the addition, the reaction mixture was stirred at 0° C. for 2 h then quenched with saturated aqueous ammonium chloride (500 mL). The resulting mixture was extracted with EtOAc (400 mL×2). The organic phases were combined, dried over anhydrous sodium sulfate, and concentrated. The residue was purified by flash column chromatography on silica gel (petroleum ether/EtOAc=100:1) to afford (S)-tert-butyl (1-(cyclopent-1-en-1-yl)-4-methyl-3-oxopent-4-en-2-yl)carbamate as colorless oil (39.3 g, 52% yield).

A solution of (S)-tert-butyl (1-(cyclopent-1-en-1-yl)-4-methyl-3-oxopent-4-en-2-yl)carbamate (10.0 g, 35.6 mmol) in DMF (180 mL) was cooled to −20° C. and bleach (54.0 mL, 71.2 mmol, 10%) was added dropwise under nitrogen. The reaction mixture was warmed to 0° C. and stirred for 1.5 h. Water (200 mL) was added and the mixture was extracted with EtOAc (200 mL×2). The organic phases were combined, washed with brine (200 mL×2), dried over anhydrous sodium sulfate, and concentrated. The residue was purified by flash column chromatography on silica gel to afford tert-butyl ((S)-3-(cyclopent-1-en-1-yl)-1-((R)-2-methyloxiran-2-yl)-1-oxopropan-2-yl)carbamate as viscous oil (5.6 g, 53% yield). $^1$H NMR (300 MHz, CDCl$_3$): δ 4.62 (s, 1H), 4.91 (d, J=7.5 Hz, 1H), 4.44-4.37 (m, 1H), 3.29 (d, J=4.8 Hz, 1H), 2.89 (d, J=4.8 Hz, 1H), 2.56-2.52 (m, 1H), 2.29-2.26 (m, 5H), 1.92-1.82 (m, 2H), 1.51 (s, 3H), 1.41 (s, 9H).

The following compound was synthesized in a similar manner:

tert-butyl ((S)-3-(cyclohex-1-en-1-yl)-1-((R)-2-methyloxiran-2-yl)-1-oxopropan-2-yl)carbamate $^1$H NMR (300 MHz, CDCl$_3$): δ 5.46 (s, 1H), 4.87 (d, J=7.5 Hz, 1H), 4.45-4.38 (m, 1H), 3.31 (d, J=5.1 Hz, 1H), 2.90 (d, J=5.1 Hz, 1H), 2.44-2.38 (m, 1H), 2.01-1.90 (m, 5H), 1.64-1.48 (m, 4H), 1.48 (s, 3H), 1.42 (s, 9H).

Example 32 tert-Butyl ((S)-3-cyclopentyl-1-((R)-2-methyloxiran-2-yl)-1-oxopropan-2-yl)carbamate

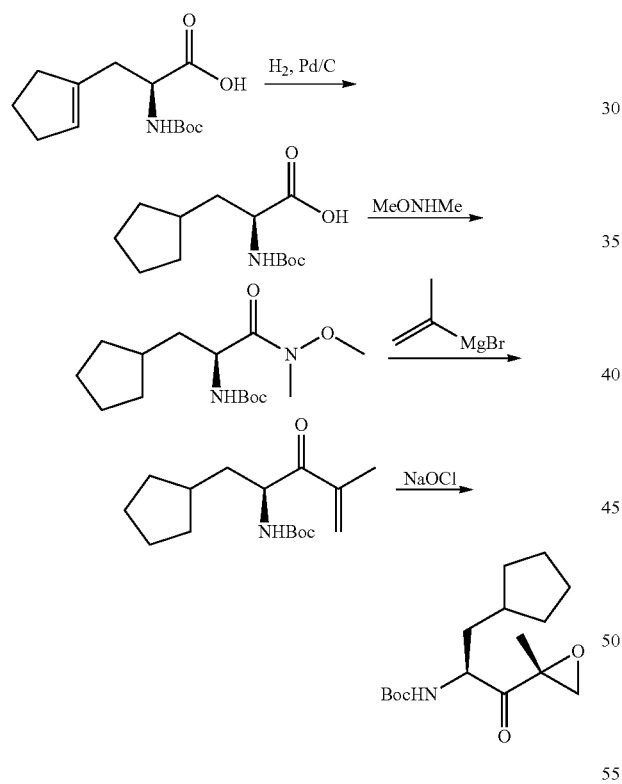

To a solution of (S)-2-(tert-butoxycarbonylamino)-3-cyclopentenylpropanoic acid (56 g, 0.22 mol) in methanol (500 mL) was added Pd/C (23 g, 0.022 mol, 10%). The mixture was stirred under a hydrogen atmosphere (1 atm) at ambient temperature overnight and then filtered through a pad of celite. The filtrate was concentrated under reduced pressure to afford (S)-2-(tert-butoxycarbonylamino)-3-cyclopentylpropanoic acid (55 g, 97% yield) as viscous oil, which was used in the next step without further purification.

The remainder of the synthesis of tert-butyl ((S)-3-cyclopentyl-1-((R)-2-methyloxiran-2-yl)-1-oxopropan-2-yl)carbamate was carried out in a similar manner to the synthesis of tert-butyl ((S)-3-(cyclopent-1-en-1-yl)-1-((R)-2-methyloxiran-2-yl)-1-oxopropan-2-yl)carbamate. $^1$H NMR (300 MHz, CDCl$_3$): δ 4.90 (m, 1H), 4.30 (m, 1H), 3.30 (d, J=5.0 Hz, 1H), 2.90 (d, J=5.0 Hz, 1H), 1.57 (s, 3H), 1.51 (s, 9H), 1.95-1.20 (m, 11H).

Example 33 tert-Butyl ((S)-3-(3,3-difluorocyclobutyl)-1-((R)-2-methyloxiran-2-yl)-1-oxopropan-2-yl)carbamate

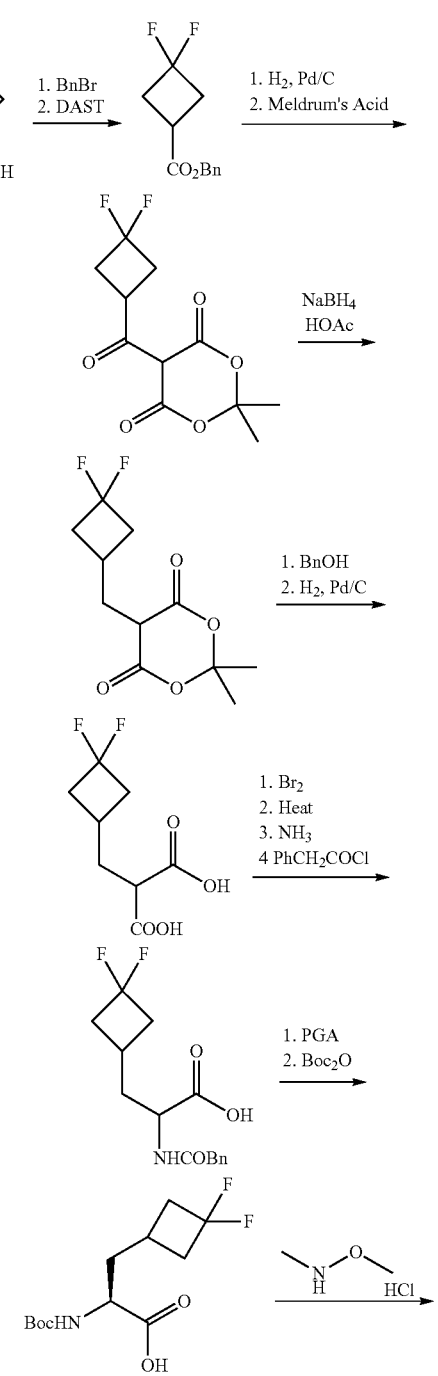

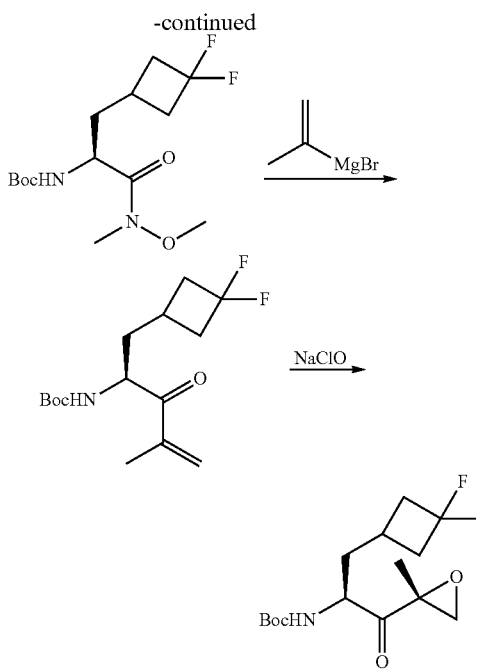

A mixture of 3-oxocyclobutanecarboxylic acid (25 g, 0.22 mol), benzyl bromide (45.14 g, 0.26 mol) and potassium carbonate (60.7 g, 0.44 mol) in DMF (200 mL) was stirred overnight at ambient temperature. The mixture was filtered off and the filtrate was poured into water (200 mL). The resulting mixture was extracted with EtOAc (200 mL×3). The organic extracts were combined, dried over anhydrous sodium sulfate, and concentrated. The residue was purified by flash column chromatography on silica gel (petroleum ether/EtOAc=100:1 to 20:1) to afford benzyl ester (38 g, 84% yield).

The benzyl ester was dissolved in dichloromethane (500 mL) and DAST (90 g, 0.56 mol) was added. The reaction mixture was stirred overnight at ambient temperature. The solution was poured into ice-cooled 10% aqueous sodium bicarbonate (400 mL). The organic layer was separated and the aqueous layer was extracted with dichloromethane (300 mL×3). The organics were combined, dried over anhydrous sodium sulfate and concentrated. The residue was purified by flash column chromatography on silica gel (petroleum ether/EtOAc=200:1 to 50:1) to afford benzyl 3,3-difluorocyclobutanecarboxylate (28 g, 67% yield).

A mixture of benzyl 3,3-difluorocyclobutanecarboxylate (28 g, 0.12 mol) and Pd/C (5 g) in methanol (150 mL) was hydrogenated for 2 h at ambient temperature. Pd/C was filtered off and the filtrate was concentrated. The residue was dissolved in dichloromethane (200 mL) and cooled to 0° C. DMAP (30.8 g, 0.250 mol), Meldrum's acid (19.6 g, 0.140 mol) and EDCI (26.9 g, 0.140 mol) were added successively. The reaction mixture was stirred overnight at ambient temperature. Water (200 mL) was added and the resulting mixture was extracted with dichloromethane (300 mL×3). The organic extracts were combined, dried over anhydrous sodium sulfate, and concentrated. The residue was purified by flash column chromatography on silica gel (dichloromethane/methanol=100:1 to 20:1) to afford 5-(3,3-difluorocyclobutanecarbonyl)-2,2-dimethyl-1,3-dioxane-4,6-dione (24 g, 74% yield).

A solution of 5-(3,3-difluorocyclobutanecarbonyl)-2,2-dimethyl-1,3-dioxane-4,6-dione (15.0 g, 57.3 mmol) in THF (200 mL) was cooled to −5° C. and acetic acid (38 g, 0.63 mol) was added. The mixture was stirred for 5 min and sodium borohydride (6.5 g, 0.17 mol) was added in portions. The reaction mixture was stirred for 2 h at −5° C. and then poured into ice water (200 mL). The resulting mixture was extracted with EtOAc (300 mL×3). The organic extracts were combined, dried over anhydrous sodium sulfate, and concentrated. The residue was purified by flash column chromatography on silica gel (dichloromethane/methanol=100:1 to 30:1) to afford 5-((3,3-difluorocyclobutyl)methyl)-2,2-dimethyl-1,3-dioxane-4,6-dione (8.2 g, 58% yield).

A solution of 5-((3,3-difluorocyclobutyl)methyl)-2,2-dimethyl-1,3-dioxane-4,6-dione (7.00 g, 28.2 mmol) and benzyl alcohol (10 mL) in toluene (10 mL) was heated at 80-90° C. overnight. Toluene was removed and the residue was purified by flash column chromatography on silica gel (dichloromethane/methanol=100:1 to 10:1) to afford the benzyl ester, which was hydrogenated in the presence of Pd/C (1 g) in methanol (30 mL) for 1 h at ambient temperature. Pd/C was filtered off and the filtrate was concentrated to afford 2-((3,3-difluorocyclobutyl)methyl)malonic acid (3.7 g, 63% yield).

Bromine (1.0 mL) was added dropwise to a solution of 2-((3,3-difluorocyclobutyl)methyl)malonic acid (3.7 g, 17.8 mmol) in diethyl ether (50 mL) while keeping the solution refluxing slightly. The mixture was stirred for 10 min and water (5 mL) was added while keeping the mixture refluxing. The organic layer was separated and concentrated.

The residue was heated at 140° C. for 2 h and then cooled to ambient temperature. Saturated aqueous sodium bicarbonate (50 mL) was added and the resulting mixture was washed with EtOAc (30 mL×2). The aqueous layer was acidified to pH=4 with saturated aqueous KHSO$_4$ and then extracted with EtOAc (50 mL×3). The organic extracts were combined, dried over anhydrous sodium sulfate, and concentrated to afford a yellow oil (2.7 g).

A solution of the yellow oil in isopropyl alcohol (100 mL) was autoclaved in the presence of NH$_3$ overnight at ambient temperature. The solvent was removed and the residue was dissolved in acetonitrile (20 mL) followed by addition of PhCH$_2$COCl (2.06 g, 13.3 mmol) and triethylamine (3.09 mL, 22.2 mmol). The reaction mixture was stirred for 6 h. Water (50 mL) was added and the resulting mixture was acidified to pH=4 and extracted with dichloromethane (50 mL×3). The organic extracts were combined, dried over anhydrous sodium sulfate and concentrated. The residue was purified by flash column chromatography on silica gel (dichloromethane/methanol=100:1 to 10:1) to afford 3-(3,3-difluorocyclobutyl)-2-(2-phenylacetamido)propanoic acid (1.4 g, 40% yield).

A mixture of 3-(3,3-difluorocyclobutyl)-2-(2-phenylacetamido)propanoic acid (1.4 g, 4.7 mmol) and PGA enzyme (1.0 g) in water (20 mL) with pH-8-9 was stirred for 3 d at 36° C. Enzyme was filtered off and the filtrate was acidified to pH=4. The resulting mixture was washed with EtOAc (50 mL×2).

The aqueous layer was treated with Boc$_2$O (0.56 g, 2.6 mmol) in acetone/water (20 mL/20 mL) with pH=8 for 5 h at ambient temperature. Acetone was removed and the aqueous solution was acidified to pH=4. The mixture was extracted with EtOAc (50 mL×3). The organic extracts were combined, dried over anhydrous sodium sulfate and concentrated. The residue was purified by flash column chromatography on silica gel (dichloromethane/methanol=100:1 to 10:1) to afford (S)-2-(tert-butoxycarbonylamino)-3-(3,3-difluorocyclobutyl)propanoic acid (0.4 g, 62% yield).

Isopropyl chloroformate (0.65 g, 4.8 mmol) was added dropwise to a solution of (S)-2-(tert-butoxycarbonylamino)-3-(3,3-difluorocyclobutyl)propanoic acid (1.2 g, 4.3 mmol) and N-methylmorpholine (0.5 g, 5.0 mmol) in dichloromethane (20 mL) at 0° C. The mixture was stirred for 1 h at 0° C. followed by addition of a mixture of N,O-dimethylhydroxylamine-HCl (0.5 g, 5.1 mmol) and triethylamine (0.69 mL, 5.0 mmol) in dichloromethane (20 mL). The reaction mixture was stirred overnight at ambient temperature and poured into 5% aqueous HCl (50 mL). The resulting mixture was extracted with EtOAc (50 mL×3). The organic extracts were combined, washed with saturated sodium bicarbonate (150 mL), dried over anhydrous sodium sulfate and concentrated. The residue was purified by flash column chromatography on silica gel (dichloromethane/methanol=100:1 to 10:1) to afford (S)-tert-Butyl 3-(3,3-difluorocyclobutyl)-1-(methoxy(methyl)amino)-1-oxo propan-2-ylcarbamate (1.2 g, 87% yield).

(S)-tert-Butyl 3-(3,3-difluorocyclobutyl)-1-(methoxy(methyl)amino)-1-oxo propan-2-ylcarbamate (1.2 g, 3.7 mmol) was dissolved in THF (20 mL) and then cooled to 0° C. Prop-1-en-2-ylmagnesium bromide (14.9 mmol) was added dropwise and the reaction mixture was stirred for 1 h at ambient temperature. The mixture was poured into ice water (50 mL) and extracted with EtOAc (50 mL×3). The organic extracts were combined, dried over anhydrous sodium sulfate and concentrated. The residue was purified by flash column chromatography on silica gel (petroleum ether/EtOAc=200:1 to 100:1) to afford (S)-tert-Butyl 1-(3,3-difluorocyclobutyl)-4-methyl-3-oxopent-4-en-2-ylcarbamate (0.8 g, 72% yield).

A solution of (S)-tert-butyl 1-(3,3-difluorocyclobutyl)-4-methyl-3-oxopent-4-en-2-ylcarbamate (0.80 g, 2.6 mmol) in DMF (20 mL) was cooled to 0° C. and 10% aqueous NaClO solution (7.90 mL, 10.6 mmol) was added while keeping the internal temperature below 5° C. The reaction mixture was stirred for 1 h at 0° C. and poured into saturated aqueous sodium bicarbonate (50 mL). The resulting mixture was extracted with EtOAc (50 mL×3). The organic extracts were combined, washed with brine (100 mL×2), dried over anhydrous sodium sulfate, and concentrated. The residue was purified by flash column chromatography on silica gel (petroleum ether/EtOAc=200:1 to 50:1) to afford tert-butyl ((S)-3-(3,3-difluorocyclobutyl)-1-((R)-2-methyloxiran-2-yl)-1-oxopropan-2-yl)carbamate (510 mg, 62% yield). $^1$H NMR (300 MHz, CDCl$_3$): δ 5.02 (d, J=8.7 Hz, 1H), 4.25 (m, 1H), 3.23 (d, J=4.5 Hz, 1H), 2.93 (d, J=4.8 Hz, 1H), 2.73 (m, 2H), 2.25 (m, 3H), 1.92 (m, 1H), 1.55 (m, 1H), 1.54 (s, 3H), 1.43 (s, 9H). MS (EI) for C$_{15}$H$_{23}$F$_2$NO$_4$, found 358.14 [M+K]$^+$.

Example 34 tert-Butyl ((S)-3-((1R,5S,6s)-bicyclo[3.1.0]hexan-6-yl)-1-((R)-2-methyloxiran-2-yl)-1-oxopropan-2-yl)carbamate

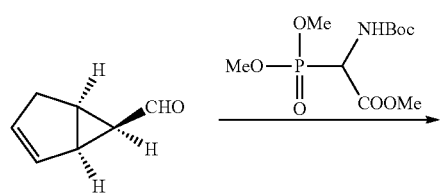

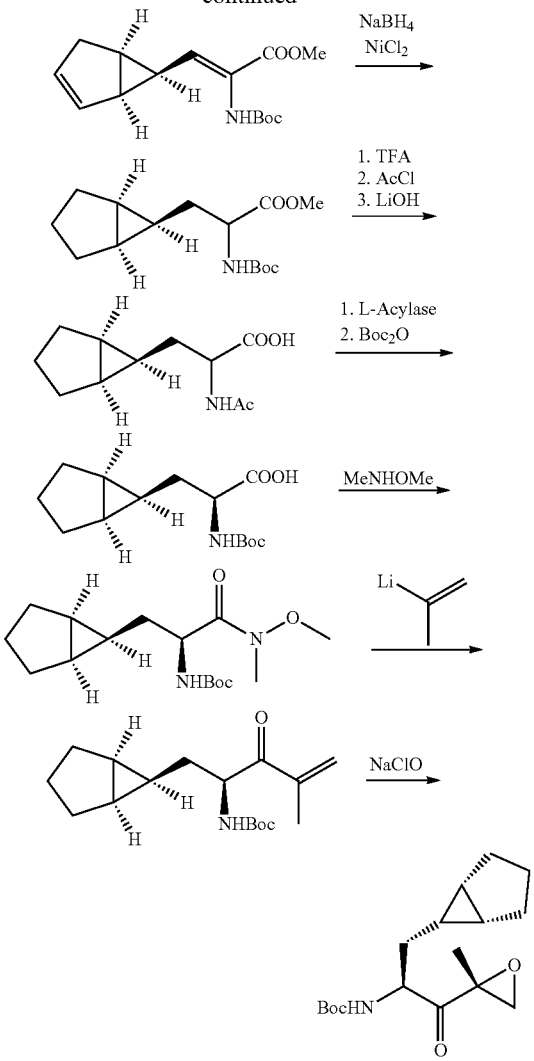

A mixture of cis-bicyclo[3.1.0]hex-2-ene-6-carbaldehyde (6.00 g, 55.5 mmol), methyl 2-(tert-butoxycarbonylamino)-2-(dimethoxyphosphoryl)acetate (10.0 g, 69.4 mol) and DBU (130 g, 85.5 mmol) in DCM (150 mL) was stirred at ambient temperature for 1 h. The mixture was poured into saturated aqueous NH$_4$Cl (150 mL) and the resulting mixture was extracted with DCM (100 mL×2). The combined organic layers were washed with saturated aqueous NH$_4$Cl (100 mL×2) and brine (100 mL), dried over anhydrous sodium sulfate, and concentrated. The residue was purified by flash column chromatography on silica gel (petroleum ether/EtOAc=10:1 to 4:1) to afford methyl 3-(cis-bicyclo[3.1.0]hex-2-en-6-yl)-2-(tert-butoxycarbonylamino)acrylate (5.6 g, 36% yield) as a colorless oil.

NaBH$_4$ (3.00 g, 78.5 mmol) was added in portions to a mixture of methyl 3-(cis-bicyclo[3.1.0]hex-2-en-6-yl)-2-(tert-butoxycarbonylamino)acrylate (4.40 g, 15.8 mmol) and NiCl$_2$·6H$_2$O (3.80 g, 15.8 mmol) in methanol (100 mL) at 0° C. The reaction mixture was stirred for 15 min and then poured into saturated aqueous NH$_4$Cl (100 mL). The resulting mixture was extracted with DCM (100 mL×2). The combined organic layers were washed with saturated aqueous NH$_4$Cl (100 mL×2) and brine (100 mL), dried over anhydrous sodium sulfate and concentrated. The residue was purified by flash column chromatography on silica gel (petroleum ether/EtOAc=10:1 to 4:1) and prep-HPLC to afford methyl 3-(cis-bicyclo[3.1.0]hexan-6-yl)-2-(tert-butoxycarbonylamino)propanoate (1.0 g, 22% yield) as a colorless oil.

The remainder of the synthesis was carried out according to the procedure for tert-butyl (S)-3-(trans-bicyclo[3.1.0]hexan-6-yl)-1-((R)-2-methyloxiran-2-yl)-1-oxopropan-2-yl-carbamate.

Example 35

(S)-Methyl 2-amino-3-(1H-indol-5-yl)propanoate

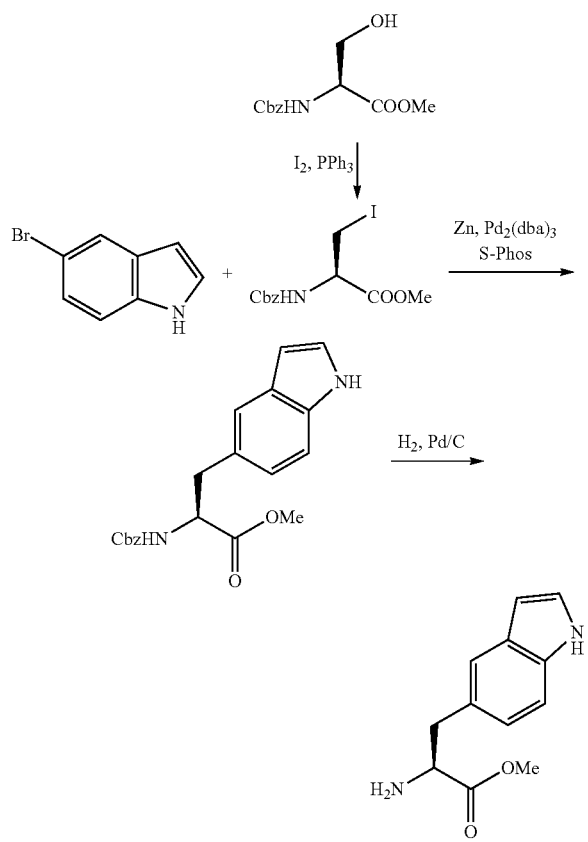

A mixture of triphenylphosphine (23.3 g, 0.890 mol) and imidazole (6.0 g, 0.89 mol) in DCM (100 mL) was cooled to 0° C. and iodide (22.6 g, 0.890 mol) was added in small portions over 0.5 h. The cooling bath was removed and the mixture was stirred for 0.5 h. After the mixture was re-cooled to 0° C., a solution of Cbz-L-Ser-OMe 15.0 g, 0.590 mol) in DCM (100 mL) was added dropwise. After the addition, the cooling bath was removed and the mixture was allowed to warm to ambient temperature and stirred for 1.5 h. The mixture was filtered and the filtrate was concentrated to remove most of the solvent. MTBE (400 mL) was added to the residue and the mixture was filtered to remove triphenylphosphine oxide. The filtrate was concentrated and the residue was purified by flash column chromatography on silica gel (petroleum ether/EtOAc=50:1 to 10:1) to afford (S)-(R)-methyl 2-(benzyloxycarbonylamino)-3-iodopropanoate (12.3 g, 57% yield) as a colorless solid.

To a suspension of zinc (2.53 g, 38.8 mmol) in DMF (20 mL) was added $I_2$ (1.10 g, 4.15 mol) followed by addition of a solution of (R)-methyl 2-(benzyloxycarbonylamino)-3-iodopropanoate (4.70 g, 13.0 mmol) in DMF (20 mL). The mixture was stirred at ambient temperature for 5 min and heated at 35° C. for 40 min. Then a solution of 5-bromo-1H-indole (3.00 g, 15.5 mmol) in DMF (10 mL), $Pd_2(dba)_3$ (0.25 g, 0.27 mmol) and S-Phos (0.25 g, 0.60 mmol) were added. The reaction mixture was stirred at 50° C. under nitrogen overnight and then cooled to ambient temperature. Brine (500 mL) was added and the resulting mixture was extracted with EtOAc (200 mL×3). The organics were combined, washed with brine (300 mL) and concentrated. The residue was purified by flash column chromatography on silica gel (petroleum ether/EtOAc=10:1 to 5:1) to afford (S)-methyl 2-(benzyloxycarbonylamino)-3-(1H-indol-5-yl)propanoate as a viscous oil (3.27 g, 60% yield).

To a solution of (S)-methyl 2-(benzyloxycarbonylamino)-3-(1H-indol-5-yl)propanoate (3.27 g, 9.39 mmol) in methanol (30 mL) was added Pd/C (10%, 200 mg). The mixture was stirred under hydrogen atmosphere at ambient temperature for 1 h and then filtered through a pad of Celite. The filtrate was concentrated to afford (S)-methyl 2-amino-3-(1H-indol-5-yl)propanoate (1.8 g, 88% yield) as a light green solid, which was used directly without further purification.

Example 36

(S)-Methyl 2-amino-3-(3-(benzyloxy)-4-methylphenyl)propanoate

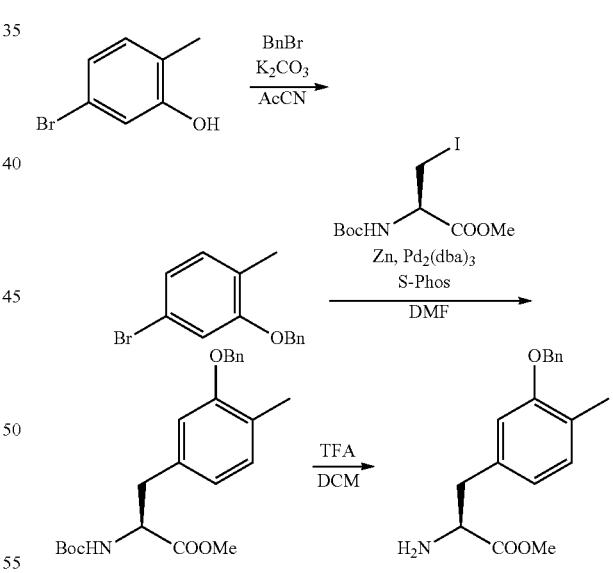

To a solution of 5-bromo-2-methylphenol (5.0 g, 27 mmol) in acetonitrile (50 mL) was added $K_2CO_3$ (4.4 g, 32 mmol) followed by benzyl bromide (5.5 g, 32 mmol). The suspension was heated at 50-60° C. for 4 h then cooled to ambient temperature. The mixture was filtered and the filtration cake was washed with acetonitrile (20 mL). The filtrate and washings were combined and concentrated to dryness. The residue was purified by flash column chromatography on silica gel (hexane/EtOAc=6:1) to afford (S)-methyl 3-(3-(benzyloxy)-4-methylphenyl)-2-(tert-butoxycarbonylamino) propanoate (7.5 g, quant.) as an oil.

Dry DMF (100 mL) was added to zinc dust (7.00 g, 108 mmol) in a flame dried flask under N$_2$. (R)-methyl 2-(tert-butoxycarbonylamino)-3-iodopropanoate (9.7 g, 29 mmol) and a catalytic amount of iodine (0.7 g, 2 mmol) were added. The mixture was stirred at ambient temperature for 0.5 h, then Pd$_2$(dba)$_3$ (1.9 g, 2.0 mmol), S-Phos (1.6 g, 4.0 mmol) and 2-(benzyloxy)-4-bromo-1-methylbenzene (7.40 g, 27.0 mmol) were added. The reaction mixture was stirred at 60° C. for 6 h then cooled to ambient temperature. EtOAc (500 mL) and water (500 mL) were added and the organic phase was separated, washed with water (300 mL×3) and brine (300 mL×1), dried over anhydrous sodium sulfate, and concentrated. The residue was purified by flash column chromatography on silica gel (hexane/EtOAc=10:1) to afford (S)-methyl 3-(3-(benzyloxy)-4-methylphenyl)-2-((tert-butoxycarbonyl)amino)propanoate (4.0 g, 37% yield).

To TFA (5 mL) was added to a solution of (S)-methyl 3-(3-(benzyloxy)-4-methylphenyl)-2-((tert-butoxycarbonyl)amino)propanoate (1.0 g, 2.5 mmol) in DCM (10 mL) at 0° C. with stirring. The mixture was stirred for 1 h and then concentrated to dryness. The residue was azeotroped with EtOAc (10 mL×3) to remove residual TFA and afford crude (S)-methyl 2-amino-3-(3-(benzyloxy)-4-methylphenyl)propanoate as its TFA salt.

Example 37

Boc-L-4-methylsulfonylphenylalanline methyl ester and Boc-L-3-methylsulfonylphenylalanline methyl ester

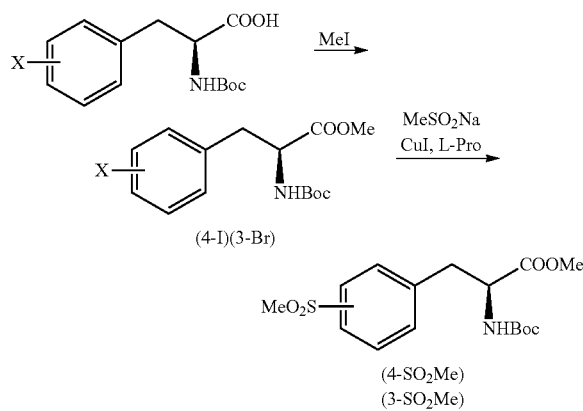

Iodomethane (3.6 g, 25 mmol) was added to a suspension of K$_2$CO$_3$ (3.5 g, 25 mmol) and Boc-L-4-iodophenylalanine (5 g, 12.5 mmol) in acetone (50 mL). The reaction mixture was heated at 40° C. for 12 h. The mixture was cooled to ambient temperature and then filtered. The filtration cake was washed with acetone (50 mL) and the filtrate and washings were combined. The solvent was removed and the residue was purified by flash column chromatography on silica gel (Hexane/EtOAc=10:1) to afford Boc-L-4-iodophenylalanline methyl ester (4.9 g, 93% yield) as a colorless solid.

Boc-L-3-bromophenylalanline methyl ester was prepared from Boc-L-3-bromophenylalanine following the same procedure for Boc-L-4-iodophenylalanline methyl ester.

A mixture of Boc-L-4-bromophenylalanline methyl ester (2.0 g, 5 mmol), sodium methanesulfinate (600 mg, 6 mmol), CuI (96 mg, 0.5 mmol) and L-proline (115 mg, 1 mmol) in DMSO (30 mL) was heated at 90° C. for 12 h under N$_2$. The mixture was cooled to ambient temperature and then diluted with water (300 mL). The resulting mixture was extracted with EtOAc (100 mL×3). The combined organic phases were washed with 1N aqueous HCl (100 mL×2), saturated aqueous NaHCO$_3$ (100 mL×3), and brine (50 mL×1), respectively. The organic solution was dried over anhydrous sodium sulfate, and concentrated. The residue was purified by flash column chromatography on silica gel (Hexane/EtOAc=2:1) to afford Boc-L-4-methylsulfonylphenylalanline methyl ester (1.1 g, 62% yield) as a colorless solid. Boc-L-3-methyl sulfonylphenylalanline methyl ester was prepared in a similar manner.

Example 38

6-Bromo-3,4-dihydro-1H-benzo[c][1,2]thiazine 2,2-dioxide

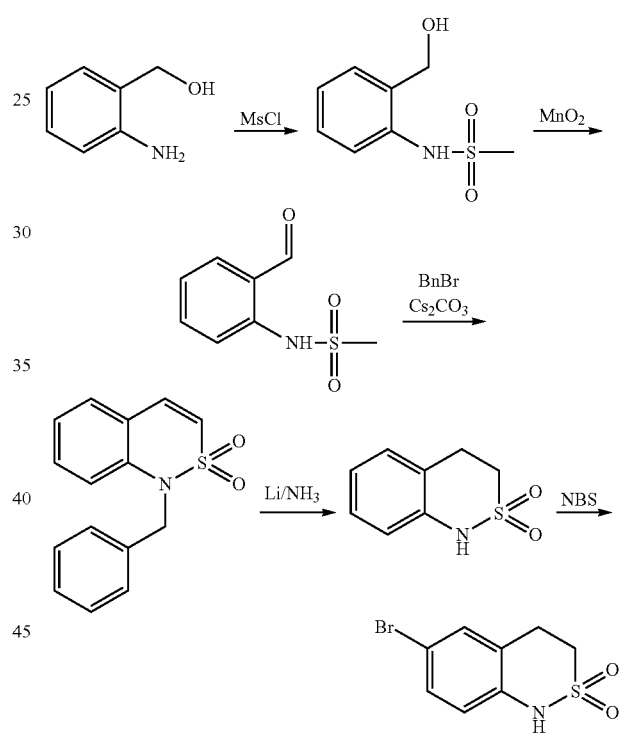

A solution of methane sulfonyl chloride (10.2 ml, 0.13 mol) in chloroform (100 mL) was added dropwise to a solution of (2-aminophenyl)methanol (15.0 g, 0.12 mol) in pyridine (100 mL) and chloroform (150 mL) under nitrogen over 1 h at 0° C. The reaction mixture was stirred for 12 h at ambient temperature and then washed with hydrochloric acid (2N, 200 ml×2). The organic phase was dried over anhydrous MgSO$_4$ and concentrated. The residue was purified by flash column chromatography on silica gel (EtOAc/hexane=1:3) to afford N-[2-(hydroxymethyl)phenyl]methanesulfonamide (13.0 g, 53% yield) as a yellow oil.

Manganese dioxide (85%, 45.0 g, 0.52 mol) was added to a solution of N-[2-(hydroxymethyl)phenyl]methanesulfonamide (13.0 g, 65 mmol) in dichloromethane (200 mL) at ambient temperature under nitrogen. The reaction mixture was stirred for 12 h and then filtered through a pad of Celite. The pad was washed with dichloromethane/methanol (1:1)

and the combined organics were concentrated to afford N-(2-Formylphenyl)methanesulfonamide (10.1 g, 78% yield) as a yellow solid.

Cesium carbonate (18.0 g, 55 mmol) and benzyl bromide (6.6 mL, 55 mmol) were added to a solution of N-(2-formylphenyl)methanesulfonamide (5.50 g, 27.6 mmol) in acetonitrile (120 mL). The reaction mixture was heated at 60° C. for 16 h and then cooled to ambient temperature. The mixture was diluted with EtOAc (200 mL) and filtered. The filtration cake was washed with EtOAc (200 mL) and the combined organics were concentrated. The residue was purified by flash column chromatography on silica gel (EtOAc/hexane=1:5) to afford 1-benzyl-1H-benzo[c][1,2]thiazine 2,2-dioxide (6.5 g, 87% yield) as a colorless oil.

Freshly polished lithium flakes (2.0 g, 0.28 mol) were added to a solution of 1-benzyl-1H-benzo[c][1,2]thiazine 2,2-dioxide (6.5 g, 24 mmol) in THF (120 mL)/EtOH (12 mL) and liquid $NH_3$ (150 mL) at −40° C. with stirring over 0.5 h. The reaction was quenched with $NH_4Cl$ powder (10 g). Water (200 mL) and EtOAc (200 mL) were added. The two layers were separated and the aqueous phase was extracted with EtOAc (100 mL×3). The combined organic phases were washed with brine (200 mL×3), dried over anhydrous sodium sulfate, and concentrated. The residue was purified by flash column chromatography on silica gel (EtOAc/hexane=1:4) to afford 3,4-dihydro-1H-benzo[c][1,2]thiazine 2,2-dioxide (1.5 g, 34% yield).

NBS (1.5 g, 8.2 mmol) was added to a solution of 3,4-dihydro-1H-benzo[c][1,2]thiazine 2,2-dioxide (1.5 g, 8.2 mmol) in DMF (15 mL). The reaction mixture was stirred overnight at ambient temperature followed by addition of water (200 mL) and EtOAc (100 mL). The two layers were separated and the aqueous phase was extracted with EtOAc (100 mL×3). The combined organic phases were washed with brine (200 mL×3), dried over anhydrous sodium sulfate, and concentrated. The residue was purified by flash column chromatography on silica gel (EtOAc/hexane=1:3) to afford 6-bromo-3,4-dihydro-1H-benzo[c][1,2]thiazine 2,2-dioxide (1.7 g, 79% yield).

Example 39

(R)-Methyl 2-((tert-butoxycarbonyl)amino)-3-(2-(2,4-dimethoxybenzyl)-1,1-dioxido-3,4-dihydro-2H-benzo[e][1,2]thiazin-6-yl)propanoate

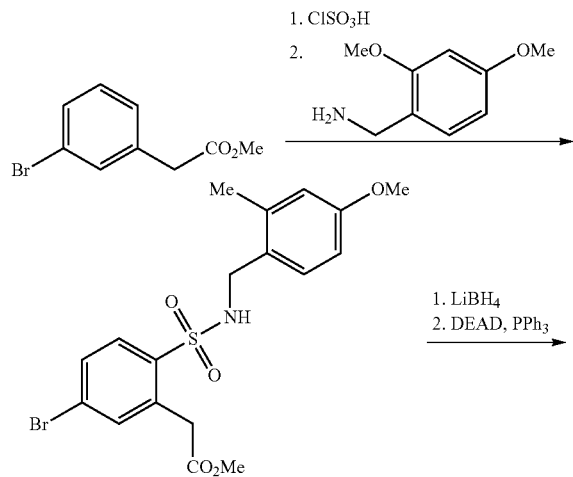

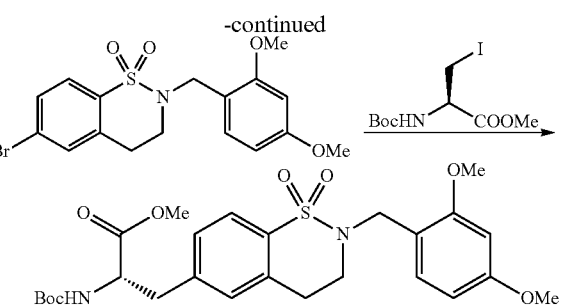

Methyl 2-(3-bromophenyl)acetate (20 g, 87 mmol) was added dropwise to $ClSO_3H$ (60 mL) at 0° C. The reaction mixture was stirred overnight at ambient temperature. The solution was poured into ice-water (100 mL) slowly and the resulting mixture was extracted with EtOAc (100 mL×3). The organic extracts were combined, dried over anhydrous sodium sulfate, and concentrated.

The resulting red oil (20 g) was dissolved in dichloromethane (100 mL) and cooled to 0° C. Triethylamine (33.1 mL, 0.240 mol) and (2,4-dimethoxyphenyl)methanamine (11.2 g, 66.0 mmol) were added slowly. The reaction mixture was stirred for 2 h at ambient temperature. The mixture was poured into water (100 mL) and the resulting mixture was extracted with dichloromethane (100 mL×3). The organic extracts were combined, dried over anhydrous sodium sulfate, and concentrated. The residue was purified by flash column chromatography on silica gel (petroleum ether/EtOAc=10:1 to 3:1) to afford methyl 2-(5-bromo-2-(N-(2,4-dimethoxybenzyl)sulfamoyl)phenyl)acetate (5.3 g, 14% yield).

$LiBH_4$ (1.02 g, 46.4 mmol) was added in portions to a solution of methyl 2-(5-bromo-2-(N-(2,4-dimethoxybenzyl)sulfamoyl)phenyl)acetate (5.30 g, 11.6 mmol) in THF/methanol (100 mL/20 mL) at 0° C. The reaction mixture was stirred for 1 h at ambient temperature and then poured into ice-water (100 mL). The resulting mixture was extracted with EtOAc (100 mL×3). The organic extracts were combined, washed with brine (200 mL), dried over anhydrous sodium sulfate, and concentrated to give the corresponding alcohol (4.70 g, 10.9 mmol).

The alcohol (1.4 g, 3.3 mmol) and DEAD (1.1 g, 6.5 mmol) were dissolved in THF (50 mL) followed by addition of $PPh_3$ (1.6 g, 6.5 mmol) in portions. The reaction mixture was stirred overnight at ambient temperature. The solvent was removed and the residue was purified by flash column chromatography on silica gel (petroleum ether/EtOAc=15:1 to 5:1) to afford 6-bromo-2-(2,4-dimethoxybenzyl)-3,4-dihydro-2H-benzo[e][1,2]thiazine 1,1-dioxide (1.3 g, 91% yield) as a yellow solid.

Iodine (0.11 g, 0.43 mmol) was added to a mixture of (R)-methyl 2-(tert-butoxycarbonylamino)-3-iodopropanoate (1.30 g, 3.58 mmol) and zinc (0.620 g, 9.75 mmol) in DMF (30 mL). The mixture was stirred for 10 min and another portion of iodine (0.11 g, 0.43 mmol) was added. The mixture was stirred for another 1 h. 6-Bromo-2-(2,4-dimethoxybenzyl)-3,4-dihydro-2H-benzo[e][1,2]thiazine 1,1-dioxide (1.34 g, 3.25 mmol), $Pd_2(dba)_3$ (0.08 g, 0.09 mmol) and S-Phos (0.070 g, 0.17 mmol) were added. The reaction mixture was stirred at 50° C. for 4 h and then cooled to ambient temperature. The mixture was filtered and the filtrate was poured into water (50 mL). The resulting mixture was extracted with EtOAc (100 mL×3). The organic extracts were combined, dried over anhydrous sodium sulfate, and concentrated. The residue was purified by flash column chromatography on silica gel (petroleum ether/EtOAc=15:1 to 3:1) to afford (R)-methyl 2-((tert-butoxycarbonyl)amino)-3-(2-(2,4-dimethoxybenzyl)-1,1-dioxido-3,4-dihydro-2H-benzo[e][1,2]thiazin-6-yl)propanoate (0.8 g, 46% yield) as a yellow oil.

Example 40

(S)-4-(3-(Benzyloxy)-2-((tert-butoxycarbonyl)amino)-3-oxopropyl)pyridine 1-oxide

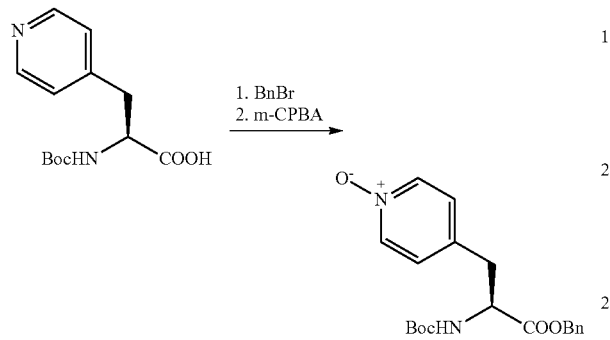

Bromomethylbenzene (965 mg, 5.64 mmol) was added dropwise to a mixture of (S)-2-(tert-butoxycarbonyl amino)-3-(pyridin-4-yl)propanoic acid (1.00 g, 3.76 mmol) and Cs₂CO₃ (1.23 g, 3.76 mmol) in DMF (20 mL) at ambient temperature. The reaction mixture was stirred at ambient temperature for 1.5 h and poured into water (50 mL). The resulting mixture was extracted with EtOAc (50 mL×2) and the combined organics were washed with water (50 mL) and brine (50 mL), dried over anhydrous sodium sulfate and concentrated. The residue was purified by flash column chromatography on silica gel (petroleum ether/EtOAc=50:1) to afford the corresponding benzyl ester (1.0 g, 74% yield) as an oil.

To a solution of the benzyl ester (1.0 g, 2.8 mmol) in CH₂Cl₂ (20 mL) was added m-CPBA (1.2 g, 5.6 mmol) at 0° C. The reaction mixture was stirred at ambient temperature overnight and poured into water (50 mL). The resulting mixture was extracted with CH₂Cl₂ (50 mL×3). The combined organic layers were washed with saturated aqueous Na₂SO₃ (100 mL) and brine (100 mL), dried over anhydrous sodium sulfate, and concentrated. The residue was purified by flash column chromatography on silica gel (DCM/methanol=50:1) to afford (S)-4-(3-(Benzyloxy)-2-(tert-butoxycarbonylamino)-3-oxopropyl)pyridine 1-oxide (900 mg, 86% yield) as a colorless solid.

Example 41

(2S,3R)-Benzyl 2-amino-3-hydroxy-3-(4-methoxyphenyl)propanoate

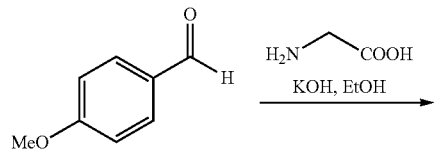

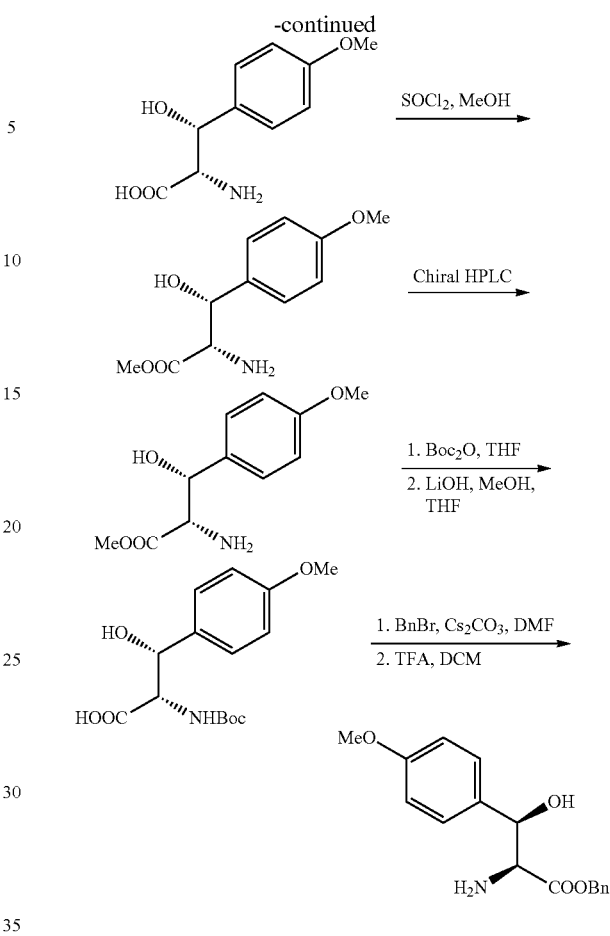

A solution of glycine (45 g, 0.60 mol) and anisaldehyde (122 g, 0.900 mol) in ethanol (1.5 L) was stirred at ambient temperature and KOH (82.7 g, 1.47 mol) was added. The reaction mixture was stirred overnight at ambient temperature. The mixture was concentrated under vacuum the majority of ethanol. The residue was dissolved in water (800 mL) and the solution was adjusted to pH=5 with 4 N aqueous HCl. The resulting mixture was washed with EtOAc (200 mL×2) to remove any impurities. The aqueous layer was concentrated to a volume of ~400 mL. The mixture was filtered and the filtration cake was washed thoroughly with water (100 mL×2) and dried to afford 2-amino-3-hydroxy-3-(4-methoxyphenyl)propanoic acid (29 g, 23% yield, threo-) as a colorless solid.

Thionyl chloride (12.3 mL, 169 mmol) was added dropwise to methanol (250 mL) at 0° C. followed by addition of 2-amino-3-hydroxy-3-(4-methoxyphenyl)propanoic acid (25.0 g, 118 mol). The reaction mixture was stirred at ambient temperature for 1 h and heated under reflux for 3 h. The mixture was cooled to ambient temperature and then concentrated to dryness. The residue was purified by flash column chromatography on silica gel (DCM/methanol=60:1) to afford (2S,3R)-methyl 2-amino-3-hydroxy-3-(4-methoxyphenyl)propanoate (15.7 g, 59% yield, threo-) as a colorless oil. Further separation by chiral preparative HPLC afforded (2S,3R)-methyl 2-amino-3-hydroxy-3-(4-methoxyphenyl)propanoate (7.0 g, 45% yield).

To THF (20 mL) was added (2S,3R)-methyl 2-amino-3-hydroxy-3-(4-methoxyphenyl)propanoate (1.00 g, 4.44 mmol) followed by Boc₂O (1.16 g, 5.33 mmol). The reaction mixture was stirred for 1 h at ambient temperature then concentrated to afford crude (2S,3R)-2-(tert-butoxycarbonylamino)-3-hydroxy-3-(4-methoxyphenyl)propanoate (1.44 g, quant.) as a colorless solid.

A mixture of (2S,3R)-2-(tert-butoxycarbonylamino)-3-hydroxy-3-(4-methoxyphenyl)propanoate (1.44 g, 4.44 mmol) and LiOH—H$_2$O (280 mg, 6.66 mmol) in MeOH/THF (30 mL, 1:1) was stirred for 1 h at ambient temperature. EtOAc/water (30 mL/50 mL) was added and the two phases were separated. The aqueous phase was washed with EtOAc (30 mL×2) then acidified with dilute HCl to pH=5. The resulting mixture was extracted with EtOAc (50 mL×2). The organics were combined, dried over anhydrous sodium sulfate, and concentrated to afford (2S,3R)-2-(tert-butoxycarbonylamino)-3-hydroxy-3-(4-methoxyphenyl)propanoic acid (0.90 g, 65% yield) as a colorless solid.

Benzyl bromide (4.40 g, 25.7 mmol) was added dropwise to a mixture of (2S,3R)-2-(tert-butoxycarbonyl amino)-3-hydroxy-3-(4-methoxyphenyl)propanoic acid (4.00 g, 12.9 mmol) and Cs$_2$CO$_3$ (4.20 g, 12.9 mmol) in DMF (80 mL) at 0° C. The reaction mixture was allowed to warm to ambient temperature and stirred for 1 h. Water (80 mL) was added and the resulting mixture was extracted with EtOAc (100 mL×2). The combined extracts were washed with water (100 mL) and brine (100 mL), dried over anhydrous sodium sulfate, and concentrated. The residue was purified by flash column chromatography on silica gel (petroleum ether/EtOAc=10:1 to 4:1) to afford (2S,3R)-benzyl 2-((tert-butoxycarbonyl)amino)-3-hydroxy-3-(4-methoxyphenyl)propanoate (3.7 g, 66% yield) as a colorless solid.

To (2S,3R)-benzyl 2-((tert-butoxycarbonyl)amino)-3-hydroxy-3-(4-methoxyphenyl)propanoate (3.0 g, 7.5 mmol) in DCM (30 mL) was added TFA (15 mL) and the mixture was stirred at 0° C. After 30 min it was diluted with DCM (100 mL). Saturated aqueous NaHCO$_3$ (100 mL) was added and the two layers were separated. The aqueous layer were extracted with DCM (100 mL×2) and the combined organics were dried over anhydrous sodium sulfate and concentrated to afford crude (2S,3R)-benzyl 2-amino-3-hydroxy-3-(4-methoxyphenyl)propanoate (2.3 g, quant.) as an oil, which was used directly in the next step without further purification.

Example 42

(2S,3S)-2-((tert-Butoxycarbonyl)amino)-3-hydroxy-3-(4-methoxyphenyl)propanoic acid

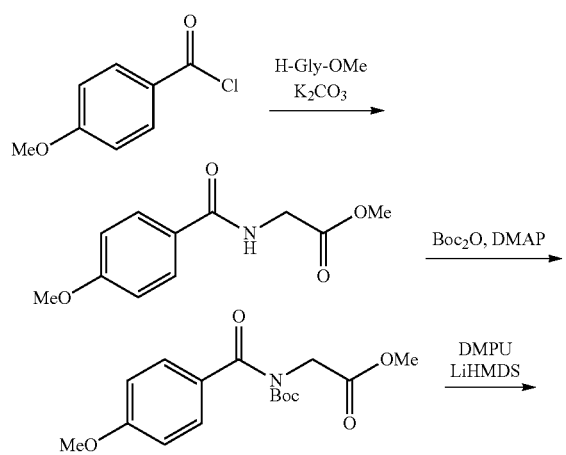

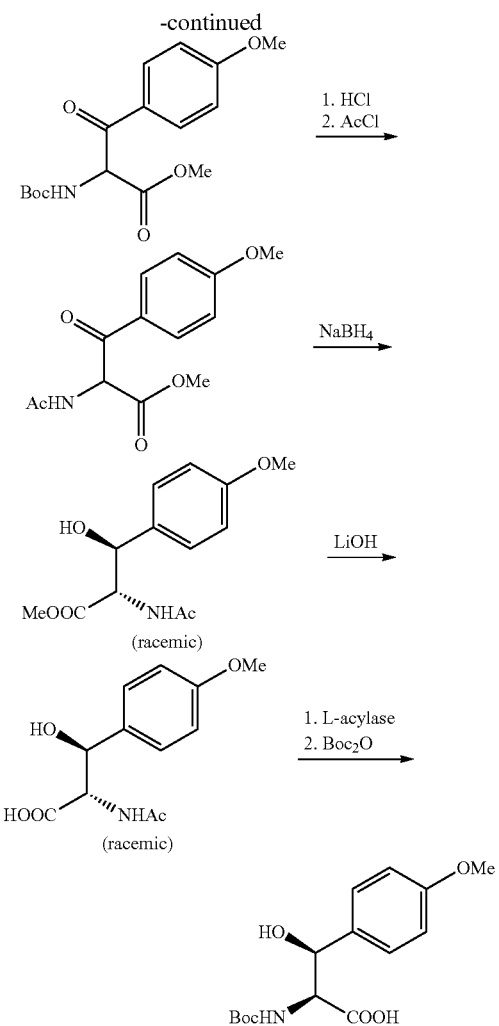

Saturated aqueous potassium carbonate (190 mL) and 4-methoxybenzoyl chloride (60.8 g, 358 mmol) were added to a solution of glycine methyl ester (30.0 g, 239 mmol) in THF (100 mL) at 0° C. The reaction mixture was stirred for 3 h at 0° C. and then poured into water (100 mL). The resulting mixture was extracted with EtOAc (200 ml×2). The combined extracts were dried over anhydrous sodium sulfate and concentrated to afford methyl 2-(4-methoxybenzamido)acetate (46.2 g, 86% yield) as a colorless solid, which was used directly without further purification.

Methyl 2-(4-methoxybenzamido)acetate (46.2 g, 207 mmol) was dissolved in acetonitrile (150 mL). Di-tert-butyl dicarbonate (69.0 g, 207 mmol) and DMAP (3.0 g, 21 mmol) were added. The reaction mixture was stirred overnight at ambient temperature and then concentrated. The residue was purified by flash column chromatographic on silica gel (petroleum ether/EtOAc=50:1) to afford methyl 2-(N-(tert-butoxycarbonyl)-4-methoxybenzamido)acetate (56 g, 92% yield) as a colorless solid.

DMPU (25.0 mL, 205 mmol) and LiHMDS (1M solution, 250 mL, 250 mmol) were added to a solution of methyl 2-(N-(tert-butoxycarbonyl)-4-methoxybenzamido)acetate (33.0 g, 102 mmol) in THF (200 mL) at −78° C. The reaction mixture was stirred for 1.5 h at −78° C. and quenched with saturated aqueous NH$_4$Cl (300 mL). The resulting mixture was extracted with EtOAc (250 mL×3). The combined extracts were washed with water (300 mL) and brine (300 mL), dried over anhydrous sodium sulfate, and concentrated. The residue was washed with petroleum ether/EtOAc (200 mL, 20:1) and dried to afford methyl 2-(tert-butoxycarbonylamino)-3-(4-methoxyphenyl)-3-oxopropanoate (23 g, 70% yield) as a colorless solid.

HCl-EtOAc (6N solution, 200 mL) was added to a solution of methyl 2-(tert-butoxycarbonylamino)-3-(4-methoxyphenyl)-3-oxopropanoate (50.0 g, 155 mmol) in EtOAc (300 mL) at ambient temperature with stirring. The reaction mixture was stirred for 30 min and then concentrated to dryness. The residue was washed with petroleum ether (200 mL×3) and dried to afford methyl 2-amino-3-(4-methoxyphenyl)-3-oxopropanoate (HCl salt, 35.5 g, 88% yield).

To a solution of methyl 2-amino-3-(4-methoxyphenyl)-3-oxopropanoate (35.5 g, 137 mmol) and Et$_3$N (57.2 mL, 411 mmol) in DCM (120 mL) at 0° C. was added AcCl (12.9 g, 164 mmol) dropwise. The reaction mixture was stirred at 0° C. for 40 min and then quenched with water (500 mL). The resulting mixture was extracted with DCM (300 mL×2) and the combined organic layers were dried over anhydrous sodium sulfate and concentrated. The residue was washed with petroleum ether/EtOAc (300 mL, 100:1) to methyl 2-acetamido-3-(4-methoxyphenyl)-3-oxopropanoate (22.0 g, 61% yield) as a colorless solid.

A solution of methyl 2-acetamido-3-(4-methoxyphenyl)-3-oxopropanoate (22.7 g, 85.7 mmol) in methanol (500 mL) was cooled to 0° C. and NaBH$_4$ (976 mg, 25.7 mmol) was added in portions. The reaction mixture was stirred for 1 h at 0° C. and then quenched with water (1 L). The resulting mixture was extracted with EtOAc (300 ml×3). The organic extracts were combined, dried over anhydrous sodium sulfate and concentrated. The residue was washed with petroleum ether/EtOAc (100 mL, 10:1) to afford methyl 2-acetamido-3-hydroxy-3-(4-methoxyphenyl)propanoate (13.5 g, 59% yield, erythro-form >95%) as a colorless solid.

To a solution of methyl 2-acetamido-3-hydroxy-3-(4-methoxyphenyl)propanoate (13.5 g, 50.5 mmol) in methanol (200 mL) was added a solution of lithium hydroxide hydrate (4.20 g, 101 mmol) in water (100 mL). The reaction mixture was stirred at ambient temperature for 1 h and then concentrated to remove the organic solvent. The residue (2-acetamido-3-hydroxy-3-(4-methoxyphenyl)propanoic acid, in aqueous solution) was used directly in the next step.

Aqueous 2-acetamido-3-hydroxy-3-(4-methoxyphenyl) propanoic acid solution (100 mL) was adjusted to pH=8.5 with 2M aqueous NaOH and the mixture was filtered. The filtrate was heated to 38° C. followed by addition of L-acylase (2.0 g). The mixture was stirred at 38° C. for 2 d and then filtered.

To the filtrate were added 1,4-dioxane (200 mL) and Boc$_2$O (13.1 g, 60 mmol). The reaction mixture was stirred overnight at ambient temperature and then concentrated. The residue was purified by flash column chromatography on silica gel (petroleum ether/EtOAc=20:1 to 5:1) to afford (2S,3S)-2-(tert-butoxycarbonylamino)-3-hydroxy-3-(4-methoxyphenyl)propanoic acid (2.8 g, 18% yield over three steps).

Example 43

5-Bromo-1-methylpyridin-2(1H)-one

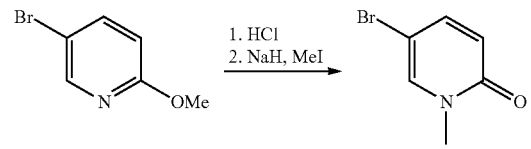

A solution of 5-bromo-2-methoxypyridine (10.0 g, 53.2 mmol) in 6N aqueous HCl (50 mL) was refluxed for 5 h. The solution was cooled to 5° C. and neutralized to pH=6.5 with 20% aqueous sodium hydroxide solution. The resulting precipitate was collected by filtration and dried to afford 5-bromopyridin-2(1H)-one (8.5 g, 91% yield) as a colorless solid.

5-Bromopyridin-2(1H)-one (2.00 g, 11.5 mmol) was added in portions to a mixture of sodium hydride (1.10 g, 27.5 mmol) in THF (100 mL) at 0° C. The mixture was stirred for 1 h at 0° C. followed by addition of iodomethane (8.20 g, 57.5 mmol). The reaction mixture was allowed to warm to ambient temperature and stirred overnight. The reaction was quenched with water (2 mL) and then concentrated. The residue was suspended in water (50 mL) and the resulting mixture was extracted with EtOAc (50 mL×3). The organic extracts were combined, dried over anhydrous sodium sulfate, and concentrated. The residue was washed with petroleum ether (30 mL) and dried to afford 5-bromo-1-methylpyridin-2(1H)-one (1.7 g, 79% yield) as a yellow solid.

Example 44

(R)-2-((1R,3S)-3-Hydroxycyclopentanecarboxamido)propanoic acid and (R)-2-((1S,3R)-3-hydroxycyclopentanecarboxamido)propanoic acid

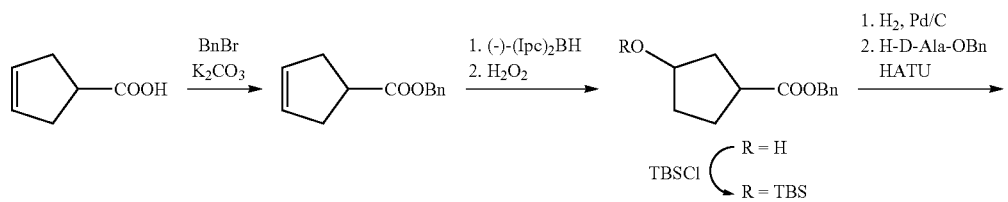

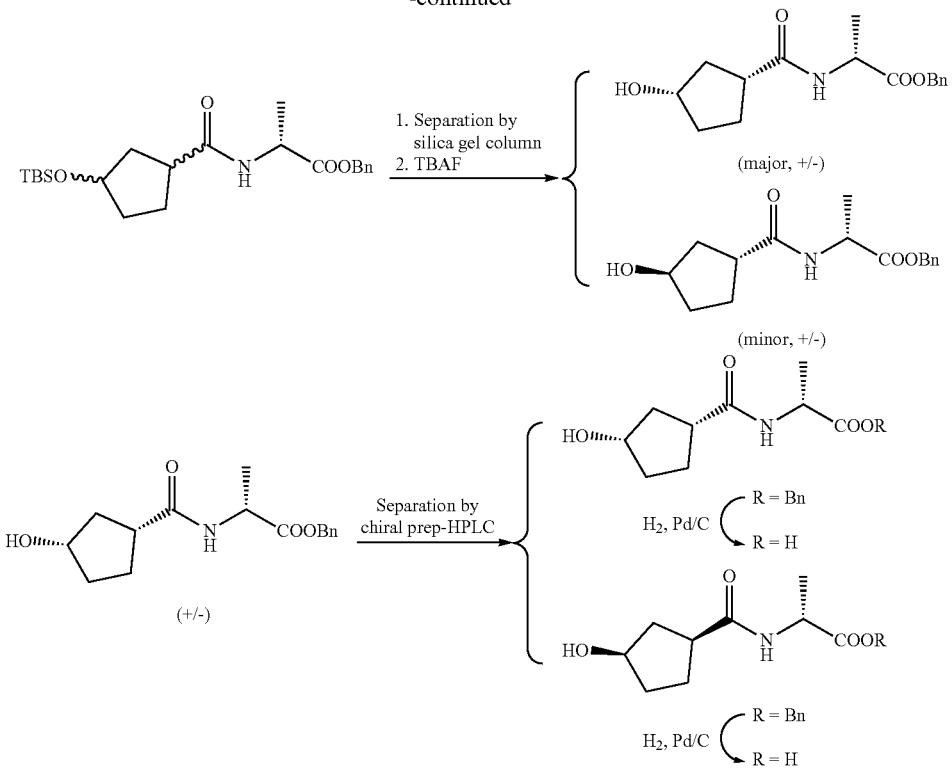

K$_2$CO$_3$ (35.0 g, 255 mmol) was added to a solution of cyclopent-3-enecarboxylic acid (20.0 g, 178 mmol) in acetonitrile (500 mL) followed by addition of benzyl bromide (36.6 g, 214 mmol). The reaction mixture was stirred for 12 h at ambient temperature. The mixture was filtered and washed with acetonitrile (200 mL). The filtrate and washings were combined and concentrated to dryness. The residue was purified by flash column chromatography on silica gel (hexane/EtOAc=10:1) to afford benzyl cyclopent-3-enecarboxylate (26.5 g, 74% yield) as an oil.

A solution of (−)-α-pinene (5.80 g, 42.6 mmol) in THF (10 mL) was cooled to 0° C. and a solution of borane-Me$_2$S (10N, 1.5 mL, 15 mmol) was added. The mixture was stirred for 4 h at 0° C. and benzyl cyclopent-3-enecarboxylate (3.5 g, 17 mmol) was added. The reaction mixture was allowed to warm to ambient temperature and stirred overnight. The mixture was cooled to 0° C. again and quenched with water (2 mL) and aqueous NaOH (3N, 15 mL). Then 30% hydrogen peroxide (20 mL) was added dropwise. The mixture was stirred for 1 h at 0° C. and diluted with water (20 mL) and EtOAc (50 mL). The two layers were separated and the aqueous phase was extracted with EtOAc (50 mL×3). The combined organic phases were washed with brine (200 mL×3), dried over anhydrous sodium sulfate, and concentrated. The residue was purified by flash column chromatography on silica gel (EtOAc/hexane=1:4) to afford benzyl 3-hydroxycyclopentanecarboxylate (1.4 g, 37% yield).

A solution of TBSCl (7.5 g, 50 mmol) in THF (50 mL) was added dropwise to a solution of benzyl 3-hydroxycyclopentanecarboxylate (10.0 g, 45.0 mmol) and imidazole (3.4 g, 50 mmol) in DMF (100 mL) at ambient temperature. The reaction mixture was stirred for 3 h and water (300 mL) was added. The resulting mixture was extracted with EtOAc (200 mL×3). The combined organic extracts were washed with 5% aqueous KHSO$_4$ (100 mL×3), saturated aqueous NaHCO$_3$ (100 mL×3), and brine (100 mL×1), respectively. The organic solution was dried over anhydrous sodium sulfate, and concentrated to dryness. The residue was purified by flash column chromatography on silica gel (EtOAc/hexane=1:20) to afford benzyl 3-(tert-butyldimethylsilyloxy)cyclopentanecarboxylate (15.2 g, quantitative) as an oil.

Pd/C (10%, 5.0 g) was added to a solution of benzyl 3-(tert-butyldimethylsilyloxy)cyclopentanecarboxylate (15.2 g, 45.5 mmol) in THF (100 mL). The suspension was stirred under hydrogen atmosphere at ambient temperature for 5 h. Pd/C was filtered off and washed with THF (50 mL). The filtrate and washings were combined and concentrated to dryness to afford the corresponding acid.

The acid (45.5 mmol) and H-D-Ala-OBn (10.0 g, HCl salt, 45.5 mmol) were dissolved in DMF (100 mL). HATU (26.5 g, 73.0 mmol) and DIPEA (16.2 mL, 118 mmol) were added at 0° C. with stirring. The reaction mixture was allowed to warm to ambient temperature and stirred for 3 h. EtOAc (500 mL) and water (500 mL) was added. The two layers were separated and the aqueous phase was extracted with EtOAc (50 mL×3). The combined organic phases were washed with brine (200 mL×3), dried over anhydrous sodium sulfate and concentrated. The residue was purified by flash column chromatography on silica gel (EtOAc/hexane=1:6) to afford (R)-benzyl 2-(3-(tert-butyldimethylsilyloxy)cyclopentanecarboxamido) propanoate (13.1 g, 71% yield).

(R)-Benzyl 2-(3-(tert-butyldimethylsilyloxy)cyclopentanecarboxamido) propanoate was separated by flash column chromatography on silica gel (EtOAc/hexane=1:10) to afford cis-(R)-benzyl 2-(3-(tert-butyldimethylsilyloxy)cyclopentanecarboxamido) propanoate (3.5 g) and trans-(R)- benzyl 2-(3-(tert-butyldimethylsilyloxy)cyclopentanecarboxamido) propanoate (0.8 g), respectively.

A solution of tetrabutylammonium fluoride (4.6 g, 17 mmol) in THF (20 mL) was added dropwise to a solution of compound cis-(R)-benzyl 2-(3-(tert-butyldimethylsilyloxy) cyclopentanecarboxamido) propanoate (3.5 g, 8.6 mmol) in THF (10 mL) at 0° C. with stirring. The reaction mixture was allowed to warm to ambient temperature and stirred for 12 h. Water (100 mL) was added and the resulting mixture was extracted with $CH_2Cl_2$ (100 mL×3). The extracts were combined and washed with 5% aqueous $KHSO_4$ (100 mL×3), saturated aqueous $NaHCO_3$ (100 mL×3), and brine (100 mL×1), respectively. The organic solution was dried over anhydrous sodium sulfate and concentrated to dryness. The residue was purified by flash column chromatography on silica gel (EtOAc/hexane=1:2) to afford cis-(R)-benzyl-3-hydroxycyclopentanecarboxamido)propanoate (1.9 g, 76% yield). The trans-(R)-benzyl 2-((1S,3R)-3-hydroxycyclopentanecarboxamido)propanoate was prepared in a similar manner.

Pd/C (10%, 1 g) was added to a solution of compound (R)-benzyl 2-((1R,3S)-3-hydroxycyclopentanecarboxamido)propanoate (500 mg, 1.7 mmol) in MeOH (20 mL). The suspension was stirred under hydrogen atmosphere at ambient temperature for 2 h. Pd/C was filtered off and washed with MeOH (5 mL). The filtrate and washings were combined and concentrated to dryness to afford (R)-2-((1R,3S)-3-hydroxycyclopentanecarboxamido)propanoic acid (450 mg, quantitative). (R)-2-((1S,3R)-3-hydroxycyclopentanecarboxamido)propanoic acid was obtained in a similar manner.

Example 45

(R)-2-((1R,3R)-3-Hydroxycyclopentanecarboxamido)propanoic acid

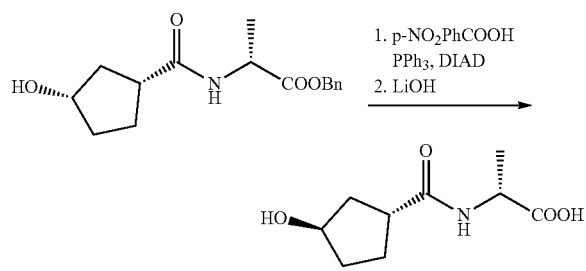

Diisopropyl azodicarboxylate (DIAD; 0.53 mL, 2.75 mmol) was added dropwise to a solution of (R)-benzyl 2-((1R,3S)-3-hydroxycyclopentanecarboxamido)propanoate (500 mg, 1.70 mmol), triphenylphosphine (676 mg, 2.60 mmol) and 4-nitrobenzoic acid (373 mg, 2.20 mmol) in dry THF (15 mL) over 0.5 h at 0-5° C. under $N_2$. The mixture was stirred for 1 h at 0-5° C. and then allowed to warm to ambient temperature and stirred for 16 h. EtOAc (50 mL) and water (50 mL) was added and the two layers were separated. The aqueous layer was extracted with EtOAc (30 mL×3) and the combined organic layers were washed with 5% aqueous $KHSO_4$ (50 mL×3), saturated aqueous $NaHCO_3$ (50 mL×3), and brine (30 mL×1), respectively. The organic solution was dried over anhydrous sodium sulfate and concentrated to dryness. The residue was purified by flash column chromatography on silica gel (EtOAc/hexane=1:2) to afford the ester (510 mg, 67% yield) as a yellow solid.

A solution of LiOH (185 mg, 4.80 mmol) in water (5 mL) was added to a solution of the ester (510 mg, 1.20 mmol) in MeOH (10 mL) at 0° C. The reaction mixture was stirred for 3 h and then acidified with 2 N aqueous HCl to pH=3. The organic solvent was removed and the remaining mixture was extracted with EtOAc/THF (1:1, 20 mL×3). The combined organic phases were washed with water (20 mL×3) and brine (20 mL×1), dried over anhydrous sodium sulfate, and concentrated to afford crude (R)-2-((1R,3R)-3-hydroxycyclopentanecarboxamido)propanoic acid (350 mg, 80% yield), which was used in the next step without further purification.

Example 46

(S)-6-Oxopiperidine-3-carboxylic acid

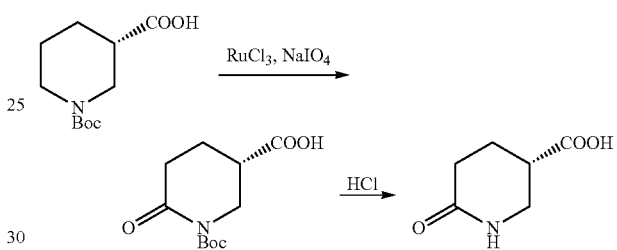

A solution of $NaIO_4$ (5.6 g, 26 mmol) in water (30 mL) and $RuCl_3$ (14 mg) were added to a solution of Boc-(R)-piperidine-3-carboxylic acid (1.5 g, 6.6 mmol) in EtOAc (30 mL). The reaction mixture was stirred overnight at ambient temperature. The two layers were separated and the aqueous phase was extracted with EtOAc (50 mL×3). The combined organic phases were washed with brine (50 mL×3), dried over anhydrous sodium sulfate, and concentrated. The residue was purified by flash column chromatography on silica gel ($CH_2Cl_2$/MeOH=20:1) to afford (S)-1-(tert-butoxycarbonyl)-6-oxopiperidine-3-carboxylic acid (790 mg, 49% yield) as a pale yellow solid.

A solution of HCl in dioxane (6M, 10 mL) was added to a solution of (S)-1-(tert-butoxycarbonyl)-6-oxopiperidine-3-carboxylic acid (700 mg, 2.90 mmol) in dioxane (5 mL) at 0° C. with stirring. The reaction mixture was stirred for 4 h and concentrated to dryness. The residue was azeotroped three times with MeOH (10 mL for each portion) to afford (S)-6-oxopiperidine-3-carboxylic acid (600 mg, quantitative) as a colorless solid. (R)-6-oxopiperidine-3-carboxylic acid was made in similar manner.

Example 47

(S)-Tetrahydro-2H-pyran-3-carboxylic acid and (R)-tetrahydro-2H-pyran-3-carboxylic acid

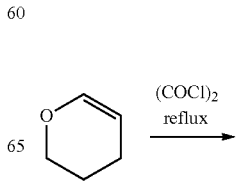

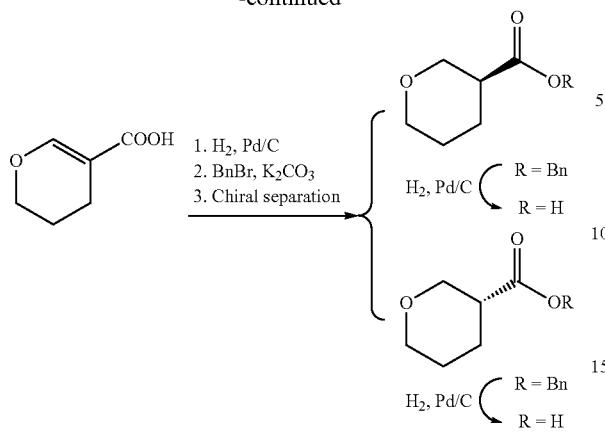

Oxalyl chloride (20 mL, 0.22 mmol) was cooled to 0° C. and 3,4-dihydro-2H-pyrane (28 mL, 0.33 mol) was added dropwise. The solution was allowed to warm to ambient temperature and stirred for 2 h. An excess of oxalyl chloride was removed under vacuum and the residue was heated at 120° C. for 0.5 h. The mixture was cooled to ambient temperature and poured into cold 10% aqueous $Na_2CO_3$ (100 mL). The resulting solution was washed with methylene chloride (50 mL×3) and then acidified with 6 N HCl to pH=3. The mixture was extracted with methylene chloride (50 mL×3) and the combined organic phases were dried over anhydrous sodium sulfate and concentrated to afford 3,4-dihydro-2H-pyran-5-carboxylic acid (9.1 g, 32% yield), which was used directly without further purification.

Pd/C (10%, 3 g) was added to a solution of 3,4-dihydro-2H-pyran-5-carboxylic acid (7.0 g, 55 mmol) in MeOH (100 mL). The suspension was stirred under hydrogen atmosphere (100 psi) at 40° C. for 10 h. The catalyst was filtered off and washed with MeOH (50 mL). The filtrate and washings were combined and concentrated to dryness to afford crude product. The crude product was dissolved in acetonitrile (200 mL) and benzyl bromide (9.9 g, 58 mmol) and $K_2CO_3$ (19.0 g, 138 mmol) were added. The resulting suspension was heated at 50-60° C. for 4 h and then cooled to ambient temperature. The mixture was filtered and the filtration cake was washed with acetonitrile (50 mL). The filtrate and washings were combined and concentrated to dryness. The residue was purified by flash column chromatography on silica gel (Hexane/EtOAc=20:1) to afford a mixture (7.1 g) of (S)-benzyl tetrahydro-2H-pyran-3-carboxylate and (R)-benzyl tetrahydro-2H-pyran-3-carboxylate, which was separated by chiral prep-HPLC to afford (S)-benzyl tetrahydro-2H-pyran-3-carboxylate (2.1 g, 17% yield) and (R)-benzyl tetrahydro-2H-pyran-3-carboxylate (2.0 g, 16% yield), respectively.

Pd/C (10%, 1 g) was added to a solution of (S)-benzyl tetrahydro-2H-pyran-3-carboxylate (1.1 g, 5 mmol) in MeOH (10 mL). The suspension was stirred under hydrogen atmosphere at ambient temperature for 2 h. The catalyst was filtered off and washed with MeOH (5 mL). The filtrate and washings were combined and concentrated to dryness to afford (S)-tetrahydro-2H-pyran-3-carboxylic acid (0.6 g, 92% yield). (R)-Tetrahydro-2H-pyran-3-carboxylic acid was made in a similar manner.

Example 48

(S)-Tetrahydrofuran-3-carboxylic acid

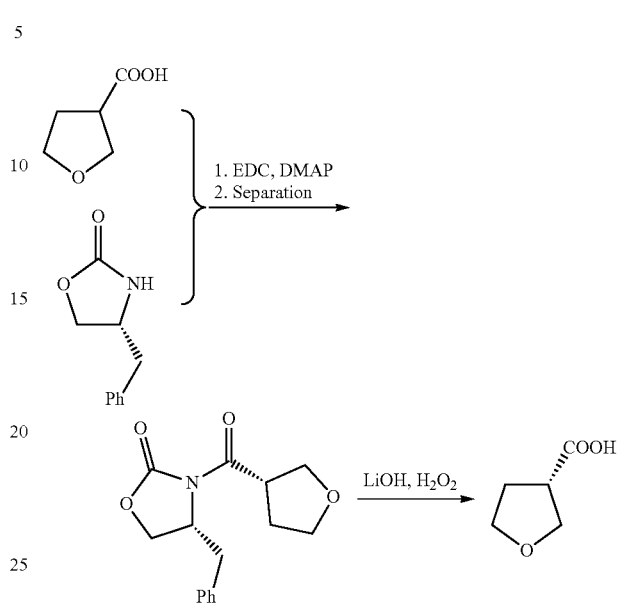

1-Ethyl-3-(3-dimethylaminopropyl)carbodiimide (EDCI; 362 mg, 1.90 mmol) and DMAP (202 mg, 1.90 mmol) were added to a solution of (R)-4-benzyl-oxazolidin-2-one (333 mg, 1.90 mmol) and tetrahydrofuran-3-carboxylic acid (200 mg, 1.70 mmol) in $CH_2Cl_2$ (20 mL) at ambient temperature. The reaction mixture was stirred for 3 h at ambient temperature and water (20 mL) was added. The two layers were separated and the aqueous phase was extracted with $CH_2Cl_2$ (20 mL×3). The combined organic phases were washed with brine (50 mL×3), dried over anhydrous sodium sulfate and concentrated. The residue was purified by flash column chromatography on silica gel ($CH_2Cl_2$/EtOAc=100:2) to afford (R)-4-benzyl-3-((S)-tetrahydrofuran-3-carbonyl)oxazolidin-2-one (120 mg, 25% yield).

$H_2O_2$ (0.44 mL, 30%, 7.0 mmol) was added dropwise to a solution of (R)-4-benzyl-3-((S)-tetrahydrofuran-3-carbonyl)oxazolidin-2-one (250 mg, 0.900 mmol) in THF (10 mL) at 0° C. with stirring over 0.5 h. The mixture was stirred for 10 min and a solution of LiOH—$H_2O$ (84 mg, 2.0 mmol) in water (0.5 mL) was added dropwise. The reaction mixture was stirred for 3 h at 0° C. and then quenched with saturated aqueous $Na_2SO_3$ (10 mL). The organic solvent was removed and the residual aqueous solution was washed with $CH_2Cl_2$ (20 mL×3) and acidified with 1N HCl to pH=3. The solution was concentrated to dryness to afford crude (S)-tetrahydrofuran-3-carboxylic acid (100 mg, quantitative), which was used directly without further purification.

Example 49

2-(3-Oxopiperazin-1-yl)acetic acid

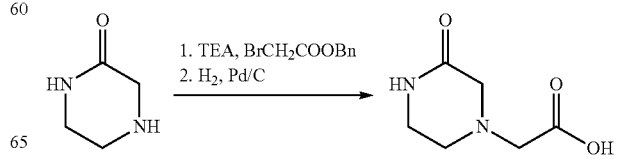

Triethylamine (4.13 mL, 30.0 mmol) was added dropwise to a solution of piperazin-2-one (1.0 g, 10 mmol) and benzyl bromoacetate (2.3 g, 10 mmol) in dichloromethane (20 mL) at 0° C. The reaction mixture was allowed to warm to ambient temperature and stirred for 2 h. Water (20 mL) was added and the resulting mixture was extracted with dichloromethane (20 mL×3). The organic extracts were combined, dried over anhydrous sodium sulfate and concentrated. The residue was purified by flash column chromatography on silica gel (dichloromethane/methanol=100:1 to 50:1) to afford the benzyl ester (1.5 g, 60% yield) as a colorless solid, which was subjected to hydrogenolysis in the presence of Pd/C (0.2 g) in methanol (10 mL) for 1 h at ambient temperature to afford 2-(3-oxopiperazin-1-yl)acetic acid (0.4 g, 42% yield).

Example 50

2-(4-Hydroxy-4-methylpiperidin-1-yl)acetic acid

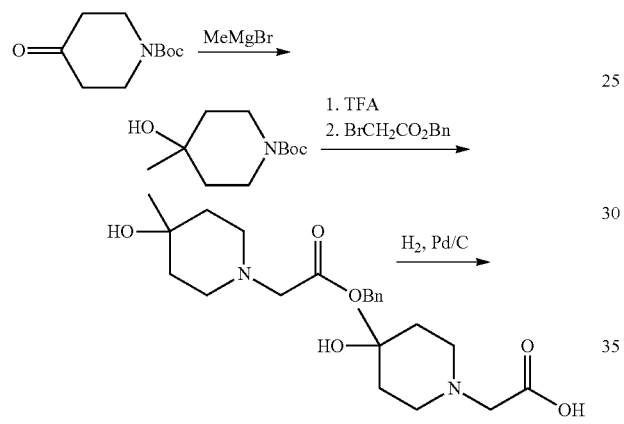

A solution of N-Boc-piperidin-4-one (1.0 g, 5.0 mmol) was dissolved in THF (20 mL) and then cooled to −40° C. MeMgBr (2.8 M, 7.2 mL, 20 mmol) was added slowly over 10 min. The reaction mixture was allowed to warm to ambient temperature and stirred for 2 h. The mixture was cooled to 0° C. and saturated aqueous NH₄Cl (50 mL) was added. The resulting mixture was extracted with EtOAc (100 mL). The organic layer was washed with water (50 mL) and brine (50 mL), dried over anhydrous sodium sulfate, and concentrated to afford tert-butyl 4-hydroxy-4-methylpiperidine-1-carboxylate (1.0 g, 92% yield) as a yellow oil.

TFA (3.0 mL) was added to a solution of tert-butyl 4-hydroxy-4-methylpiperidine-1-carboxylate (1.0 g, 4.7 mmol) in CH₂Cl₂ (5 mL) at 0° C. with stirring. The reaction mixture was stirred for 1 h and then concentrated to dryness. The residue was azeotroped three times with EtOAc (3 mL for each portion) to remove residual TFA to afford compound the amine (1.0 g, quantitative) as its TFA salt.

K₂CO₃ (6.9 g, 50 mmol) was added to a solution of the TFA salt (2.50 g, 16.6 mmol) and benzyl 2-bromoacetate (4.30 g, 18.8 mmol) in DMF (10 mL). The reaction mixture was stirred at ambient temperature for 3 h and then pound into water (300 mL). The resulting mixture was extracted with EtOAc (300 mL×3) and the combined organic layers were washed with water (400 mL) and concentrated. The residue was purified by flash column chromatography on silica gel (DCM/MeOH=50:1) to afford (3.0 g, 68% yield) as a yellow oil.

To a solution of compound benzyl 2-(4-hydroxy-4-methylpiperidin-1-yl)acetate (400 mg, 1.61 mmol) in methanol (10 mL) was added Pd/C (10%, 100 mg) and the mixture was stirred under hydrogen atmosphere at ambient temperature for 1 h. The mixture was filtered through a pad of Celite and the filtrate was concentrated to afford 2-(4-hydroxy-4-methylpiperidin-1-yl)acetic acid (250 mg, quantitative) as a colorless solid, which was used directly without further purification.

Example 51

(S)-4,5,6,7-Tetrahydro-1H-indazole-5-carboxylic acid and (R)-4,5,6,7-tetrahydro-1H-indazole-5-carboxylic acid

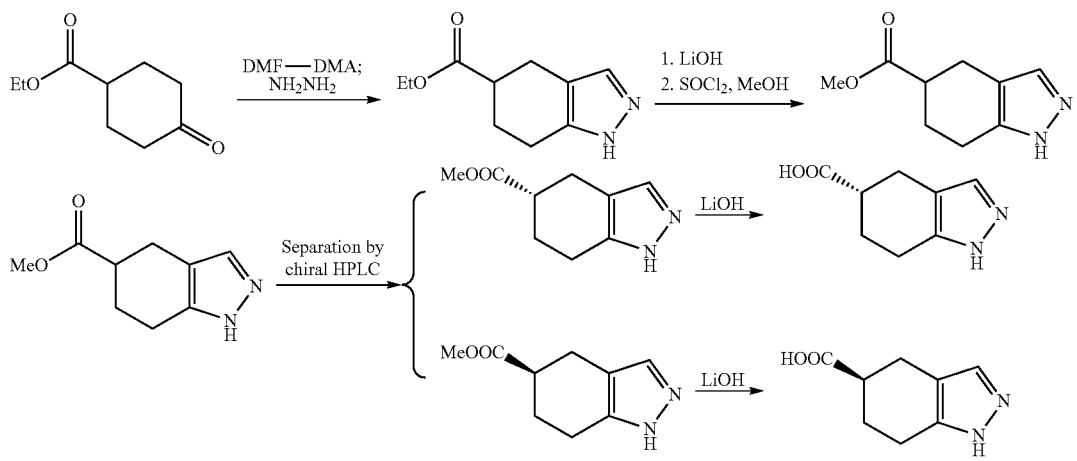

A solution of ethyl 4-oxocyclohexanecarboxylate (50 g, 0.29 mol) in DMF-DMA (275 mL) was heated at 110° C. for 12 h. The mixture was concentrated and hydrazine hydrate (73.5 g, 1.47 mol) in ethanol (1000 mL) was heated under reflux overnight. Most of ethanol was removed and the remaining mixture was treated with water (400 mL). The resulting mixture was extracted with EtOAc (400 ml×2).

The combined organic layers were washed with brine (400 mL) and concentrated. The residue was purified by flash column chromatography on silica gel (DCM/MeOH=30:1) to afford crude ethyl 4,5,6,7-tetrahydro-1H-indazole-5-carboxylate (18 g) as a colorless solid.

To a solution of ethyl 4,5,6,7-tetrahydro-1H-indazole-5-carboxylate (3.00 g, 15.5 mmol) in methanol (10 mL) was added water (10 mL) and lithium hydroxide hydrate (780 mg, 5.90 mmol). The reaction mixture was stirred at ambient temperature overnight and then concentrated to remove most of methanol. The remaining mixture was acidified with diluted aqueous HCl to pH=4 and then concentrated. The residue was dried under vacuum to afford the corresponding acid (1.7 g, 66% yield) as a colorless solid, which was used directly without further purification.

A mixture of the acid (1.7 g, 10 mmol) and SOCl$_2$ (2.5 g, 21 mmol) in methanol (20 mL) was heated under reflux for 2 h. The mixture was cooled to ambient temperature and then concentrated. The residue was purified by flash column chromatography on silica gel (DCM/MeOH=30:1) to afford the crude product (1.0 g, 55% yield) as a light yellow solid, which was further separated by preparative chiral-HPLC to afford (S)-methyl 4,5,6,7-tetrahydro-1H-indazole-5-carboxylate (0.2 g) and (R)-methyl 4,5,6,7-tetrahydro-1H-indazole-5-carboxylate (0.2), respectively.

To a solution of (S)-methyl 4,5,6,7-tetrahydro-1H-indazole-5-carboxylate (500 mg, 2.80 mmol) in methanol (20 mL) were added water (10 mL) and lithium hydroxide hydrate (234 mg, 5.57 mmol) at 0° C. The reaction mixture was stirred at ambient temperature for 2 h and then concentrated to remove most of methanol. The remaining mixture was acidified with diluted aqueous HCl to pH=4 and then concentrated. The residue was dried under vacuum to afford (S)-4,5,6,7-tetrahydro-1H-indazole-5-carboxylic acid (380 mg, 81% yield) as a colorless solid, which was used directly without further purification. (R)-methyl 4,5,6,7-tetrahydro-1H-indazole-5-carboxylate was synthesized in a similar manner.

Example 52

(S)-2-(2-Morpholinoacetamido)propanoic acid

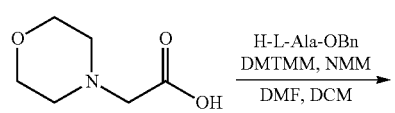

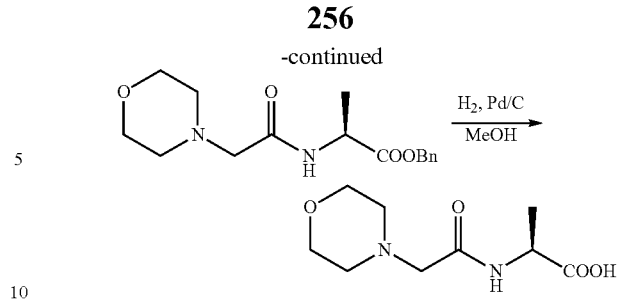

To DMTMM (76.1 g, 0.276 mol) and N-methylmorpholine (NMM; 32.9 mL, 0.300 mol) was added to a 0° C. solution of 2-morpholinoacetic acid (20.0 g, 0.138 mmol) and L-alanine benzyl ester hydrochloride (35.7 g, 0.166 mol) in DMF (100 mL) and DCM (200 mL). The reaction mixture was stirred for 4 h at ambient temperature then concentrated. EtOAc (500 mL) and water (500 mL) was added to the residue. The resulting two layers were separated and the aqueous phase was extracted with EtOAc (3×300 mL). The combined organic layers were washed with brine (3×500 mL), dried over anhydrous sodium sulfate, and concentrated. The residue was purified by flash column chromatography on silica gel (DCM/MeOH=100:3) to afford (S)-benzyl 2-(2-morpholinoacetamido)propanoate (21.1 g, 50% yield).

To Pd/C (10%, 5.0 g) was added a solution of (S)-benzyl 2-(2-morpholinoacetamido)propanoate (20.0 g, 69.0 mmol) in MeOH (200 mL). The mixture was stirred under a hydrogen atmosphere at ambient temperature for 4 h, then it was filtered and rinsed with MeOH (200 mL). The filtrate and washings were combined and concentrated to dryness to afford crude product which was washed with EtOAc (2×100 mL) and dried under vacuum to afford (S)-2-(2-morpholinoacetamido)propanoic acid (12.8 g, 86% yield) as an off-white solid. $^1$H NMR (300 MHz, DMSO-d$_6$): δ 7.95 (m, 1H), 4.25 (m, 1H), 3.70 (m, 4H), 3.08 (d, J=15.4 Hz, 2H), 2.40-2.55 (m, 4H), 1.30 (d, J=6.6 Hz, 3H).

Example 53

(R)-1-(2,4-Dimethoxybenzyl)-5-oxopyrrolidine-3-carboxylic acid and (S)-1-(2,4-dimethoxybenzyl)-5-oxopyrrolidine-3-carboxylic acid

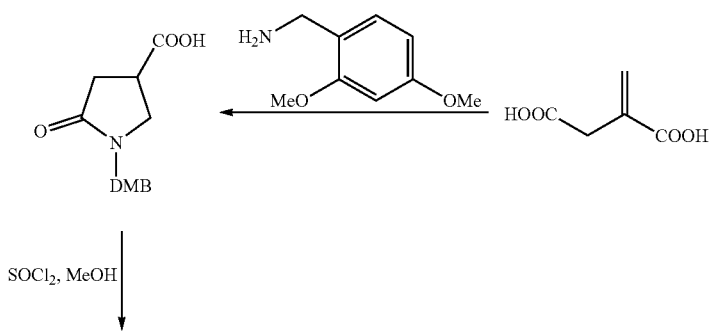

-continued

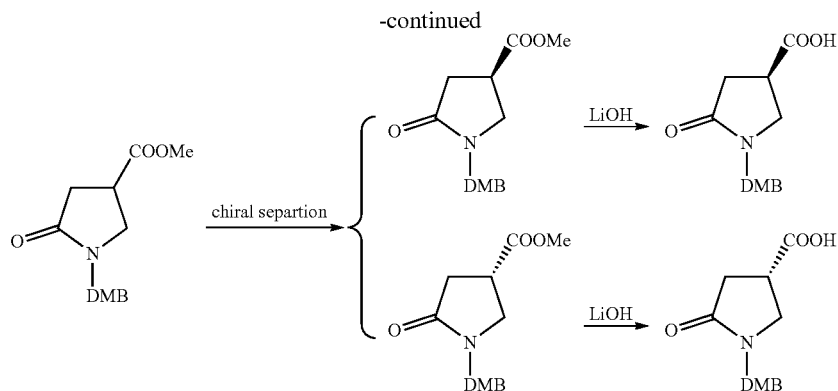

To a solution of itaconic acid (13.0 g, 100 mmol) in toluene (50 ml) was added a solution of 2,4-dimethoxybenzylamine (17.54 g, 105.0 mmol) in toluene (50 mL) and the reaction mixture was stirred for 15 h under reflux. The mixture was cooled to ambient temperature and then concentrated under reduced pressure. The residue was treated with diethyl ether (100 mL) and the resulting precipitate was collected by filtration, washed with diethyl ether and EtOAc and dried to afford 1-(2,4-dimethoxybenzyl)-5-oxopyrrolidine-3-carboxylic acid (20.0 g, 71% yield) as a colorless solid.

$SOCl_2$ (6.4 g, 54 mmol) was added dropwise to methanol (40 mL) followed by addition of 1-(2,4-dimethoxybenzyl)-5-oxopyrrolidine-3-carboxylic acid (5.0 g, 18 mmol) at 0° C. The reaction mixture was stirred at ambient temperature for 1 h and then heated under reflux for 7 h. The mixture was cooled to ambient temperature and concentrated. The residue was purified by flash column chromatography on silica gel (petroleum ether/EtOAc=6:1 to 2:1) to afford methyl 1-(2,4-dimethoxybenzyl)-5-oxopyrrolidine-3-carboxylate (a mixture of two enantiomers, 4.3 g, 81% yield) as a colorless oil. The two enantiomers were separated by chiral prep-HPLC.

LiOH (1.36 g, 32.5 mmol) was added to a solution of (R)-methyl 1-(2,4-dimethoxybenzyl)-5-oxopyrrolidine-3-carboxylate (3.18 g, 10.9 mmol) in $THF/H_2O$ (1:1, 40 mL) at 0° C. and the reaction mixture was stirred for 1 h. THF was removed and the remaining aqueous solution was washed with diethyl ether (50 mL×2). The aqueous phase was adjusted to pH=5 with 3 N aqueous HCl and the resulting mixture was extracted with DCM (40 ml×3). The combined extracts were washed with water (100 mL×3) and brine (100 mL×1), dried over anhydrous sodium sulfate and concentrated to afford compound (R)-1-(2,4-dimethoxybenzyl)-5-oxopyrrolidine-3-carboxylic acid (2.76 g, 88% yield) as a colorless solid. (S)-1-(2,4-dimethoxybenzyl)-5-oxopyrrolidine-3-carboxylic acid was prepared using the same method.

Example 54

(1r,4r)-4-Hydroxy-1-methylcyclohexanecarboxylic acid

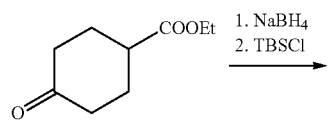

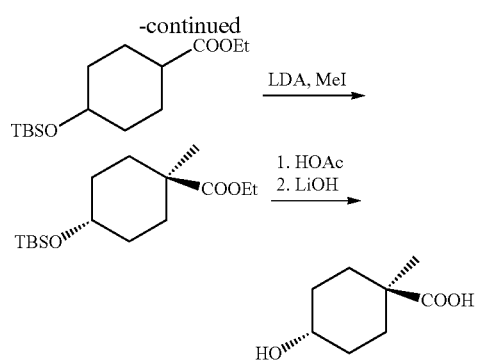

$NaBH_4$ (12.7 g, 0.34 mol) was added in portions to a solution of ethyl 4-oxocyclohexanecarboxylate (52.0 g, 0.31 mol) in ethanol (300 mL) at 0° C. over a period of 0.5 h with stirring. The suspension was stirred overnight at ambient temperature and then quenched with 1N aqueous HCl (100 mL). The solvent was removed under reduced pressure and the residue was dissolved in $CH_2Cl_2$ (500 mL). The resulting solution was washed with saturated aqueous $NaHCO_3$ (300 mL×3) and brine (300 mL×1), dried over anhydrous sodium sulfate, and concentrated to dryness to give the corresponding alcohol.

The alcohol was dissolved in DMF (300 mL) and imidazole (51.4 g, 0.450 mol) was added. A solution of TBSCl (54.4 g, 0.360 mol) in THF (100 mL) was added dropwise and the reaction mixture was stirred at ambient temperature for 12 h. Water (300 mL) was added and the resulting mixture was extracted with EtOAc (300 mL×2). The combined organic extracts were washed with 5% aqueous $KHSO_4$ (300 mL×3), saturated aqueous $NaHCO_3$ (300 mL×3), and brine (300 mL×1), respectively. The organic solution was dried over anhydrous sodium sulfate and concentrated to dryness. The residue was purified by flash column chromatography on silica gel (EtOAc/Hexane=1:30) to afford ethyl 4-(tert-butyldimethylsilyloxy)cyclohexanecarboxylate (48.0 g, 54% yield over two steps) as an oil.

LDA (2M solution, 7.70 mL, 15.4 mmol) was added dropwise to a solution of ethyl 4-(tert-butyldimethylsilyloxy)cyclohexanecarboxylate (4.0 g, 14 mmol) in THF (30 mL) at −78° C. with stirring. The mixture was stirred for 1 h followed by addition of iodomethane (2.20 g, 15.4 mmol) dropwise. The reaction mixture was stirred at −78° C. for 0.5 h and then allowed to warm to ambient temperature and stirred overnight. The reaction was quenched with water (200 mL) and the resulting mixture was extracted with $CH_2Cl_2$ (200 mL×3). The combined organic phases were washed with brine (500 mL×1), dried over anhydrous sodium sulfate and concentrated. The residue was purified by flash column chromatography on silica gel (Hexane/EtOAc=100:1) to afford trans-ethyl 4-(tert-butyldimethylsilyloxy)-1-methylcyclohexanecarboxylate (2.3 g, 60% yield) as an oil.

Acetic acid (2.0 mL) was added dropwise to a solution of trans-ethyl 4-(tert-butyldimethyl silyloxy)-1-methylcyclohexanecarboxylate (2.0 g, 7.0 mmol) in THF (10 mL) at ambient temperature. The reaction mixture was heated at 50° C. for 3 h. The mixture was concentrated and then diluted with water (100 mL). The resulting mixture was extracted with $CH_2Cl_2$ (50 mL×3). The combined extracts were washed with saturated aqueous $NaHCO_3$ (50 mL×3) and brine (100 mL×1), dried over anhydrous sodium sulfate, and concentrated to afford the alcohol.

The alcohol was treated with a solution of lithium hydroxide-$H_2O$ (100 mg, 25 mmol) in water/THF (10 mL/4 mL) for 30 min. THF was removed and the aqueous solution was acidified to pH=3-4 with 1N aqueous HCl. The resulting mixture was concentrated to dryness to afford crude trans-4-hydroxy-1-methylcyclohexanecarboxylic acid (150 mg, 13% yield), which was used directly without further purification.

Example 55

(1r,4r)-4-Hydroxy-4-methylcyclohexanecarboxylic acid reaction mixture was stirred at 0° C. for 12 h. The mixture was concentrated to afford the corresponding acid as its sodium salt.

Benzyl bromide (3.3 g, 19 mmol) was added to a suspension of the acid (sodium salt) in DMF (40 mL). The reaction mixture was stirred at ambient temperature for 1 h and water (100 mL) was added. The resulting mixture was extracted with EtOAc (100 mL×2). The combined organic layers were washed with brine (150 mL) and water (150 mL), dried over anhydrous sodium sulfate, and concentrated. The residue was purified by flash column chromatography on silica gel (petroleum ether/EtOAc=6:1 to 4:1) to afford (507 mg, 21% yield) and cis-benzyl 4-hydroxy-4-methylcyclohexanecarboxylate (748 mg, 31% yield), respectively.

To a solution of (1r,4r)-benzyl 4-hydroxy-4-methylcyclohexanecarboxylate (500 mg, 2.00 mmol) in THF (20 mL) was added Pd/C (50 mg, 10%). The mixture was stirred under a hydrogen atmosphere (1 atm) at ambient temperature for 2 h. The mixture was filtered through a pad of Celite and the filtrate was concentrated under reduced pressure to afford (1r,4r)-4-hydroxy-4-methylcyclohexanecarboxylic acid (260 mg, 82% yield) as a colorless solid, which was used in the next step without further purification. (1s,4s)-4-hydroxy-4-methylcyclohexanecarboxylic acid was synthesized in a similar manner.

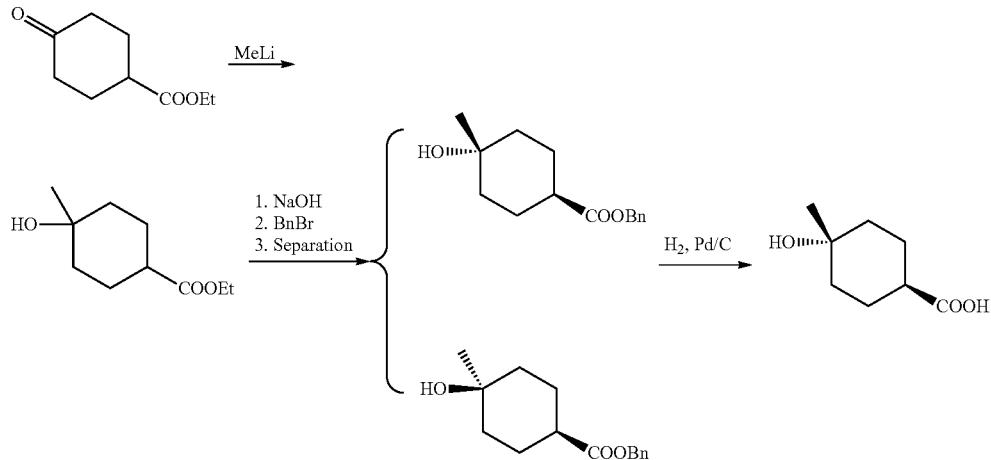

To a solution of ethyl 4-oxocyclohexanecarboxylate (4.00 g, 23.5 mmol) in diethyl ether (80 mL) was added MeLi (37.6 mL, 1M in diethyl ether) at −60° C. under nitrogen atmosphere. The reaction mixture was stirred at −60° C. for 30 min. Saturated aqueous $NH_4Cl$ (50 mL) was added and the resulting mixture was extracted with EtOAc (100 mL×2). The combined organic layers were washed with brine (150 mL) and water (150 mL), dried over anhydrous sodium sulfate, and concentrated. The residue was purified by flash column chromatography on silica gel (petroleum ether/EtOAc=10:1) to afford ethyl 4-hydroxy-4-methylcyclohexanecarboxylate (1.8 g, 41% yield) as an oil.

NaOH (0.58 g, 14.5 mmol) was added to a solution of ethyl 4-hydroxy-4-methylcyclohexanecarboxylate (1.8 g, 9.7 mmol) in ethanol/$H_2O$ (30 mL/15 mL) at 0° C. and the Example 56

(1s,4s)-4-Hydroxy-1-methylcyclohexanecarboxylic acid

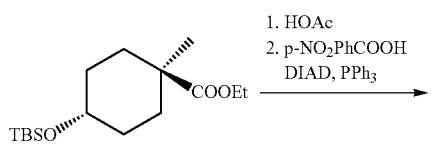

-continued

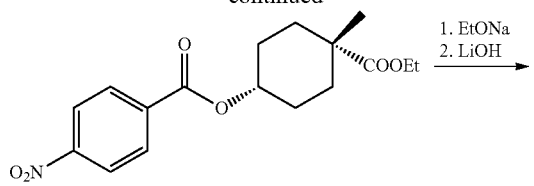

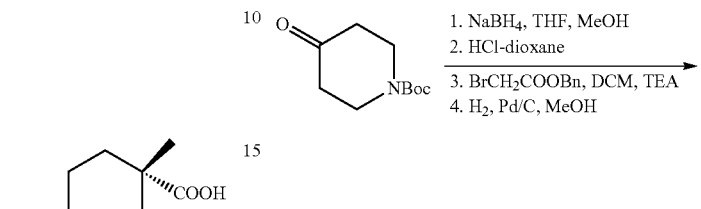

Acetic acid (2 mL) was added dropwise to a solution of (1r,4r)-ethyl 4-((tert-butyldimethylsilyl)oxy)-1-methylcyclohexanecarboxylate (2.0 g, 7 mmol) in THF (10 mL) at ambient temperature. The reaction mixture was heated at 50° C. for 3 h. The mixture was concentrated and water (100 mL) was added. The resulting mixture was extracted with $CH_2Cl_2$ (50 mL×3) and the combined extracts were washed with saturated aqueous $NaHCO_3$ (50 mL×3) and brine (100 mL×1), dried over anhydrous sodium sulfate, and concentrated. The residue was purified by flash column chromatography on silica gel (hexane/EtOAc=3:1) to afford the corresponding alcohol (1.1 g, 84% yield) as an oil.

The alcohol (1.0 g, 5.4 mmol), 4-nitrobenzoic acid (1.2 g, 7.0 mmol) and triphenylphosphine (2.11 g, 8.10 mmol) were dissolved in THF (40 mL). The mixture was cooled to 0° C. under $N_2$ and DIAD (1.74 g, 8.60 mmol) was added dropwise over 0.5 h. The reaction mixture was stirred for 1 h at 0° C. and then allowed to warm to ambient temperature and stirred for 16 h. EtOAc (100 mL) and water (100 mL) were added and two layers were separated. The aqueous layer was extracted with EtOAc (100 mL×3). The combined organic layers were washed with brine (100 mL×1), dried over anhydrous sodium sulfate and concentrated. The residue was purified by flash column chromatography on silica gel (hexane/EtOAc=5:1) to afford cis-4-(ethoxycarbonyl)-4-methylcyclohexyl 4-nitrobenzoate (1.2 g, 66% yield).

cis-4-(Ethoxycarbonyl)-4-methylcyclohexyl 4-nitrobenzoate (970 mg, 2.90 mmol) was added to a freshly prepared solution of NaOEt (14.5 mmol) in EtOH (40 mL) at 0° C. The mixture was stirred for 6 h at ambient temperature and then concentrated. The residue was purified by flash column chromatography on silica gel (hexane/EtOAc=3:1) to afford (1s,4s)-ethyl 4-hydroxy-1-methylcyclohexanecarboxylate (400 mg, 74% yield).

(1s,4s)-Ethyl 4-hydroxy-1-methylcyclohexanecarboxylate was treated with a solution of lithium hydroxide-$H_2O$ (361 mg, 8.6 mmol) in water/THF (10 mL/4 mL) for 30 min. THF was removed and the aqueous solution was acidified to pH=3-4 with 1N HCl. The mixture was concentrated to dryness to afford crude compound cis-4-hydroxy-1-methylcyclohexanecarboxylic acid (quantitative), which was used directly without further purification.

Example 57

2-(4-Hydroxypiperidin-1-yl)acetic acid

Sodium borohydride (5.7 g, 0.15 mol) was added in portions to a solution of tert-butyl 4-oxopiperidine-1-carboxylate (15 g, 75 mmol) in THF/MeOH (150 mL/30 mL) at −10° C. The reaction mixture was stirred for 30 min at −10° C. and then poured into ice-water (300 mL). The resulting mixture was extracted with EtOAc (300 mL×3) and the combined extracts were dried over anhydrous sodium sulfate and concentrated to afford tert-butyl 4-hydroxypiperidine-1-carboxylate (13.2 g, 87% yield).

tert-Butyl 4-hydroxypiperidine-1-carboxylate was treated a 6 N HCl/dioxane solution (20 mL) and the mixture was allowed to stand for 20 min at ambient temperature. The solvent was removed to afford piperidin-4-ol (HCl salt, 9.0 g, quant.).

To piperidin-4-ol (HCl salt, 9.0 g) was added a solution of benzyl 2-bromoacetate (15.0 g, 65.7 mmol) in dichloromethane (100 mL). The mixture was cooled to 0° C. and triethylamine (27.6 mL, 0.200 mol) was added. The reaction mixture was allowed to warm to ambient temperature and stirred for 2 h. Water (100 mL) was added and the resulting mixture was extracted with dichloromethane (100 mL×3). The organic extracts were combined, dried over anhydrous sodium sulfate, and concentrated. The residue was purified by flash column chromatography on silica gel (dichloromethane/methanol=20:1 to 10:1) to afford benzyl 2-(4-hydroxypiperidin-1-yl)acetate (8.3 g, 51% yield).

A mixture of benzyl 2-(4-hydroxypiperidin-1-yl)acetate (1.0 g, 4.0 mmol) and Pd/C (0.1 g) in methanol (20 mL) was hydrogenated for 1 h at ambient temperature. The Pd/C was filtered off and the filtrate was concentrated to dryness to afford 2-(4-hydroxypiperidin-1-yl)acetic acid (0.6 g, 94% yield).

Example 58

2-(3,3-Difluoropiperidin-1-yl)acetic acid, 2-(4,4-difluoropiperidin-1-yl)acetic acid, 2-(3,3-difluoropyrrolidin-1-yl)acetic acid, 2-(4-(trifluoromethyl)piperidin-1-yl)acetic acid, and 2-(4-chloropiperidin-1-yl)acetic acid

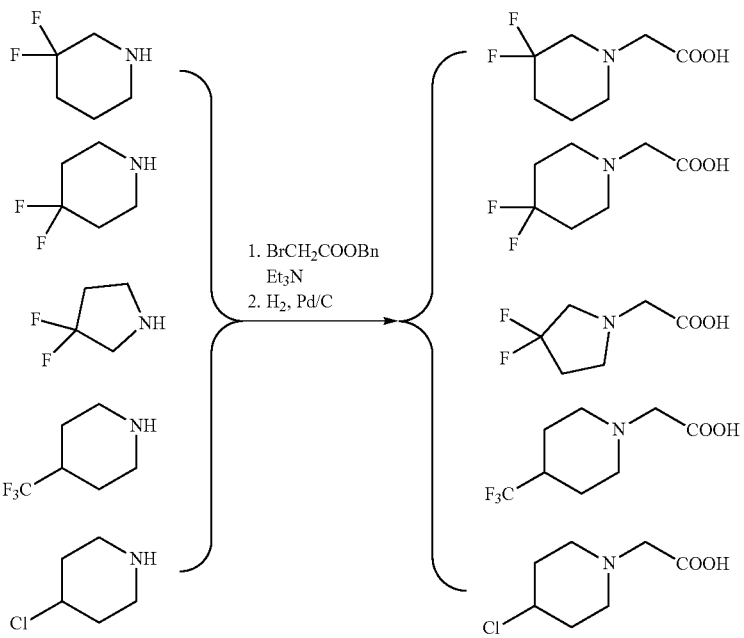

Triethylamine (0.660 mL, 4.76 mmol) was added to a solution of 3,3-difluoropiperidine-HCl (500 mg, 3.17 mmol) and benzyl 2-bromoacetate (763 mg, 3.33 mmol) in methylene chloride (10 mL). The reaction mixture was stirred at ambient temperature for 2 h. The mixture was washed with 1 N aqueous sodium hydroxide and water, successively. The organic layer was concentrated and the residue was purified by flash column chromatography on silica gel (Hexane/EtOAc=25:1) to afford benzyl ester of 2-(3,3-difluoropiperidin-1-yl)acetic acid (486 mg, 56% yield) as a yellow oil.

To a solution of benzyl ester of 2-(3,3-difluoropiperidin-1-yl)acetic acid (486 mg, 0.850 mmol) in methanol (20 mL) was added Pd/C (10%, 100 mg). The suspension was stirred under hydrogen atmosphere at ambient temperature for 1 h. The catalyst was filtered off and washed with MeOH (5 mL). The filtrate and washings were combined and concentrated to dryness to afford 2-(3,3-difluoropiperidin-1-yl)acetic acid (292 mg, 90% yield) as a greenish yellow solid, which was used directly without further purification.

The following compounds were synthesized in a similar manner: 2-(4,4-difluoropiperidin-1-yl)acetic acid, 2-(3,3-difluoropyrrolidin-1-yl)acetic acid, 2-(4-(trifluoromethyl)piperidin-1-yl)acetic acid, 2-(4-chloropiperidin-1-yl)acetic acid

Example 59

(S)-2-((R)-2-((1r,3R)-3-Hydroxycyclobutanecarboxamido)propanamido)-3-(4-methoxyphenyl)propanoic acid

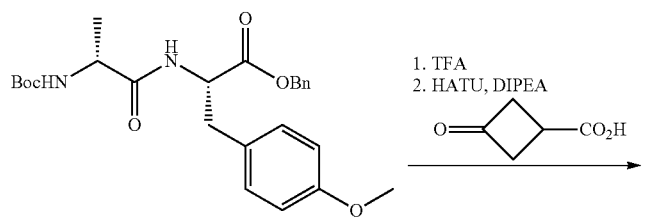

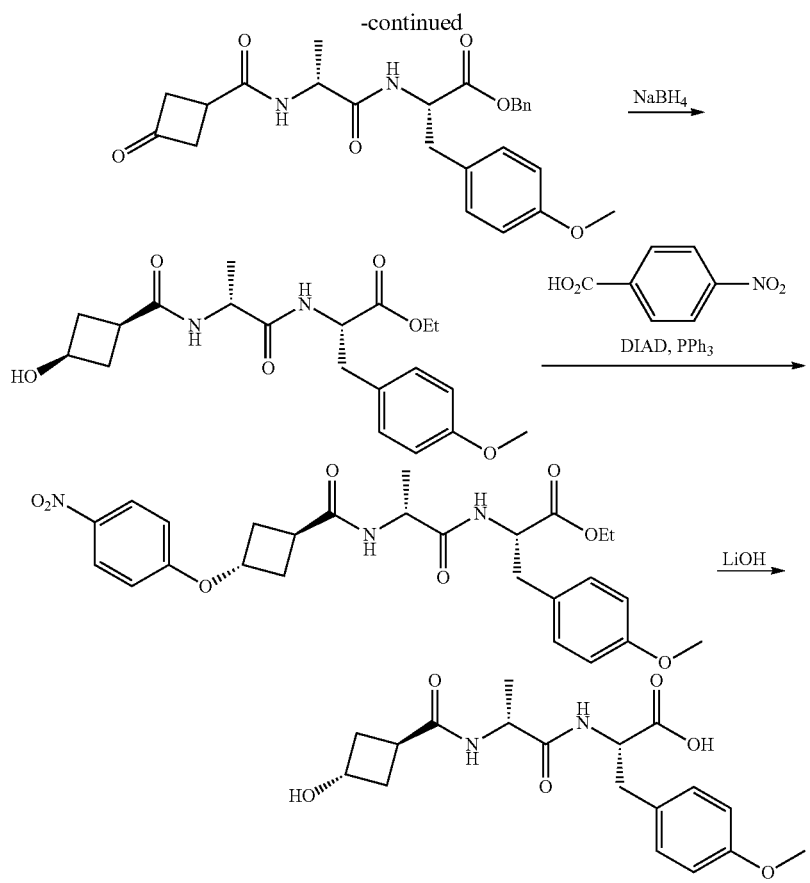

To a solution of (S)-benzyl 2-((R)-2-((tert-butoxycarbonyl)amino)propanamido)-3-(4-methoxy phenyl)propanoate (1.2 g, 2.6 mmol) in DCM (10 mL) was added TFA (3 mL). The mixture was stirred at ambient temperature for 0.5 h and then concentrated to dryness to the crude amine (TFA salt).

To the amine (TFA salt) was suspended in DCM (20 mL) and 3-oxocyclobutanecarboxylic acid (0.36 g, 3.15 mmol) and HATU (1.09 g, 1.43 mmol) were added. The mixture was cooled to 0° C. followed by addition of DIPEA to pH=8. The reaction mixture was stirred at ambient temperature for 30 min and water (50 mL) was added. The organic layer was dried over anhydrous sodium sulfate and concentrated. The residue was purified by flash column chromatography on silica gel (petroleum ether/EtOAc=2:1 to 1:1) to afford (S)-benzyl 3-(4-methoxyphenyl)-2-((R)-2-(3-oxocyclobutanecarboxamido)propanamido)propanoate (0.99 g, 83% yield over two steps) as a colorless solid.

To a solution of (S)-benzyl 3-(4-methoxyphenyl)-2-((R)-2-(3-oxocyclobutanecarboxamido)propanamido)propanoate (0.99 g, 2.2 mmol) in ethanol (20 mL) was added NaBH$_4$ (0.17 g, 4.4 mmol) in three portions over 20 min. After complete addition, the reaction mixture was stirred at ambient temperature for 2 h and then quenched with saturated aqueous ammonium chloride (50 mL). Ethanol was removed under reduced pressure and the residue was extracted with DCM (50 mL×2). The organics were combined, dried over anhydrous sodium sulfate, and concentrated. The residue was purified by flash column chromatography on silica gel (DCM/methanol=10:1) to afford (S)-Ethyl 2-((R)-2-((1s,3S)-3-hydroxycyclobutanecarboxamido)propanamido)-3-(4-methoxyphenyl)propanoate (0.62 g, 63% yield) as a colorless solid.

To a solution of (S)-ethyl 2-((R)-2-((1s,3S)-3-hydroxycyclobutanecarboxamido)propanamido)-3-(4-methoxyphenyl)propanoate (0.62 g, 1.6 mmol), 4-nitrobenzoic acid (0.53 g, 3.2 mmol) and triphenylphosphine (0.88 g, 3.4 mmol) in THF (20 mL) was added DIAD (0.660 mL, 3.36 mmol). The reaction mixture was stirred under nitrogen for 2 d and quenched with saturated aqueous NaHCO$_3$ (50 mL). The resulting mixture was extracted with EtOAc (50 mL×2) and the organics were combined, dried over anhydrous sodium sulfate, and concentrated. The residue was purified by flash column chromatography on silica gel to afford (S)-ethyl 3-(4-methoxyphenyl)-2-((R)-2-((1r,3R)-3-(4-nitrophenoxy)cyclobutane carboxamido)propanamido)propanoate (0.59 g, 73% yield) as a colorless solid.

To a solution of (S)-ethyl 3-(4-methoxyphenyl)-2-((R)-2-((1r,3R)-3-(4-nitrophenoxy)cyclobutane carboxamido)propanamido)propanoate (0.59 g, 1.1 mmol) in CH$_3$OH/H$_2$O (15 mL, 2:1) was added LiOH—H$_2$O (0.14 g, 3.3 mmol). The reaction mixture was stirred at ambient temperature for 1 h and then concentrated. Water (50 mL) was added to the residue and the resulting mixture was washed with DCM (50 mL×2). The aqueous phase was acidified with diluted aqueous HCl to pH=3-4 and then washed again with DCM (50 mL×2). The aqueous phase was concentrated under vacuum to afford crude (S)-2-((R)-2-((1r,3R)-3-hydroxycyclobutanecarboxamido)propanamido)-3-(4-methoxyphenyl)propanoic acid (0.46 g, 84% yield) as a colorless solid, which was used for the next step without further purification.

Example 60

(S)-2-((tert-Butoxycarbonyl)amino)-3-cyanopropanoic acid

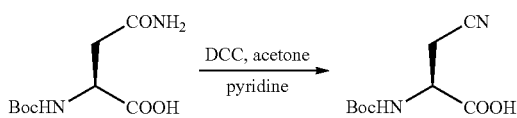

A solution of dicyclohexylcarbodiimide (DCC, 8.3 g, 40 mmol) in acetone (100 ml) was added dropwise a suspension of Boc-asparagine (9.3 g, 40 mmol) in pyridine (50 mL) at 0° C. under nitrogen. The reaction mixture was stirred at ambient temperature for 3 h. The mixture was filtered and the filtrate was concentrated. The residue was dissolved in dichloromethane (400 mL) and the solution was washed with 2 N aqueous HCl (20 mL×3) and brine (200 mL), dried over anhydrous sodium sulfate, and concentrated to afford (S)-2-(tert-butoxycarbonylamino)-3-cyanopropanoic acid (5.5 g, 56% yield), which was used directly without further purification.

Example 61

2-((tert-Butoxycarbonyl)amino)-3,3,3-trifluoropropanoic acid

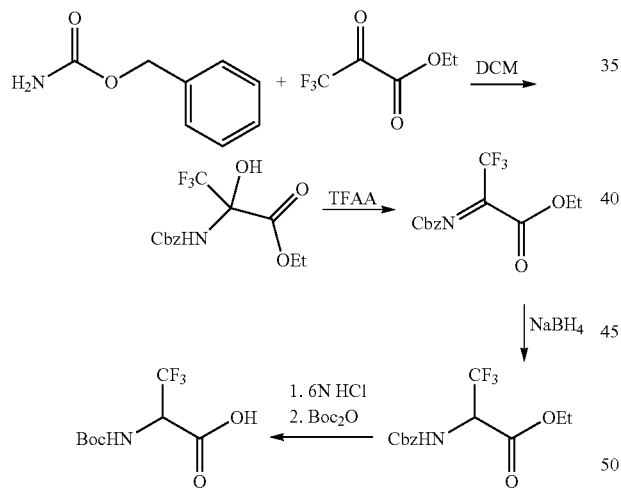

To a solution of ethyl 3,3,3-trifluoro-2-oxopropanoate (30 g, 176 mmol) in dichloromethane (1 L) was added benzyl carbamate (26.6 g). The reaction mixture was stirred at ambient temperature for 24 h and the resulting precipitate was collected by filtration and dried under vacuum to afford ethyl 2-(benzyloxycarbonylamino)-3,3,3-trifluoro-2-hydroxypropanoate (49.0 g, 87% yield), which was used directly without further purification.

To a solution of ethyl 2-(benzyloxycarbonylamino)-3,3,3-trifluoro-2-hydroxypropanoate (49.0 g, 153 mmol) in diethyl ether (350 mL) was added dropwise TFAA (35.3 g, 168 mmol) at 0° C. followed by addition of pyridine dropwise (26.5 g, 336 mmol) at 0° C. The reaction mixture was allowed to warm to ambient temperature and stirred for 6 h. The mixture was filtered and the filtrate was concentrated to afford ethyl 2-(benzyloxycarbonylimino)-3,3,3-trifluoropropanoate (45.0 g, 97% yield), which was used directly without further purification.

To a solution of ethyl 2-(benzyloxycarbonylimino)-3,3,3-trifluoropropanoate (45.0 g, 148.5 mmol) in diethyl ether (300 mL) was added sodium borohydride (11.3 g 297 mmol) in portions at 0° C. The reaction mixture was allowed to warm to ambient temperature and stirred for 16 h. The reaction was quenched with water (100 mL) carefully and the organic layer was separated. The aqueous layer was extracted with EtOAc (100 mL×3). The organic layers were combined, washed with brine (200 mL×2), dried over anhydrous sodium sulfate and concentrated. The residue was purified by flash column chromatography on silica gel (EtOAc/petroleum ether=1:9) to afford ethyl 2-(benzyloxycarbonylamino)-3,3,3-trifluoropropanoate (22.0 g, 48% yield).

A suspension of ethyl 2-(benzyloxycarbonylamino)-3,3,3-trifluoropropanoate (5.0 g, 16.4 mmol) in 6N aqueous HCl (200 mL) was refluxed for 6 h. The mixture was cooled to ambient temperature and then concentrated under reduced pressure.

The residue was suspended in acetonitrile (100 mL) and triethylamine (4.96 mL, 36 mmol) and di-tert-butyl dicarbonate (3.9 g, 18 mmol) were added. The pale yellow solution was stirred at ambient temperature overnight and then diluted with dichloromethane (400 mL). The resulting solution was washed with 1N aqueous HCl (100 mL) and brine (200 mL), dried over anhydrous sodium sulfate and concentrated. The residue was washed with petroleum ether (100 mL) to afford 2-(tert-Butoxycarbonylamino)-3,3,3-trifluoropropanoic acid (3.0 g, 75% yield) as a colorless solid.

Example 62

(S)-3-(3,4-Bis(benzyloxy)phenyl)-2-((S)-2-(2-morpholinoacetamido)propanamido)propanoic acid

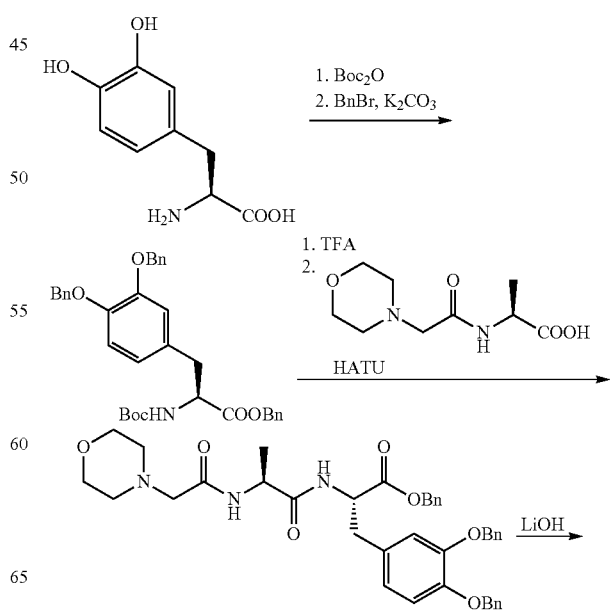

-continued

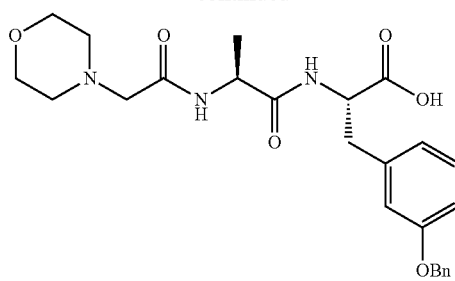

L-Dopa (10.0 g, 50 mmol) was suspended in water (100 mL) and acetone (100 mL) and 2N aqueous NaOH was added to adjust pH=8. Boc$_2$O (10.5 g, 50 mmol) was added and the reaction mixture was stirred for 12 h at ambient temperature. The organic solvent was removed. The aqueous solution was washed with ethyl ether (100 mL×3) and then acidified with 2N aqueous hydrochloric acid to pH=3. The resulting mixture was extracted with EtOAc (200 mL×3). The combined organic phases were washed with brine (100 mL×1), dried over anhydrous sodium sulfate, and concentrated to afford Boc-L-dopa (15.1 g, quantitative), which was used directly for the next step without further purification.

K$_2$CO$_3$ (21.0 g, 150 mmol) was added to a solution of Boc-L-dopa (10.0 g, 33 mmol) in acetonitrile (100 mL) followed by addition of benzyl bromide (21.0 g, 123 mmol). The suspension was heated at 50-60° C. for 4 h and then cooled to ambient temperature. The mixture was filtered and the filtration cake was washed with acetonitrile (50 mL). The filtrate and washings were combined and concentrated to dryness. The residue was purified by flash column chromatography on silica gel (Hexane/EtOAc=20:1) to afford (S)-benzyl 3-(3,4-bis(benzyloxy)phenyl)-2-(tert-butoxycarbonylamino)propanoate (15.3 g, yield 80%).

TFA (2 mL) was added to a solution of (S)-benzyl 3-(3,4-bis(benzyloxy)phenyl)-2-(tert-butoxycarbonylamino)propanoate (1.9 g, 3.1 mmol) in CH$_2$Cl$_2$ (5 mL) at 0° C. with stirring. The mixture was stirred for 1 h and concentrated to dryness. The residue was azeotroped three times with EtOAc (5 mL for each portion) to remove residual TFA and the amine was obtained as its TFA salt, which was used directly without further purification.

HATU (1.9 g, 5.1 mmol) and N-methylmorpholine (1.5 g, 15 mmol) were added to a solution of amine (TFA salt, 3.4 mmol) and (S)-2-(2-morpholinoacetamido)propanoic acid (800 mg, 3.70 mmol) in methylene chloride (20 mL) and DMF (10 mL) at 0° C. with stirring. The suspension was stirred for 1 h at ambient temperature and then concentrated. The residue was purified by flash column chromatography on silica gel (methylene chloride/methanol=20:1) to afford (S)-benzyl 3-(3,4-bis(benzyloxy)phenyl)-2-((S)-2-(2-morpholinoacetamido) propanamido)propanoate (1.70 g, yield 82%) as a colorless solid.

A solution of LiOH (279 mg, 6.6 mmol) in water (6 mL) was added to a solution of (S)-benzyl 3-(3,4-bis(benzyloxy) phenyl)-2-((S)-2-(2-morpholinoacetamido) propanamido) propanoate (1.1 g, 1.66 mmol) in MeOH (30 mL) at 0° C. with stirring. The reaction mixture was stirred for 3 h and then acidified with 2 N aqueous HCl to pH=3. The resulting mixture was concentrated and the residue was carried forward without further purification.

Example 63

(S)-2-Amino-N—((S)-3-(cyclopent-1-en-1-yl)-1-((R)-2-methyloxiran-2-yl)-1-oxopropan-2-yl)-3-(4-methoxyphenyl)propanamide TFA salt

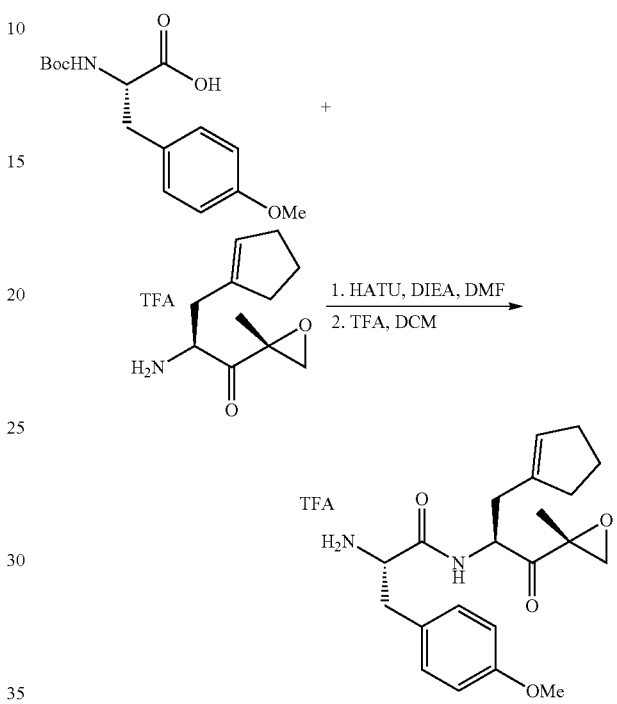

To (S)-2-((tert-butoxycarbonyl)amino)-3-(4-methoxyphenyl)propanoic acid (2.00 g, 6.78 mmol) and (S)-2-amino-3-(cyclopent-1-en-1-yl)-1-((R)-2-methyloxiran-2-yl) propan-1-one (1.98 g, 6.78 mmol) in DMF (10 mL) at 0° C. was added HATU (3.00 g, 8.36 mmol) followed by DIEA (5.90 mL, 33.9 mmol) and the mixture was stirred for 15 min then quenched with NaHCO$_3$ (sat., aq.), extracted with EtOAc (2×), washed with brine, dried with sodium sulfate, filtered, and concentrated. Purification by column chromatography (1:1 hexanes/EtOAc) provided tert-butyl ((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)carbamate (2.62 g, 82%) as a colorless oil. MS(EI) for C$_{26}$H$_{36}$N$_2$O$_6$, found 473.3 (MH)$^+$.

To tert-butyl ((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)carbamate (0.99 g, 2.1 mmol) was added DCM (5 mL) and TFA (5 mL). The mixture was allowed to stand at ambient temperature for 30 min then it was concentrated to provide crude (S)-2-amino-N—((S)-3-(cyclopent-1-en-1-yl)-1-((R)-2-methyloxiran-2-yl)-1-oxopropan-2-yl)-3-(4-methoxyphenyl)propanamide (quant.) and carried forward without further purification. MS(EI) for C$_{21}$H$_{28}$N$_2$O$_4$, found 373.2 (MH)$^+$.

(S)-2-amino-N—((S)-3-cyclohexenyl-1-((R)-2-methyloxiran-2-yl)-1-oxopropan-2-yl)-3-(4-(methylsulfonyl)phenyl)propanamide was synthesized in a similar manner.

Example 64

(S)-2-((S)-2-Aminopropanamido)-N—((S)-3-(cyclopent-1-en-1-yl)-1-((R)-2-methyloxiran-2-yl)-1-oxopropan-2-yl)-3-(4-methoxyphenyl)propanamide (TFA salt)

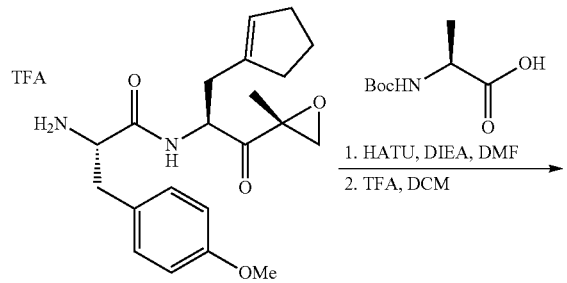

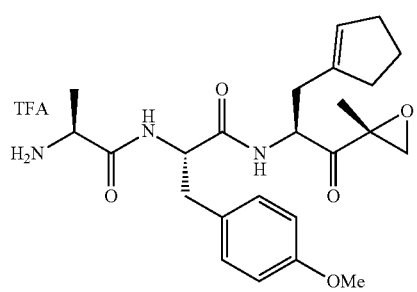

To (S)-2-amino-N—((S)-3-(cyclopent-1-en-1-yl)-1-((R)-2-methyloxiran-2-yl)-1-oxopropan-2-yl)-3-(4-methoxyphenyl)propanamide (TFA salt, 2.00 g, 4.26 mmol) and (S)-2-((tert-butoxycarbonyl)amino)propanoic acid (805 mg, 4.26 mmol) in DMF (10 mL) at 0° C. was added HATU (1.94 g, 5.11 mmol) followed by DIEA (4.37 mL, 25.6 mmol) and the mixture was stirred for 15 min then quenched with NaHCO$_3$ (sat., aq.), extracted with EtOAc (2×), washed with brine, dried with sodium sulfate, filtered, and concentrated. Purification by column chromatography (1:1 hexanes/EtOAc) provided tert-butyl ((S)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)carbamate (1.94 g, 84%) as a colorless oil. MS(EI) for C$_{29}$H$_{41}$N$_3$O$_7$, found 544.3 (MH)$^+$.

To tert-butyl ((S)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)carbamate (1.94 g, 2.18 mmol) was added DCM (10 mL) and TFA (10 mL). The mixture was allowed to stand at ambient temperature for 30 min then it was concentrated to provide crude tert-butyl ((S)-1-(((S)-1-(((S)-3-(cyclopent-1-en-1-yl)-1-((R)-2-methyloxiran-2-yl)-1-oxopropan-2-yl)amino)-3-(4-methoxyphenyl)-1-oxopropan-2-yl)amino)-1-oxopropan-2-yl)carbamate (quant.) which was carried forward without further purification. MS(EI) for C$_{24}$H$_{33}$N$_3$O$_5$, found 444.2 (MH)$^+$.

Example 65

(S)-3-Hydroxy-2-(2-morpholinoacetamido)propanoic acid

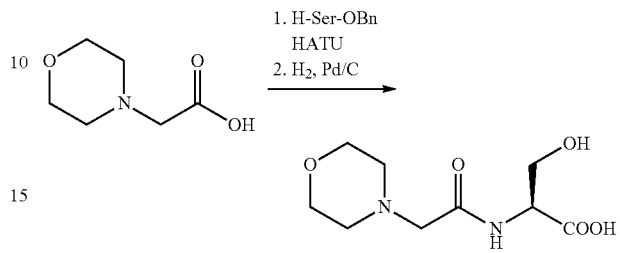

HATU (25.2 g, 66.0 mmol) and DIPEA (20 mL) were added to a solution of 2-morpholinoacetic acid (8.00 g, 55.0 mmol) and L-serine benzyl ester (HCl salt, 12.7 g, 55.0 mmol) in DMF (150 mL) at 0° C. with stirring. The reaction mixture was allowed to warm to ambient temperature and stirred for 8 h. EtOAc (500 mL) and water (500 mL) was added and two layers were separated. The aqueous phase was extracted with EtOAc (300 mL×3) and the combined organic phases were washed with brine (200 mL×3), dried over anhydrous sodium sulfate, and concentrated. The residue was purified by flash column chromatography on silica gel (CH$_2$Cl$_2$/MeOH=20:1) to afford the benzyl ester (8.1 g, 47% yield).

Pd/C (3 g, 10%) was added to a solution of ester (8.1 g, 25 mmol) in THF (80 mL) and H$_2$O (20 mL). The mixture was stirred under hydrogen atmosphere (1 atm) at ambient temperature overnight and then filtered through a pad of celite. The filtrate was concentrated under reduced pressure to afford (S)-3-hydroxy-2-(2-morpholinoacetamido)propanoic acid (5.5 g, 85% yield) as a colorless solid.

Example 66

(S)-2-amino-1-((R)-2-methyloxiran-2-yl)-3-phenylpropan-1-one TFA salt was prepared using methods described in the following reference: WO2007/149512A2, which is incorporated herein by reference in its entirety.

Additional Synthetic Procedures

Example 67

(S)-3-cyclopropyl-N—((S)-1-((R)-2-methyloxiran-2-yl)-1-oxo-3-phenylpropan-2-yl)-2-((S)-2-(2-morpholinoacetamido)propanamido)propanamide (C-1224)

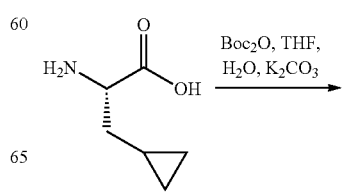

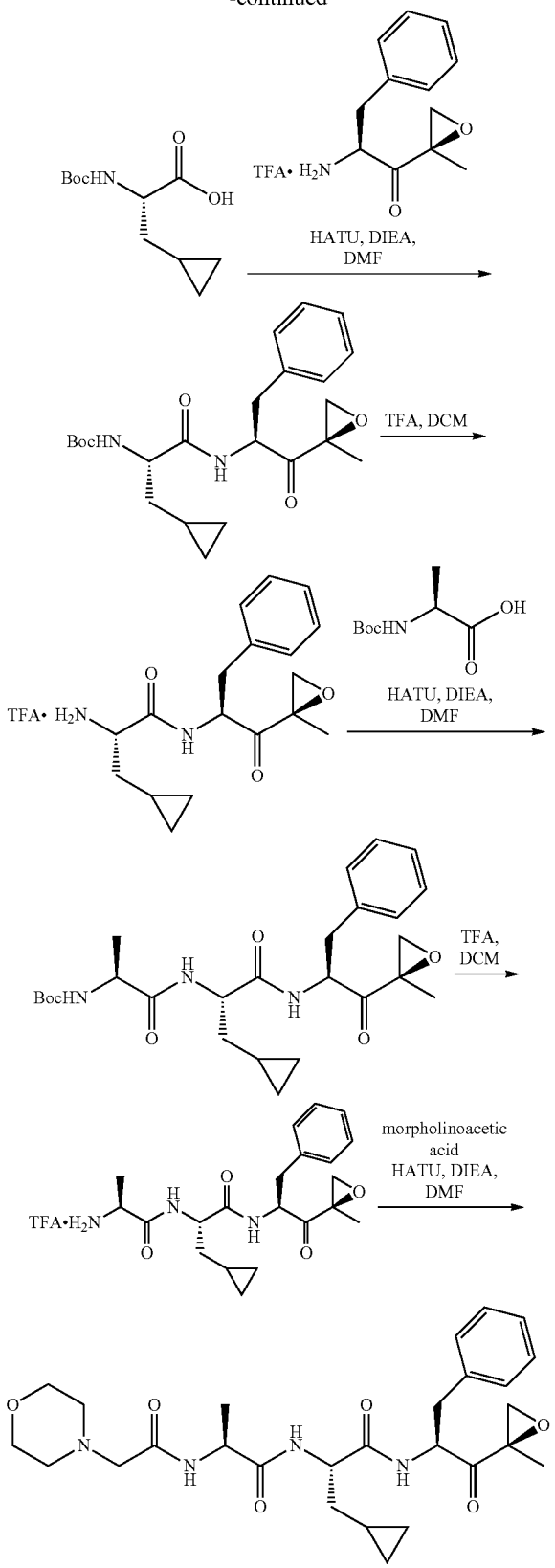

To (S)-2-amino-3-cyclopropylpropanoic acid (600 mg, 4.65 mmol) in THF (3 mL) and water (3 mL) was added K₂CO₃ (2.20 g, 16.0 mmol) and di-tert-butyl dicarbonate (1.31 g, 6.03 mmol). After stirring at ambient temperature for 12 h the mixture was concentrated and washed with diethyl ether. The aqueous layer was acidified with citric acid to pH ~3 then extracted with DCM (3×), dried with sodium sulfate, filtered, and concentrated. The crude (S)-2-((tert-butoxycarbonyl)amino)-3-cyclopropylpropanoic acid (1.13 g, quant.) was provided as a colorless oil that was carried forward without further purification. MS (EI) for $C_{11}H_{19}NO_4$, found 230.1 (MH⁺).

To (S)-2-((tert-butoxycarbonyl)amino)-3-cyclopropylpropanoic acid (1.02 g, 4.44 mmol) was added (S)-2-amino-1-((R)-2-methyloxiran-2-yl)-3-phenylpropan-1-one TFA salt (1.34 g, 4.44 mmol), HATU (2.02 g, 5.33 mmol), and DMF (10 mL). The mixture was cooled to 0° C. and DIEA (3.09 mL, 17.8 mmol) was added. The reaction mixture was stirred at ambient temperature for 30 min then quenched with sodium bicarbonate (sat.), extracted with ethyl acetate (2×), dried with sodium sulfate, filtered, and concentrated. Purification by column chromatography (0-70% ethyl acetate/heptane) provided tert-butyl ((S)-3-cyclopropyl-1-(((S)-1-((R)-2-methyloxiran-2-yl)-1-oxo-3-phenylpropan-2-yl)amino)-1-oxopropan-2-yl)carbamate (1.33 g, 72%) as a colorless solid. MS (EI) for $C_{23}H_{32}N_2O_5$, found 417.3 (MH⁺).

To tert-butyl ((S)-3-cyclopropyl-1-(((S)-1-((R)-2-methyloxiran-2-yl)-1-oxo-3-phenylpropan-2-yl)amino)-1-oxopropan-2-yl)carbamate (663 mg, 1.59 mmol) was added DCM (2.5 mL) and TFA (2.5 mL). The mixture was allowed to stand at ambient temperature for 30 min before it was concentrated to provide (S)-2-amino-3-cyclopropyl-N—((S)-1-((R)-2-methyloxiran-2-yl)-1-oxo-3-phenylpropan-2-yl)propanamide TFA salt (657 mg, quant.) as a yellow oil that was carried forward without further purification. MS (EI) for $C_{20}H_{24}F_3N_2O_4$, found 317.2 [M-TFA]⁺.

To (S)-2-amino-3-cyclopropyl-N—((S)-1-((R)-2-methyloxiran-2-yl)-1-oxo-3-phenylpropan-2-yl)propanamide TFA salt (657 mg, 1.59 mmol) was added (S)-2-((tert-butoxycarbonyl)amino)propanoic acid (601 mg, 3.18 mmol), HATU (1.40 g, 3.67 mmol), and DMF (5 mL). The mixture was cooled to 0° C. and DIEA (1.11 mL, 6.36 mmol) was added. The reaction mixture was stirred at ambient temperature for 30 min then quenched with sodium bicarbonate (sat.), extracted with ethyl acetate (2×), dried with sodium sulfate, filtered, and concentrated. Purification by column chromatography (0-80% ethyl acetate/heptane) provided tert-butyl ((S)-1-(((S)-3-cyclopropyl-1-(((S)-1-((R)-2-methyloxiran-2-yl)-1-oxo-3-phenylpropan-2-yl)amino)-1-oxopropan-2-yl)amino)-1-oxopropan-2-yl)carbamate (380 mg, 49%) as a colorless solid. MS (EI) for $C_{26}H_{37}N_3O_6$, found 488.4 (MH⁺).

To tert-butyl ((S)-1-(((S)-3-cyclopropyl-1-(((S)-1-((R)-2-methyloxiran-2-yl)-1-oxo-3-phenylpropan-2-yl)amino)-1-oxopropan-2-yl)amino)-1-oxopropan-2-yl)carbamate (380 mg, 0.779 mmol) was added DCM (2.5 mL) and TFA (2.5 mL). The mixture was allowed to stand at ambient temperature for 30 min before it was concentrated to provide (S)-2-((S)-2-aminopropanamido)-3-cyclopropyl-N—((S)-1-((R)-2-methyloxiran-2-yl)-1-oxo-3-phenylpropan-2-yl)propanamide TFA salt (377 mg, quant.) as a yellow oil that was carried forward without further purification. MS (EI) for $C_{23}H_{29}F_3N_3O_5$, found 388.3 [M-TFA]⁺.

To (S)-2-((S)-2-aminopropanamido)-3-cyclopropyl-N—((S)-1-((R)-2-methyloxiran-2-yl)-1-oxo-3-phenylpropan-2-yl)propanamide TFA salt (377 mg, 0.779 mmol) was added 2-morpholinoacetic acid (226 mg, 1.56 mmol), HATU (622 mg, 1.64 mmol), and DMF (4 mL). The mixture was cooled to 0° C. and DIEA (0.68 mL, 3.9 mmol) was added. The reaction mixture was stirred at ambient temperature for 30 min then quenched with sodium bicarbonate (sat.), extracted with ethyl acetate (2×), dried with sodium sulfate, filtered, and concentrated. Purification by column chromatography (3:1 DCM/ethyl acetate+0-10% methanol) provided (S)-3-cyclopropyl-N—((S)-1-((R)-2-methyloxiran-2-yl)-1-oxo-3-phenylpropan-2-yl)-2-((S)-2-(2-morpholinoacetamido)propanamido)propanamide (320 mg, 80%) as a colorless solid. $^1$H NMR (400 MHz, CDCl$_3$): δ 7.54 (d, J=7.6 Hz, 1H), 7.32-7.22 (m, 3H), 7.16-7.14 (m, 2H), 6.67 (d, J=7.6 Hz, 1H), 6.47 (d, J=7.6 Hz, 1H), 4.86-4.81 (m, 1H), 4.43 (q, J=6.8 Hz, 2H), 4.34 (dd, J=14.4, 6.8 Hz, 1H), 3.74-3.72 (m, 4H), 3.30 (d, J=4.8 Hz, 1H), 3.14 (dd, J=14.0, 5.2 Hz, 1H), 3.04 (d, J=4.8 Hz, 2H), 2.92 (d, J=4.8 Hz, 1H), 2.83 (dd, J=14.0, 7.8 Hz, 1H), 2.54-2.52 (m, 4H), 1.56 (t, J=6.8 Hz, 2H), 1.50 (s, 3H), 1.35 (d, J=7.2 Hz, 3H), 0.41-0.36 (m, 2H), 0.05-0.00 (m, 2H). MS (EI) for C$_{27}$H$_{38}$N$_4$O$_6$, found 515.4 (MH$^+$).

Example 68

(S)—N—((S)-1-((R)-2-methyloxiran-2-yl)-1-oxo-3-phenylpropan-2-yl)-2-((S)-2-(2-morpholinoacetamido)propanamido)-3-(pyridin-2-yl)propanamide (C-1505)

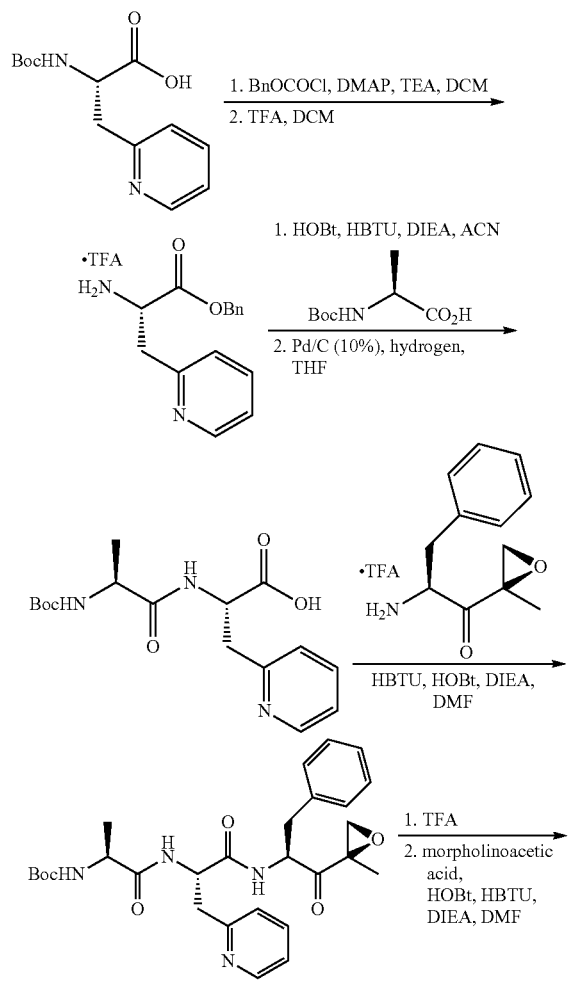

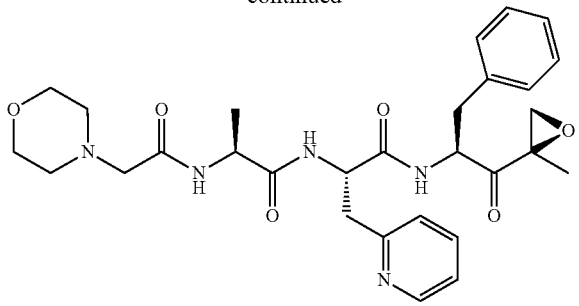

To (S)-2-((tert-butoxycarbonyl)amino)-3-(pyridin-2-yl)propanoic acid (1.00 g, 3.76 mmol) in DCM (10 mL) was added TEA (0.974 mL, 7.52 mmol) and DMAP (23 mg, 0.188 mmol) and the reaction mixture was cooled to 0° C. and BnCOCl (635 mL, 4.51 mmol) was added via an addition funnel over 20 min. The mixture was allowed to warm to ambient temperature overnight at which time it was quenched with sodium bicarbonate (sat.), extracted with ethyl acetate (2×), dried with sodium sulfate, filtered, and concentrated. Purification by column chromatography (0-50% ethyl acetate/hexanes+1% TEA) provided (S)-benzyl 2-((tert-butoxycarbonyl)amino)-3-(pyridin-2-yl)propanoate (0.558 g, 42%) as a light brown solid. MS (EI) for C$_{20}$H$_{24}$N$_2$O$_4$, found 257.2 [M-Boc]$^+$.

To (S)-benzyl 2-((tert-butoxycarbonyl)amino)-3-(pyridin-2-yl)propanoate (0.558 g, 1.57 mmol) was added DCM (2 mL) followed by TFA (2 mL). The reaction mixture was allowed to stand for 1 h at which time it was concentrated to provide (S)-benzyl 2-amino-3-(pyridin-2-yl)propanoate TFA salt (quant. yield) as a yellow oil. MS (EI) for C$_{17}$H$_{16}$F$_3$N$_2$O$_3$, found 257.2 [M-TFA]$^+$.

To (S)-2-((tert-butoxycarbonyl)amino)propanoic acid (495 mg, 2.62 mmol) was added (S)-benzyl 2-amino-3-(pyridin-2-yl)propanoate TFA salt (0.82 g, 2.22 mmol), HOBt (482 mg, 3.57 mmol), HBTU (1.35 g, 3.57 mmol), and ACN (10 mL). The mixture was cooled to 0° C. and DIEA (1.46 mL, 8.88 mmol) was added. The reaction mixture was stirred at ambient temperature for 30 min then quenched with sodium bicarbonate (sat.), extracted with ethyl acetate (2×), dried with sodium sulfate, filtered, and concentrated to provided crude (S)-benzyl 2-((S)-2-((tert-butoxycarbonyl)amino)propanamido)-3-(pyridin-2-yl)propanoate as a colorless solid (0.46 g) that was carried forward without further purification. MS (EI) for C$_{23}$H$_{29}$N$_3$O$_5$, found 428.3 (MH$^+$).

To (S)-benzyl 2-((S)-2-((tert-butoxycarbonyl)amino)propanamido)-3-(pyridin-2-yl)propanoate (0.460 g, 1.08 mmol) in THF (10 mL) was added Pd/C (10%, 500 mg) and a hydrogen atmosphere was established (balloon). After 4 h the reaction was filtered through Celite and concentrated to provide (S)-3-(4-methoxyphenyl)-2-(2-methyl-2-(2-morpholinoacetamido)propanamido)propanoic acid (0.310 g) as a colorless solid. MS (EI) for C$_{16}$H$_{23}$N$_3$O$_5$, found 337.2 (M$^+$).

To (S)-3-(4-methoxyphenyl)-2-(2-methyl-2-(2-morpholinoacetamido) propanamido)propanoic acid (0.310 g, 0.920 mmol) was added (S)-2-amino-1-((R)-2-methyloxiran-2-yl)-3-phenylpropan-1-one TFA salt (278 mg, 0.920 mmol), HOBt (199 mg, 1.47 mmol), HBTU (558 mg, 1.47 mmol) and DMF (3 mL). The mixture was cooled to 0° C. and DIEA (0.607 mL, 3.68 mmol) was added. The reaction mixture was stirred at ambient temperature for 30 min then quenched with sodium bicarbonate (sat.), extracted with ethyl acetate (2x), dried with sodium sulfate, filtered, and concentrated. Purification by column chromatography (50-100% ethyl acetate/heptane) provided tert-butyl ((S)-1-(((S)-1-(((S)-1-((S)-2-methyloxiran-2-yl)-1-oxo-3-phenyl-propan-2-yl)amino)-1-oxo-3-(pyridin-2-yl)propan-2-yl)amino)-1-oxopropan-2-yl)carbamate (315 mg, 65%) as a colorless amorphous solid. MS (EI) for $C_{28}H_{36}N_4O_6$, found 525.3 (M-).

To tert-butyl ((S)-1-(((S)-1-(((S)-1-((S)-2-methyloxiran-2-yl)-1-oxo-3-phenylpropan-2-yl)amino)-1-oxo-3-(pyridin-2-yl)propan-2-yl)amino)-1-oxopropan-2-yl)carbamate (315 mg, 0.600 mmol) was added DCM (4 mL) followed by TFA (2 mL). The reaction mixture was allowed to stand for 2 h at which time it was concentrated to provide (S)-2-((S)-2-aminopropanamido)-N—((S)-1-((S)-2-methyloxiran-2-yl)-1-oxo-3-phenylpropan-2-yl)-3-(pyridin-2-yl)propanamide TFA salt as a yellow oil that was carried forward without further purification. MS (EI) for $C_{25}H_{28}F_3N_4O_5$, found 425.3 [M-TFA]+.

To (S)-2-((S)-2-aminopropanamido)-N—((S)-1-((S)-2-methyloxiran-2-yl)-1-oxo-3-phenylpropan-2-yl)-3-(pyridin-2-yl)propanamide TFA salt (0.601 mmol assumed) was added morpholinoacetic acid (174 mg, 1.20 mmol), HOBt (130 mg, 0.962 mmol), HBTU (365 mg, 0.962 mmol) and DMF (3 mL). The mixture was cooled to 0° C. and DIEA (0.627 mL, 3.61 mmol) was added. The reaction mixture was stirred at ambient temperature for 30 min then quenched with sodium bicarbonate (sat.), extracted with ethyl acetate (2x), dried with sodium sulfate, filtered, and concentrated. Purification by column chromatography (3:1 DCM/ethyl acetate+0-15% methanol) provided (S)—N—((S)-1-((R)-2-methyloxiran-2-yl)-1-oxo-3-phenylpropan-2-yl)-2-((S)-2-(2-morpholinoacetamido)propanamido)-3-(pyridin-2-yl)propanamide (121 mg, 37%) as a colorless solid. $^1$H NMR (400 MHz, CDCl$_3$) δ 8.39 (ddd, J=4.9, 1.8, 0.9 Hz, 1H), 7.89 (d, J=6.7 Hz, 2H), 7.60 (ddt, J=7.7, 5.6, 1.8, 1.8 Hz, 2H), 7.25-7.09 (m, 5H), 7.09-6.99 (m, 2H), 4.88-4.65 (m, 2H), 4.47 (p, J=7.1, 7.1, 7.0, 7.0 Hz, 1H), 3.88-3.61 (m, 4H), 3.34-3.23 (m, 2H), 3.14 (dd, J=15.2, 6.3 Hz, 1H), 3.08-2.94 (m, 3H), 2.88 (d, J=5.0 Hz, 1H), 2.76 (dd, J=14.1, 7.9 Hz, 1H), 2.66-2.42 (m, 4H), 1.45 (s, 3H), 1.35 (d, J=7.1 Hz, 3H). MS (EI) for $C_{29}H_{37}N_5O_6$, found 552.4 (MH+).

The following compound was synthesized in a similar manner:

(S)-3-(4-methoxyphenyl)-N—((S)-1-((R)-2-methyloxiran-2-yl)-1-oxo-3-phenylpropan-2-yl)-2-(2-(2-morpholino-acetamido)acetamido)propanamide (C-1153):

$^1$H NMR (400 MHz, CDCl$_3$) δ 7.66 (t, J=5.8, 5.8 Hz, 1H), 7.26-7.19 (m, 3H), 7.07 (s, 2H), 7.00 (s, 2H), 6.86-6.76 (m, 2H), 6.54 (s, 1H), 6.19 (d, J=7.4 Hz, 1H), 4.71 (td, J=7.8, 7.7, 4.9 Hz, 1H), 4.50 (q, J=6.9, 6.9, 6.8 Hz, 1H), 3.86 (dd, J=5.7, 4.0 Hz, 2H), 3.78 (s, 3H), 3.76-3.67 (m, 4H), 3.24 (d, J=5.0 Hz, 1H), 3.07 (dd, J=14.0, 4.9 Hz, 1H), 2.99 (d, J=2.9 Hz, 2H), 2.95 (d, J=6.3 Hz, 1H), 2.93-2.83 (m, 2H), 2.68 (dd, J=14.0, 8.3 Hz, 1H), 2.60-2.43 (m, 4H), 1.48 (s, 3H). MS (EI) for $C_{30}H_{38}N_4O_7$, found 567.4 (MH+).

Example 69

(S)-3-(3,4-dimethoxyphenyl)-N—((S)-1-((R)-2-methyloxiran-2-yl)-1-oxo-3-phenylpropan-2-yl)-2-((S)-2-(2-morpholinoacetamido)propanamido)propanamide (C-1160)

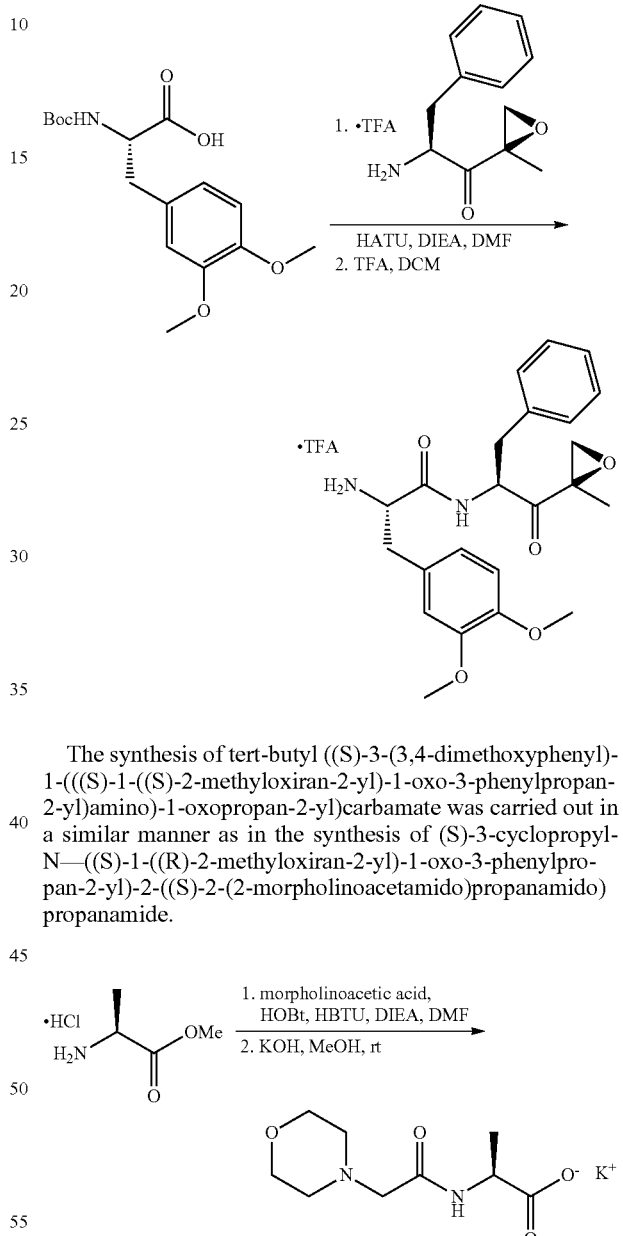

The synthesis of tert-butyl ((S)-3-(3,4-dimethoxyphenyl)-1-(((S)-1-((S)-2-methyloxiran-2-yl)-1-oxo-3-phenylpropan-2-yl)amino)-1-oxopropan-2-yl)carbamate was carried out in a similar manner as in the synthesis of (S)-3-cyclopropyl-N—((S)-1-((R)-2-methyloxiran-2-yl)-1-oxo-3-phenylpropan-2-yl)-2-((S)-2-(2-morpholinoacetamido)propanamido)propanamide.

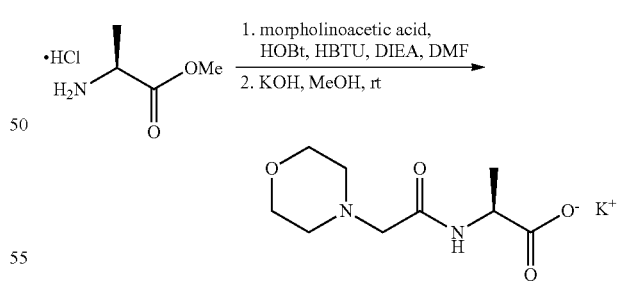

To (S)-methyl 2-aminopropanoate HCl salt (5.0 g, 35.8 mmol) in DMF (30 mL) at 0° C. was added morpholinoacetic acid (5.19 g, 35.8 mmol), HOBt (7.74 g, 57.3 mmol), HBTU (21.7 g, 57.3 mmol), followed by DIEA (24.9 mL, 0.143 mol). The mixture was allowed to stir for 15 min at which time it was quenched with sodium bicarbonate (sat.), extracted with ethyl acetate (2x), dried with sodium sulfate, filtered, and concentrated to provide (S)-methyl 2-(2-morpholinoacetamido)propanoate (quant. yield) as a colorless solid. MS (EI) for $C_{10}H_{18}N_2O_4$, found 231.2 (MH+).

Crude (S)-methyl 2-(2-morpholinoacetamido)propanoate was dissolved in methanol (10 mL) and KOH (20 mL of a 1N solution, 0.020 mmol). The reaction mixture was stirred for 3 h then concentrated, dissolved in methanol, and filtered. The filtrate was concentrated to provide potassium (S)-2-(2-morpholinoacetamido)propanoate (8.38 g, 92% over 2 steps) as a colorless oil. MS (EI) for $C_9H_{15}KN_2O_4$, found 217.2 [M-K]$^+$.

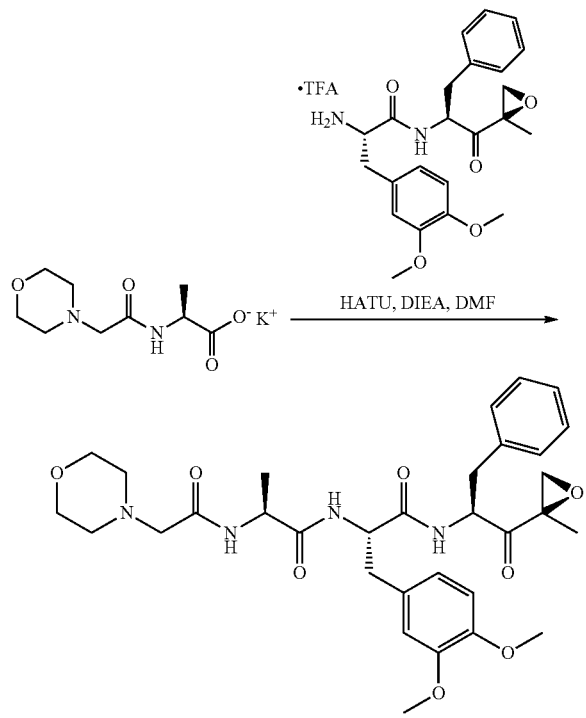

To (S)-2-amino-3-(3,4-dimethoxyphenyl)-N—((S)-1-((S)-2-methyloxiran-2-yl)-1-oxo-3-phenylpropan-2-yl)propanamide TFA salt (784 mg, 1.54 mmol) in DMF (5 mL) was added potassium (S)-2-(2-morpholinoacetamido)propanoate (470 mg, 1.85 mmol), HATU (702 mg, 1.85 mmol), DIEA (1.02 mL, 6.16 mmol). The mixture was allowed to stir for 15 min at which time it was quenched with sodium bicarbonate (sat.), extracted with ethyl acetate (2×), dried with sodium sulfate, filtered, and concentrated. Purification by column chromatography (3:1 DCM/ethyl acetate+0-10% methanol) followed by trituration from ethyl acetate/heptane (1:1) provided (S)-3-(3,4-dimethoxyphenyl)-N—((S)-1-((S)-2-methyloxiran-2-yl)-1-oxo-3-phenylpropan-2-yl)-2-((R)-2-(2-morpholinoacetamido)propanamido)propanamide (322 mg, 34%) as a colorless amorphous solid. $^1$H NMR (400 MHz, CDCl$_3$) δ 7.41 (d, J=7.7 Hz, 1H), 7.26-7.20 (m, 2H), 6.99 (dd, J=7.5, 1.8 Hz, 2H), 6.86-6.68 (m, 3H), 6.64 (d, J=7.3 Hz, 1H), 6.16 (d, J=7.0 Hz, 1H), 4.78-4.64 (m, 1H), 4.48 (q, J=7.1, 7.1, 7.0 Hz, 1H), 4.42-4.28 (m, 1H), 3.86 (d, J=4.0 Hz, 6H), 3.69 (t, J=4.6, 4.6 Hz, 4H), 3.27 (d, J=5.0 Hz, 1H), 3.08 (dd, J=14.0, 4.9 Hz, 1H), 3.02-2.79 (m, 5H), 2.64 (dd, J=14.0, 8.3 Hz, 1H), 2.45 (q, J=4.0, 3.9, 3.9 Hz, 4H), 1.49 (s, 2H), 1.30 (d, J=7.1 Hz, 3H). MS (EI) for $C_{32}H_{42}N_4O_8$, found 611.3 (MH$^+$).

The following compound was synthesized in a similar manner:

(S)-3-(4-(dimethylamino)phenyl)-N—((S)-1-((R)-2-methyloxiran-2-yl)-1-oxo-3-phenylpropan-2-yl)-2-((S)-2-(2-morpholinoacetamido)propanamido)propanamide (C-1161):

$^1$H NMR (400 MHz, CDCl$_3$) δ 7.45 (d, J=8.8 Hz, 1H), 7.25-7.20 (m, 3H), 7.06 (d, J=8.7 Hz, 2H), 7.03-6.91 (m, 2H), 6.67-6.60 (m, 2H), 6.52 (d, J=7.6 Hz, 1H), 6.16 (d, J=7.0 Hz, 1H), 4.71 (ddd, J=8.1, 7.2, 4.9 Hz, 1H), 4.45 (q, J=6.9, 6.9, 6.9 Hz, 1H), 4.43-4.31 (m, 1H), 3.82-3.63 (m, 4H), 3.28 (d, J=5.0 Hz, 1H), 3.15-3.02 (m, 1H), 3.02-2.88 (m, 9H), 2.83 (dd, J=14.1, 7.0 Hz, 2H), 2.66 (dd, J=14.0, 8.2 Hz, 1H), 2.57-2.37 (m, 4H), 1.49 (s, 3H), 1.29 (d, J=7.0 Hz, 3H). MS (EI) for $C_{32}H_{43}N_5O_6$, found 594.3 (MH$^+$).

(S)-3-(5-fluoropyridin-2-yl)-N—((S)-1-((R)-2-methyloxiran-2-yl)-1-oxo-3-phenylpropan-2-yl)-2-((S)-2-(2-morpholinoacetamido)propanamido)propanamide (C-1154):

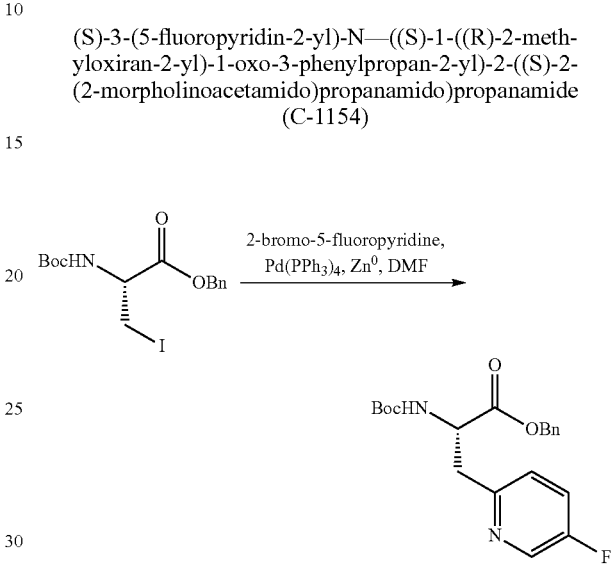

To (R)-benzyl 2-((tert-butoxycarbonyl)amino)-3-iodopropanoate (1 g, 2.47 mmol) and zinc (355 mg, 5.45 mmol) was added DMF (2.5 mL) and mixture was stirred for 30 min under N$_2$ at ambient temperature then Pd(PPh$_3$)$_4$ (175 mg, 0.247 mmol) was added. The mixture was stirred at ambient temperature for an additional 48 h under N$_2$ then diluted with water and ethyl acetate, extracted with ethyl acetate (2×), dried with sodium sulfate, filtered, and concentrated to provide (S)-benzyl 2-((tert-butoxycarbonyl)amino)-3-(5-fluoropyridin-2-yl)propanoate (1.108 g, quant. yield) as an orange oil that was carried forward without further purification. MS (EI) for $C_{20}H_{23}FN_2O_4$, found 375.2 (MH$^+$).

The remainder of the synthesis of (S)-3-(5-fluoropyridin-2-yl)-N—((S)-1-((R)-2-methyloxiran-2-yl)-1-oxo-3-phenylpropan-2-yl)-2-((S)-2-(2-morpholinoacetamido)propanamido)propanamide (8) was carried out in a similar manner as (S)—N—((S)-3-cyclohexyl-1-((R)-2-methyloxiran-2-yl)-1-oxopropan-2-yl)-3-(4-methoxyphenyl)-2-((S)-2-(2-morpholinoacetamido)propanamido)propanamide (4). $^1$H NMR (400 MHz, DMSO-d6) δ 8.49-8.37 (m, 2H), 8.11 (d, J=8.5 Hz, 1H), 7.71 (d, J=7.7 Hz, 1H), 7.58 (td, J=8.8, 8.8, 3.0 Hz, 1H), 7.40-7.08 (m, 6H), 4.66 (td, J=9.0, 8.7, 5.0 Hz, 1H), 4.54 (ddd, J=9.3, 7.4, 4.2 Hz, 1H), 4.28-4.14 (m, 1H), 3.65-3.48 (m, 4H), 3.19 (d, J=5.1 Hz, 1H), 3.09 (dd, J=13.9, 4.8 Hz, 1H), 3.00 (d, J=5.1 Hz, 1H), 2.98-2.79 (m, 4H), 2.70 (dd, J=13.9, 9.3 Hz, 1H), 2.44-2.28 (m, 4H), 1.36 (s, 3H), 1.09 (d, J=7.0 Hz, 3H). MS (EI) for $C_{29}H_{36}F_5O_6$, found 568.1 (MH$^+$).

(S)—N—((S)-3-(4-hydroxyphenyl)-1-((R)-2-methyloxiran-2-yl)-1-oxopropan-2-yl)-3-(4-methoxyphenyl)-2-((S)-2-(2-morpholinoacetamido)propanamido)propanamide (C-1162):

Synthesized following methods used in the synthesis of C-1003. $^1$H NMR (400 MHz,) δ 7.43 (d, J=7.1 Hz, 1H), 7.11-7.01 (m, 2H), 6.91-6.83 (m, 2H), 6.83-6.75 (m, 2H), 6.75-6.66 (m, 2H), 6.57 (d, J=7.7 Hz, 1H), 6.22 (d, J=7.6 Hz, 1H), 4.70 (dt, J=7.8, 4.1, 4.1 Hz, 1H), 4.48 (q, J=7.2, 7.2, 7.1 Hz, 1H), 4.38 (p, J=7.0, 7.0, 6.9, 6.9 Hz, 1H), 3.77 (s, 3H), 3.69 (t, J=4.6, 4.6 Hz, 4H), 3.22 (d, J=4.9 Hz, 1H), 3.03 (dd, J=14.4, 5.0 Hz, 1H), 2.99-2.82 (m, 5H), 2.58 (dd, J=14.1, 8.3 Hz, 1H), 2.54-2.38 (m, 4H), 1.51 (s, 3H), 1.30 (d, J=7.1 Hz, 3H). MS (EI) for $C_{31}H_{40}N_4O_8$, found 597.3 (MH+).

Example 70

(S)-3-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)-2-(2-morpholinoacetamido)propanamide (C-1159):

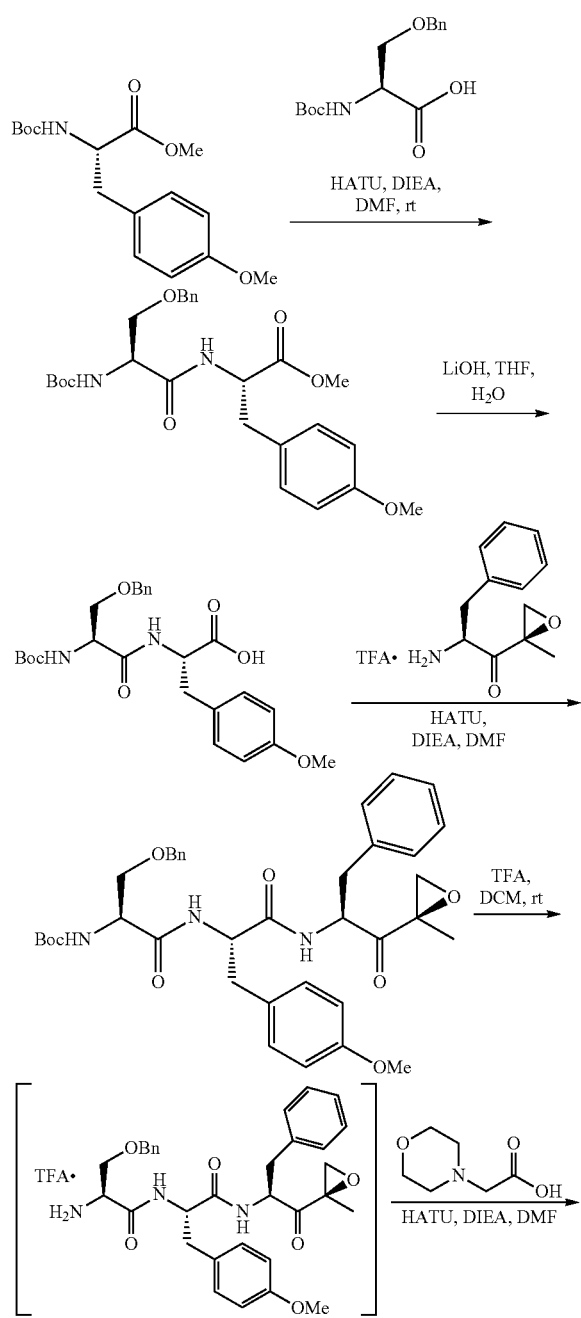

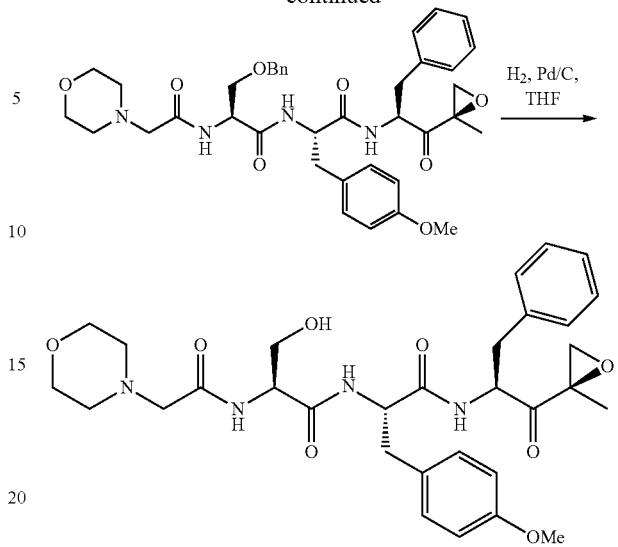

To (S)-3-(benzyloxy)-2-((tert-butoxycarbonyl)amino) propanoic acid (1.00 g, 3.39 mmol) in DMF (10 mL) at 0° C. was added HATU (1.42 g, 3.73 mmol). The mixture was stirred for 5 min to dissolve the solids at which time (S)-methyl 2-((tert-butoxycarbonyl)amino)-3-(4-methoxyphenyl)propanoate (0.708 g, 3.39 mmol) and DIEA (1.77 mL, 10.2 mmol) was added. The reaction mixture was stirred at ambient temperature for 30 min then quenched with sodium bicarbonate (sat.), extracted with ethyl acetate (2×), dried with sodium sulfate, filtered, and concentrated to provide crude (S)-methyl 2-((S)-3-(benzyloxy)-2-((tert-butoxycarbonyl)amino)propanamido)-3-(4-methoxyphenyl) propanoate as a yellow oil that was carried forward without further purification. MS (EI) for $C_{26}H_{34}N_2O_7$, found 387.1 (M-Boc).

To crude (S)-methyl 2-((S)-3-(benzyloxy)-2-((tert-butoxycarbonyl)amino) propanamido)-3-(4-methoxyphenyl)propanoate (3.39 mmol assumed) was added aqueous lithium hydroxide (5 mL of a 2 N solution) and methanol (5 mL). The reaction mixture was stirred for 5 h then diluted with ethyl acetate and water, washed with ethyl acetate (1×), acidified with citric acid, extracted with DCM, washed with brine, dried with sodium sulfate, filtered, and concentrated to provide (S)-2-((S)-3-(benzyloxy)-2-((tert-butoxycarbonyl) amino)propanamido)-3-(4-methoxyphenyl)propanoic acid as an amorphous off-white solid. MS (EI) for $C_{25}H_{32}N_2O_7$, found 471.1 (MH−).

To (S)-2-((S)-3-(benzyloxy)-2-((tert-butoxycarbonyl) amino)propanamido)-3-(4-methoxyphenyl)propanoic acid (3.39 mmol assumed) and HATU (1.45 g, 3.82 mmol) in DMF (10 mL) at 0° C. was added (S)-2-amino-1-((R)-2-methyloxiran-2-yl)-3-phenylpropan-1-one TFA salt (1.05 g, 3.47 mmol). The mixture was stirred for 5 min to dissolved the solids and DIEA (2.41 mL, 13.88 mmol) was added. The reaction mixture was stirred at this temperature for 15 min then quenched with sodium bicarbonate (sat.), extracted with ethyl acetate (2×), dried with sodium sulfate, filtered, and concentrated to provide crude tert-butyl ((S)-3-(benzyloxy)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)carbamate (quant.) as a yellow oil that was carried forward without further purification. MS (EI) for $C_{37}H_{45}N_3O_8$, found 660.4 (MH+).

283

To tert-butyl ((S)-3-(benzyloxy)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)carbamate (2.94 mmol assumed) was added DCM (10 mL) and TFA (10 mL). The reaction mixture was stirred for 30 min at ambient temperature at which time it was concentrated and carried forward without further purification. MS (EI) for $C_{32}H_{37}N_3O_6$, found 559.7 (M-TFA).

To (S)-2-amino-3-(benzyloxy)-N—((S)-3-(4-methoxyphenyl)-1-(((S)-1-((R)-2-methyloxiran-2-yl)-1-oxo-3-phenylpropan-2-yl)amino)-1-oxopropan-2-yl)propanamide TFA salt (2.94 mmol assumed) was added 2-morpholinoacetic acid (647 mg, 4.46 mmol), HATU (1.86 g, 4.91 mmol), and DMF (5 mL). The mixture was cooled to 0° C. and DIEA (3.10 mL, 17.8 mmol) was added. The reaction mixture was stirred at ambient temperature for 30 min then quenched with sodium bicarbonate (sat.), extracted with ethyl acetate (2×), dried with sodium sulfate, filtered, and concentrated. Purification by column chromatography (3:1 DCM/ethyl acetate+0-10% methanol) provided (S)-3-(benzyloxy)-N—((S)-3-(4-methoxyphenyl)-1-(((S)-1-((R)-2-methyloxiran-2-yl)-1-oxo-3-phenylpropan-2-yl)amino)-1-oxopropan-2-yl)-2-(2-morpholinoacetamido)propanamide (660 mg, 28% over 5 steps) as an amorphous colorless solid. MS (EI) for $C_{38}H_{46}N_4O_8$, found 687.4 (MH$^+$).

To (S)-3-(benzyloxy)-N—((S)-3-(4-methoxyphenyl)-1-(((S)-1-((R)-2-methyloxiran-2-yl)-1-oxo-3-phenylpropan-2-yl)amino)-1-oxopropan-2-yl)-2-(2-morpholinoacetamido)propanamide (330 mg, 0.480 μmol) was added methanol (20 mL) and Pd/C (10%, 500 mg). The reaction mixture was stirred under a hydrogen atmosphere (balloon) for 16 h at 40° C. before it was cooled to ambient temperature and filtered through Celite. Purification by column chromatography (3:1 DCM/ethyl acetate+0-10% methanol) provided (S)-3-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)-2-(2-morpholinoacetamido)propanamide (119 mg, 42%) as a colorless amorphous solid. $^1$H NMR (400 MHz,) δ 7.89 (d, J=7.7 Hz, 1H), 7.26-7.19 (m, 3H), 7.10-7.06 (m, 2H), 7.01-6.96 (m, 2H), 6.82-6.79 (m, 2H), 6.73 (d, J=8.0 Hz 1H), 6.50 (d, J=7.8 Hz, 1H), 4.80 (td, J=7.7, 7.7, 5.4 Hz, 1H), 4.64-4.48 (m, 1H), 4.45-4.31 (m, 1H), 3.92 (dd, J=11.0, 3.9 Hz, 1H), 3.79-3.74 (m, 5H), 3.73-3.67 (m, 3H), 3.54 (dd, J=11.0, 6.7 Hz, 1H), 3.27 (d, J=4.9 Hz, 1H), 3.15-2.84 (m, 6H), 2.72 (dd, J=14.0, 7.8 Hz, 1H), 2.55-2.39 (m, 4H), 1.48 (s, 3H). MS (EI) for $C_{31}H_{40}N_4O_8$, found 597.1 (MH$^+$).

Example 71

(2S,3S)-3-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)-2-((3-morpholinoprop-1-en-2-yl)amino)butanamide (C-1174)

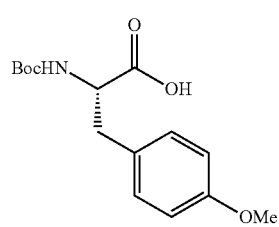

+

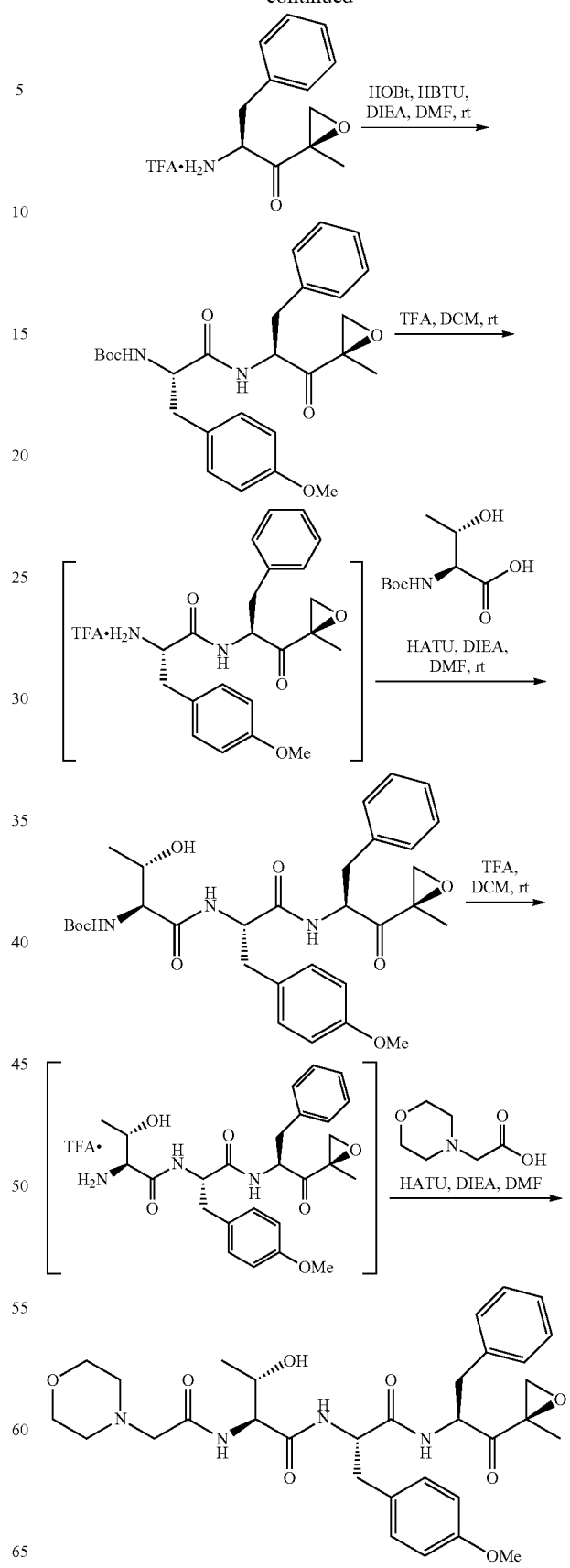

To (S)-2-((tert-butoxycarbonyl)amino)-3-(4-methoxyphenyl)propanoic acid (10.0 g, 33.9 mmol) in DMF (10 mL) at 0° C. was added HOBt (4.81 g, 37.3 mmol) and HBTU (14.1 g, 37.3 mmol). The mixture was stirred for 5 min to the dissolve solids at which time (S)-2-amino-1-((R)-2-methyloxiran-2-yl)-3-phenylpropan-1-one TFA salt (10.2 g, 33.9 mmol) and DIEA (17.4 mL, 0.101 mol) was added. The reaction mixture was stirred at ambient temperature for 30 min then quenched with sodium bicarbonate (sat.), extracted with ethyl acetate (2×), dried with sodium sulfate, filtered, and concentrated. Purification by column chromatography (0-60% ethyl acetate/heptane) provided tert-butyl ((S)-3-(4-methoxyphenyl)-1-(((S)-1-((R)-2-methyloxiran-2-yl)-1-oxo-3-phenylpropan-2-yl)amino)-1-oxopropan-2-yl)carbamate (13.4 g, 82%) as an colorless amorphous solid. MS (EI) for $C_{27}H_{34}N_2O_6$, found 483.3 (MH$^+$).

To tert-butyl ((S)-3-(4-methoxyphenyl)-1-(((S)-1-((R)-2-methyloxiran-2-yl)-1-oxo-3-phenylpropan-2-yl)amino)-1-oxopropan-2-yl)carbamate (1.00 g, 2.07 mmol) was added DCM (5 mL) and TFA (5 mL). The reaction mixture was stirred for 15 min at ambient temperature at which time it was concentrated and carried forward without further purification. (S)-2-amino-3-(4-methoxyphenyl)-N—((S)-1-((R)-2-methyloxiran-2-yl)-1-oxo-3-phenylpropan-2-yl)propanamide TFA salt was immediately carried forward into the subsequent step (quant. yield). MS (EI) for $C_{22}H_{26}N_2O_4$, found 383.2 (MH$^+$).

To (2S,3S)-2-((tert-butoxycarbonyl)amino)-3-hydroxybutanoic acid (453 mg, 2.07 mmol) in DMF (10 mL) at 0° C. was added HATU (865 mg, 2.28 mmol). The mixture was stirred for 5 min to dissolve the solids at which time (S)-2-amino-3-(4-methoxyphenyl)-N—((S)-1-((R)-2-methyloxiran-2-yl)-1-oxo-3-phenylpropan-2-yl)propanamide TFA salt (2.07 mmol assumed) and DIEA (1.71 mL, 10.35 mmol) was added. The reaction mixture was stirred at ambient temperature for 30 min then quenched with sodium bicarbonate (sat.), extracted with ethyl acetate (2×), dried with sodium sulfate, filtered, and concentrated to provide crude tert-butyl ((2S,3S)-3-hydroxy-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxobutan-2-yl)carbamate as a yellow oil that was carried forward without further purification.

To tert-butyl ((2S,3S)-3-hydroxy-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxobutan-2-yl)carbamate (2.07 mmol assumed) was added DCM (2.5 mL) and TFA (2.5 mL). The reaction mixture was stirred for 15 min at ambient temperature at which time it was concentrated and crude (2S,3S)-2-amino-3-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)butanamide TFA salt was carried forward without further purification.

To (2S,3S)-2-amino-3-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)butanamide TFA salt (0.207 mmol assumed) was added 2-morpholinoacetic acid (48.0 mg, 0.331 mmol), HATU (0.126 g, 0.331 mmol), and DMF (1 mL). The mixture was cooled to 0° C. and DIEA (0.177 mL, 0.104 mmol) was added. The reaction mixture was stirred at ambient temperature for 30 min then quenched with sodium bicarbonate (sat.), extracted with ethyl acetate (2×), dried with sodium sulfate, filtered, and concentrated. Purification by column chromatography (3:1 DCM/ethyl acetate+0-10% methanol) provided (2S,3S)-3-hydroxy-N—((S)-3-(4-methoxyphenyl)-1-(((S)-1-((R)-2-methyloxiran-2-yl)-1-oxo-3-phenylpropan-2-yl)amino)-1-oxopropan-2-yl)-2-(2-morpholinoacetamido)butanamide (80 mg, 63%) as a colorless solid. $^1$H NMR (400 MHz, DMSO-d6): δ 8.40 (d, J=7.6 Hz, 1H), 8.10 (d, J=8.0 Hz, 1H), 7.62 (d, J=8.8 Hz, 1H), 7.32-7.21 (m, 4H), 7.09 (d, J=7.6 Hz, 1H), 6.75 (d, J=8.4 Hz, 1H), 5.02 (d, J=4.8 Hz, 1H), 4.57-4.56 (m, 1H), 4.31-4.23 (m, 1H), 4.26-4.22 (m, 1H), 3.77-3.74 (m, 1H), 3.69 (s, 3H), 3.34-3.30 (m, 4H), 3.19-3.18 (m, 1H), 2.99-2.84 (m, 6H), 2.72-2.64 (m, 2H), 2.40-2.33 (m, 4H), 1.34 (s, 3H), 0.95 (d, J=6.4 Hz, 3H). MS (EI) for $C_{32}H_{42}N_4O_8$, found 611.6 (MH$^+$).

Example 72

Synthesis of (R)—N—((S)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)tetrahydrofuran-2-carboxamide (C-1166)

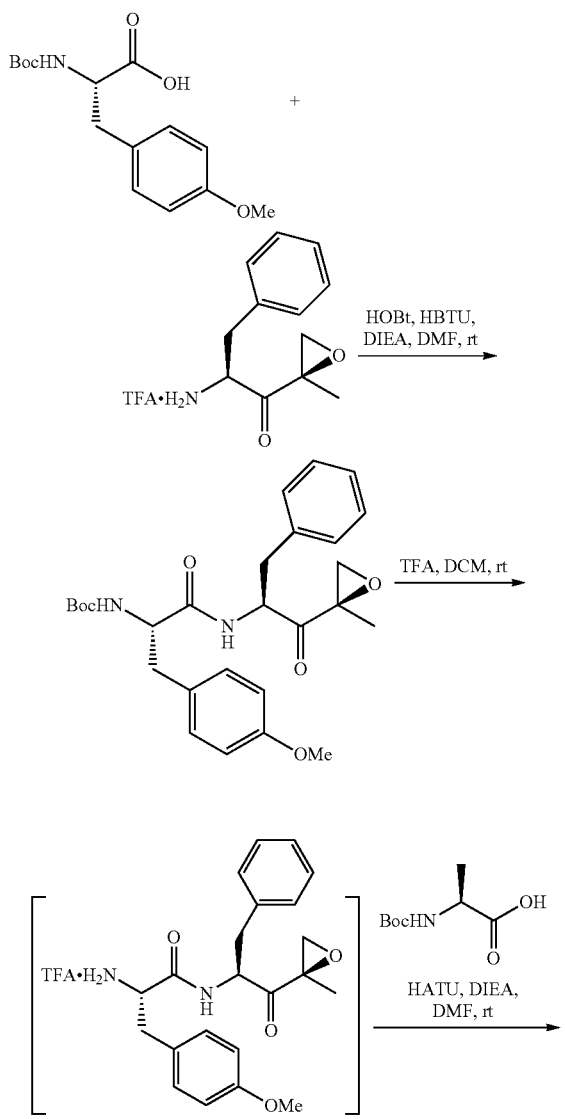

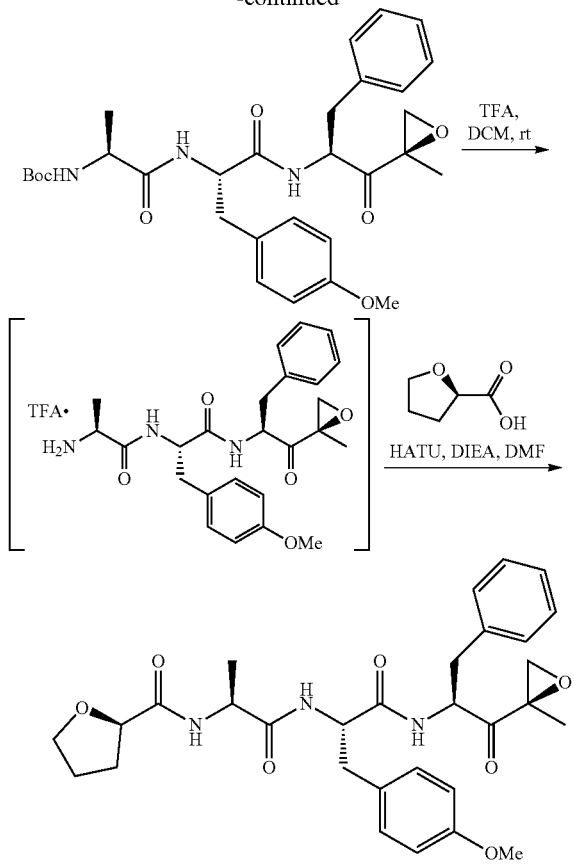

To (S)-2-((tert-butoxycarbonyl)amino)-3-(4-methoxyphenyl)propanoic acid (10.0 g, 33.9 mmol) in DMF (10 mL) at 0° C. was added HOBt (4.81 g, 37.3 mmol) and HBTU ((14.1 g, 37.3 mmol). The mixture was stirred for 5 min to the dissolve solids at which time (S)-2-amino-1-((R)-2-methyloxiran-2-yl)-3-phenylpropan-1-one TFA salt (10.2 g, 33.9 mmol) and DIEA (17.4 mL, 0.101 mol) was added. The reaction mixture was stirred at ambient temperature for 30 min then quenched with sodium bicarbonate (sat.), extracted with ethyl acetate (2×), dried with sodium sulfate, filtered, and concentrated. Purification by column chromatography (0-60% ethyl acetate/heptane) provided tert-butyl ((S)-3-(4-methoxyphenyl)-1-(((S)-1-((R)-2-methyloxiran-2-yl)-1-oxo-3-phenylpropan-2-yl)amino)-1-oxopropan-2-yl)carbamate (13.4 g, 82%) as an colorless amorphous solid. MS (EI) for $C_{27}H_{34}N_2O_6$, found 483.3 (MH$^+$).

To tert-butyl ((S)-3-(4-methoxyphenyl)-1-(((S)-1-((R)-2-methyloxiran-2-yl)-1-oxo-3-phenylpropan-2-yl)amino)-1-oxopropan-2-yl)carbamate (1.00 g, 2.07 mmol) was added DCM (5 mL) and TFA (5 mL). The reaction mixture was stirred for 15 min at ambient temperature at which time it was concentrated and carried forward without further purification. (S)-2-amino-3-(4-methoxyphenyl)-N—((S)-1-((R)-2-methyloxiran-2-yl)-1-oxo-3-phenylpropan-2-yl)propanamide TFA salt was immediately carried forward into the subsequent step (quant. yield). MS (EI) for $C_{22}H_{26}N_2O_4$, found 383.2 (MH$^+$).

To (S)-2-amino-3-(4-methoxyphenyl)-N—((S)-1-((R)-2-methyloxiran-2-yl)-1-oxo-3-phenylpropan-2-yl)propanamide TFA salt (2.07 mmol) was added (S)-2-((tert-butoxycarbonyl)amino)propanoic acid (782 mg, 4.14 mmol), HATU (1.82 g, 4.77 mmol), and DMF (7 mL). The mixture was cooled to 0° C. and DIEA (3.54 mL, 20.7 mmol) was added. The reaction mixture was stirred at ambient temperature for 30 min then quenched with sodium bicarbonate (sat.), extracted with ethyl acetate (2×), dried with sodium sulfate, filtered, and concentrated. Purification by column chromatography (0-80% ethyl acetate/heptane) provided tert-butyl ((S)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)carbamate (897 mg, 89%) as a colorless solid. MS (EI) for $C_{26}H_{37}N_3O_6$, found 488.4 (MH$^+$).

To tert-butyl ((S)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)carbamate (190 mg, 0.412 mmol) was added DCM (2 mL) and TFA (2 mL). The reaction mixture was stirred for 15 min at ambient temperature at which time it was concentrated and crude (S)-2-((S)-2-aminopropanamido)-3-(4-methoxyphenyl)-N—((S)-1-((R)-2-methyloxiran-2-yl)-1-oxo-3-phenylpropan-2-yl)propanamide TFA salt was carried forward without further purification. MS (EI) for $C_{27}H_{31}F_3N_3O_7$, found 470.3 (MH$^+$).

To (S)-2-((S)-2-aminopropanamido)-3-(4-methoxyphenyl)-N—((S)-1-((R)-2-methyloxiran-2-yl)-1-oxo-3-phenylpropan-2-yl)propanamide (0.412 mmol assumed) was added a mixture of (R)-tetrahydrofuran-2-carboxylic acid (57 mg, 0.494 mmol), HATU (187 mg, 0.494 mmol), and DMF (3 mL). The mixture was cooled to 0° C. and DIEA (0.352 mL, 2.06 mmol) was added. The reaction mixture was stirred at ambient temperature for 15 min then quenched with sodium bicarbonate (sat.), extracted with ethyl acetate (2×), dried with sodium sulfate, filtered, and concentrated. Purification by column chromatography (3:1 DCM/ethyl acetate+0-10% methanol) provided (R)—N—((S)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)tetrahydrofuran-2-carboxamide (130 mg, 57%) as a colorless amorphous solid. $^1$H NMR (400 MHz, DMSO-d6): δ 8.46 (d, J=7.6 Hz, 1H), 7.93 (d, J=8.0 Hz, 1H), 7.54 (d, J=8.0 Hz, 1H), 7.31-7.20 (m, 5H), 7.08 (d, J=8.4 Hz, 1H), 6.77 (d, J=8.4 Hz, 1H), 4.59-4.54 (m, 1H), 4.48-4.42 (m, 1H), 4.21-4.16 (m, 2H), 3.80-3.69 (m, 5H), 3.18 (d, J=5.2 Hz, 1H), 2.98 (d, J=6.4 Hz, 1H), 2.95-2.86 (m, 2H), 2.73-2.59 (m, 2H), 2.05-1.99 (m, 1H), 1.80-1.66 (m, 3H), 1.11 (d, J=7.2 Hz, 3H). MS (EI) for $C_{30}H_{37}N_3O_7$, found 552.3 (MH$^-$).

Characterization of (S)—N—((S)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)tetrahydrofuran-2-carboxamide (C-1167)

$^1$H NMR (400 MHz, DMSO-d6): δ 8.46 (d, J=7.2 Hz, 1H), 8.00 (d, J=8.4 Hz, 1H), 7.59 (d, J=7.6 Hz, 1H), 7.31-7.20 (m, 5H), 7.08 (d, J=8.4 Hz, 1H), 6.77 (d, J=8.8 Hz, 1H), 4.58-4.56 (m, 1H), 4.51-4.42 (m, 1H), 4.22-4.15 (m, 2H), 3.84-3.67 (m, 5H), 3.18 (d, J=5.2 Hz, 1H), 2.99 (d, J=5.2 Hz, 1H), 2.95-2.87 (m, 2H), 2.72-2.62 (m, 2H), 2.08-2.05 (m, 1H), 1.78-1.74 (m, 3H), 1.09 (d, J=7.2 Hz, 3H). MS (EI) for $C_{30}H_{37}N_3O_7$, found 552.3 (MH$^+$).

Characterization of N—((S)-1-(((S)-3-(4-methoxyphenyl)-1-(((S)-1-((R)-2-methyloxiran-2-yl)-1-oxo-3-phenylpropan-2-yl)amino)-1-oxopropan-2-yl)amino)-1-oxopropan-2-yl)-1-methylazetidine-3-carboxamide (C-1172)

$^1$H NMR (400 MHz, DMSO-d6) δ 8.57 (d, J=7.6 Hz, 1H), 8.40 (d, J=8.4 Hz, 1H), 7.53 (d, J=6.4 Hz, 1H), 7.31-7.10 (m, 5H), 6.84 (d, J=8.8 Hz, 1H), 4.59-4.48 (m, 2H), 3.94-3.91 (m, 1H), 3.72 (s, 3H), 3.20-3.02 (m, 1H), 3.03-2.95 (m, 2H), 2.85-2.82 (m, 6H), 2.73-2.67 (m, 1H), 2.46-2.36 (m, 1H), 1.38 (s, 3H), 1.24 (d, J=6.8 Hz, 3H). MS (EI) for $C_{30}H_{38}N_4O_6$, found 550.6 (M+).

Assays

Example 73—Proteasome Active-Site ELISA

An ELISA-based technique, the proteasome constitutive/immunoproteasome subunit enzyme-linked immunosorbent (ProCISE) assay, was utilized for quantitative assessment of subunit-specific activity, as previously described in Parlati F, Lee S J, Aujay M, et al. *Blood* (2009) 114:3439-3447. Test compounds were serially diluted in DMSO at 100× concentration, then diluted to 10× in aqueous hypotonic lysis buffer. Lysate from the human acute lymphoblastic leukemia cell line, MOLT-4, was treated for 1 hour at 25° C. with compound at a final 1× concentration. Treated cell lysate was then incubated with a biotinylated proteasome active-site binding probe for 2 hours at 25° C. Following, lysate was denatured in guanidine hydrochloride, and subunits bound to probe were isolated with streptavidin-conjugated sepharose beads. Individual subunits (e.g., β5, LMP7, LMP2, MECL-1) were probed with subunit-specific primary antibodies, followed by HRP-conjugated secondary antibodies. A chemiluminescent substrate was used to generate signal associated with HRP binding, which was detected on a plate reader. Luminescent signal was normalized to protein content, then, percent activity calculated relative to DMSO-treated controls to generate $IC_{50}$ curves.

Results for select compounds provided herein are shown in the following table:

| Cmpd | ProCISE beta5 MOLT4 lysate Hu 1 h CONT: $IC_{50}$ (nM) | ProCISE LMP7 MOLT4 lysate Hu 1 h CONT: $IC_{50}$ (nM) | Solubility pH 7 (μg/mL) |
|---|---|---|---|
| C-1001 | NT | NT | 2635.1 |
| C-1002 | NT | NT | 3187.2 |
| C-1003 | 4199.91 | 254.21 | 629 |
| C-1004 | 1867.2 | 540.63 | 2499.9 |
| C-1005 | 1942.38 | 184.61 | 1764.6 |
| C-1006 | 5242.51 | 5146.61 | 2589.5 |
| C-1007 | 2361.73 | 314.34 | 877.5 |
| C-1008 | NT | NT | 1431.1 |
| C-1009 | 926.25 | 83.09 | 2730.8 |
| C-1010 | 695.18 | 99.6 | 185.3 |
| C-1011 | 6965.7 | 556.06 | 1115.3 |
| C-1012 | 1275.1 | 166.74 | 1724.65 |
| C-1013 | NT | NT | 911 |
| C-1014 | NT | NT | 1017.9 |
| C-1015 | 1136.99 | 498.13 | 212.2 |
| C-1016 | NT | NT | 6886.3 |
| C-1017 | 21738.87 | 1089.99 | 11716.4 |
| C-1018 | 1731.06 | 183.61 | 5835 |
| C-1019 | 9333.32 | 299.33 | 1757.15 |
| C-1020 | 45029.73 | 1164.16 | 6435.7 |
| C-1021 | 1901.31 | 113.02 | 19.3 |
| C-1022 | 1114.54 | 85.06 | 4047.5 |
| C-1023 | NT | NT | 3866.2 |
| C-1024 | NT | NT | 4762.55 |
| C-1025 | NT | NT | >10 |
| C-1027 | 1045.6 | 165.41 | 5750.9 |
| C-1028 | 807.08 | 52.61 | 214.9 |
| C-1029 | 3790.84 | 303.09 | 822.5 |
| C-1030 | 496.51 | 11.25 | 220.1 |
| C-1031 | NT | NT | 462 |
| C-1032 | NT | NT | 251.4 |
| C-1033 | NT | NT | 3211.9 |
| C-1034 | NT | NT | 2780.2 |
| C-1035 | NT | NT | >10 |
| C-1036 | NT | NT | 277.3 |
| C-1037 | NT | NT | 1326 |
| C-1038 | 289.27 | 9.07 | 230.5 |
| C-1039 | NT | NT | 7014.8 |
| C-1040 | NT | NT | 12339.3 |
| C-1041 | 12535.15 | 439.53 | 1826.7 |
| C-1042 | NT | NT | 8775.5 |
| C-1043 | NT | NT | 79.2 |
| C-1044 | NT | NT | 1899.6 |
| C-1045 | NT | NT | 50.2 |
| C-1046 | 198.23 | 37.88 | 151.9 |
| C-1047 | NT | NT | 24.1 |
| C-1048 | NT | NT | 152.9 |
| C-1049 | 796.47 | 153.49 | 3510.1 |
| C-1050 | 764.71 | 115.86 | 1277.5 |
| C-1051 | 705.31 | 90.8 | 702 |
| C-1052 | 511.92 | 101.3 | 705.6 |
| C-1053 | 4543.31 | 269.9 | 647.6 |
| C-1054 | 805.42 | 131.37 | 2859.6 |
| C-1055 | 7147.69 | 953.3 | 1296.5 |
| C-1056 | 17.44 | 2.72 | 298.1 |
| C-1057 | 2550.39 | 34.02 | 491.3 |
| C-1058 | NT | NT | 3009.8 |
| C-1059 | NT | NT | 6005.3 |
| C-1060 | 422.61 | 12.37 | 1375.3 |
| C-1061 | 978.49 | 70.76 | 2052.5 |
| C-1062 | 388.46 | 38.39 | 139.8 |
| C-1063 | 443.45 | 90.69 | 1310.35 |
| C-1064 | 4050.97 | 60.5 | NT |
| C-1065 | 1482.63 | 34.635 | 2662.6 |
| C-1066 | 335.37 | 47.12 | 3196.85 |
| C-1067 | NT | NT | 4592.5 |
| C-1068 | NT | NT | 4409.5 |
| C-1069 | NT | NT | 3541.65 |
| C-1070 | 1813.48 | 209.12 | 2140.35 |
| C-1071 | 3889.49 | 105.52 | 4295.55 |
| C-1072 | 3391.44 | 39.71 | 4742.65 |
| C-1073 | NT | NT | 2175.85 |
| C-1074 | 777.73 | 26.24 | 1153 |
| C-1075 | 787.62 | 92.14 | 1647.3 |
| C-1076 | NT | NT | 1041.1 |
| C-1077 | NT | NT | 1536 |
| C-1078 | NT | NT | 873 |
| C-1079 | 2227.99 | 34.575 | 2050.7 |
| C-1080 | 1181.45 | 25.155 | NT |
| C-1081 | NT | NT | 2759.7 |
| C-1082 | 3531.94 | 86.63 | 6130.4 |
| C-1083 | 561.17 | 40.325 | 7072.1 |
| C-1084 | NT | NT | 125.3 |
| C-1085 | 1841.14 | 157.67 | 8193.5 |
| C-1086 | NT | NT | 3864.7 |
| C-1087 | 1745.09 | 59.89 | 1126.5 |
| C-1088 | 2249.42 | 132.04 | 1414.6 |
| C-1089 | 8970.55 | 57.58 | 984.9 |
| C-1090 | 6627.39 | 261.88 | 979.1 |
| C-1091 | NT | NT | 230.5 |
| C-1092 | 2043.07 | 29.29 | 3068.2 |
| C-1093 | NT | NT | 6110.5 |
| C-1094 | NT | NT | 1669.6 |
| C-1095 | NT | NT | NT |
| C-1096 | 867.54 | 25.2 | 916.6 |
| C-1097 | 322.28 | 21.64 | 256.5 |
| C-1098 | NT | NT | 7833.2 |
| C-1099 | NT | NT | 7310.5 |
| C-1100 | NT | NT | 4571.7 |
| C-1101 | NT | NT | 4091.2 |
| C-1102 | NT | NT | 3408.7 |
| C-1103 | 1964.34 | 38.7 | 2145.5 |
| C-1104 | 2206.35 | 72.38 | 3266.5 |
| C-1105 | 3230.39 | 49.51 | 5694.7 |
| C-1106 | 284.33 | 49.77 | 960.2 |
| C-1107 | NT | NT | 199.9 |
| C-1108 | NT | NT | 4730.9 |
| C-1109 | 4087.5 | 181.18 | 3824.5 |

| Cmpd | ProCISE beta5 MOLT4 lysate Hu 1 h CONT: IC$_{50}$ (nM) | ProCISE LMP7 MOLT4 lysate Hu 1 h CONT: IC$_{50}$ (nM) | Solubility pH 7 (μg/mL) |
|---|---|---|---|
| C-1110 | 4337.92 | 217.31 | 8380.3 |
| C-1111 | NT | NT | 1072.4 |
| C-1112 | NT | NT | 1113.6 |
| C-1113 | NT | NT | 3785.2 |
| C-1114 | NT | NT | 792.9 |
| C-1115 | NT | NT | 495.8 |
| C-1116 | 2935.85 | 50.56 | 8225.7 |
| C-1117 | 1104.4 | 100.52 | 1564.2 |
| C-1118 | 406.61 | 43.82 | 6257.4 |
| C-1119 | 1386.93 | 833.1 | 10558.7 |
| C-1120 | NT | NT | 8002.4 |
| C-1121 | NT | NT | 286.9 |
| C-1122 | NT | NT | 1825.6 |
| C-1123 | NT | NT | 1465.7 |
| C-1124 | NT | NT | 56.5 |
| C-1125 | 566.21 | 97.63 | 7717.2 |
| C-1126 | NT | NT | 7275.7 |
| C-1127 | 4167.71 | 315.04 | 1517.7 |
| C-1128 | NT | NT | 1367.6 |
| C-1129 | 793.2 | 76.45 | 1757.6 |
| C-1130 | NT | NT | 1138.4 |
| C-1131 | NT | NT | 1700.8 |
| C-1132 | NT | NT | 158.9 |
| C-1133 | NT | NT | 182.5 |
| C-1135 | 288.66 | 30.95 | 1864.4 |
| C-1136 | 401.86 | 46.16 | 54.4 |
| C-1137 | NT | NT | >10000 |
| C-1138 | 408.87 | 45.29 | 2350.5 |
| C-1139 | NT | NT | 172.1 |
| C-1140 | NT | NT | >10000 |
| C-1141 | NT | NT | 9011.2 |
| C-1142 | NT | NT | 2341.3 |
| C-1144 | 266.19 | 20.11 | >10000 |
| C-1153 | 4166.35 | 208.5 | 3273 |
| C-1154 | NT | NT | 1909.3 |
| C-1155 | NT | NT | 2090.4 |
| C-1156 | 175.35 | 50.84 | NT |
| C-1158 | 873.57 | 161.48 | 3033.3 |
| C-1159 | 454.38 | 43.12 | 1914.7 |
| C-1160 | 660.32 | 156.97 | 1527.7 |
| C-1161 | 408.55 | 51.17 | 2114.5 |
| C-1162 | 595.14 | 43.43 | 1273.6 |
| C-1163 | NT | NT | 2460.5 |
| C-1164 | 581.35 | 82.125 | 2667.6 |
| C-1165 | NT | NT | 2146.1 |
| C-1166 | 961.3 | 359.92 | 535.8 |
| C-1167 | 526.2 | 154.83 | 790.5 |
| C-1168 | NT | NT | 212.7 |
| C-1171 | 251.82 | 50.97 | 1681.9 |
| C-1172 | | | 1902.9 |
| C-1173 | 113.82 | 28.91 | 2343.7 |
| C-1174 | 149.53 | 22.93 | 1781.5 |
| C-1175 | 440.95 | 107.14 | 2476.1 |
| C-1176 | | | 1890.6 |
| C-1178 | 3835.17 | 510.43 | 1189.7 |
| C-1179 | 525.81 | 119.31 | 1299 |
| C-1180 | 312.21 | 21 | 1380.2 |
| C-1181 | 120.38 | 13.54 | 937.6 |
| C-1183 | 101.4 | 17.14 | 4537.9 |
| C-1184 | 63.9 | 19.5 | 2732.1 |
| C-1185 | 283.17 | 30.35 | 150.5 |
| C-1186 | 781.81 | 23.2 | 240 |
| C-1187 | 43.41 | 10.5 | 130.4 |
| C-1188 | 185.07 | 29.23 | 12.1 |
| C-1189 | 476.27 | 58.55 | 22.7 |
| C-1190 | 204.98 | 16.78 | 456.6 |
| C-1191 | 678.01 | 24.71 | 4245.5 |
| C-1224 | NT | NT | 257.1 |
| C-1225 | 204.8 | 49.52 | 3446.9 |
| C-1226 | NT | NT | 3821.8 |
| C-1227 | NT | NT | 1976.35 |
| C-1228 | NT | NT | 682.3 |
| C-1229 | NT | NT | 3623.1 |

NT—Not Tested

Example 74-20S Proteasome Assays

Proteasome chymotrypsin-like, caspase-like, and trypsin-like activities for various compounds provided herein were determined using succinyl-Leu-Leu-Val-Tyr-AMC (10 Amol/L), Z-Leu-Leu-Glu-AMC (10 Amol/L), and Boc-Leu-Arg-Arg-AMC (50 Amol/L), respectively, with purified human 20S proteasome (2, 4, and 8.0 nmol/L, respectively) or HT-29 cell lysate (0.125, 0.25, and 0.25 Ag protein/mL, respectively). Assay buffer consisted of TE buffer [20 mmol/L Tris (pH 8.0), 0.5 mmol/L EDTA] with (20S) or without (cell lysate) 0.03% SDS. Reactions were initiated by enzyme or lysate addition and monitored for AMC product formation at 27j C with a plate-based spectofluorometer (Tecan). IC$_{50}$ values were determined based on the reaction velocity measured between 60 and 75 min. See also Demo, S. D. et al., *Cancer Res.* 2007, 67, 6383-6391.

Results for select compounds provided herein are shown in the following table:

| Compound | LLVY i20S Hu 1 h CONT: IC$_{50}$ (nM) | LLVY c20S Hu 1 h CONT: IC$_{50}$ (nM) |
|---|---|---|
| C-1001 | 3230 | >10000 |
| C-1003 | 463 | 3800 |
| C-1235 | 390 | 195 |
| C-1153 | 278 | 2430 |
| C-1154 | 113 | 301 |
| C-1155 | 252 | 495 |
| C-1160 | 246 | 909 |
| C-1161 | 146 | 807 |
| C-1171 | 63.1 | 338.9 |
| C-1162 | 27.9 | 1610 |
| C-1159 | 43 | 473 |
| C-1220 | 11 | 44 |
| C-1174 | 23 | 161 |
| C-1234 | 1498 | 1648 |
| C-1173 | 33.6 | 152 |
| C-1005 | 70.4 | 519 |
| C-1007 | 106 | 440 |
| C-1008 | 2500 | 3380 |
| C-1009 | 46.2 | 351 |
| C-1010 | 24.4 | 119 |
| C-1011 | 98.8 | 1550 |
| C-1012 | 92.5 | 470 |
| C-1013 | 445 | 548 |
| C-1014 | 289 | 806 |
| C-1015 | 167 | 506 |
| C-1018 | 170. | 656 |
| C-1021 | 144 | 3540 |
| C-1022 | 115 | 729 |
| C-1024 | 707 | 715 |
| C-1027 | 108 | 775 |
| C-1028 | 53.8 | 1010 |
| C-1029 | 214 | 4110 |
| C-1030 | 7.93 | 201 |
| C-1031 | 2980 | >250000 |
| C-1033 | 3104 | 121000 |
| C-1034 | 1050 | 25400 |
| C-1036 | 480 | 16500 |
| C-1039 | 202 | 694 |

-continued

| Compound | LLVY i20S Hu 1 h CONT: IC$_{50}$ (nM) | LLVY c20S Hu 1 h CONT: IC$_{50}$ (nM) |
| --- | --- | --- |
| C-1041 | 232 | 7030 |
| C-1032 | 436 | 24800 |
| C-1043 | 251 | 404 |
| C-1044 | 2580 | 9090 |
| C-1045 | 308 | 470 |
| C-1046 | 63.5 | 361 |
| C-1047 | 438 | 707 |
| C-1048 | 549 | 2630 |
| C-1037 | 356 | 5860 |
| C-1049 | 66.8 | 305 |
| C-1050 | 53.5 | 277 |
| C-1051 | 45.1 | 978 |
| C-1052 | 44.5 | 515 |
| C-1053 | 98.9 | 3770 |
| C-1054 | 76.5 | 667 |
| C-1055 | 149 | 4440 |
| C-1056 | 4.7 | 46.8 |
| C-1057 | 5.3 | 595 |
| C-1058 | 1610 | 54800 |
| C-1023 | 322 | 1880 |
| C-1059 | 1650 | 38400 |
| C-1061 | 15.4 | 756 |
| C-1062 | 20.2 | 232 |
| C-1063 | 14.9 | 169 |
| C-1175 | 129 | 501 |
| C-1178 | 241 | 3830 |
| C-1180 | 25.9 | 374 |
| C-1181 | 13.5 | 160. |
| C-1225 | 18.6 | 59.3 |
| C-1227 | 649 | 1030 |
| C-1183 | 21.5 | 63.8 |
| C-1184 | 10.5 | 57.3 |

What is claimed is:

1. A method of inhibiting activity of immunoproteasome of a cell comprising contacting the cell with a compound of Formula (X) or a pharmaceutically acceptable salt thereof in an amount effective to inhibit the immunoproteasome:

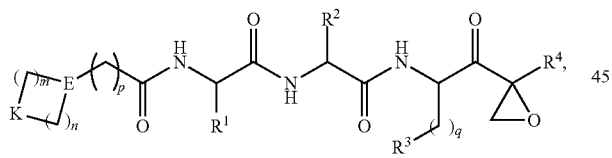

(X)

wherein:
m and n each independently are 0, 1 or 2, and m+n=2, 3, or 4;
p is 0 or 1;
q is 0, 1, or 2;
K is selected from the group consisting of $CR^5R^6$, $NR^7$, $N(C=O)OR^7$, —NH—(C=O)—, O, S, SO, and $SO_2$;
E is N or $CR^7$;
$R^1$ is selected from the group consisting of H, $C_{1-6}$alkyl, $C_{2-6}$alkenyl, $C_{2-6}$alkynyl, $C_{3-6}$cycloalkyl, and 3-6 membered heterocycloalkyl, wherein $R^1$ is optionally substituted with one or more substituents selected from the group consisting of halo, $OR^7$, $SR^7$, $N(R^7)_2$, CN, and $(C=O)N(R^7)_2$;
$R^2$ is $C_{1-2}$alkylene-G or (C=O)-G; wherein G is selected from the group consisting of aryl, heteroaryl, and pyridinone, with the proviso that when $R^2$ is $CH_2$phenyl, the phenyl is substituted with one or more substituents selected from the group consisting of $OR^7$, halo, $C_{1-3}$alkyl, $OCF_3$, $SO_2R^7$, $(C=O)N(R^7)_2$, CN, and $SO_2N(R^7)_2$;
$R^3$ is selected from the group consisting of $C_{3-7}$cycloalkyl, $C_{3-7}$cycloalkenyl, a 3-7 membered heterocycloalkyl, and a 3-7 membered heterocycloalkenyl, wherein $R^3$ is optionally substituted with one or more substituents selected from the group consisting of halo, =O, $OR^7$, $SR^7$, $N(R^7)_2$, $O(C=O)N(R^7)_2$, and $C_{1-6}$alkyl;
$R^4$ is H or $C_{1-3}$alkyl;
$R^5$ and $R^6$ are each independently selected from the group consisting of H, OH, halo, $C_{1-3}$alkyl, and $CF_3$, or $R^5$ and $R^6$ together with the carbon to which they are attached form C=O or

wherein W is O or $NR^7$, and r is 1, 2 or 3; and
each $R^7$ is independently H or $C_{1-6}$alkyl.

2. The method of claim 1, wherein

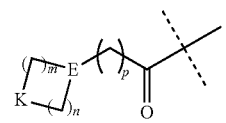

is selected from the group consisting of:

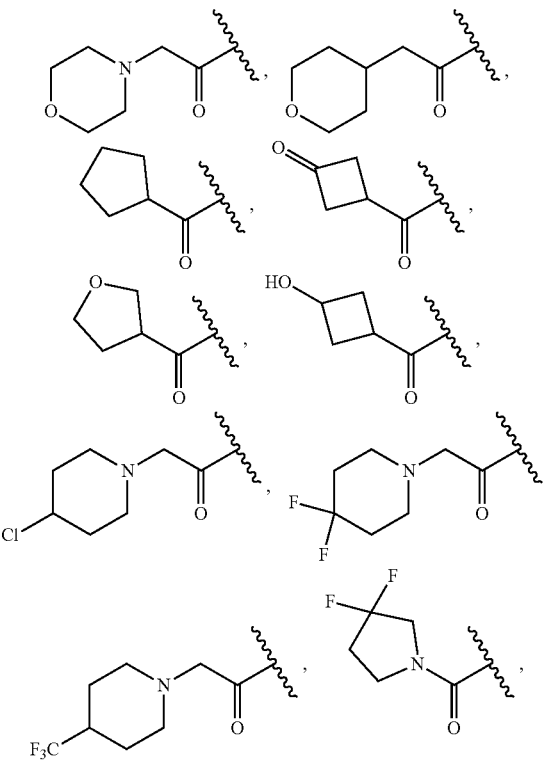

-continued
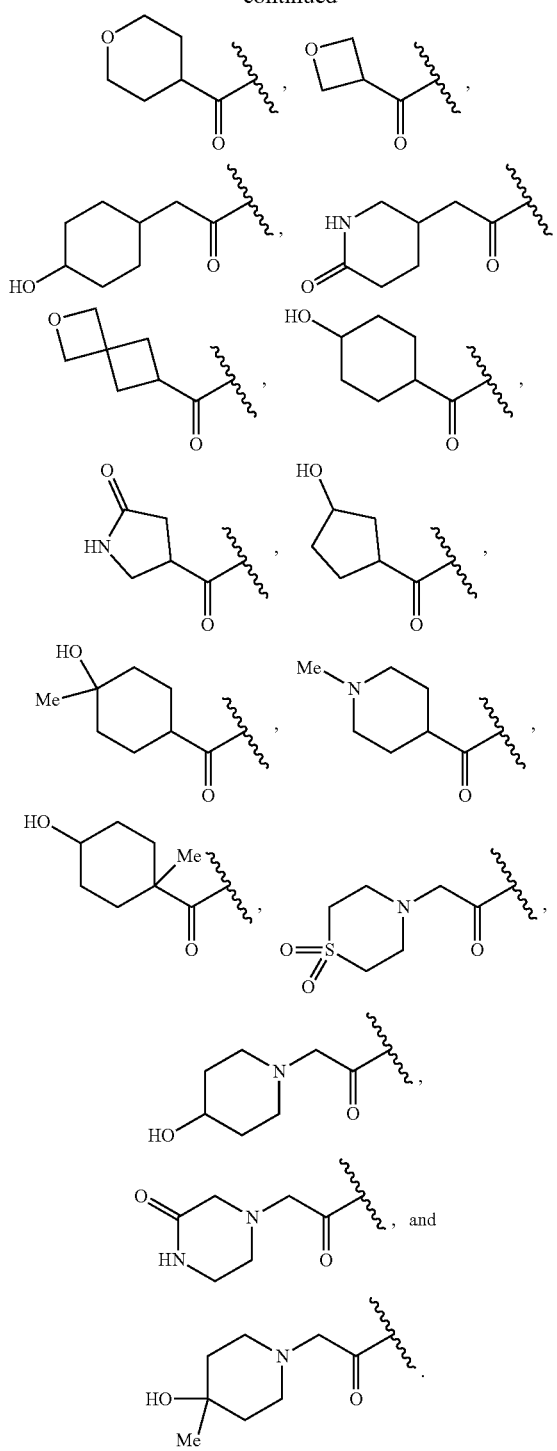
3. The method of claim 1, wherein
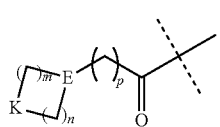
is selected from the group consisting of:
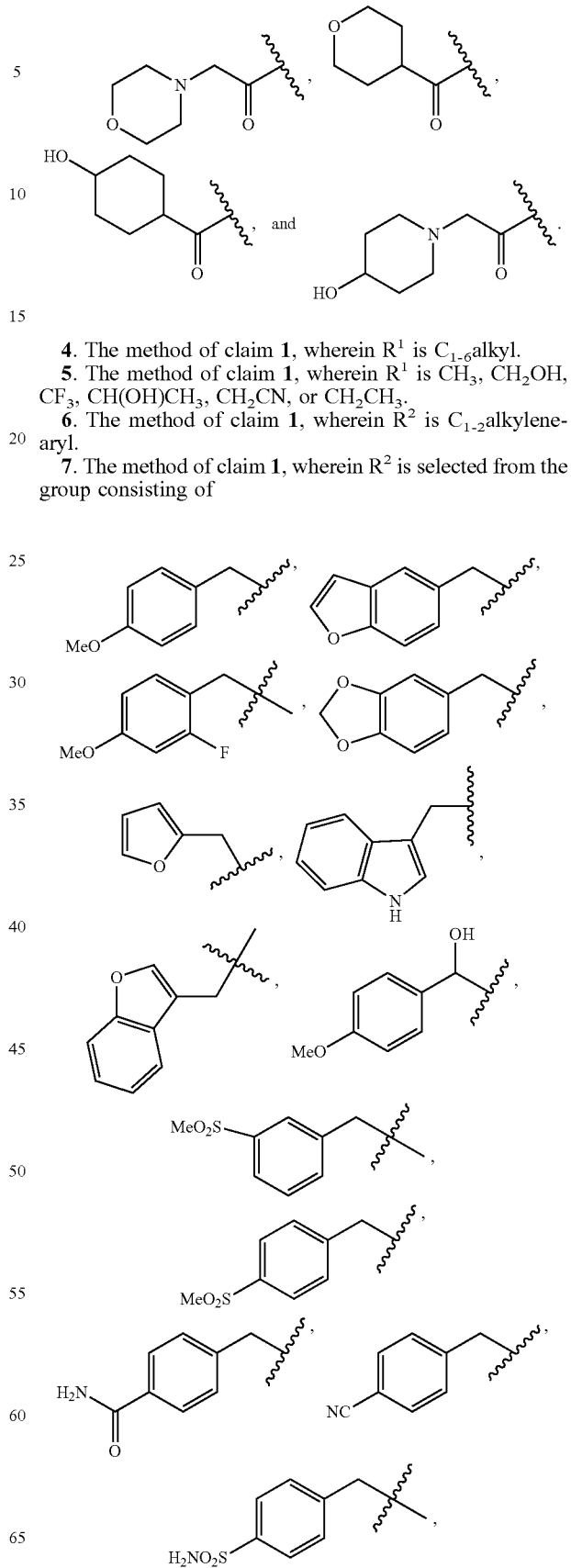
4. The method of claim 1, wherein $R^1$ is $C_{1-6}$alkyl.
5. The method of claim 1, wherein $R^1$ is $CH_3$, $CH_2OH$, $CF_3$, $CH(OH)CH_3$, $CH_2CN$, or $CH_2CH_3$.
6. The method of claim 1, wherein $R^2$ is $C_{1-2}$alkylene-aryl.
7. The method of claim 1, wherein $R^2$ is selected from the group consisting of

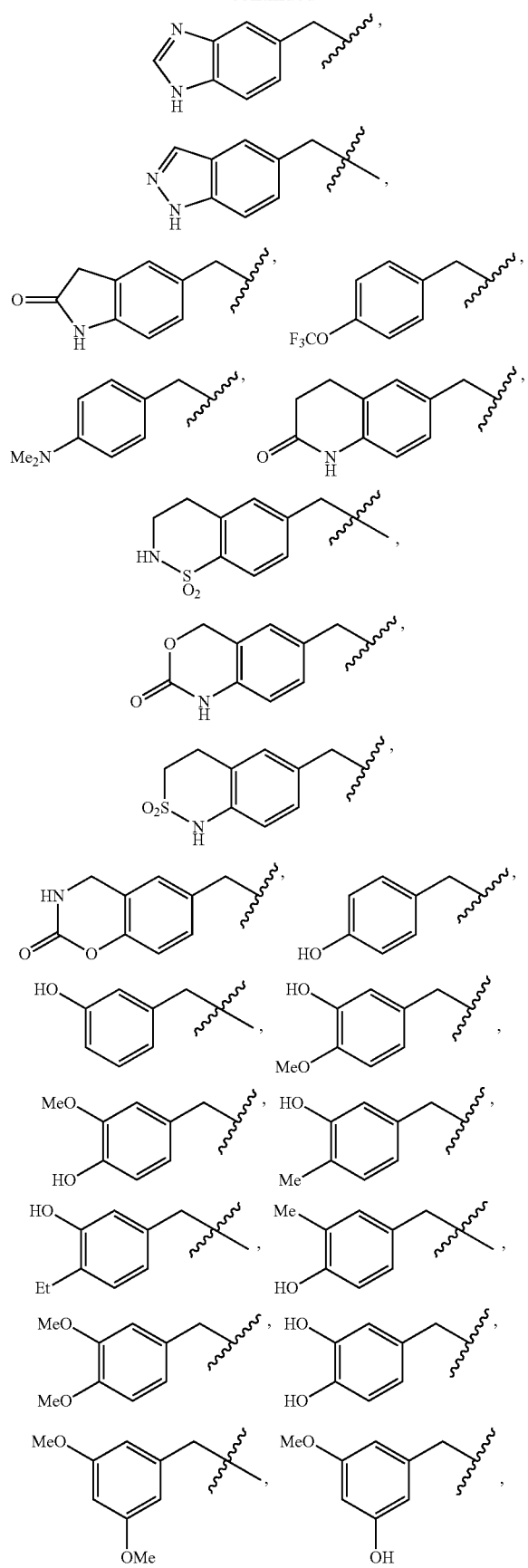
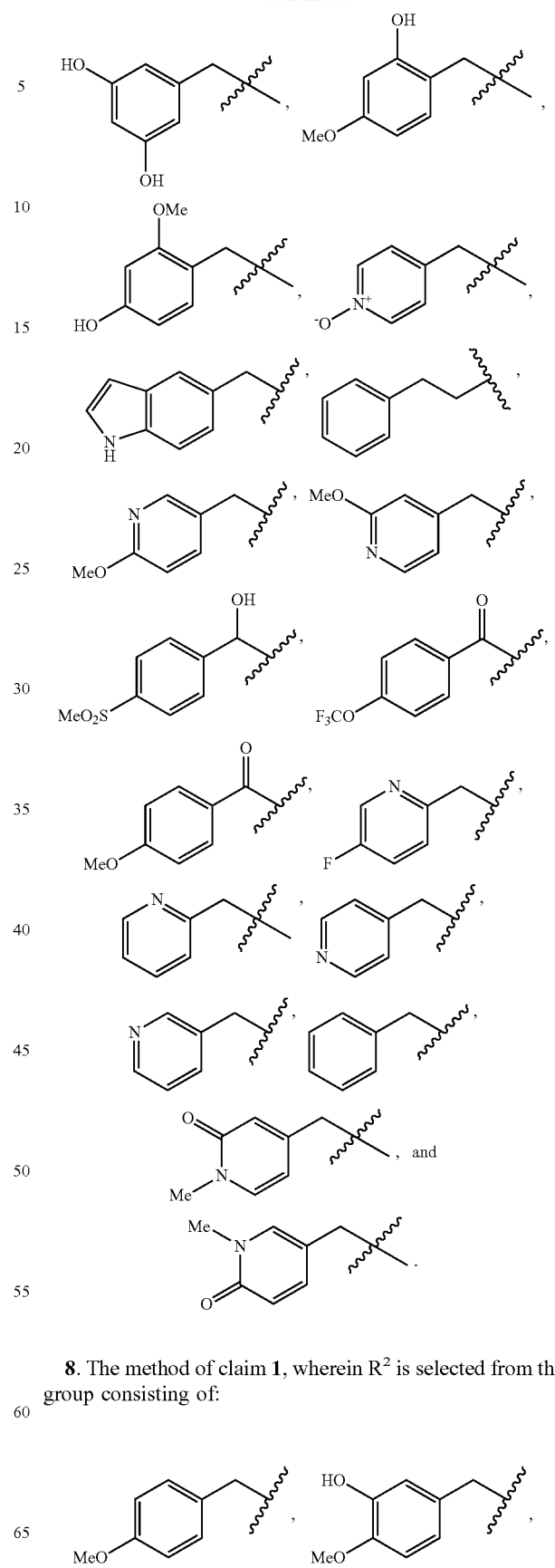
8. The method of claim 1, wherein $R^2$ is selected from the group consisting of:

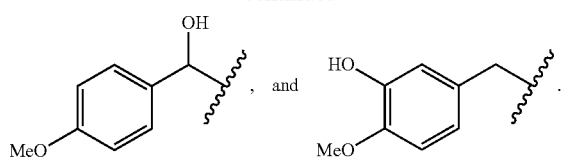

9. The method of claim 1, wherein $R^3$ is $C_{3-7}$cycloalkyl.

10. The method of claim 1, wherein $R^3$ is $C_{3-7}$cycloalkenyl.

11. The method of claim 1, wherein $R^3$ is selected from the group consisting of:

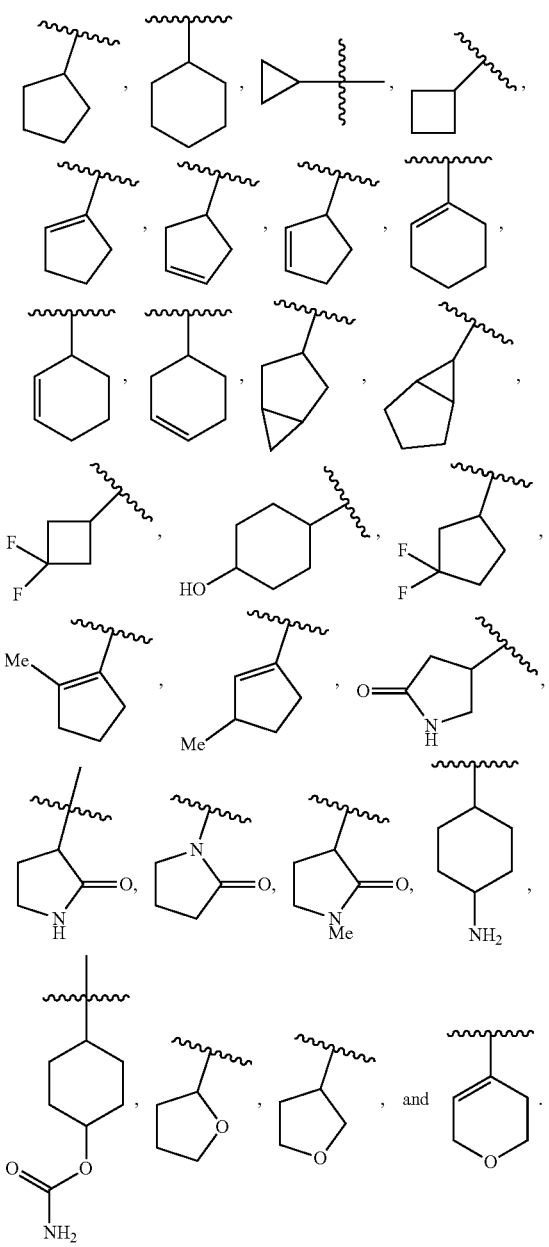

12. The method of claim 1, wherein $R^3$ is selected from the group consisting of

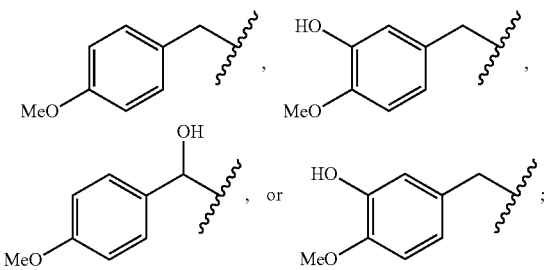

13. The method of claim 1, wherein $R^4$ is methyl.

14. The method of claim 1, wherein:
m and n are each independently 2;
p is 1;
q is 1;
K is $CR^5R^6$ or O;
E is N or $CR^7$;
$R^1$ is $CH_3$, $CH_2OH$, $CH(OH)CH_3$, or $CH_2CN$;
$R^2$ is

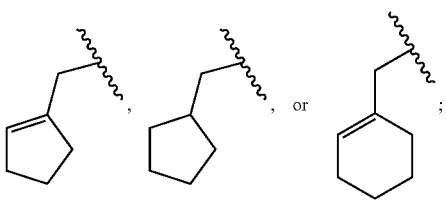 [SMILES: *CC1=CCCC1 ; *CC1CCCC1 ; *CC1=CCCCC1]

$R^3$ is

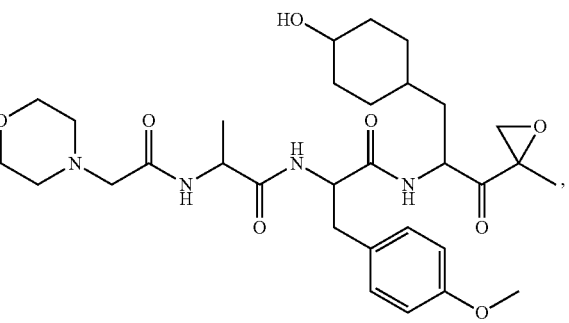

$R^4$ is methyl;
$R^5$ is H;
$R^6$ is OH; and,
$R^7$ is H.

15. The method of claim 1, wherein the compound of formula (X) has a structure selected from the group consisting of:

301
-continued
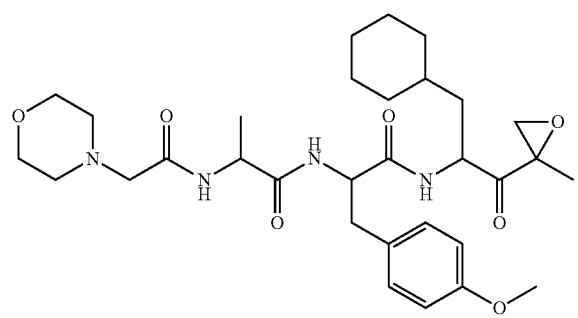
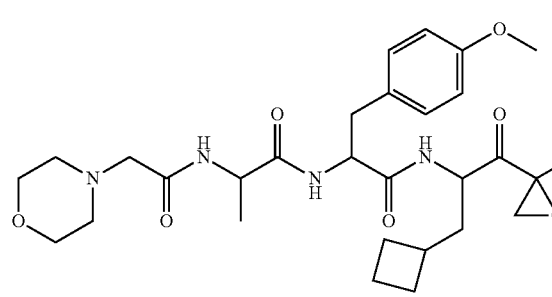
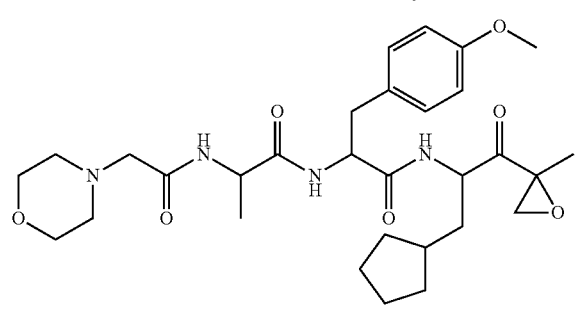
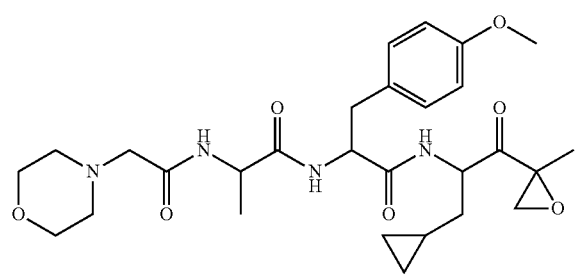
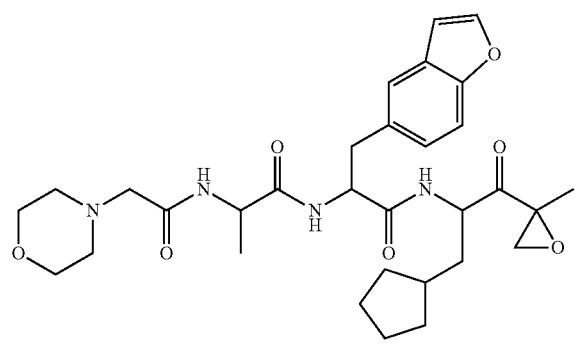
302
-continued
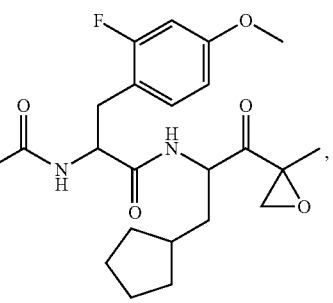
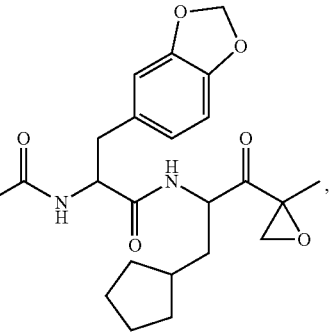
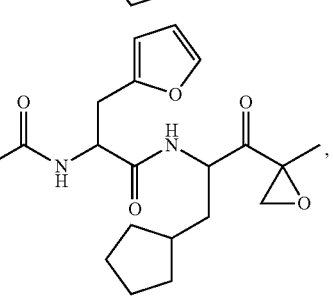

303
-continued
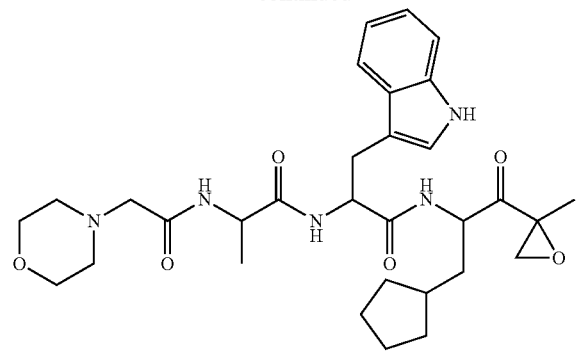
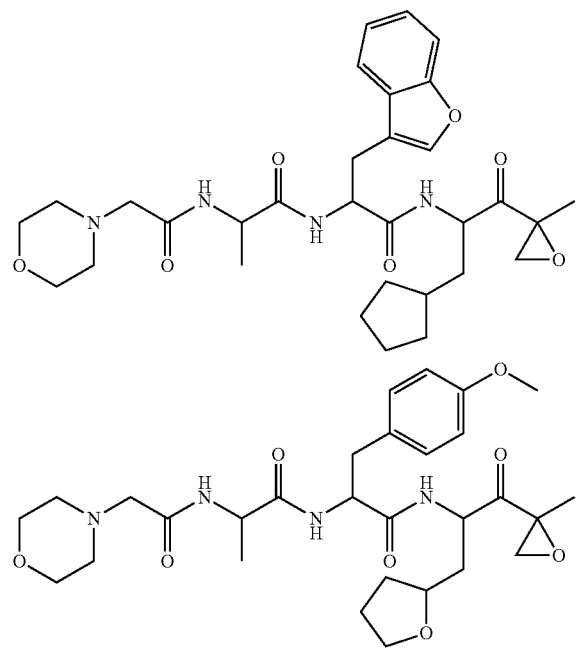
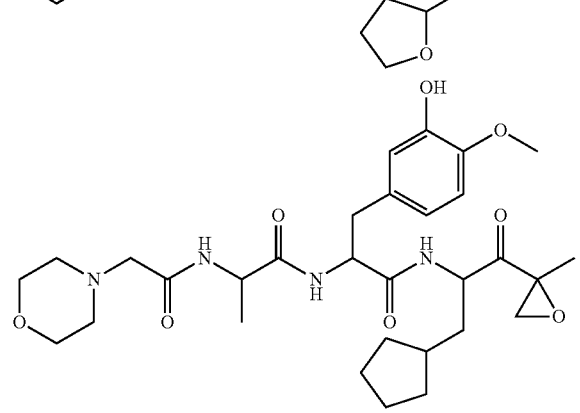
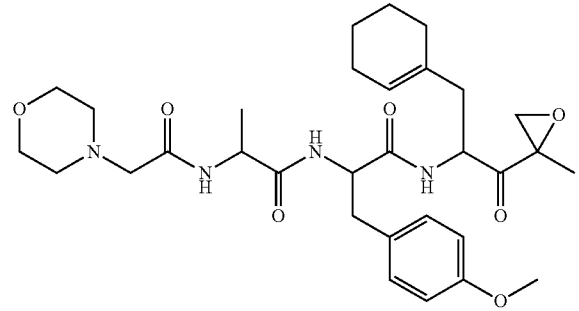
304
-continued
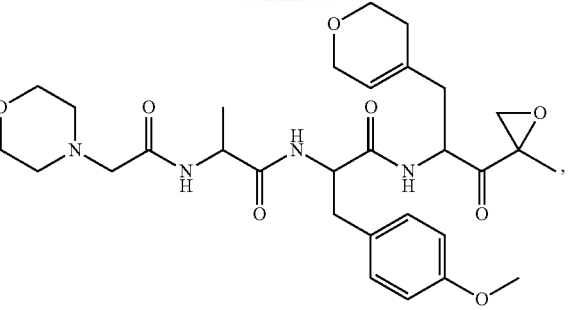
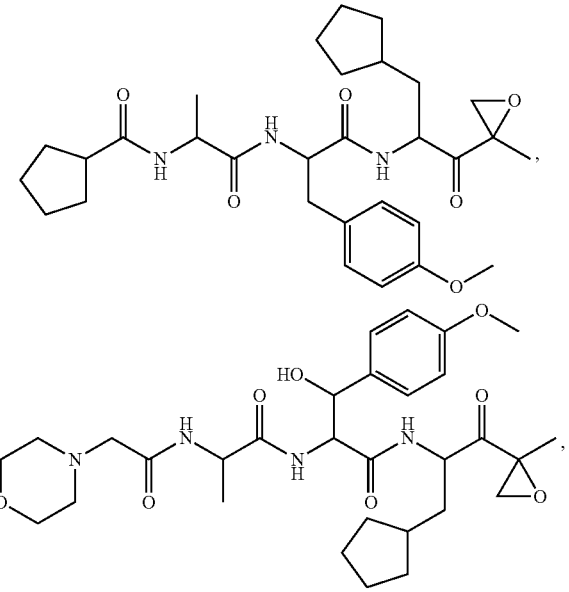
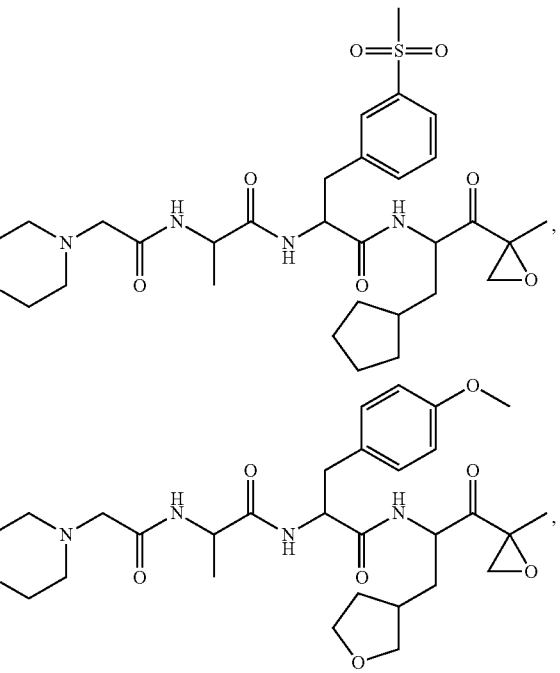

305
-continued
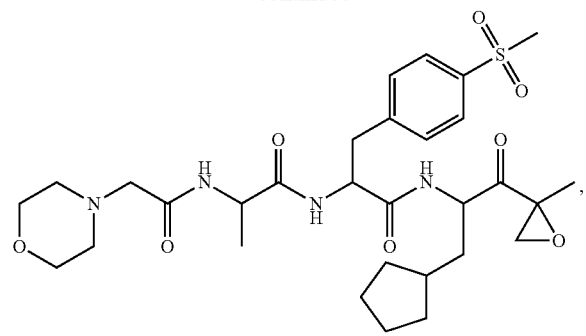
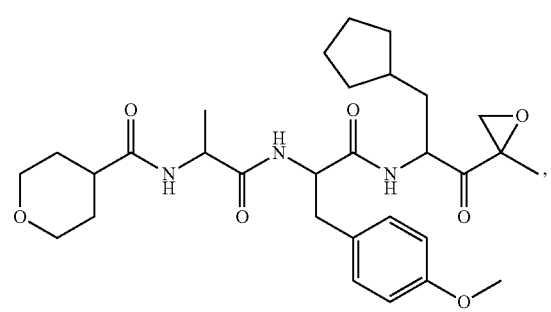
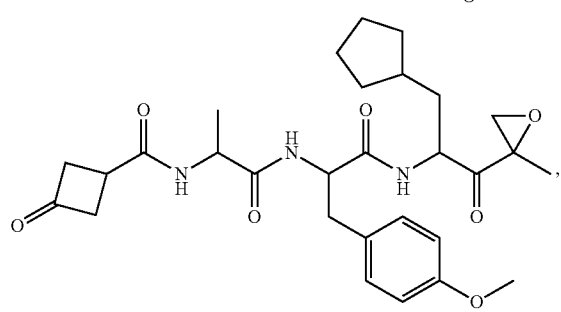
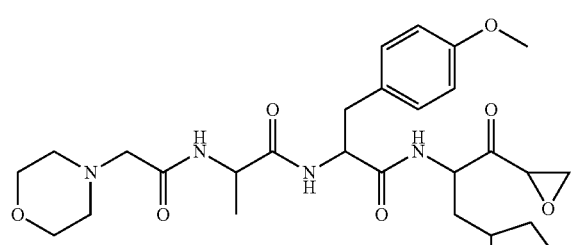
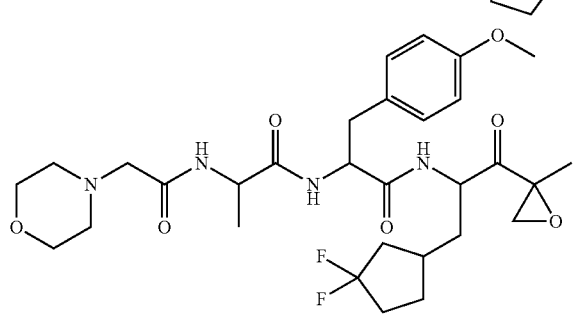
306
-continued
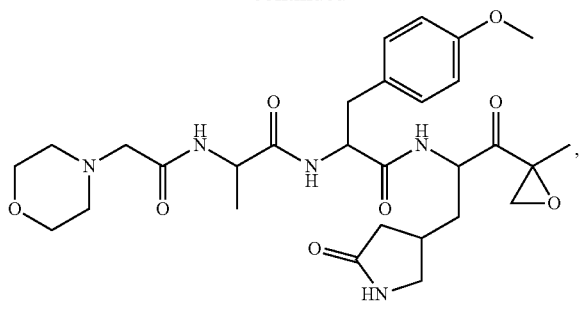
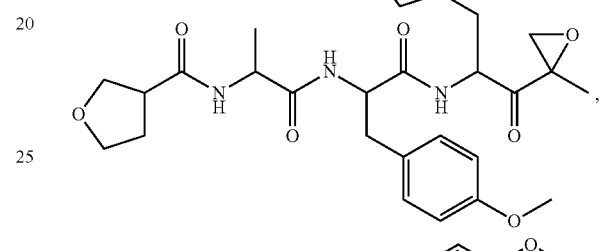
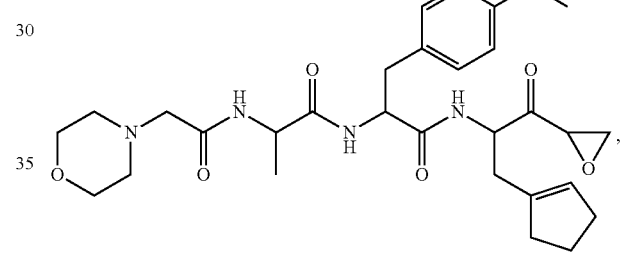
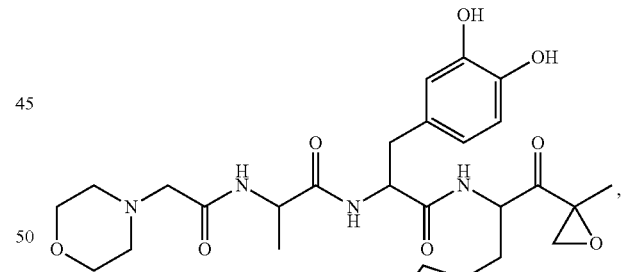
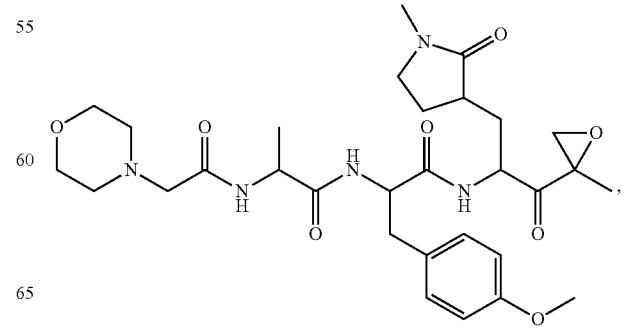

307
-continued
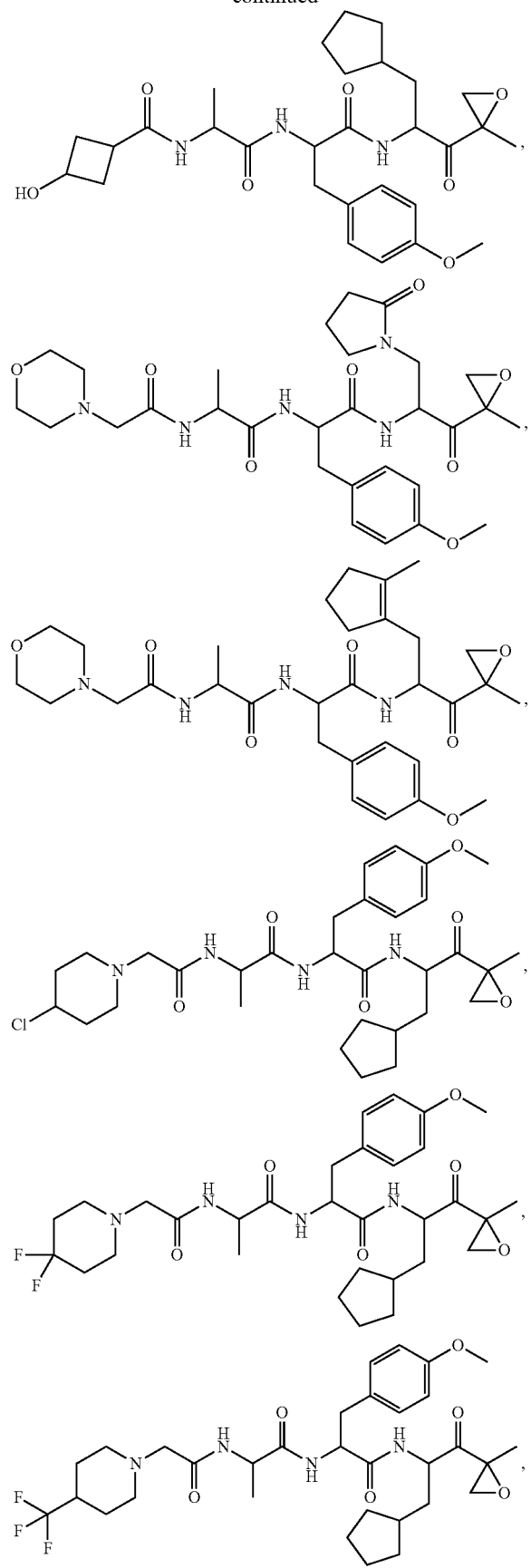
308
-continued
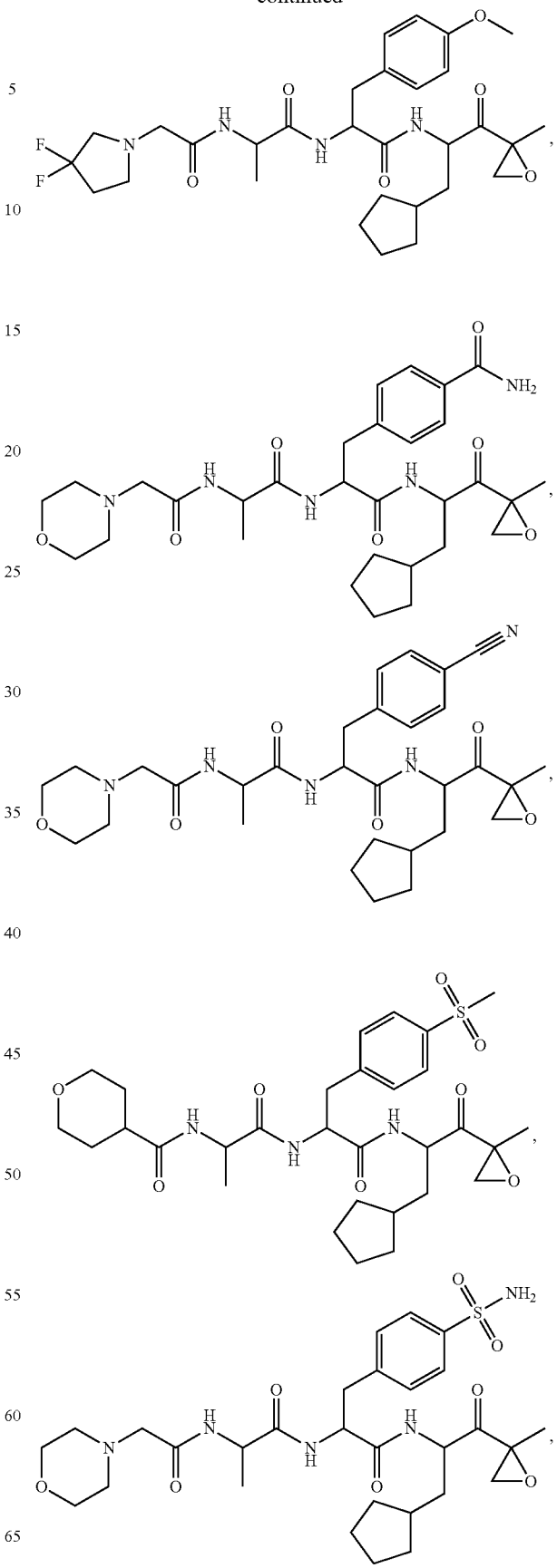

309
-continued
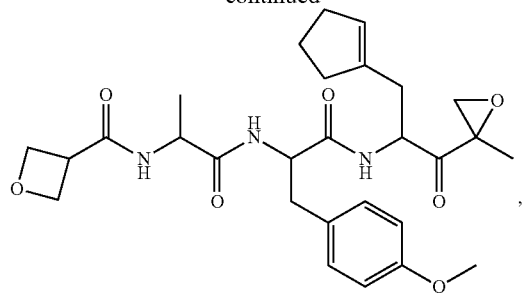
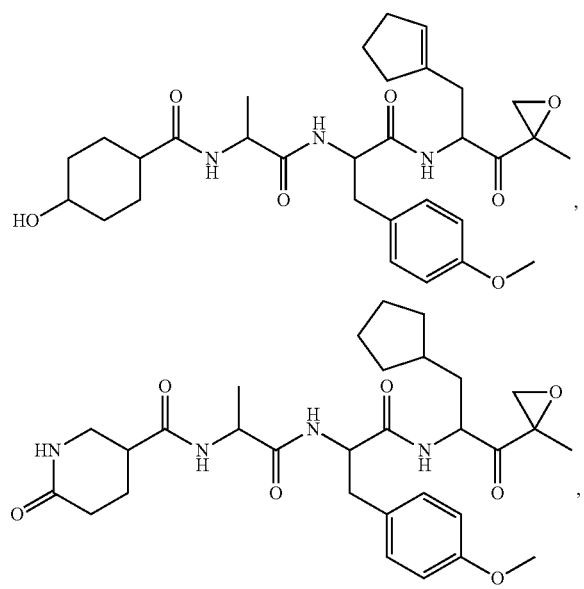
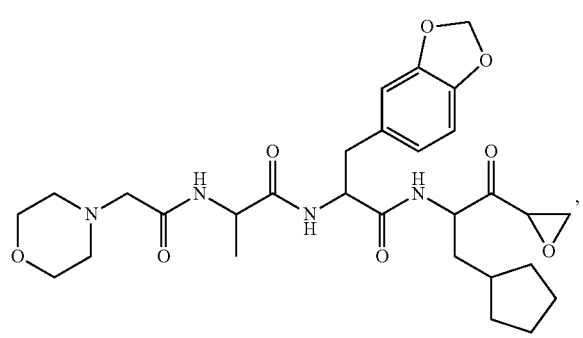
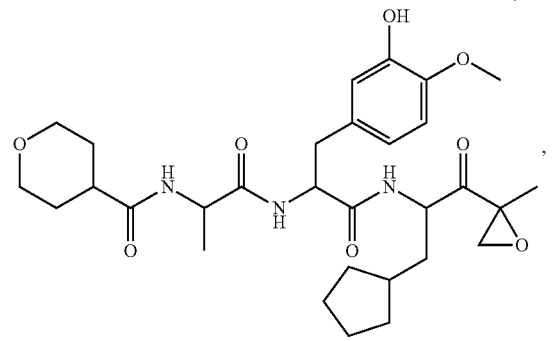
310
-continued
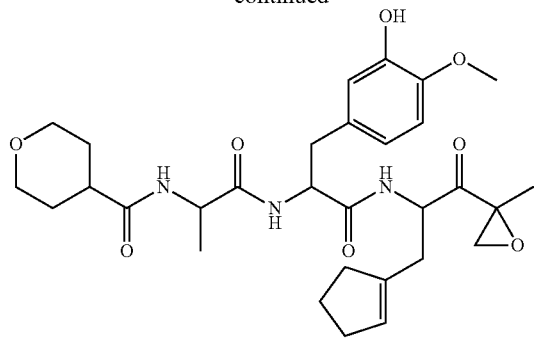
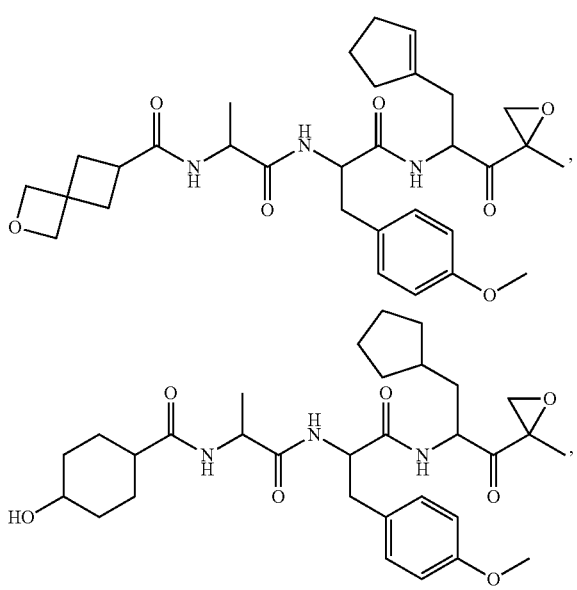
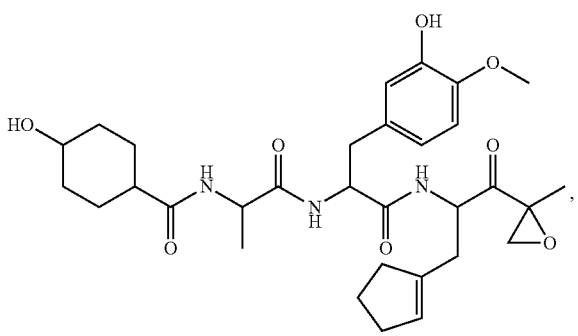
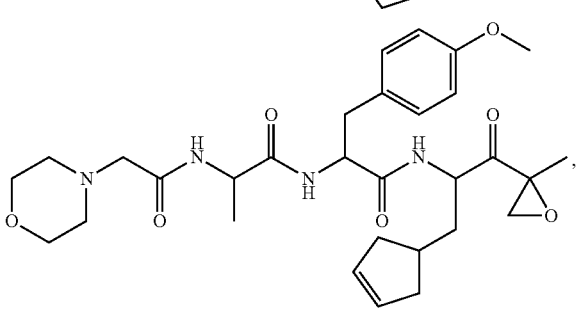

311
-continued
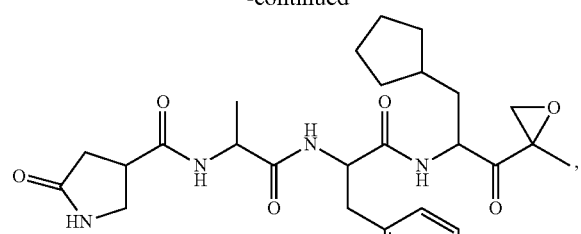
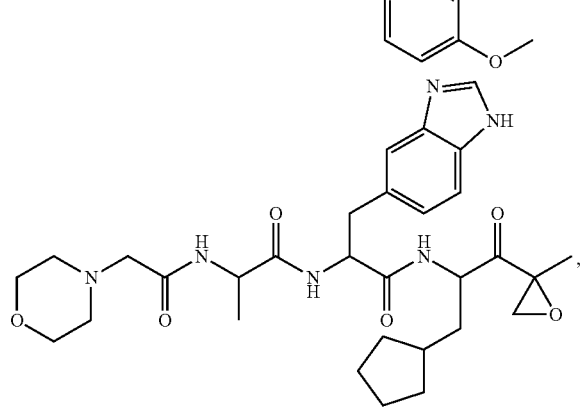
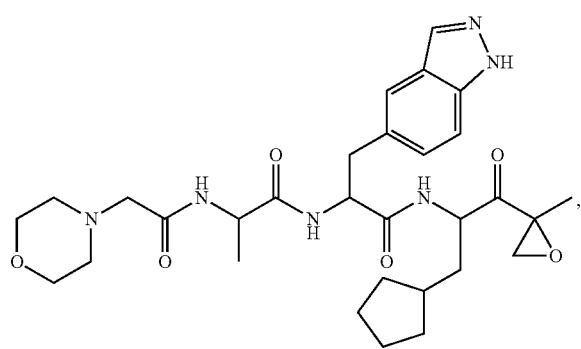
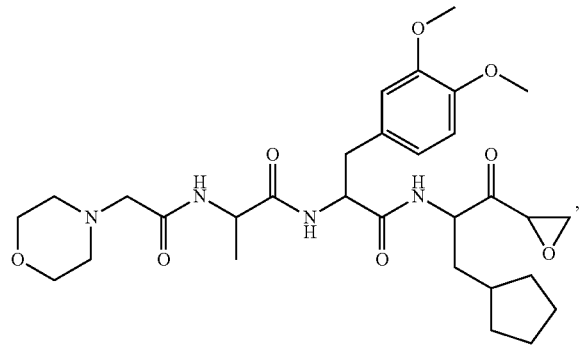
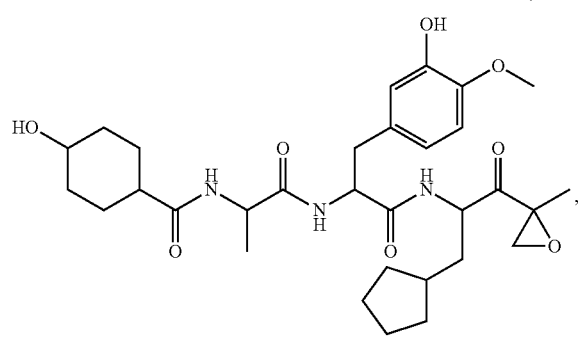
312
-continued
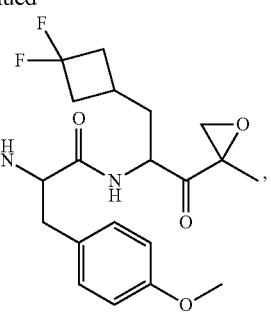
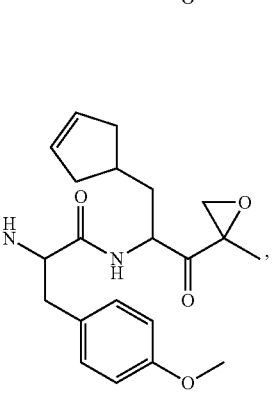
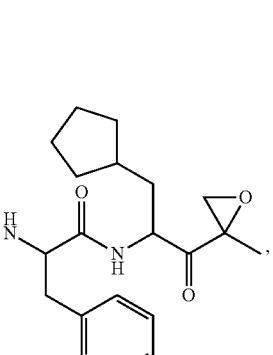
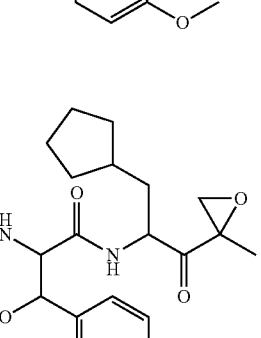
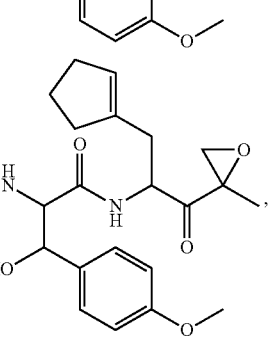

313
-continued
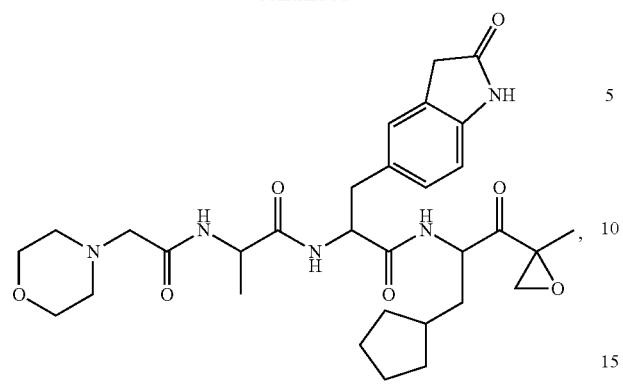
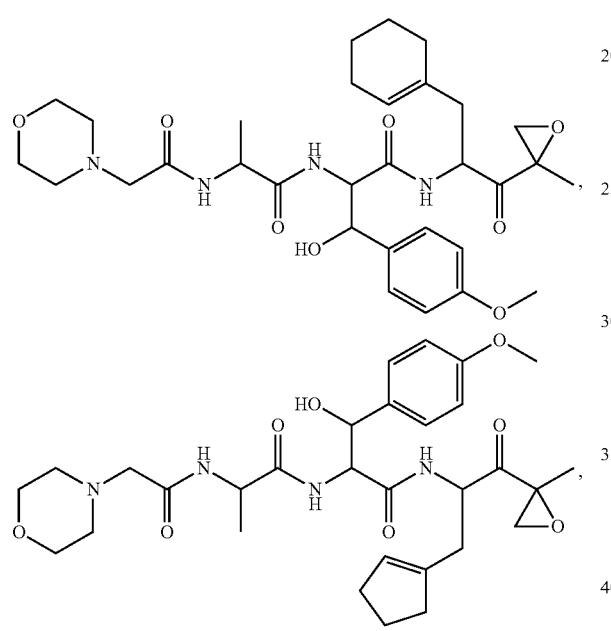
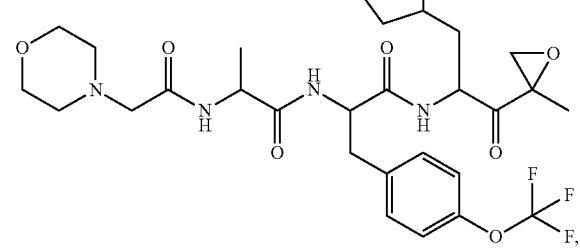
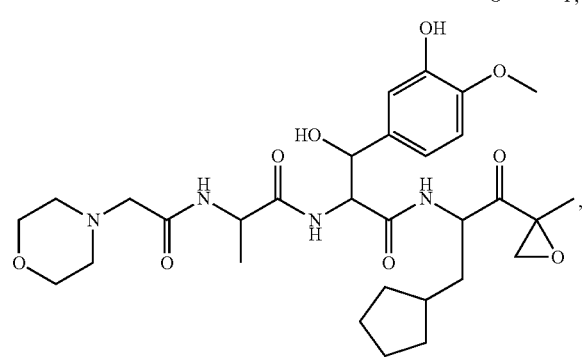
314
-continued
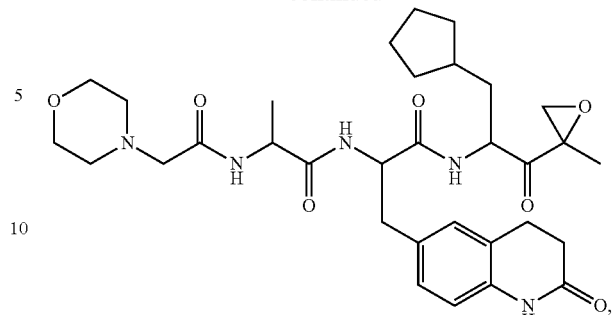
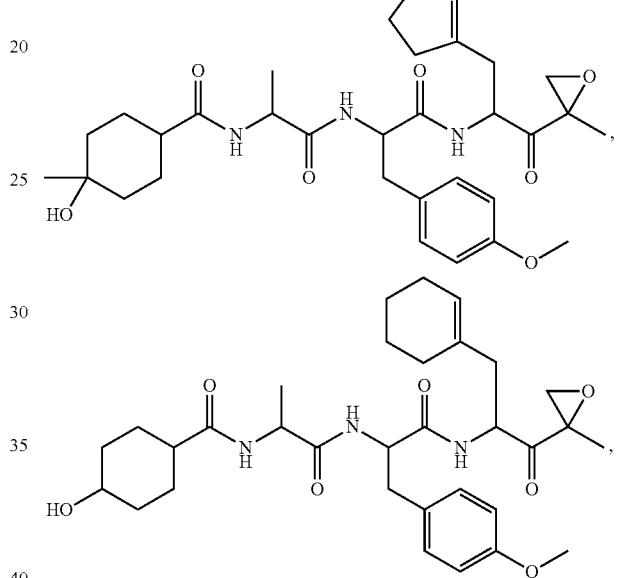
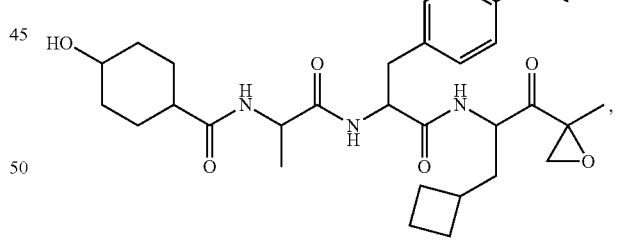
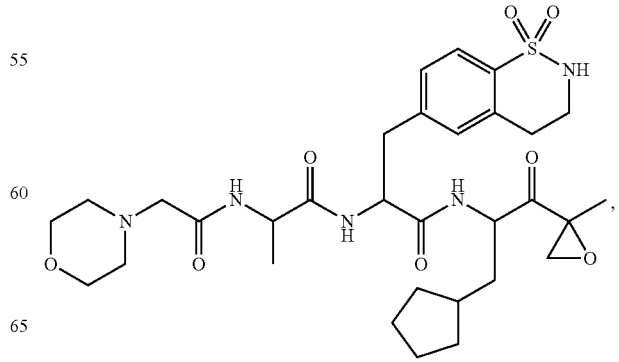

315
-continued
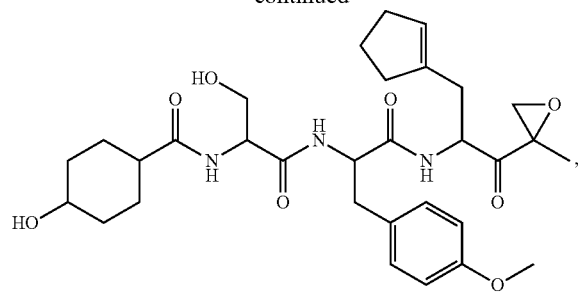
316
-continued
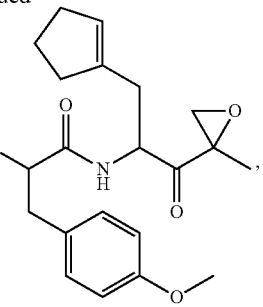
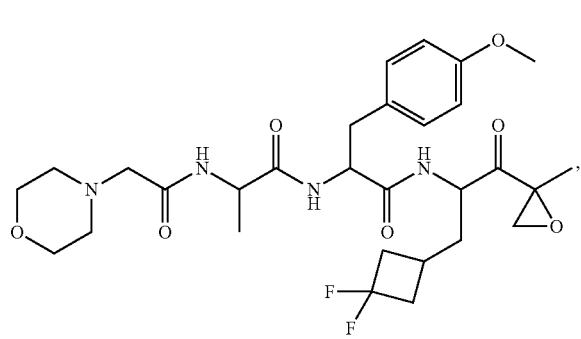
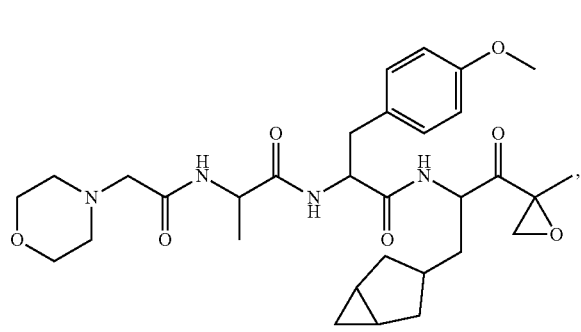
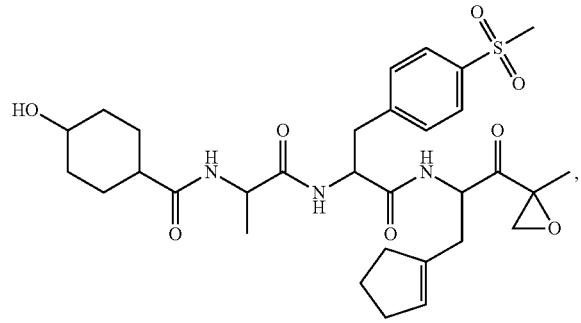

317
-continued
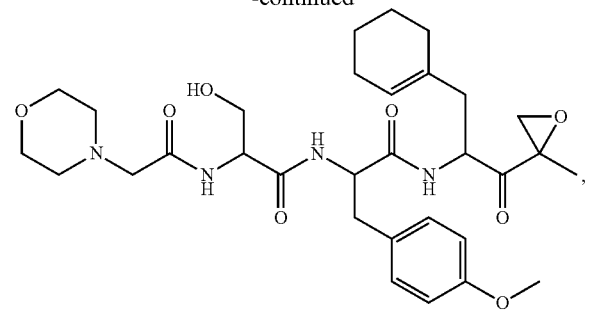
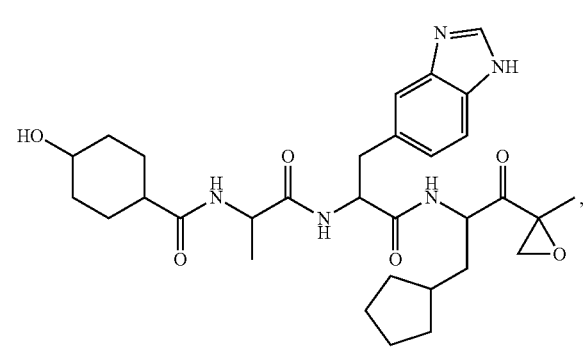
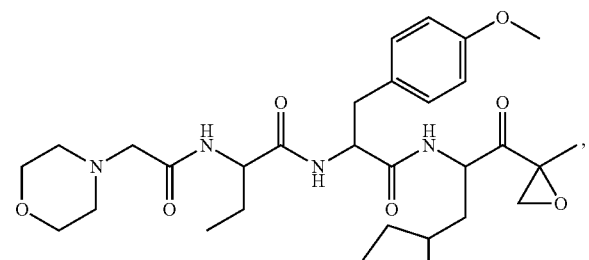
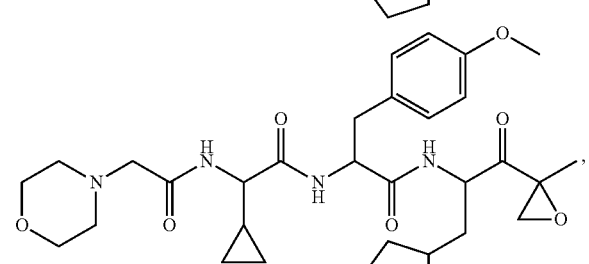
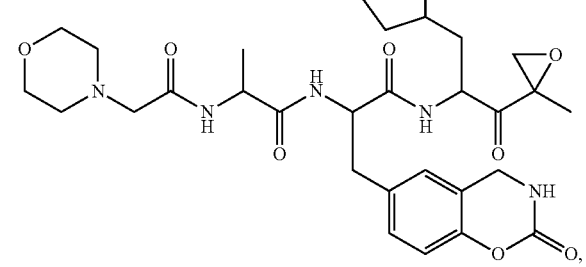
318
-continued
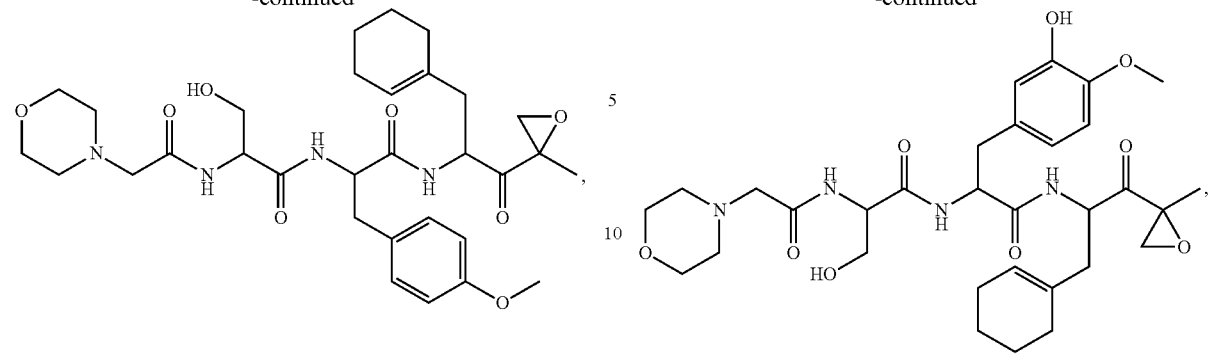
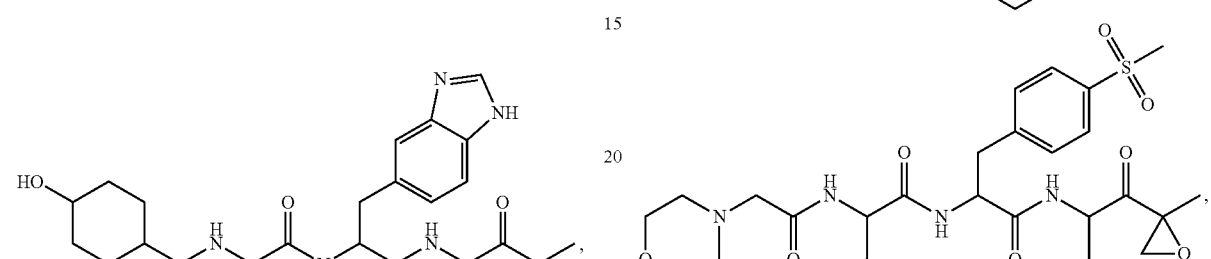
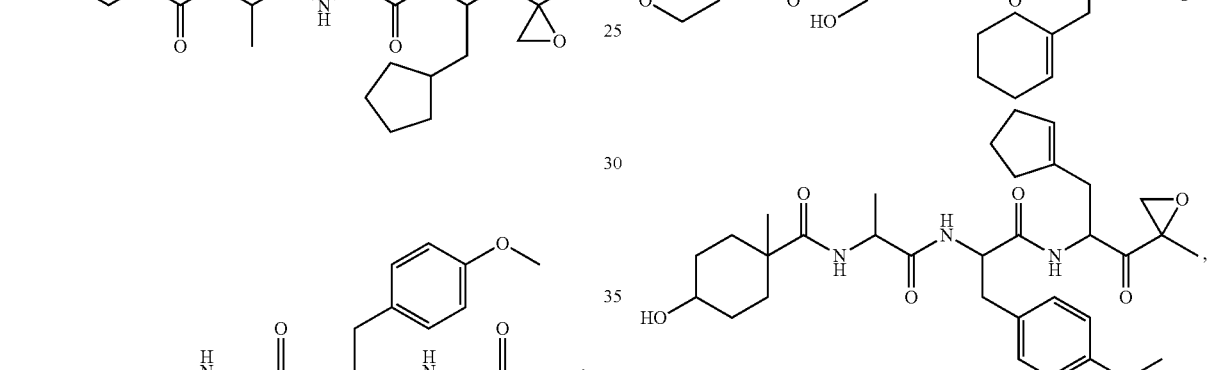
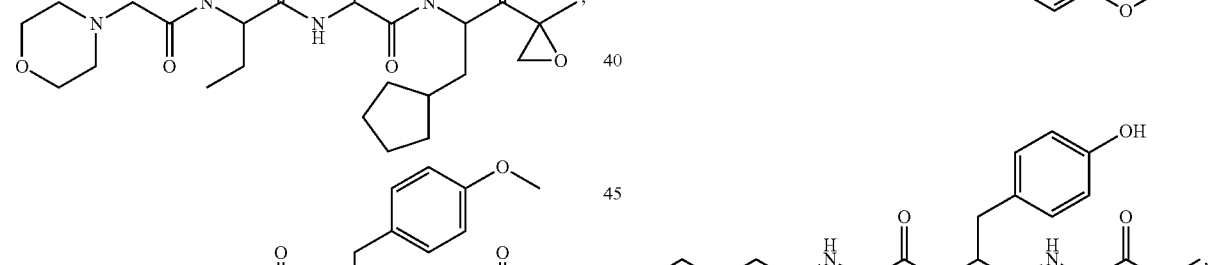
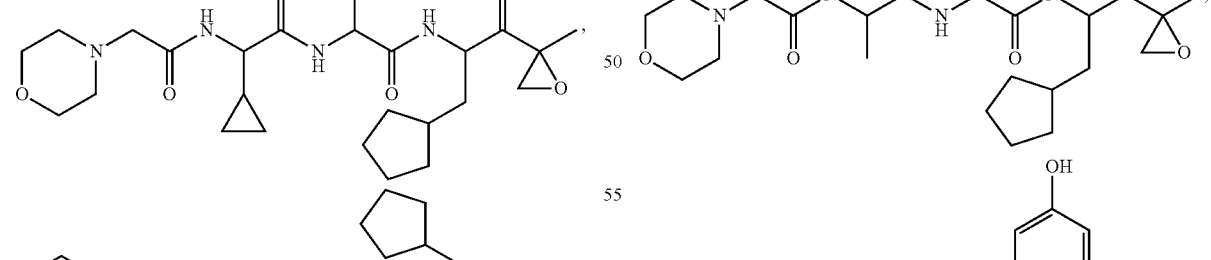
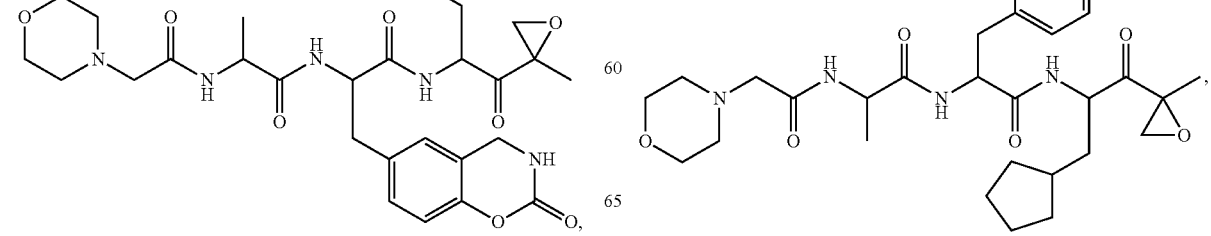

319
-continued
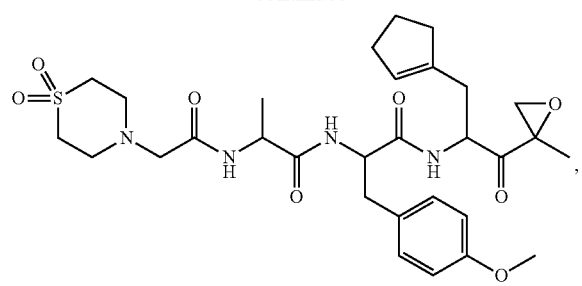
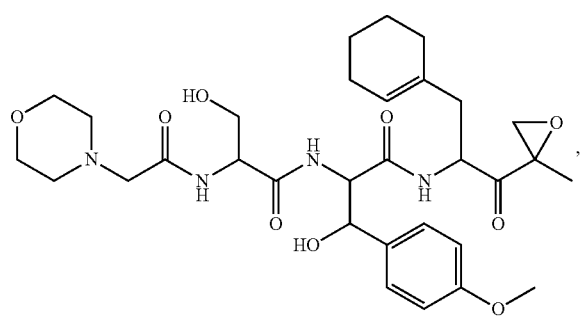
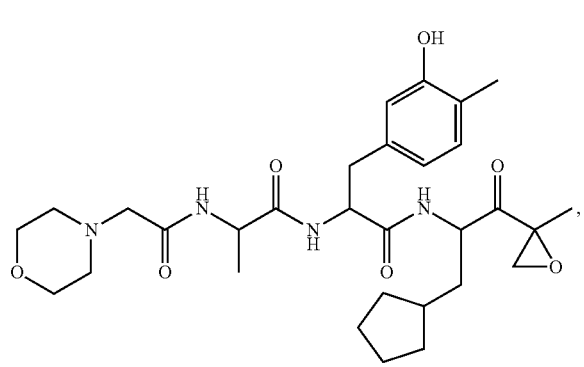
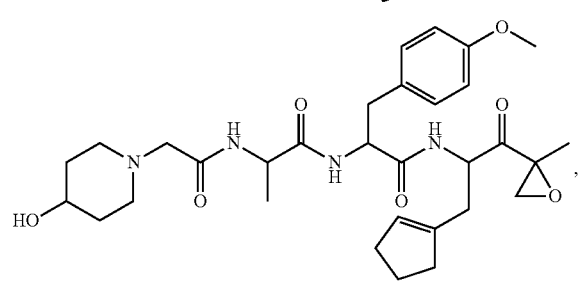
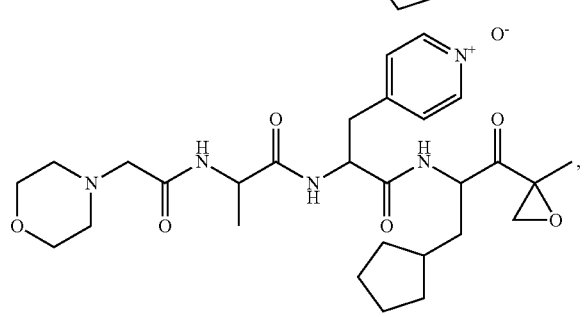
320
-continued
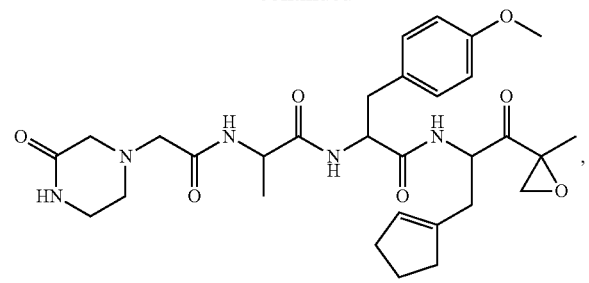
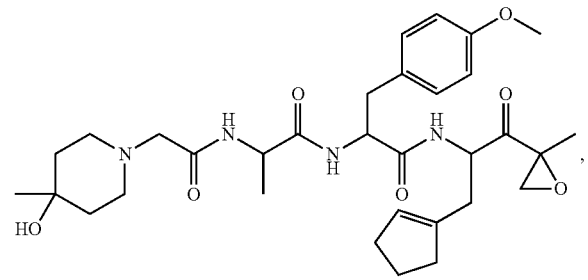
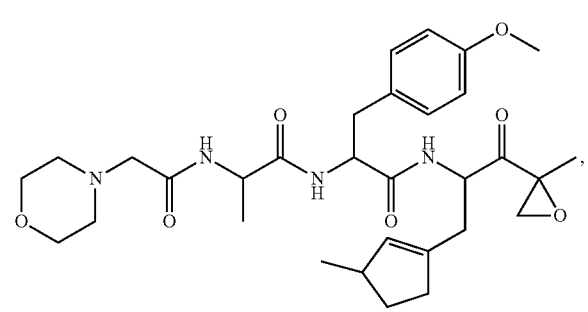
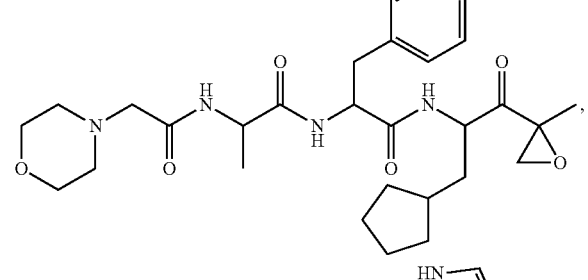
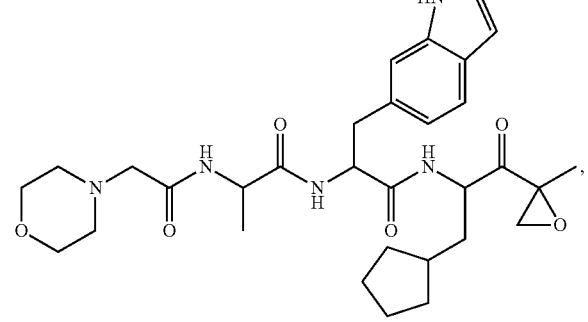

321
-continued
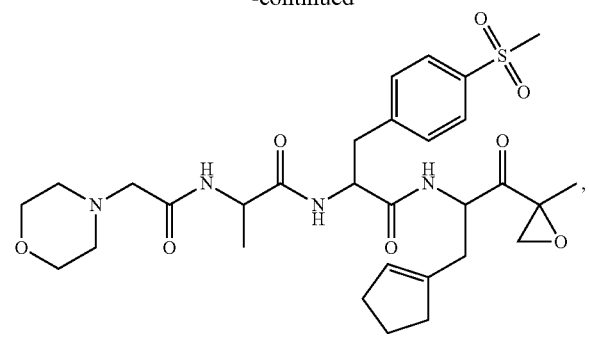
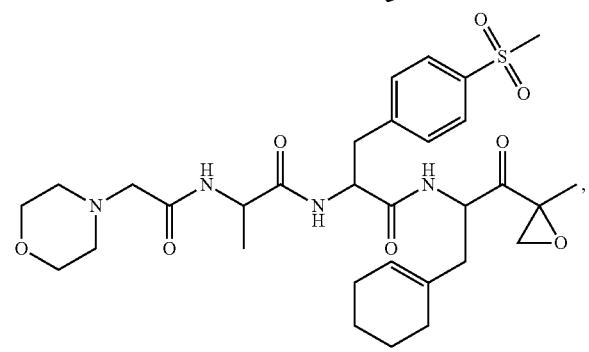
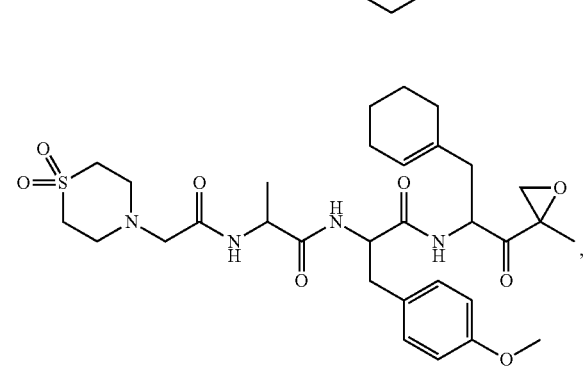
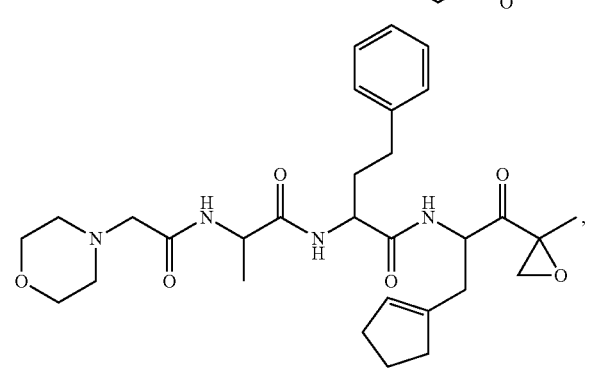
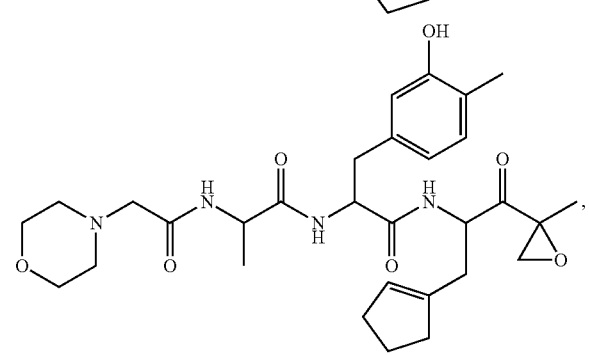
322
-continued
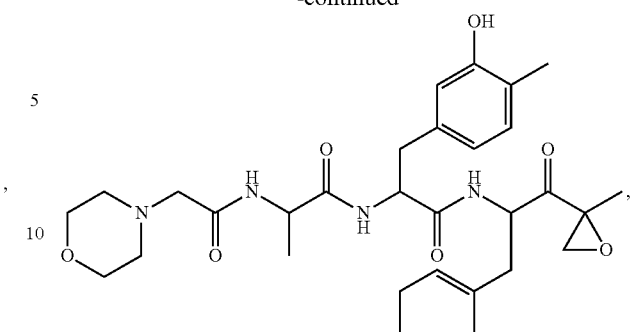
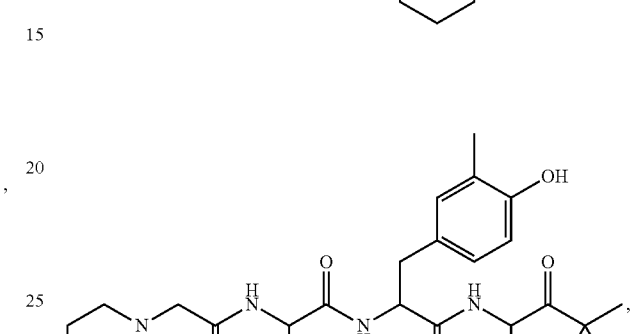
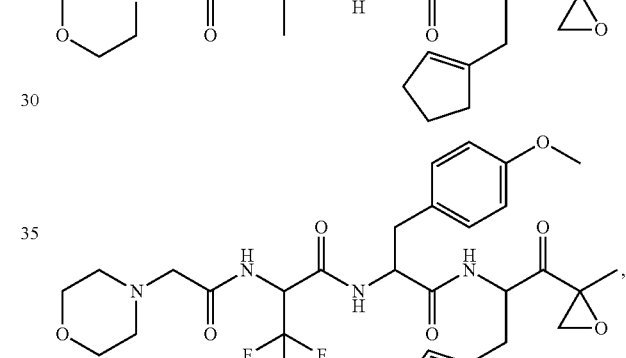
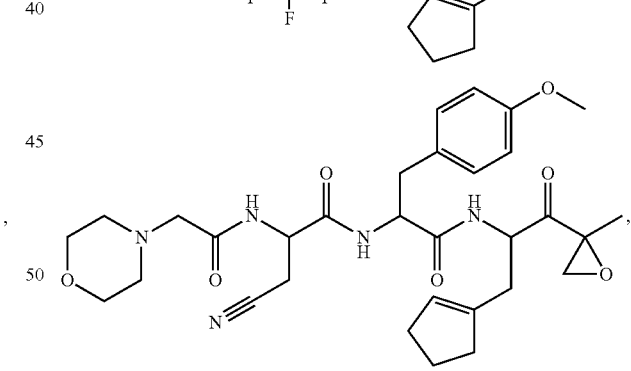
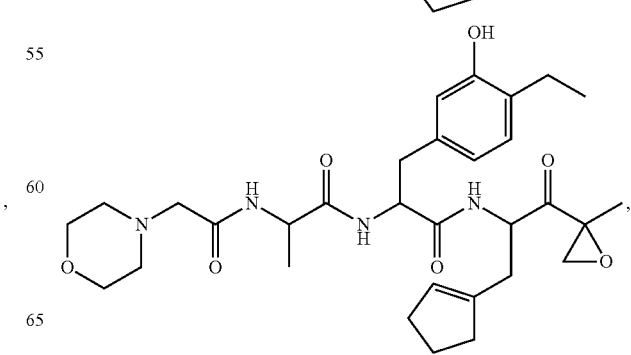

323
-continued
324
-continued
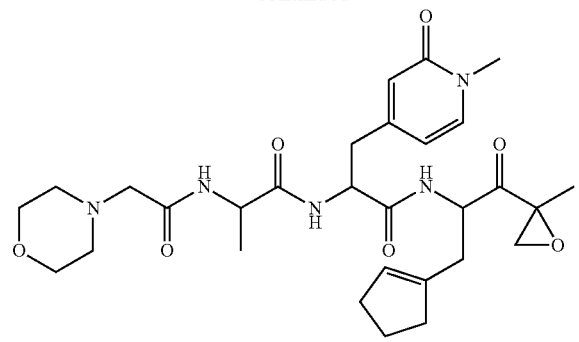
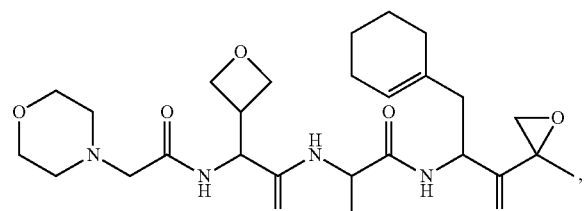
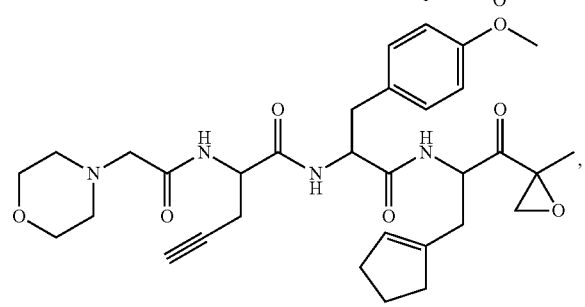
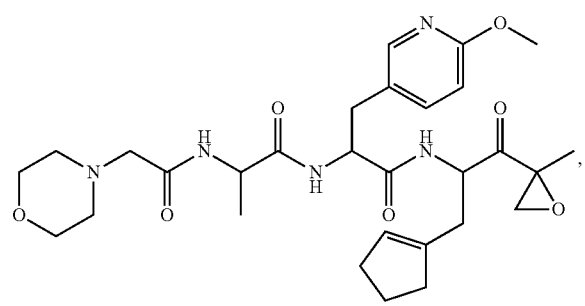
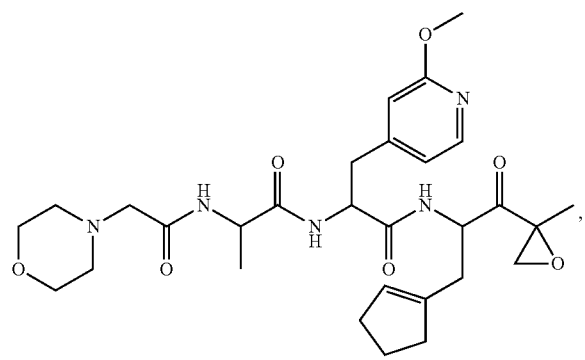
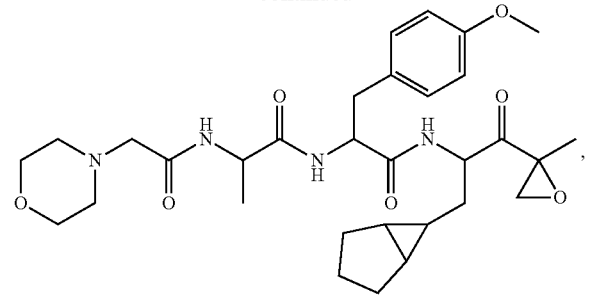

-continued
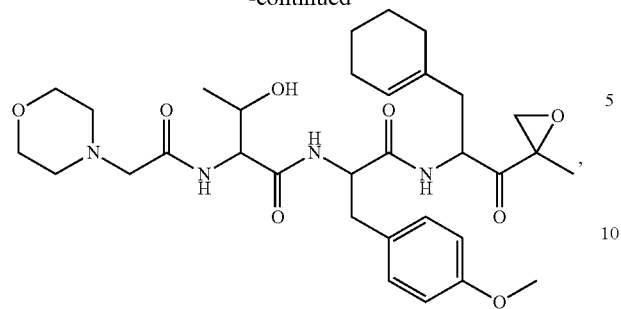
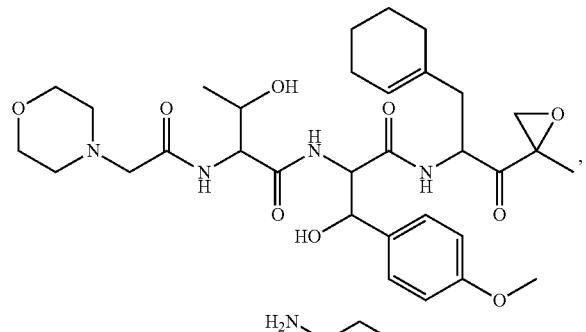
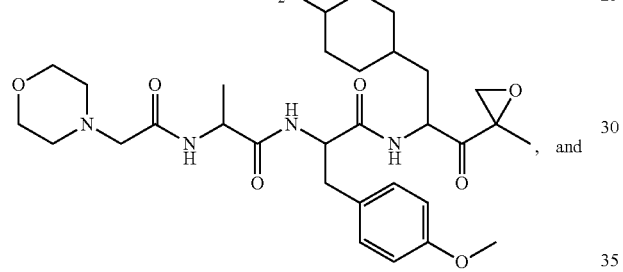
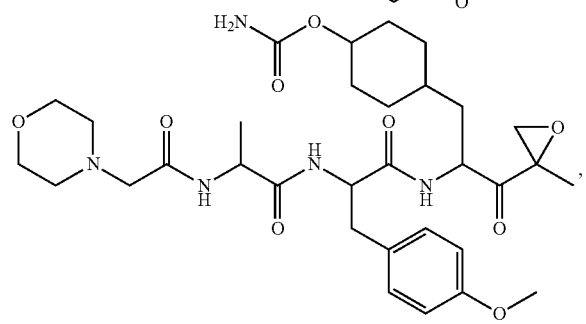
or a pharmaceutically acceptable salt thereof.
16. The method of claim 1, wherein the compound of formula (X) has a structure selected from the group consisting of:
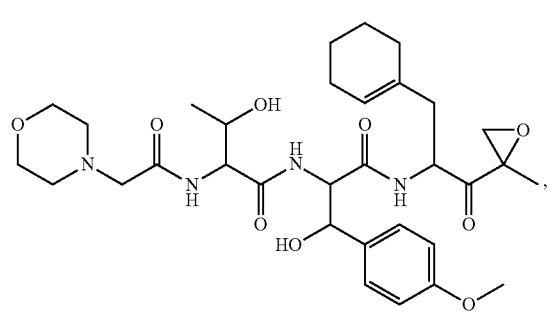
-continued
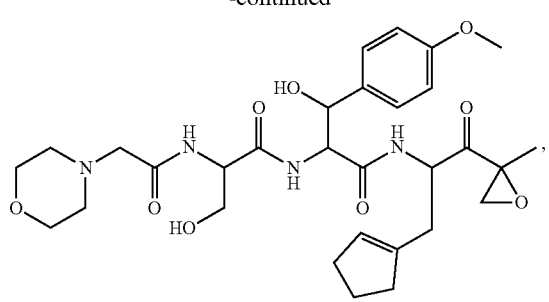
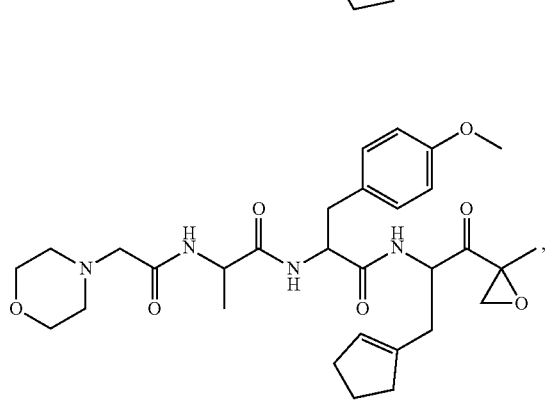
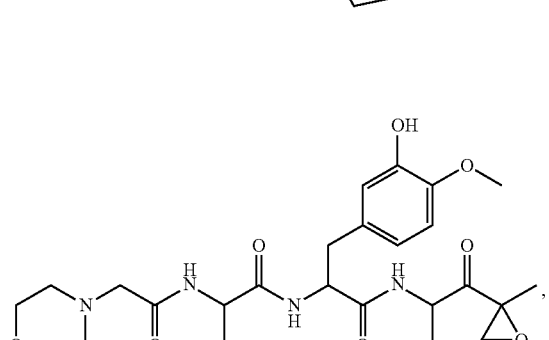
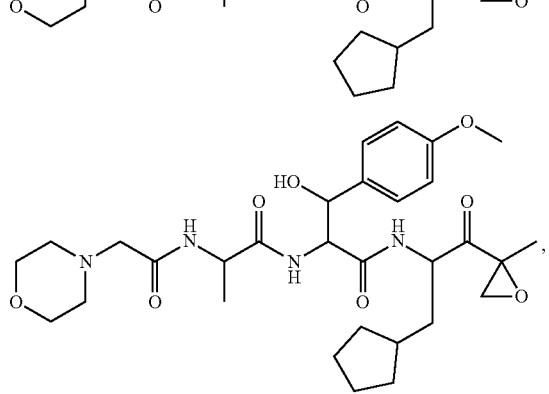
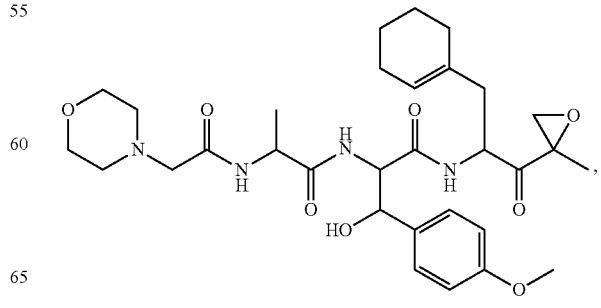

-continued

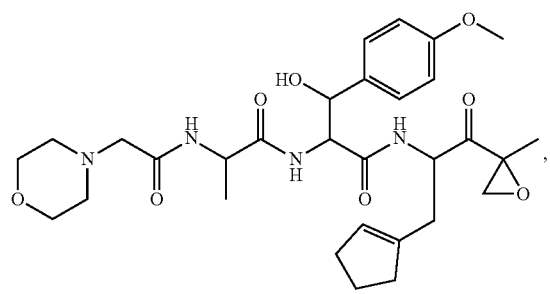

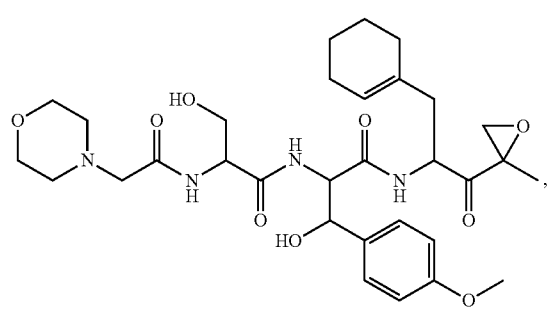

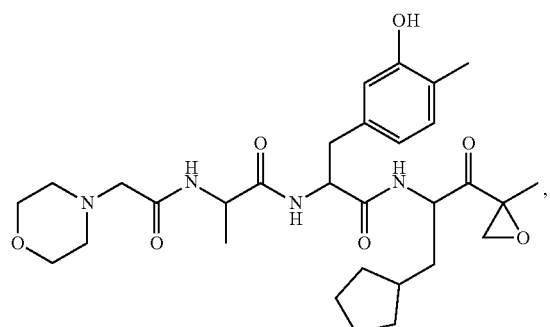

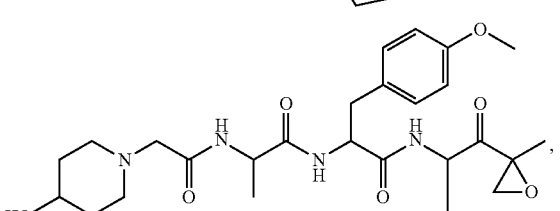

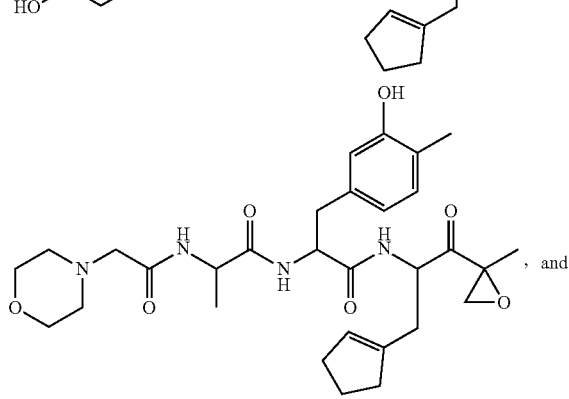

-continued

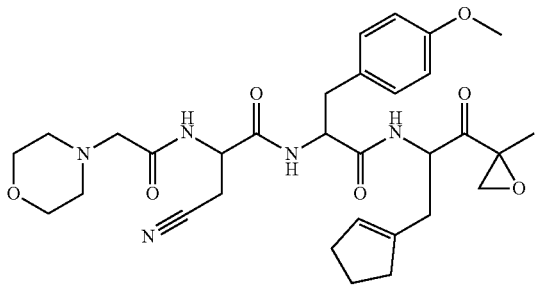

or a pharmaceutically acceptable salt thereof.

17. The method of claim 1, wherein the compound has a stereochemical configuration:

or a pharmaceutically acceptable salt thereof.

18. The method of claim 1, wherein the compound or salt inhibits β5i (LMP7).

19. The method of claim 1, wherein the contacting is in vivo.

20. The method of claim 19, wherein the contacting comprises administering the compound or salt to a subject suffering from an autoimmune disease.

21. The method of claim 20, wherein the autoimmune disease is psoriasis, dermatitis, systemic scleroderma, sclerosis, Crohn's disease, ulcerative colitis; respiratory distress syndrome, meningitis; encephalitis; uveitis; colitis; glomerulonephritis; eczema, asthma, chronic inflammation; atherosclerosis; leukocyte adhesion deficiency; rheumatoid arthritis; systemic lupus erythematosus (SLE); diabetes mellitus; multiple sclerosis; Reynaud's syndrome; autoimmune thyroiditis; allergic encephalomyelitis; Sjorgen's syndrome; juvenile onset diabetes; tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia; myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; or autoimmune thrombocytopenia (ITP).

22. The method of claim 1, wherein the compound is

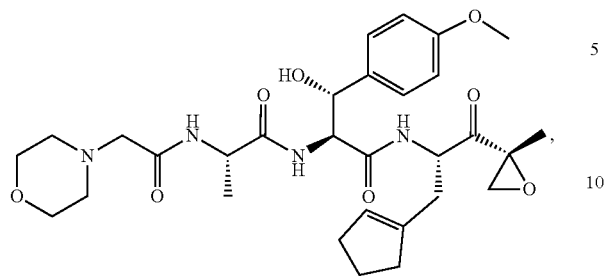

or a pharmaceutically acceptable salt thereof.

23. The method of claim 22, wherein the contacting comprises administering the compound or salt to a subject suffering from an autoimmune disease selected from the group consisting of systemic lupus erythematosus (SLE), polymyositis, hemolytic anemia, and autoimmune thrombocytopenia (ITP).

24. The method of claim 23, wherein the autoimmune disease is SLE.

25. The method of claim 23, wherein the autoimmune disease is polymyositis.

26. The method of claim 23, wherein the autoimmune disease is hemolytic anemia.

27. The method of claim 23, wherein the autoimmune disease is ITP.

* * * * *

UNITED STATES PATENT AND TRADEMARK OFFICE
CERTIFICATE OF CORRECTION

PATENT NO. : 11,078,233 B2  
APPLICATION NO. : 16/818731  
DATED : August 3, 2021  
INVENTOR(S) : Dustin McMinn et al.

Page 1 of 1

It is certified that error appears in the above-identified patent and that said Letters Patent is hereby corrected as shown below:

In the Claims

At Column 313, Lines 53-66, " 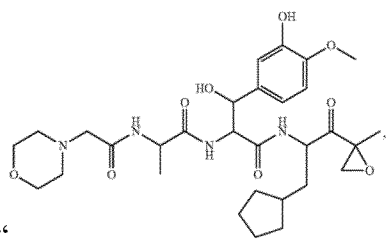 " should be

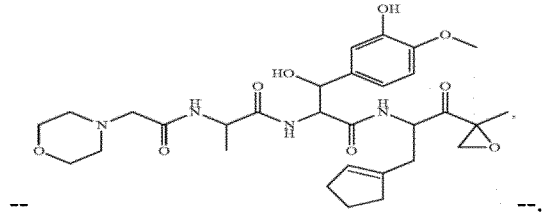

-- --.

At Column 328, Lines 25-32, " 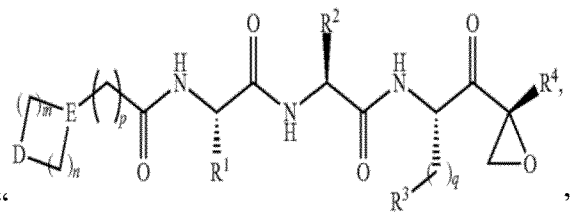 " should be

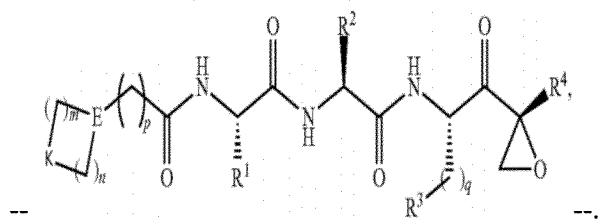

-- --.

Signed and Sealed this  
Seventeenth Day of May, 2022

*Katherine Kelly Vidal*

Katherine Kelly Vidal  
*Director of the United States Patent and Trademark Office*